US011856843B2

(12) United States Patent
Mun et al.

(10) Patent No.: US 11,856,843 B2
(45) Date of Patent: Dec. 26, 2023

(54) COMPOUND FOR ORGANIC ELECTRIC ELEMENT, ORGANIC ELECTRIC ELEMENT USING THE SAME, AND ELECTRONIC DEVICE THEREFOR

(71) Applicant: DUK SAN NEOLUX CO., LTD., Cheonan-si (KR)

(72) Inventors: Soung Yun Mun, Cheonan-si (KR); Sun Hee Lee, Hwaseong-si (KR); Jong Gwang Park, Cheonan-si (KR); Ki Ho So, Cheonan-si (KR); Won Sam Kim, Hwaseong-si (KR); Jung Hwan Park, Hwaseong-si (KR); Chi Hyun Park, Cheonan-si (KR); Mi Young Chae, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 616 days.

(21) Appl. No.: 17/043,595

(22) PCT Filed: Mar. 18, 2019

(86) PCT No.: PCT/KR2019/003116

§ 371 (c)(1),
(2) Date: Sep. 29, 2020

(87) PCT Pub. No.: WO2019/190101

PCT Pub. Date: Oct. 3, 2019

(65) Prior Publication Data

US 2021/0028370 A1 Jan. 28, 2021

(30) Foreign Application Priority Data

Mar. 29, 2018 (KR) ........................ 10-2018-0036886
Mar. 14, 2019 (KR) ........................ 10-2019-0029346

(51) Int. Cl.

*C07D 405/14* (2006.01)
*H10K 85/60* (2023.01)
*C09K 11/02* (2006.01)
*C07D 409/14* (2006.01)
*H10K 50/11* (2023.01)
(Continued)

(52) U.S. Cl.

CPC ......... *H10K 85/636* (2023.02); *C07D 405/14* (2013.01); *C07D 409/14* (2013.01);
(Continued)

(58) Field of Classification Search

None
See application file for complete search history.

(56) References Cited

U.S. PATENT DOCUMENTS

2011/0147717 A1* 6/2011 LeCloux .............. H10K 85/633
564/429
2016/0099422 A1* 4/2016 Zeng ...................... H10K 50/15
252/301.16

(Continued)

FOREIGN PATENT DOCUMENTS

CN 108250189 A * 7/2018 ........... C07D 307/91
JP 2013243266 A * 12/2013 ............. C09K 11/06

(Continued)

*Primary Examiner* — Robert S Loewe
(74) *Attorney, Agent, or Firm* — Vorys, Sater, Seymour and Pease LLP; Mih Suhn Koh

(57) ABSTRACT

Provided is a novel mixture capable of improving luminous efficiency, stability, and lifespan of an element, an organic electric element using the same, and an electronic device therefor.

24 Claims, 1 Drawing Sheet

(51) Int. Cl.

| | |
|---|---|
| *H10K 50/15* | (2023.01) |
| *H10K 101/10* | (2023.01) |
| *H10K 101/00* | (2023.01) |

(52) U.S. Cl.

CPC .......... *C09K 11/025* (2013.01); *H10K 85/633* (2023.02); *H10K 85/654* (2023.02); *H10K 85/6574* (2023.02); *H10K 85/6576* (2023.02); *H10K 50/11* (2023.02); *H10K 50/15* (2023.02); *H10K 85/6572* (2023.02); *H10K 2101/10* (2023.02); *H10K 2101/90* (2023.02)

(56) References Cited

U.S. PATENT DOCUMENTS

| | | | | |
|---|---|---|---|---|
| 2016/0126472 | A1* | 5/2016 | Oh | H10K 85/622 252/500 |
| 2016/0293843 | A1* | 10/2016 | Itoi | H10K 85/615 |
| 2017/0125699 | A1* | 5/2017 | Ahn | H10K 85/654 |
| 2018/0114906 | A1* | 4/2018 | Itoi | H10K 85/615 |
| 2018/0301639 | A1* | 10/2018 | Zeng | C07D 487/04 |
| 2019/0198771 | A1* | 6/2019 | Lui | H10K 85/6574 |
| 2019/0296248 | A1* | 9/2019 | Mun | C07D 209/82 |
| 2019/0372012 | A1* | 12/2019 | Cho | H10K 85/6572 |
| 2020/0266355 | A1* | 8/2020 | Park | H10K 85/615 |
| 2020/0388766 | A1* | 12/2020 | Kim | H10K 85/342 |
| 2021/0083198 | A1* | 3/2021 | Han | H10K 99/00 |

FOREIGN PATENT DOCUMENTS

| | | | |
|---|---|---|---|
| KR | 10-2014-0101661 | A | 8/2014 |
| KR | 10-2016-0107975 | A | 9/2016 |
| KR | 10-2017-0089599 | A | 8/2017 |
| WO | 2018/012780 | A1 | 1/2018 |
| WO | 2018/016742 | A1 | 1/2018 |

* cited by examiner

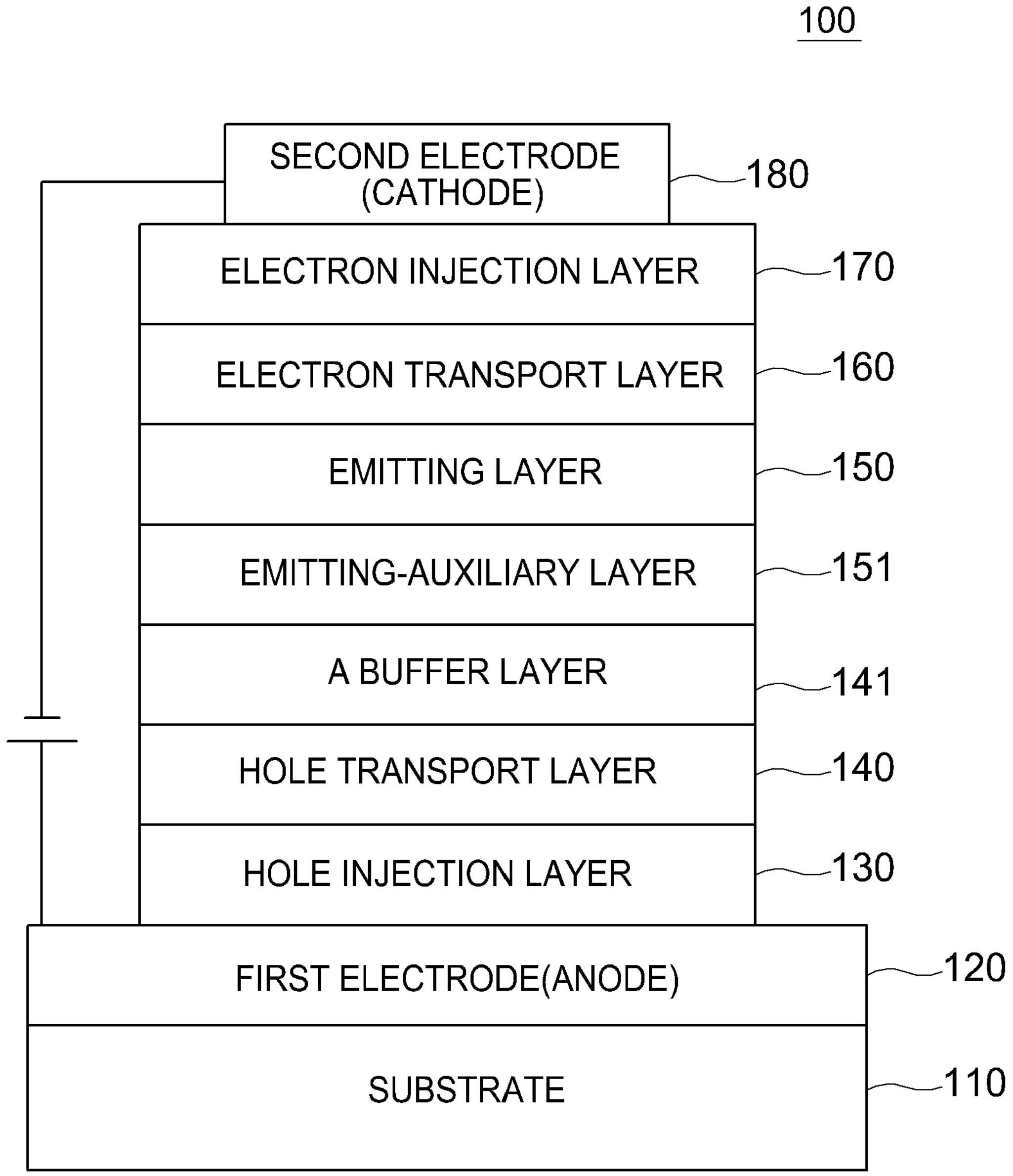
100
SECOND ELECTRODE (CATHODE)
180
ELECTRON INJECTION LAYER
170
ELECTRON TRANSPORT LAYER
160
EMITTING LAYER
150
EMITTING-AUXILIARY LAYER
151
A BUFFER LAYER
141
HOLE TRANSPORT LAYER
140
HOLE INJECTION LAYER
130
FIRST ELECTRODE(ANODE)
120
SUBSTRATE
110

COMPOUND FOR ORGANIC ELECTRIC ELEMENT, ORGANIC ELECTRIC ELEMENT USING THE SAME, AND ELECTRONIC DEVICE THEREFOR

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electric element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

Bis-type cyclic compounds including heteroatoms have a very large difference in properties depending on the material structure, and are therefore applied to various layers as materials for organic electric elements. In particular, the band gap (HOMO, LUMO), electrical properties, chemical properties, and physical properties are different depending on the number of rings and the fused position, and the type and arrangement of heteroatoms, therefore application development for layers of various organic electric elements using the same has been progressed. In a phosphorescent organic electric element using a phosphorescent dopant material, the LUMO and HOMO levels of the host material have a great influence on the efficiency and life span of the organic electric element, and depending on whether electron and hole injection in the emission layer can be efficiently controlled, charge balance in the emission layer, dopant quenching, and reduction in efficiency and lifespan due to light emission at the hole transport layer interface can be prevented.

For fluorescent and phosphorescent host materials, recently we have been studying the increase of efficiency and life span of organic electric elements using TADF (thermal activated delayed fluorescent), exciplex, etc., particularly, and many studies have been carried out to identify the energy transfer method from the host material to the dopant material.

Although there are various methods for identifying the energy transfer in the emitting layer for TADF (thermally activated delayed fluorescent) and exciplex, it can be easily confirmed by the PL lifetime (TRTP) measurement method.

The TRTP (Time Resolved Transient PL) measurement method is a method of observing a decay time after irradiating a pulsed light source onto a host thin film, and is a measurement method that can identify the energy transfer method by observing energy transfer and emission delay time. The TRTP measurement is a measurement method capable of distinguishing fluorescence and phosphorescence, and an energy transfer method in a mixed host material, an exciplex energy transfer method, and a TADF energy transfer method.

As such, there are various factors that affect the efficiency and lifespan depending on how energy is transferred from the host material to the dopant material.

Since the energy transfer method is different depending on the material, the development of a stable and efficient host material for an organic electric element has not been sufficiently performed. Therefore, development of new materials is continuously required, and especially development of a host material for an emitting layer is urgently required.

Reference KR101170666 B1 was used as a prior art document.

DETAILED DESCRIPTION OF THE INVENTION

Summary

The present invention has been proposed in order to solve the problems of the phosphorescent host material, and an object of the present invention is, by controlling the HOMO level of a host material of a phosphorescent emitting organic electric element including a phosphorescent dopant, to provide a compound capable of controlling charge balance and of improving efficiency and lifespan in an emitting layer, and an organic electric element using the same and an electronic device thereof.

Technical Solution

In order to control the efficient hole injection in the emitting layer of the phosphorescent emitting organic electric element, by containing a second host material in combination with a first host material as a main component, the energy barrier between the emitting layer and the adjacent layer can be reduced, and the charge balance in the emitting layer is maximized to provide high efficiency and high lifespan of the organic electric element.

The present invention provides an organic electronic element comprising a first electrode, a second electrode, and an organic material layer formed between the first electrode and the second electrode, wherein the organic material layer comprises an emitting layer, wherein the emitting layer is a phosphorescent emitting layer and comprises a first host compound represented by Formula 1 and a second host compound represented by Formula 2.

Formula 1

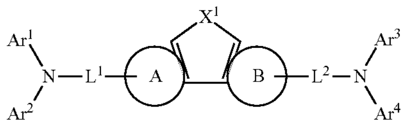

-continued

Formula 2

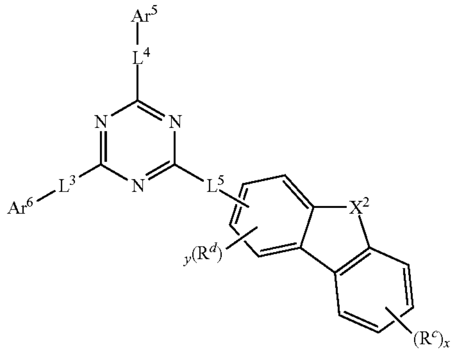

The present invention also provides organic electric elements and electronic devices using the compounds represented by the Formulas.

Effects of the Invention

By using the mixture according to the present invention as a phosphorescent host material, it is possible to achieve a high luminous efficiency and a low driving voltage of an organic electric element, and the life span of the device can be greatly improved.

BRIEF DESCRIPTION OF THE DRAWINGS

The FIGURE is an illustration of an organic electroluminescent device according to the present invention.

| | | | |
|---|---|---|---|
| 100: | organic electric element, | 110: | substrate |
| 120: | the first electrode(anode), | 130: | the hole injection layer |
| 140: | the hole transport layer, | 141: | a buffer layer |
| 150: | the emitting layer, | 151: | the emitting auxiliary layer |
| 160: | the electron transport layer, | 170: | the electron injection layer |
| 180: | the second electrode(cathode) | | |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxyl group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms. Unless otherwise stated, the term "heteroaryl group" or "heteroarylene group", as used herein, means a C2 to C60 aryl containing one or more of hetero atoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphadic ring and/or heteroaromatic ring. Also, the heterocyclic group may also be formed in conjunction with an adjacent group. Unless otherwise stated, the term "heteroatom", as used herein, represents at least one of N, O, S, P, or Si.

Also, the term "heterocyclic group" may include a ring containing $SO_2$ instead of carbon consisting of cycle. For example, "heterocyclic group" includes compound below.

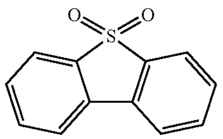 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these. Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

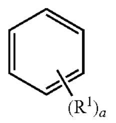

Here, when a is an integer of 0, it means that the substituent $R^1$ is absent, that is, when a is 0, it means that all hydrogens are bonded to carbons forming the benzene ring, and in this case, the display of hydrogen bonded to carbon may be omitted and the chemical formula or compound may be described.

When a is an integer of 1, one substituent $R^1$ is bonded to any one of carbons forming a benzene ring, and when a is an integer of 2 or 3, they are respectively combined as follows, in which $R^1$ may be the same as or different from each other, and when a is an integer of 4 to 6, and it is bonded to the carbon of the benzene ring in a similar manner, whereas the indication of hydrogen bonded to the carbon forming the benzene ring is omitted.

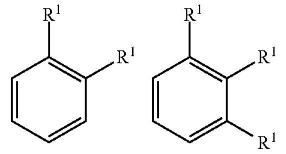

(a = 2) (a = 3)

Hereinafter, a compound according to an aspect of the present invention and an organic electric element comprising the same will be described.

The present invention provides an organic electronic element comprising a first electrode, a second electrode, and an organic material layer formed between the first electrode and the second electrode, wherein the organic material layer comprises an emitting layer, wherein the emitting layer comprises a first host compound represented by Formula 1 and a second host compound represented by Formula 2 as the phosphorescent emitting layer.

Formula 1

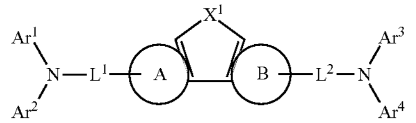

Formula 2

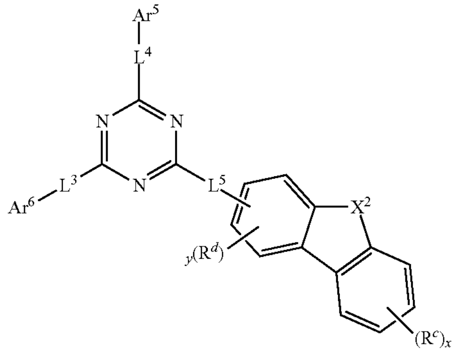

{In Formula 1 and Formula 2,

1) $Ar^1$, $Ar^2$, $Ar^3$, $Ar^4$, $Ar^5$, $Ar^6$ and Ar' are each independently selected from the group consisting of hydrogen; deuterium; halogen; a $C_6$-$C_{60}$ aryl group; a fluorenyl group; a $C_2$-$C_{60}$ heterocyclic group including at least one hetero atom of O, N, S, Si, P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R^a$)($R^b$), and $Ar^1$ and $Ar^2$, or $Ar^3$ and $Ar^4$ may be bonded to each other to form a ring, 2) wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R^a$ and $R^b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P, 3) $L^1$, $L^2$, $L^3$, $L^4$ and $L^5$ are independently selected from the group consisting of a single bond; a $C_6$-$C_{60}$ arylene group; a fluorenylene group; or a $C_2$-$C_{60}$ heteroarylene group containing at least one hetero atom of O, N, S, Si, and P;

4) $X^1$ is O or S,

5) Ring A and B are independently a $C_6$-$C_{60}$ aryl group; or a $C_2$-$C_{20}$ heterocyclic group, 6) $X^2$ is a single bond, N-$L^6$-$Ar^7$, O, S or CR'R", wherein R' and R" are independently hydrogen; a $C_6$-$C_{60}$ aryl group; a fluorenyl group; a $C_3$-$C_{60}$ heterocyclic group; or a $C_1$-$C_{50}$ alkyl group; R' and R" may be bonded to each other to form a spiro, 7) X is an integer of 0 to 4, y is an integer of 0 to 3, $R^c$ and $R^d$ are each independently selected from the group consisting of hydrogen; a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R^a$)($R^b$), 8) wherein, the aryl group, fluorenyl group, arylene group, heterocyclic group, fluorenylene group, fused ring group, alkyl group, alkenyl group, alkoxy group and aryloxy group may be substituted with one or more substituents selected from the group consisting of deuterium; halogen; a silane group; siloxane group; boron group; germanium group; cyano group; nitro group; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the present invention provides an organic electric element, wherein A and B in Formula 1 each independently include a compound represented by any one of the following formulas a-1 to a-7

Formula a-1

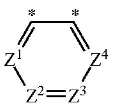

-continued

Formula a-2

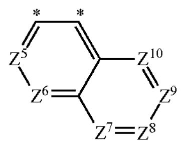

Formula a-3

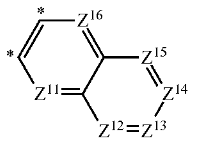

Formula a-4

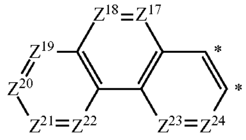

Formula a-5

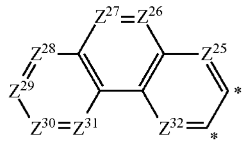

Formula a-6

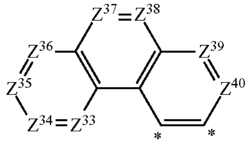

Formula a-7

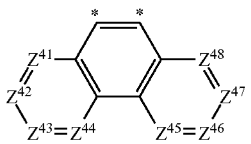

In Formulas a-1 to a-7, $Z^1$ to $Z^{48}$ are each independently $CR^c$ or N, $Z^1$ to $Z^{48}$ bonded to $L^1$ to $L^3$ are carbon (C), $R^c$ is the same as the definition of $R^a$,

* indicates the position to be condensed.

The present invention provides an organic electric element including a compound wherein $L^1$ to $L^5$ in Formula 1 or Formula 2 are represented by any one of the following Formulas b-1 to b-13.

Formula b-1

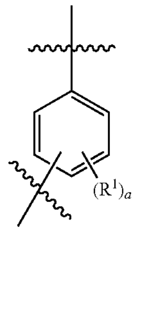

-continued
Formula b-2
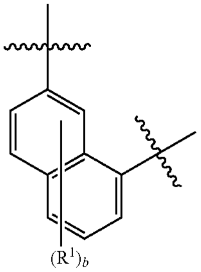
Formula b-3
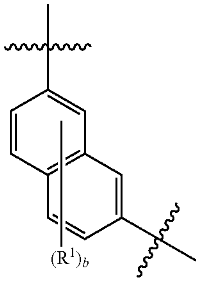
Formula b-4
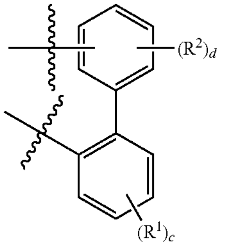
Formula b-5
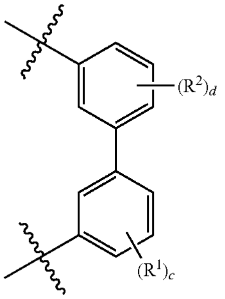
Formula b-6
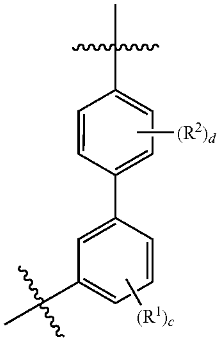
-continued
Formula b-7
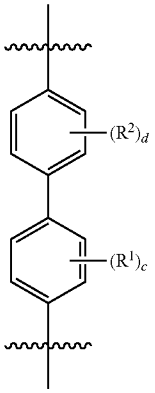
Formula b-8
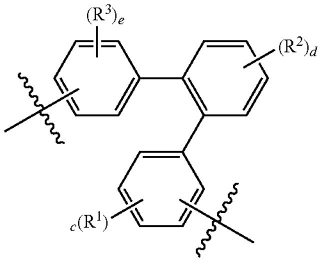
Formula b-9
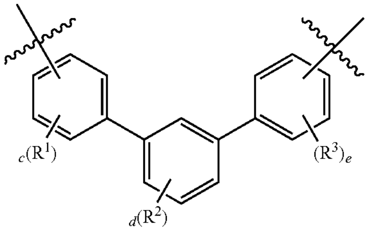
Formula b-10
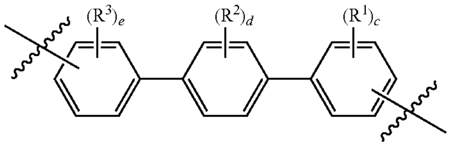
Formula b-11
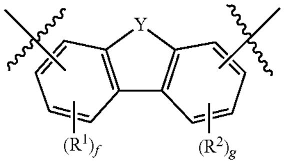
Formula b-12
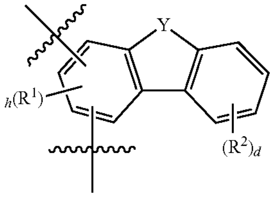

-continued

Formula b-13

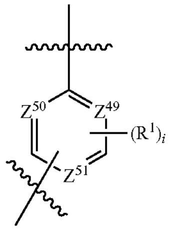

In Formulas b-1 to b-13,

Y is N-$L^5$-$Ar^7$, O, S or $CR^dR^e$, $L^5$ is the same as the definition of $L^3$, $Ar^7$ is the same as the definition of $Ar^5$, $R^d$ and $R^e$ are the same as the definition of $R^a$, a, c, d and e are each independently an integer of 0 to 4, b is an integer of 0 to 6, f and g are each independently an integer of 0 to 3, h is an integer of 0 to 2, i is an integer of 0 or 1, $C_3$-$C_{60}$ aliphatic ring and a $C_6$-$C_{60}$ aromatic ring; and $C_3$-$C_{60}$ aliphatic hydrocarbon group;

$R^f$ and $R^g$ are each independently selected from the group consisting of a $C_6$-$C_{60}$ aryl group; a fluorenyl group; a $C_2$-$C_{60}$ heterocyclic group containing at least one hetero atom of O, N, S, Si, and P; a fused ring group of a $C_3$-$C_{60}$ aliphatic ring and a $C_6$-$C_{60}$ aromatic ring, $Z^{49}$, $Z^{50}$, and $Z^{51}$ are each independently $CR^h$ or N, at least one of $Z^{49}$, $Z^{50}$, and $Z^{51}$ is N, $R^h$ is selected from the group consisting of hydrogen; deuterium; tritium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and adjacent $R^1$ and $R^h$ may be bonded to each other to form an aromatic or a heteroaromatic ring, The present invention provides a compound wherein the first host compound represented by Formula 1 comprises the compound represented by any one of the following Formulas 3 to Formula 5.

Formula 3

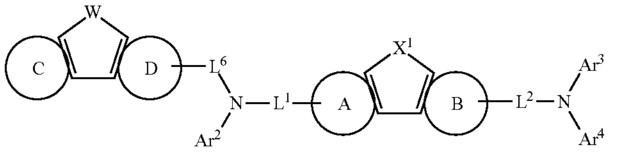

Formula 4

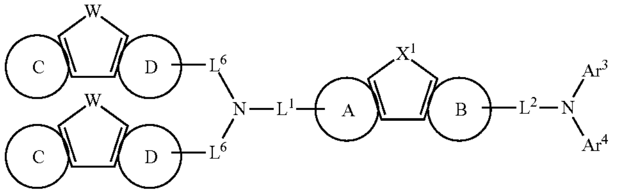

Formula 5

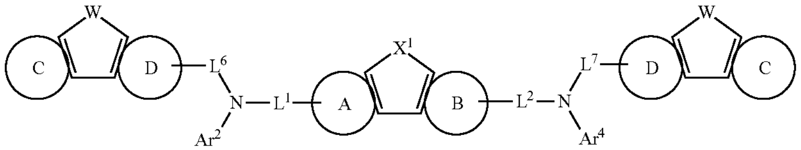

$R^1$, $R^2$ and $R^3$ are each independently hydrogen; deuterium; tritium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -$L^a$-N($R^f$)($R^g$); or in case a, b, c, d, e, f and g are 2 or more, and h is 2 or more, each as plurality are the same as or different from each other, and a plurality of $R^1$ or a plurality of $R^2$ or a plurality of $R^3$ or adjacent $R^1$ and $R^2$, or adjacent $R^2$ and $R^3$ may be bonded to each other to form an aromatic or a heteroaromatic ring, where, $L^a$ is selected from the group consisting of a single bond; a $C_6$-$C_{60}$ arylene group; a fluorenylene group; a $C_2$-$C_{60}$ heterocyclic group containing at least one hetero atom of O, N, S, Si, and P; a fused ring group of a In Formulas 3 to 5, $X^1$, A, B, $L^1$, $L^2$, $Ar^2$, $Ar^3$ and $Ar^4$ are the same as defined above, C and D are the same as the definition of A, W is N-$L^7$-$Ar^8$, O, S, or $CR^iR^j$ $L^6$ and $L^7$ are the same as the definition of $L^4$, $Ar^8$ is the same as the definition of $Ar^5$, $R^i$ and $R^j$ are the same as the definition of $R^a$, The two $Ar^8$ are each the same or different, the two W are each the same or different, the two C are each the same or different, the two D are each the same or different.

The present invention provides a compound wherein the first host compound represented by Formula 1 comprises the compound represented by Formula 6.

Formula 6

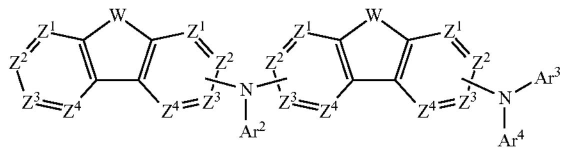

In Formula 6, $X^1$, $Ar^2$, $Ar^3$ and $Ar^4$ are the same as defined above, $Z^1$, $Z^2$, $Z^3$ and $Z^4$ are each independently $CR^c$ or N, $Z^1$ to $Z^4$ bonded to N is carbon (C), $R^c$ is the same as the definition of $R^a$, W is N-$L^7$-$Ar^8$, O, S, or $CR^iR^j$ $L^7$ are the same as the definition of $L^4$, $Ar^8$ is the same as the definition of $Ar^5$, $R^i$ and $R^j$ are the same as the definition of $R^a$.

In the present invention, as another example, the first host compound represented by Formula 1 comprises the compound represented by Formula 7 or 8 or 9.

Formula 7

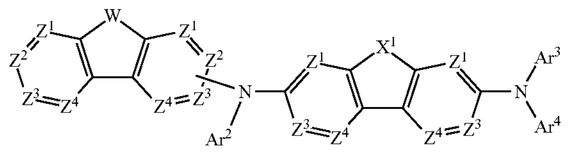

Formula 8

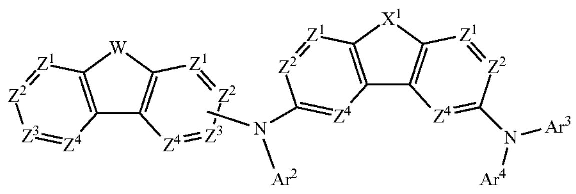

Formula 9

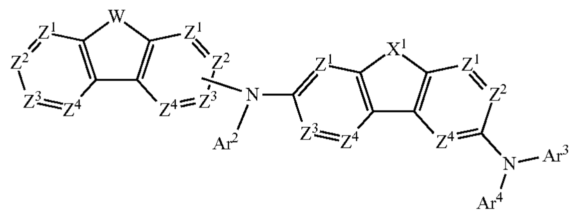

In Formulas 7 to 9, $X^1$, $Ar^2$, Ara and $Ar^4$, $Z^1$, $Z^2$, $Z^3$, $Z^4$ and W are the same as defined above.

In another aspect, a second host compound represented by Formula 2 comprises a compound represented by any one of Formulas 10 to 13.

Formula 10

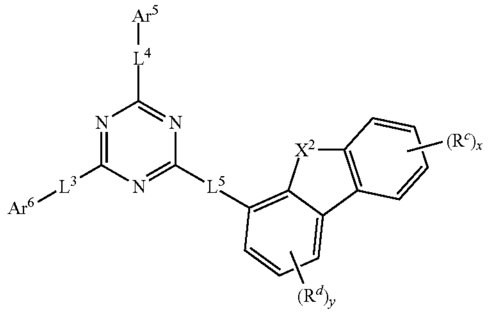

Formula 11

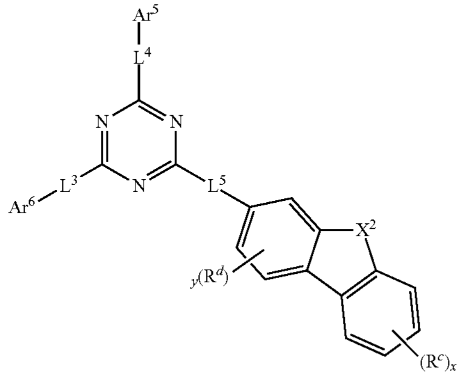

Formula 12

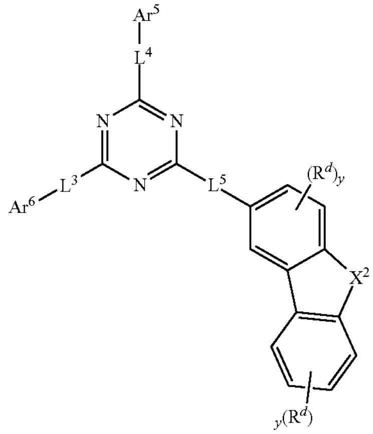

Formula 13

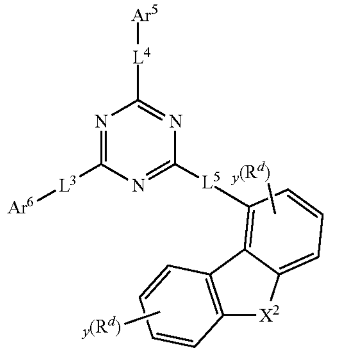

In Formulas 10 to 13, $X^2$, $L^3$, $L^4$, $L^5$, $Ar^5$, $Ar^6$, $R^c$, $R^d$, x, y are the same as defined above.

Also, the second host compound represented by Formula 2 comprises a compound represented by Formula 14.

Formula 14

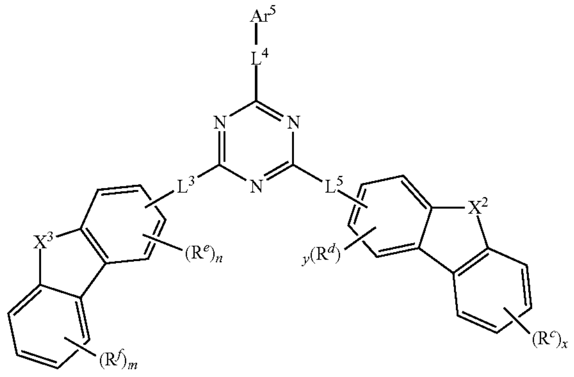

In Formula 14,

1) $X^2$, $L^3$, $L^4$, $L^5$, $Ar^5$, $R^c$, $R^d$, x, y are the same as defined above, 2) $X^3$ is the same as the definition of $X^2$, 3) $R^e$ and $R^f$ are the same as the definition of $R^d$ and $R^c$, 4) n is the same as the definition of y, m is the same as the definition of x, The second host compound represented by Formula 2 comprises a compound represented by Formulas 15 to 18.

Formula 15

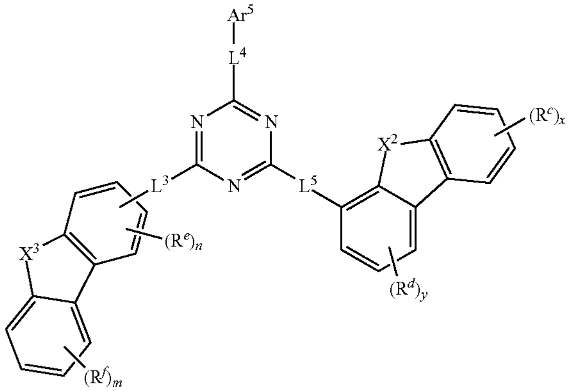

Formula 16

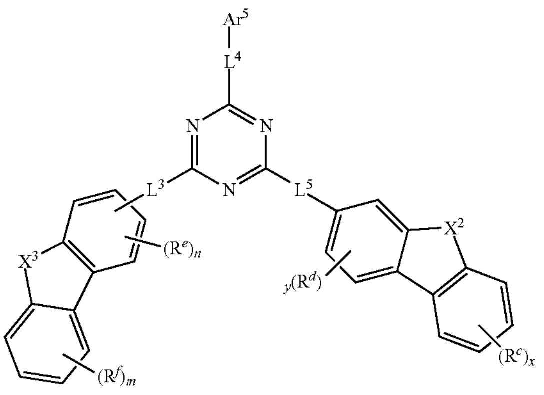

-continued

Formula 17

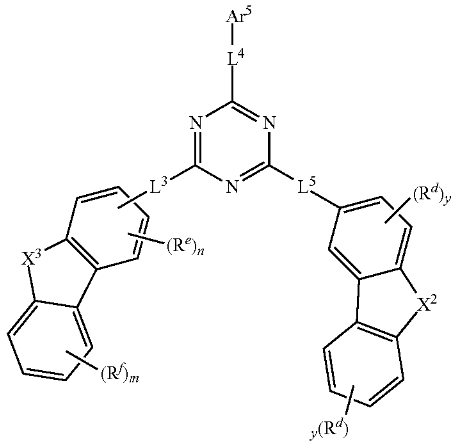

Formula 18

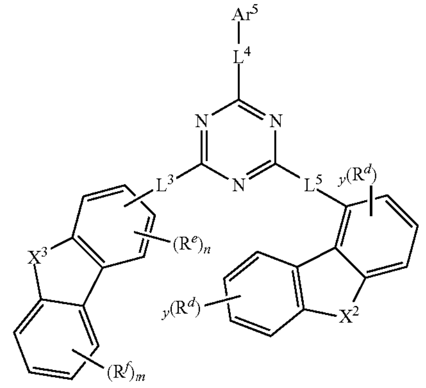

In Formulas 15 to 18, $X^2$, $L^3$, $L^4$, $L^5$, $Ar^5$, $R^c$, $R^d$, x, y, $X^3$, $R^e$, $R^f$, m, n are the same as defined above.

Also, the compound represented by Formula 2 comprises a compound represented by Formula 19.

Formula 19

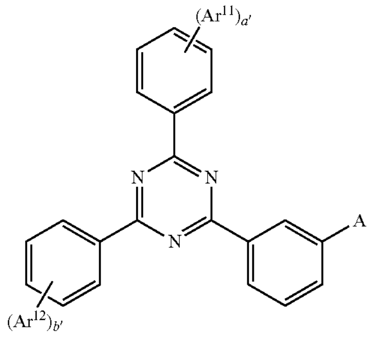

In Formula 19,
A is the following Formula A-1 or Formula A-2,
<Formula A-1>
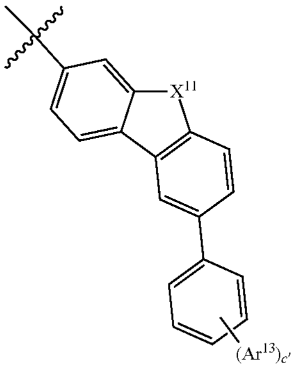
-continued
<Formula A-2>
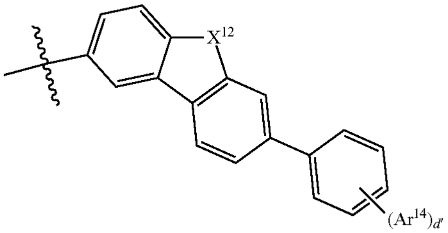
$X^{11}$ and $X^{12}$ are each independently O or S,
a', b', c' and d' are each independently O or 1,
$Ar^{11}$, $Ar^{12}$, $Ar^{13}$ and $Ar^{14}$ are each independently $C_6$-$C_{18}$ aryl group.
The compound represented by Formula 19 comprises a compound represented by the following Formula 20 or 21
<Formula 20>
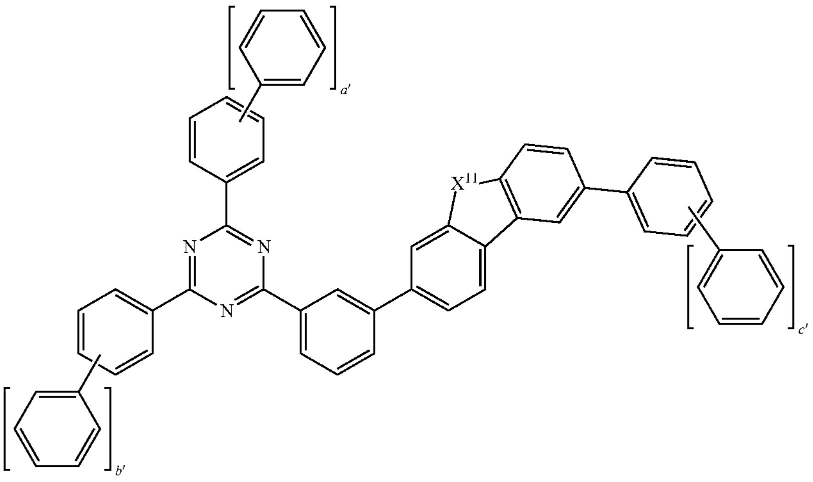
<Formula 21>
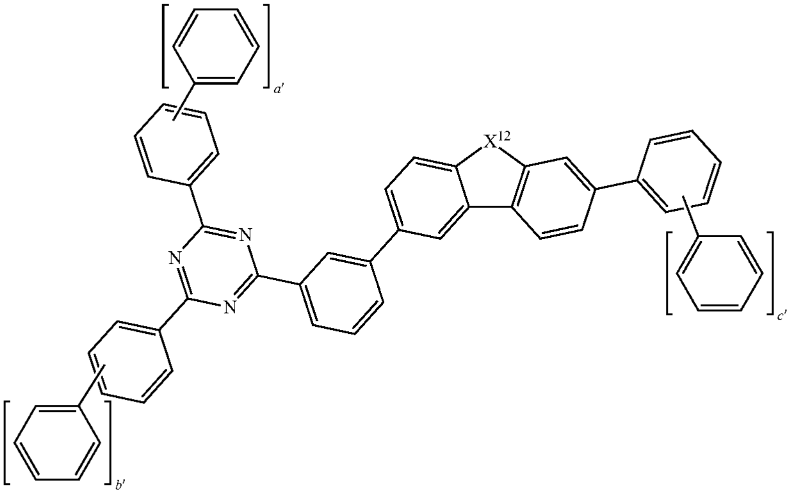

In Formula 20 and 21, $X^{11}$, $X^{12}$, a', b', c'및 d' are the same as defined above.

As another example, the compound represented by Formula 2 comprises the compound represented by Formula 22.

These compounds may be mixed with the second host such as Bis-carbazole, tertiary amine, and polycyclic heterocyclic compound to be used in the emitting layer.

<Formula 22>

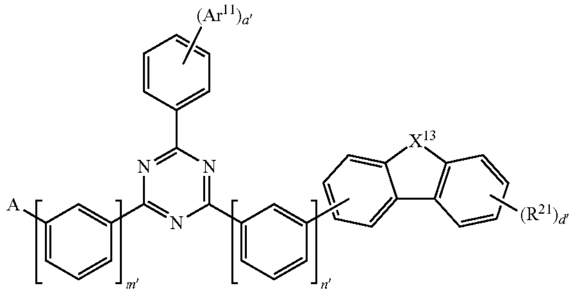

In Formula 22,

A is the following Formula A-1 or A-2,

<Formula A-1>

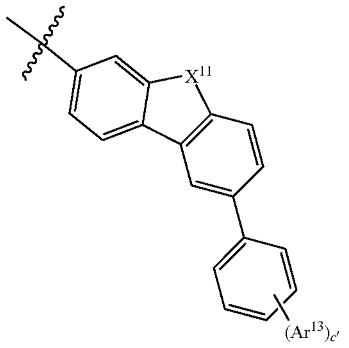

-continued

<Formula A-2>

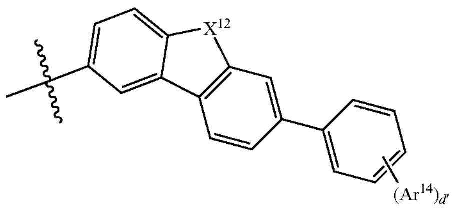

$Ar^{11}$ is a $C_6$-$C_{18}$ aryl group, $X^{11}$, $X^{12}$ and $X^{13}$ are each independently O or S, m' and n' are each independently O or 1, a' and c' each independently an integer of any one of 0 to 5, d' is an integer of any one of 0 to 4, $R^{21}$ is a $C_6$-$C_{18}$ aryl group, $Ar^{13}$ and $Ar^{14}$ are each independently a $C_6$-$C_{18}$ aryl group.

Also, the compound represented by Formula 22 may be represented by the following Formula 23 or Formula 24.

Formula 23

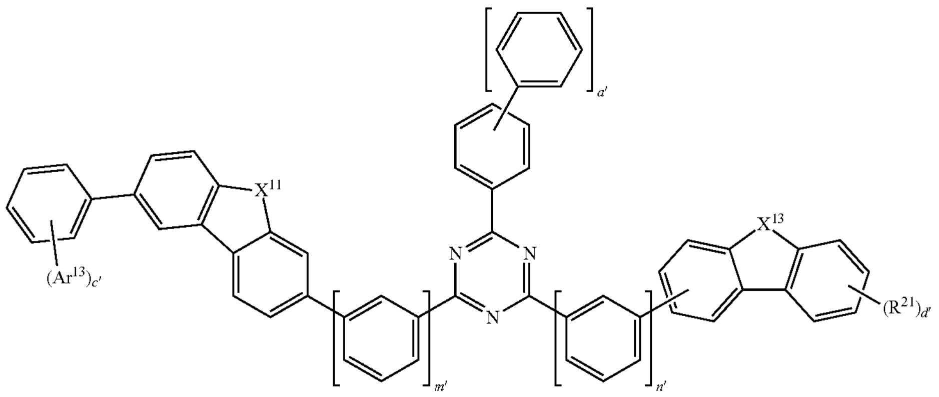

-continued

Formula 24

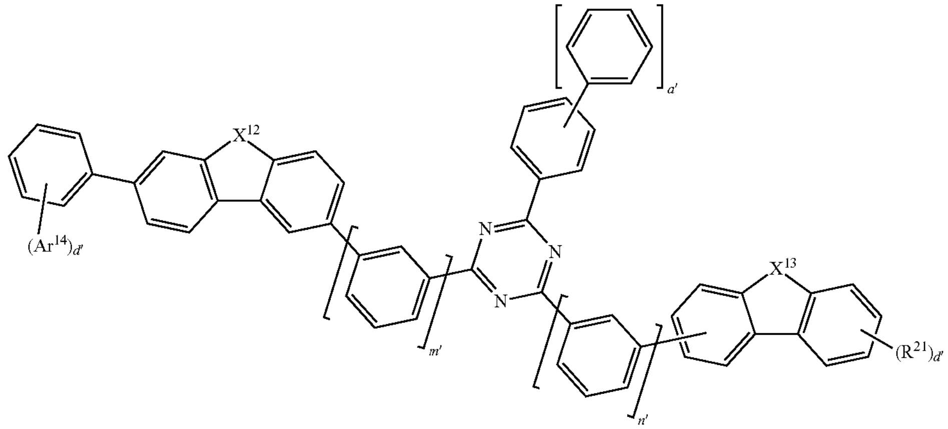

In Formula 23 and 24, $X^{11}$, $X^{12}$, $X^{13}$, a', c', d', m', n', $Ar^{13}$, $Ar^{14}$, $R^{21}$ are the same as defined above.

The compound comprised in Formula 2 may be mixed with the second host such as Bis-carbazole, a tertiary amine, and a polycyclic heterocyclic compound to be used in the emitting layer, and more specifically, a compound included in Formula 19 or Formula 22 may be used.

As another example, the first host compound represented by Formula 1 comprises Compound 1-1 to Compound 1-175.

1-1

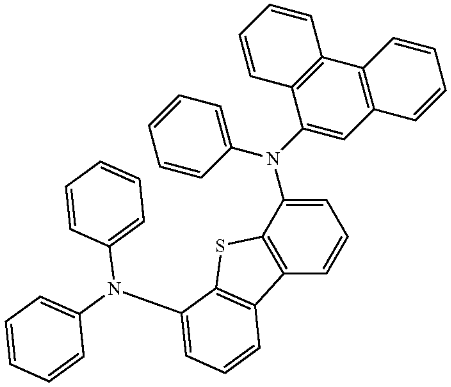

-continued 1-2

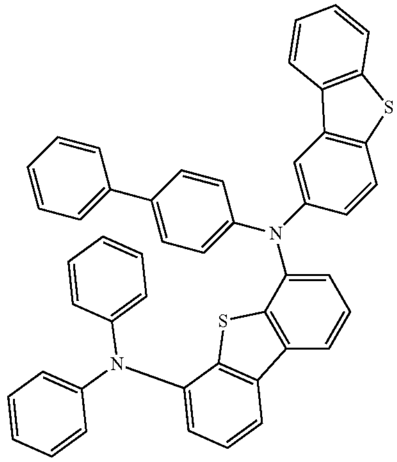

1-3

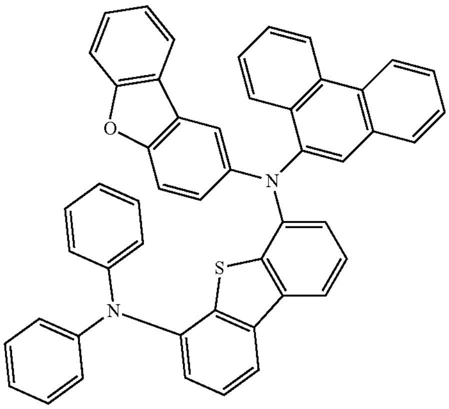

-continued
1-4
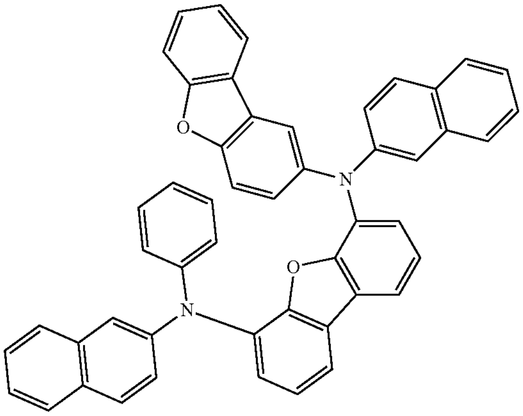
1-5
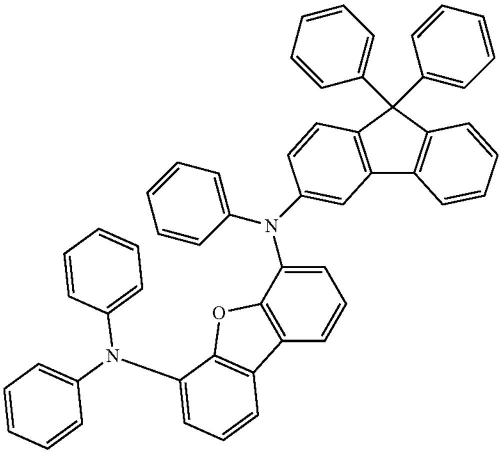
1-6
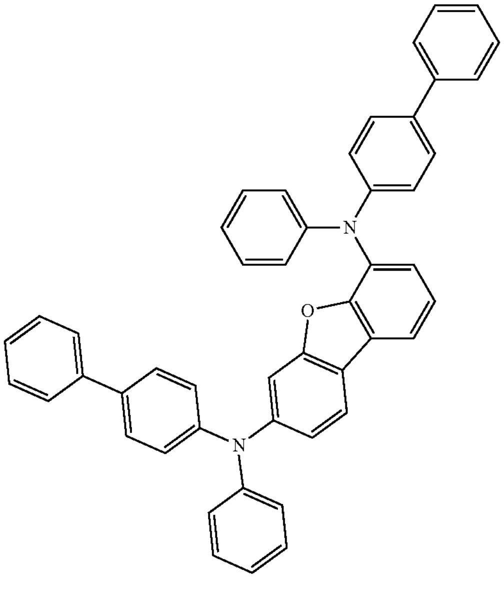
-continued
1-7
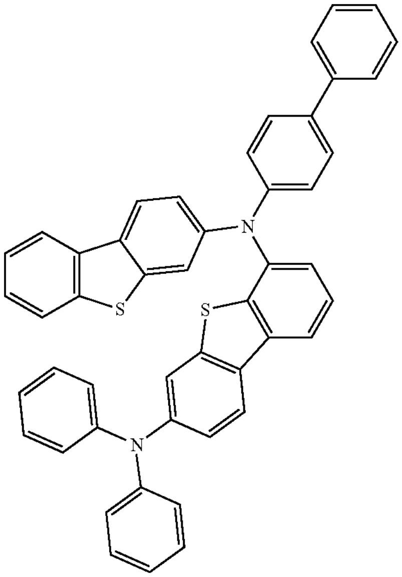
1-8
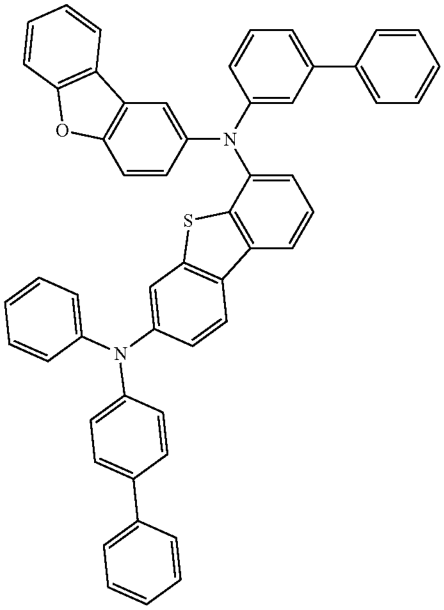

-continued
1-9
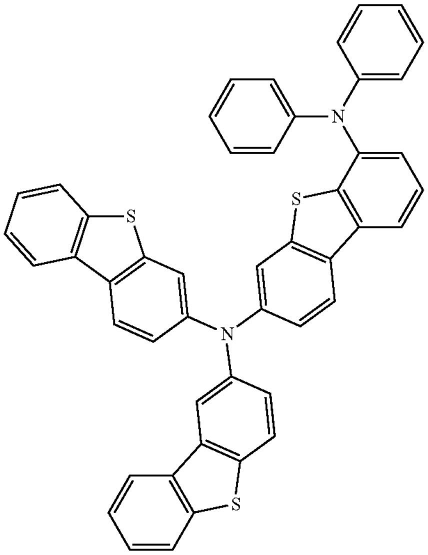
1-10
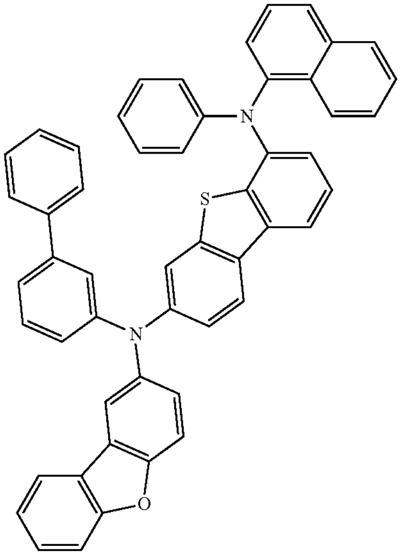
-continued
1-11
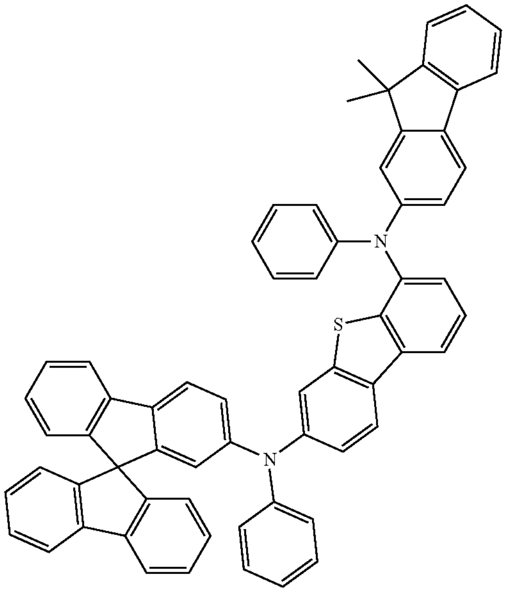
1-12
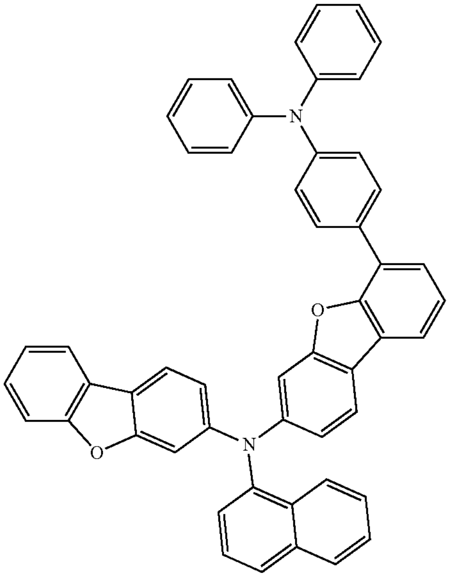

-continued
1-13
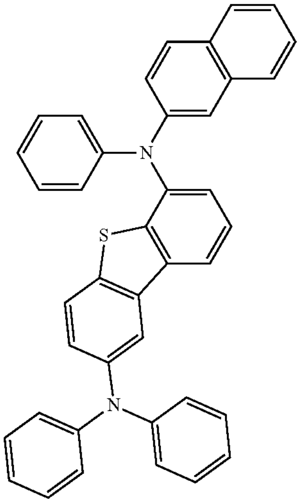
1-14
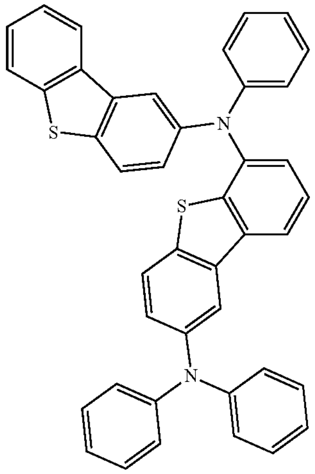
1-15
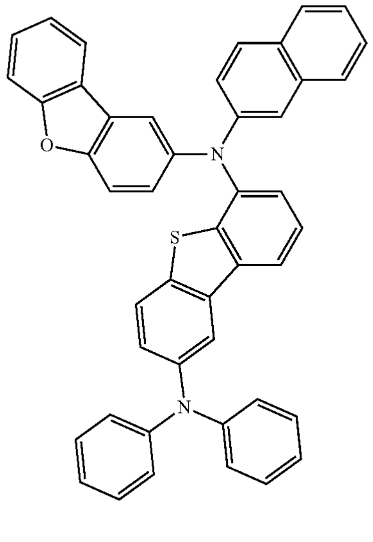
-continued
1-16
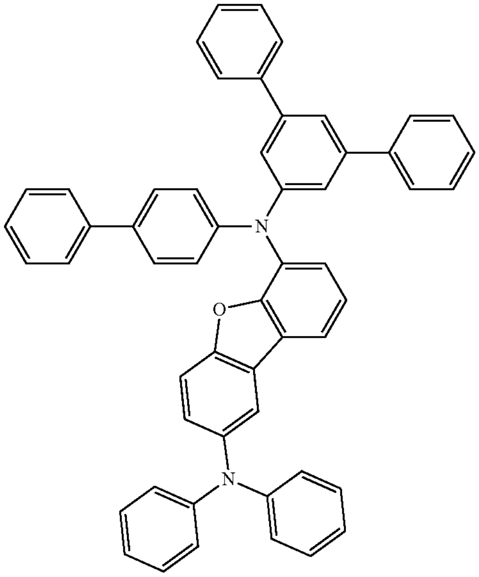
1-17
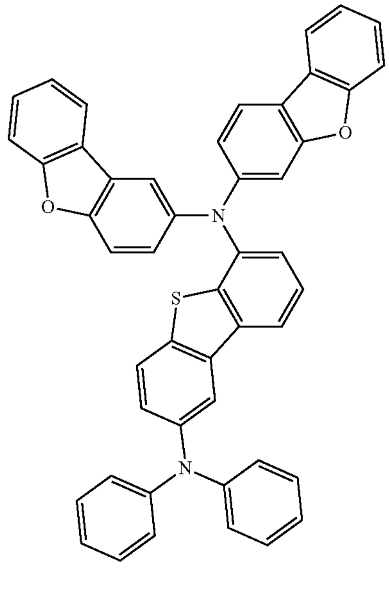

-continued
1-18
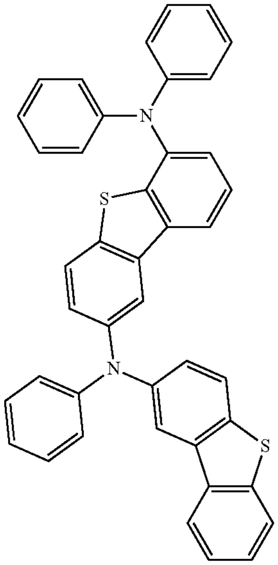
1-19
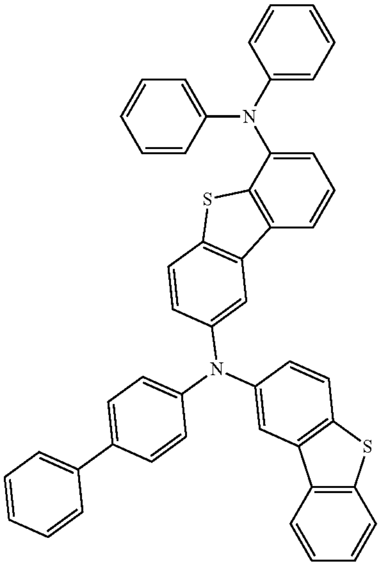
-continued
1-20
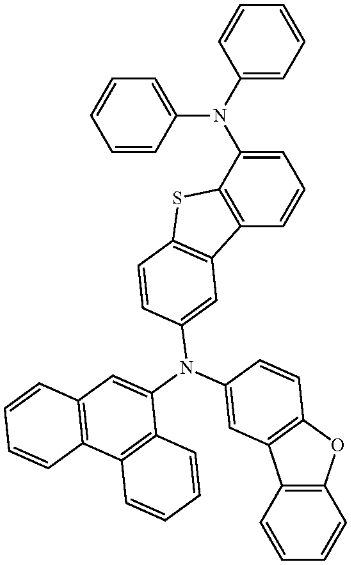
1-21
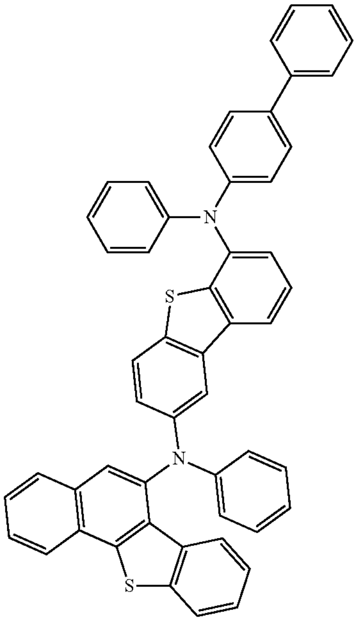

-continued
1-22
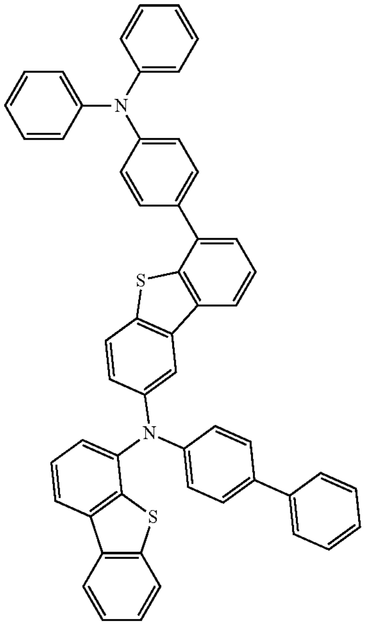
1-23
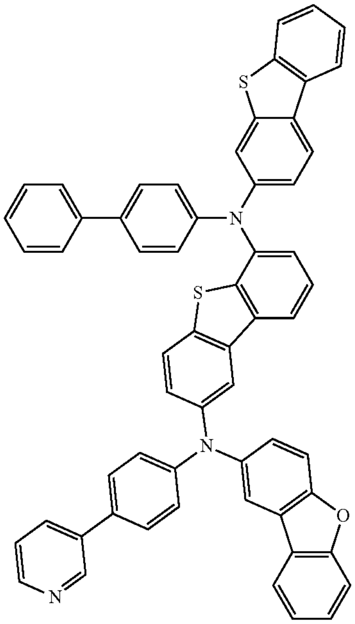
-continued
1-24
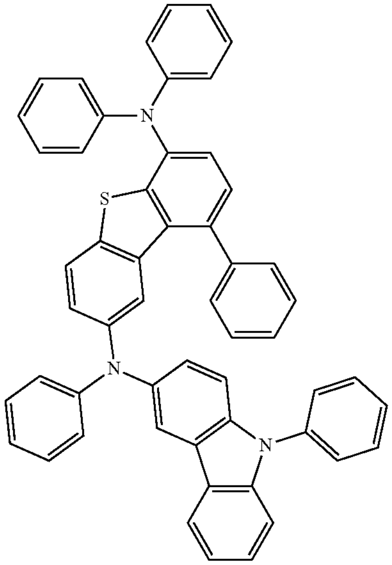
1-25
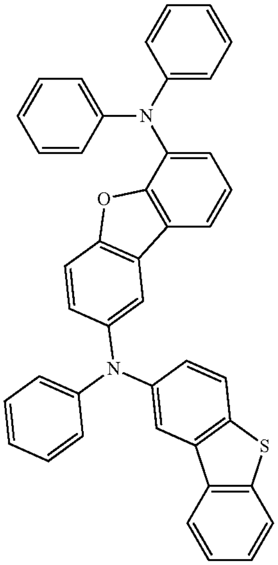
1-26
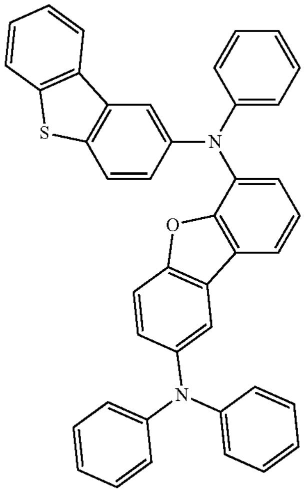

-continued
1-27
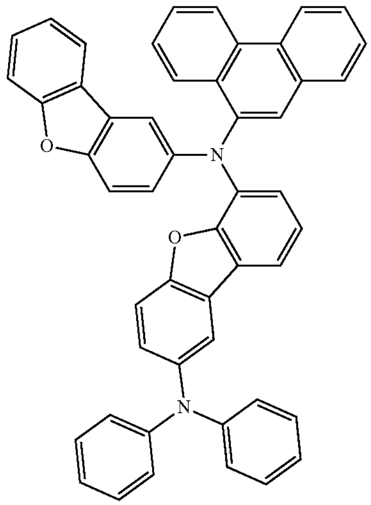
1-28
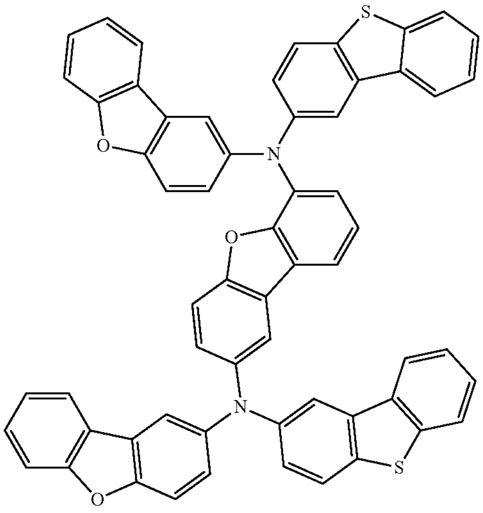
1-29
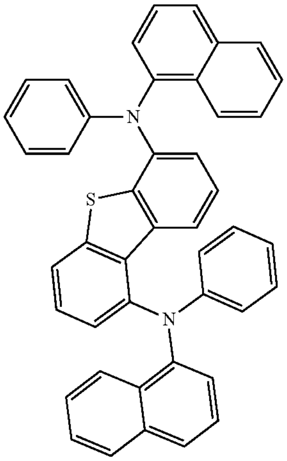
-continued
1-30
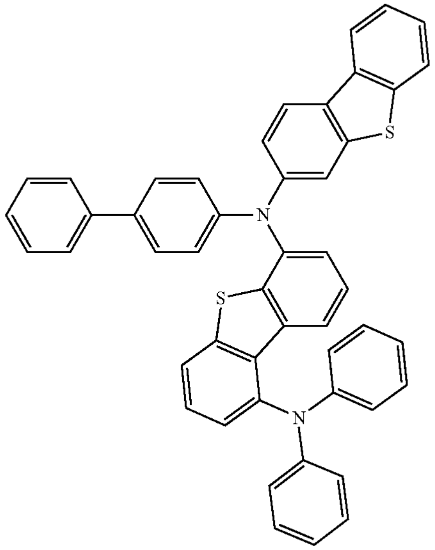
1-31
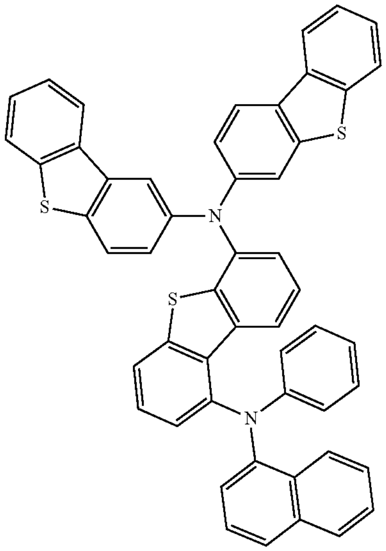
1-32
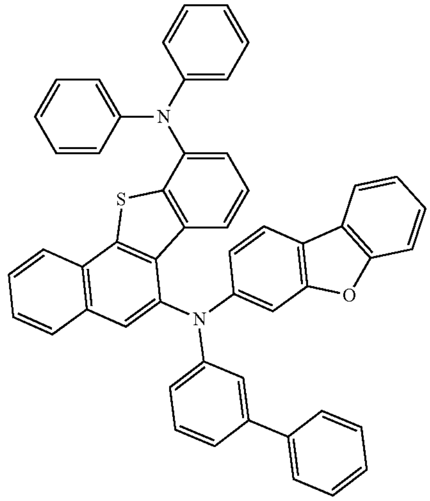

-continued
1-33
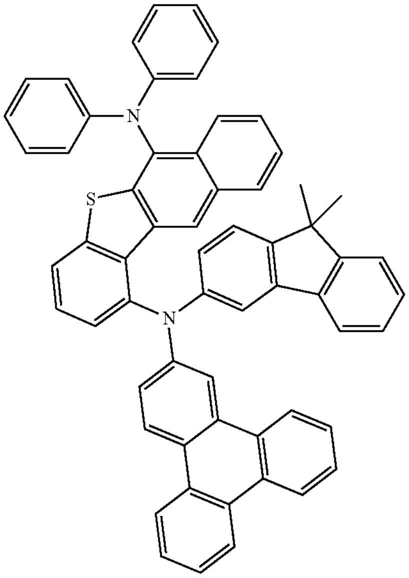
1-34
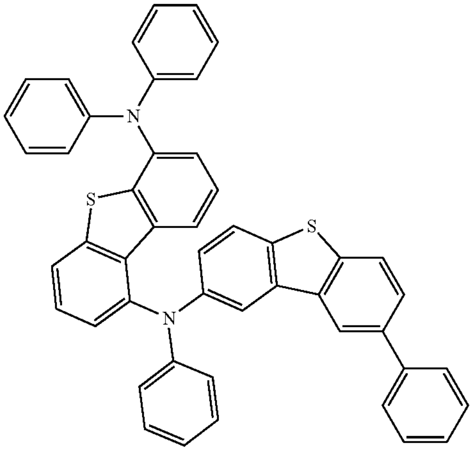
1-35
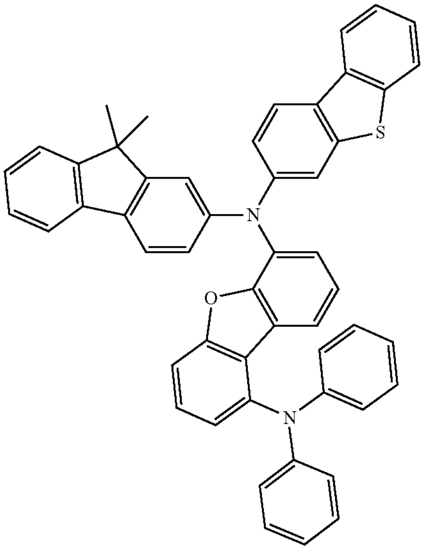
-continued
1-36
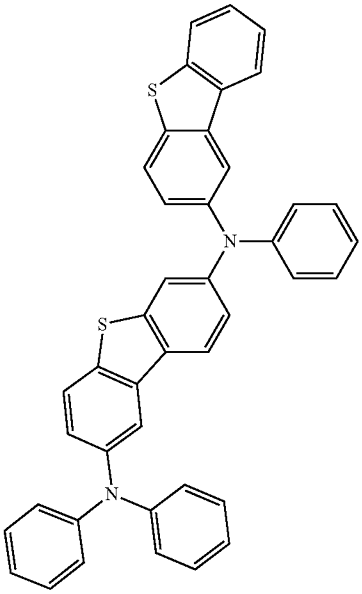
1-37
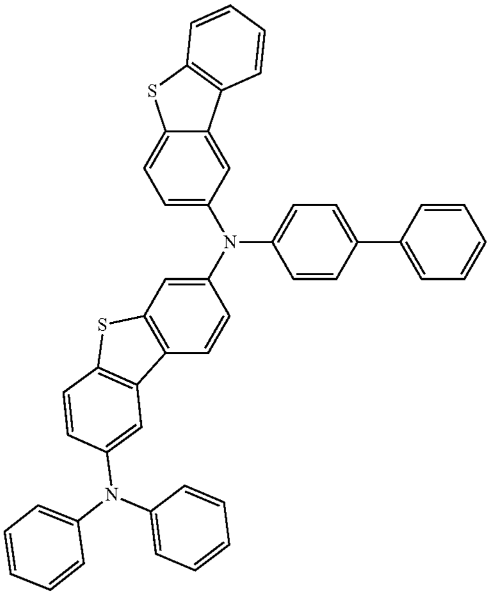

-continued
1-38
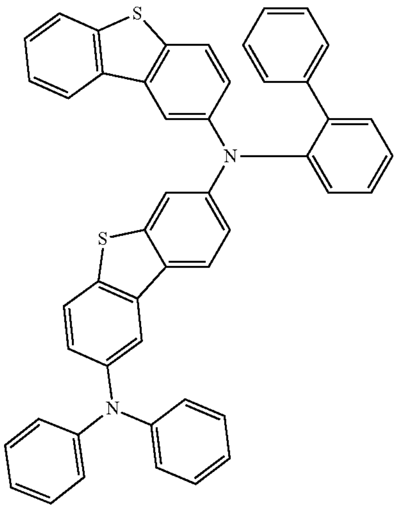
1-39
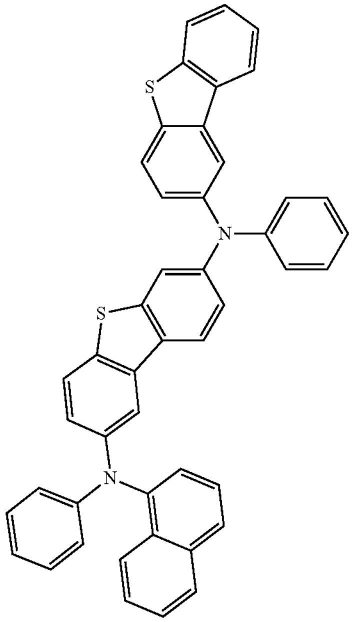
-continued
1-40
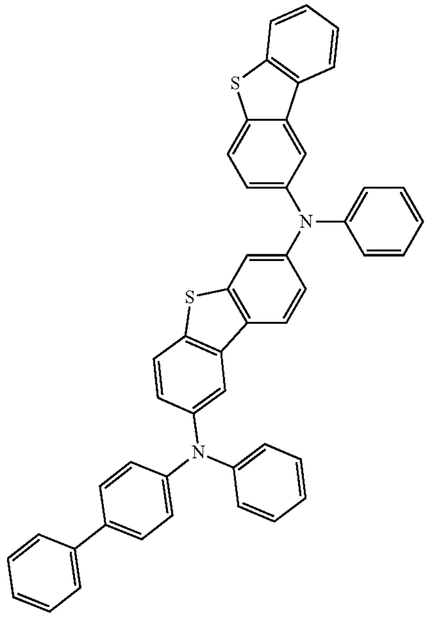
1-41
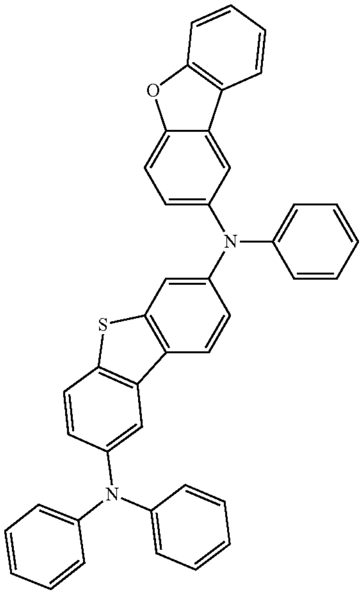

-continued
1-42
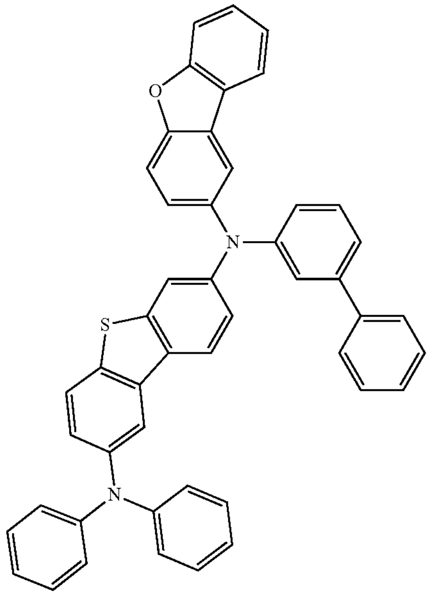
1-43
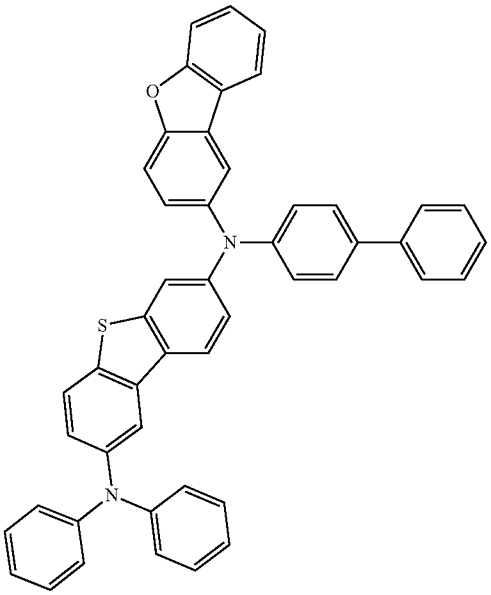
-continued
1-44
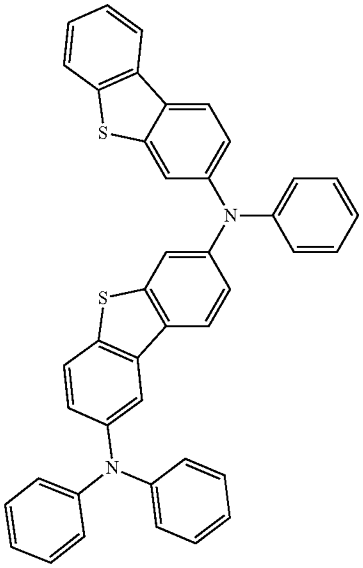
1-45
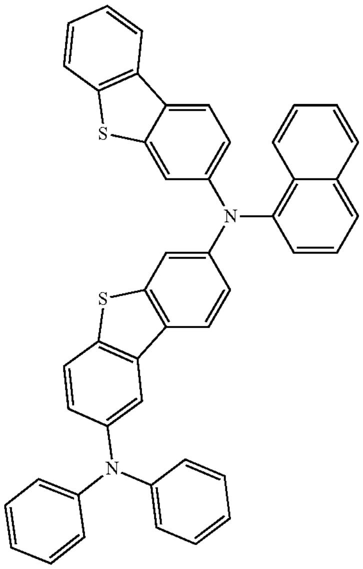

-continued
1-46
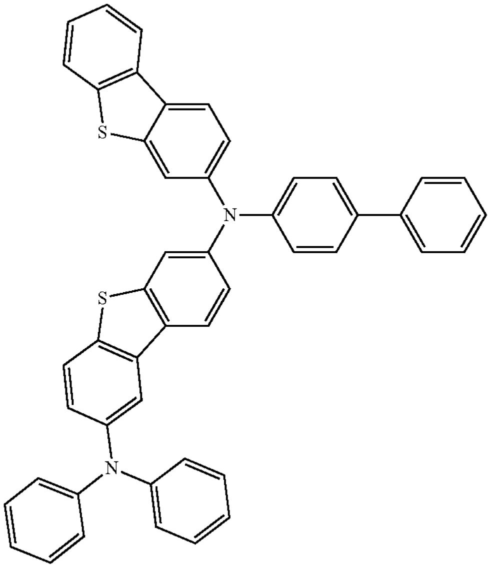
1-47
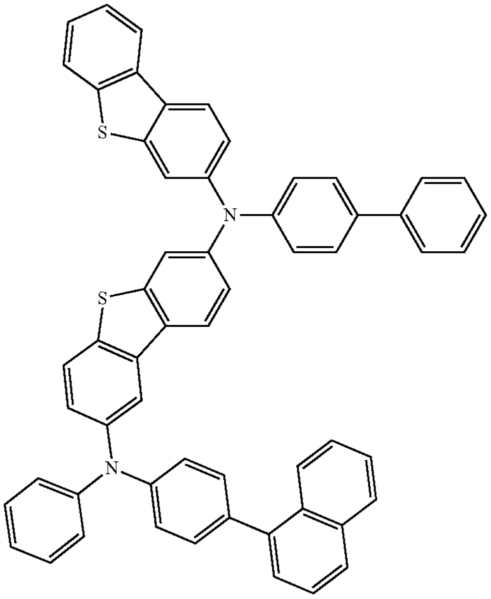
-continued
1-48
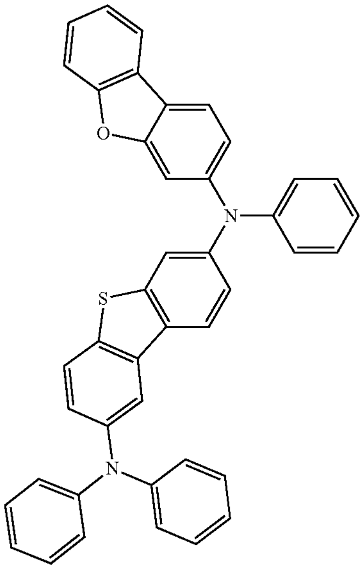
1-49
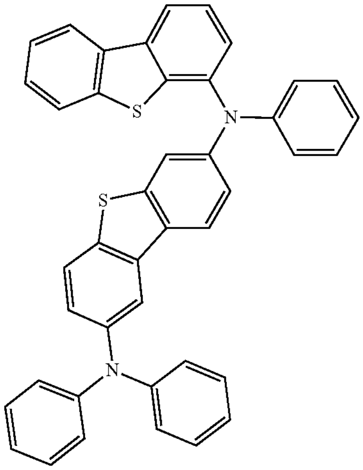
1-50
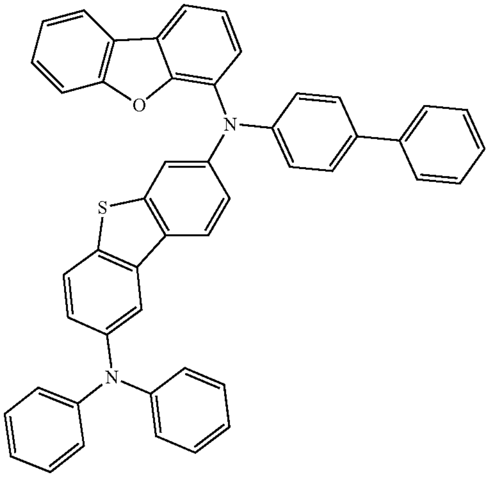

-continued
1-51
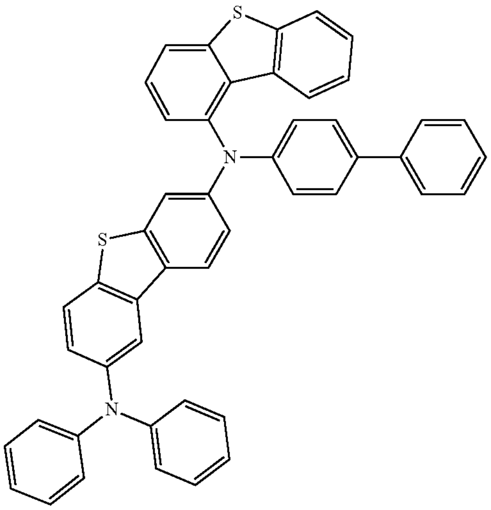
1-52
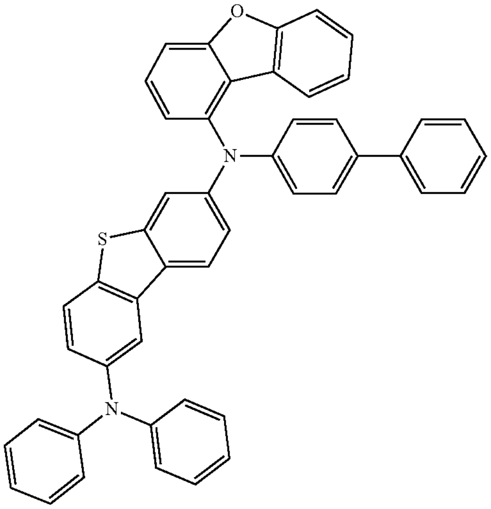
-continued
1-53
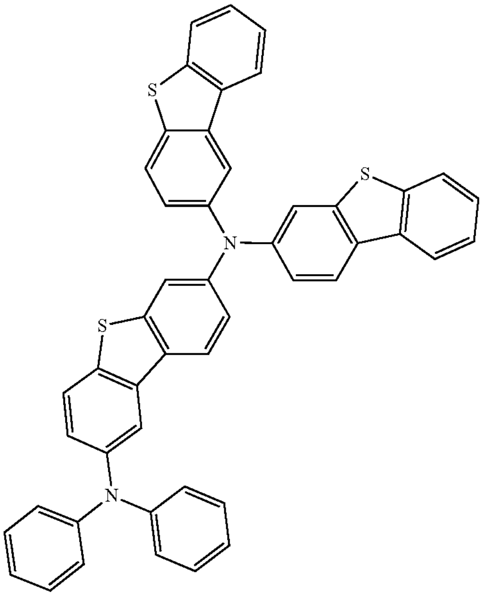
1-54
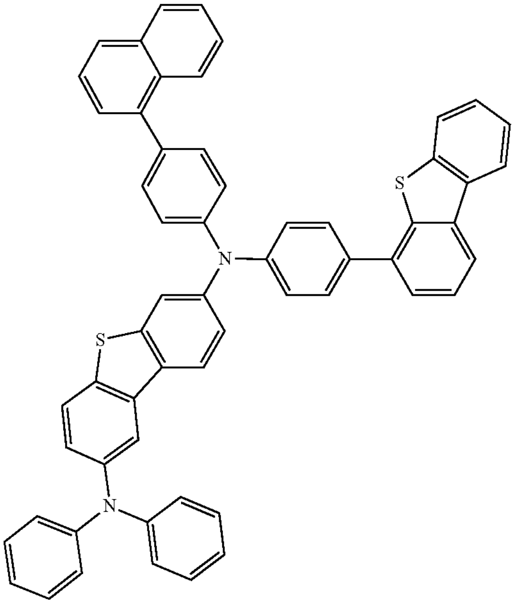

-continued
1-55
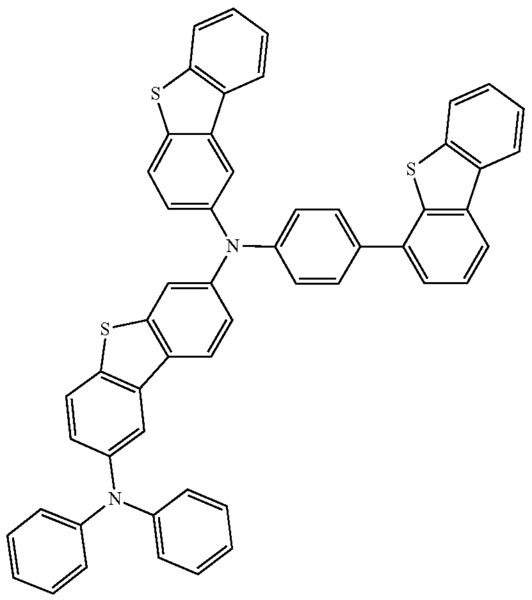
1-56
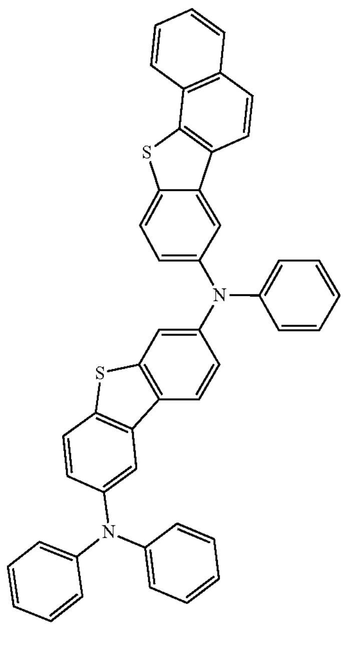
-continued
1-57
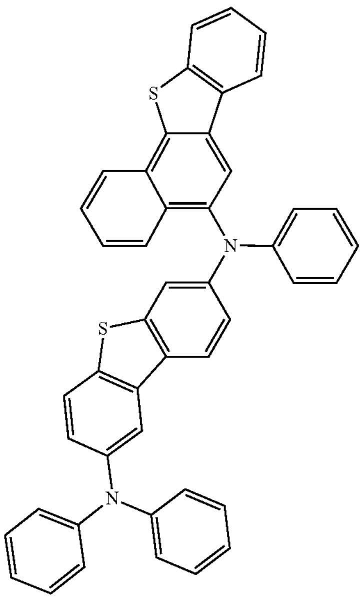
1-58
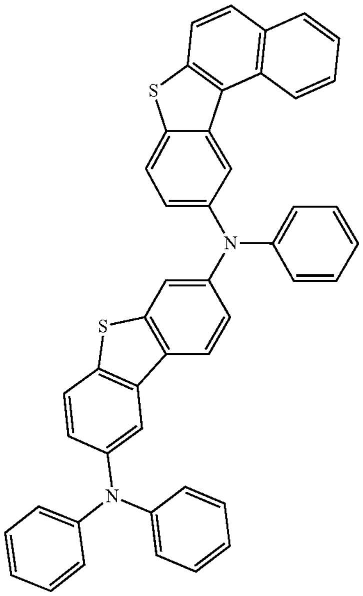

-continued
1-59
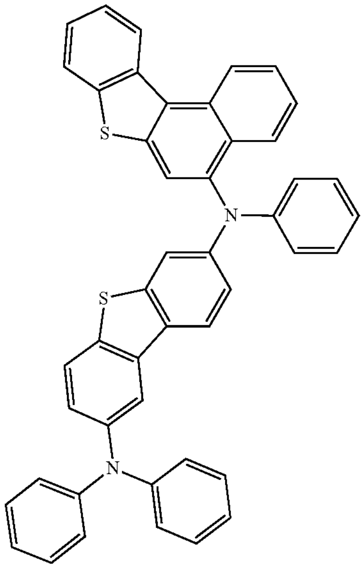
1-60
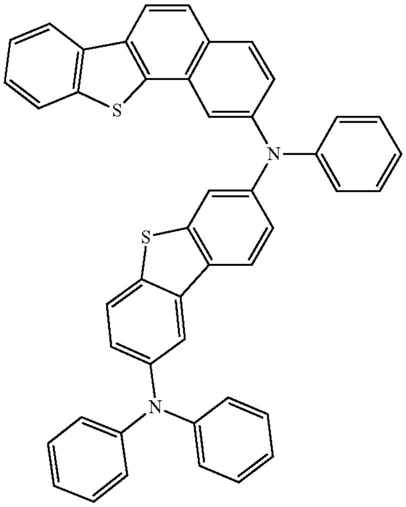
-continued
1-61
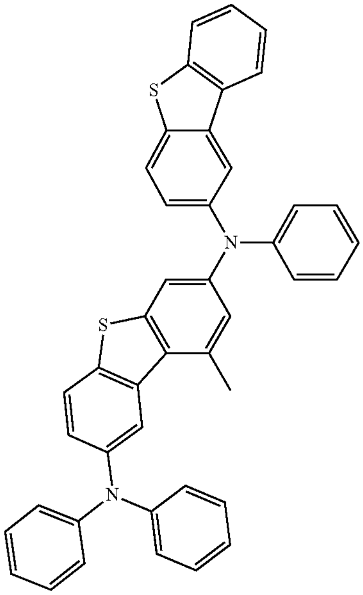
1-62
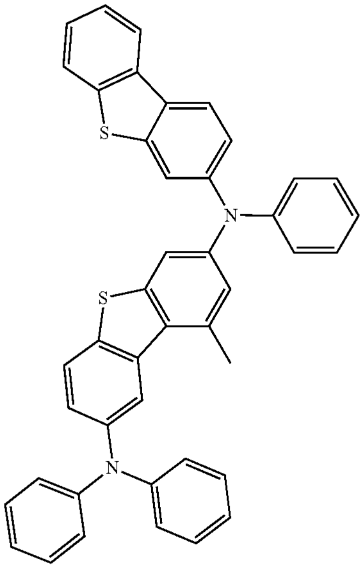

-continued
1-63
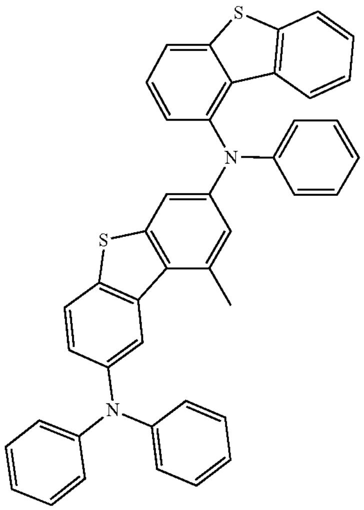
1-64
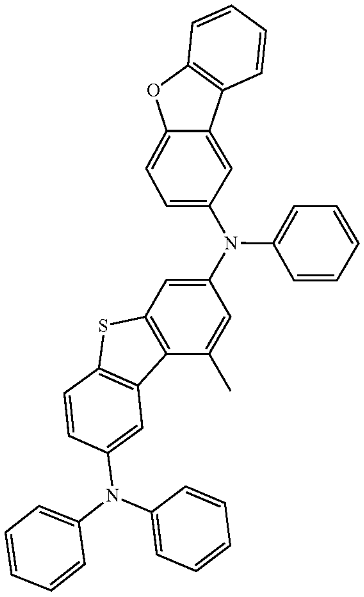
-continued
1-65
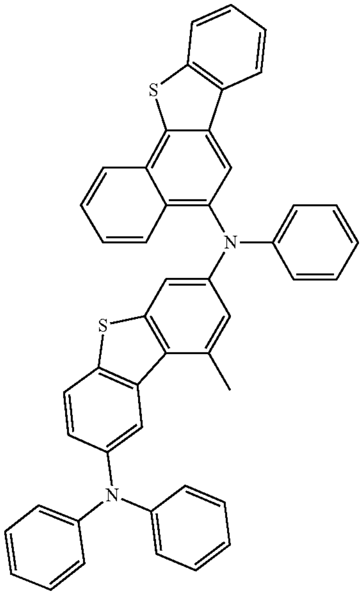
1-66
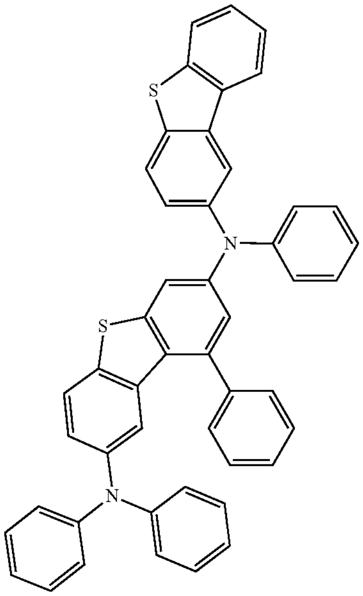

-continued
1-67
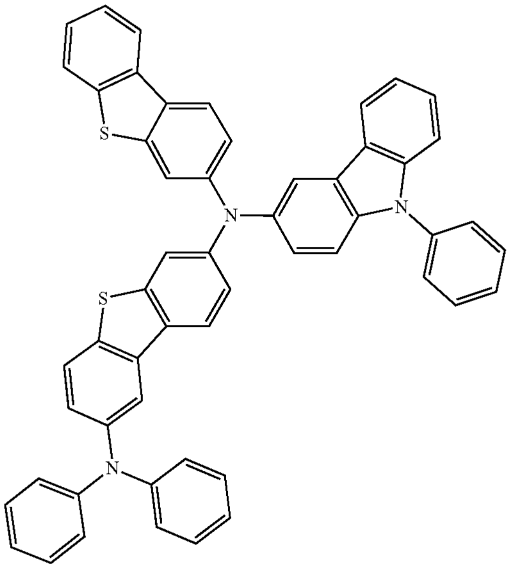
1-68
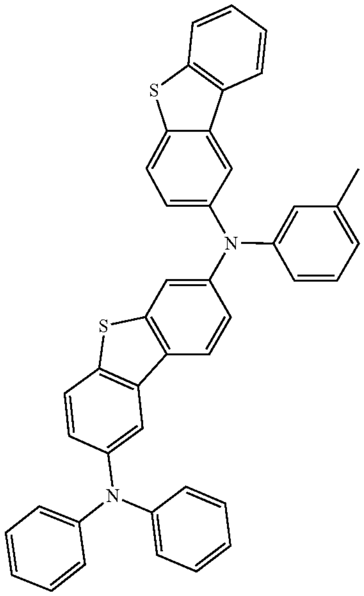
-continued
1-69
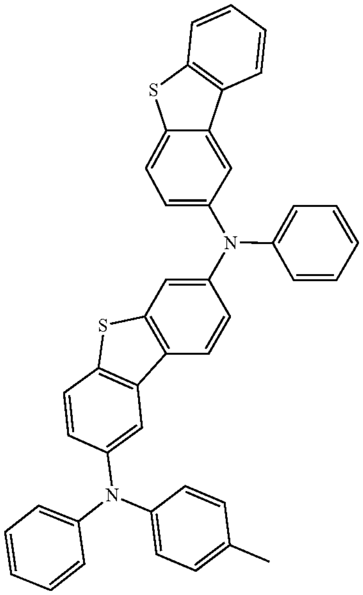
1-70
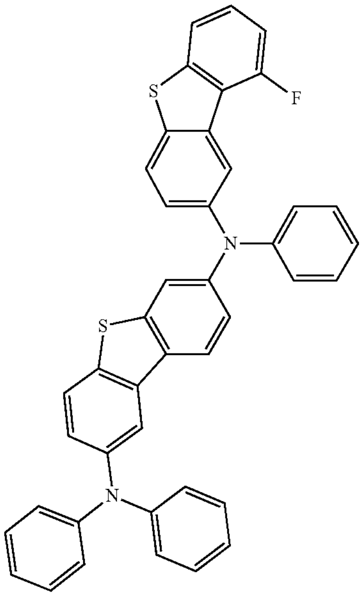

-continued
1-71
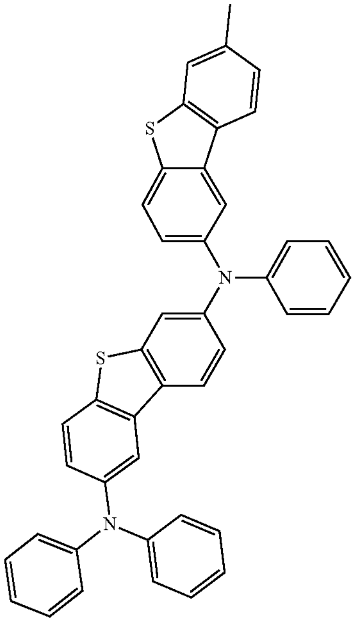
1-72
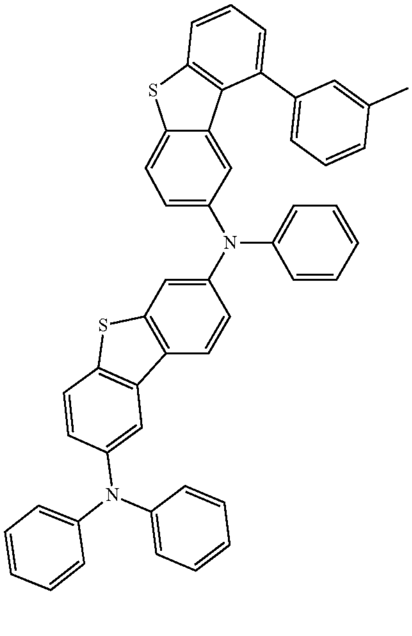
-continued
1-73
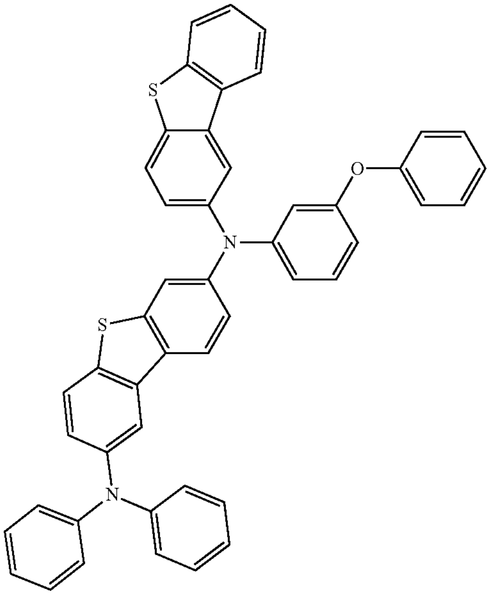
1-74
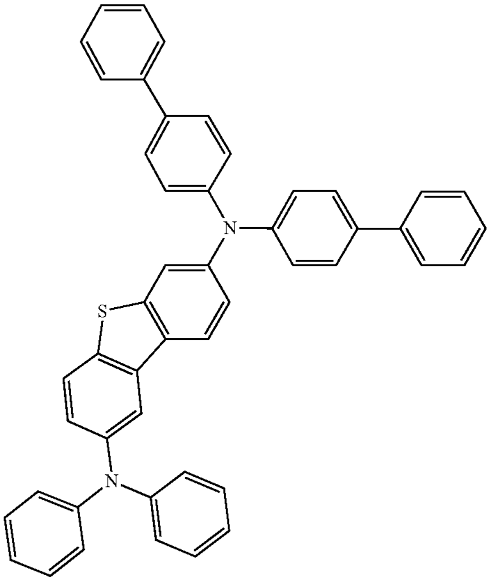
1-75
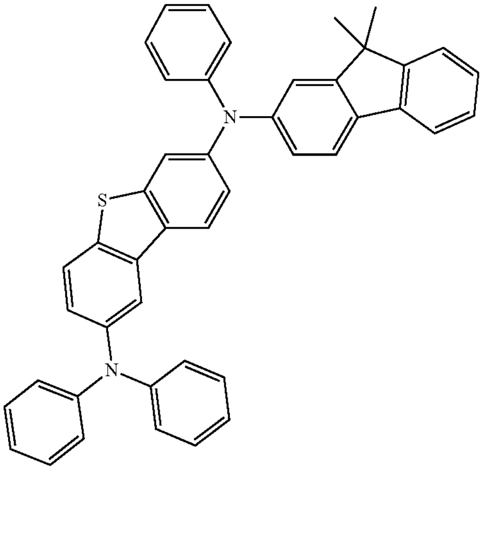

-continued
1-76
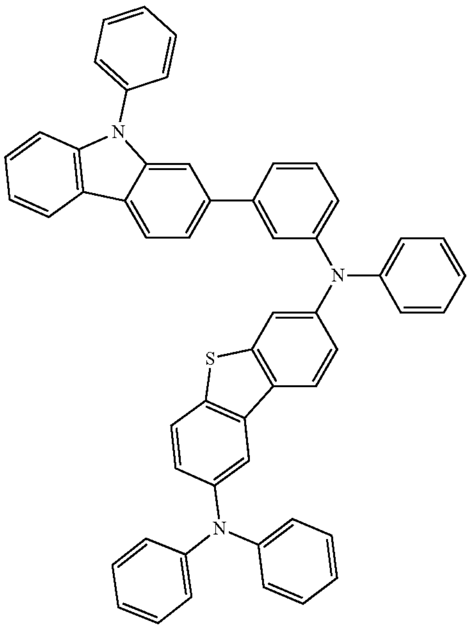
1-77
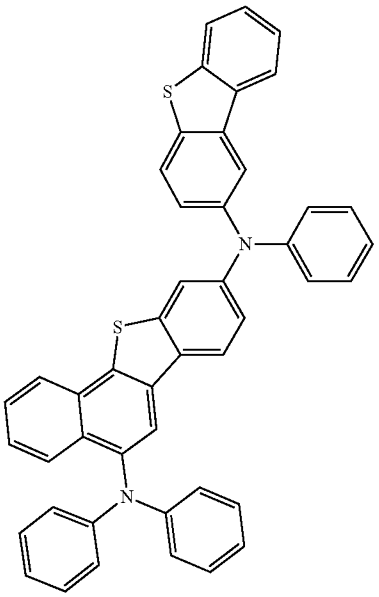
-continued
1-78
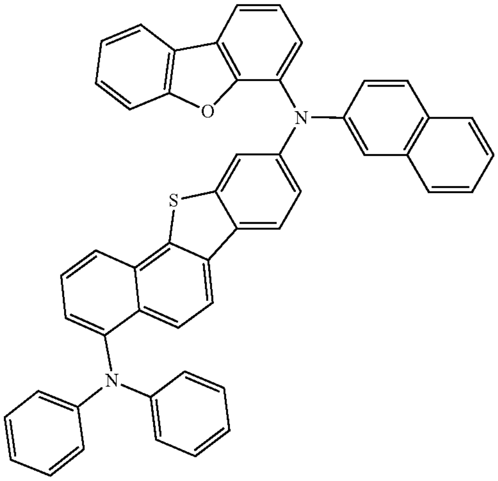
1-79
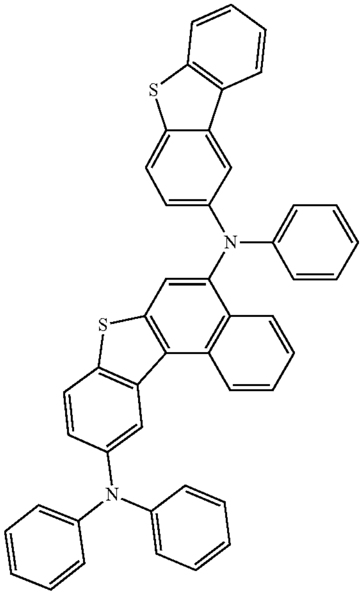

-continued
1-80
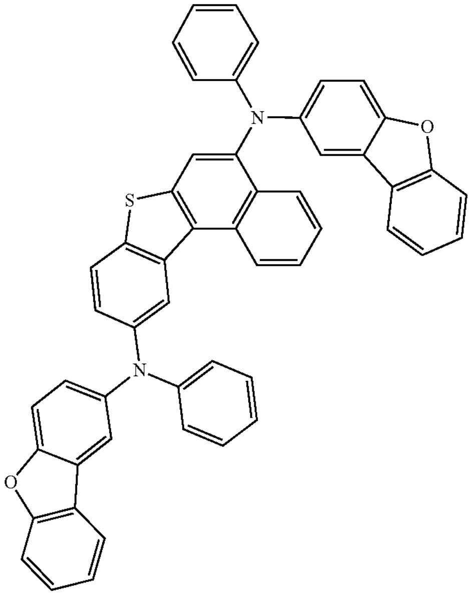
1-81
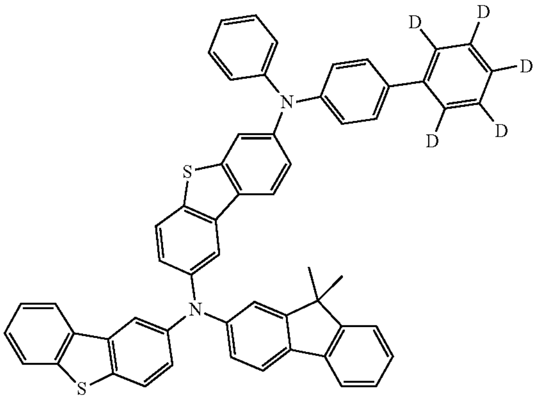
1-82
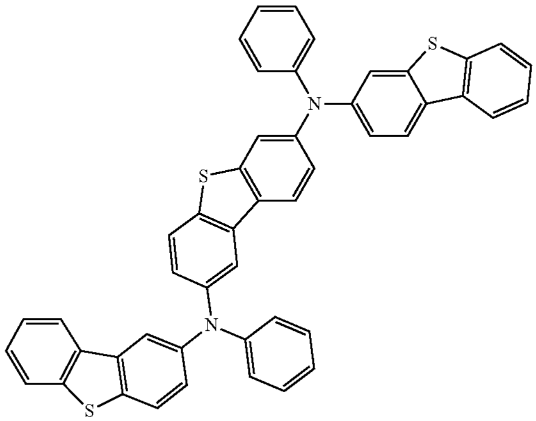
-continued
1-83
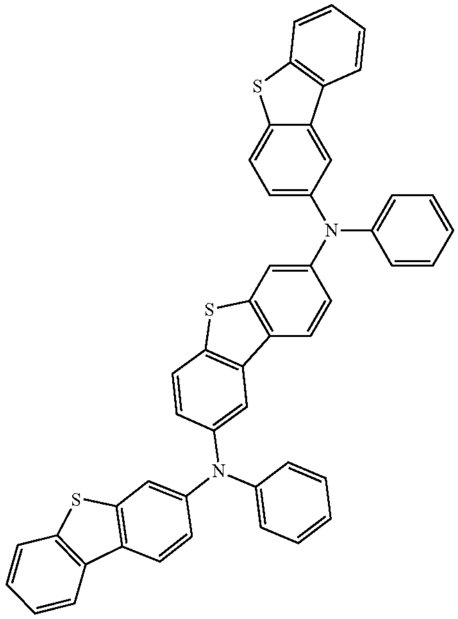
1-84
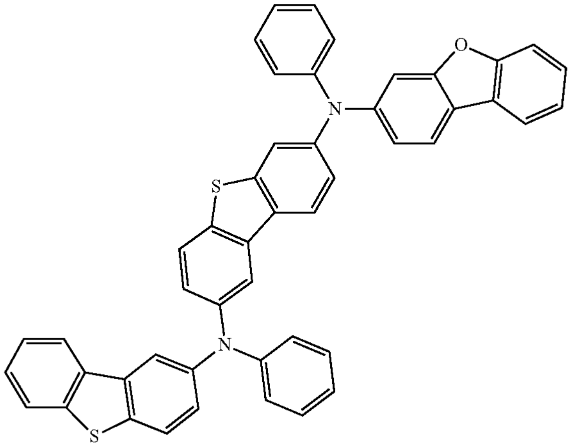

-continued
1-85
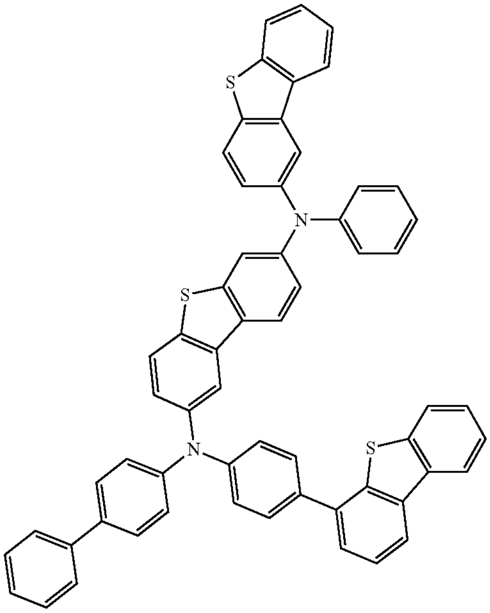
1-86
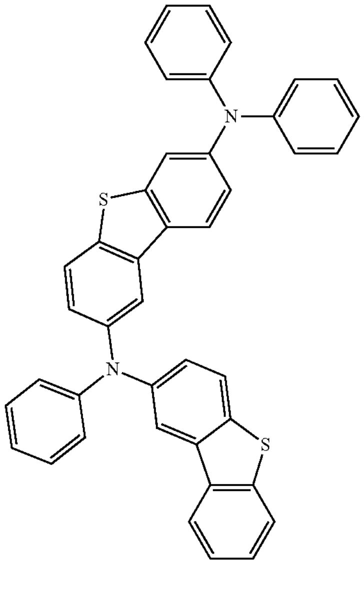
-continued
1-87
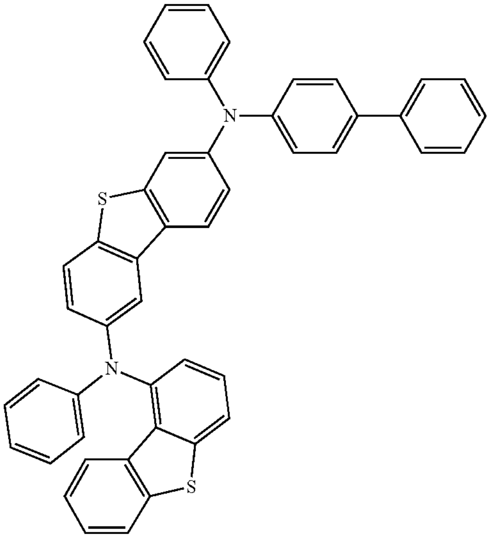
1-88
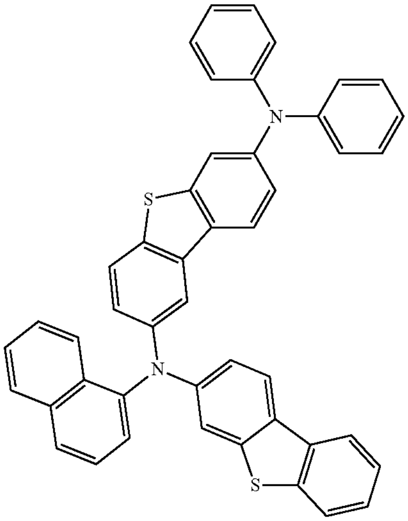
1-89
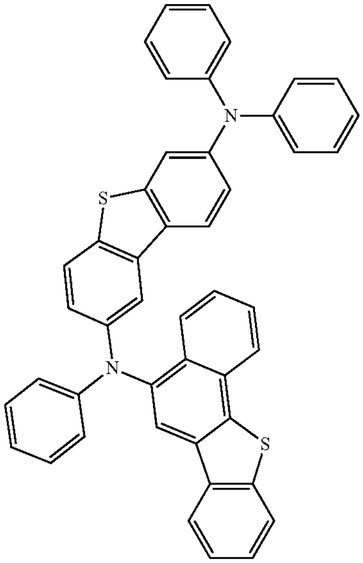

-continued
1-90
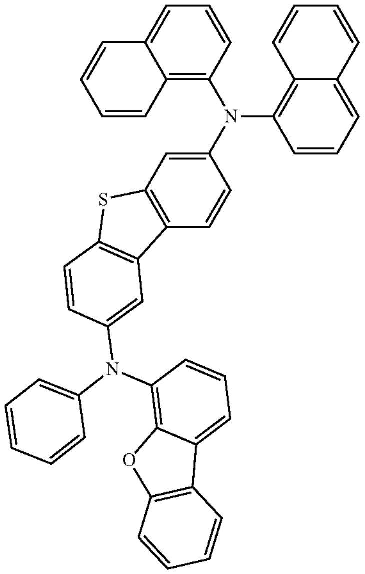
1-91
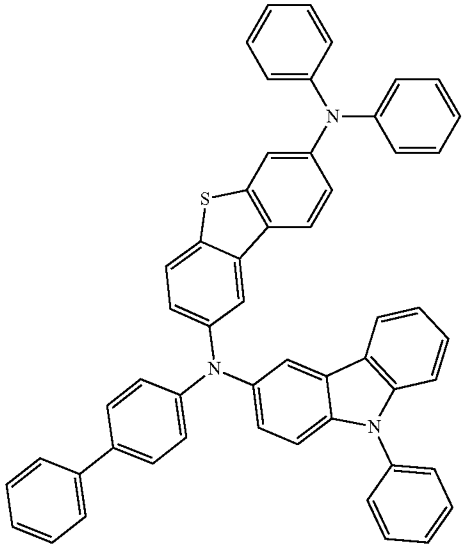
-continued
1-92
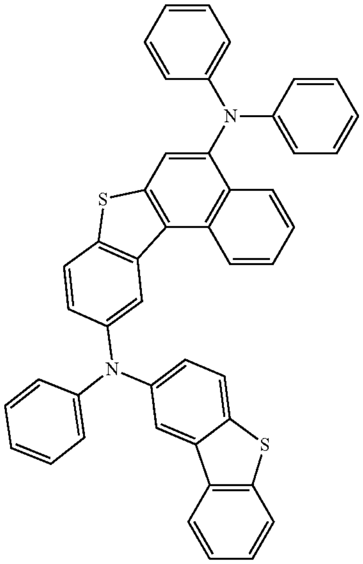
1-93
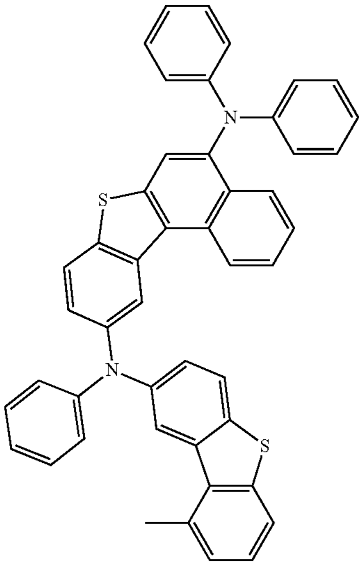

-continued
1-94
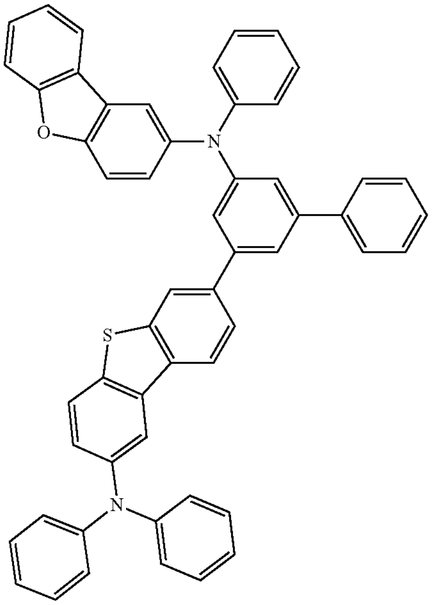
1-95
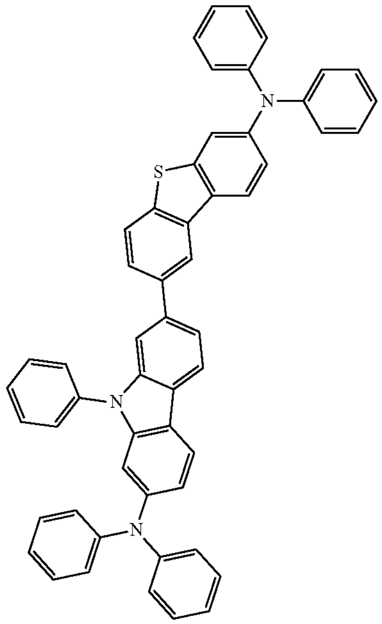
-continued
1-96
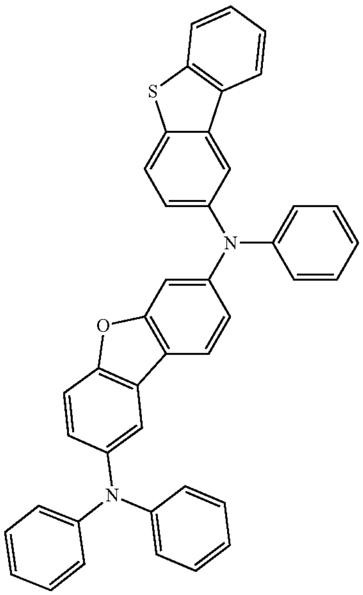
1-97
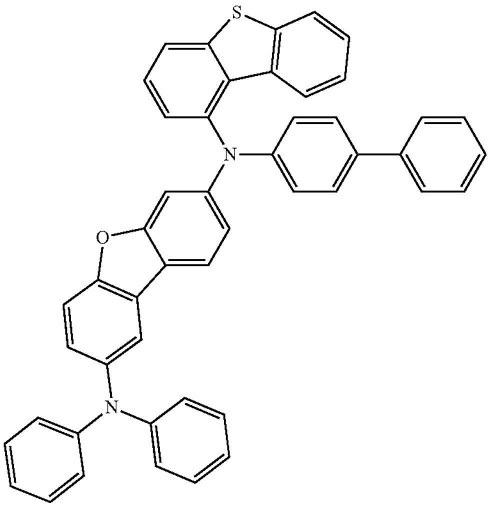

-continued
1-98
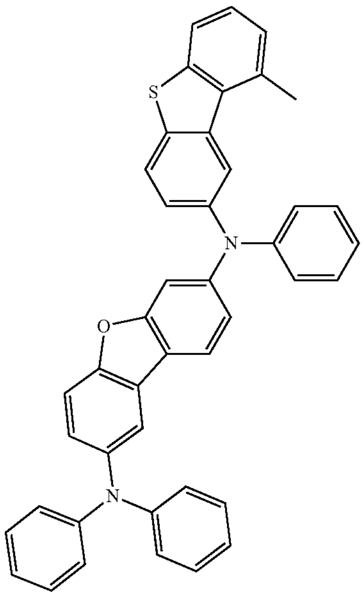
1-99
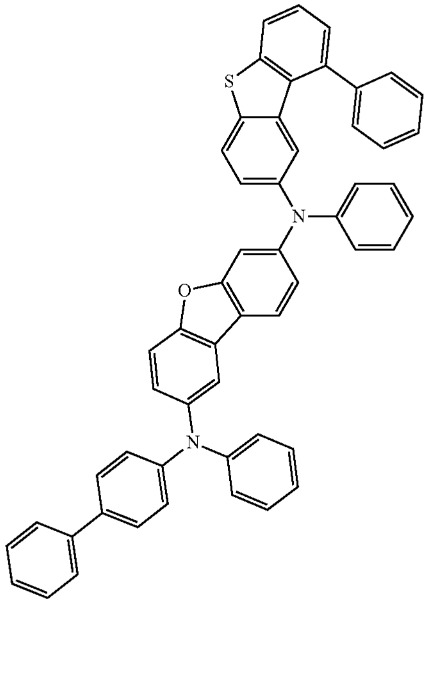
-continued
1-100
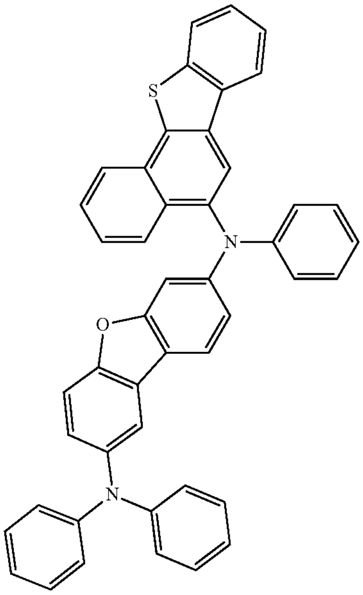
1-101
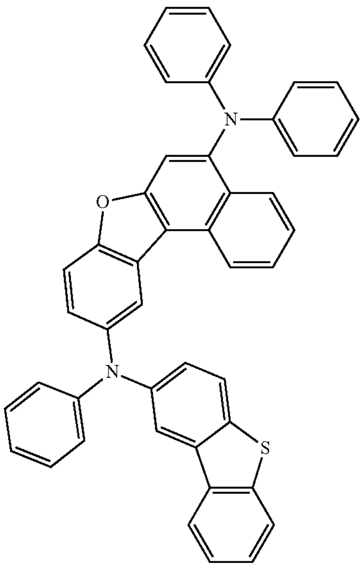

-continued
1-102
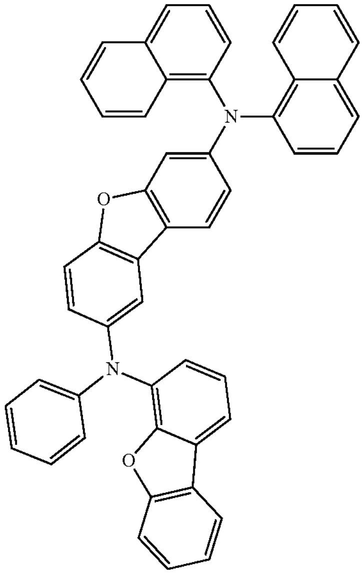
1-103
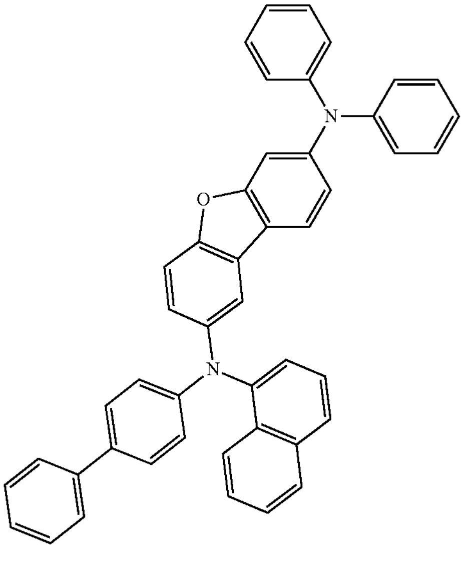
-continued
1-104
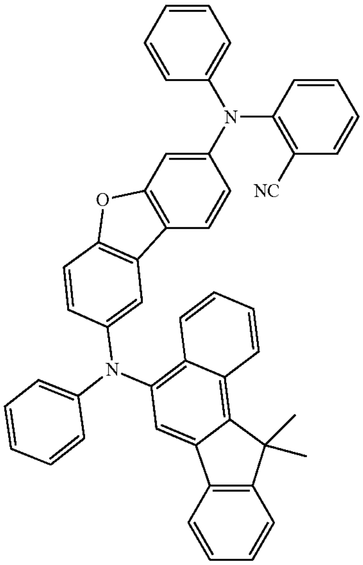
1-105
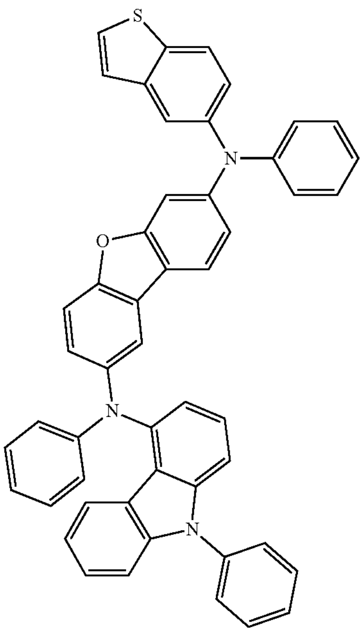

-continued
1-106
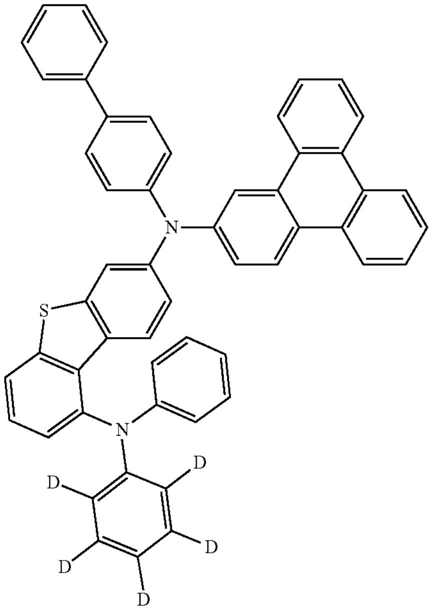
1-107
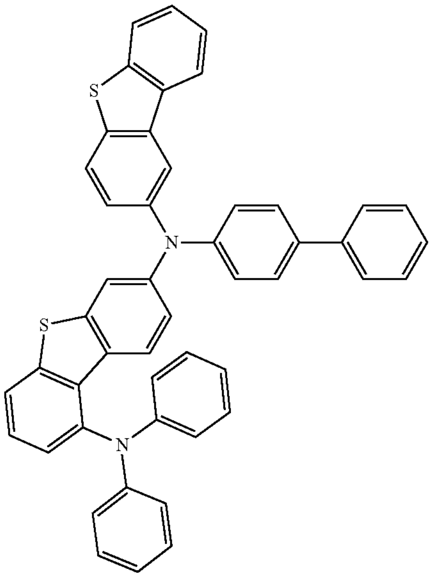
-continued
1-108
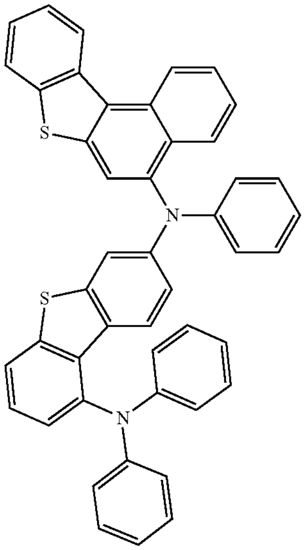
1-109
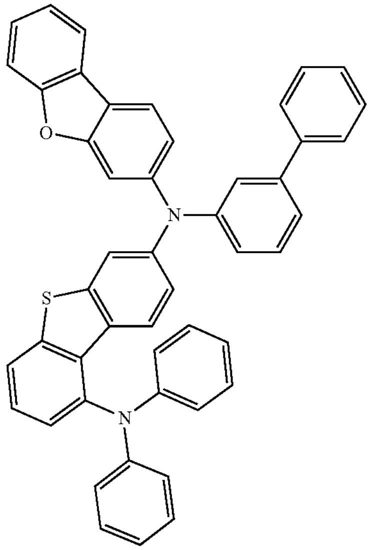
1-110
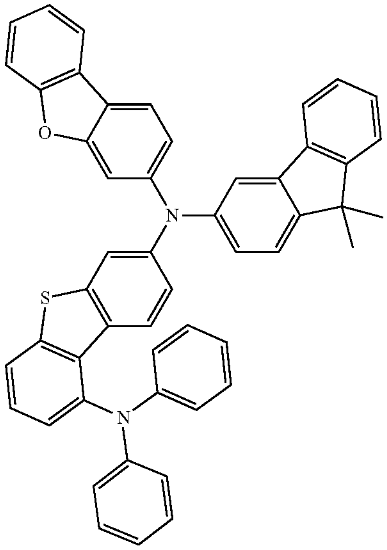

-continued
1-111
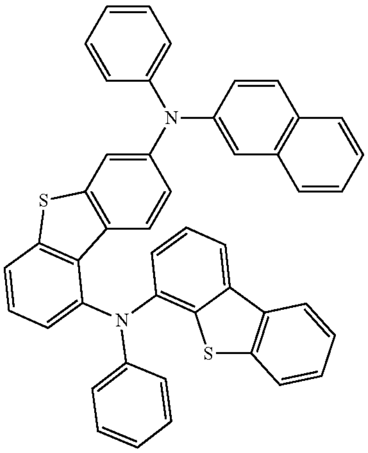
1-112
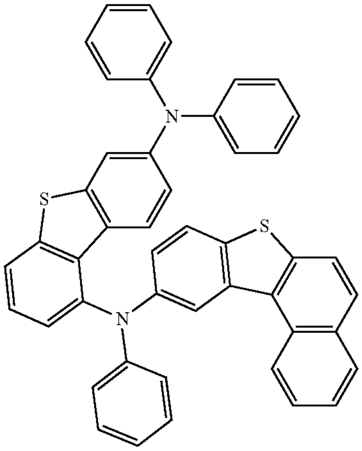
1-113
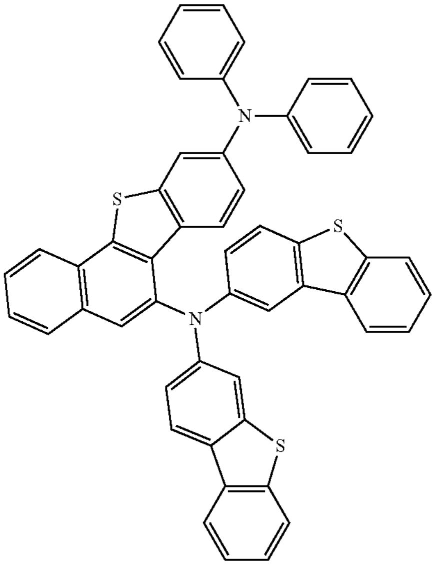
-continued
1-114
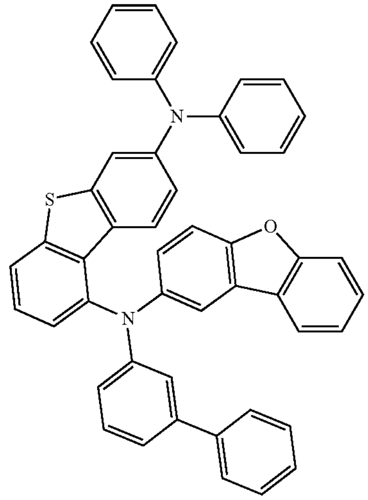
1-115
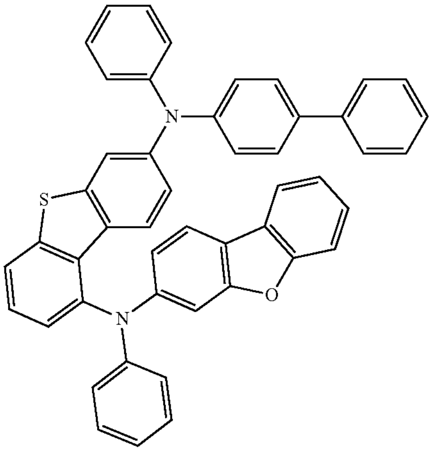
1-116
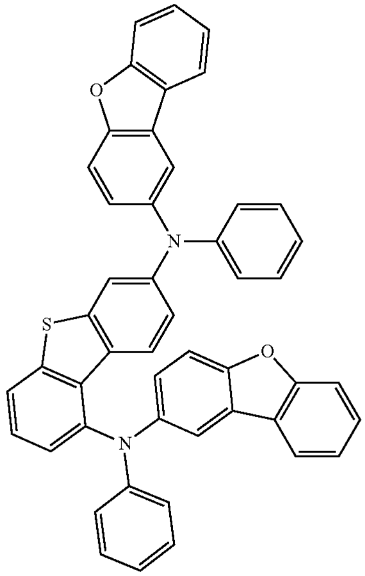

-continued
1-117
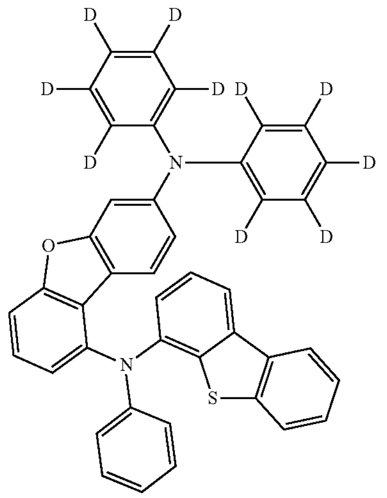
1-118
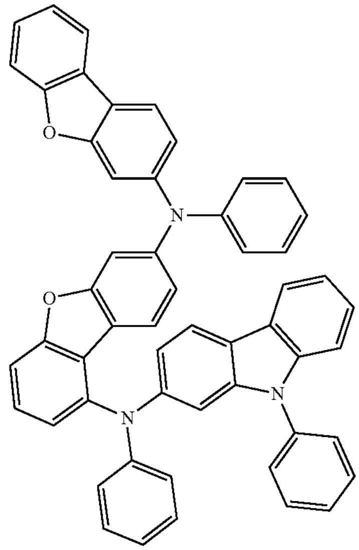
1-119
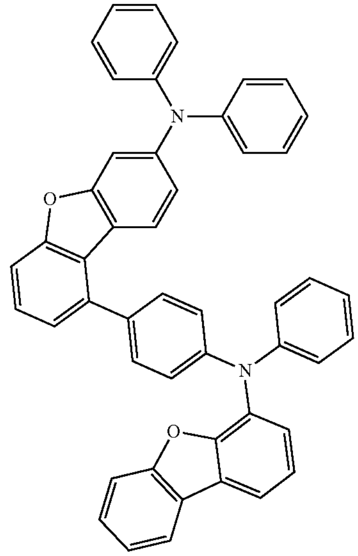
-continued
1-120
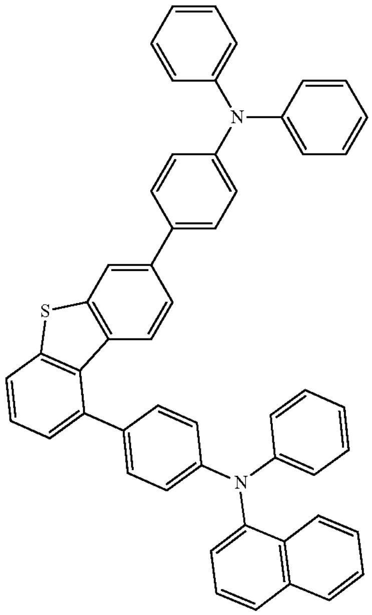
1-121
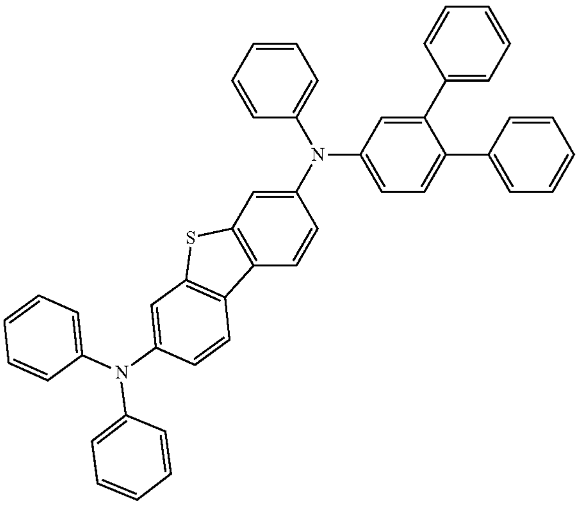

-continued
1-122
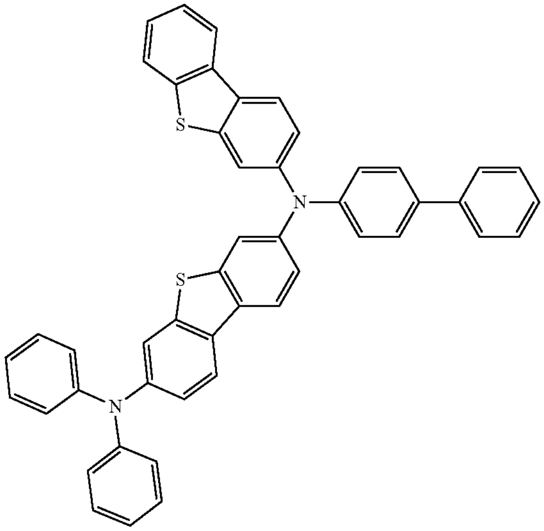
1-123
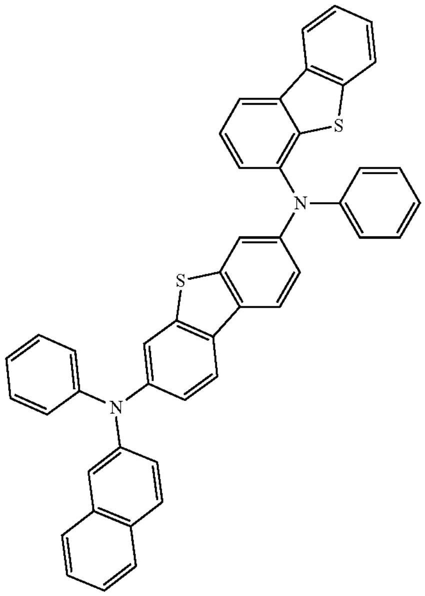
-continued
1-124
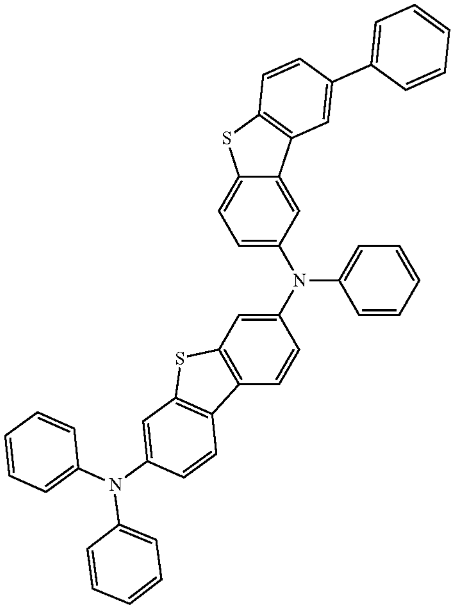
1-125
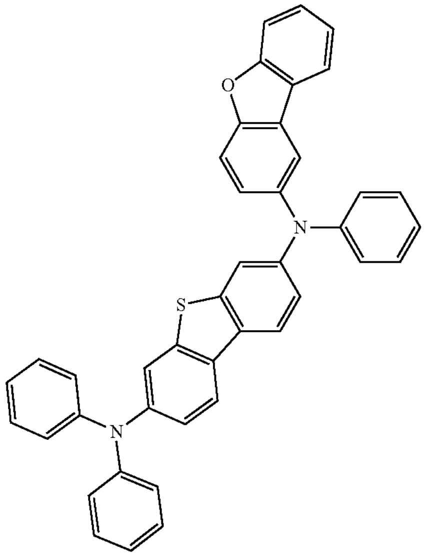

-continued
1-126
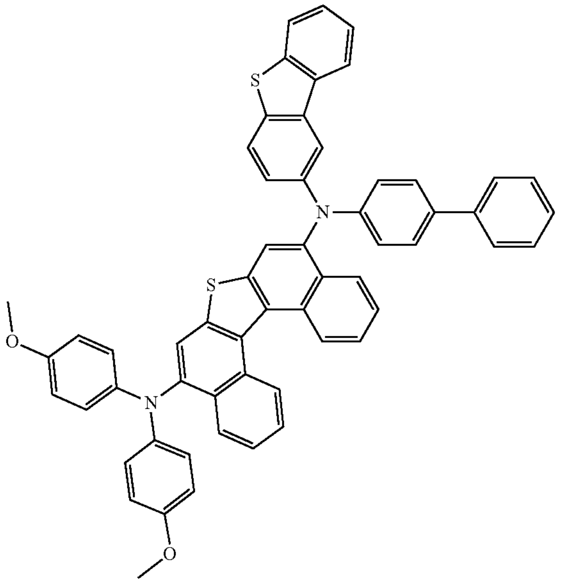
1-127
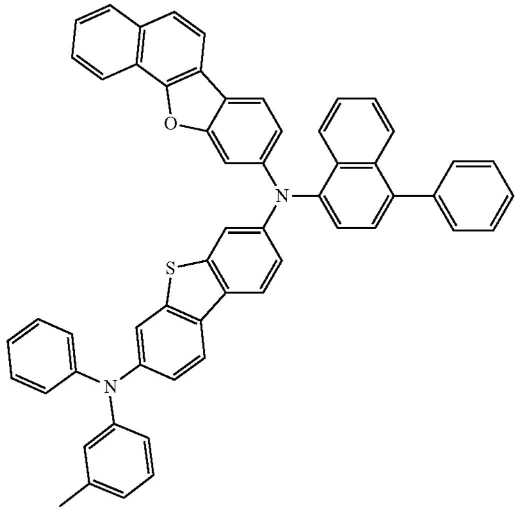
-continued
1-128
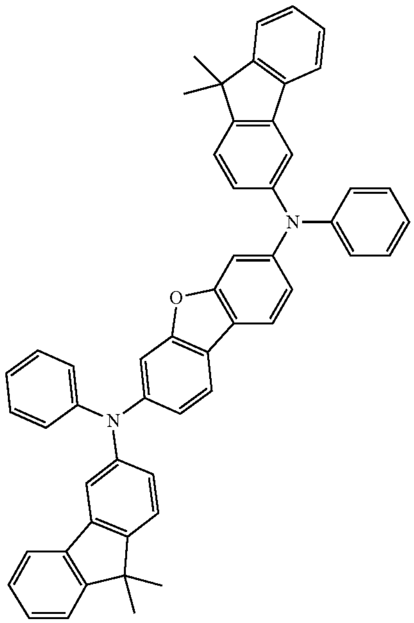
1-129
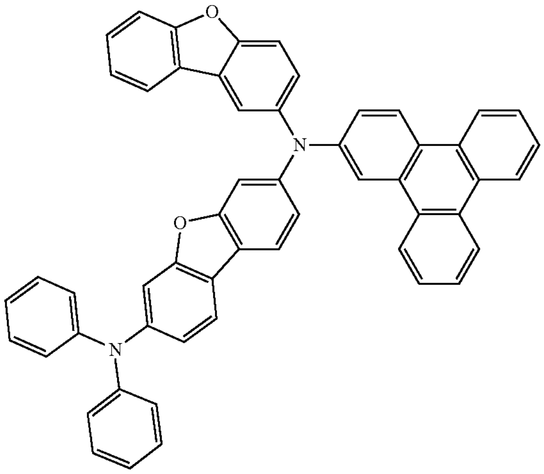

-continued
1-130
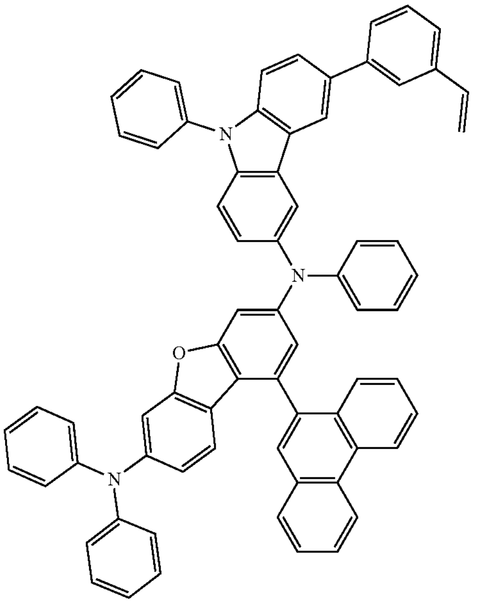
1-131
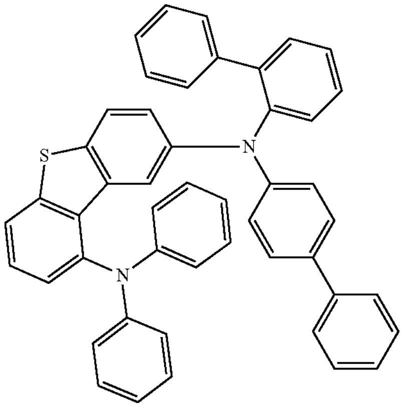
1-132
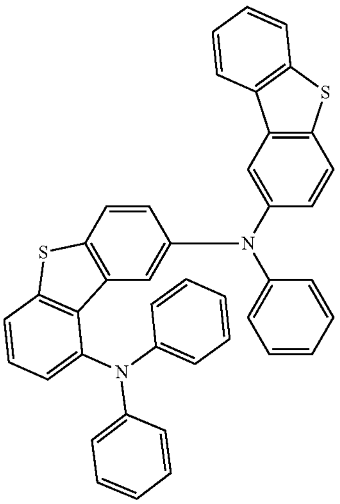
-continued
1-133
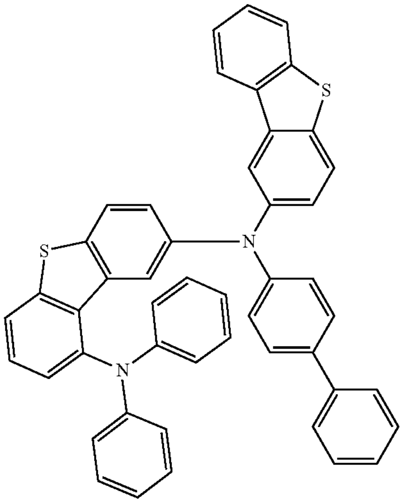
1-134
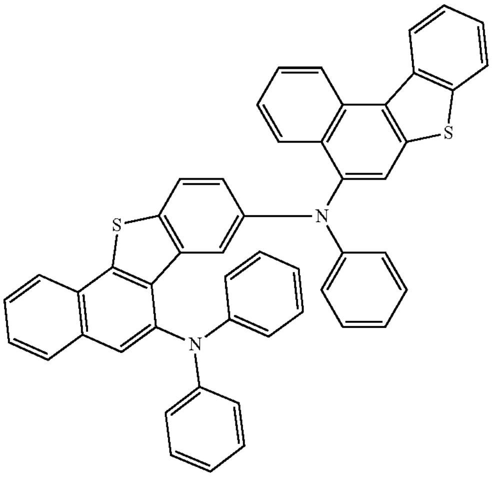
1-135
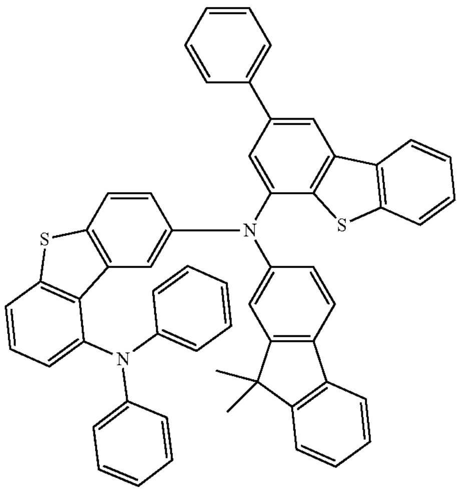

-continued
1-136
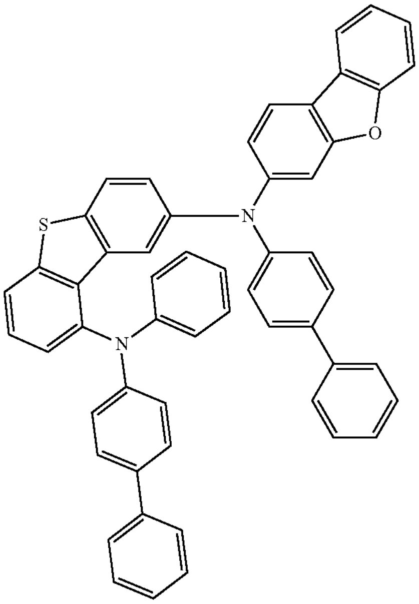
1-137
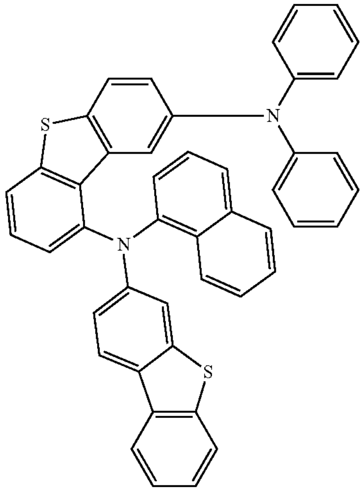
1-138
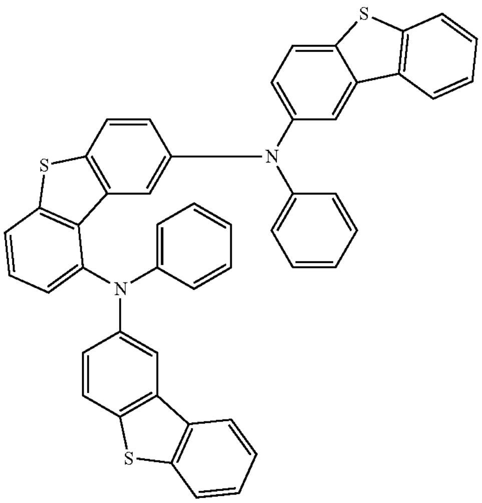
-continued
1-139
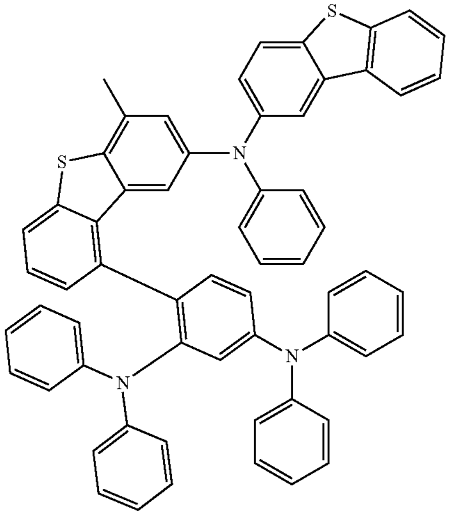
1-140
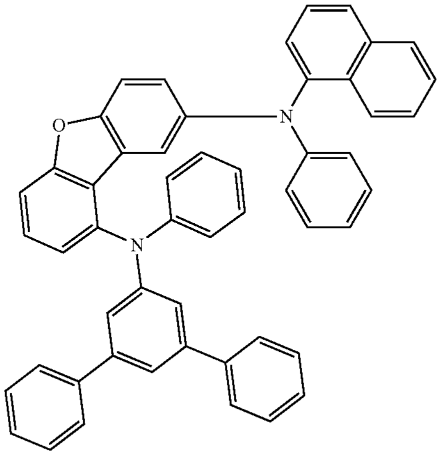
1-141
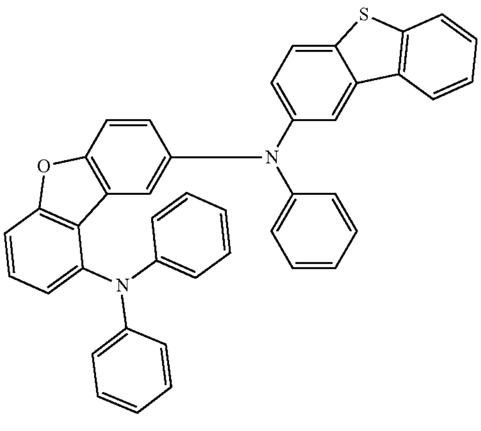

-continued
1-142
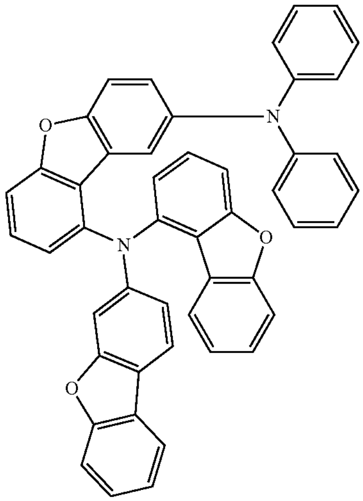
1-143
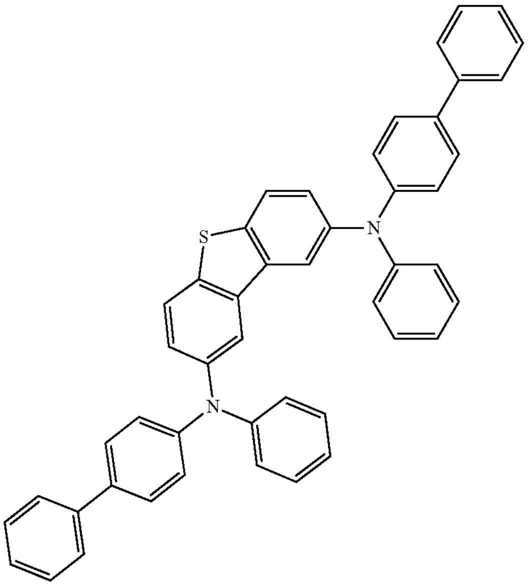
1-144
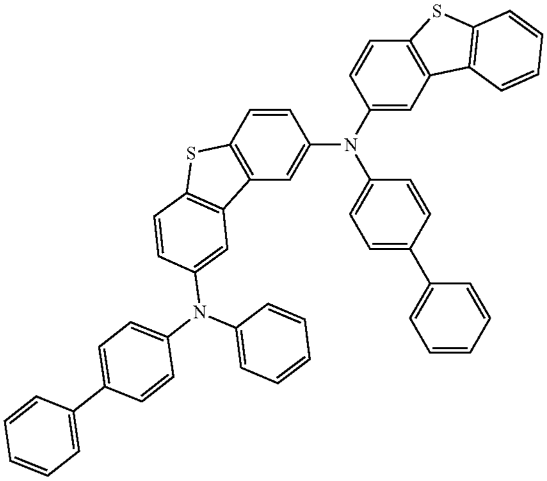
-continued
1-145
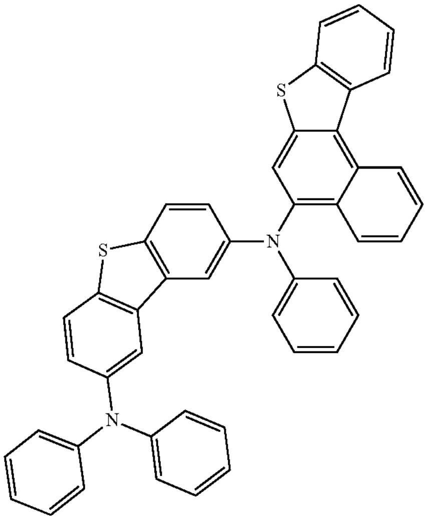
1-146
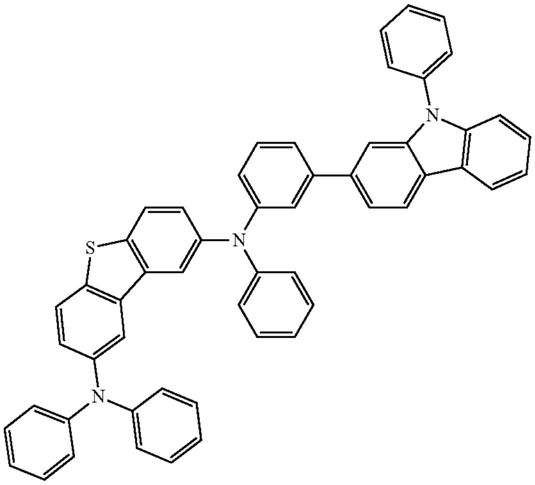
1-147
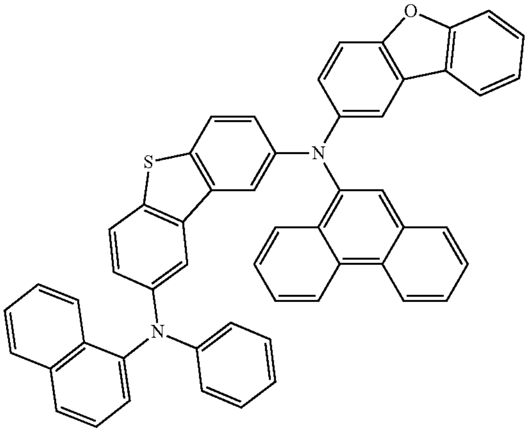

-continued
1-148
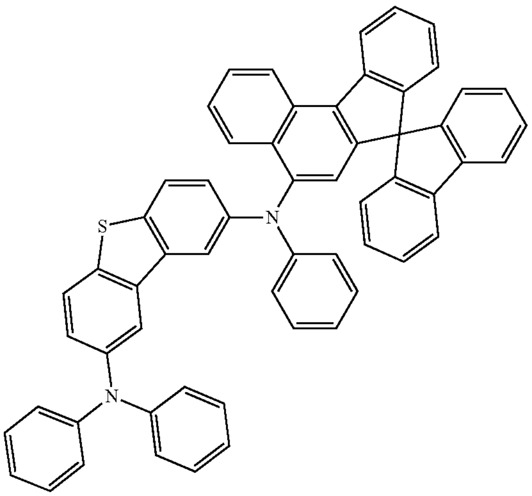
1-149
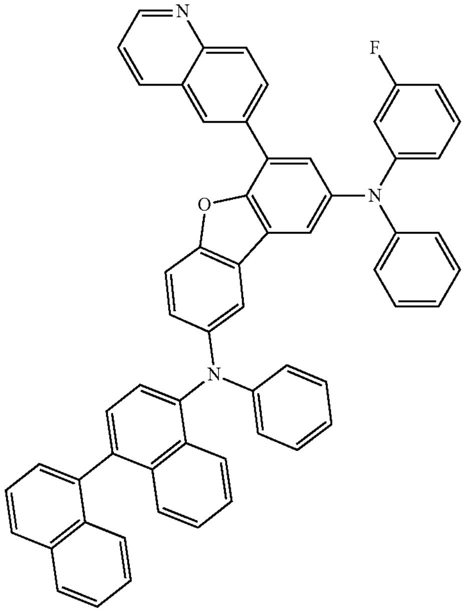
-continued
1-150
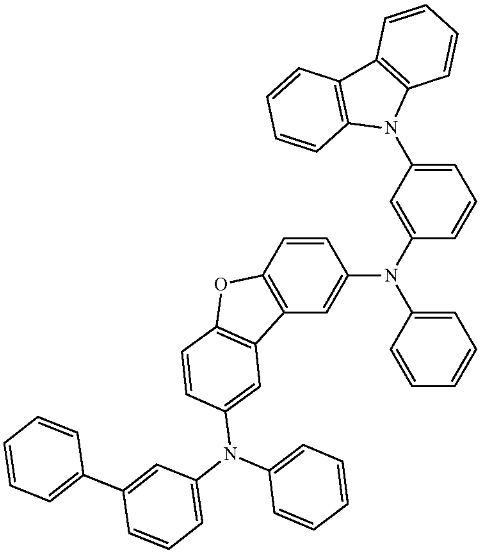
1-151
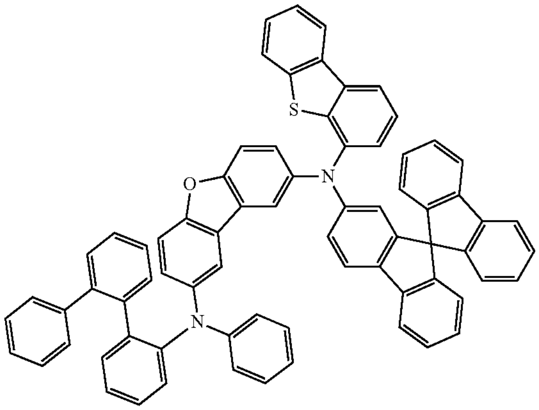
1-152
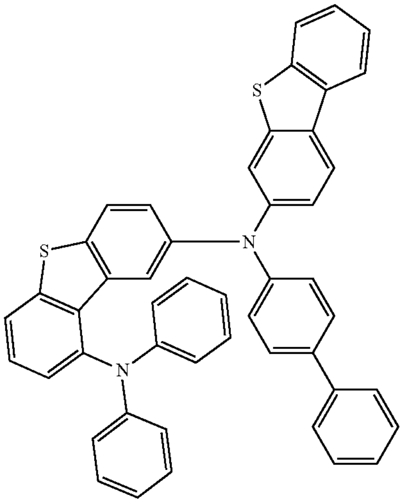

-continued
1-153
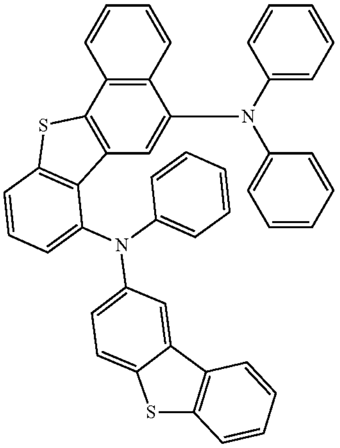
1-154
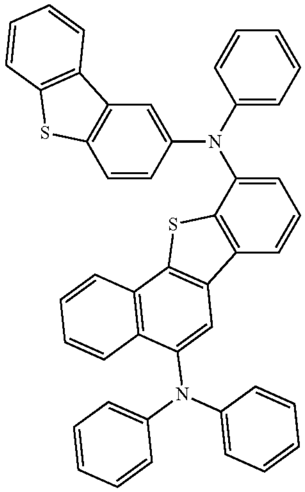
1-155
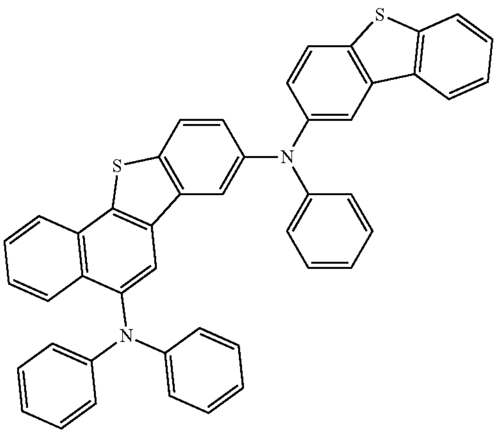
-continued
1-156
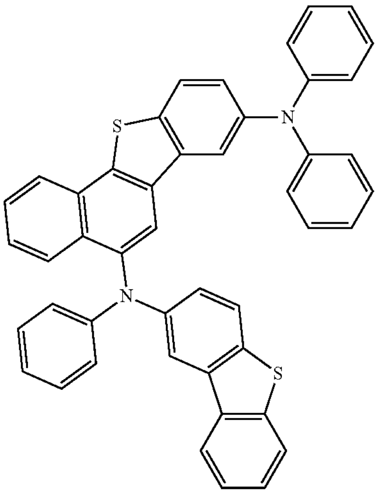
1-157
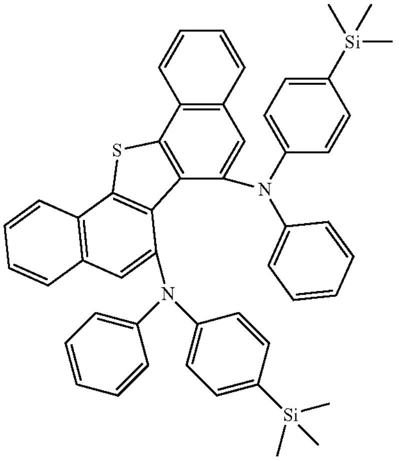
1-158
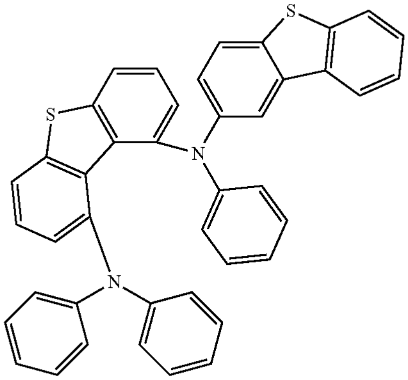

-continued
1-159
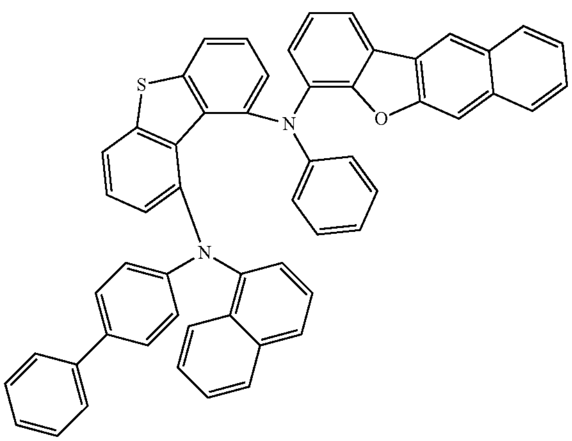
1-160
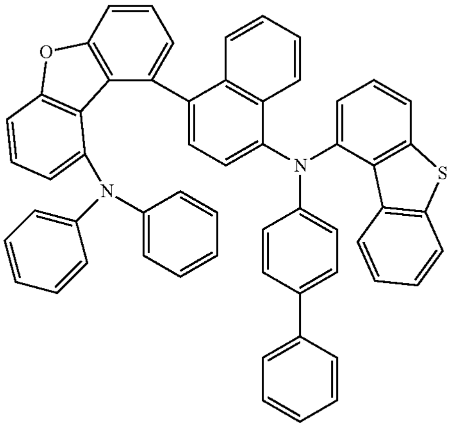
1-161
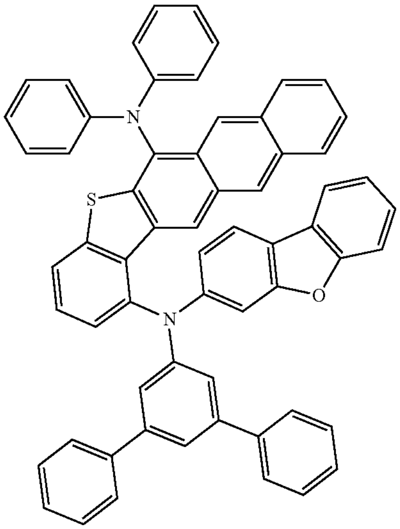
-continued
1-162
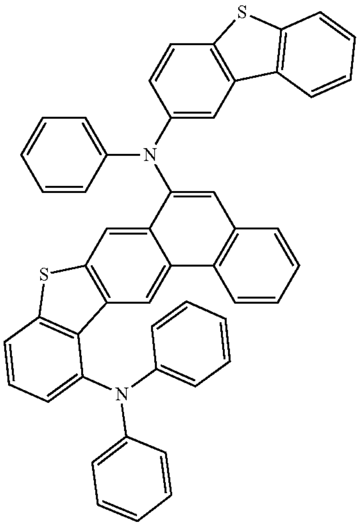
1-163
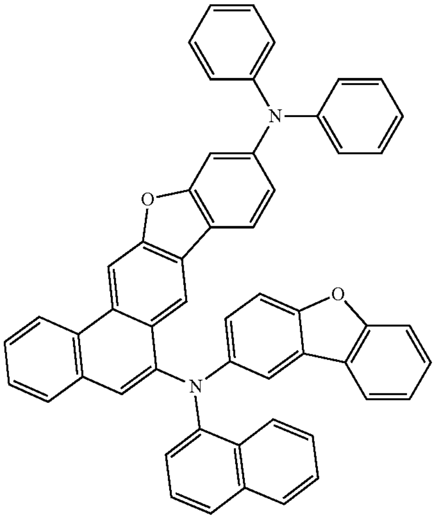
1-164
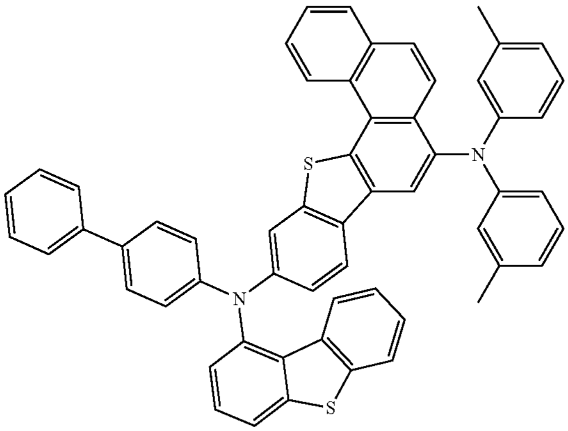

-continued
1-165
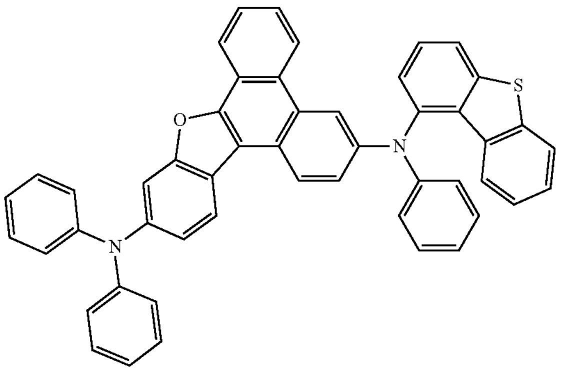
1-166
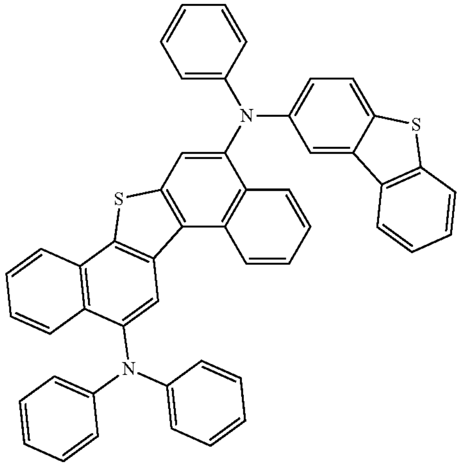
1-167
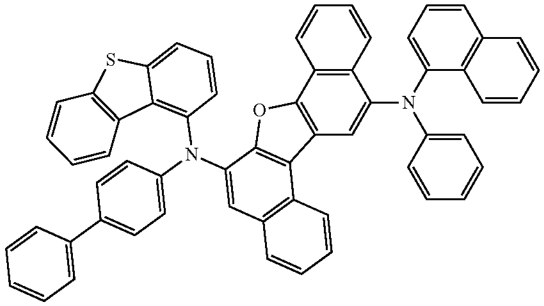
1-168
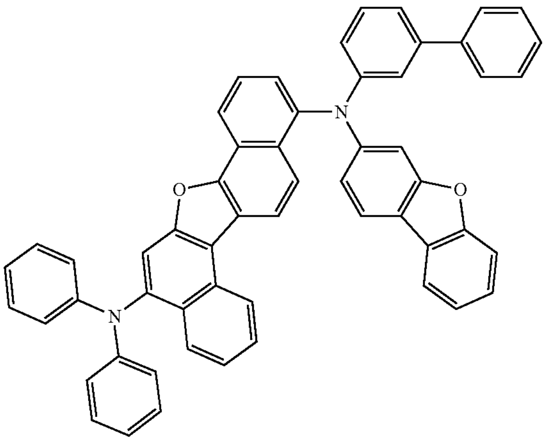
-continued
1-169
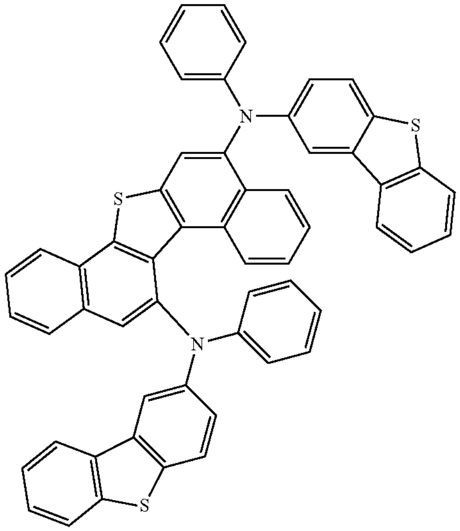
1-170
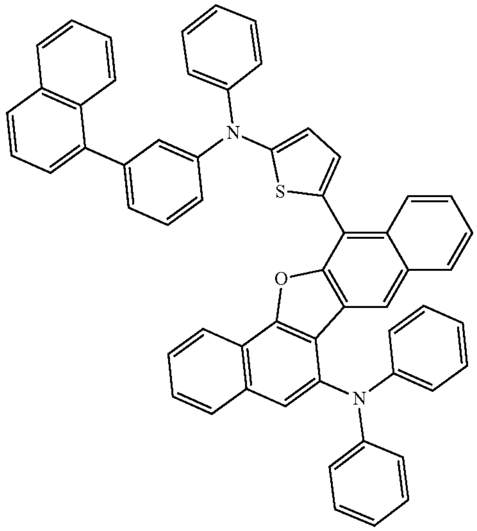
1-171
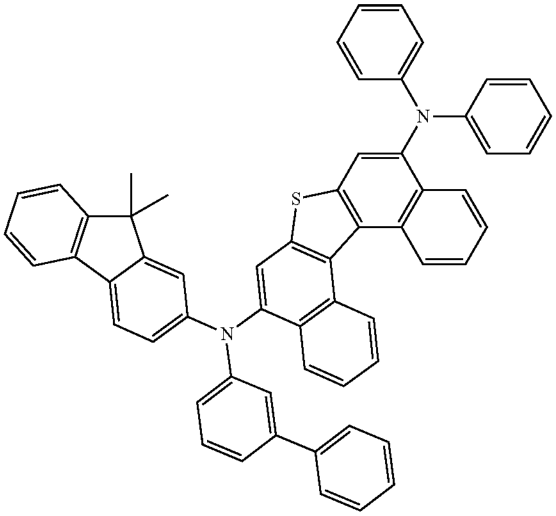

-continued
1-172
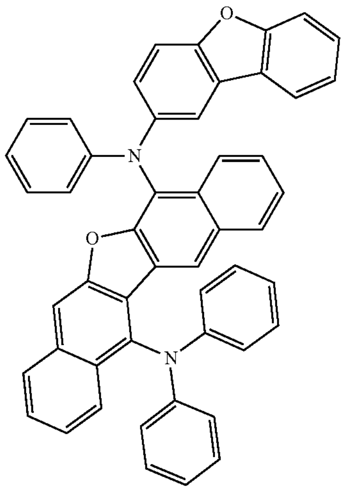
1-173
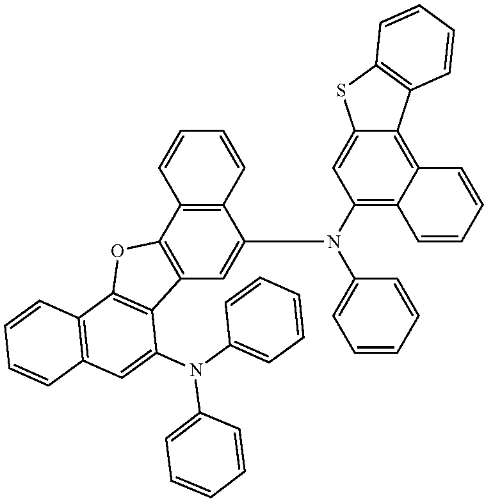
-continued
1-174
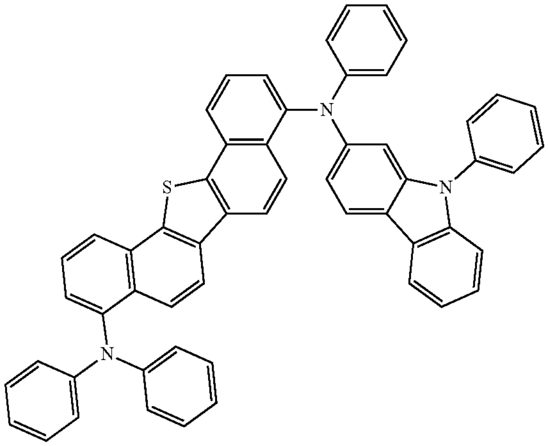
1-175
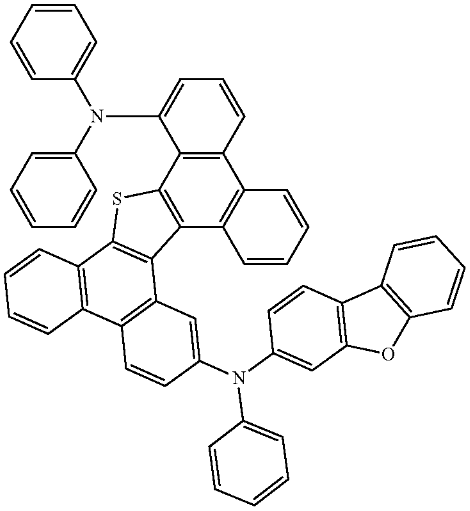
As another example, the second host compound represented by Formula 2 comprises the following compounds. That is, Compounds 1'-1 to 1'-84, 2-1 to 2-60, 3-1 to 3-36, P-1 to P-120, 4-1 to 4-12, 5-1 to 5-20, 6-1 to 6-16 and 7-1 to 7-24.

1'-1
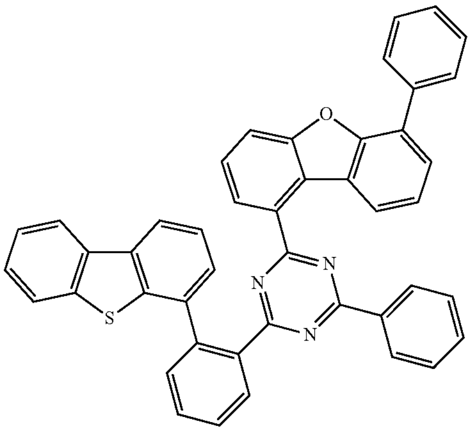
1'-2
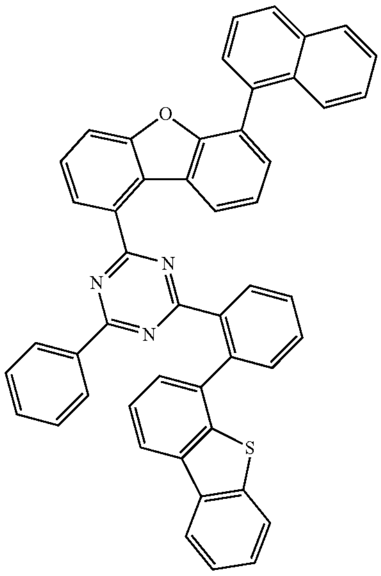
1'-3
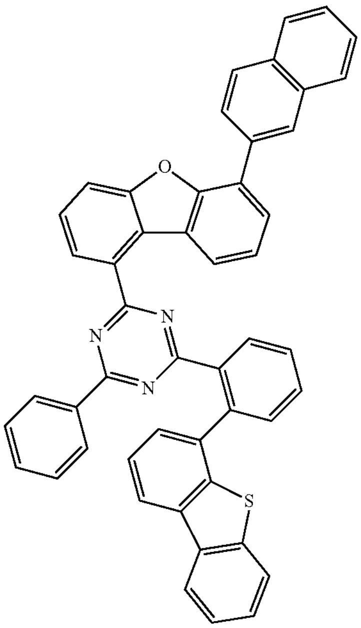
1'-4
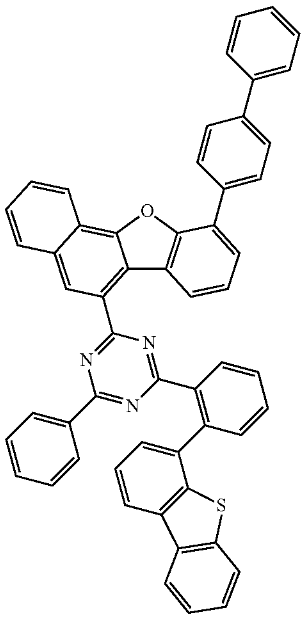
1'-5
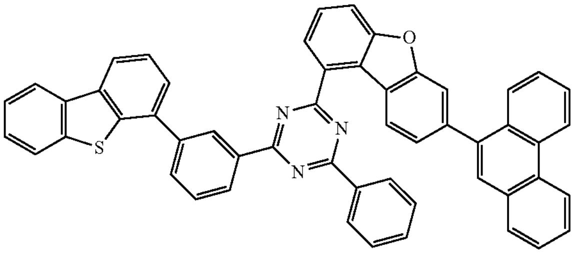
1'-6
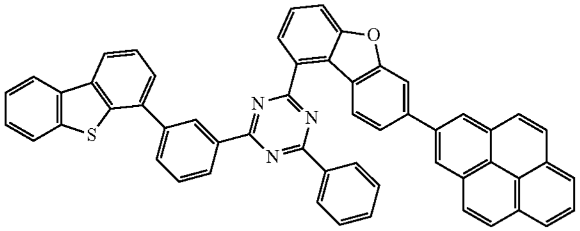

-continued
1'-7
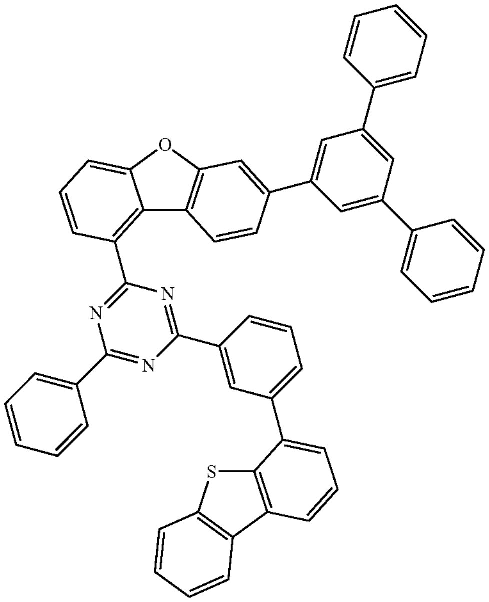
1'-8
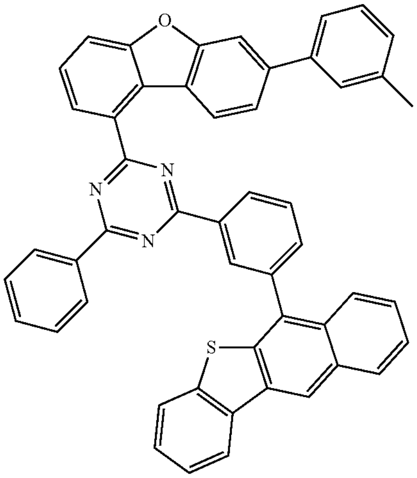
1'-9
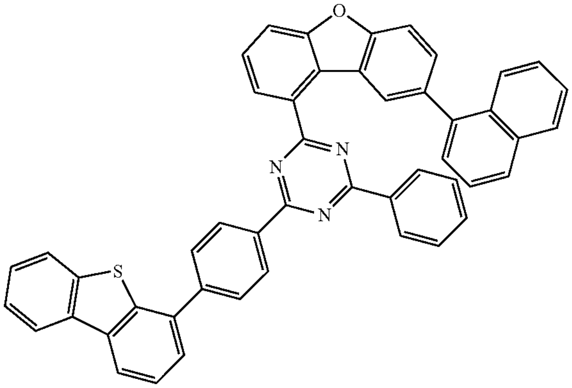
1'-10
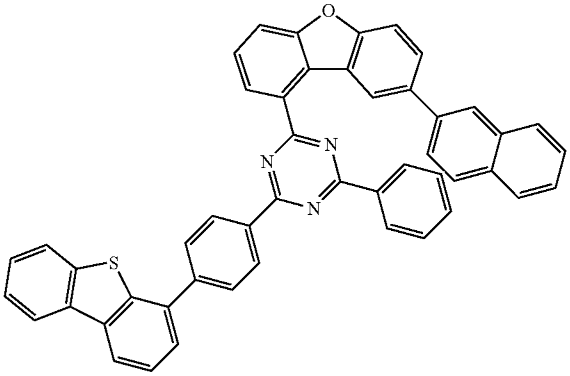
1'-11
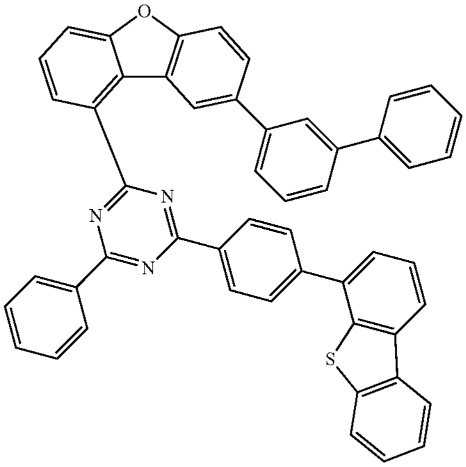
1'-12
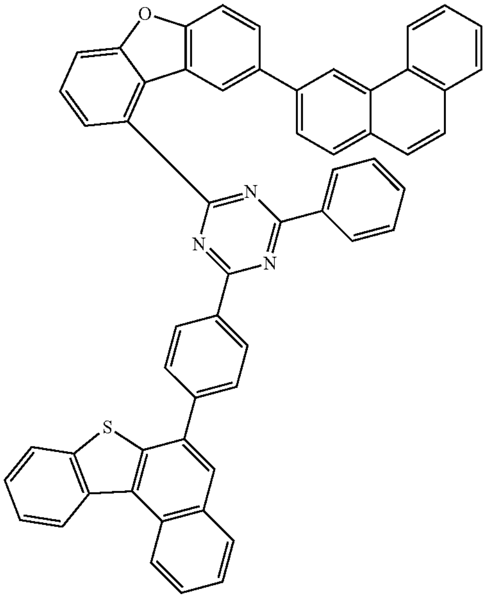

-continued
1′-13
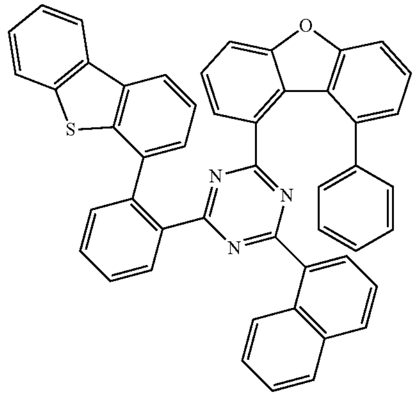
1′-14
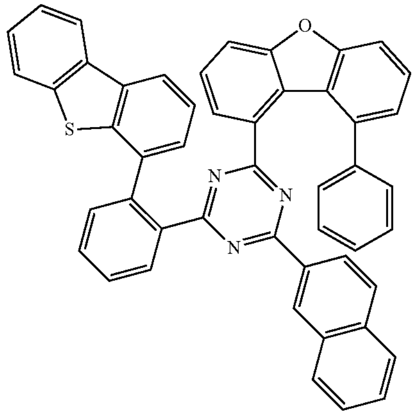
1′-15
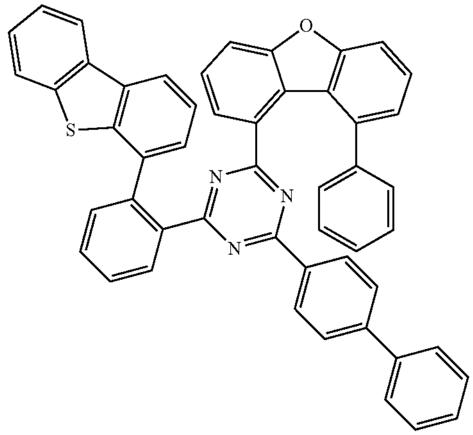
1′-16
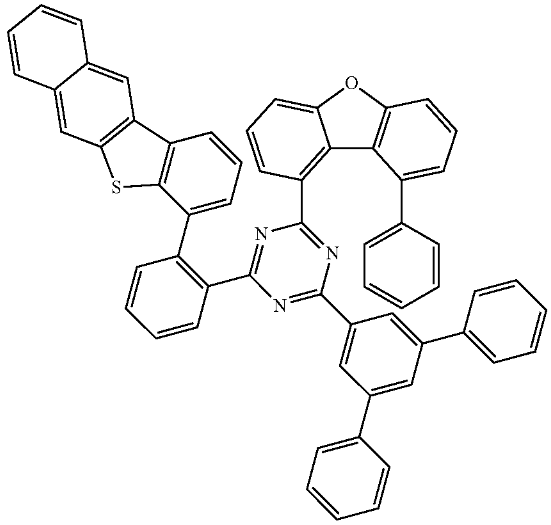
1′-17
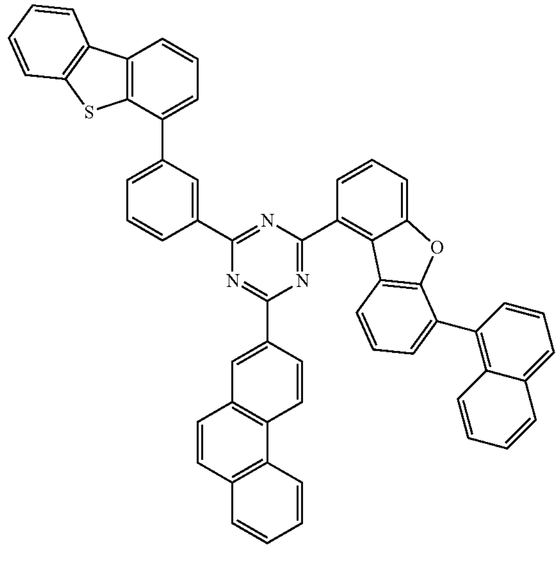
1′-18
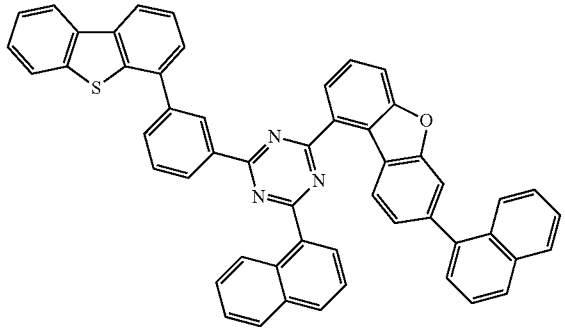

-continued
1′-19
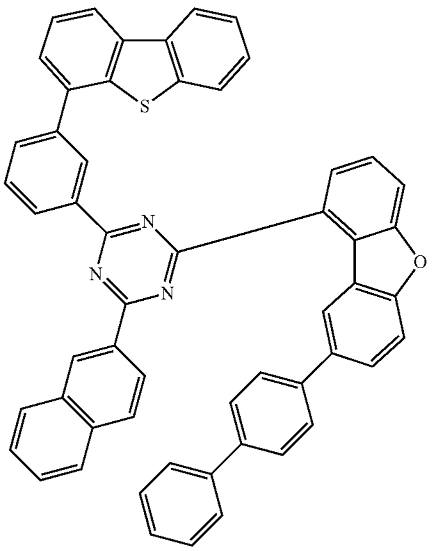
1′-20
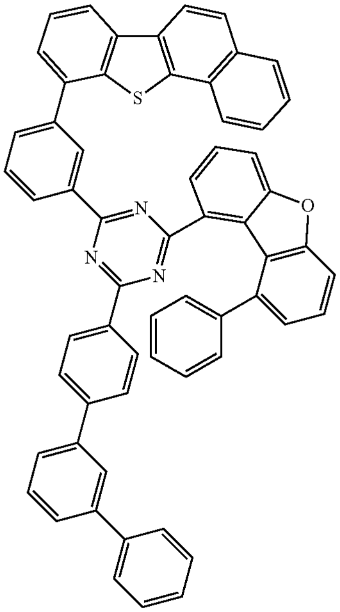
1′-21
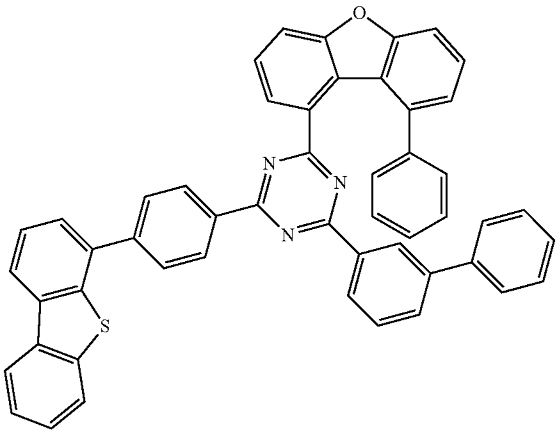
1′-22
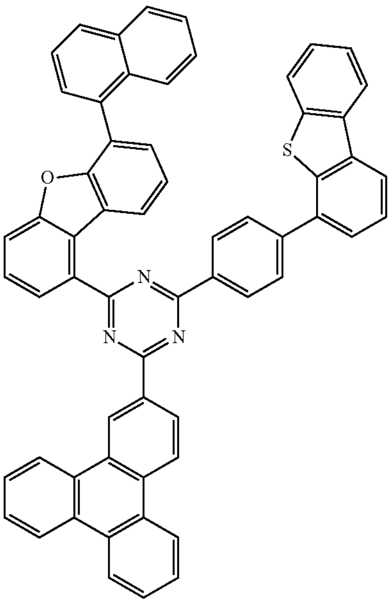

-continued
1'-23
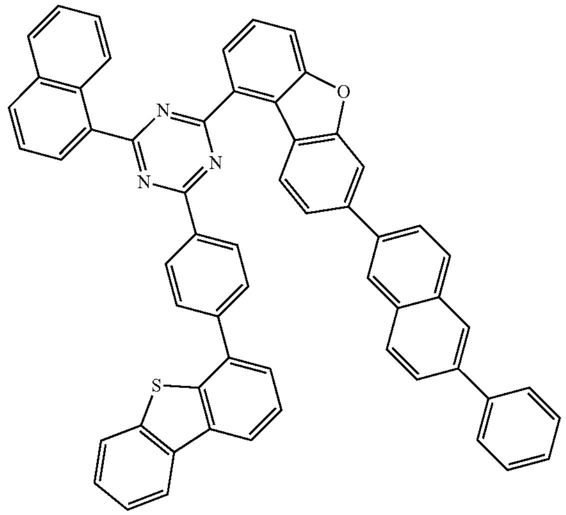
1'-24
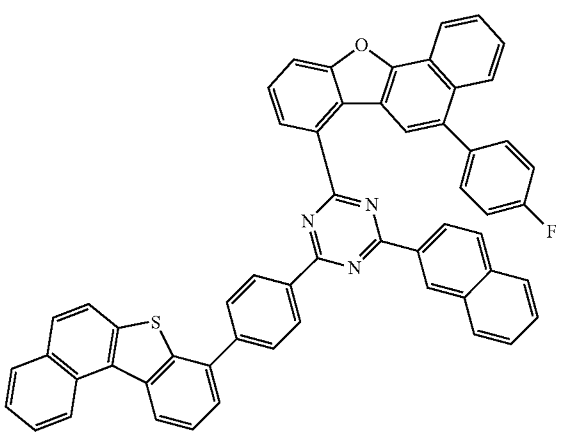
1'-25
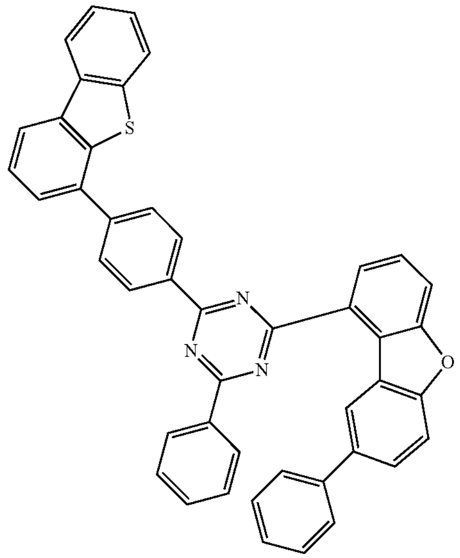
1'-26
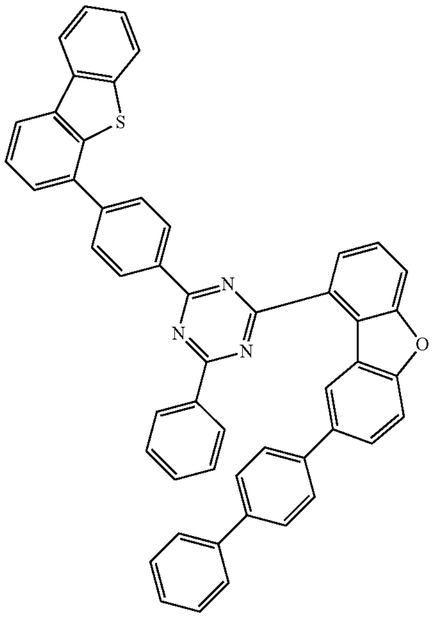

-continued
1′-27
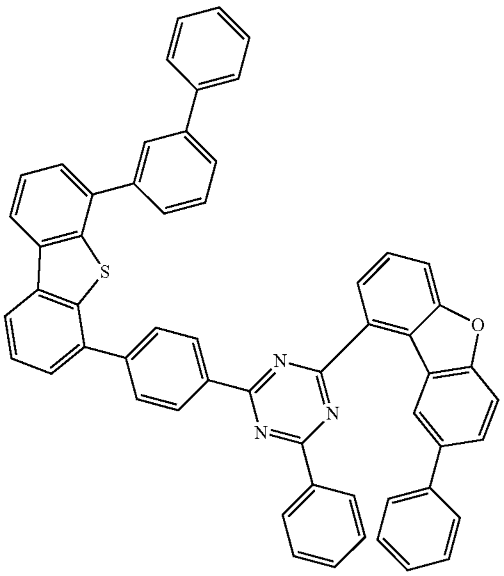
1′-28
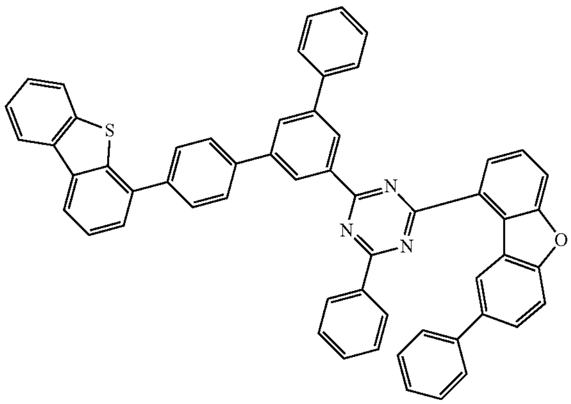
1′-29
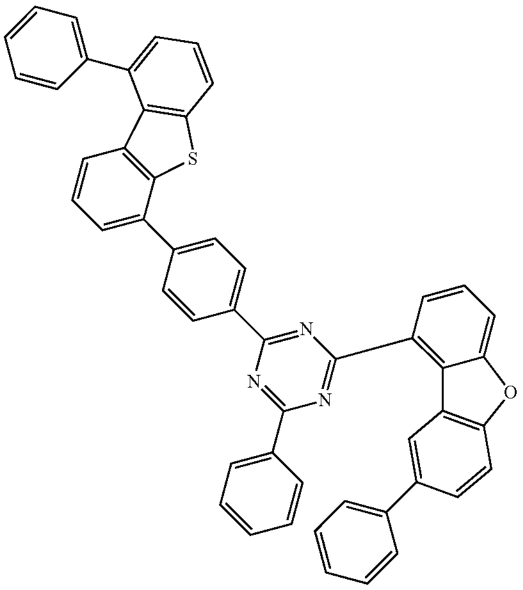
1′-30
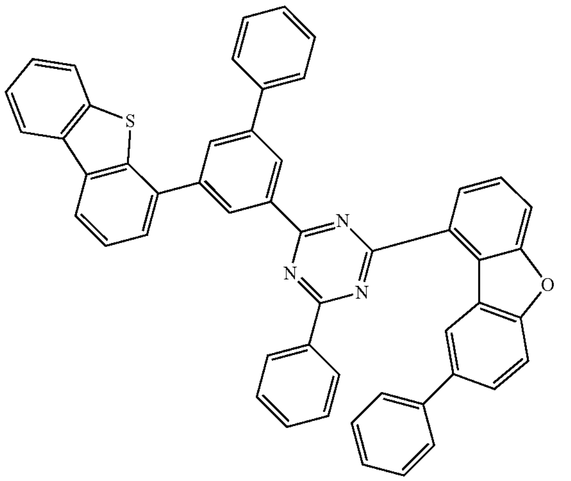

-continued
1′-31
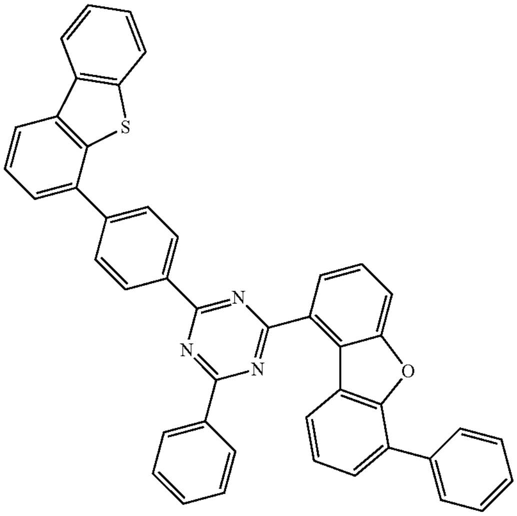
1′-32
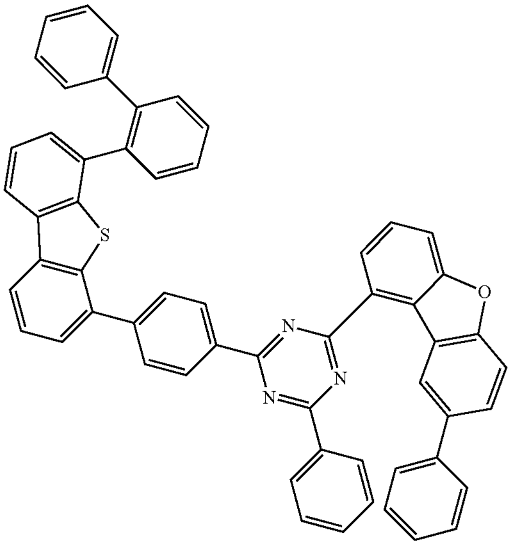
1′-33
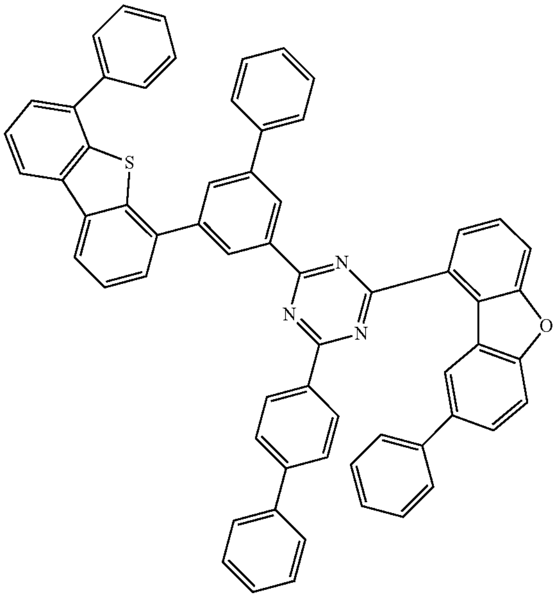
1′-34
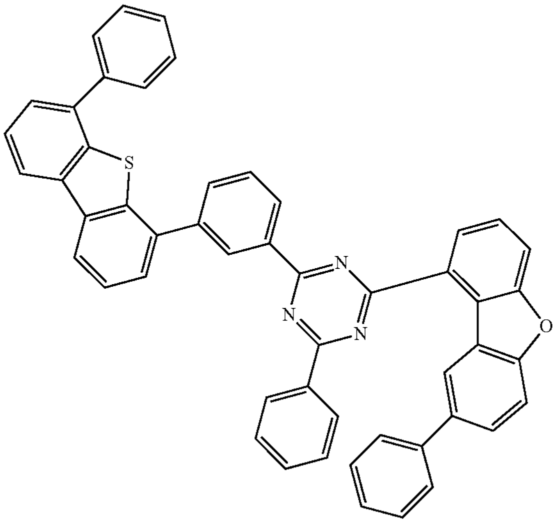

-continued
1′-35
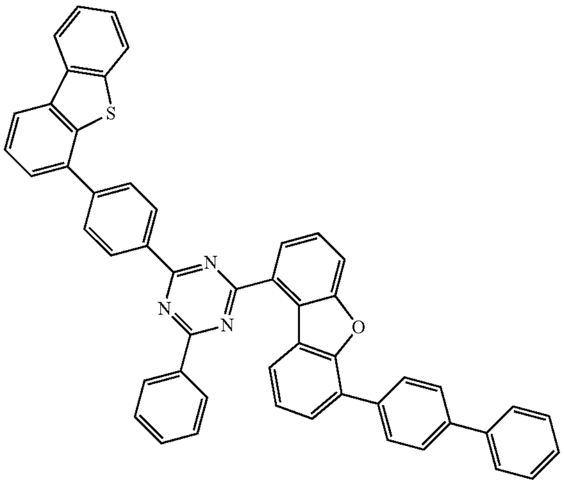
1′-36
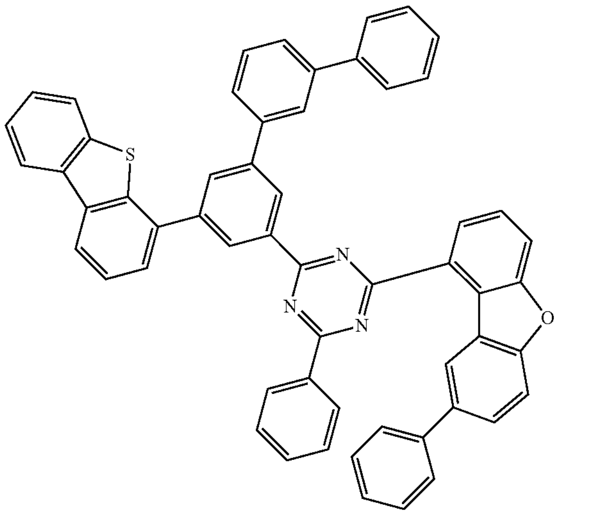
1′-37
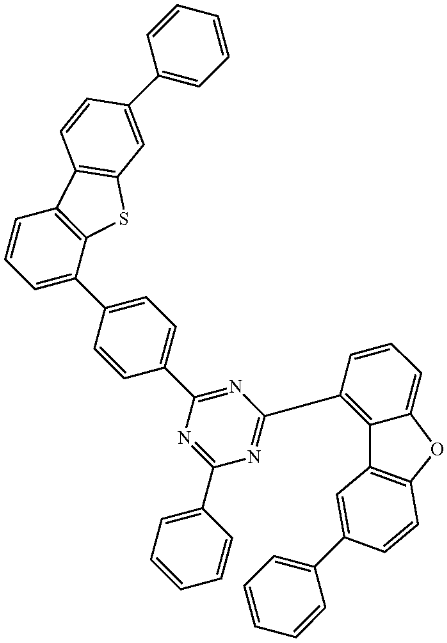
1′-38
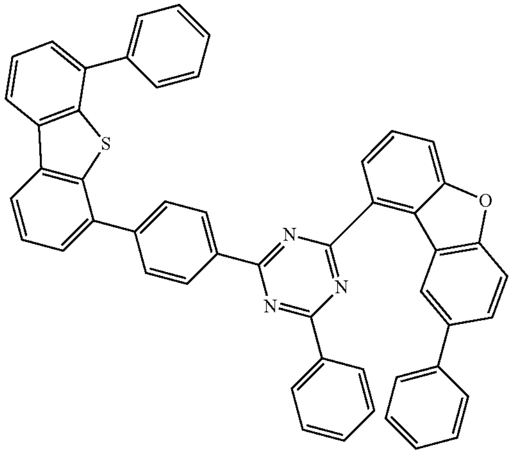
1′-39
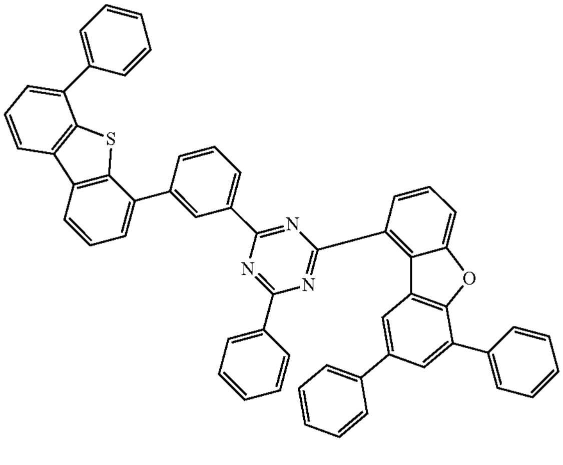
1′-40
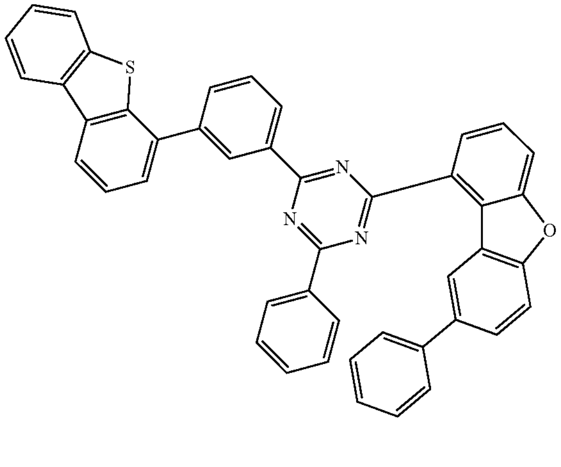

-continued
1′-41
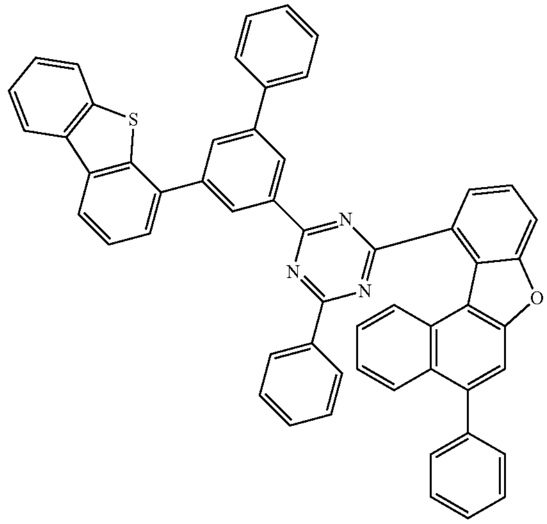
1′-42
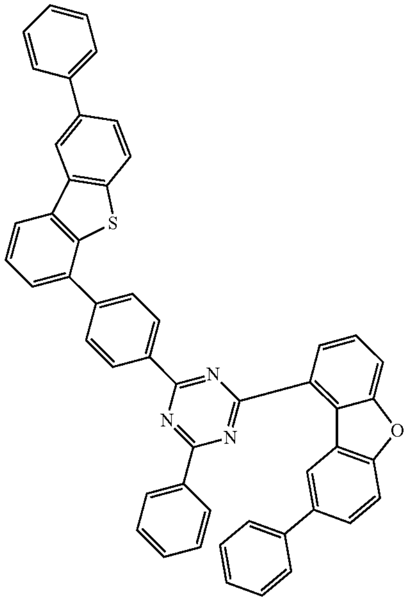
1′-43
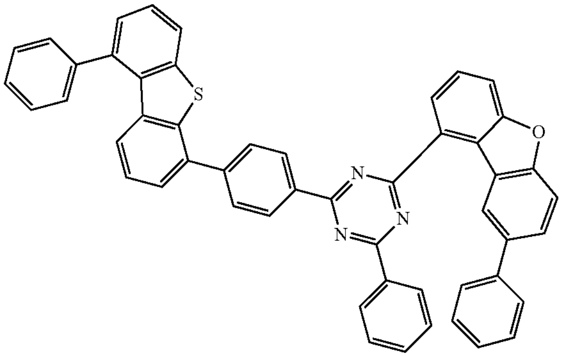
1′-44
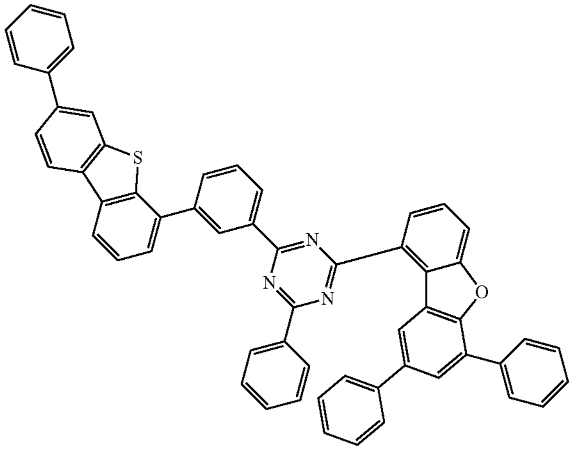
1′-45
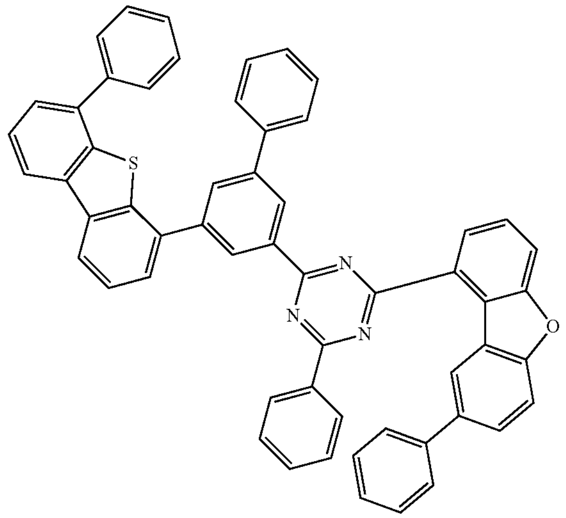
1′-46
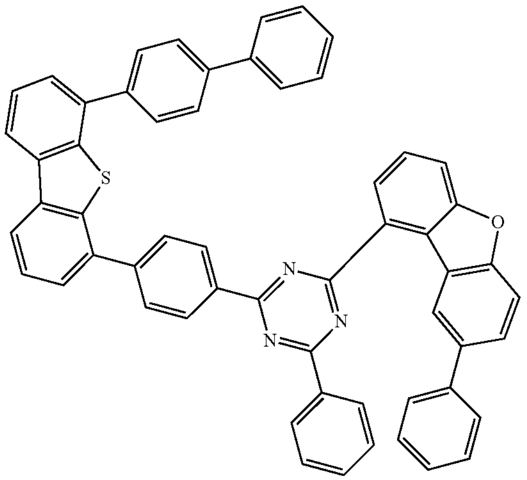

-continued
1'-47
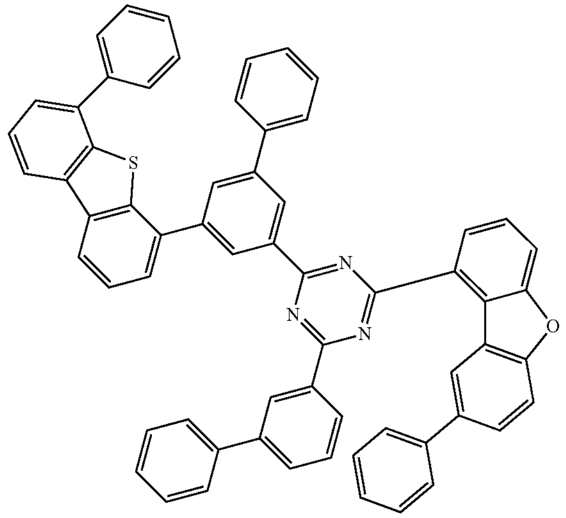
1'-48
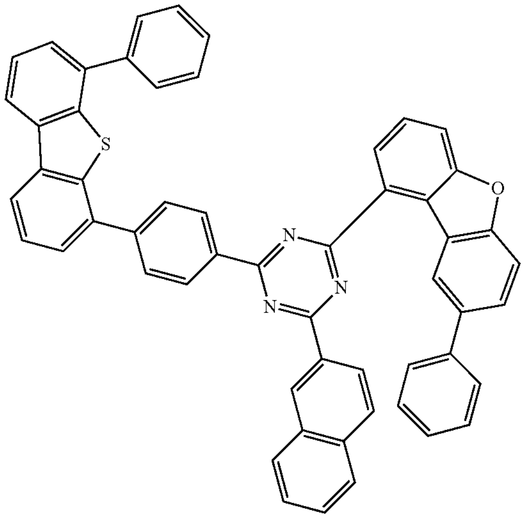
1'-49
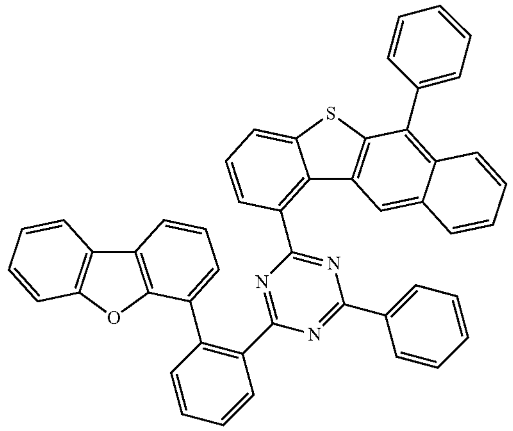
1'-50
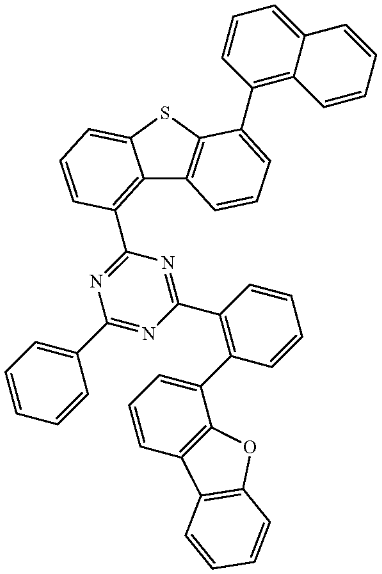

-continued
1′-51
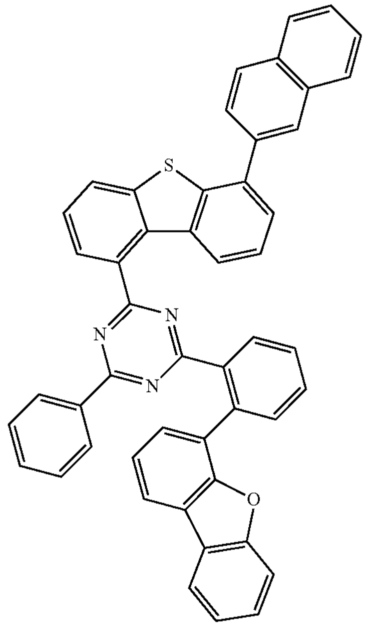
1′-52
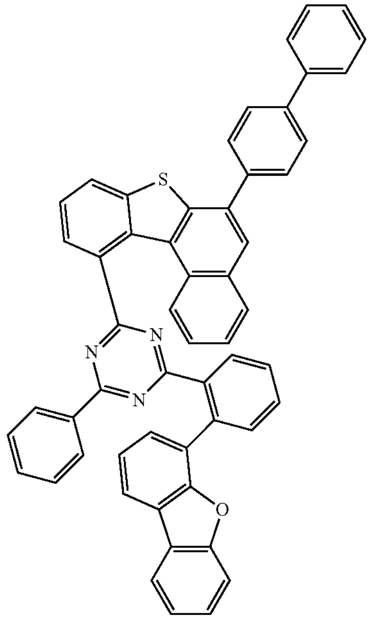
1′-53
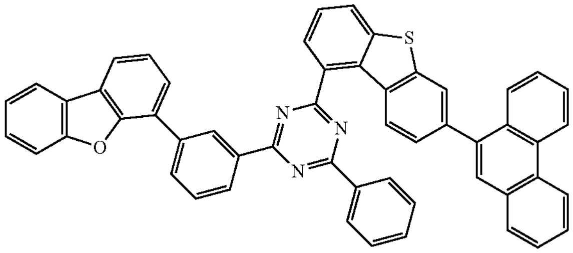
1′-54
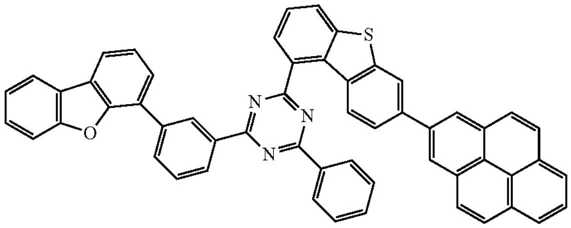
1′-55
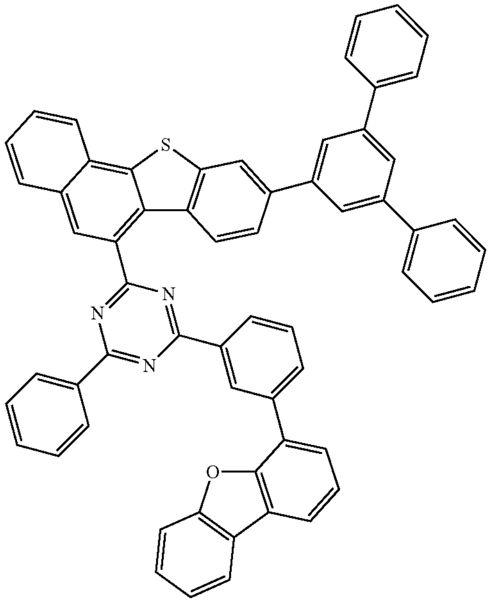
1′-56
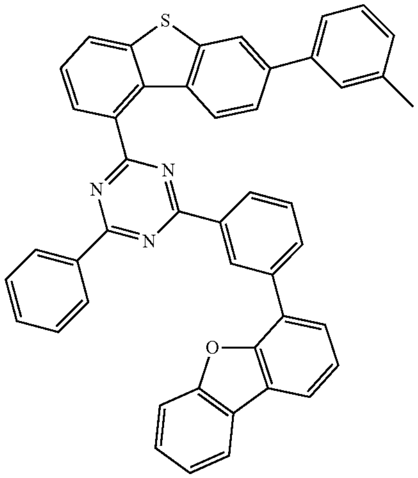

-continued
1′-57
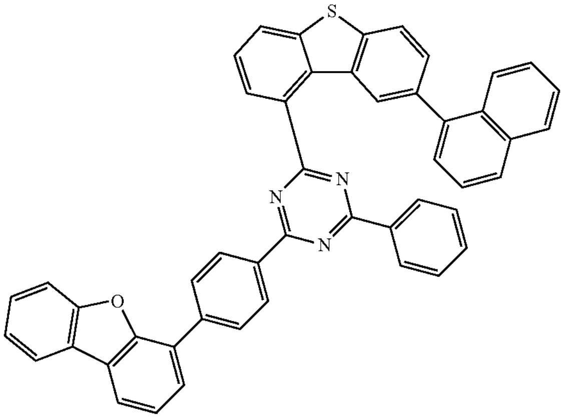
1′-58
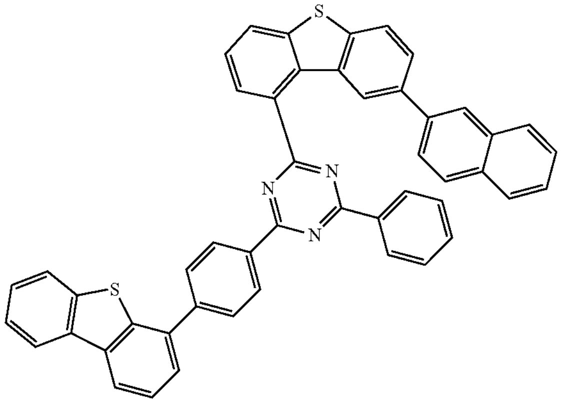
1′-59
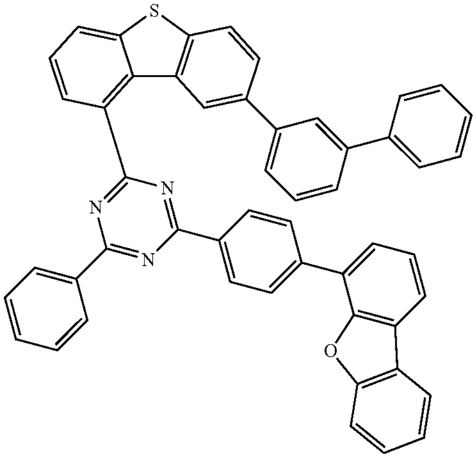
1′-60
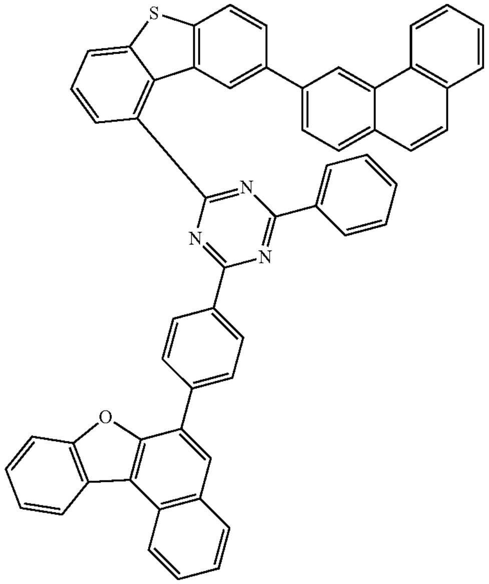
1′-61
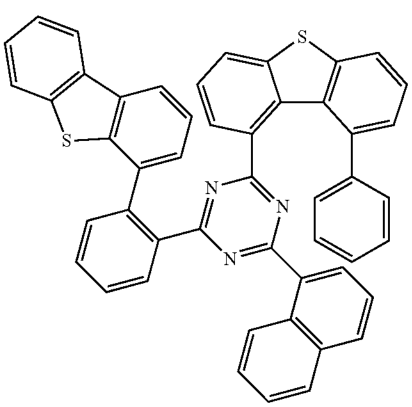
1′-62
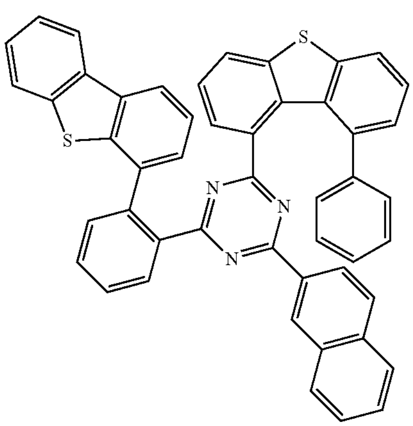

-continued
1'-63
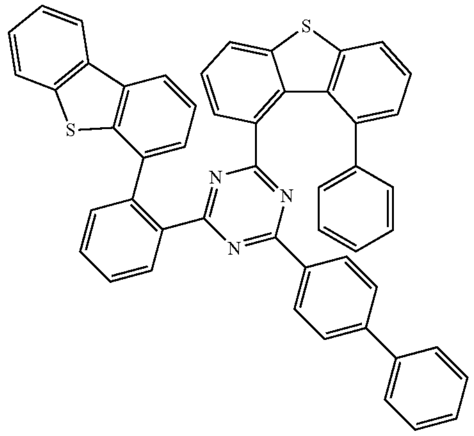
1'-64
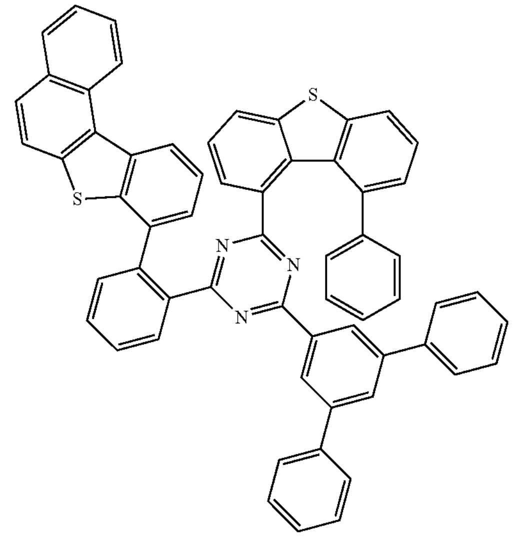
1'-65
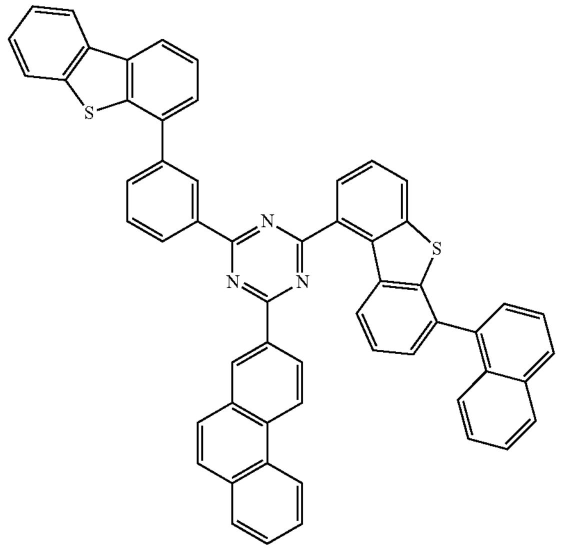
1'-66
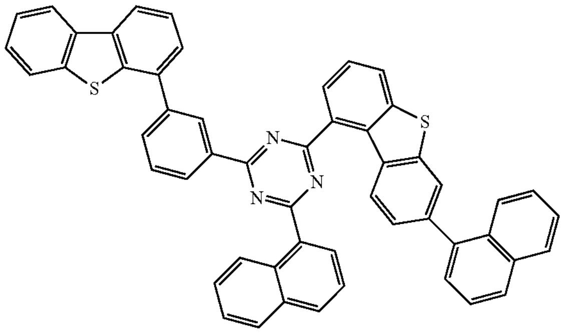

-continued
1′-67
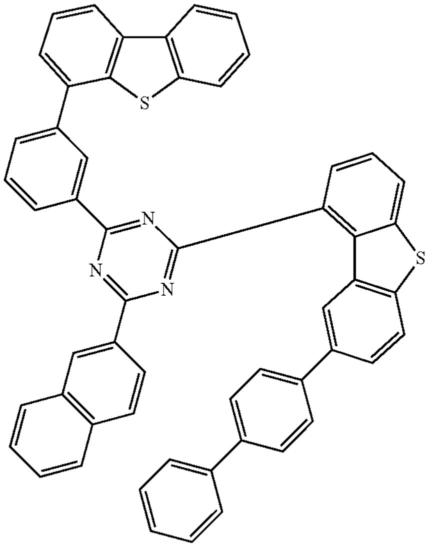
1′-68
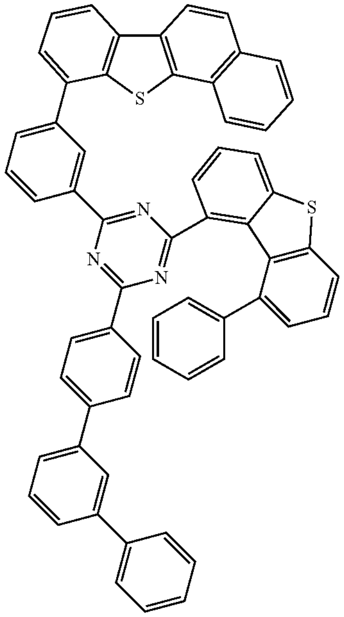
1′-69
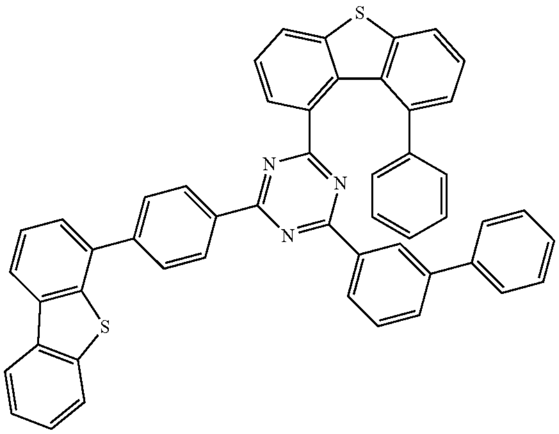
1′-70
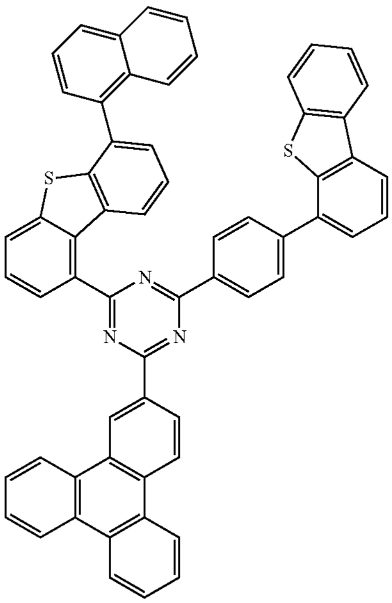

-continued
1′-71
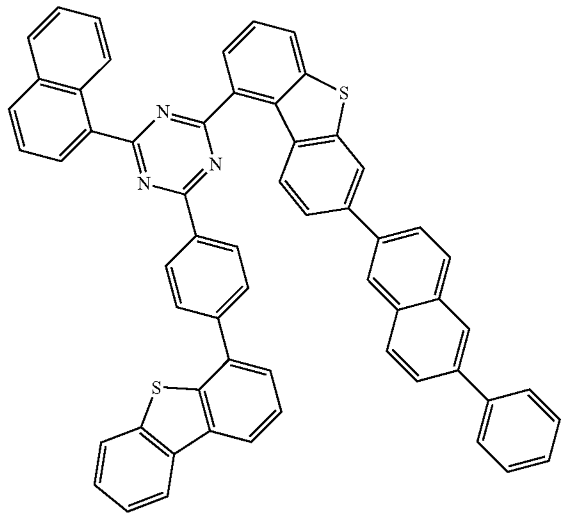
1′-72
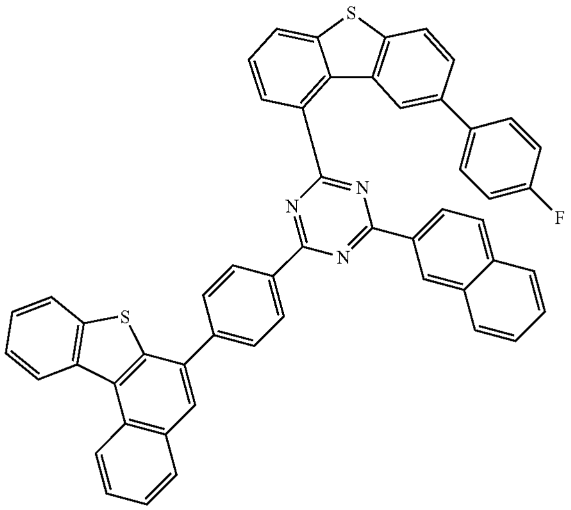
1′-73
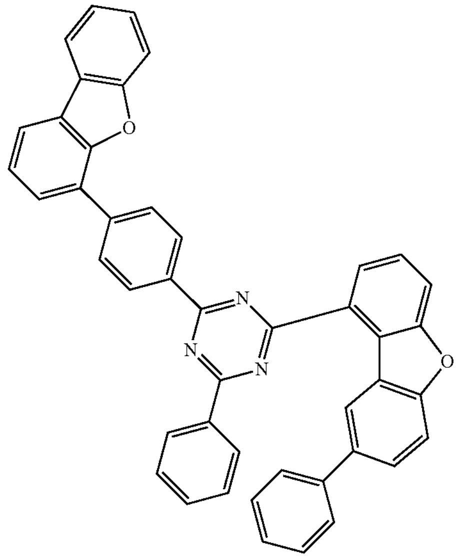
1′-74
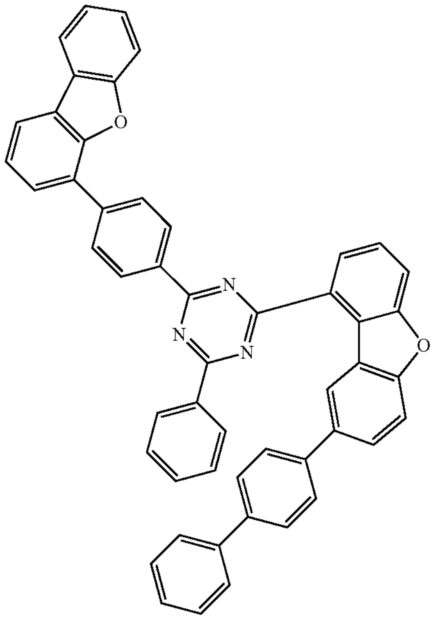

-continued
1′-75
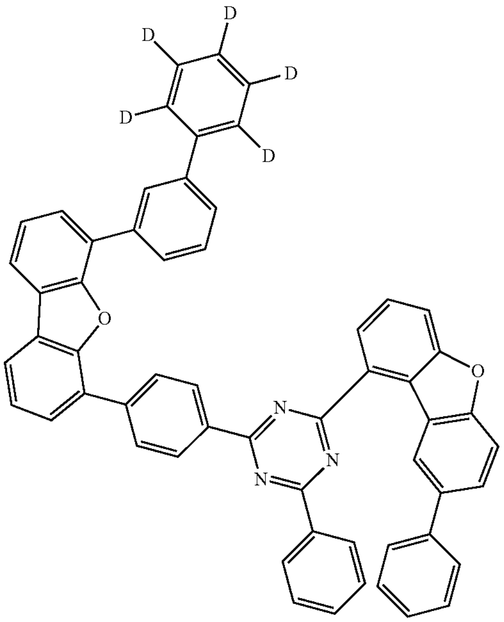
1′-76
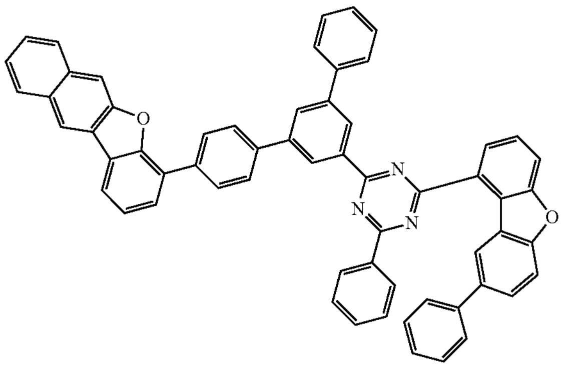
1′-77
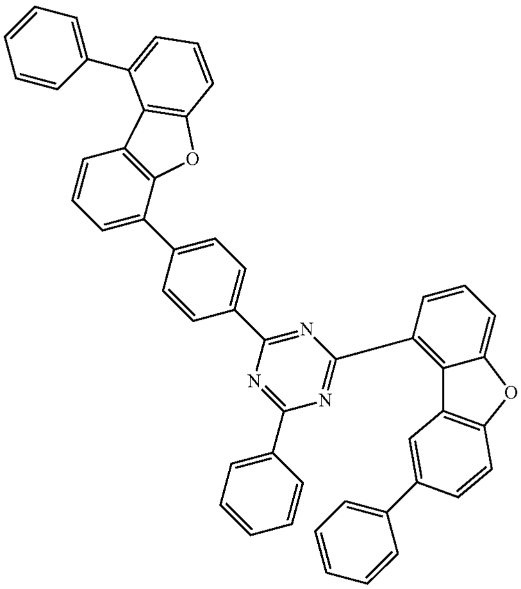
1′-78
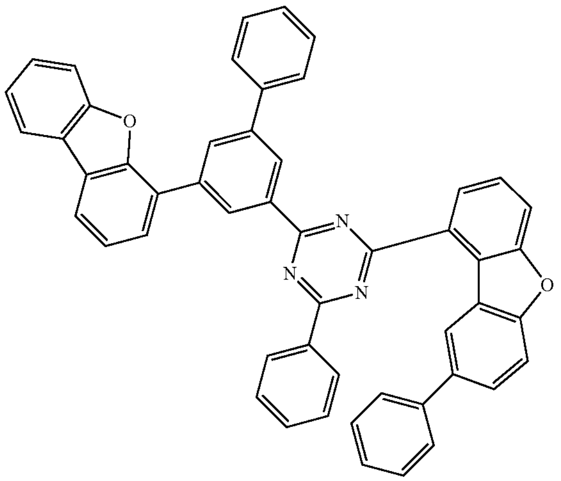

-continued
1′-79
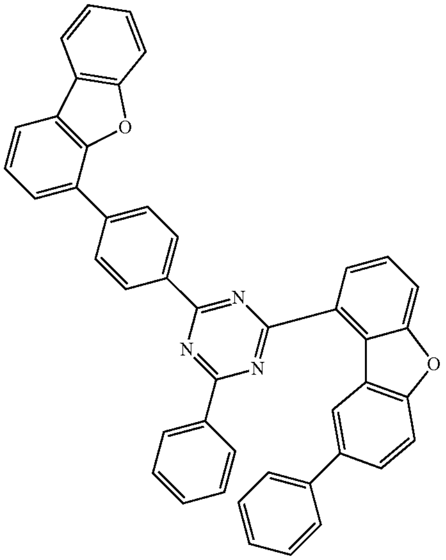
1′-80
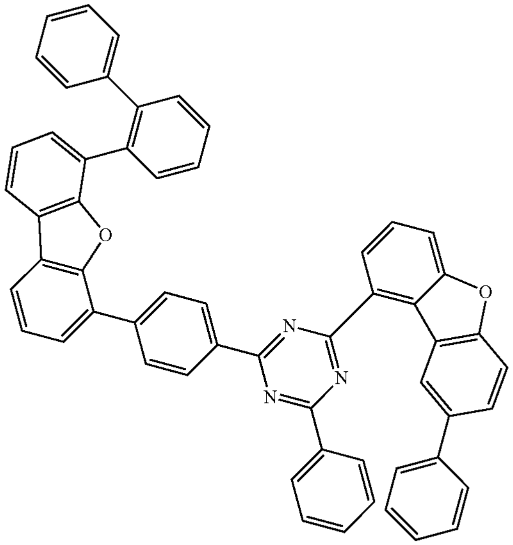
1′-81
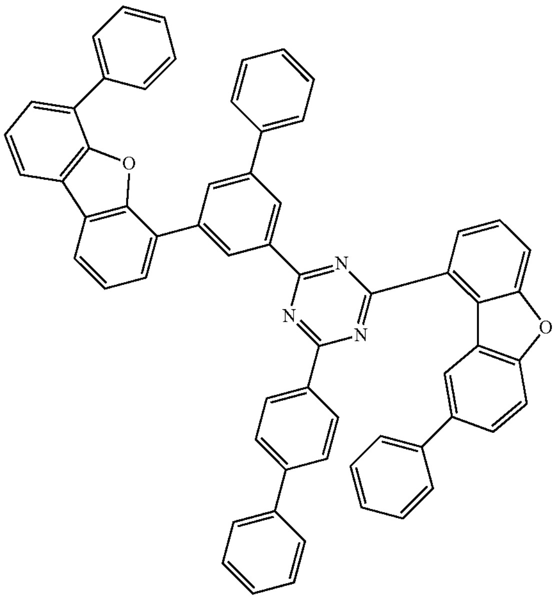
1′-82
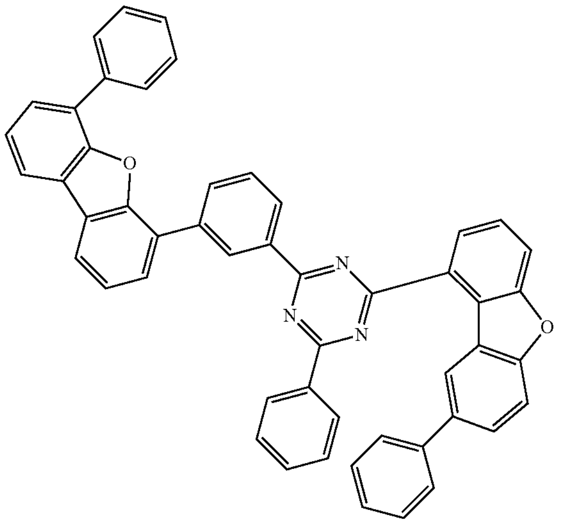

-continued
1′-83
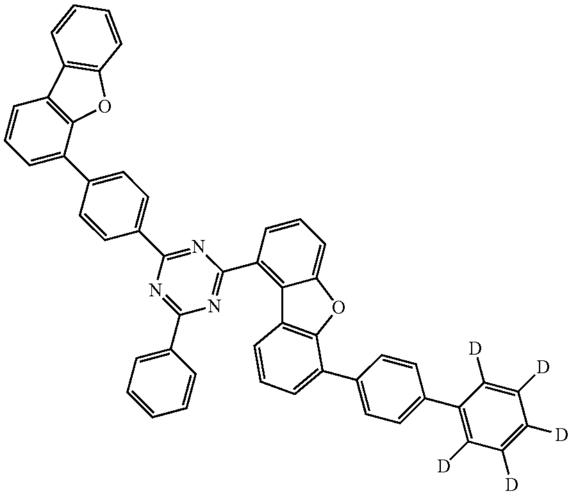
1′-84
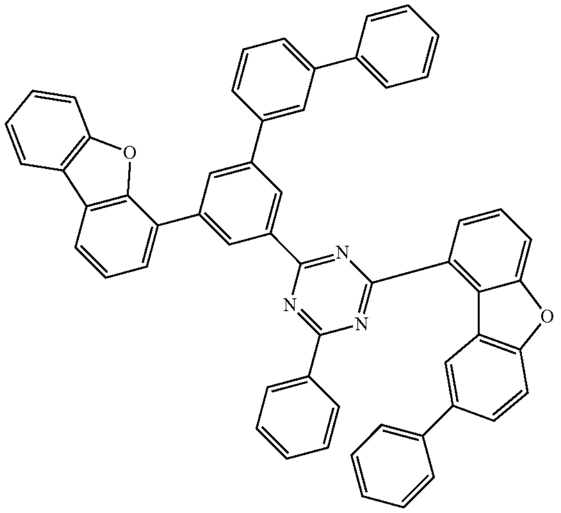
2-1
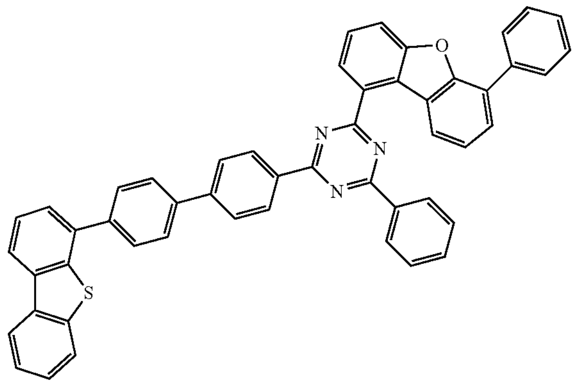
2-2
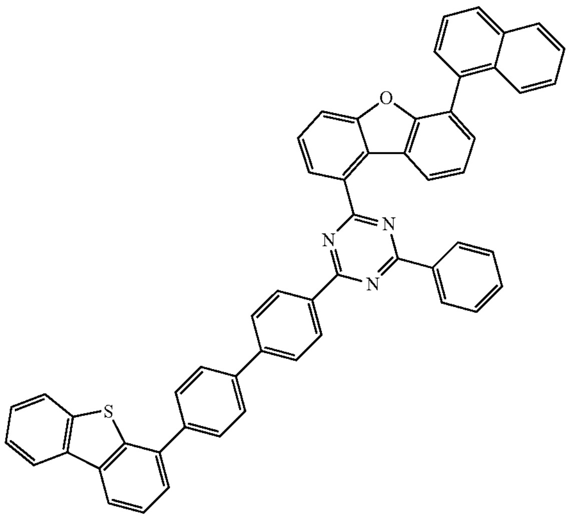
2-3
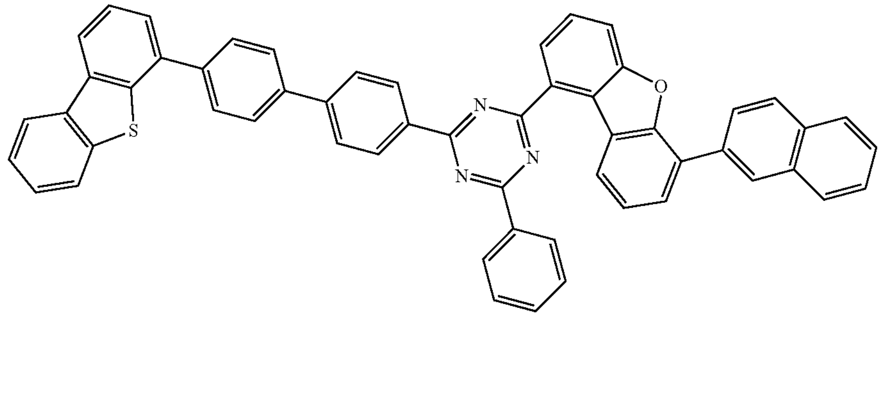

-continued
2-4
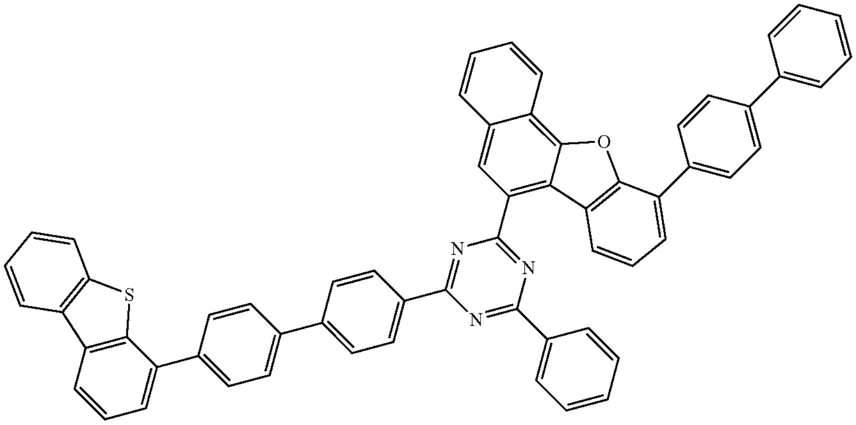
2-5
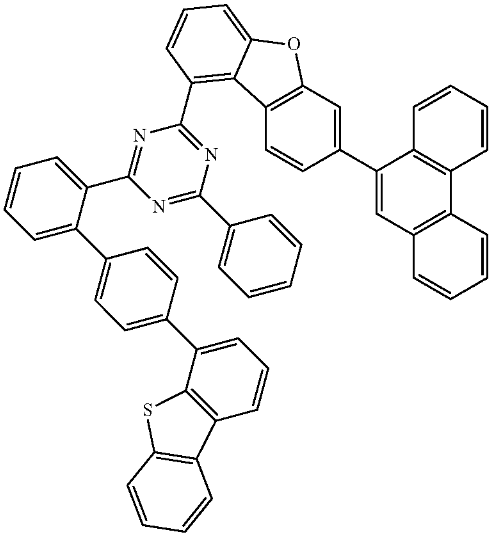
2-6
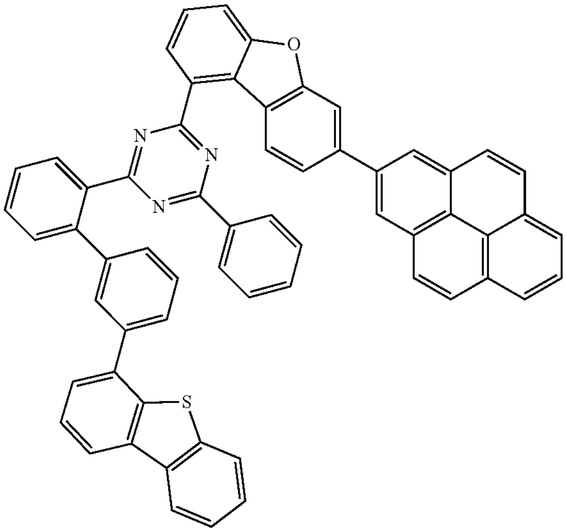
2-7
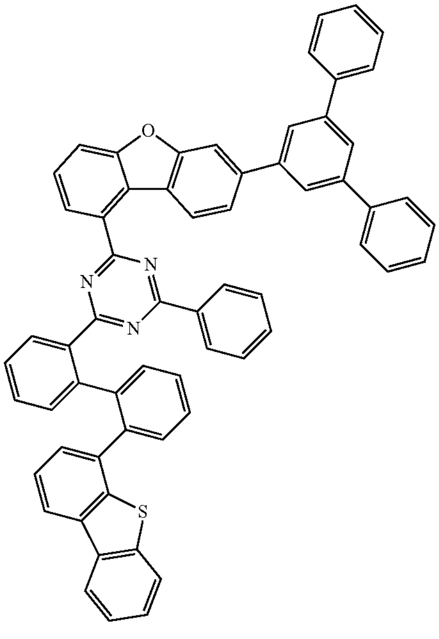
2-8
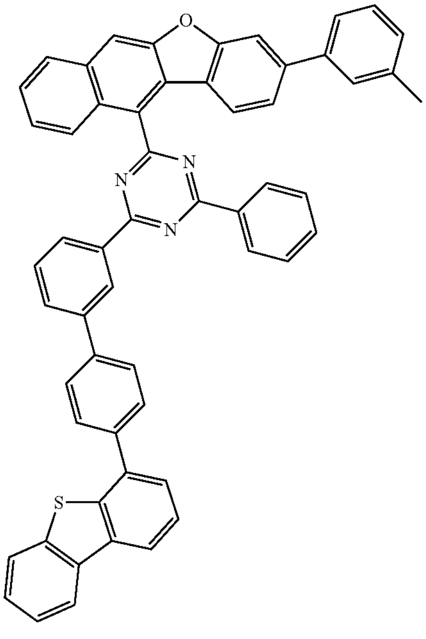

-continued
2-9
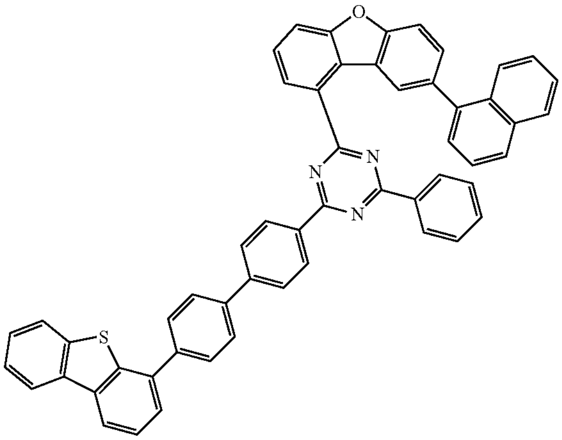
2-10
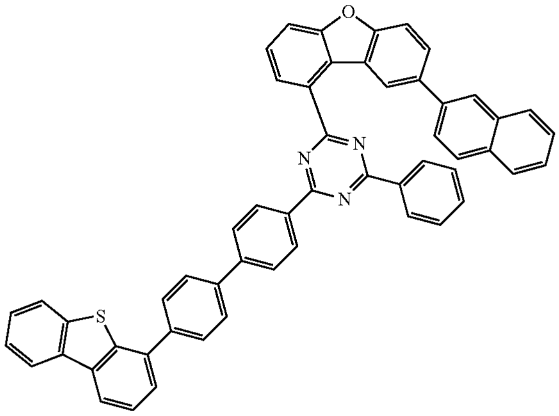
2-11
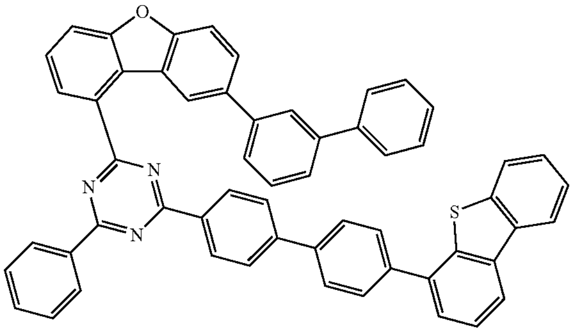
2-12
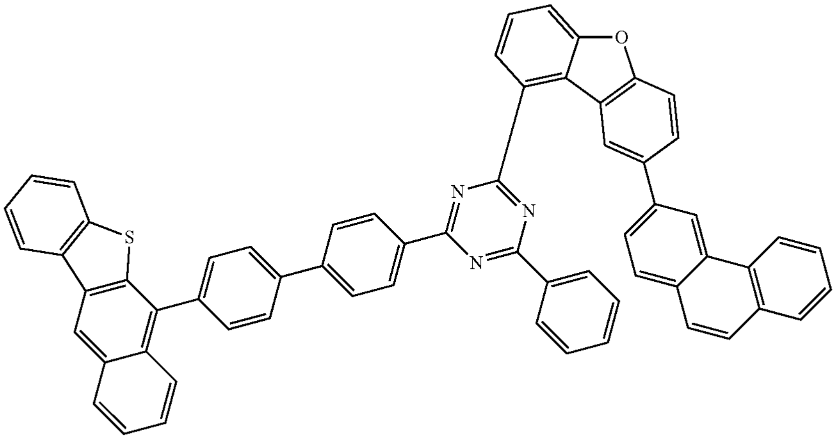

-continued
2-13
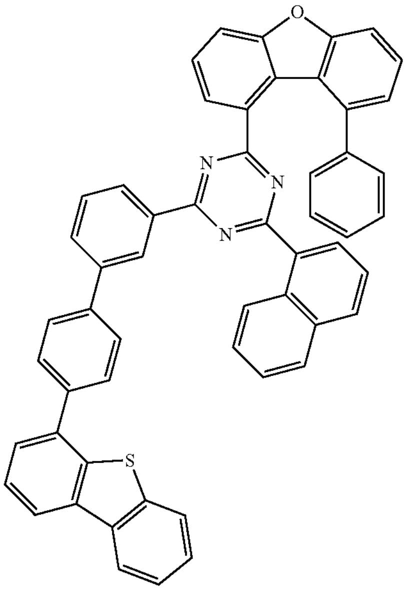
2-14
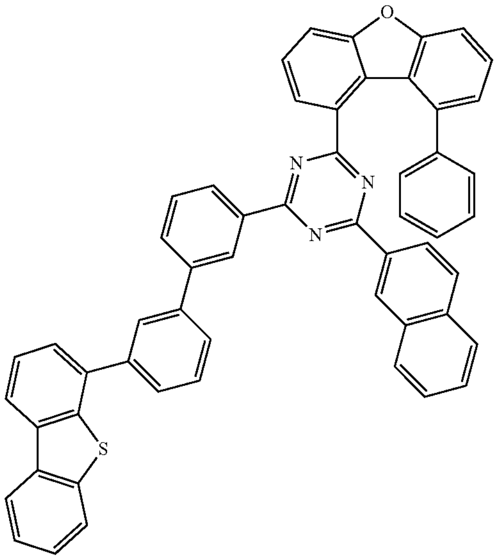
2-15
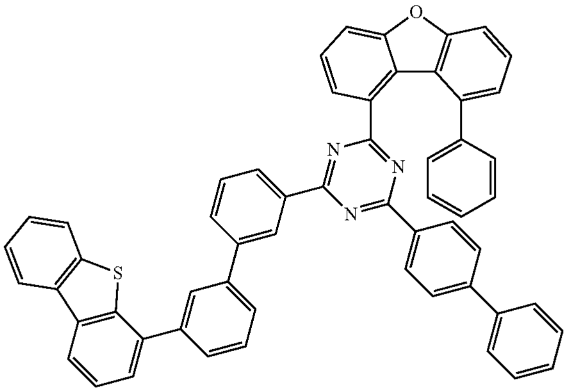
2-16
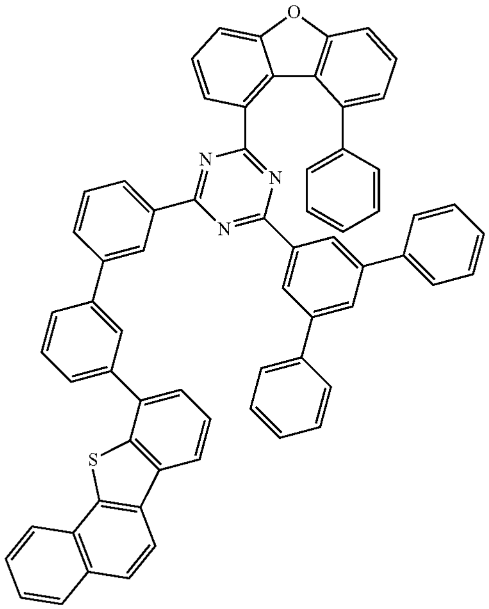
2-17
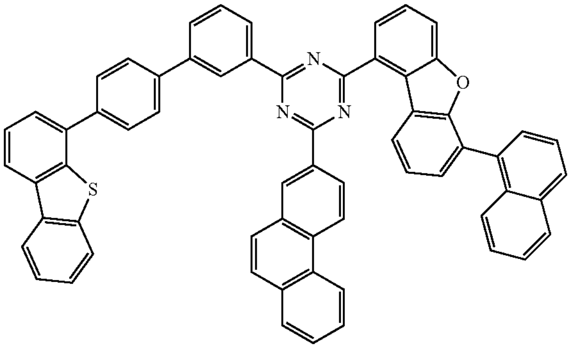
2-18
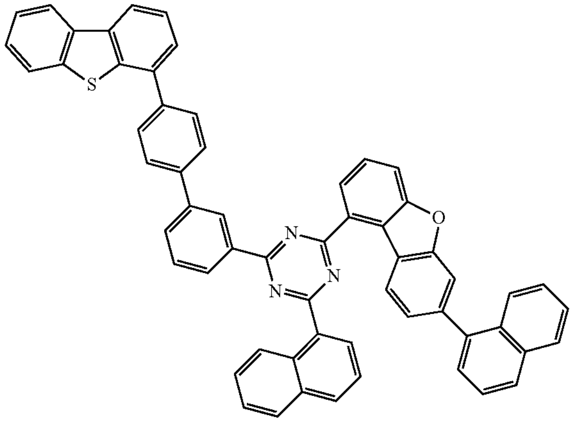

-continued
2-19
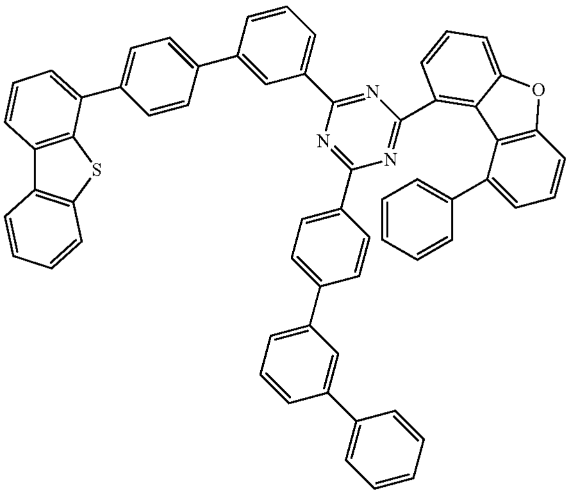
2-20
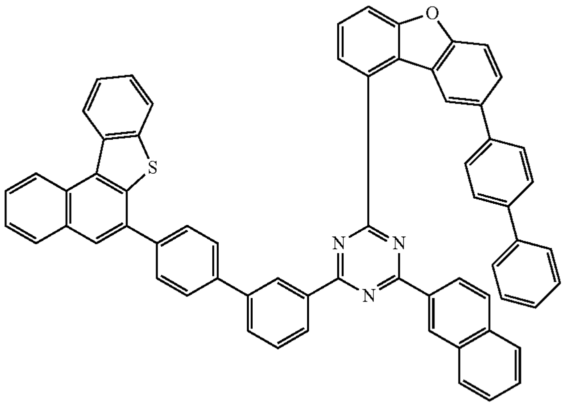
2-21
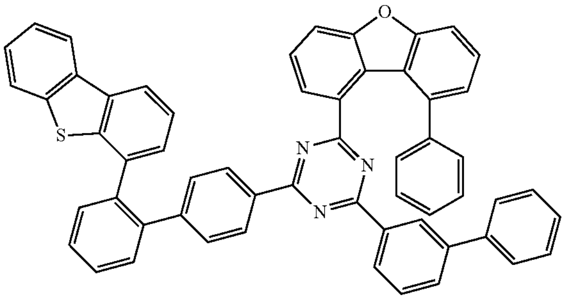
2-22
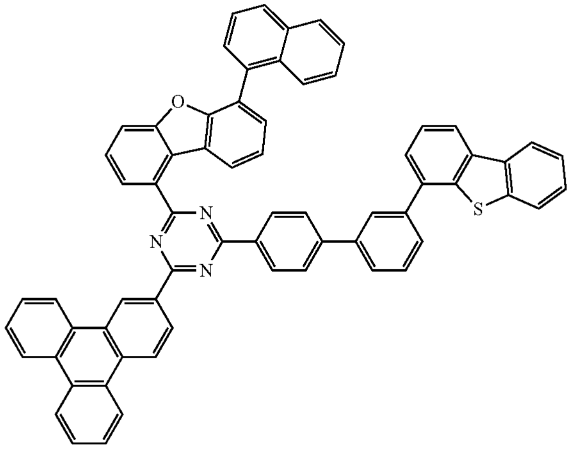
2-23
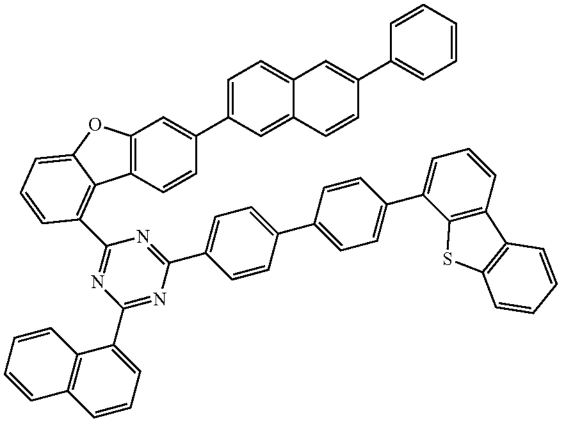
2-24
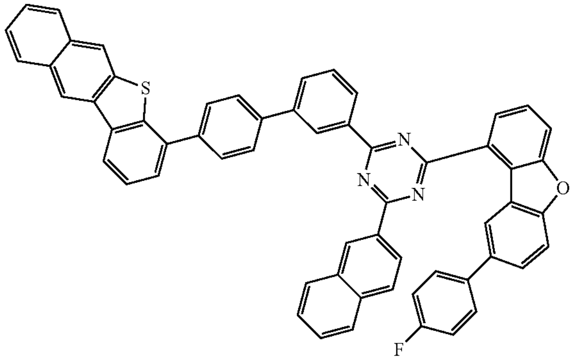

-continued
2-25
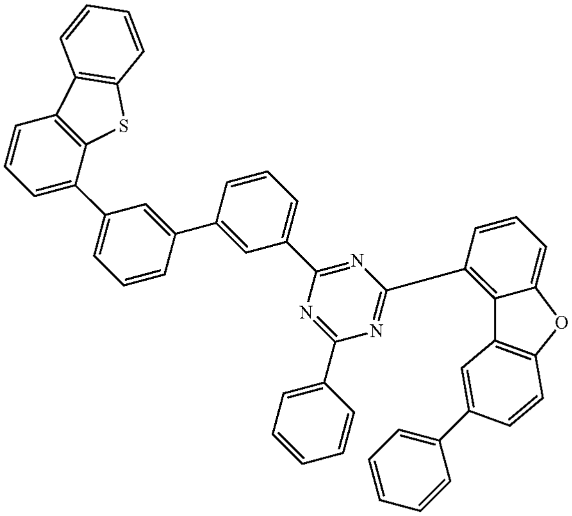
2-26
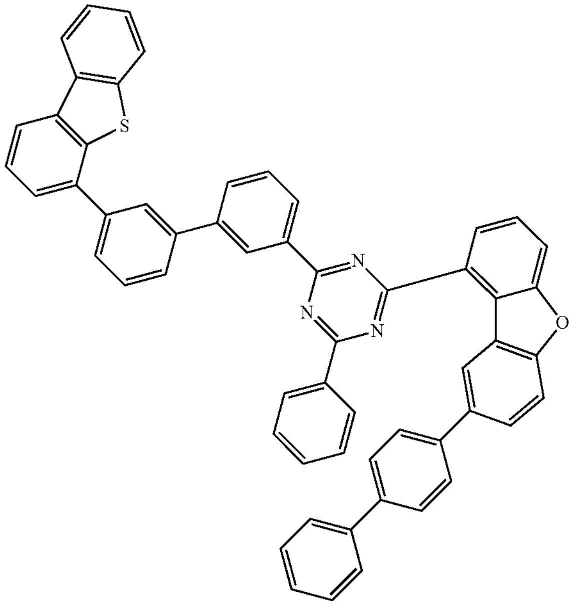
2-27
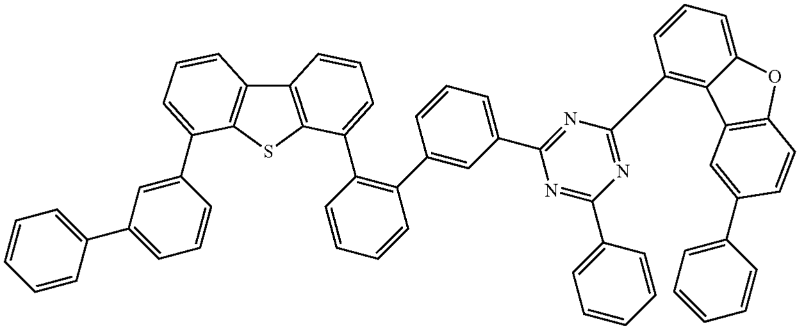
2-28
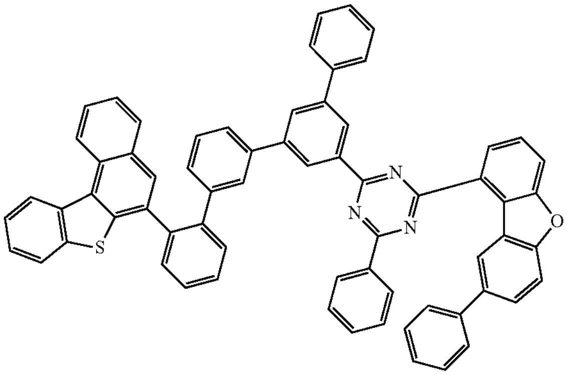
2-29
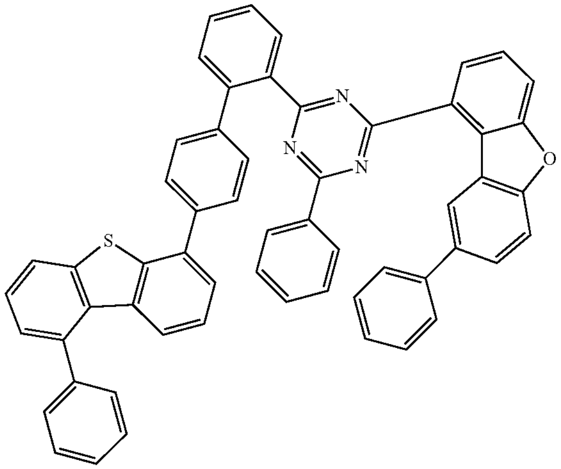

-continued
2-30
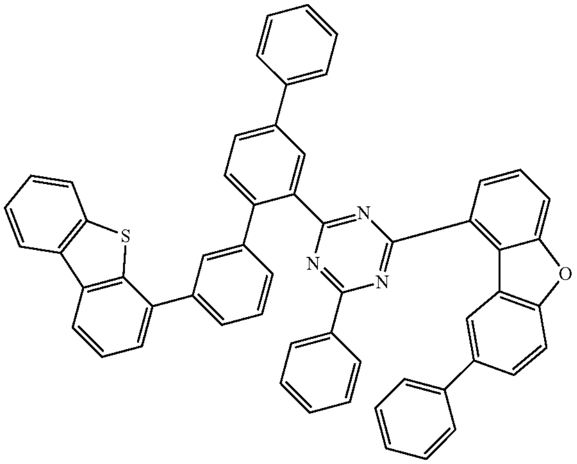
2-31
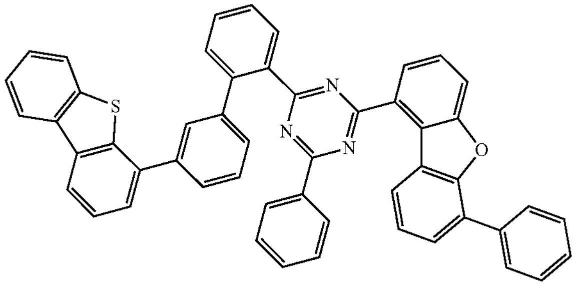
2-32
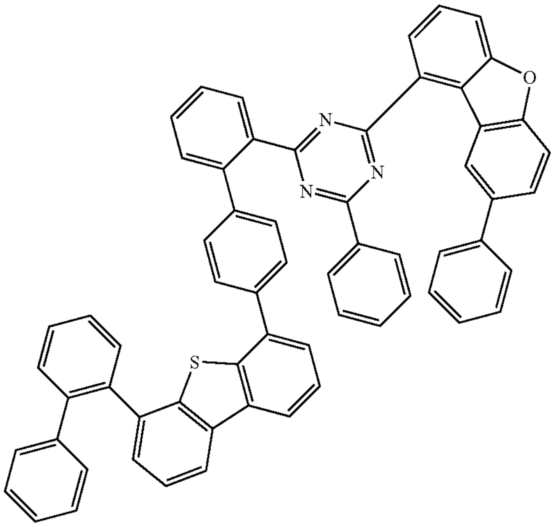
2-33
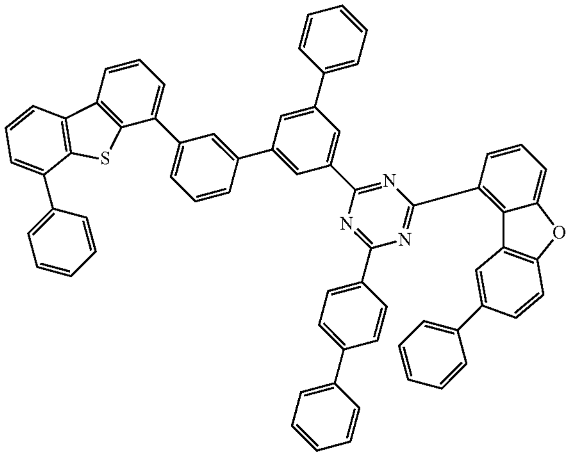
2-34
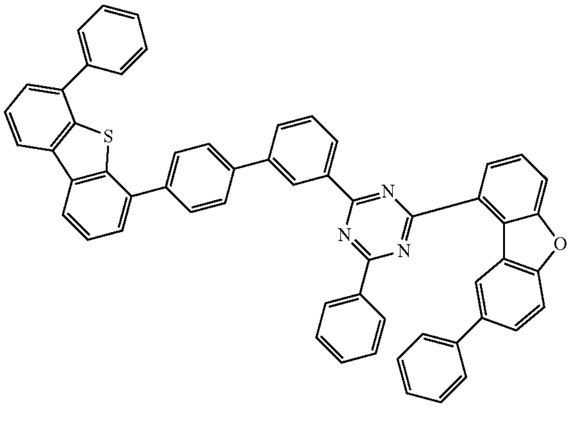
2-35
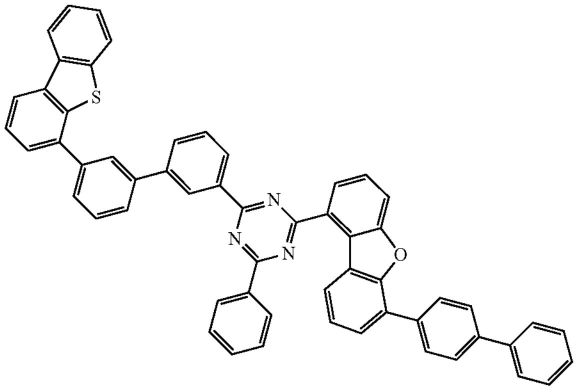

-continued
2-36
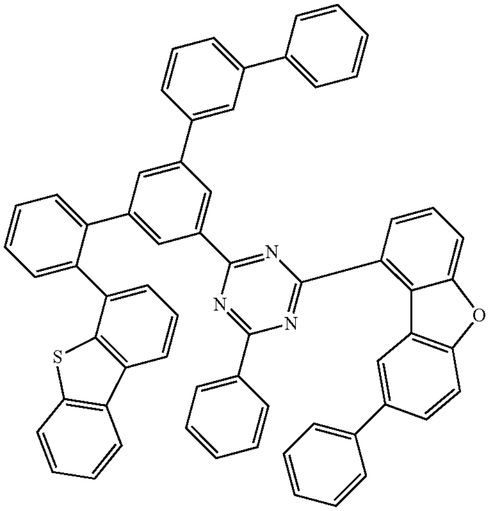
2-37
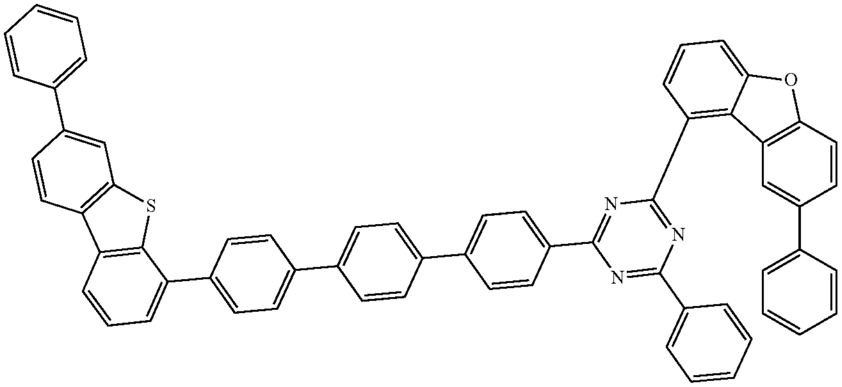
2-38
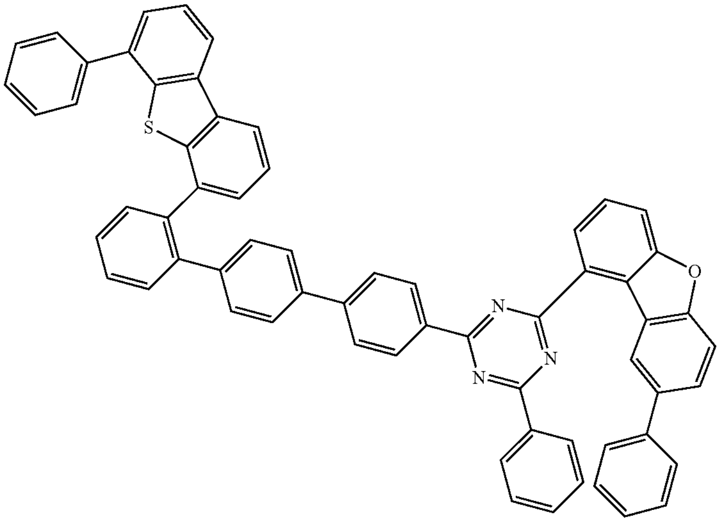

-continued
2-39
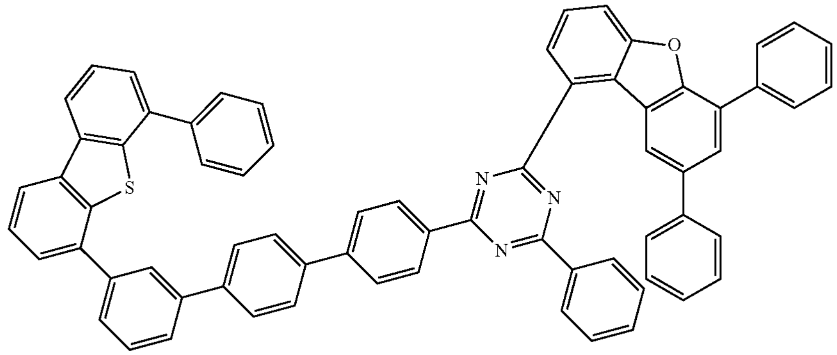
2-40
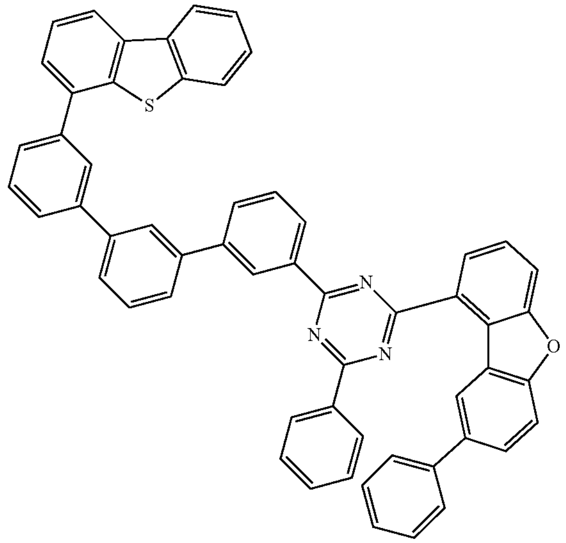
2-40
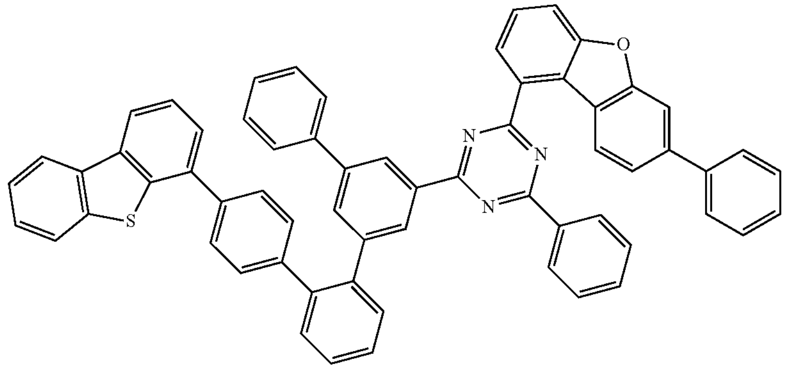

-continued
2-42
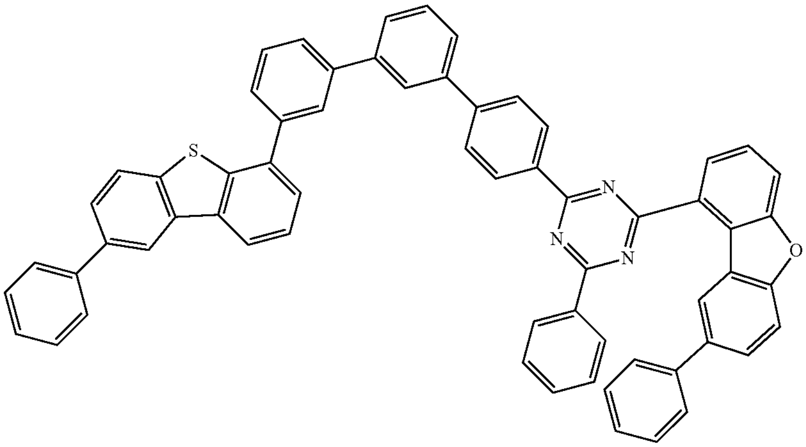
2-43
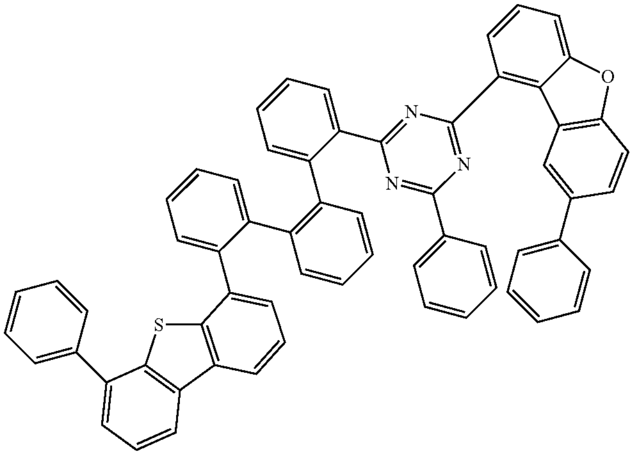
2-44
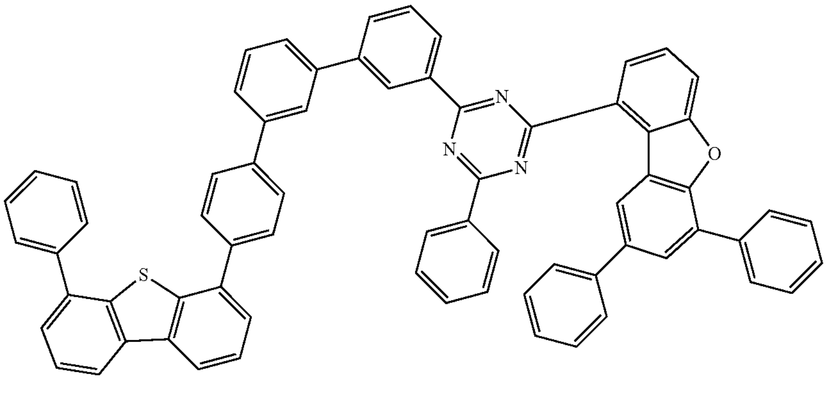

-continued
2-45
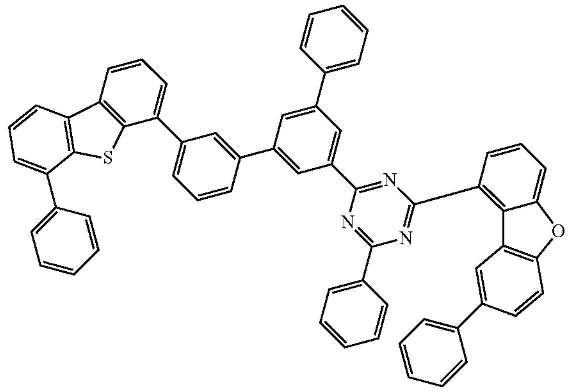
2-46
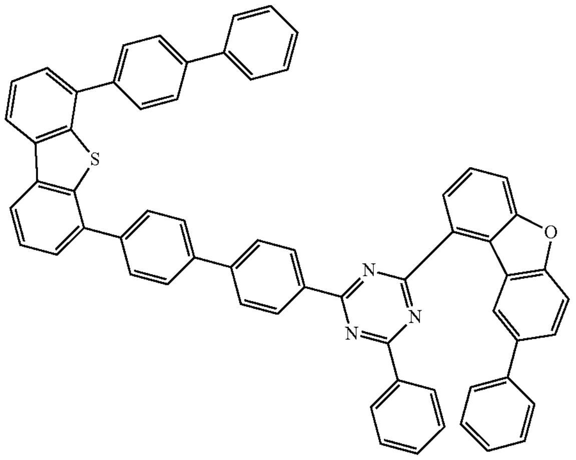
2-47
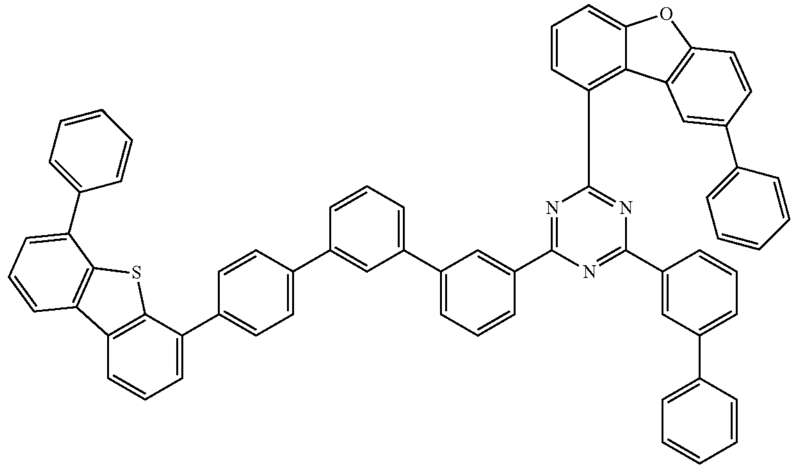
2-48
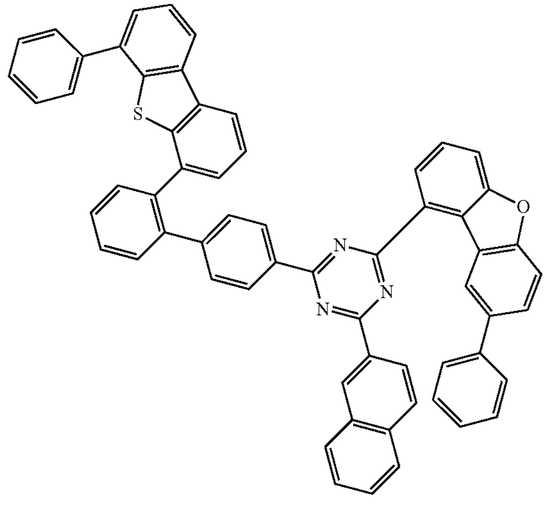
2-49
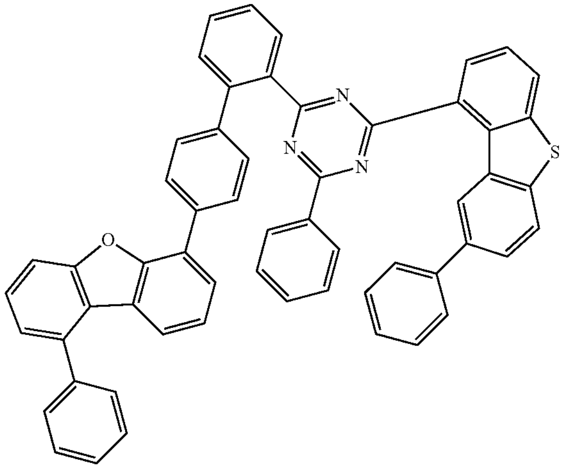

-continued
2-50
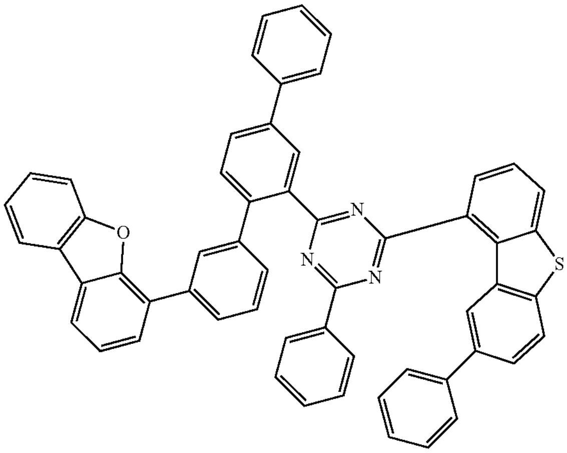
2-51
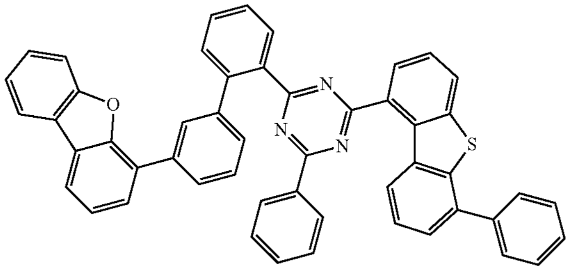
2-52
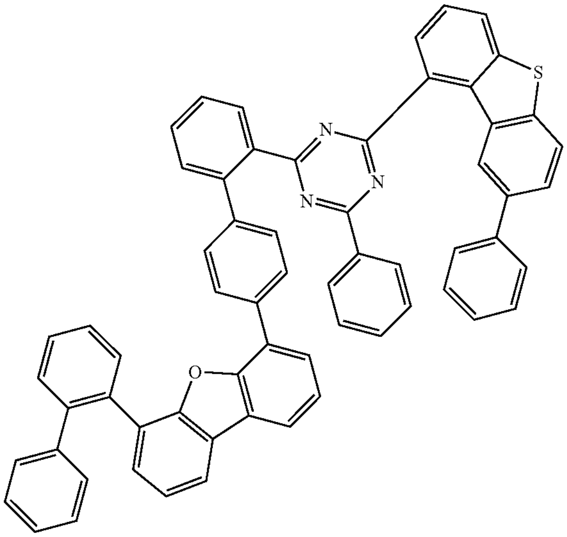
2-53
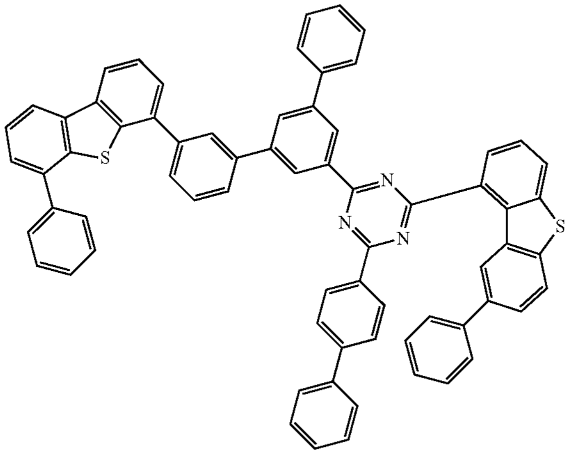
2-54
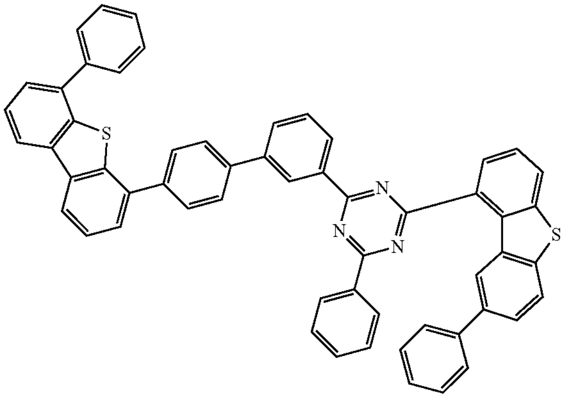
2-55
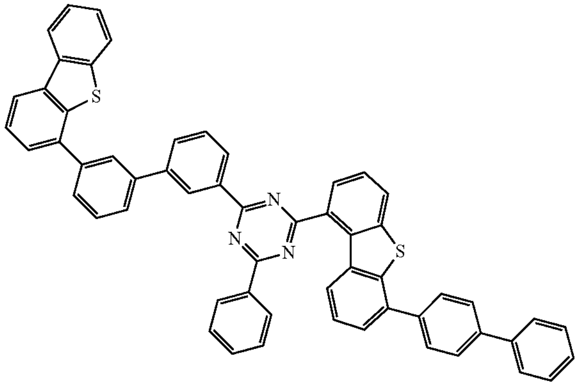

-continued
2-56
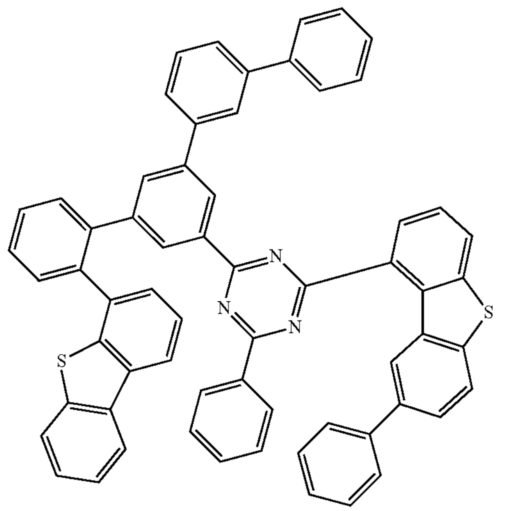
2-57
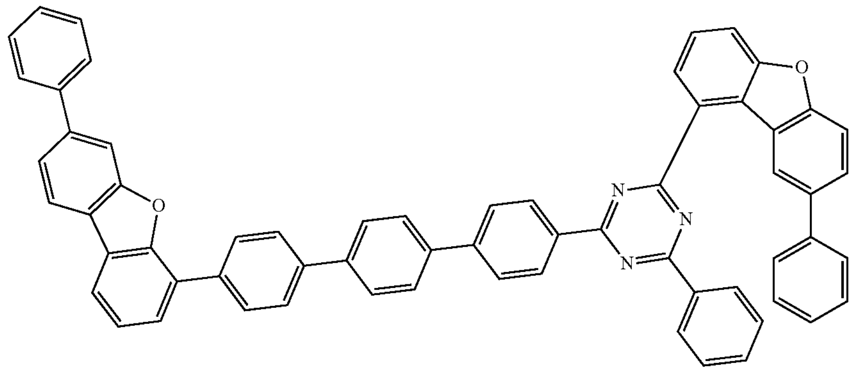
2-58
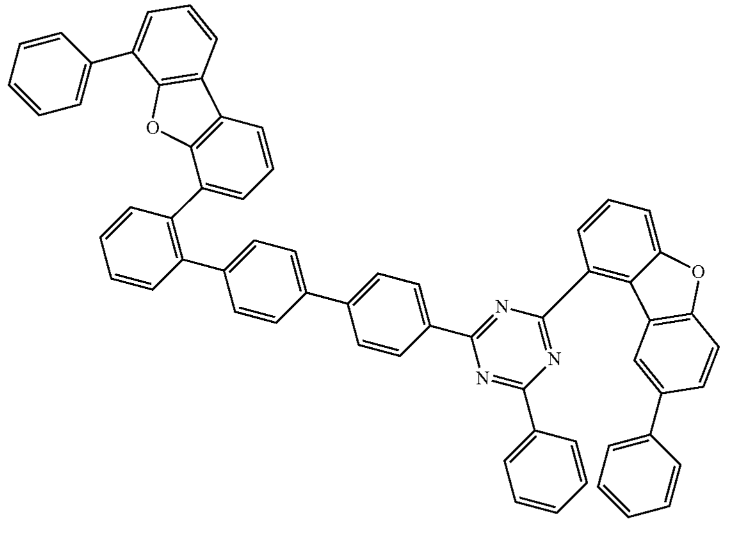

-continued
2-59
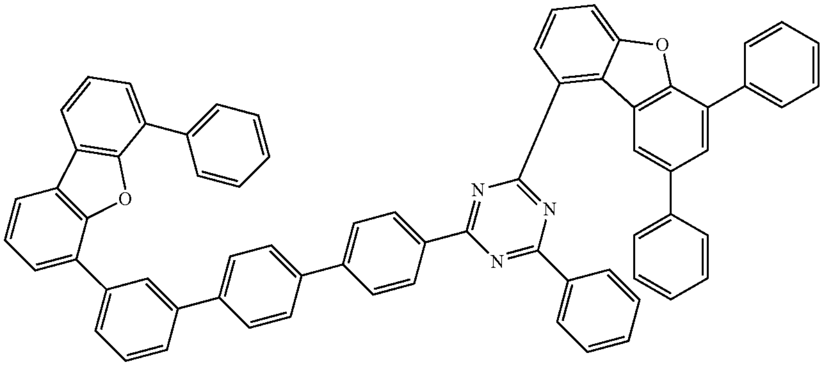
2-60
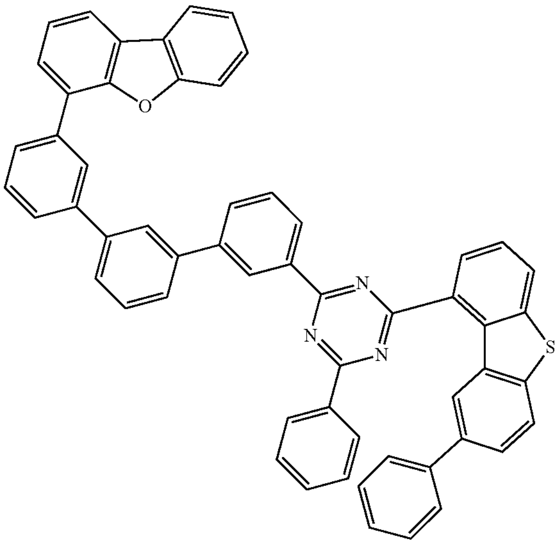
3-1
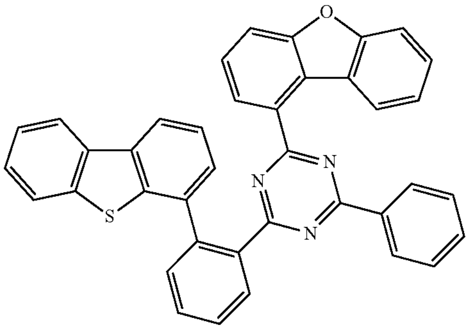
3-2
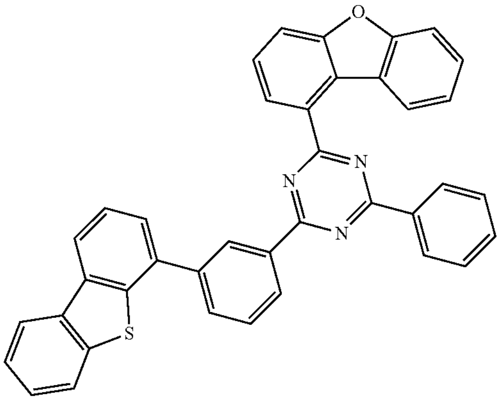

-continued
3-3
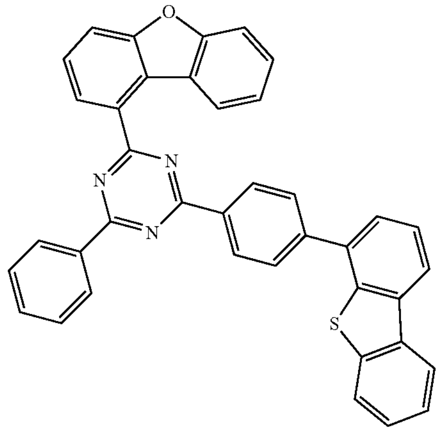
3-4
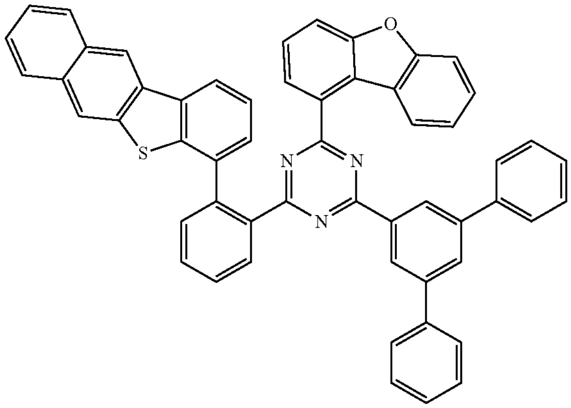
3-5
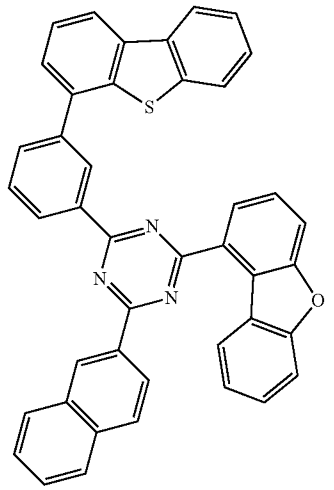
3-6
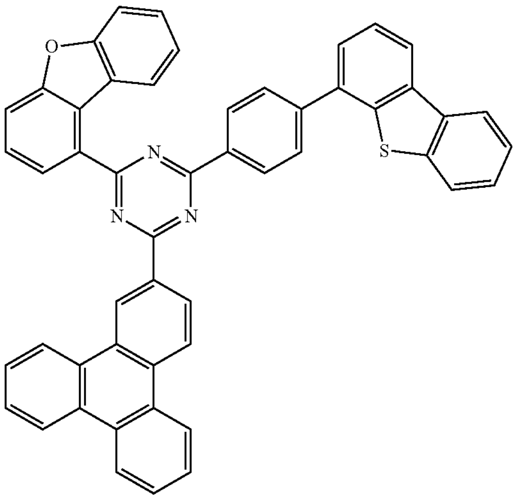
3-7
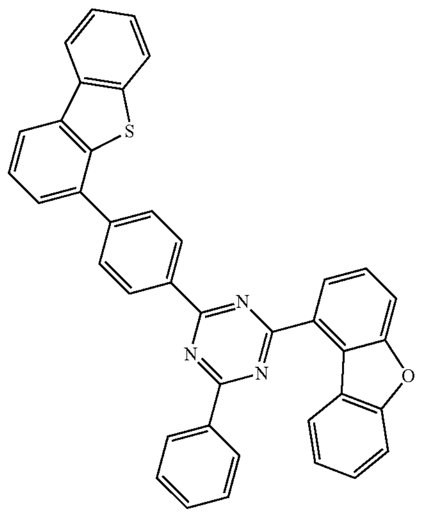
3-8
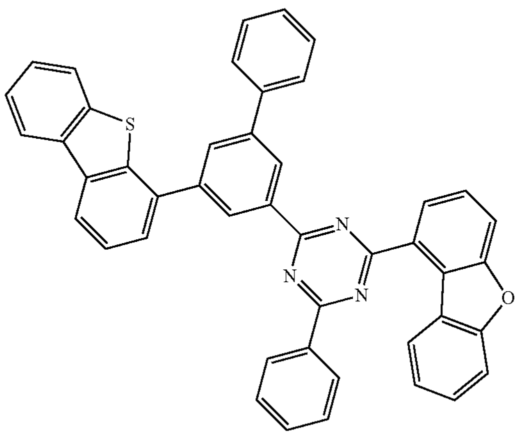

-continued
3-9
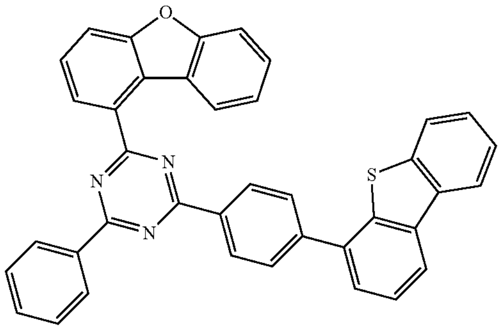
3-10
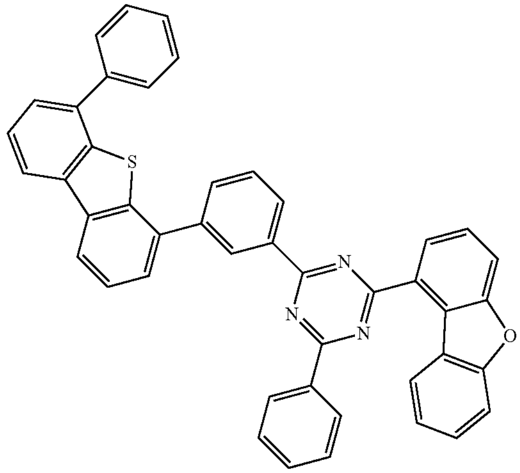
3-11
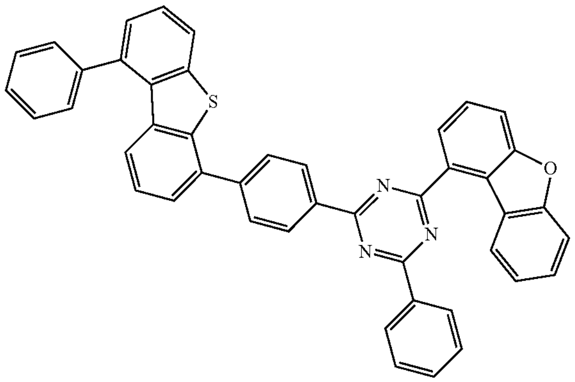
3-12
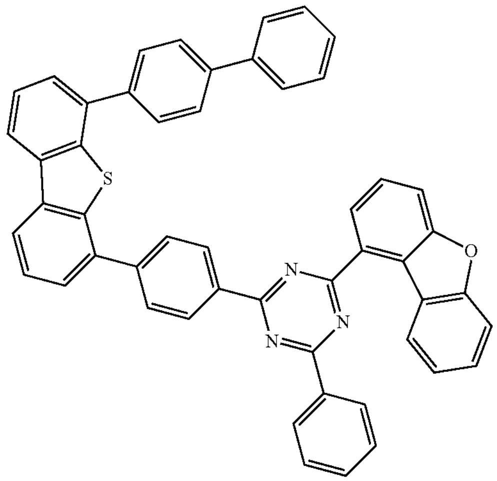
3-13
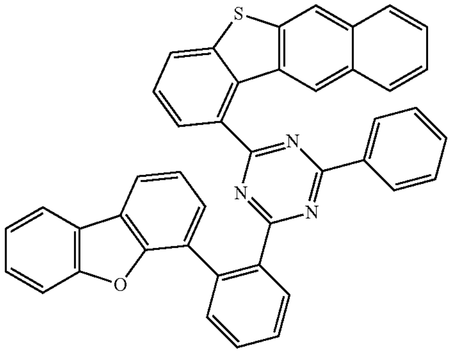
3-14
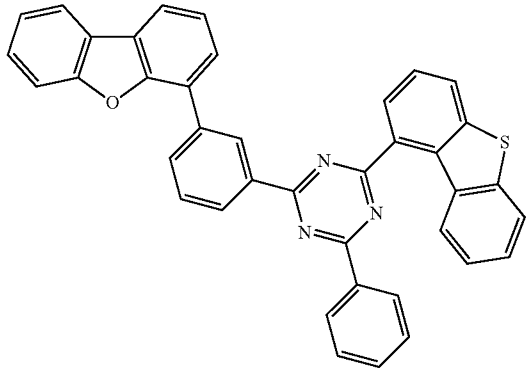

-continued
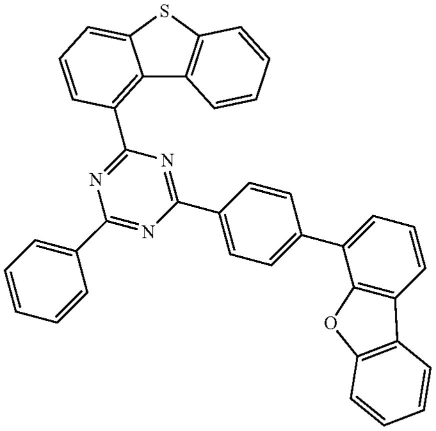
3-15
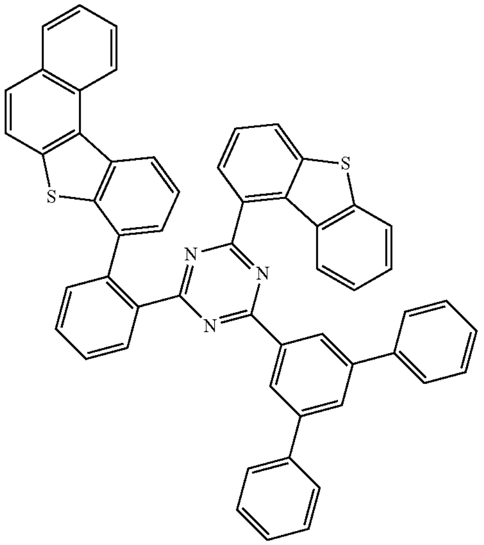
3-16
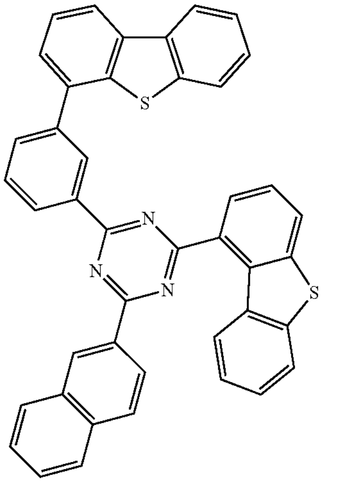
3-17
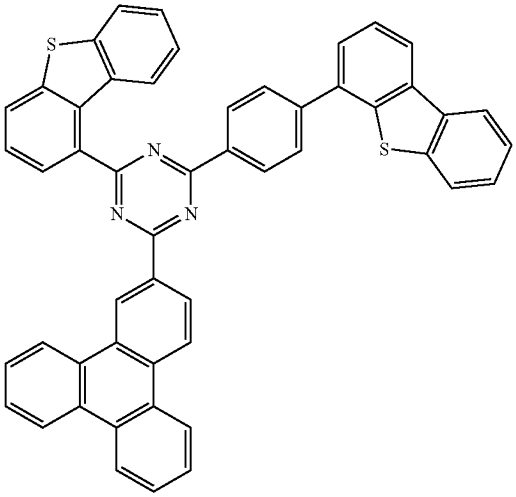
3-18
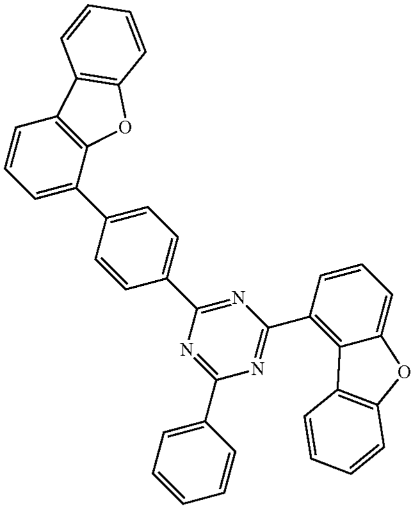
3-19
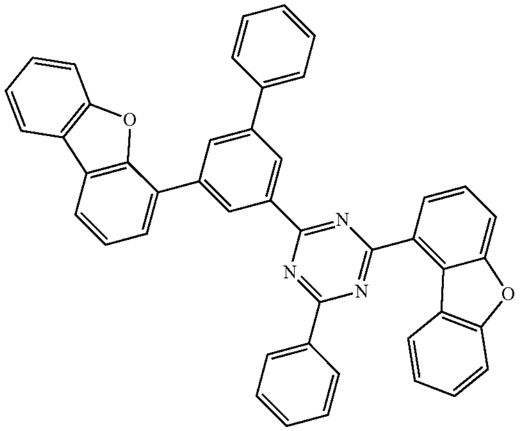
3-20

-continued
3-21
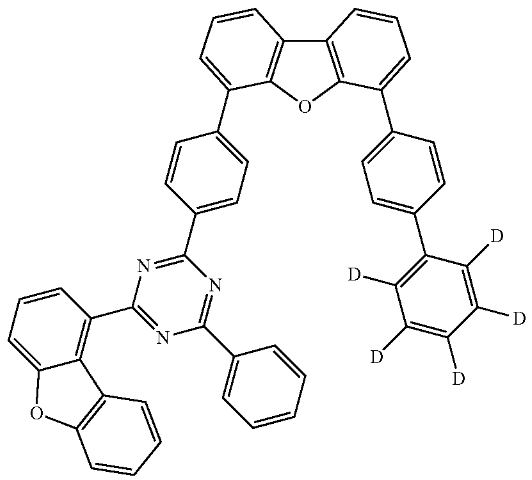
3-22
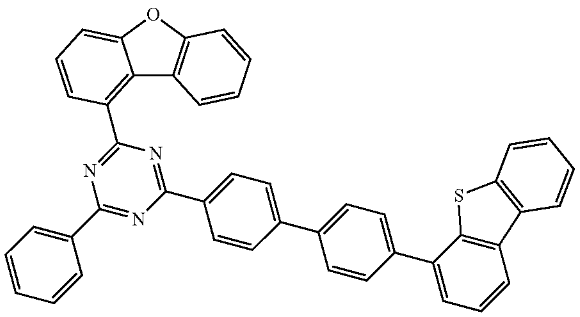
3-23
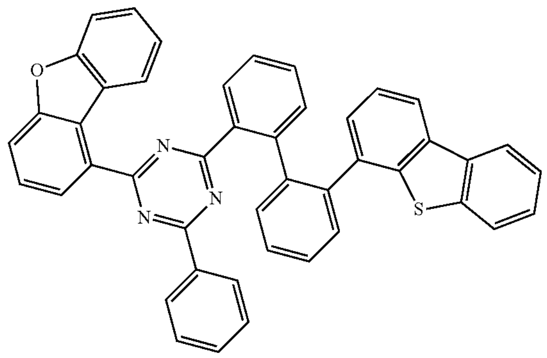
3-24
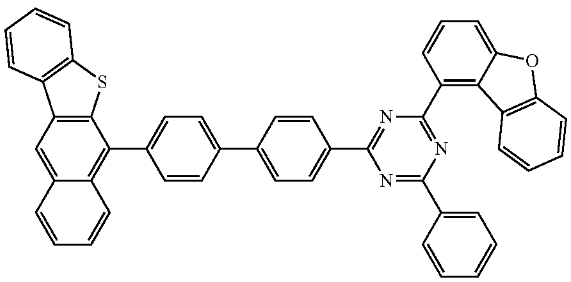
3-25
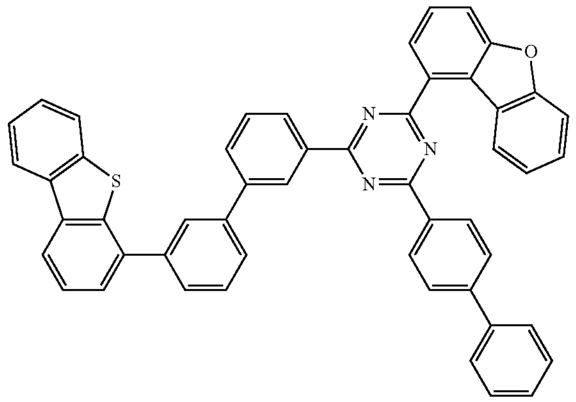
3-26
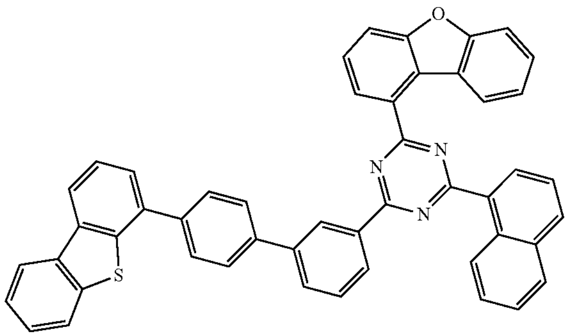

-continued
3-27
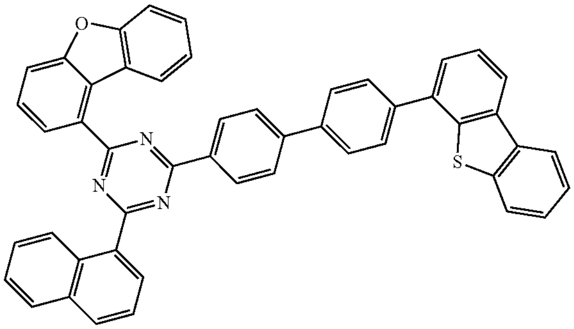
3-28
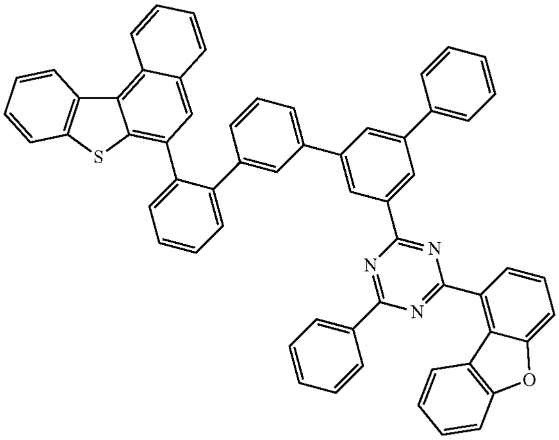
3-29
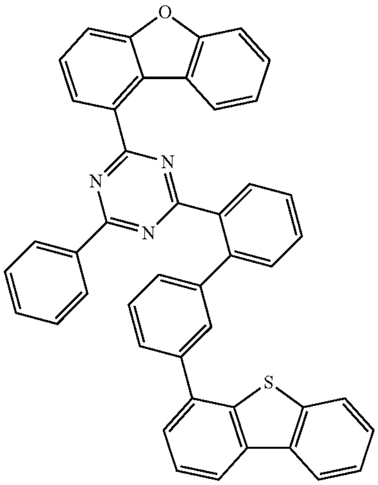
3-30
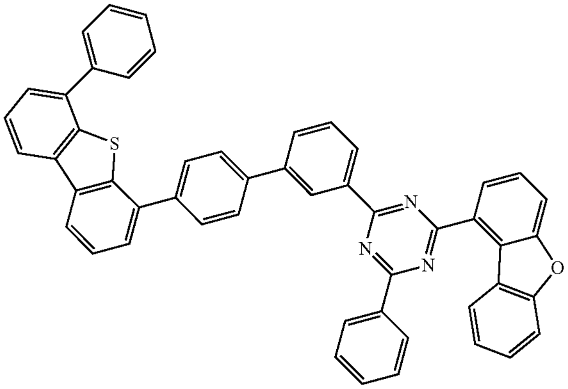
3-31
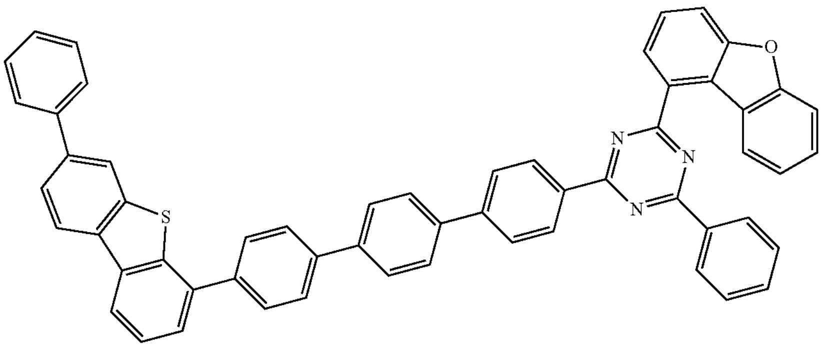

-continued
3-32
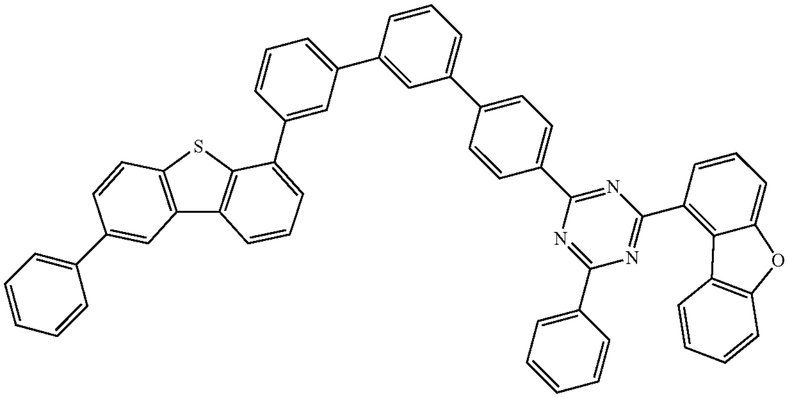
3-33
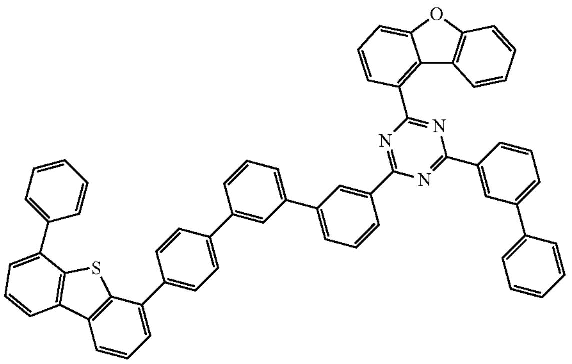
3-34
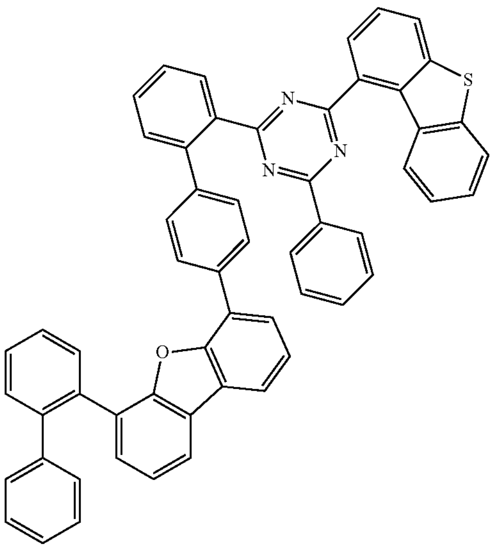
3-35
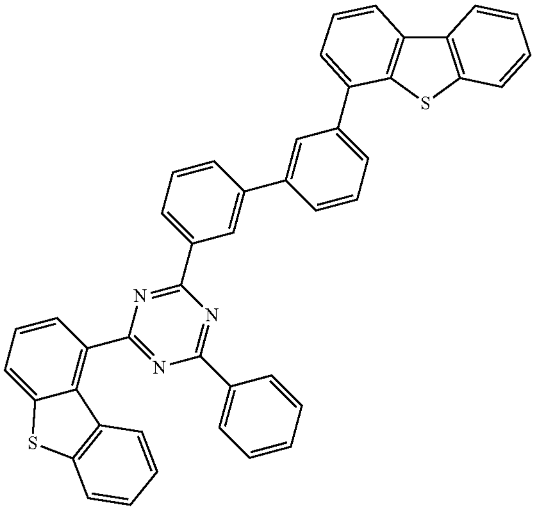
3-36
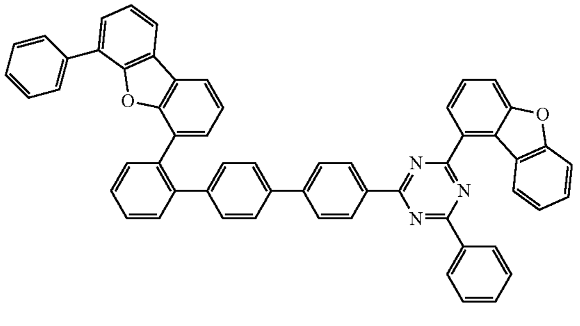

-continued
P-1
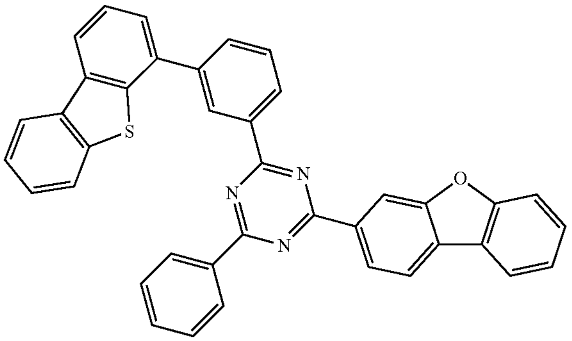
P-2
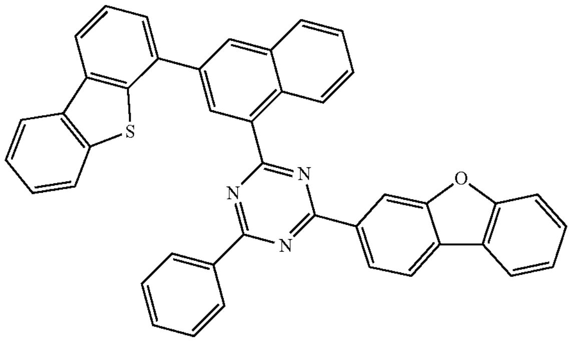
P-3
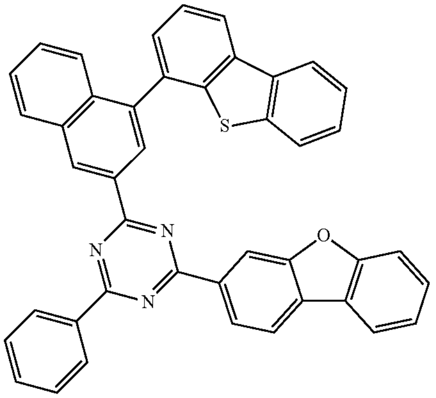
P-4
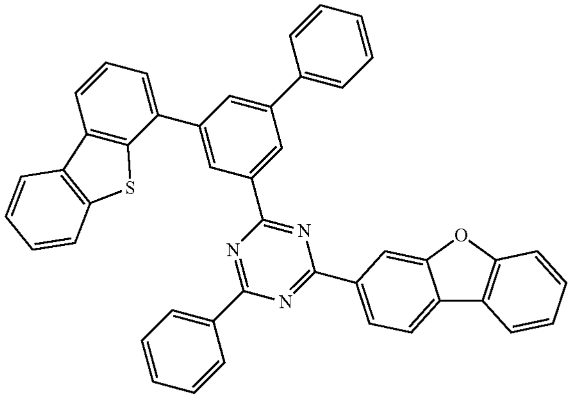
P-5
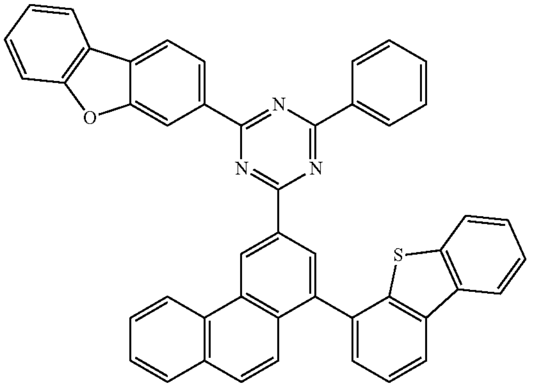
P-6
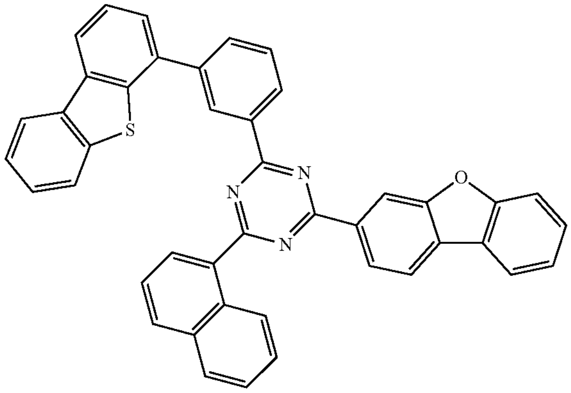
P-7
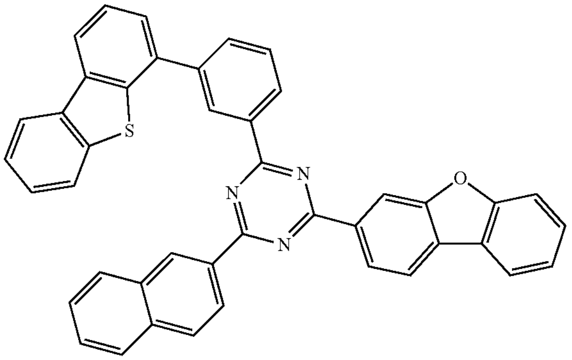
P-8
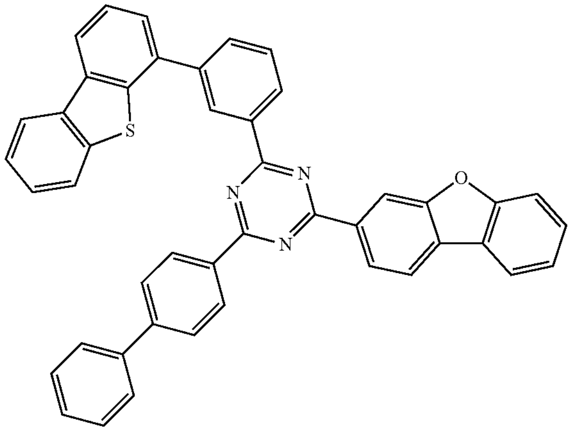

-continued
P-9
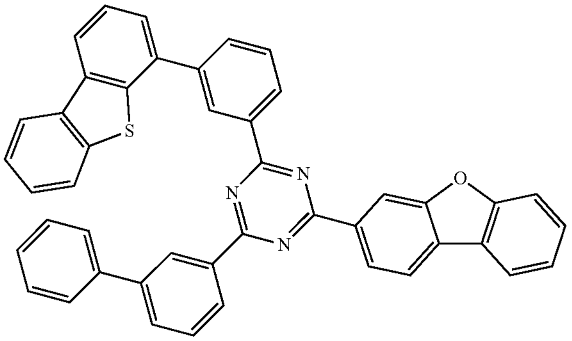
P-10
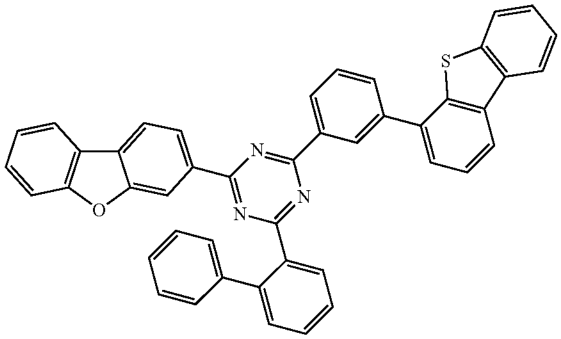
P-11
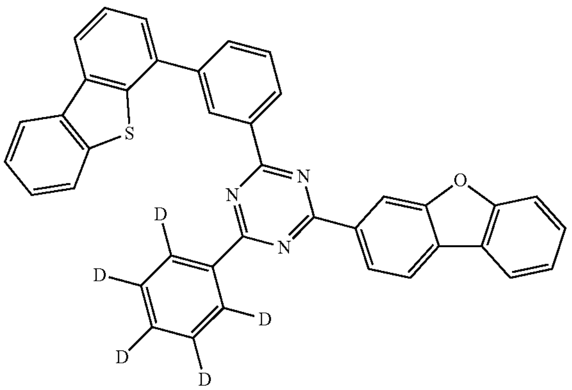
P-12
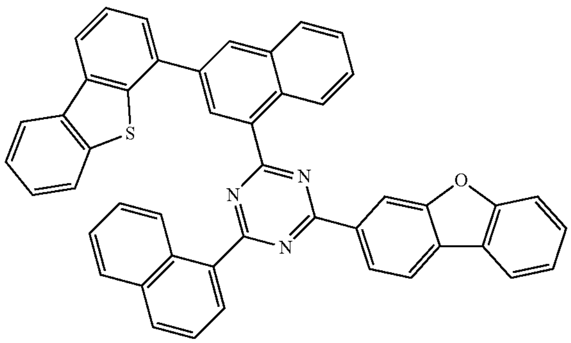
P-13
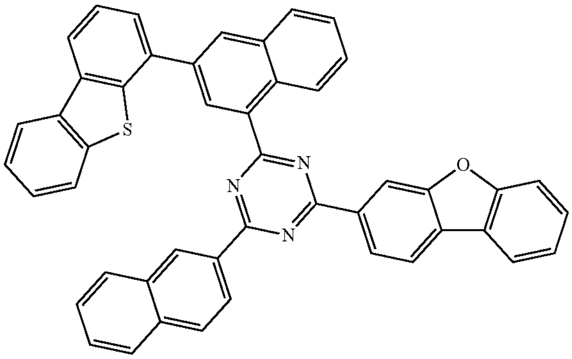
P-14
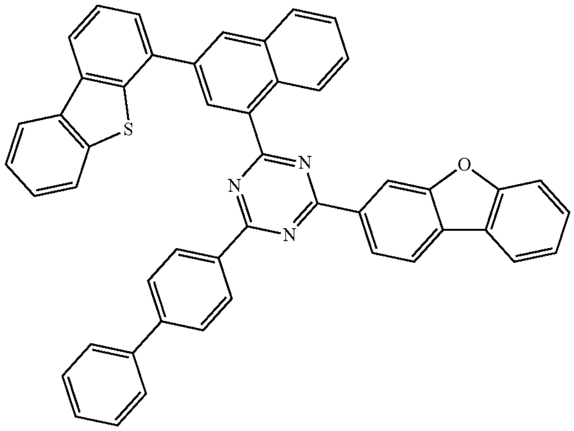

-continued
P-15
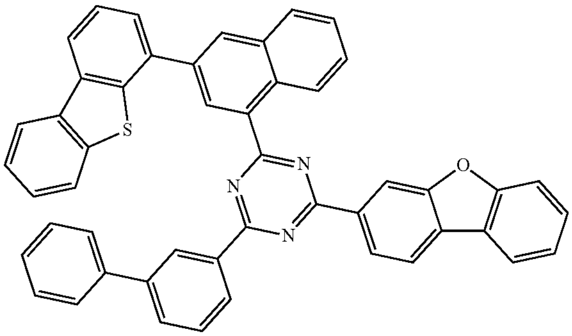
P-16
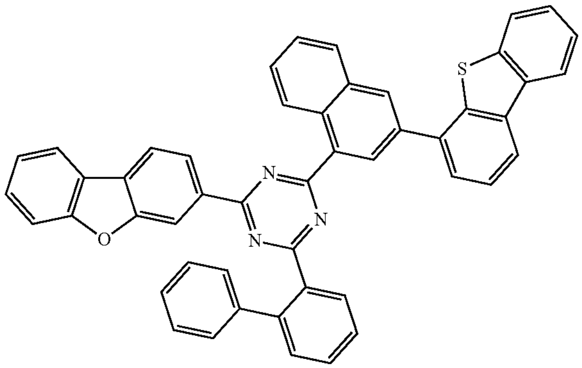
P-17
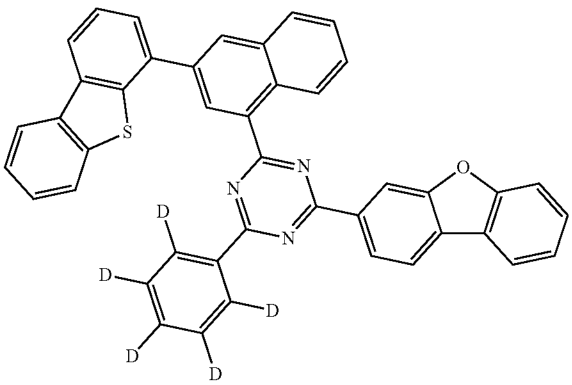
P-18
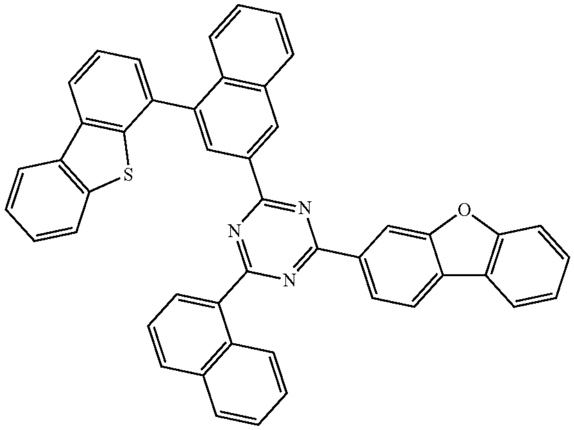
P-19
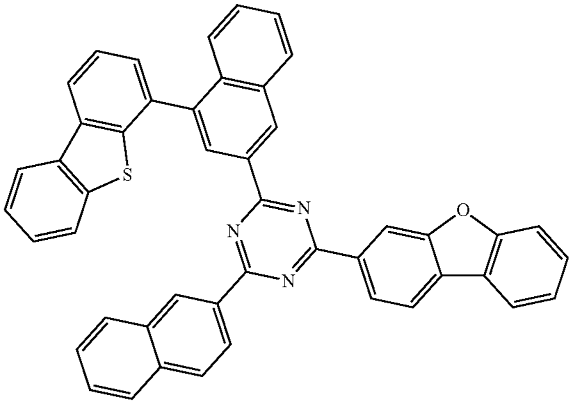
P-20
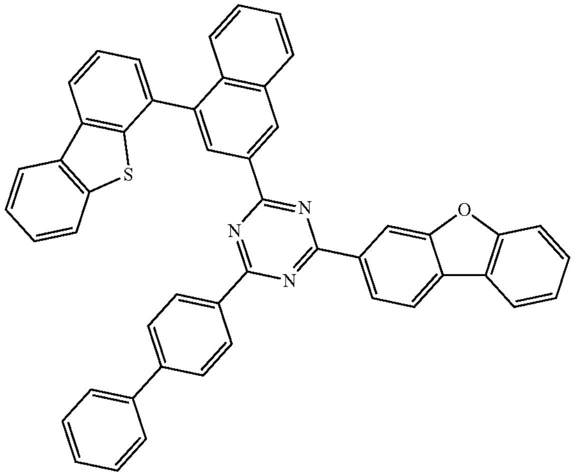

-continued
P-21
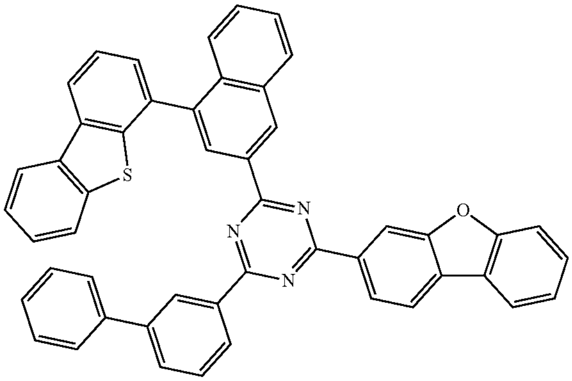
P-22
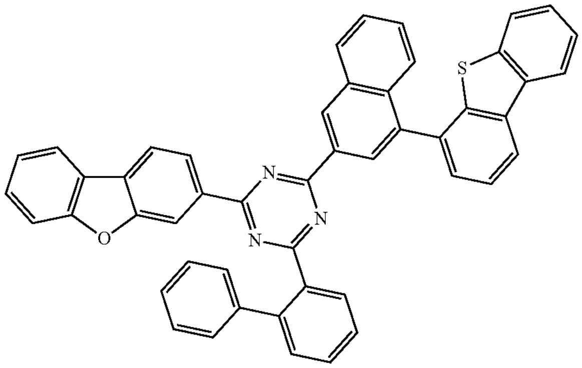
P-23
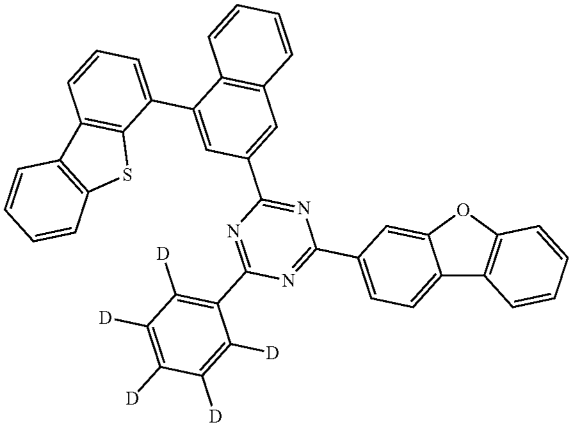
P-24
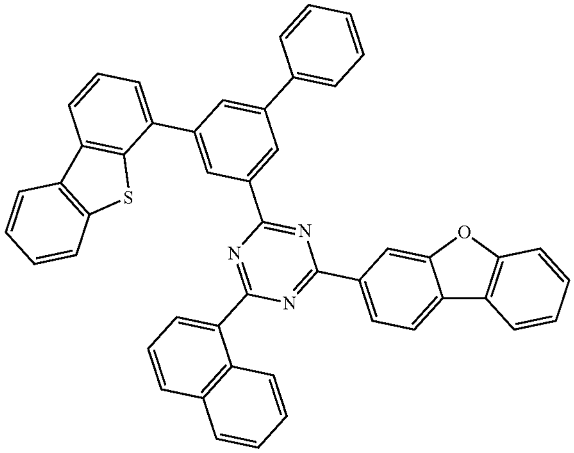
P-25
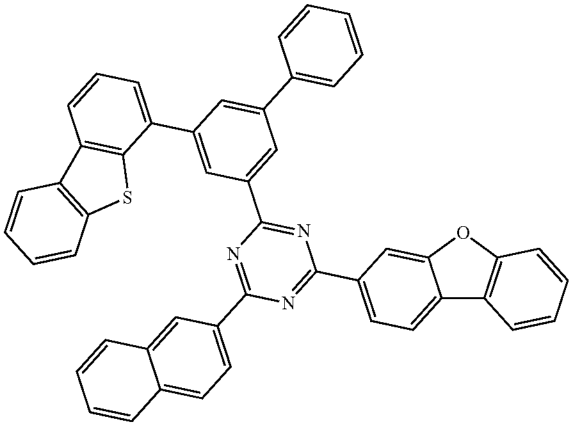
P-26
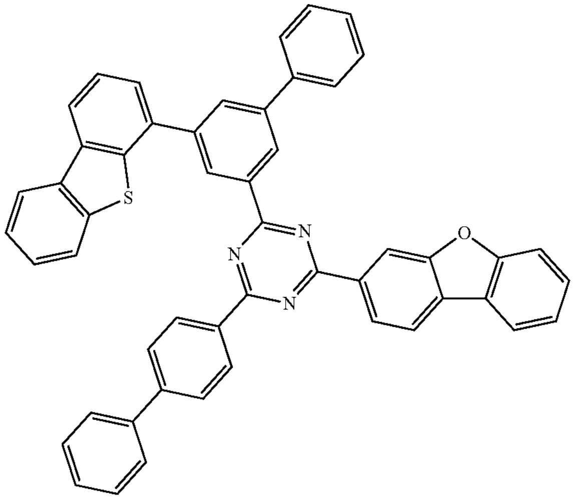

-continued
P-27
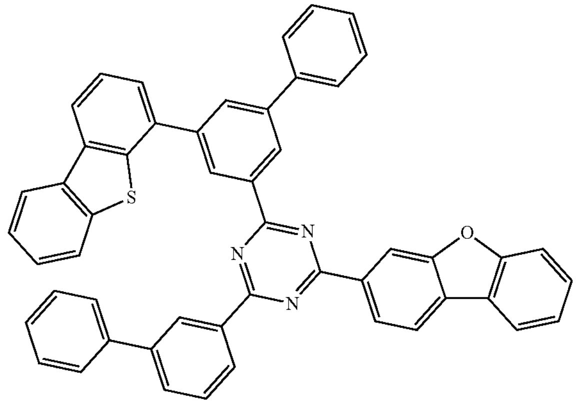
P-28
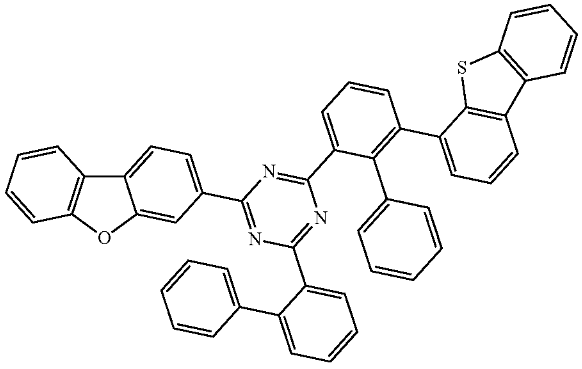
P-29
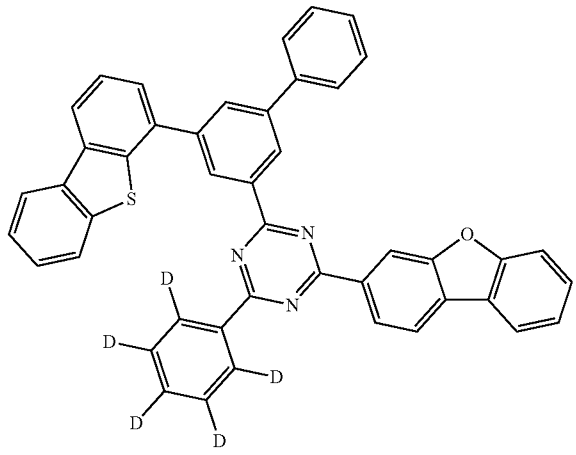
P-30
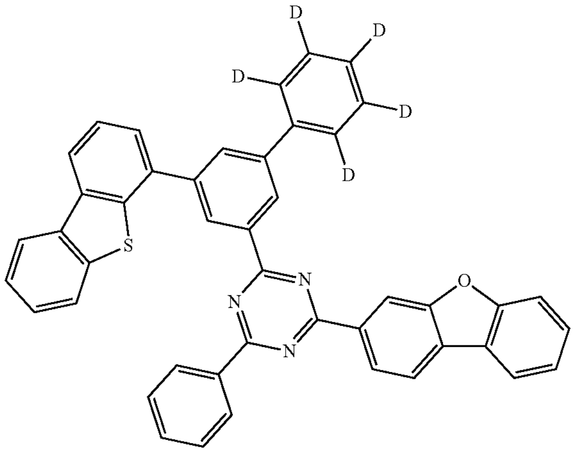
P-31
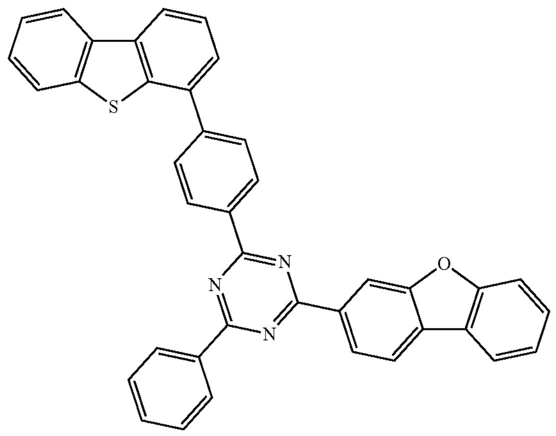
P-32
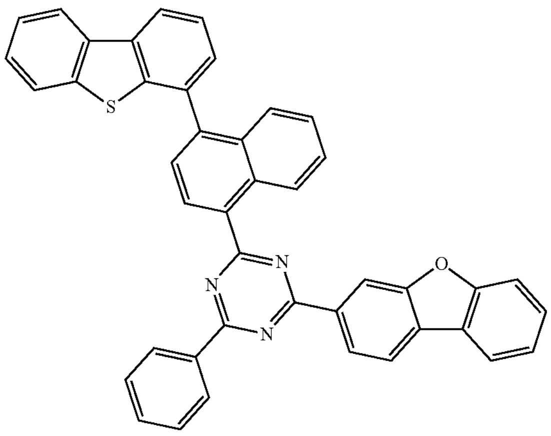

-continued
P-33
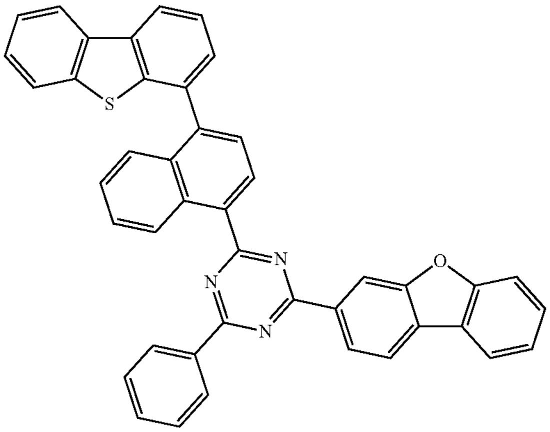
P-34
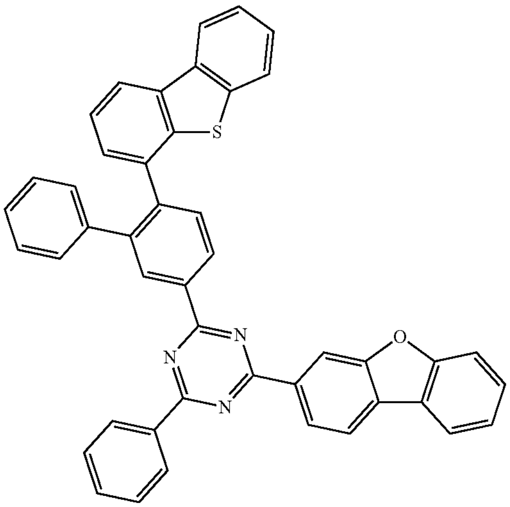
P-35
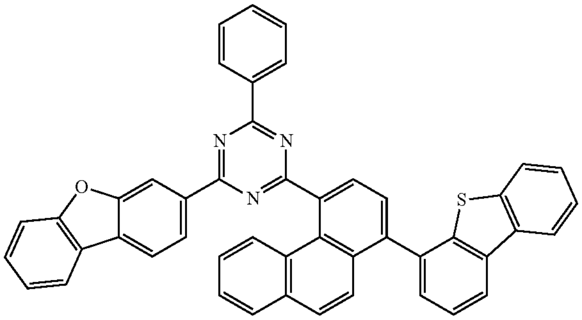
P-36
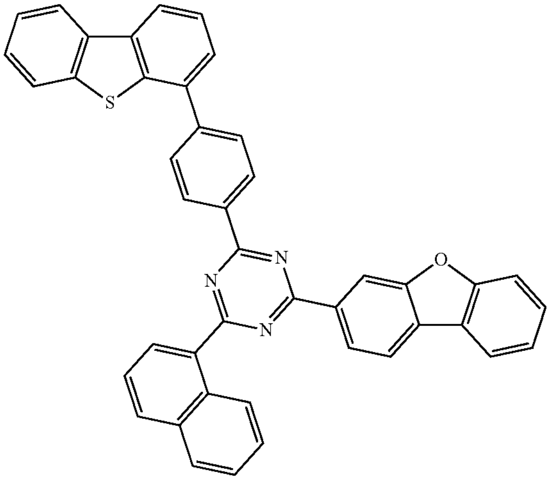
P-37
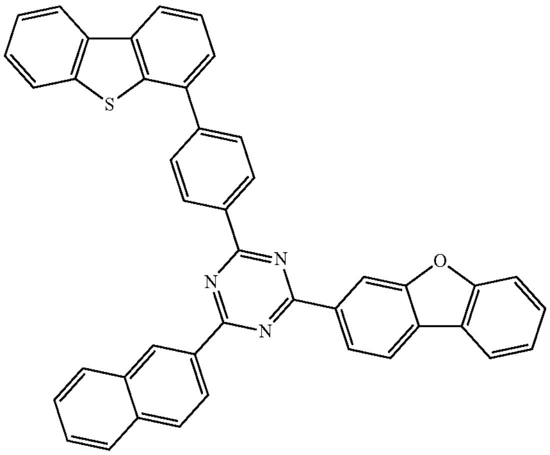
P-38
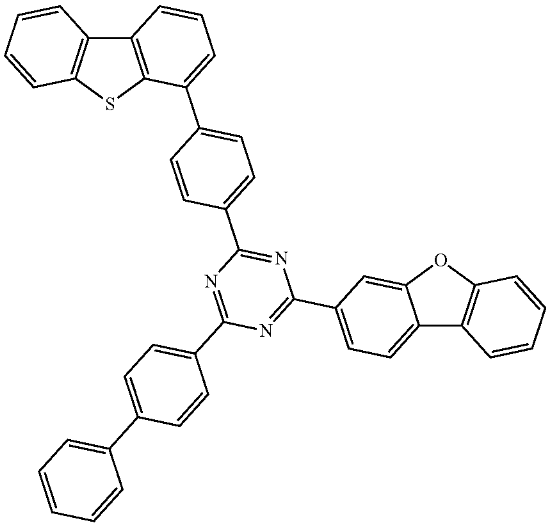

-continued
P-39
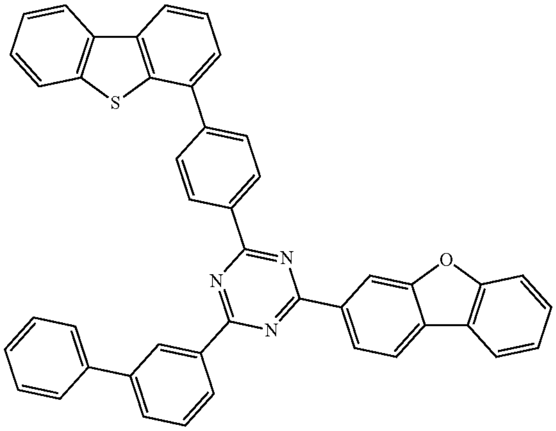
P-40
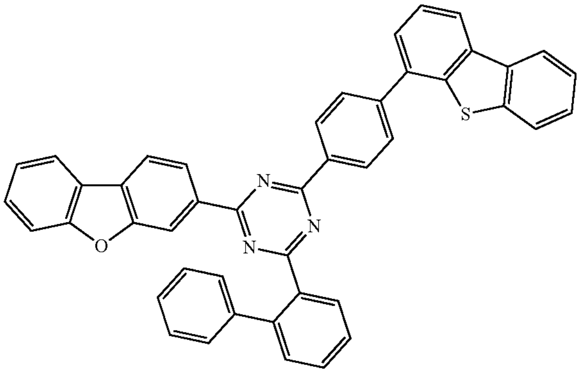
P-41
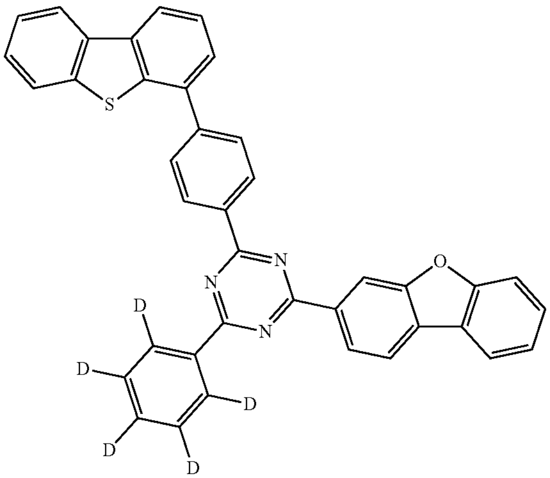
P-42
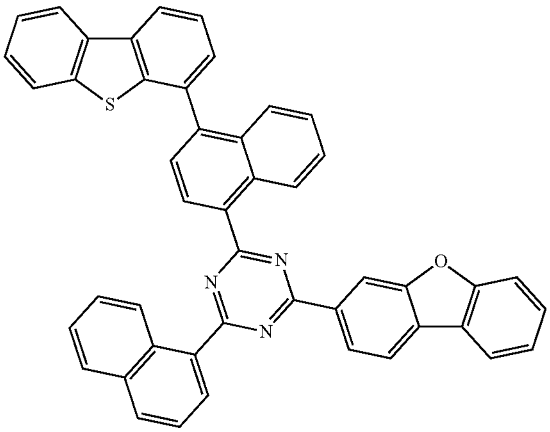
P-43
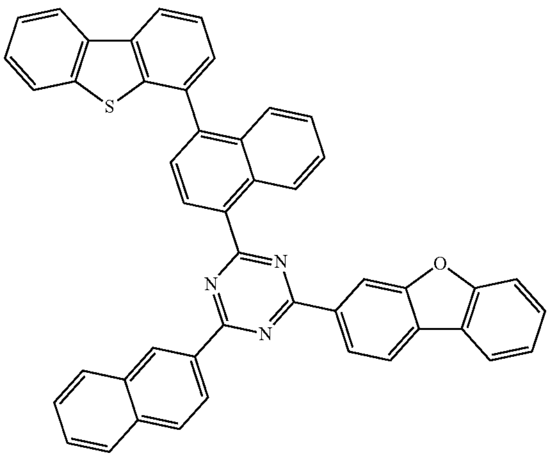
P-44
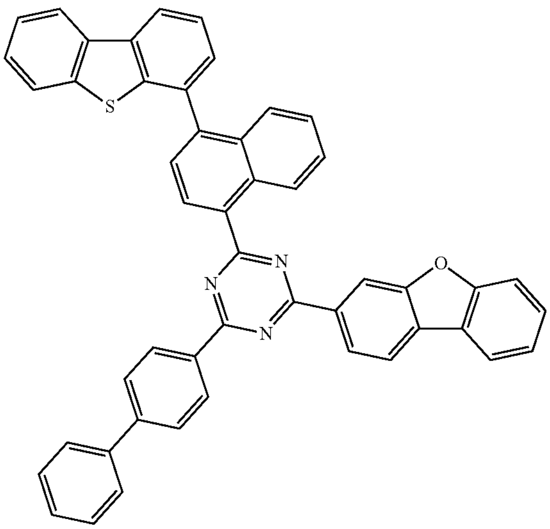

-continued
P-45
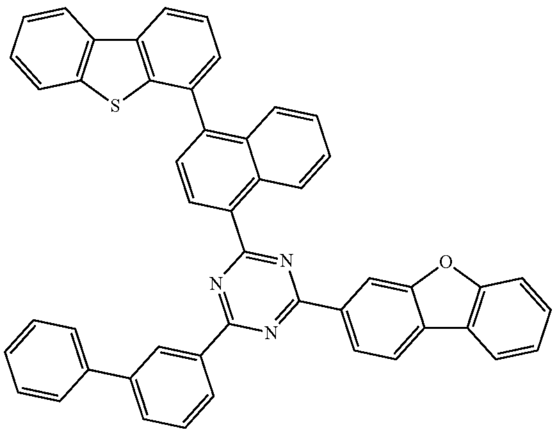
P-46
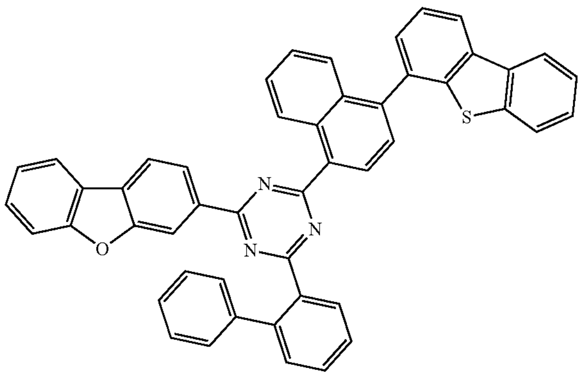
P-47
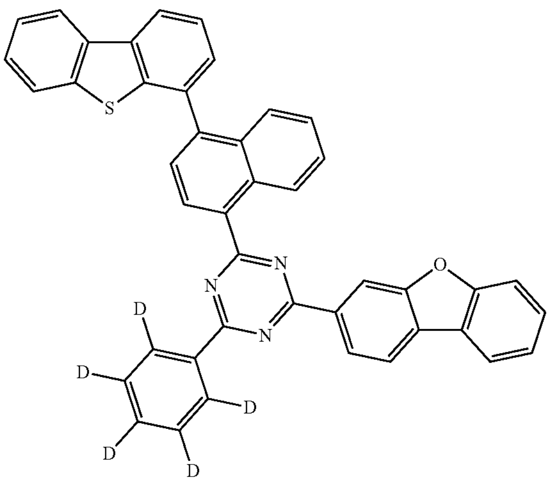
P-48
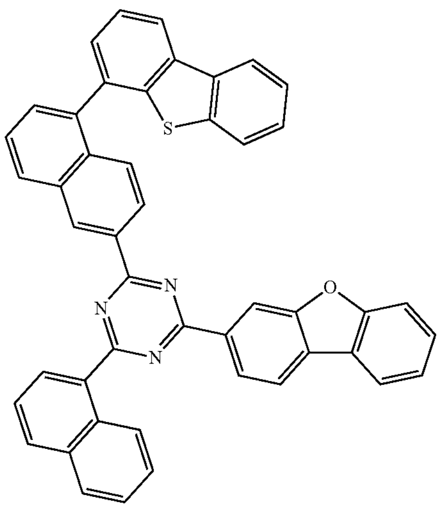
P-49
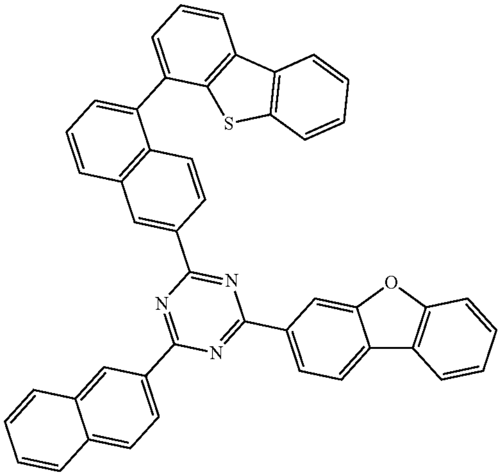
P-50
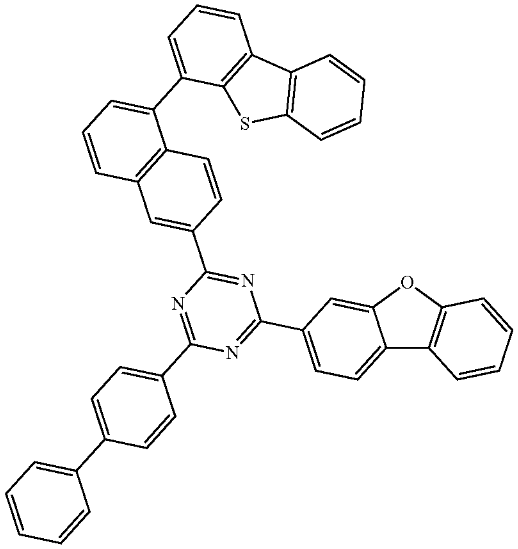

-continued
P-51
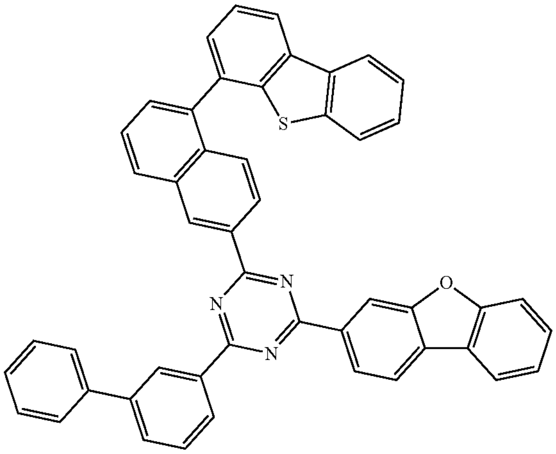
P-52
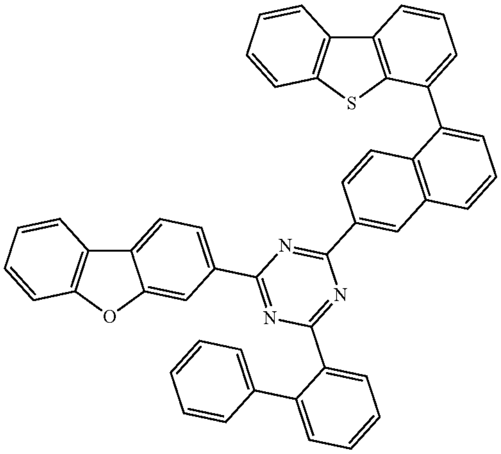
P-53
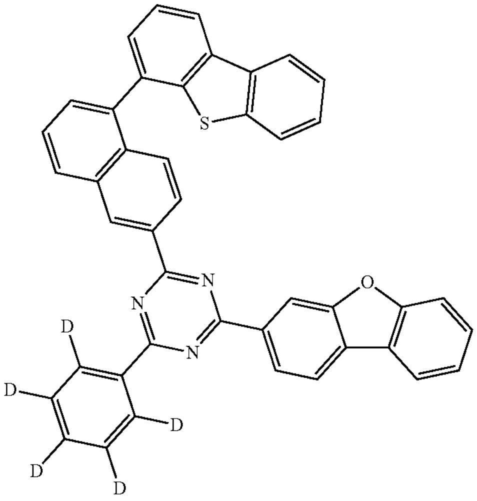
P-54
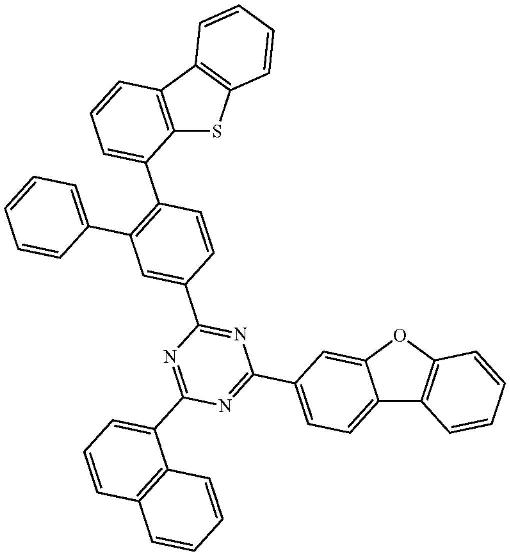
P-55
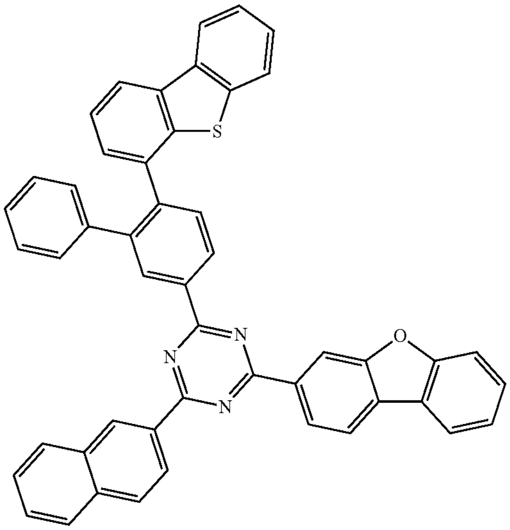
P-56
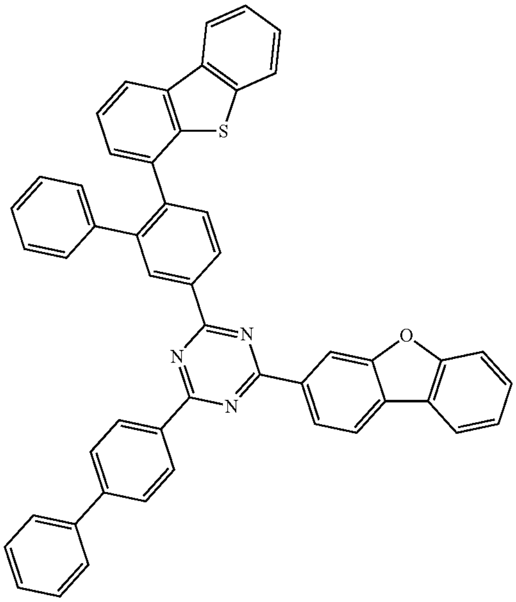

-continued
P-57
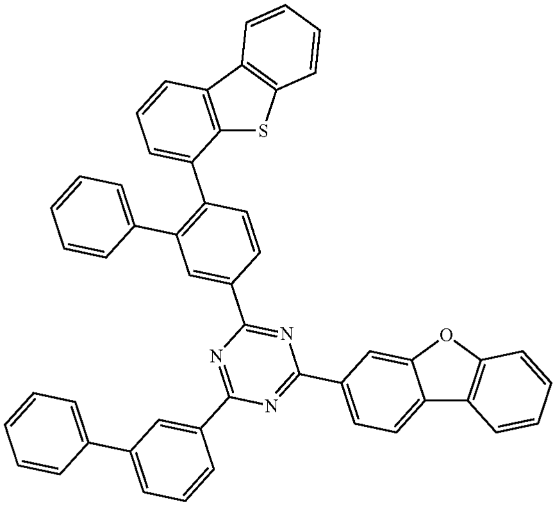
P-58
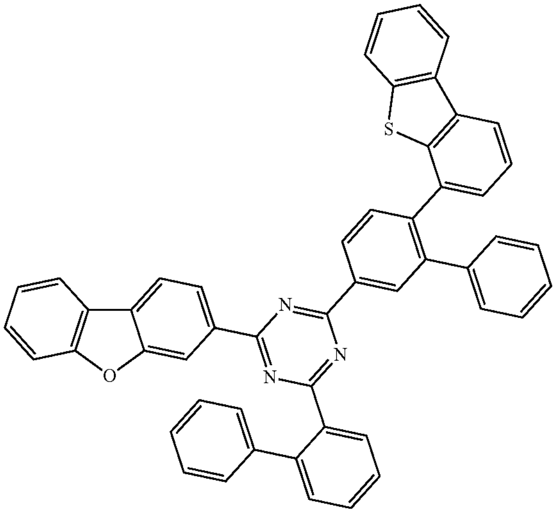
P-59
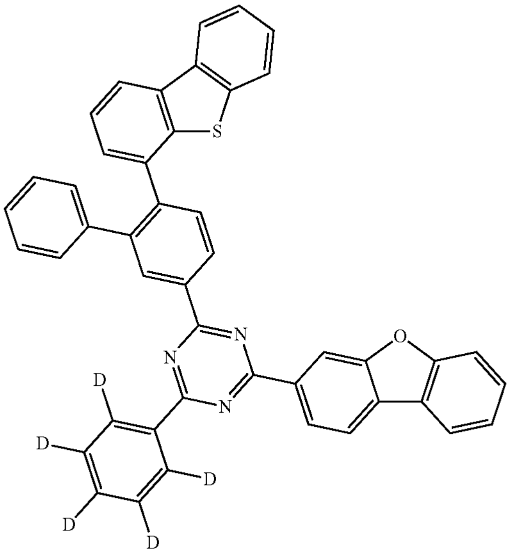
P-60
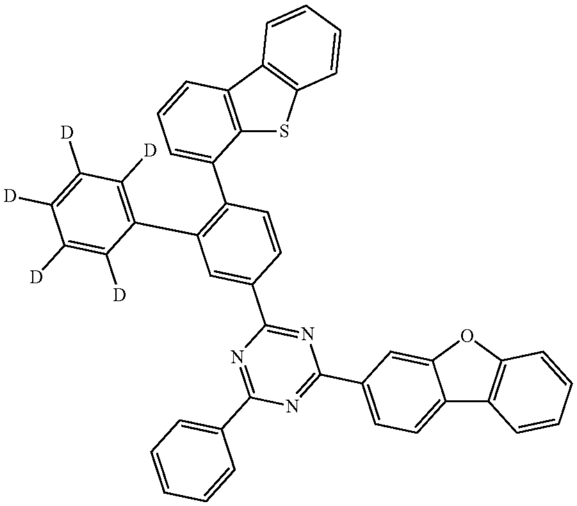
P-61
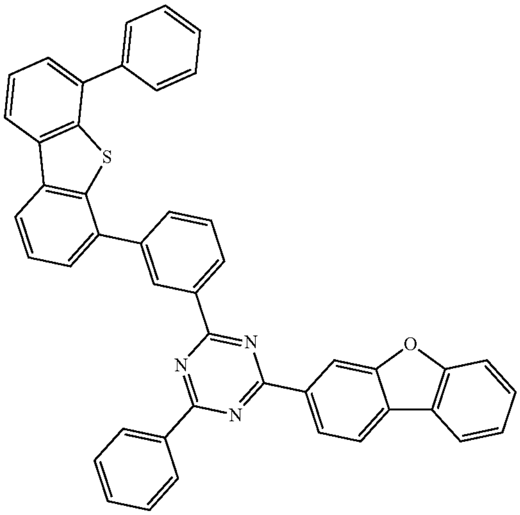
P-62
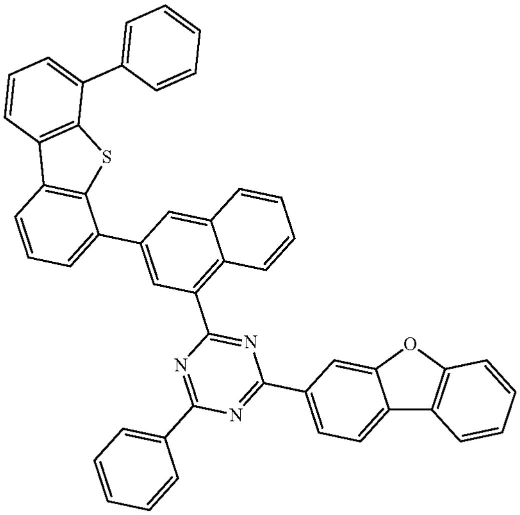

-continued
P-63
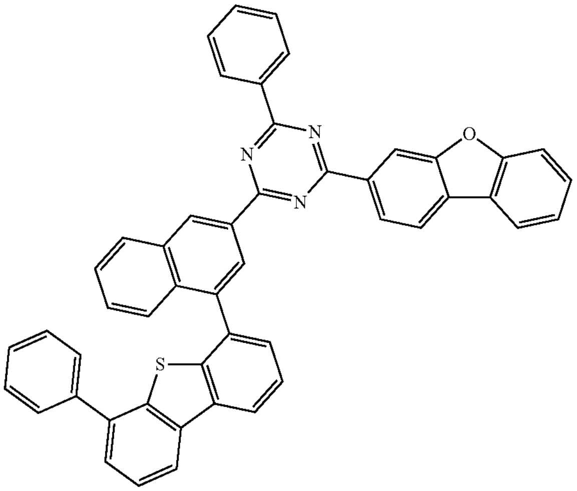
P-64
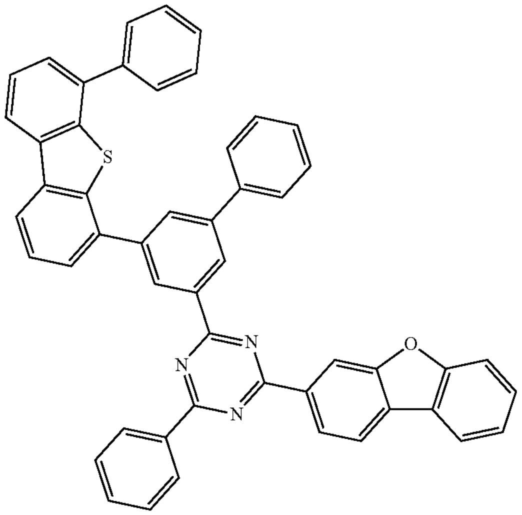
P-65
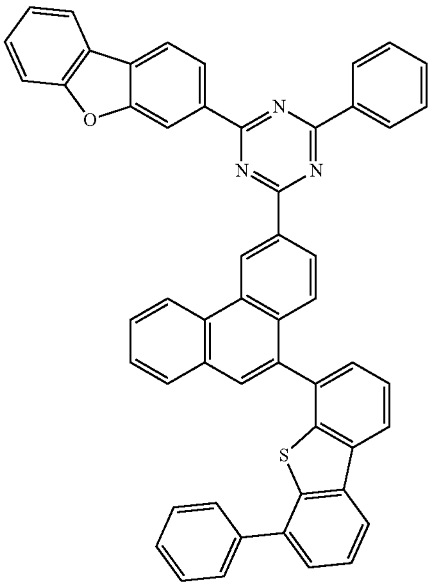
P-66
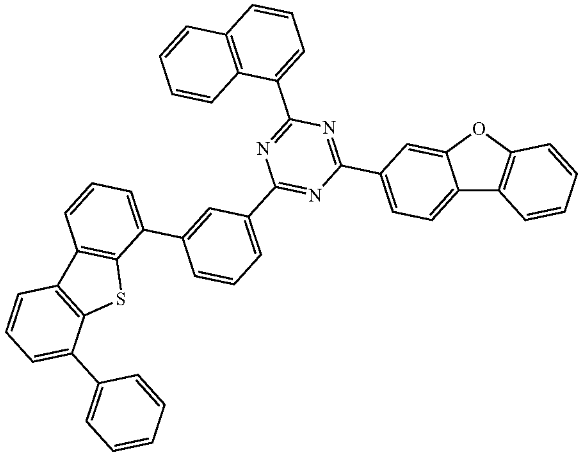

-continued
P-67
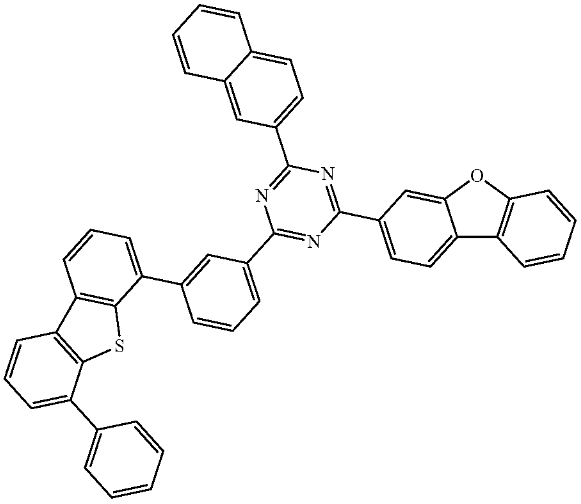
P-68
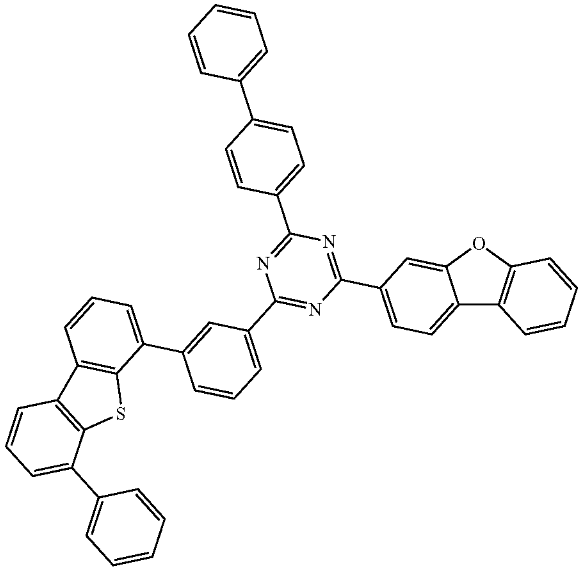
P-69
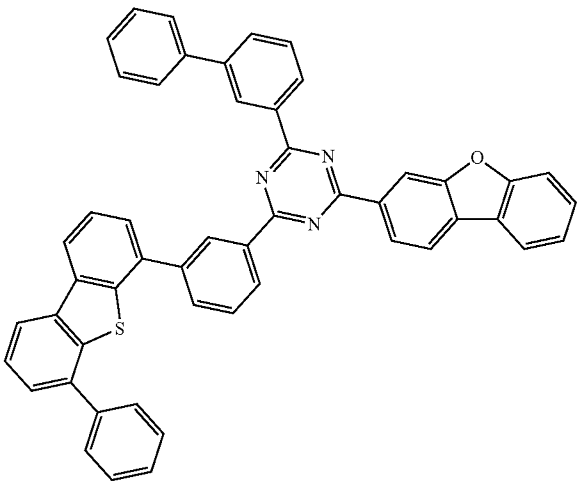
P-70
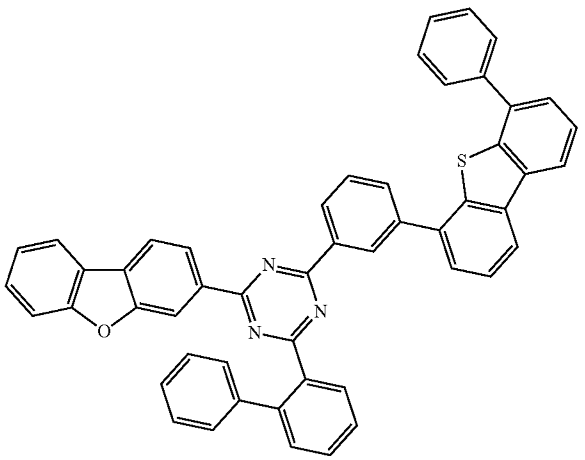
P-71
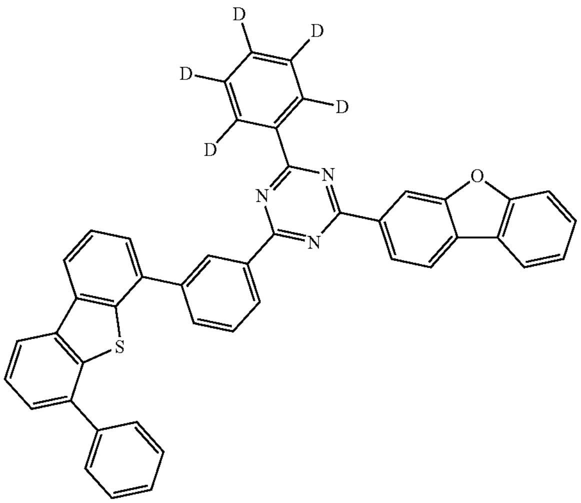
P-72
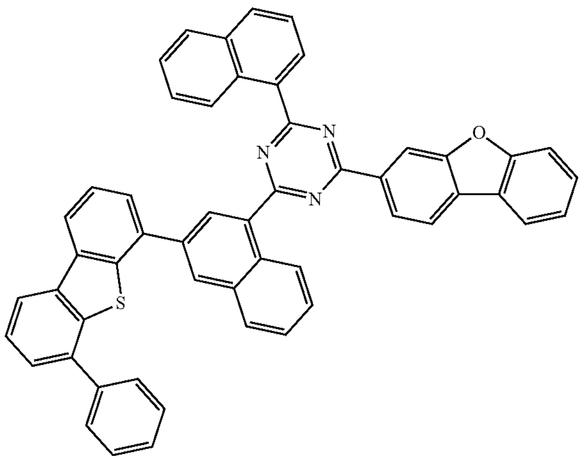

-continued
P-73
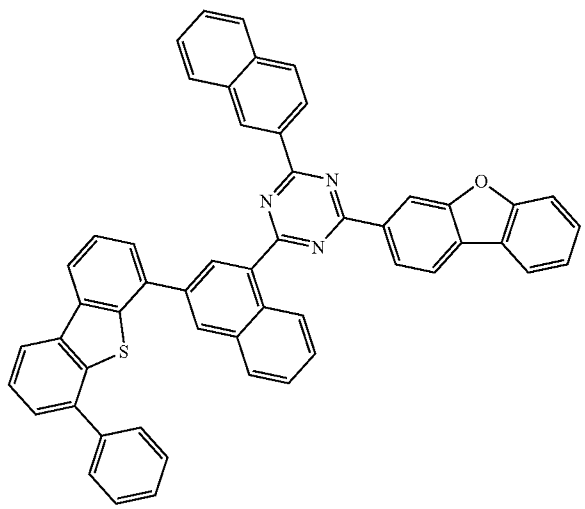
P-74
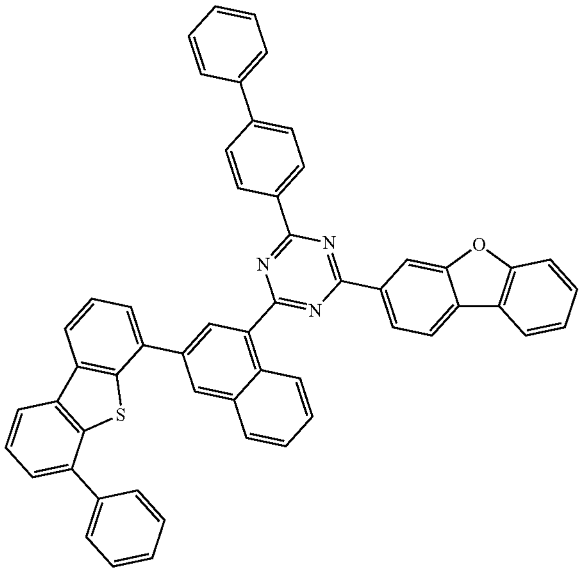
P-75
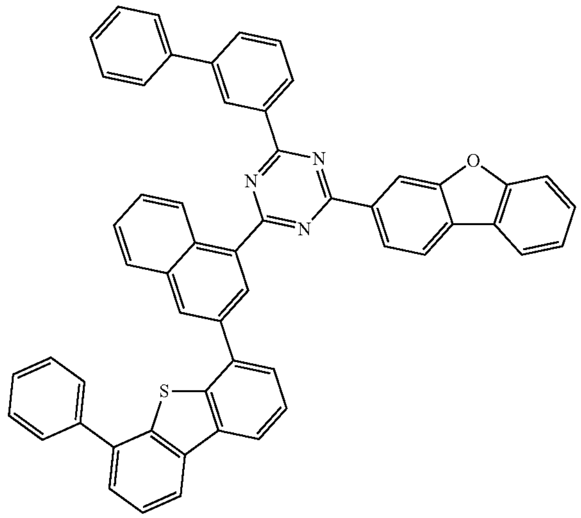
P-76
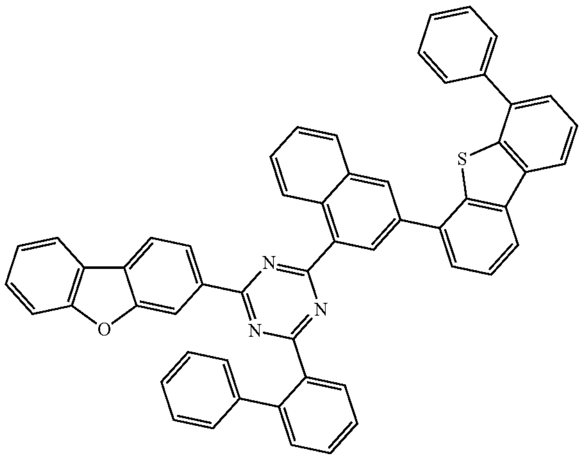
P-77
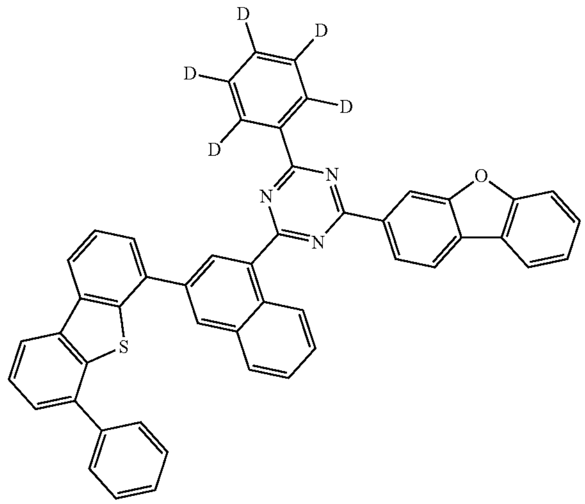
P-78
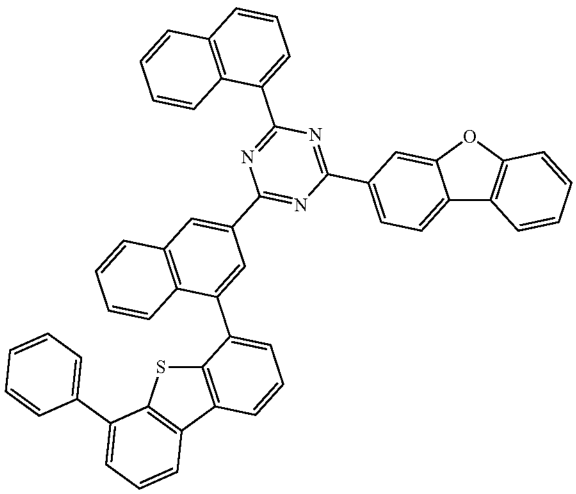

-continued
P-79
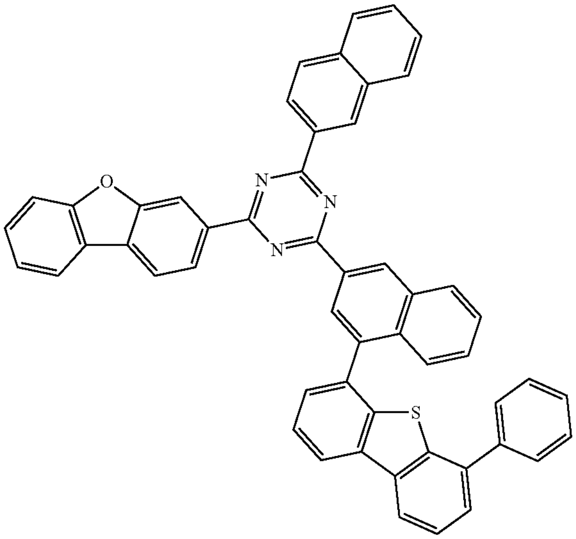
P-80
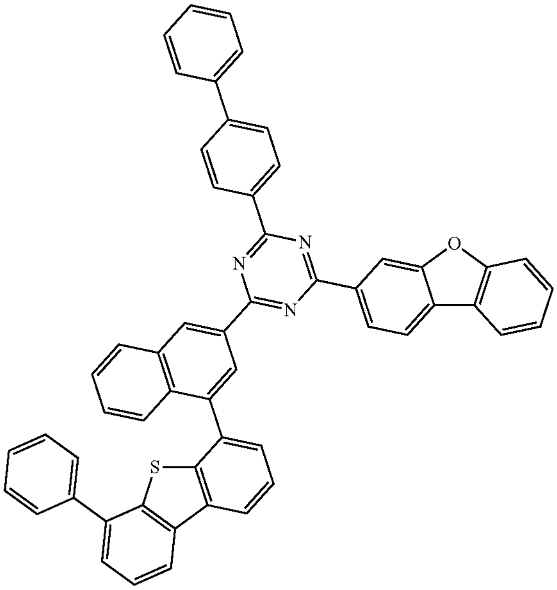
P-81
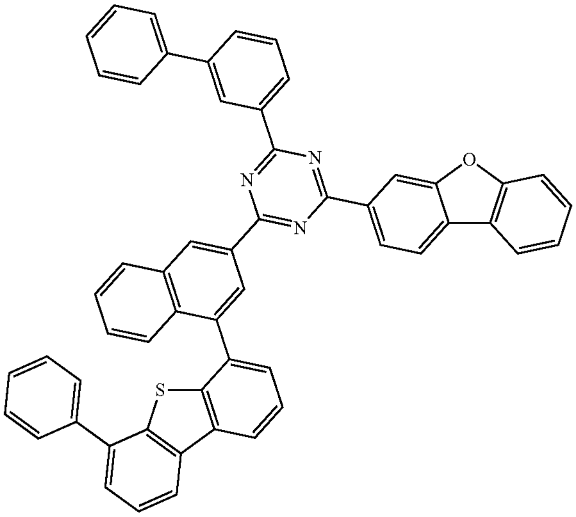
P-82
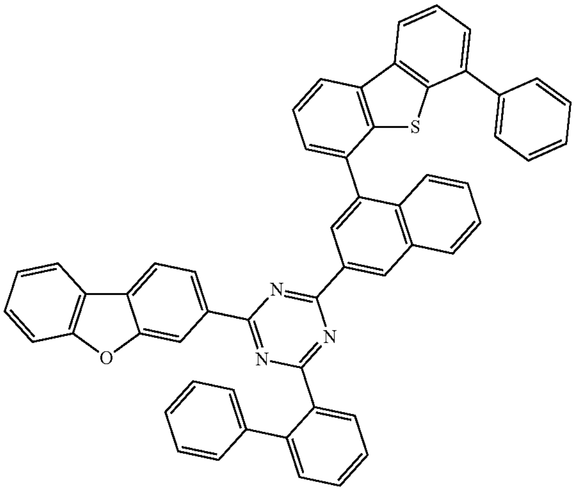

-continued
P-83
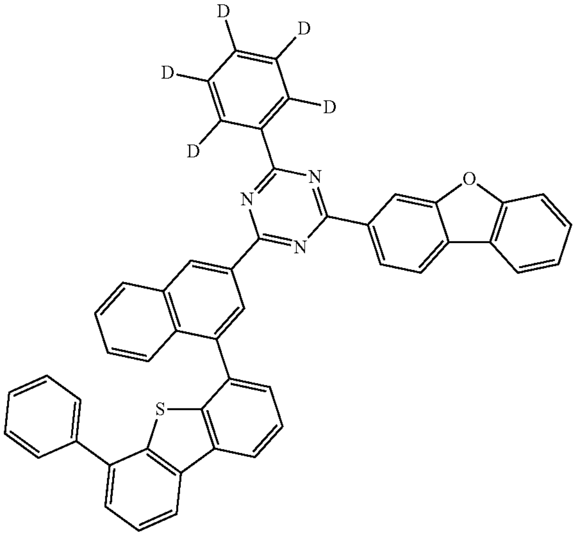
P-84
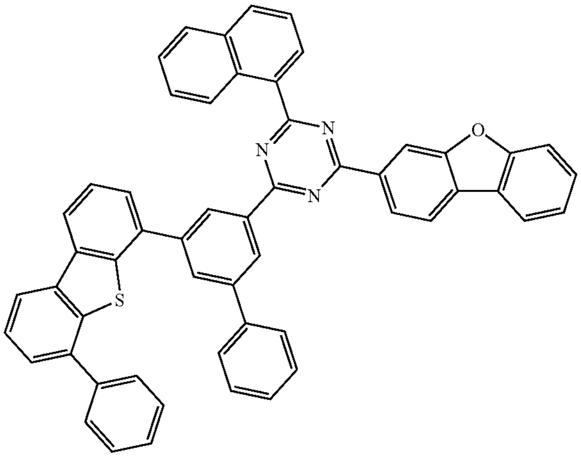
P-85
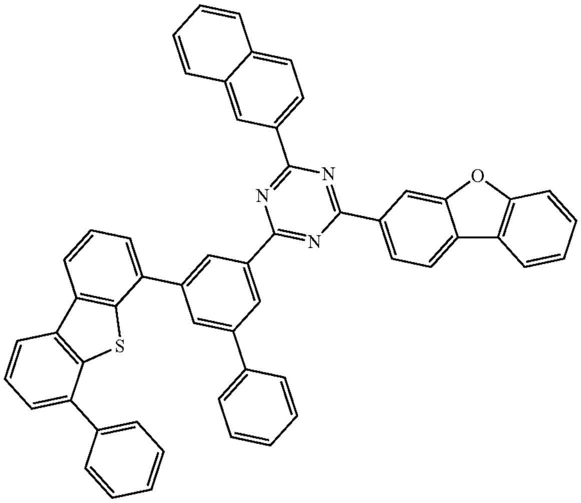
P-86
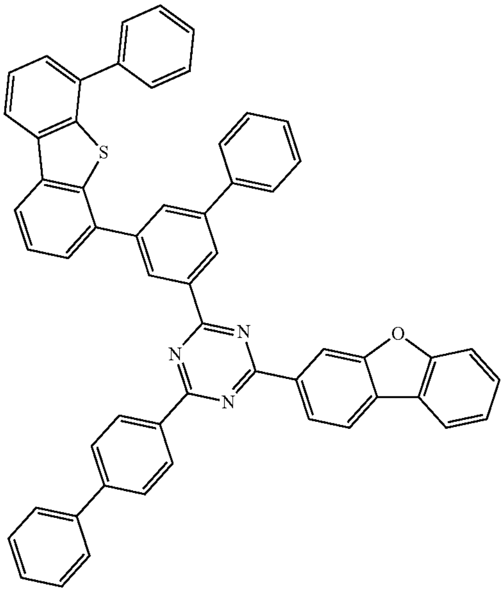

-continued
P-87
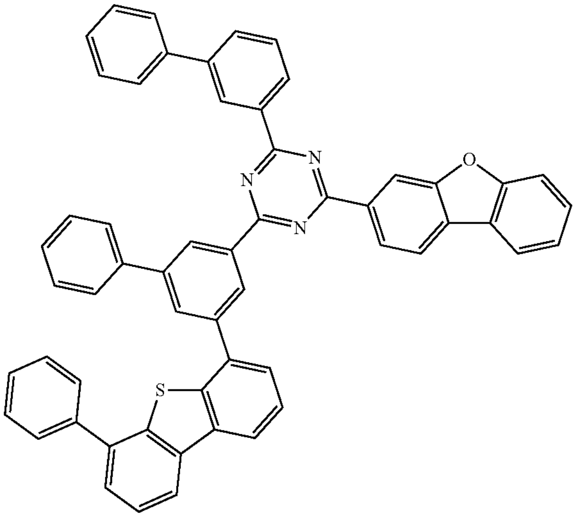
P-88
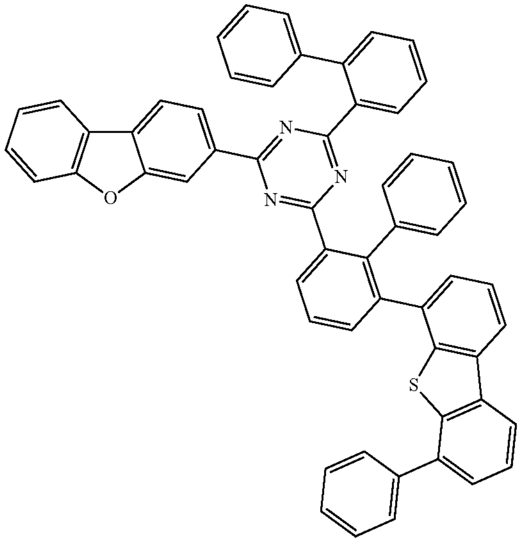
P-89
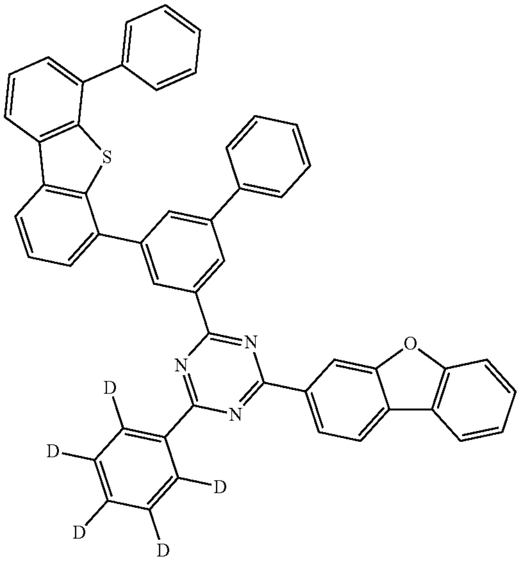
P-90
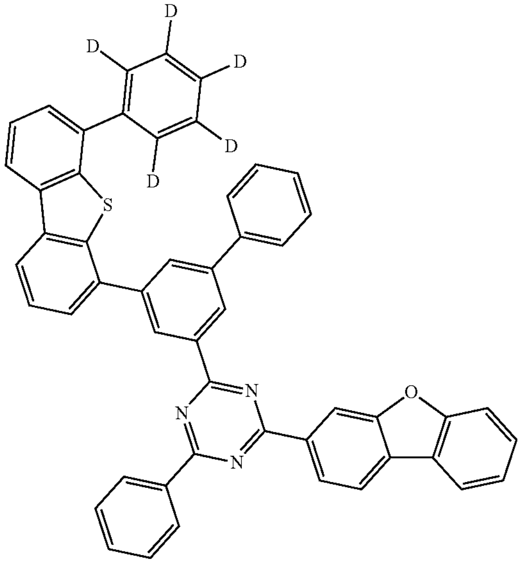
P-91
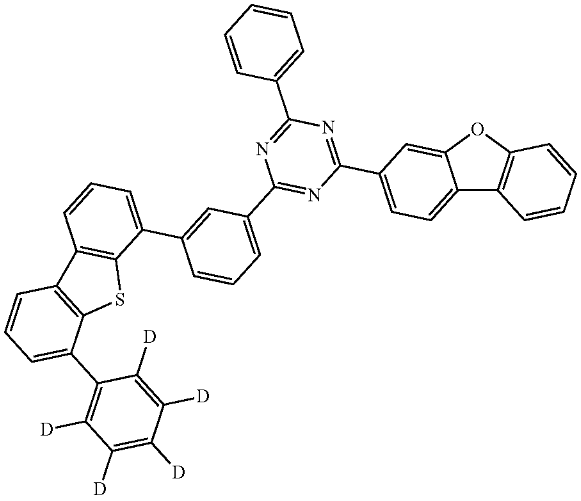
P-92
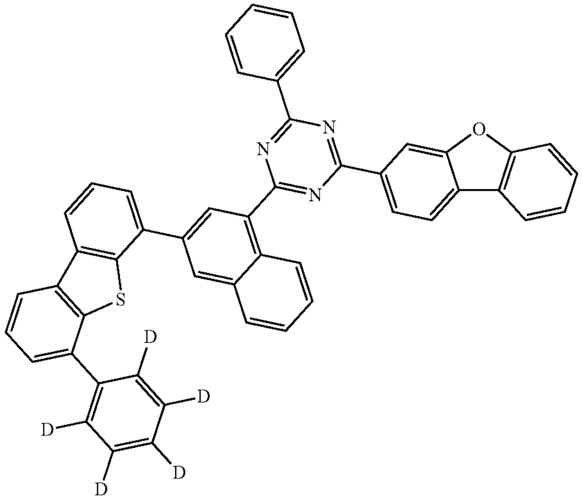

-continued
P-93
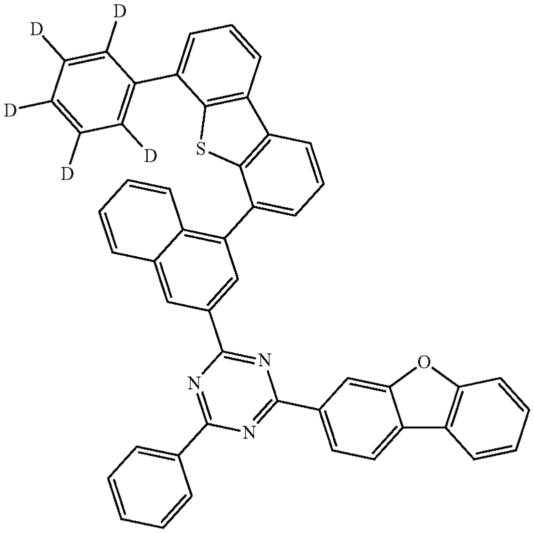
P-94
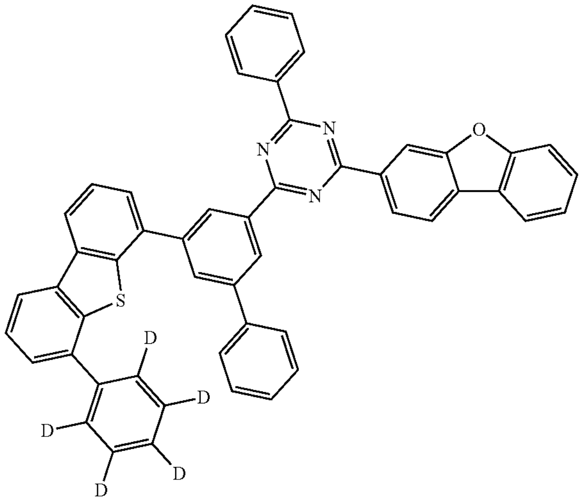
P-95
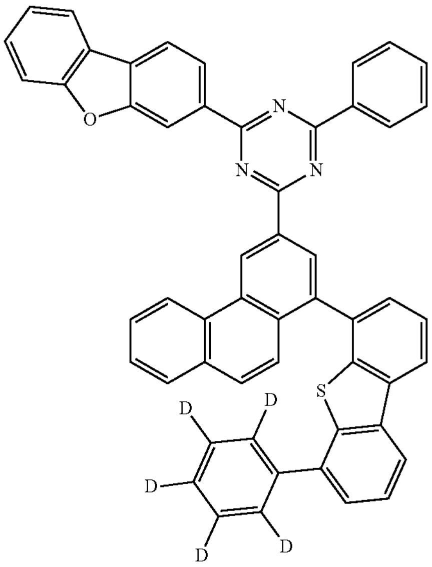
P-96
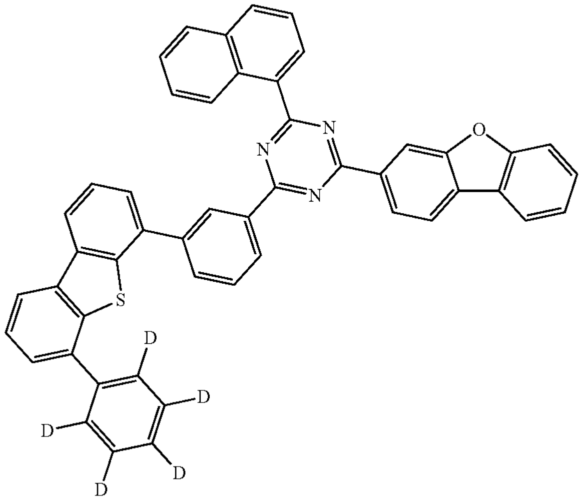

-continued
P-97
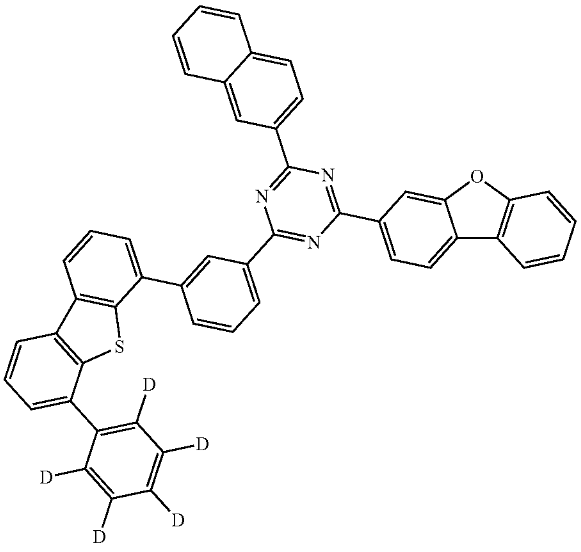
P-98
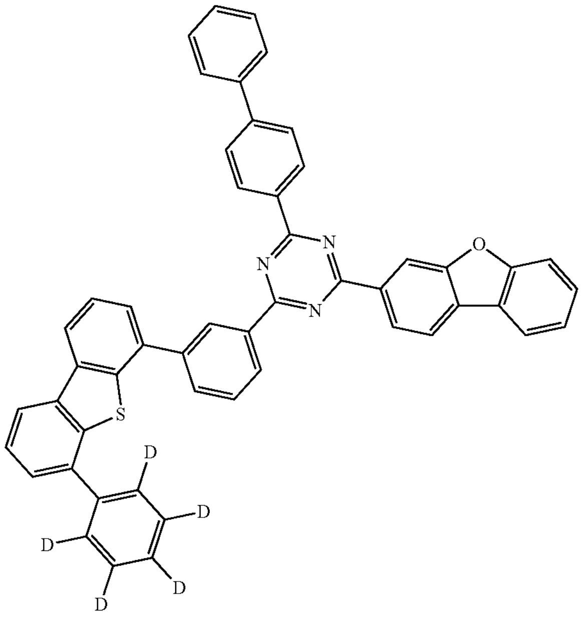
P-99
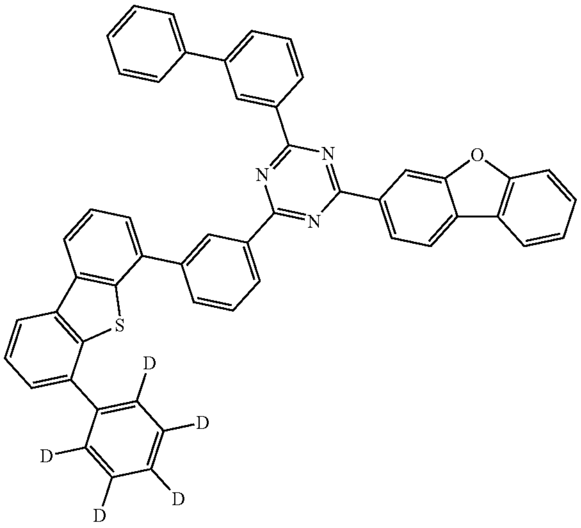
P-100
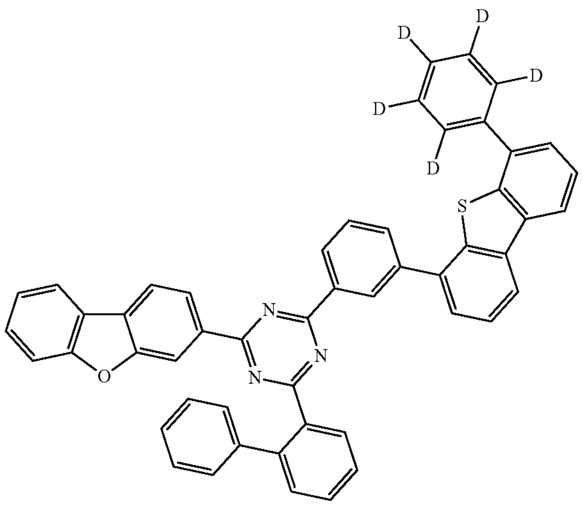

-continued
P-101
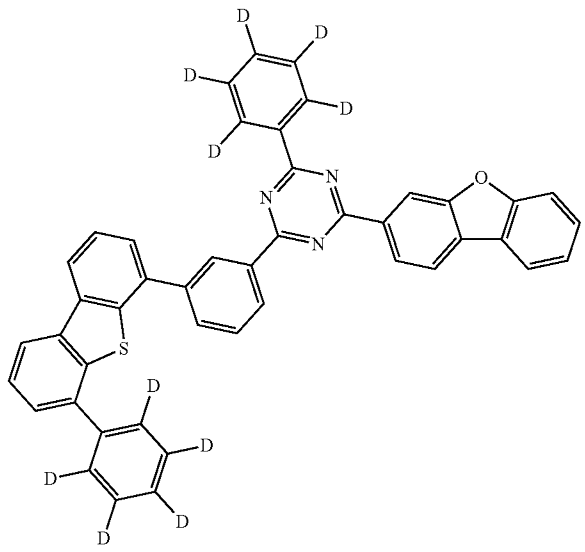
P-102
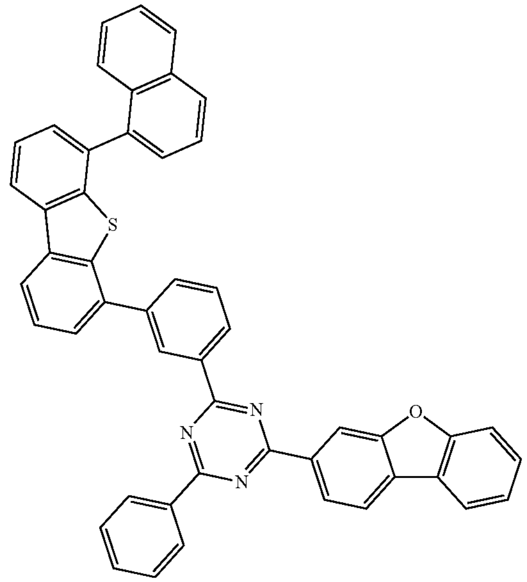
P-103
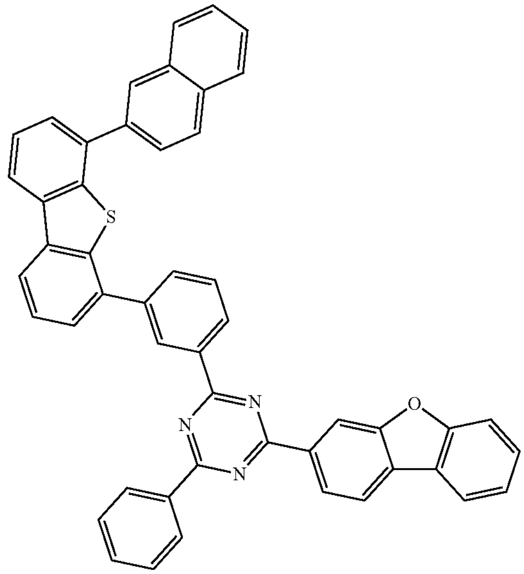
P-104
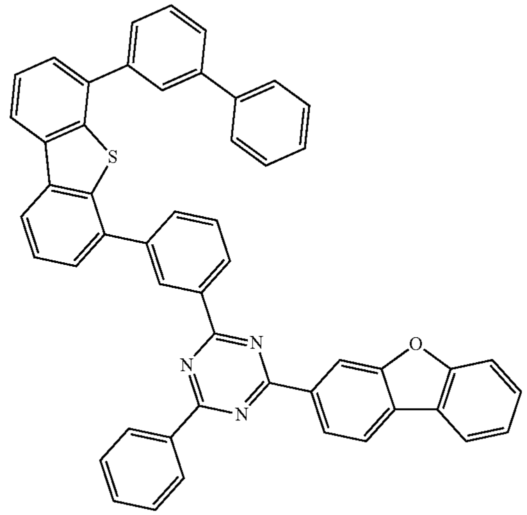

-continued
P-105
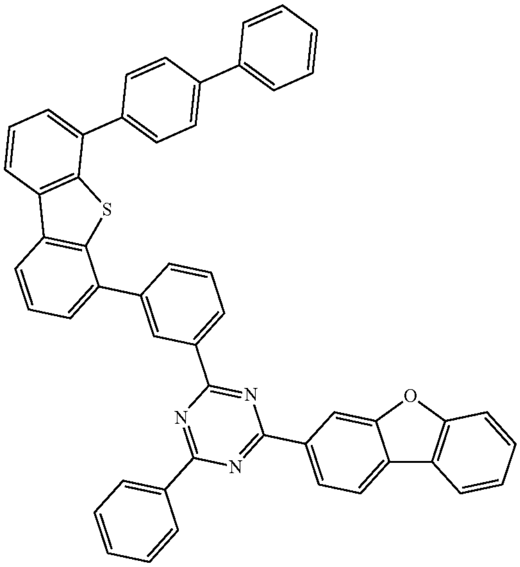
P-106
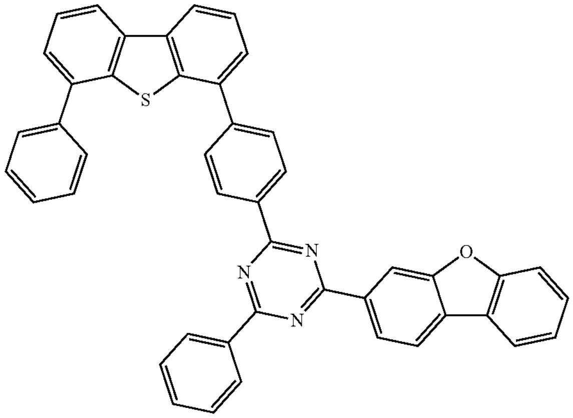
P-107
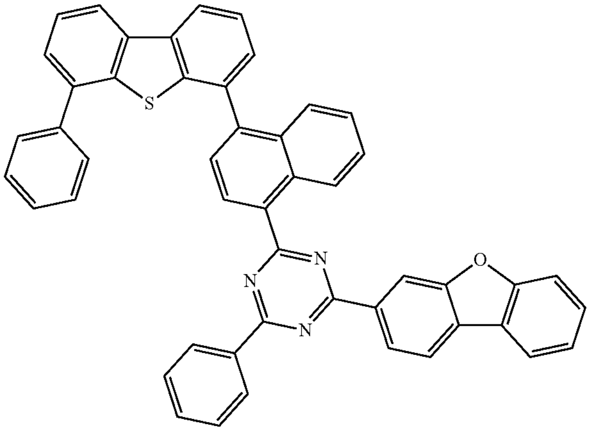
P-108
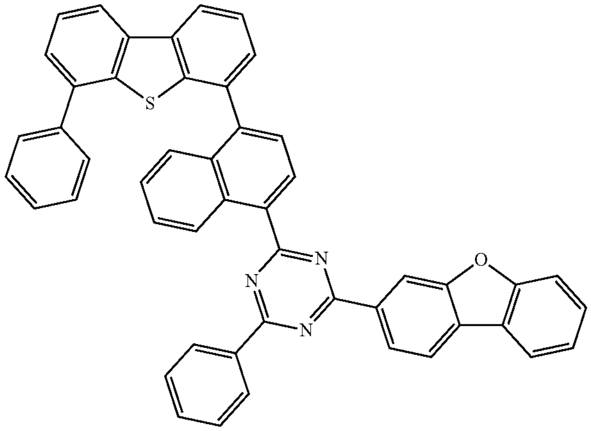
P-109
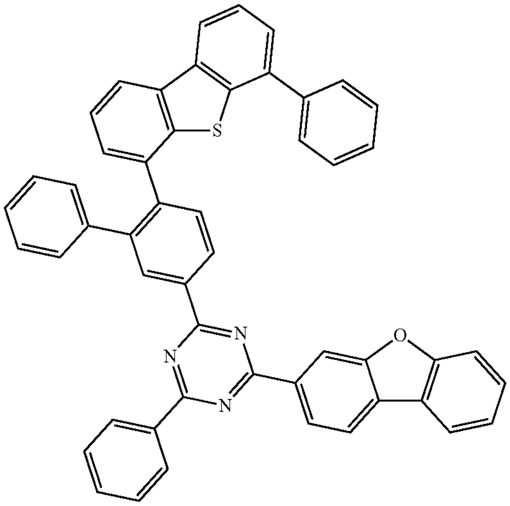
P-110
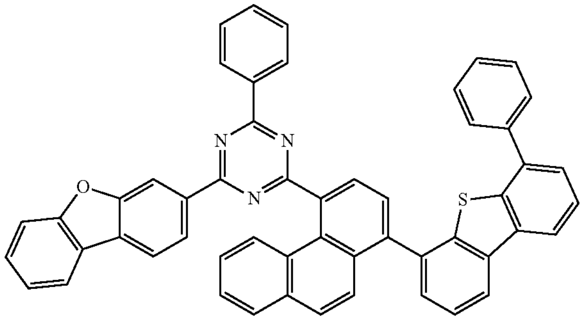

-continued
P-111
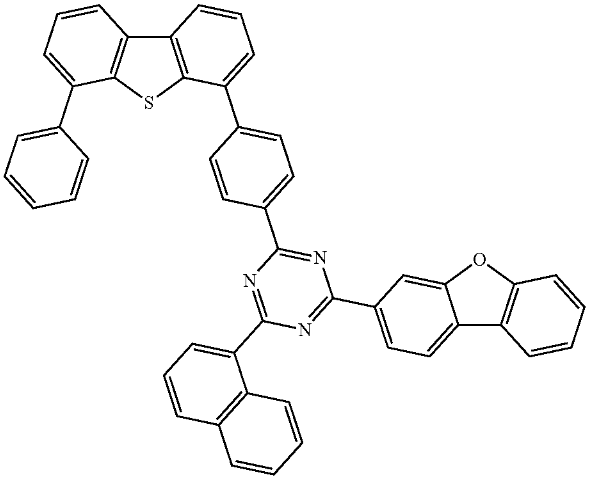
P-112
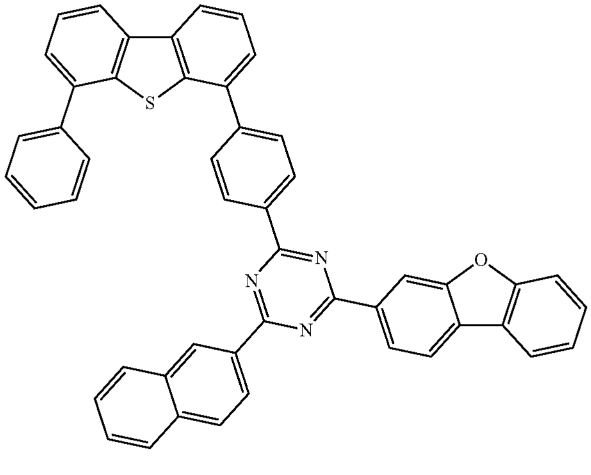
P-113
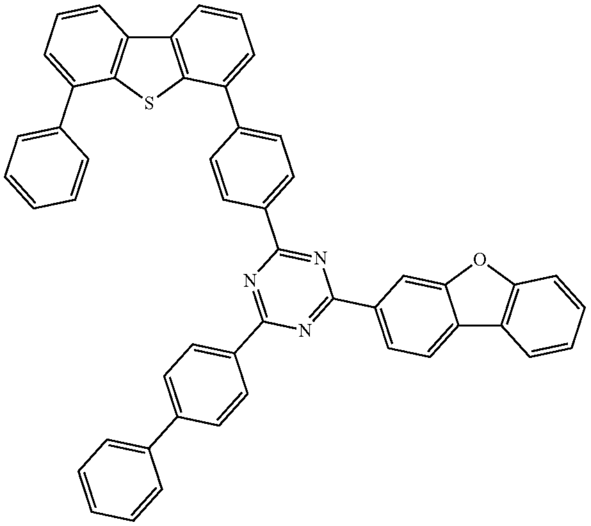
P-114
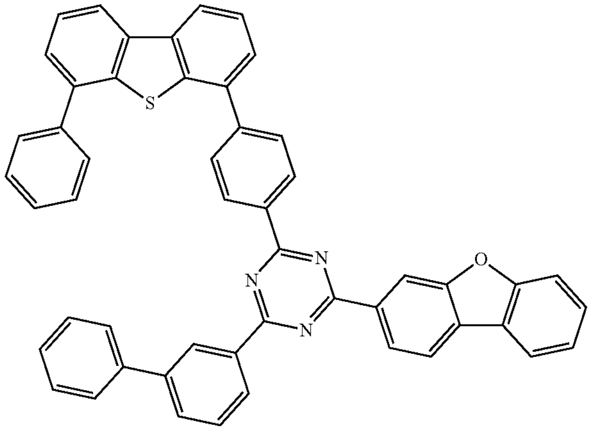
P-115
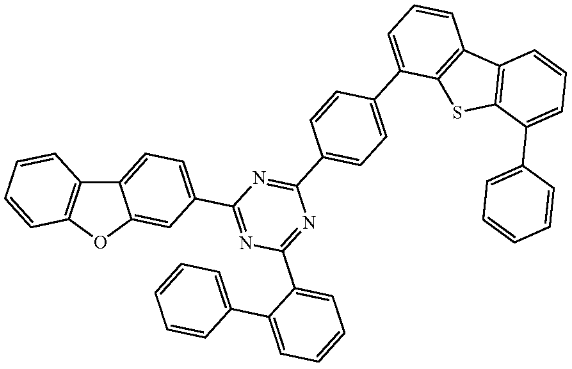
P-116
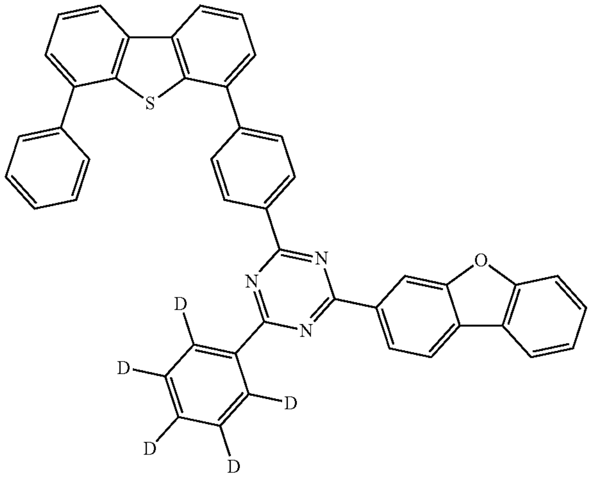

-continued
P-117
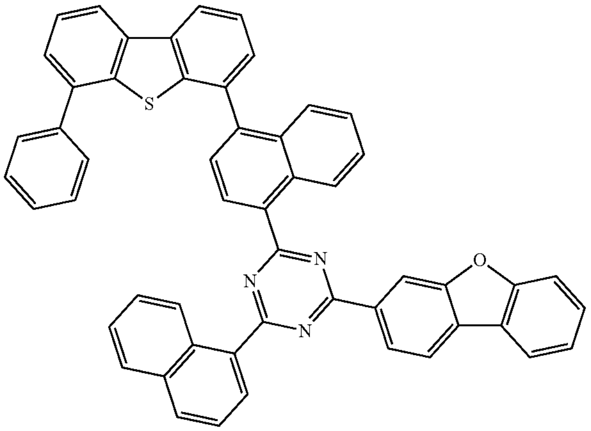
P-118
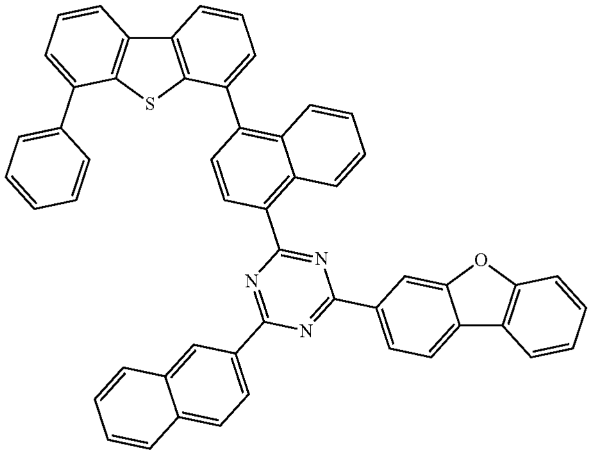
P-119
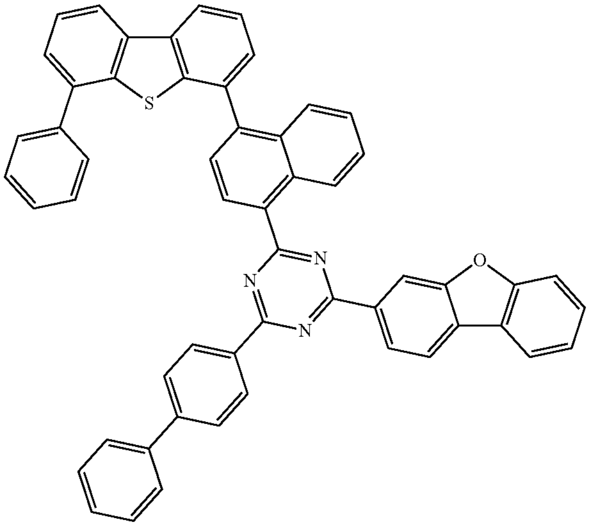
P-120
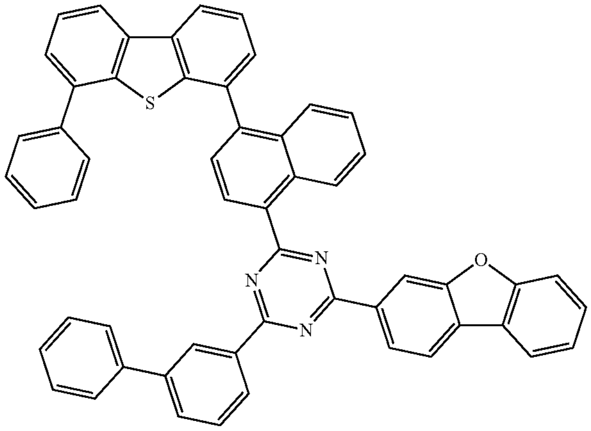
4-1
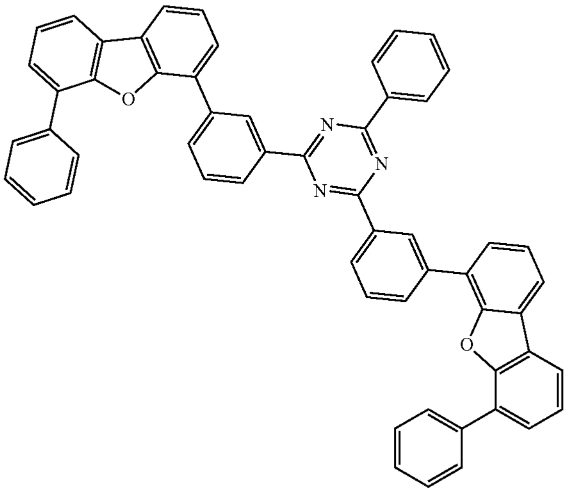
4-2
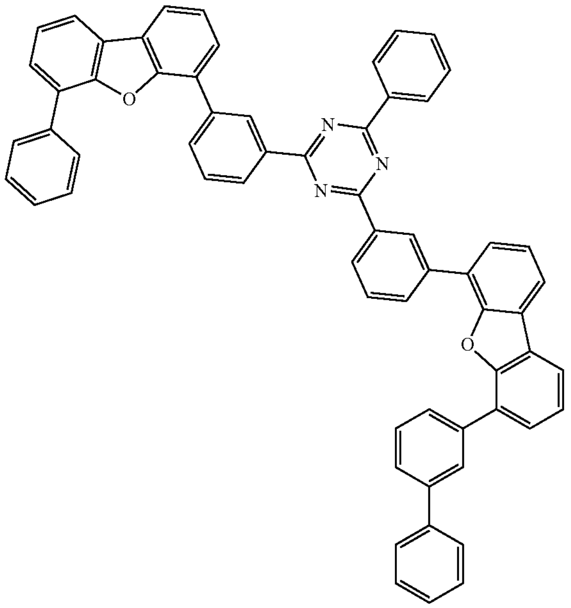

-continued
4-3
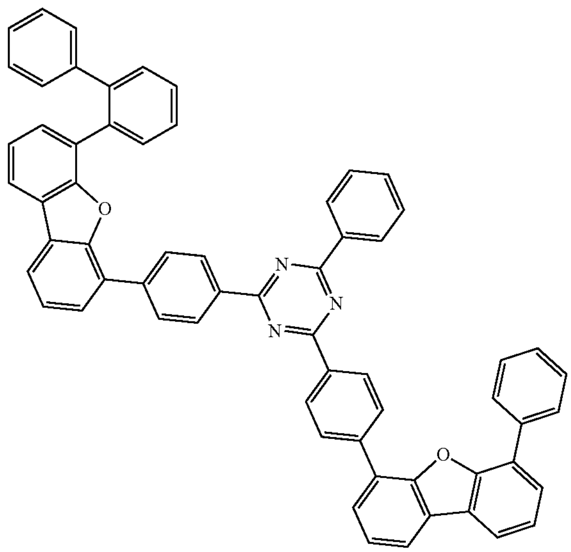
4-4
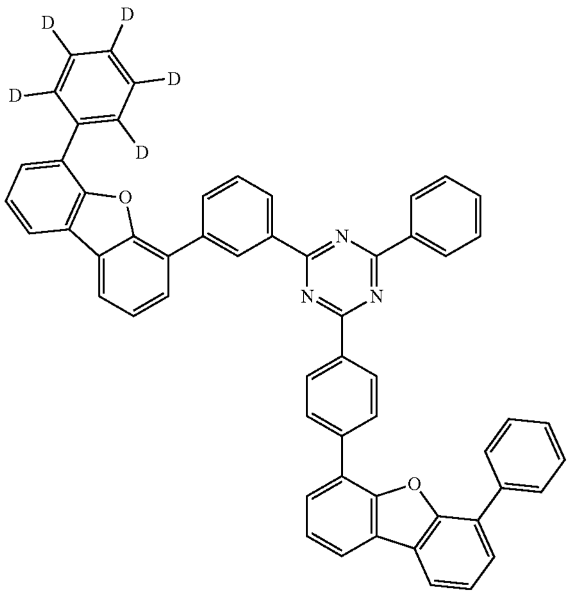
4-5
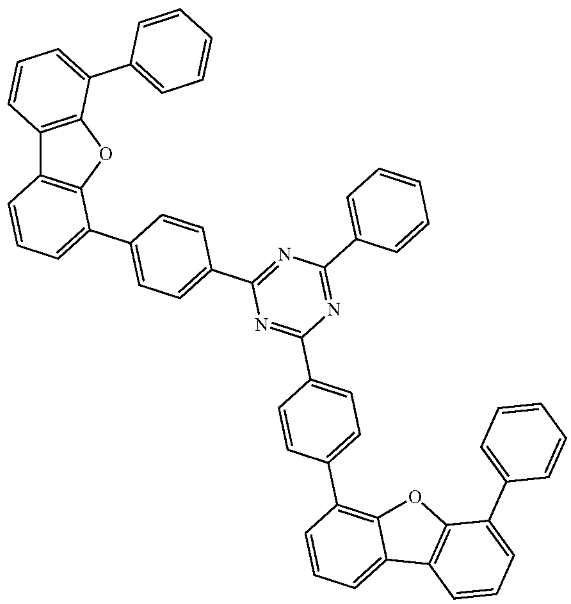
4-6
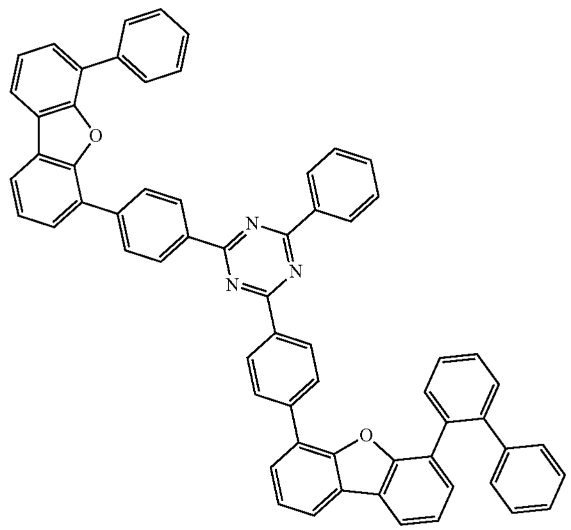

-continued
4-7
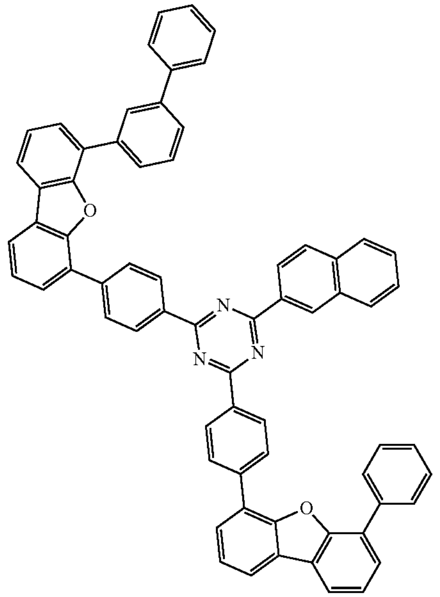
4-8
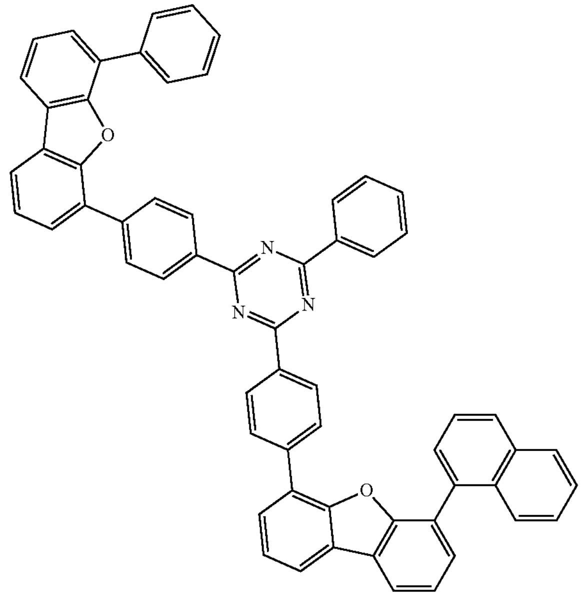
4-9
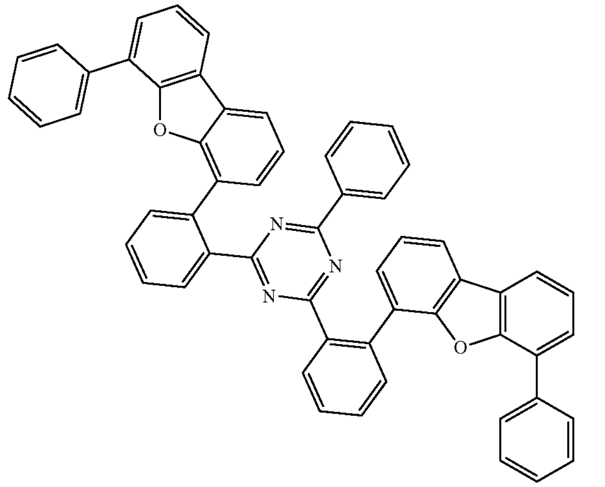
4-10
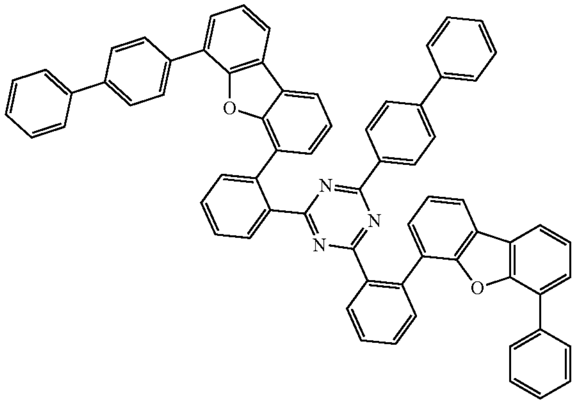
4-11
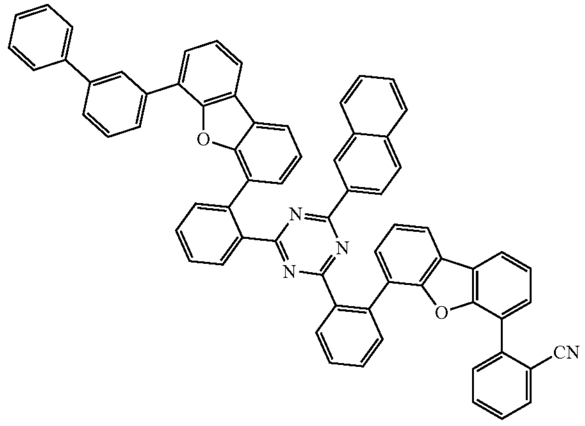
4-12
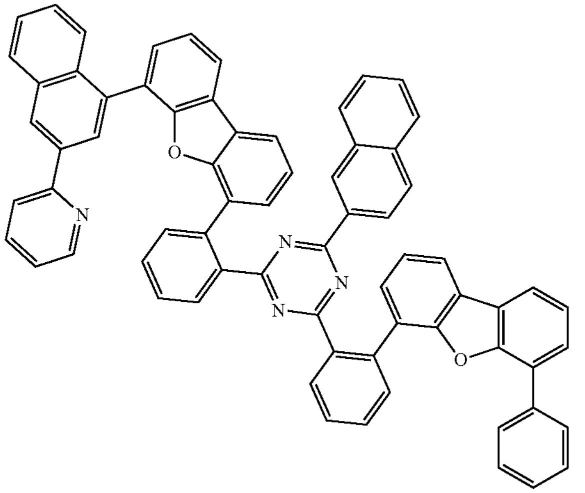

-continued
5-1
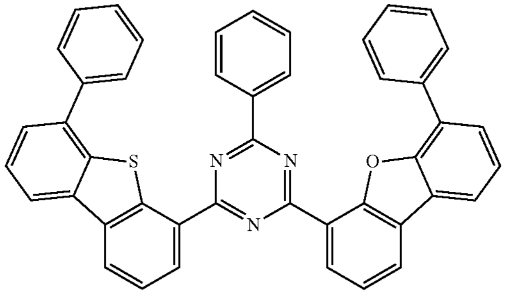
5-2
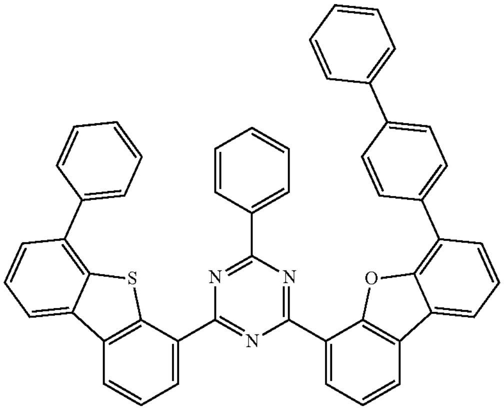
5-3
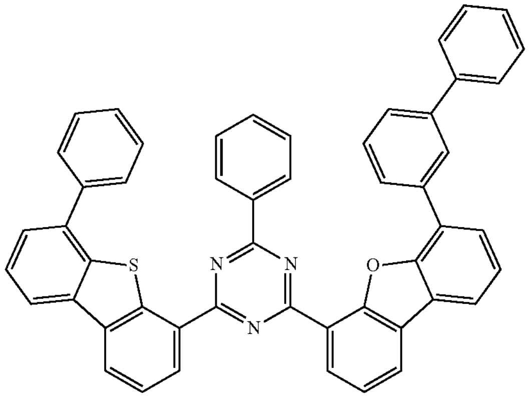
5-4
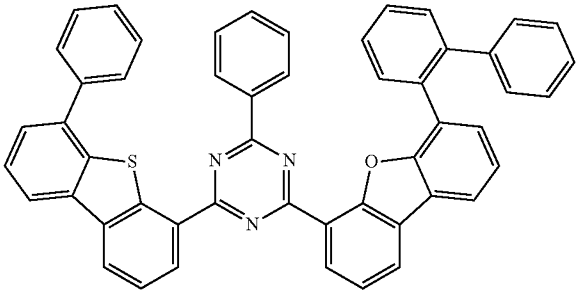
5-5
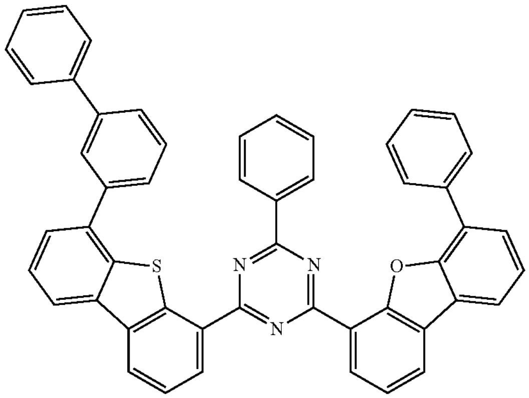
5-6
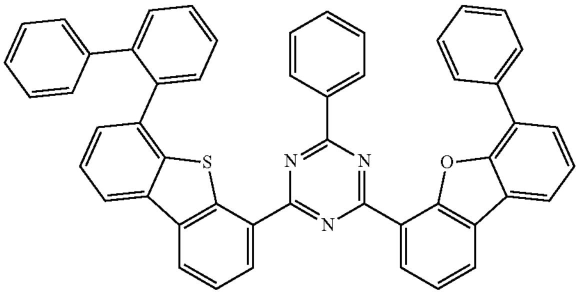
5-7
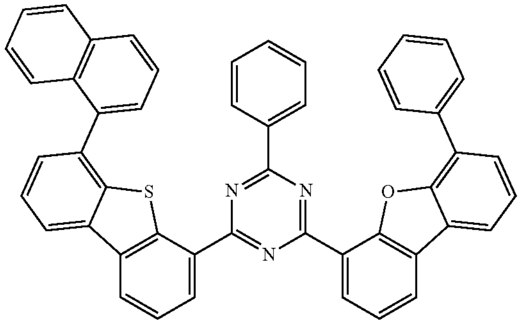
5-8
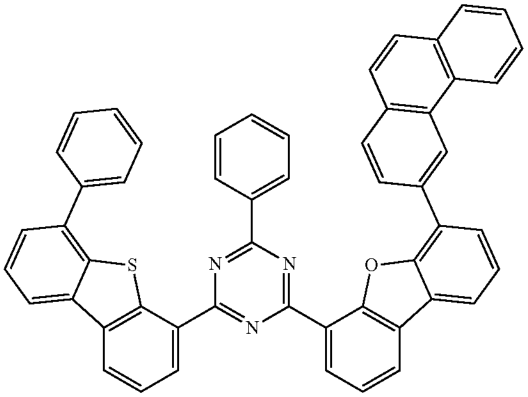

-continued
5-9
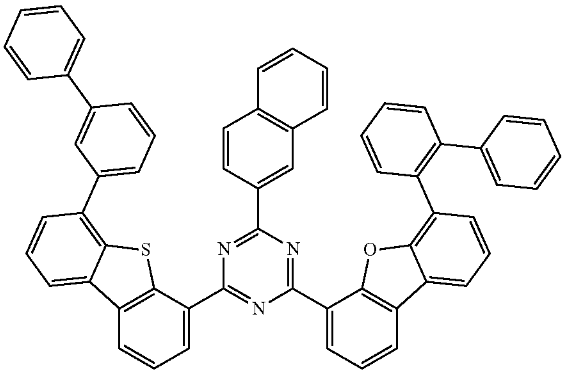
5-10
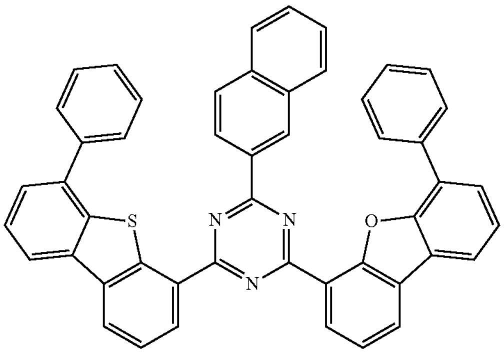
5-11
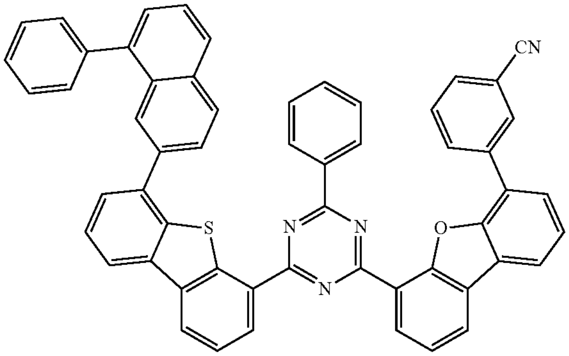
5-12
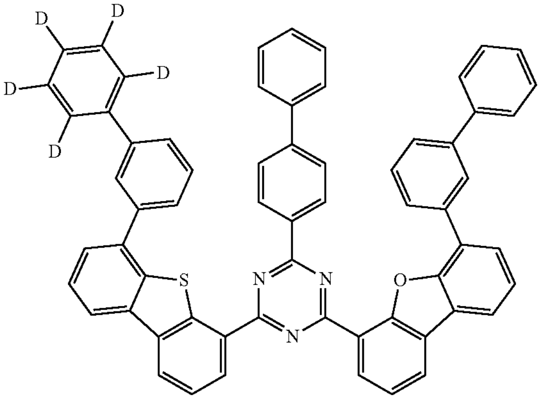
5-13
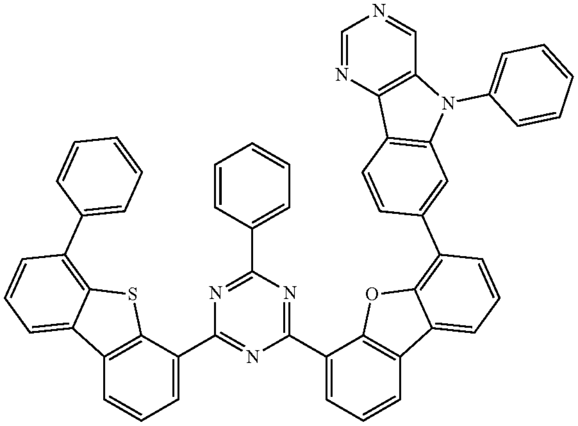
5-14
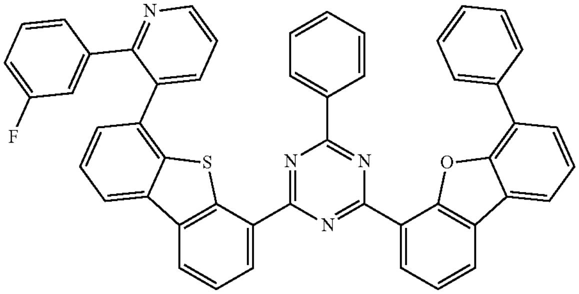
5-15
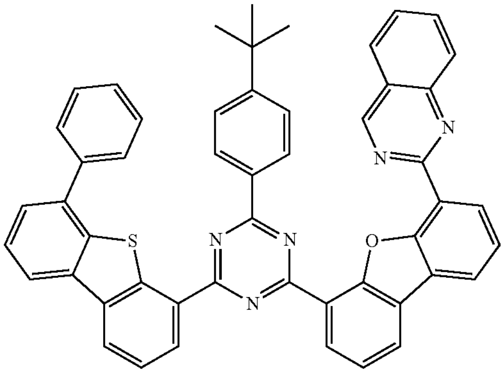
5-16
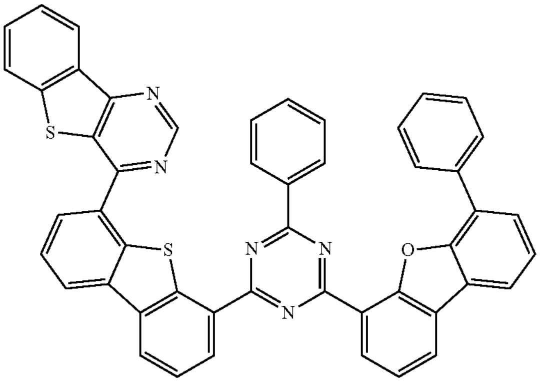

-continued
5-17
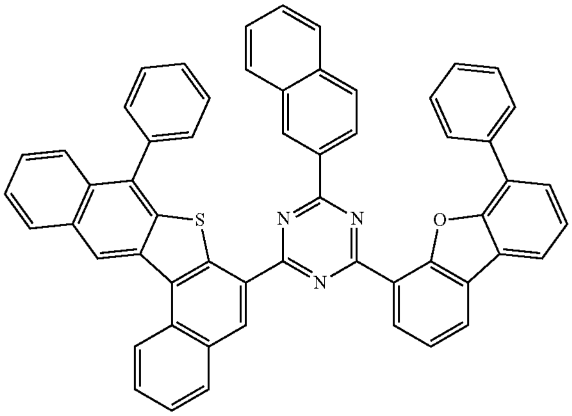
5-18
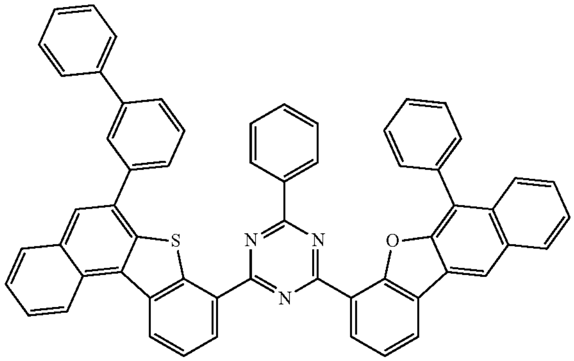
5-19
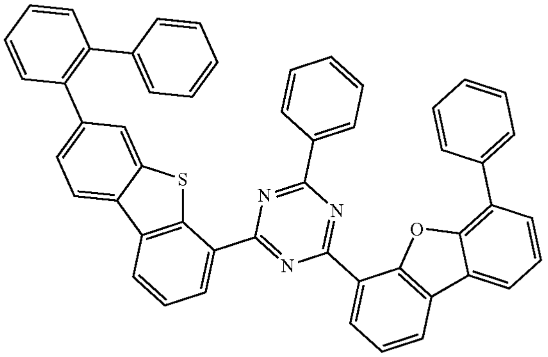
5-20
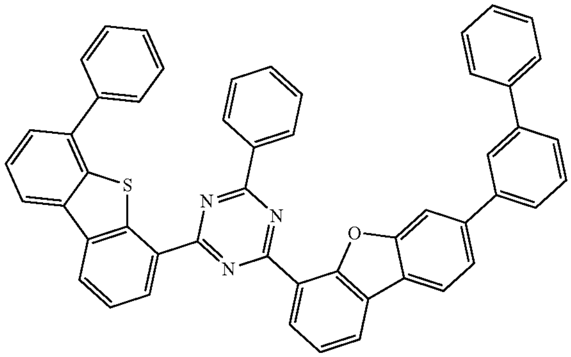
6-1
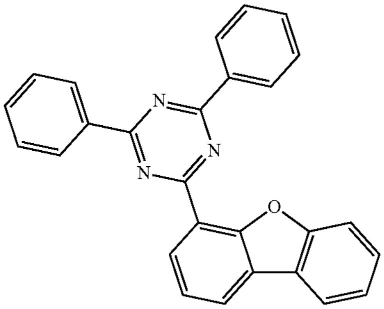
6-2
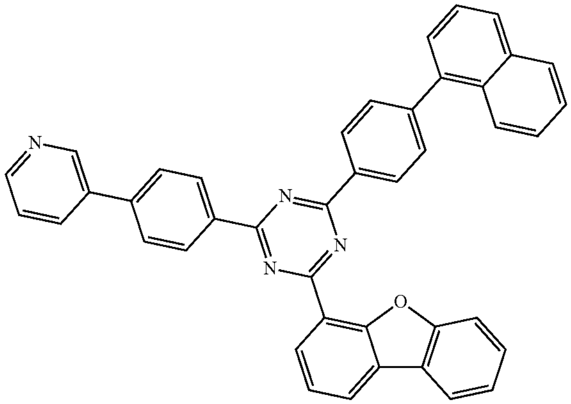

-continued
6-3
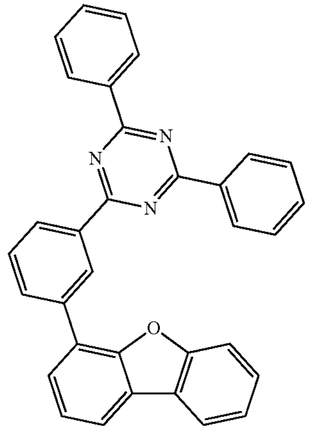
6-4
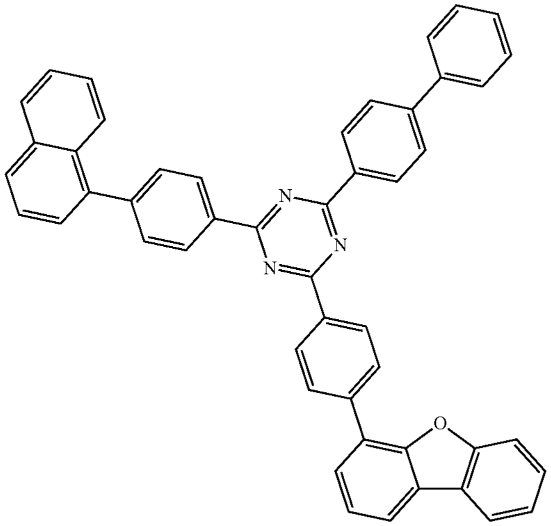
6-5
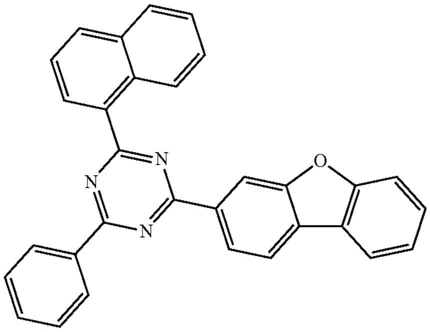
6-6
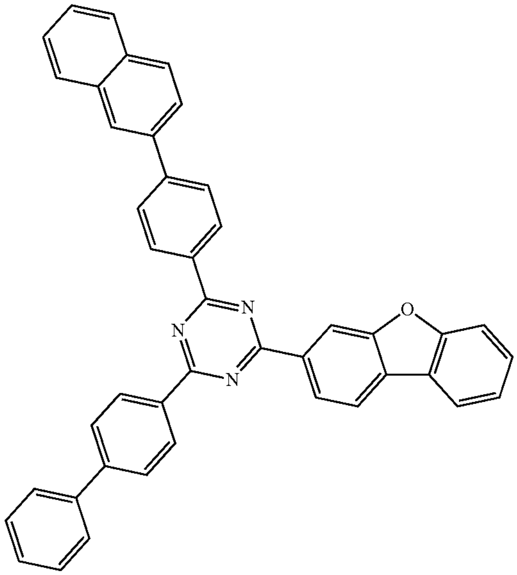
6-7
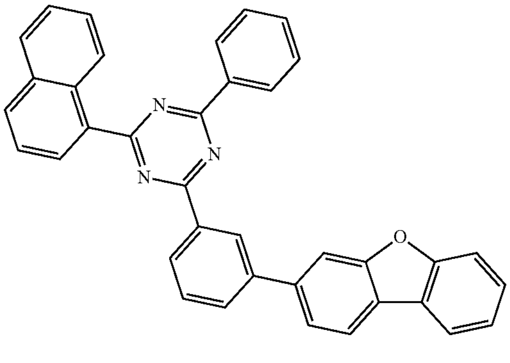
6-8
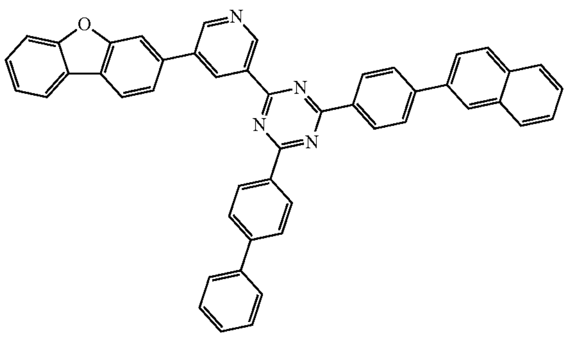

-continued
6-9
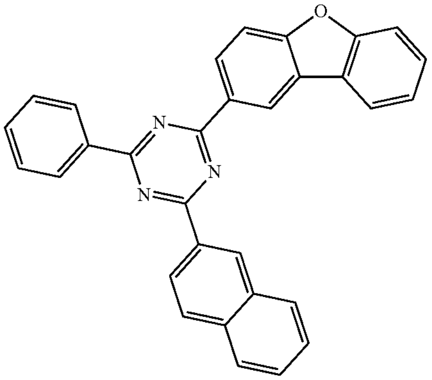
6-10
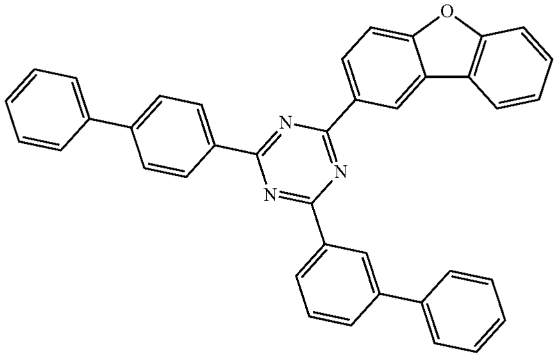
6-11
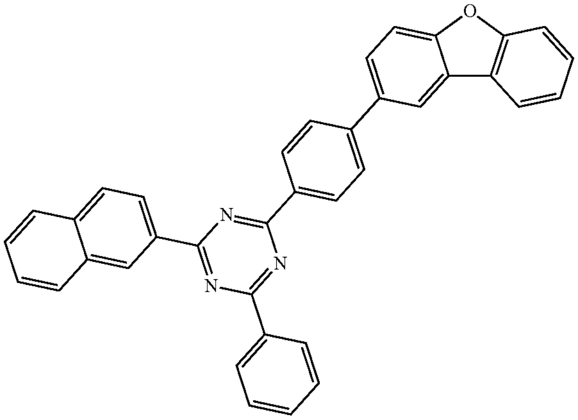
6-12
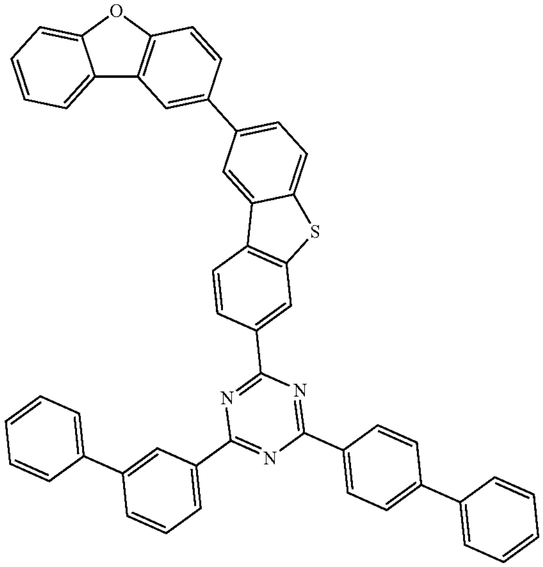
6-13
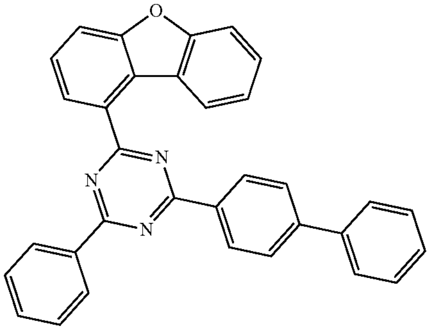
6-14
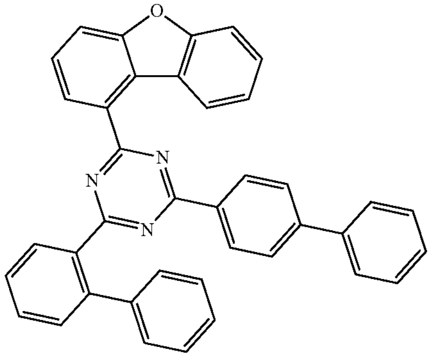

-continued
6-15
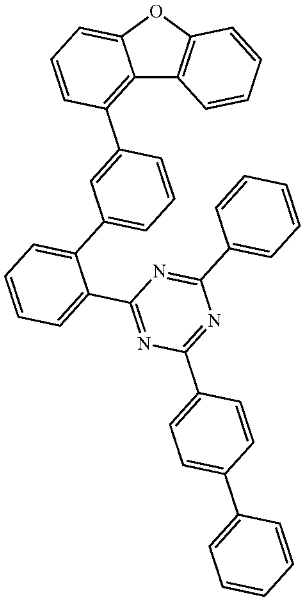
6-16
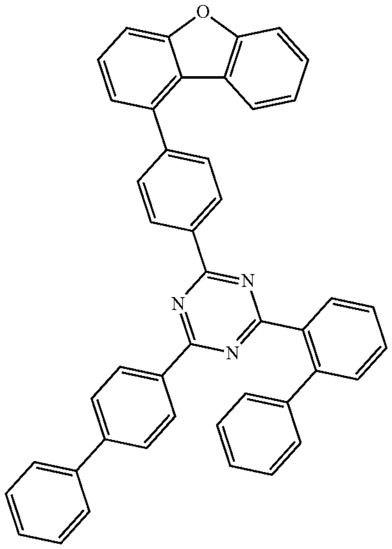
7-1
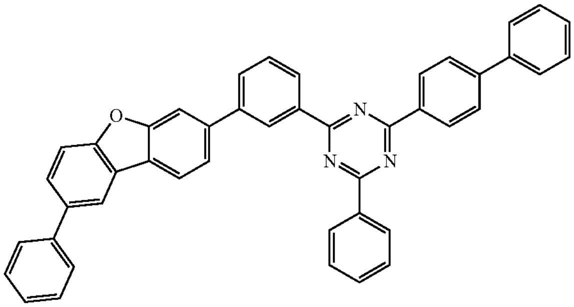
7-2
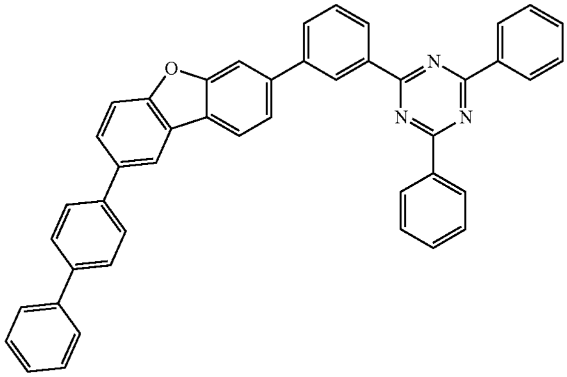
7-3
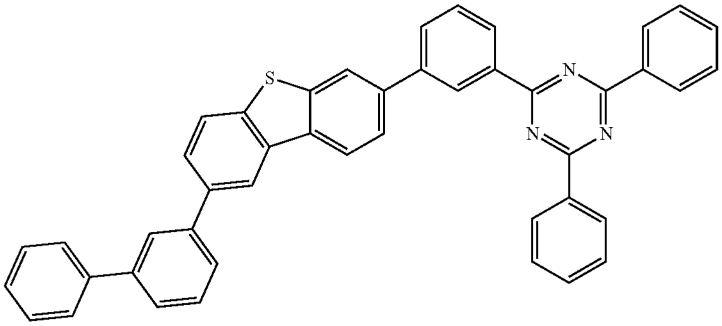

-continued
7-4
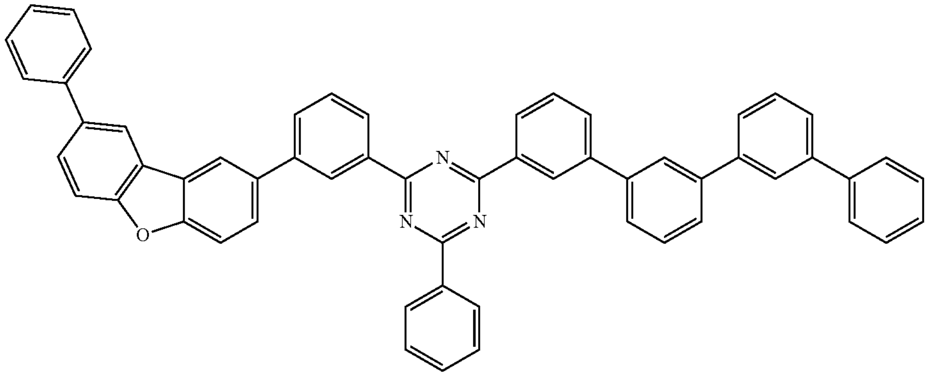
7-5
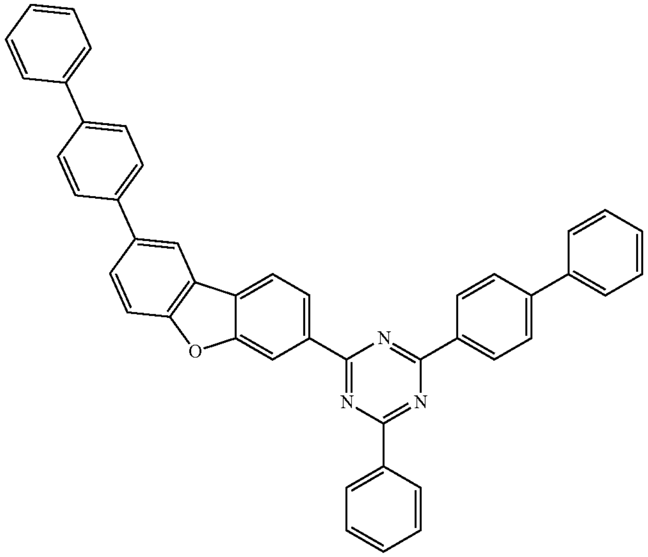
7-6
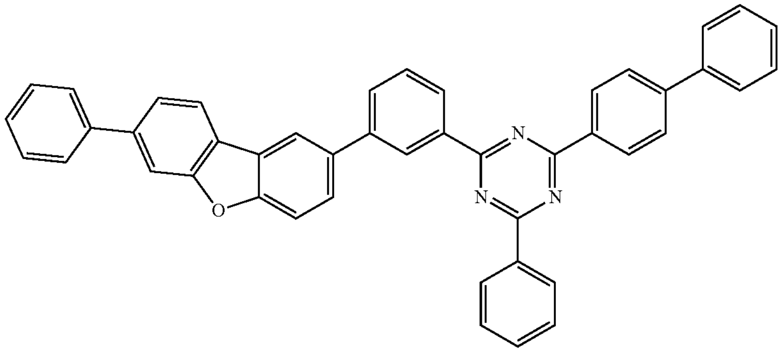

-continued
7-7
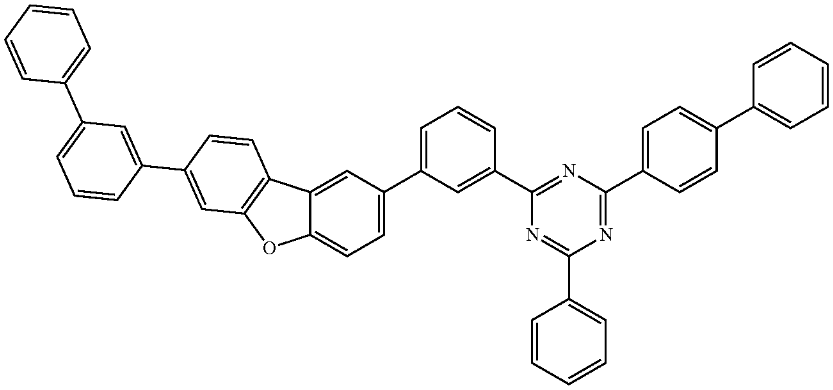
7-8
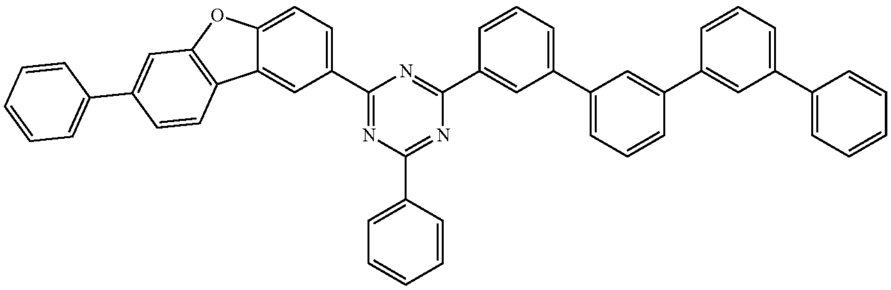
7-9
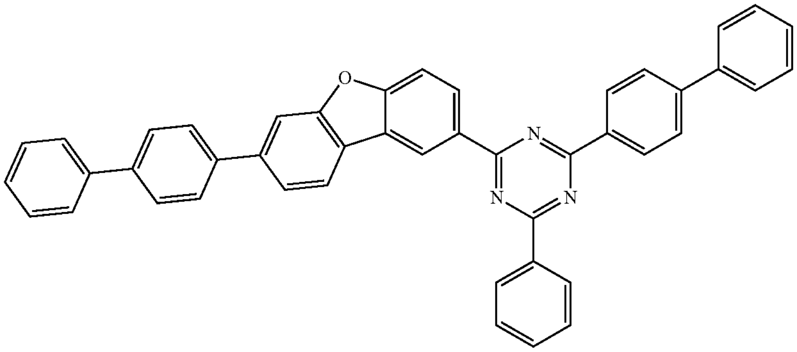
7-10
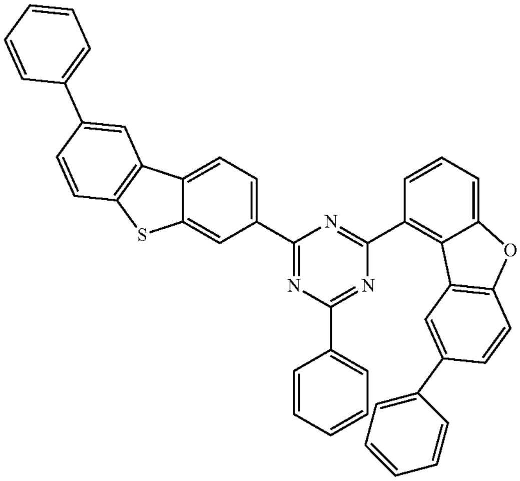
7-11
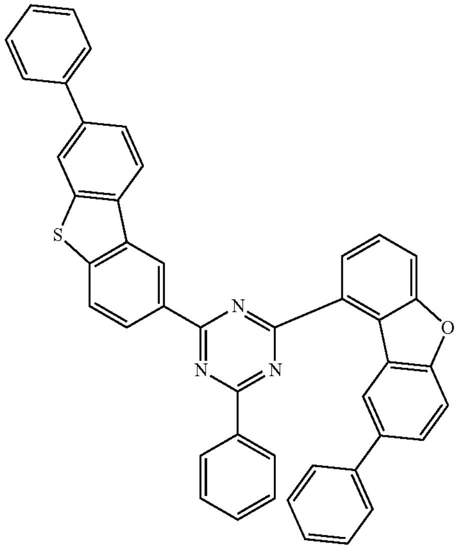

-continued
7-12
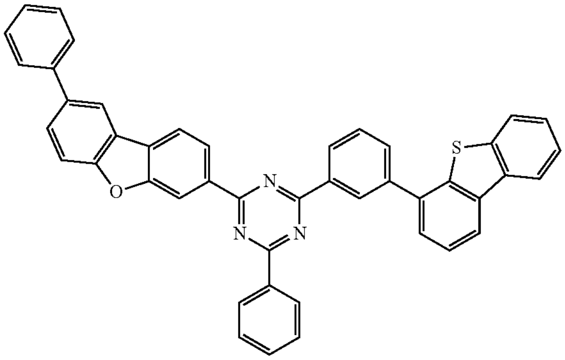
7-13
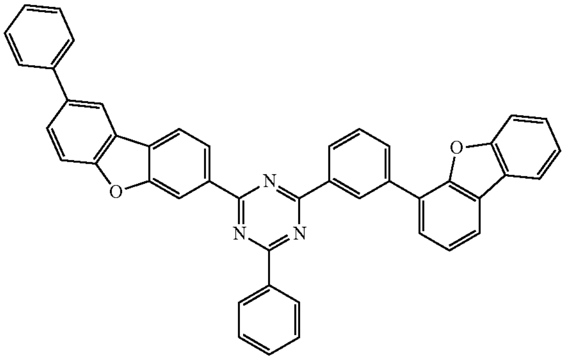
7-14
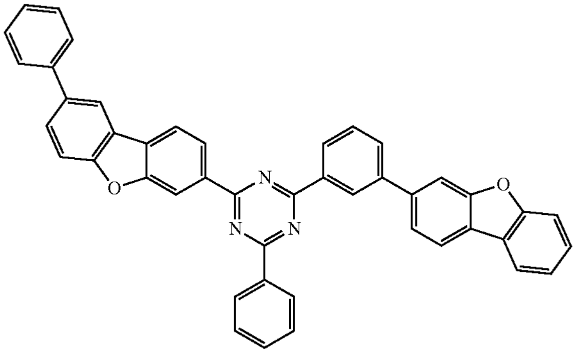
7-15
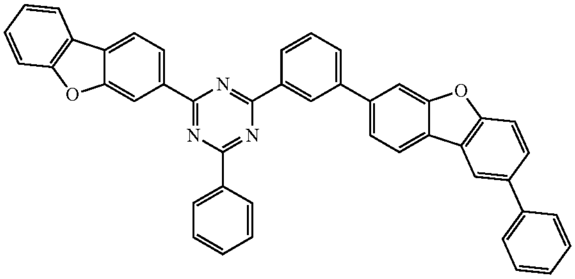
7-16
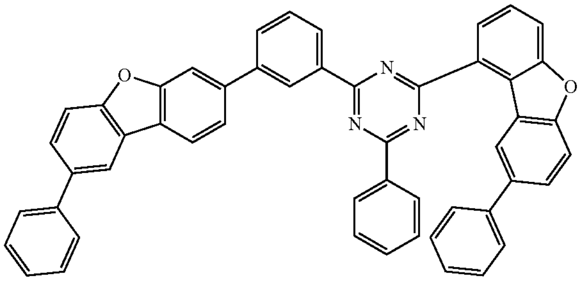
7-17
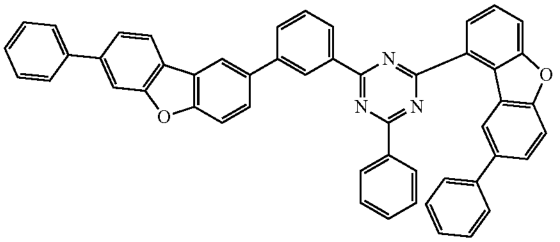
7-18
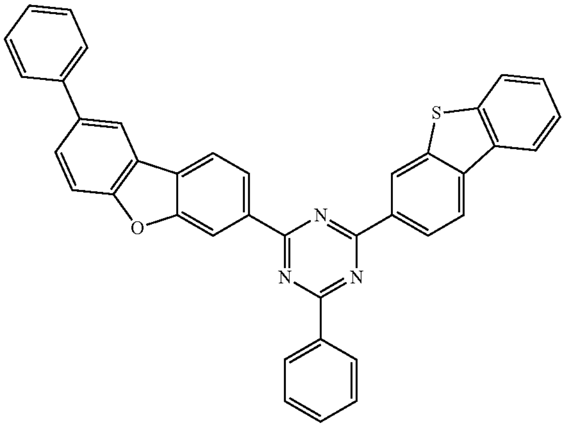
7-19
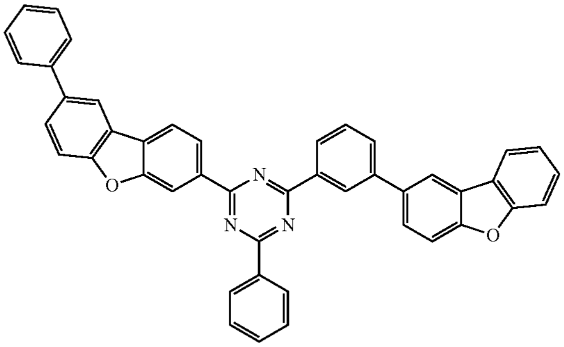

-continued
7-20
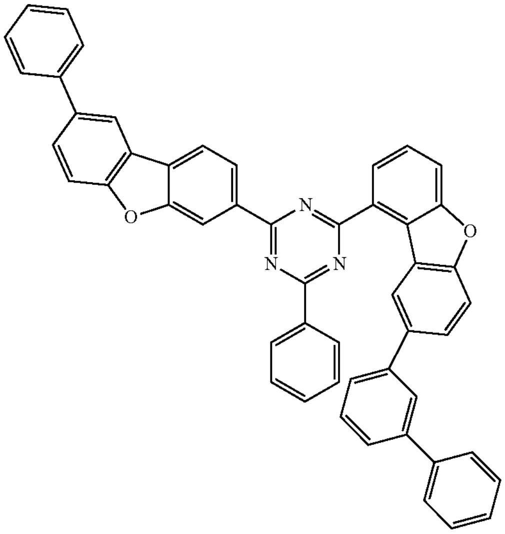
7-21
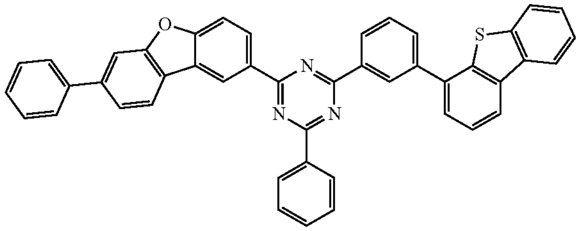
7-22
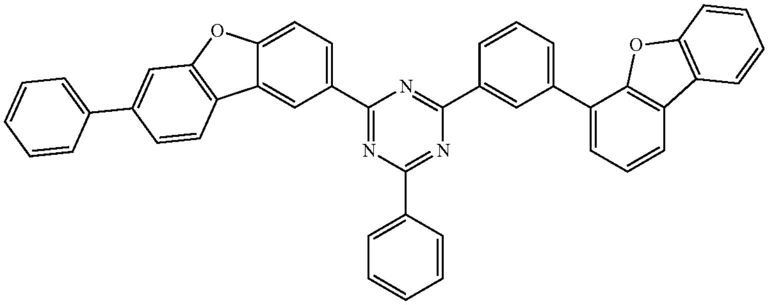
7-23
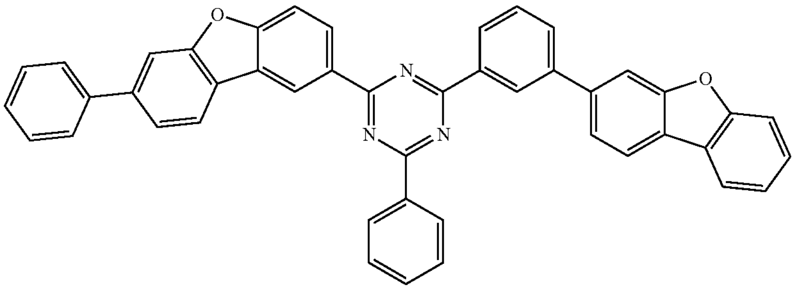
7-24
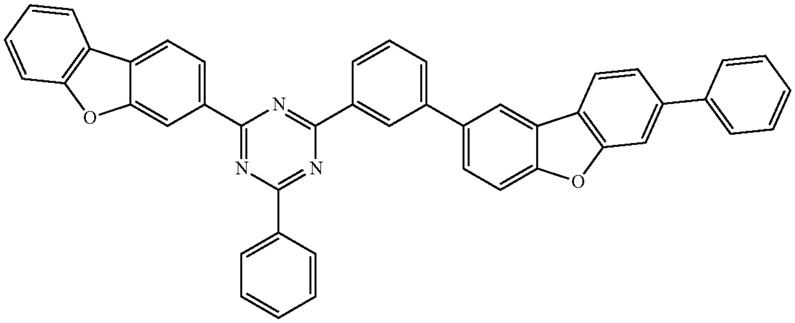

Referring to the FIGURE, the organic electric element (100) according to the present invention includes a first electrode(120) formed on a substrate(110), a second electrode(180), and an organic material layer including the compound represented by Formula 1 between the first electrode(120) and the second electrode(180). Here, the first electrode(120) may be an anode (positive electrode), and the second electrode(180) may be a cathode (negative electrode). In the case of an inverted organic electric element, the first electrode may be a cathode, and the second electrode may be an anode.

The organic material layer may include a hole injection layer(130), a hole transport layer(140), an emitting layer (150), an emitting-auxiliary layer(151), an electron transport layer(160), and an electron injection layer(170) formed in sequence on the first electrode(120). Here, the remaining layers except the emitting layer(150) may not be formed. The organic material layer may further include a hole blocking layer, an electron blocking layer, an emitting-auxiliary layer(151), an electron transport auxiliary layer, a buffer layer(141), etc., and the electron transport layer(160) and the like may serve as a hole blocking layer.

Although not shown, the organic electric element according to the present invention may further include a protective layer formed on at least one side of the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials(mobility, interfacial characteristics, etc.) of each organic material layer is achieved, a long lifespan and high efficiency can be achieved at the same time.

The organic electroluminescent device according to an embodiment of the present invention may be manufactured using a PVD (physical vapor deposition) method. For example, an anode is formed by depositing a metal or a conductive metal oxide or an alloy thereof on a substrate, and after forming an organic material layer including the hole injection layer(130), the hole transport layer(140), the emitting layer(150), the electron transport layer(160) and the electron injection layer(170) thereon, the organic electroluminescent device according to an embodiment of the present invention can be manufactured by depositing a material that can be used as a cathode thereon.

In addition, an emission auxiliary layer(151) may be further formed between the hole transport layer(140) and the emitting layer(150), and an electron transport auxiliary layer may be further formed between the emitting layer(150) and the electron transport layer (160).

Accordingly, the present invention includes at least one hole transport layer between the first electrode and the emitting layer, wherein the hole transport layer includes a hole transport layer, an emitting auxiliary layer, or both, and wherein the hole transport layer includes the compound represented by Formula 1.

Also, the compounds represented by Formula 1 and by Formula 2 are mixed in a ratio of any one of 1:9 to 9:1 to be included in the emitting layer, preferably mixed in a ratio of 1:9 to 5:5, more preferably in a ratio of 2:8 or 3:7 to be included in the emitting layer.

The present invention may further include a light efficiency enhancing layer formed on at least one of the opposite side to the organic material layer among one side of the first electrode, or one of the opposite side to the organic material layer among one side of the second electrode. Also, the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

The organic electric element according to an embodiment of the present invention may be a front emission type, a back emission type, or a both-sided emission type, depending on the material used.

WOLED (White Organic Light Emitting Device) is easy to realize high resolution and excellent processability, while there is an advantage that can be manufactured using the existing LCD color filter technology. Various structures for a white organic light emitting device mainly used as a backlight device have been proposed and patented. Typically, R(Red), G(Green), B(Blue) light emitting parts are arranged in a side-by-side manner, and R, G, B light emitting layers are stacked up and down, and blue (B) electroluminescence by organic emitting layer and, there is a color conversion material (CCM) method using photo-luminescence of an inorganic phosphor using light from this, and the present invention may be applied to such WOLED.

The present invention also provides an electronic device comprising a display device including the organic electric element; and a control unit for driving the display device. According to another aspect, the present invention provides an electronic device wherein the organic electric element is at least one of an OLED, an organic solar cell, an organic photo conductor, an organic transistor and an element for monochromic or white illumination. At this time, the electronic device may be a current or future wired/wireless communication terminal, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, Synthesis Examples of the compound represented by Formula 1 and Formula 2 according to the present invention and preparation examples of the organic electric element of the present invention will be described in detail by way of example, but are not limited to the following examples of the invention.

Synthesis Example 1

The final products 1 represented by Formula 1 of the present invention can be synthesized by reaction between Sub 1 and Sub 2 as illustrated in the following Reaction Scheme 1, but is not limited thereto. $X^1$, A, B, $L^1$, $L^2$, $Ar^1$ to $Ar^4$ are the same as defined in Formula 1, and Hal1 is Br or Cl.

<Reaction Scheme 1>

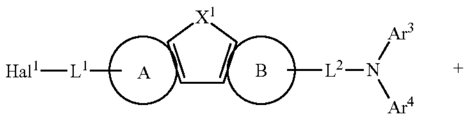

Sub 1

-continued
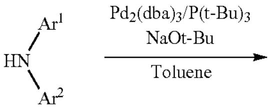
Sub 2
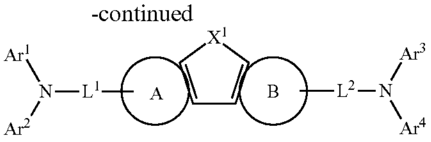
Final Product 1
I. Synthesis Examples of Sub 1
Sub 1 of Reaction Scheme 1 is synthesized by the reaction path of Reaction Scheme 2 below, but is not limited thereto.
<Reaction Scheme 2>
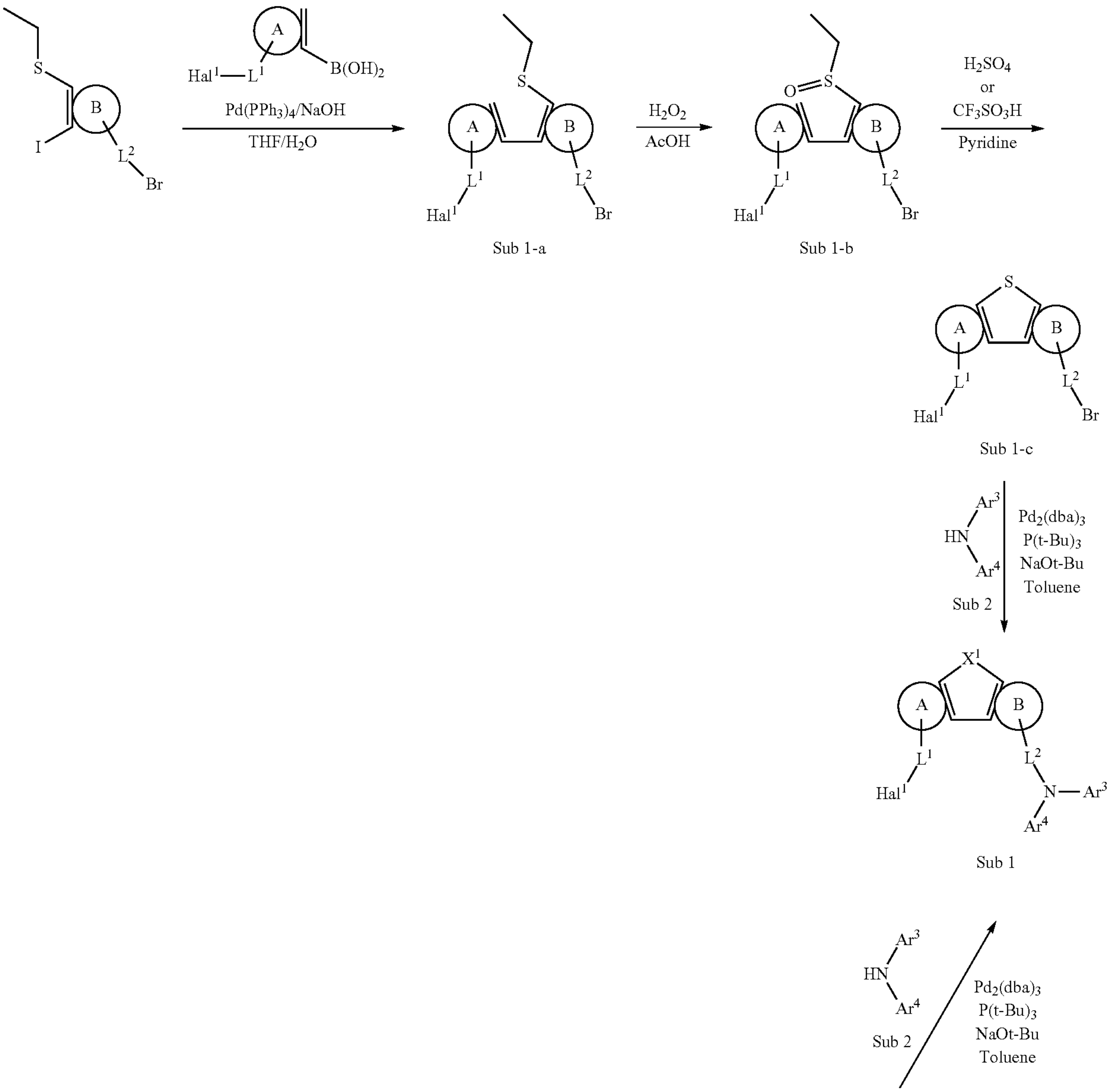
Sub 1-a
Sub 1-b
Sub 1-c
Sub 2
Sub 1
Sub 2

-continued

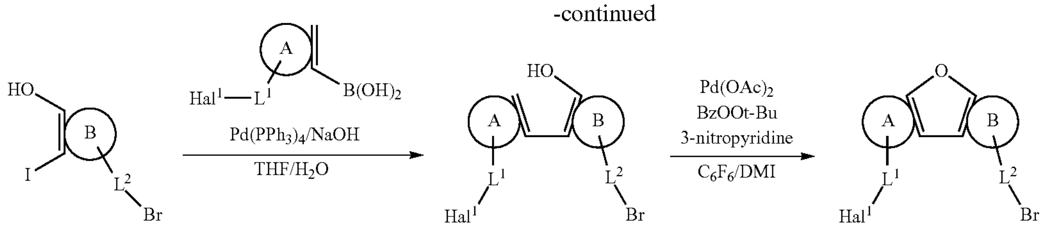

Sub 1-d

Sub 1-e

1. Synthesis Examples of Sub 1-1

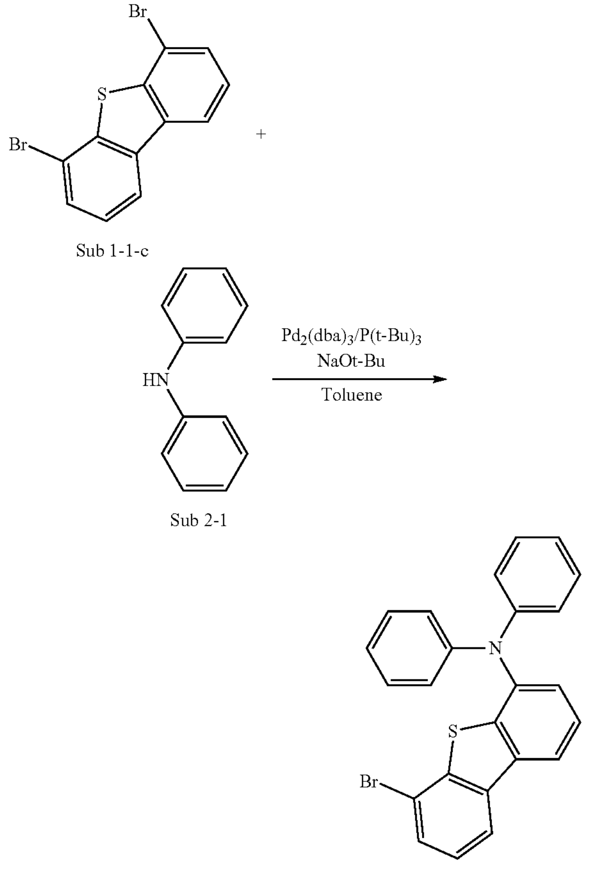

Sub 1-1-c

Sub 2-1

Sub 1-1

Starting material Sub 2-1 (15.22 g, 89.94 mmol) was added in a round bottom flask and dissolved in toluene (750 mL), Sub 1-1-c (CAS Registry Number: 669773-34-6) (46.14 g, 134.91 mmol), $Pd_2(dba)_3$ (2.47 g, 2.70 mmol), $P(t\text{-}Bu)_3$ (1.46 g, 7.19 mmol), NaOt-Bu (25.93 g, 269.81 mmol) were added and stirred at 80° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 23.61 g of the product. (yield:61%)

2. Synthesis Examples of Sub 1-3

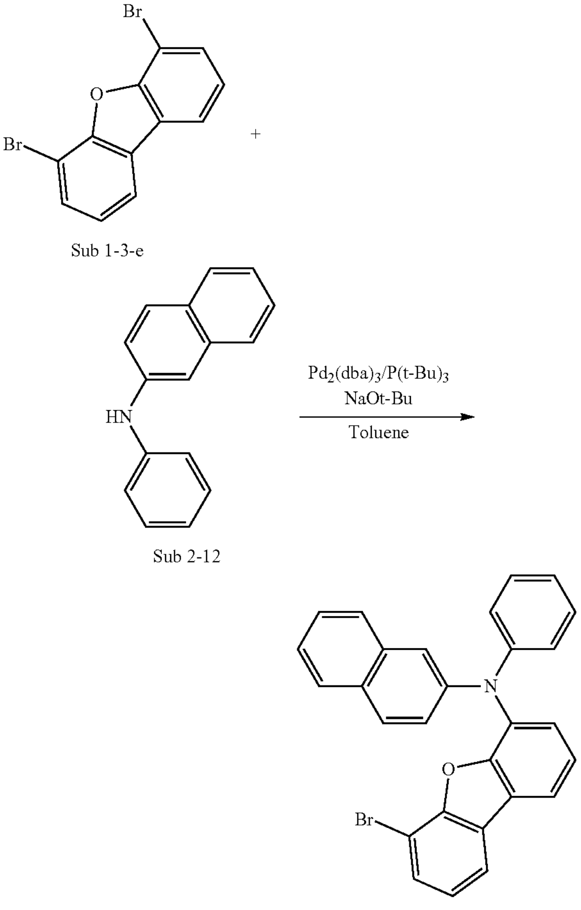

Sub 1-3-e

Sub 2-12

Sub 1-3

To the starting material Sub 2-12 (13.94 g, 63.57 mmol), Sub 1-3-e (CAS Registry Number: 201138-91-2) (31.08 g, 95.35 mmol), $Pd_2(dba)_3$ (1.75 g, 1.91 mmol) $P(t\text{-}Bu)_3$ (1.03 g, 5.09 mmol), NaOt-Bu (18.33 g, 190.71 mmol), toluene (530 ml) were added, the same procedure as described in the synthesis method of Sub 1-1 was carried out to obtain 19.78 g of the product. (yield:67%).

3. Synthesis Examples of Sub 1-5

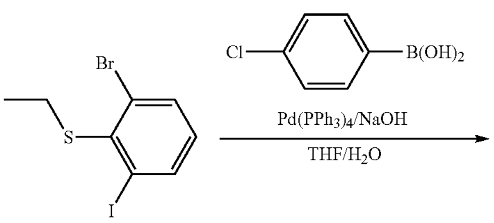

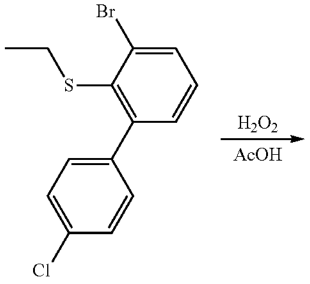

Sub 1-5-a

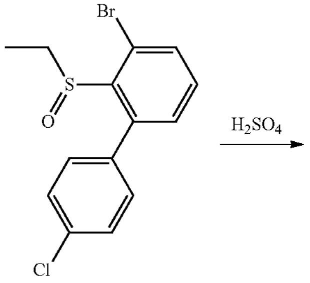

Sub 1-5-b

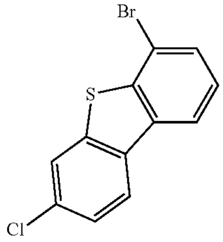

Sub 1-5-c

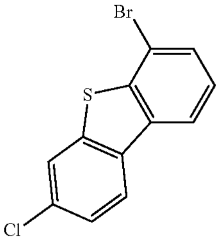

\+

Sub 1-5-c

-continued

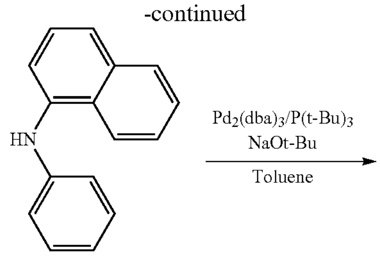

Sub 2-11

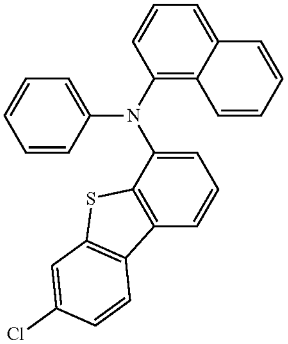

Sub 1-5

(1) Synthesis of Sub 1-5-a

Starting material (2-bromo-6-iodophenyl)(ethyl)sulfane (9.94 g, 28.98 mmol) was added in a round bottom flask and dissolved in THF (100 mL), (4-chlorophenyl)boronic acid (4.53 g, 28.98 mmol), $Pd(PPh_3)_4$ (1.00 g, 0.87 mmol), NaOH (2.32 g, 57.96 mmol), water (50 ml) were added and stirred at 80° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 8.55 g of the product. (yield:90%)

(2) Synthesis of Sub 1-5-b

To Sub 1-5-a (8.55 g, 26.09 mmol) obtained in the above synthesis, acetic acid (90 ml) was added, 35% hydrogen peroxide (H2O2) (2.66 g, 78.28 mmol) was added and stirred at room temperature. When the reaction was completed, after neutralization with NaOH aqueous solution, extraction was performed with EA and washed with water. The organic layer was dried over $MgSO_4$ and concentrated. The resulting compound was separated by silicagel column chromatography to obtain 8.70 g of the product. (yield:97%)

(3) Synthesis of Sub 1-5-c

To Sub 1-5-b (8.70 g, 25.32 mmol) obtained in the above synthesis, sulfuric acid (H2SO4) (50 ml) was added and stirred at room temperature. When the reaction was completed, after neutralization with NaOH aqueous solution, extraction was performed with MC and washed with water. The organic layer was dried over $MgSO_4$ and concentrated. The resulting compound was separated by silicagel column chromatography to obtain 7.16 g of the product. (yield: 95%)

(4) Synthesis of Sub 1-5

The obtained Sub 1-5-c (7.16 g, 24.06 mmol) was added in a round bottom flask and dissolved in toluene (240 mL), Sub 2-11 (5.28 g, 24.06 mmol), $Pd_2(dba)_3$ (0.66 g, 0.72 mmol), $P(t-Bu)_3$ (0.49 g, 2.41 mmol), NaOt-Bu (4.62 g, 48.12 mmol) were added and stirred at 80° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 8.08 g of the product. (yield:77%)

4. Synthesis Examples of Sub 1-17

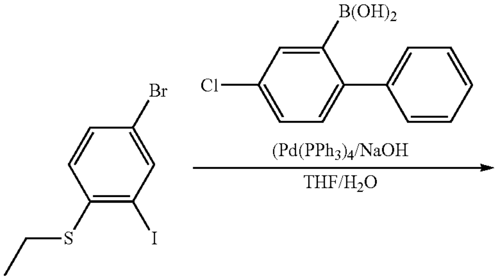

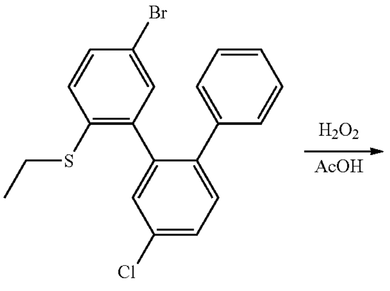

Sub 1-17-a

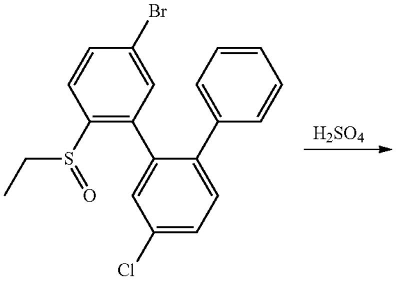

Sub 1-17-b

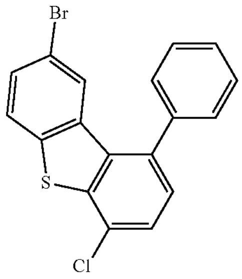

Sub 1-17-c

-continued

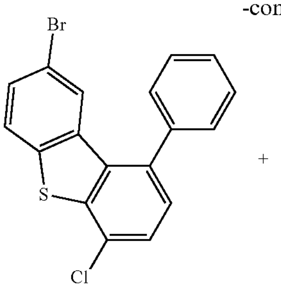

Sub 1-17-c

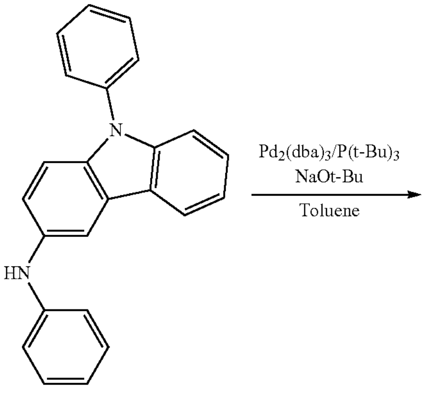

Sub 2-78

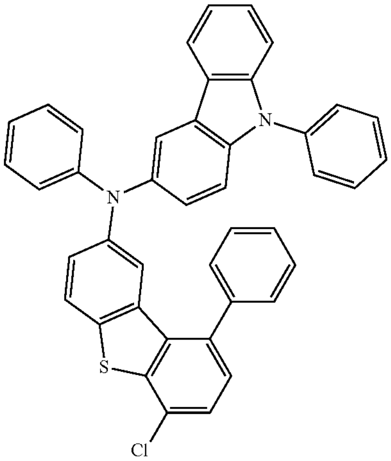

Sub 1-17

(1) Synthesis of Sub 1-17-a

In the starting material (4-bromo-2-iodophenyl)(ethyl) sulfane (10.65 g, 31.05 mmol), (4-chloro-[1,1'-biphenyl]-2-yl)boronic acid (7.22 g, 31.05 mmol)), Pd(PPh3)4 (1.08 g, 0.93 mmol), NaOH (2.48 g, 62.10 mmol), THF (100 ml), water (50 ml) were added, and the same procedure as described in the synthesis method of Sub 1-5-a was carried out to obtain 9.90 g of the product. (yield:79%).

(2) Synthesis of Sub 1-17-b

Sub 1-17-a (9.90 g, 24.52 mmol), acetic acid (80 ml), 35% hydrogen peroxide (H2O2) (2.50 g, 73.56 mmol) obtained in the above synthesis were used in the synthesis method of Sub 1-5-b. Thus, the product 9.78 g (yield:95%) was obtained.

(3) Synthesis of Sub 1-17-c

Sub 1-17-b (9.78 g, 23.30 mmol) and sulfuric acid (H2SO4) (50 ml) obtained in the above synthesis were used in the synthesis method of Sub 1-5-c. Thus, the product 7.84 g (yield:90%) was obtained.

(4) Synthesis of Sub 1-17

To Sub 1-17-c (7.84 g, 20.98 mmol) obtained in the above synthesis, Sub 2-78 (7.02 g, 20.98 mmol), Pd2(dba)3 (0.58 g, 0.63 mmol) P(t-Bu)3 (0.42 g, 2.10 mmol), NaOt-Bu (4.03 g, 41.96 mmol), and toluene (210 ml) were added, and the same procedure as described in the synthesis method of Sub 1-5 was carried out to obtain 10.79 g of the product. (yield:82%).

5. Synthesis Examples of Sub 1-82

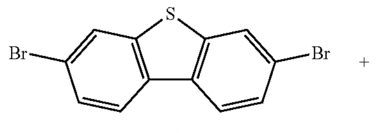

Sub 1-82-c

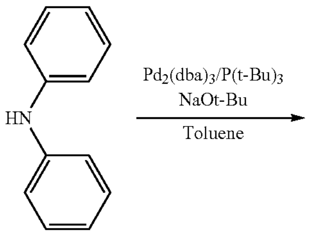

Sub 2-1

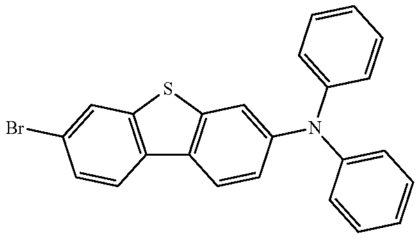

Sub 1-82

In the starting material Sub 2-1 (16.48 g, 97.38 mmol), Sub 1-82-c (CAS Registry Number: 83834-10-0) (49.96 g, 146.07 mmol), Pd2(dba)3 (2.68 g, 2.92 mmol) P(t-Bu)3 (1.58 g, 7.79 mmol), NaOt-Bu (28.08 g, 292.15 mmol), toluene (810 ml) were added and the same procedure as described in the synthesis method of Sub 1-1 was carried out to obtain 26.40 g of the product. (yield:63%).

6. Synthesis Examples of Sub 1-102

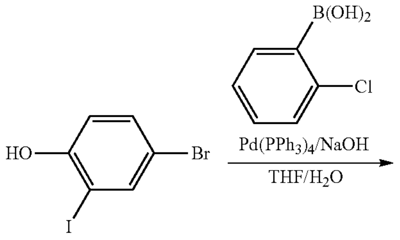

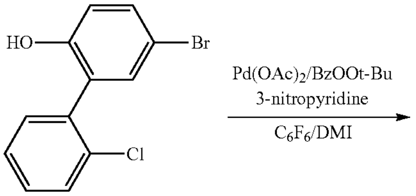

Sub 1-102-d

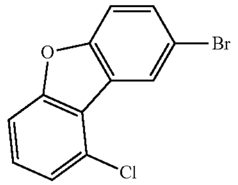

Sub 1-102-e

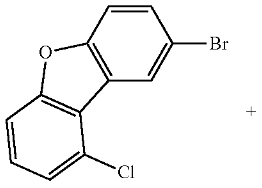

Sub 1-102-e

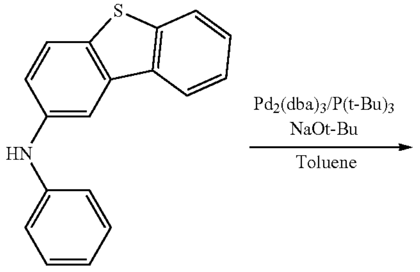

Sub 2-29

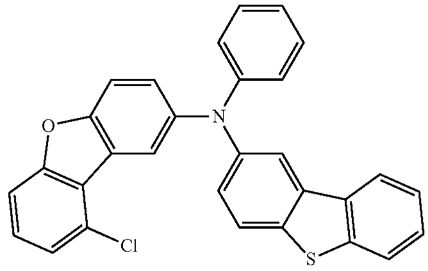

Sub 1-102

(1) Synthesis of Sub 1-102-d

In the starting material 4-bromo-2-iodophenol (39.85 g, 133.32 mmol), (2-chlorophenyl)boronic acid (20.85 g, 133.32 mmol), $Pd(PPh_3)_4$ (4.62 g, 4.00 mmol), NaOH (10.67 g, 266.64 mmol), THF (440 ml), water(220 ml) were added and the same procedure as described in the synthesis method of Sub 1-5-a was carried out to obtain 28.73 g of the product. (yield:76%).

(2) Synthesis of Sub 1-102-e

To Sub 1-102-d (28.73 g, 101.32 mmol) obtained in the above synthesis, $Pd(OAc)_2$ (2.27 g, 10.13 mmol), 3-nitropyridine (1.26 g, 10.13 mmol), BzOOtBu (tert-butyl peroxybenzoate) (39.36 g, 202.65 mmol), $C_6F_6$ (hexafluorobenzene) (150 ml), DMI (N,N'-dimethylimidazolidinone) (100 ml) were added and refluxed at 90° C. for 3 hours. When the reaction is completed, the temperature of the reaction product is cooled to room temperature, extracted with EA, and washed with water. The organic layer was dried over $MgSO_4$ and concentrated, and the resulting organic material was separated using a silicagel column to obtain 13.69 g (48%) of the product.

(3) Synthesis of Sub 1-102

To Sub 1-102-e (13.69 g, 48.63 mmol) obtained in the above synthesis, Sub 2-29 (13.39 g, 48.63 mmol), $Pd_2(dba)_3$ (1.34 g, 1.46 mmol) $P(t\text{-}Bu)_3$ (0.98 g, 4.86 mmol), NaOt-Bu (9.35 g, 97.25 mmol), toluene (490 ml) were added, and the same procedure as described in the synthesis method of Sub 1-5 was carried out to obtain 19.67 g of the product. (yield:85%).

7. Synthesis Examples of Sub 1-104

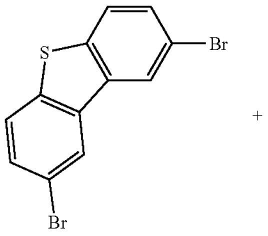

Sub 1-104-c

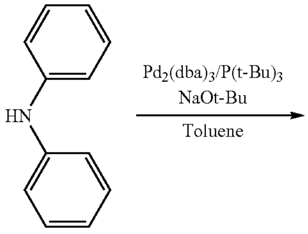

Sub 2-1

-continued

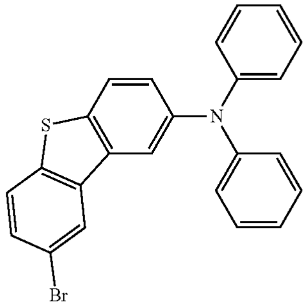

Sub 1-104

In the starting material Sub 2-1 (9.15 g, 54.04 mmol), Sub 1-104-c (CAS Registry Number: 31574-87-5) (27.73 g, 81.07 mmol), $Pd_2(dba)_3$ (1.48 g, 1.62 mmol) $P(t\text{-}Bu)_3$ (0.87 g, 4.32 mmol), NaOt-Bu (15.58 g, 162.13 mmol), toluene (450 ml) were added and the same procedure as described in the synthesis method of Sub 1-1 was carried out to obtain 15.12 g of the product. (yield:65%).

8. Synthesis Examples of Sub 1-112

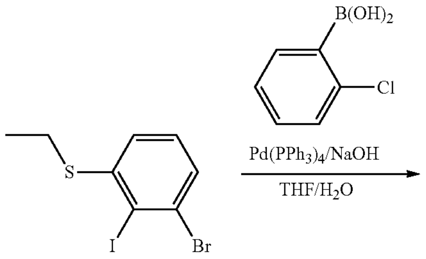

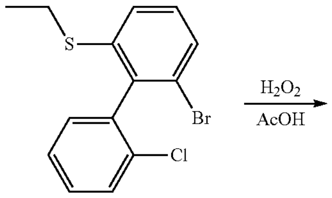

Sub 1-112-a

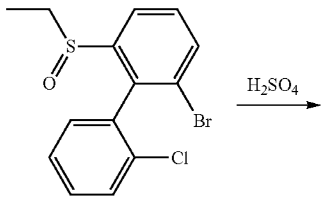

Sub 1-112-b

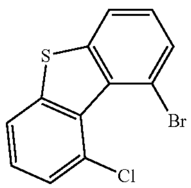

Sub 1-112-c

-continued

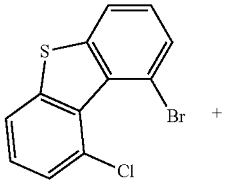

Sub 1-112-c

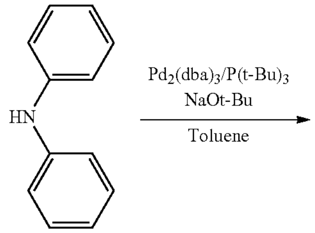

Sub 2-1

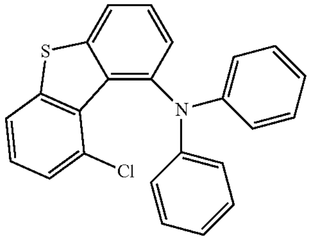

Sub 1-112

(1) Synthesis of Sub 1-112-a

In the starting material (3-bromo-2-iodophenyl)(ethyl) sulfane (12.73 g, 37.11 mmol), (2-chlorophenyl)boronic acid (5.80 g, 37.11 mmol), $Pd(PPh_3)_4$ (1.29 g, 1.11 mmol), NaOH (2.97 g, 74.22 mmol), THF (120 ml), water (60 ml) were added and the same procedure as described in the synthesis method of Sub 1-5-a was carried out to obtain 9.48 g of the product. (yield:78%).

(2) Synthesis of Sub 1-112-b

Sub 1-112-a (9.48 g, 28.93 mmol) obtained in the above synthesis, acetic acid (95 ml), 35% hydrogen peroxide ($H_2O_2$) (2.95 g, 86.80 mmol) were added, and the same procedure as described in the synthesis method of Sub 1-5-b was carried out to obtain 9.74 g of the product. (yield:98%).

(3) Synthesis of Sub 1-112-c

Sub 1-112-b (9.74 g, 28.34 mmol), sulfuric acid (H2SO4) (60 ml) obtained in the above synthesis were added, and the same procedure as described in the synthesis method of Sub 1-5-c was carried out to obtain 7.76 g of the product. (yield:92%).

(4) Synthesis of Sub 1-112

To Sub 1-112-c (7.76 g, 26.08 mmol) obtained in the above synthesis, Sub 2-1 (4.41 g, 26.08 mmol), $Pd_2(dba)_3$ (0.72 g, 0.78 mmol) $P(t\text{-}Bu)_3$ (0.53 g, 2.61 mmol), NaOt-Bu (5.01 g, 52.15 mmol), toluene (260 ml) were added, and the same procedure as described in the synthesis method of Sub 1-5 was carried out to obtain 5.84 g of the product. (yield: 58%).

The compound belonging to Sub 1 may be a compound as follows, but is not limited thereto, and Table 1 shows FD-MS (Field Desorption-Mass Spectrometry) values of some compounds belonging to Sub 1.

Sub 1-1

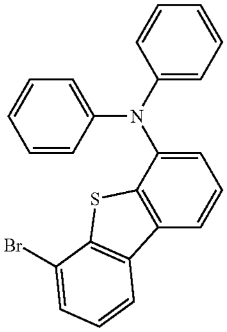

Sub 1-2

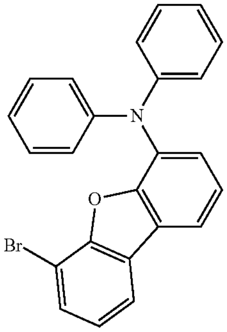

Sub 1-3

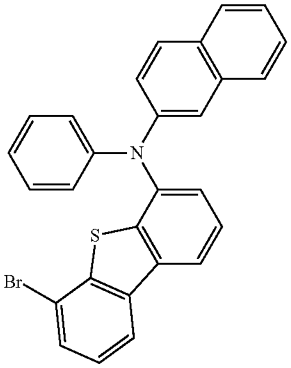

Sub 1-4

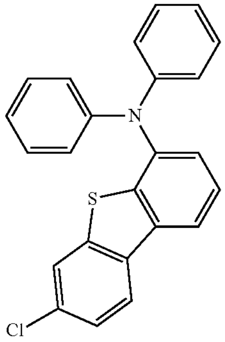

-continued
Sub 1-5
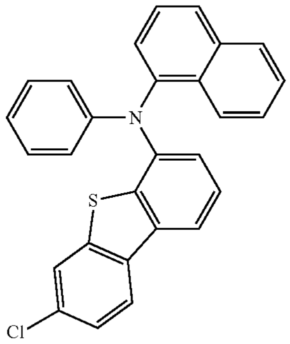
Sub 1-6
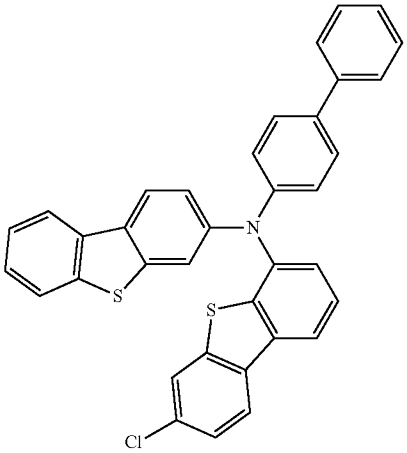
Sub 1-7
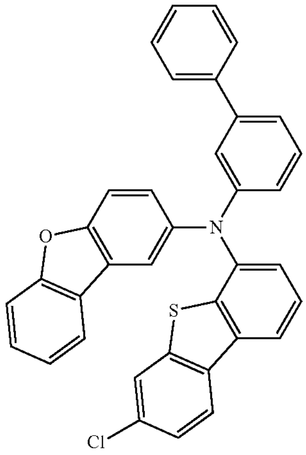
-continued
Sub 1-8
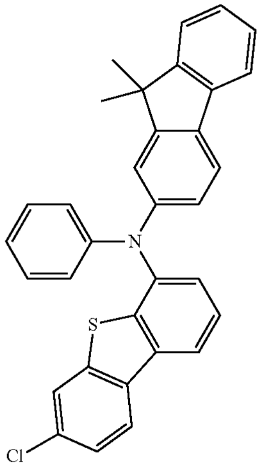
Sub 1-9
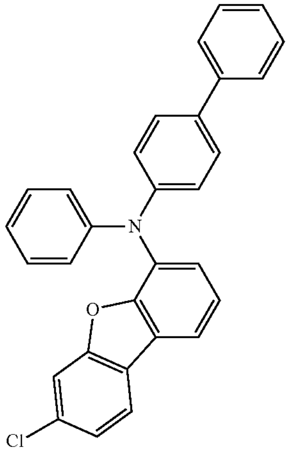
Sub 1-10
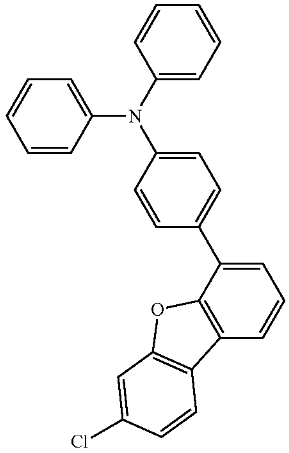

-continued
Sub 1-11
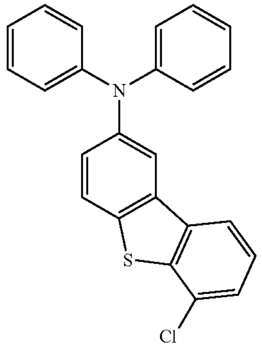
Sub 1-12
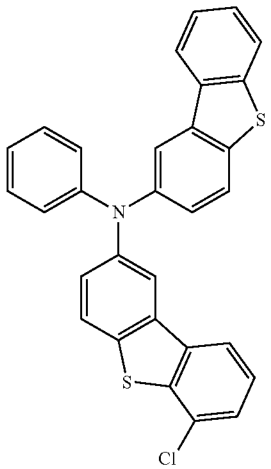
Sub 1-13
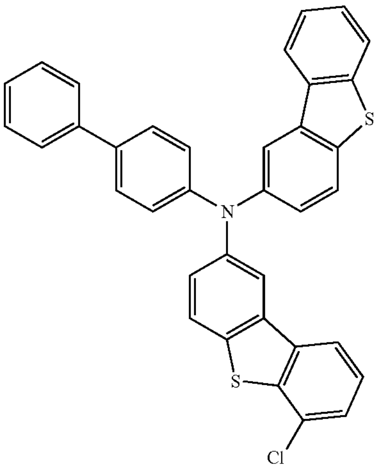
-continued
Sub 1-14
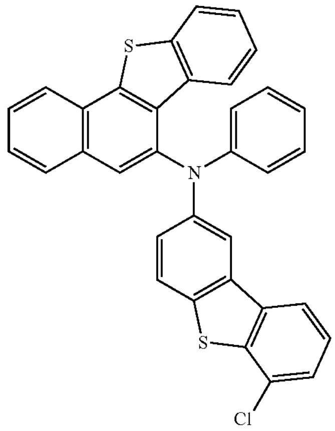
Sub 1-15
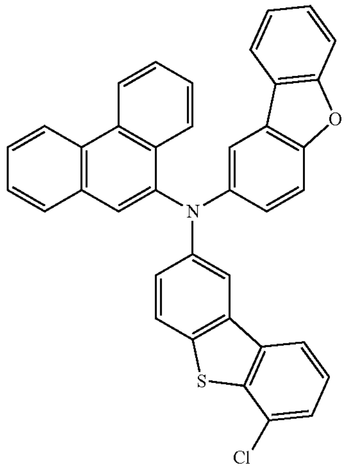
Sub 1-16
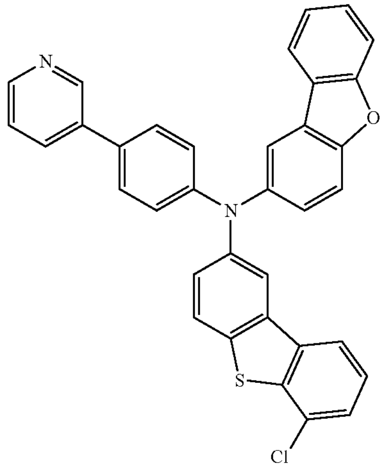

-continued
Sub 1-17
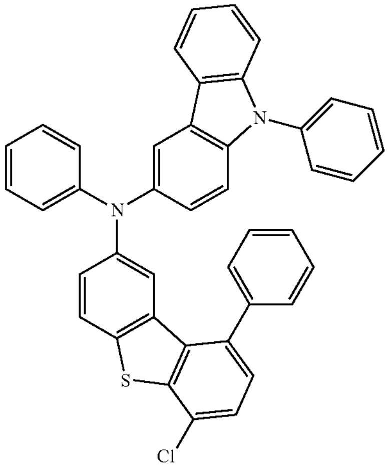
Sub 1-18
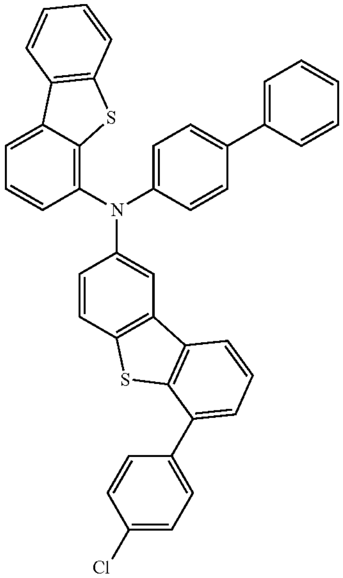
Sub 1-19
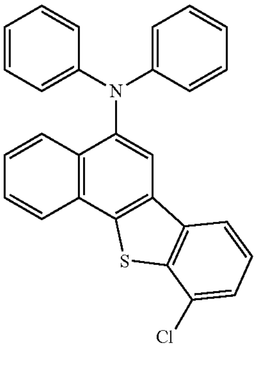
-continued
Sub 1-20
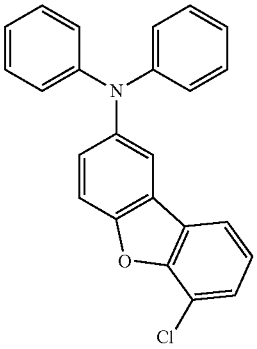
Sub 1-21
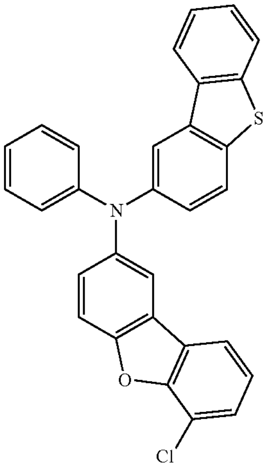
Sub 1-22
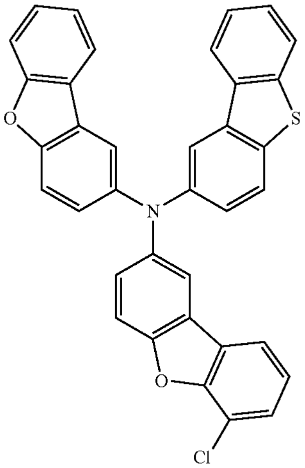

-continued
Sub 1-23
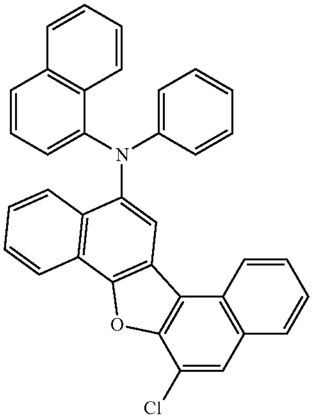
Sub 1-24
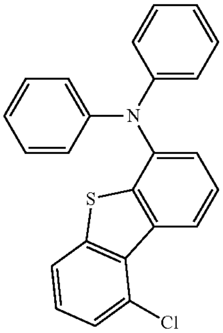
Sub 1-25
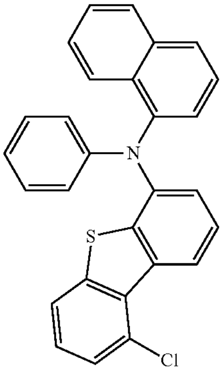
Sub 1-26
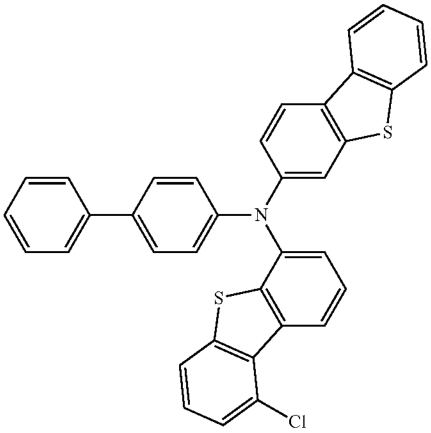
-continued
Sub 1-27
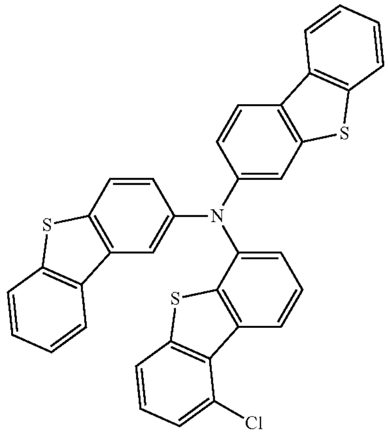
Sub 1-28
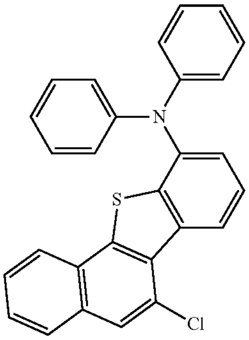
Sub 1-29
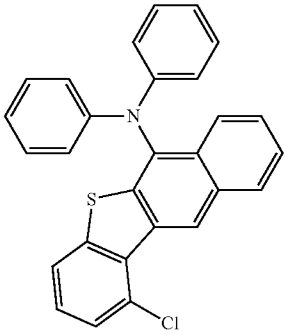
Sub 1-30
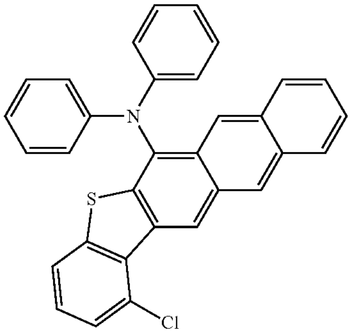

-continued
Sub 1-31
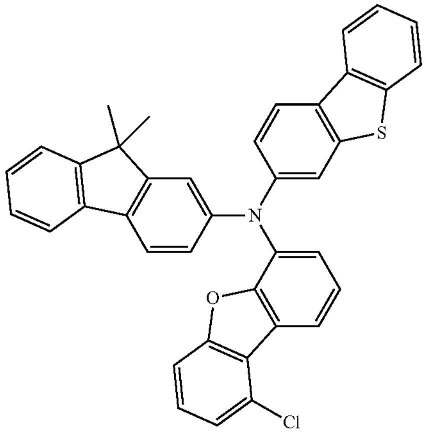
Sub 1-32
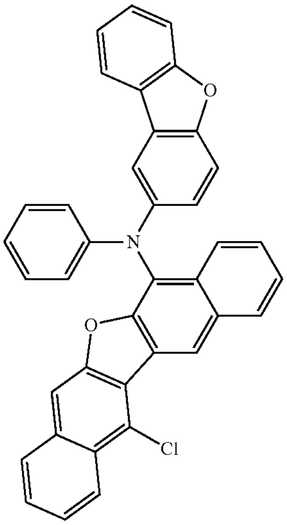
Sub 1-33
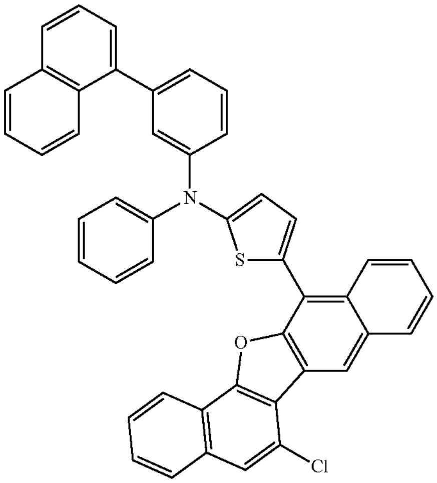
-continued
Sub 1-34
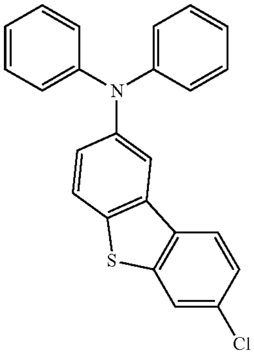
Sub 1-35
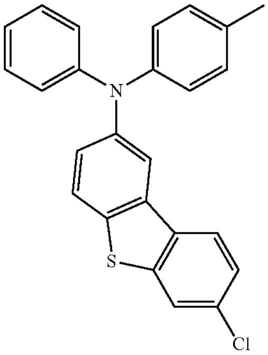
Sub 1-36
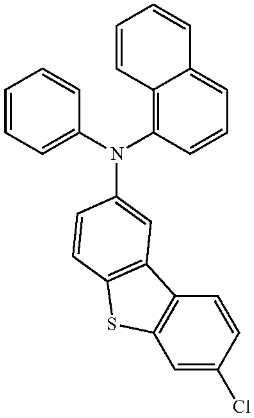
Sub 1-37
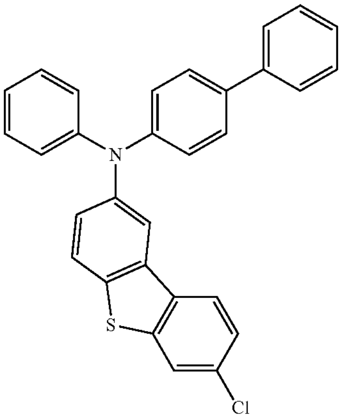

-continued
Sub 1-38
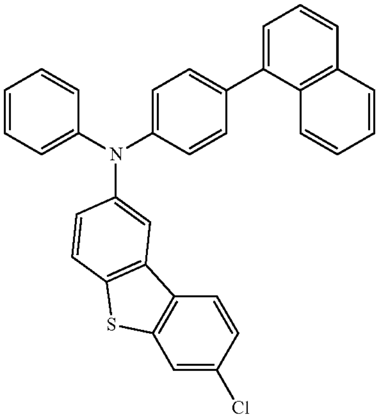
Sub 1-39
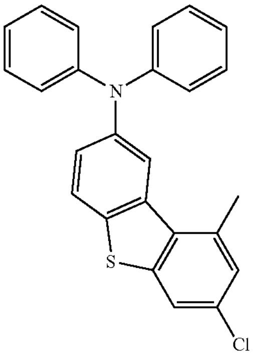
Sub 1-40
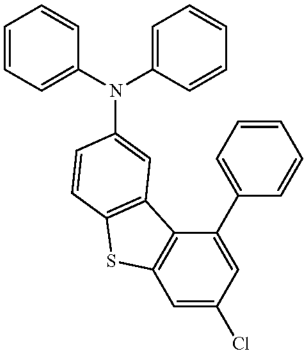
Sub 1-41
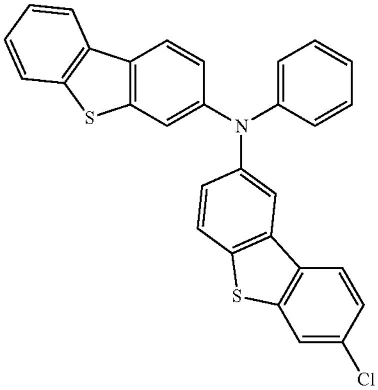
-continued
Sub 1-42
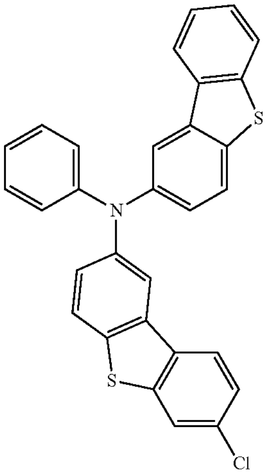
Sub 1-43
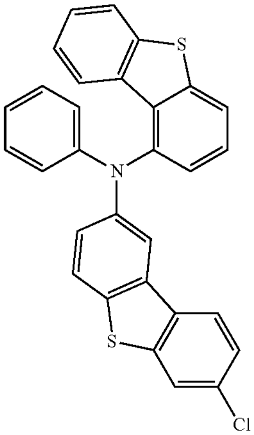
Sub 1-44
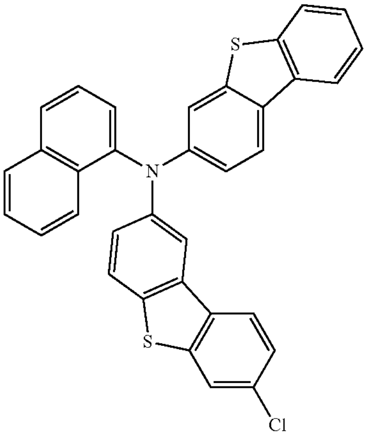

-continued
Sub 1-45
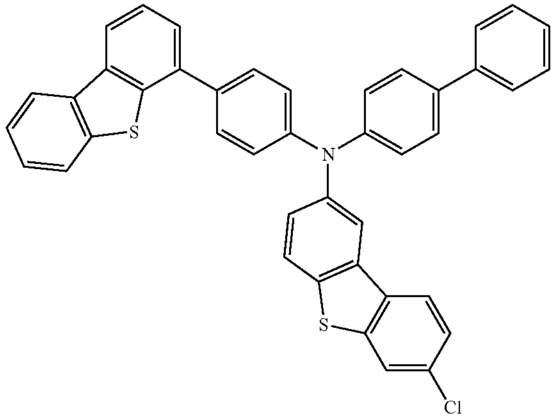
Sub 1-46
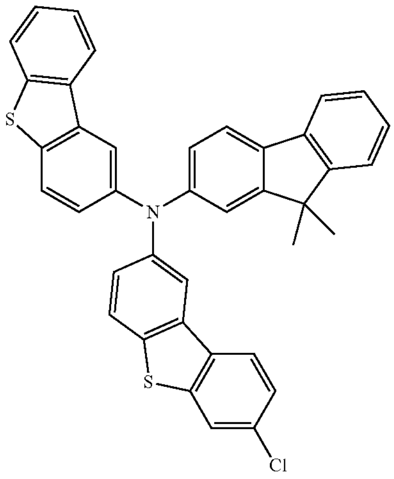
Sub 1-47
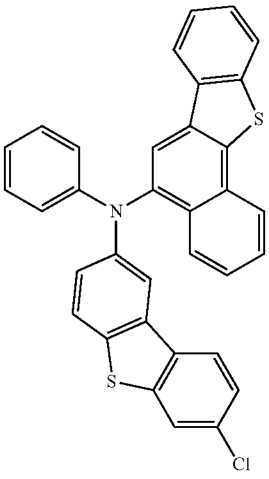
-continued
Sub 1-48
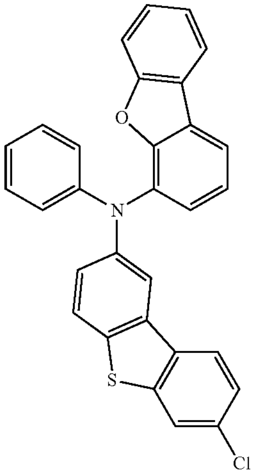
Sub 1-49
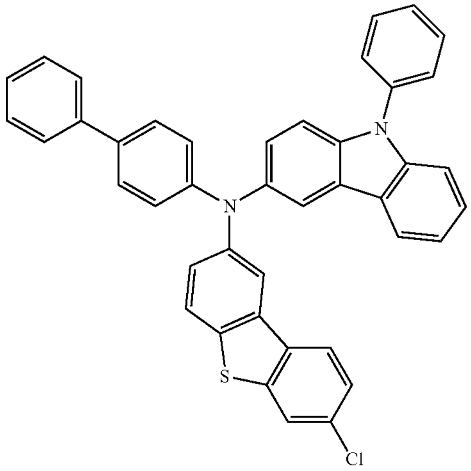
Sub 1-50
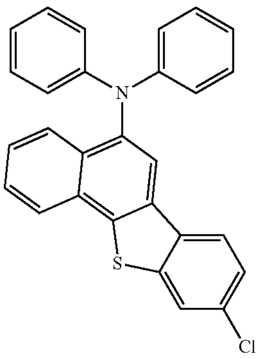

-continued
Sub 1-51
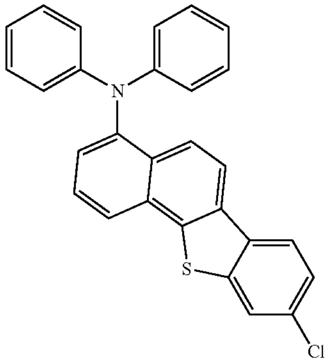
Sub 1-52
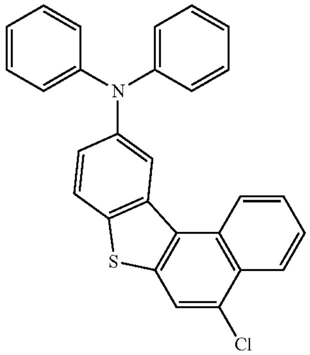
Sub 1-53
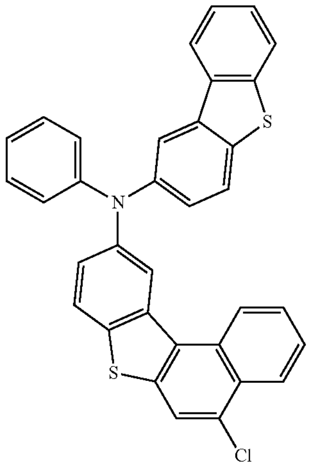
Sub 1-54
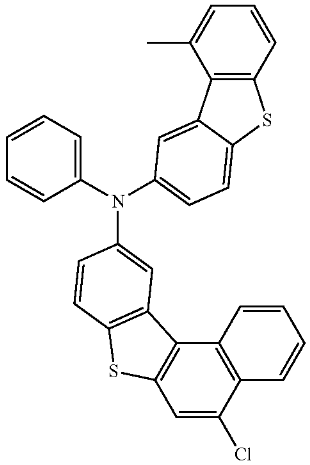
-continued
Sub 1-55
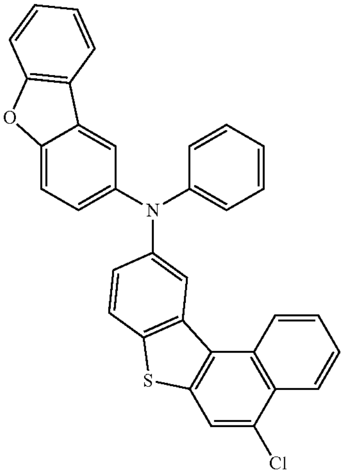
Sub 1-56
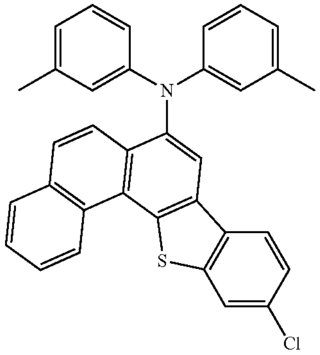
Sub 1-57
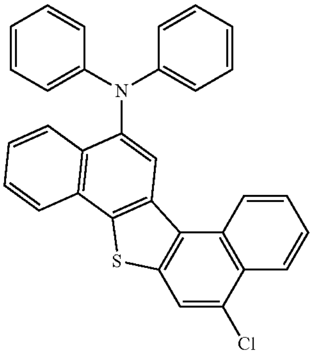

-continued
Sub 1-58
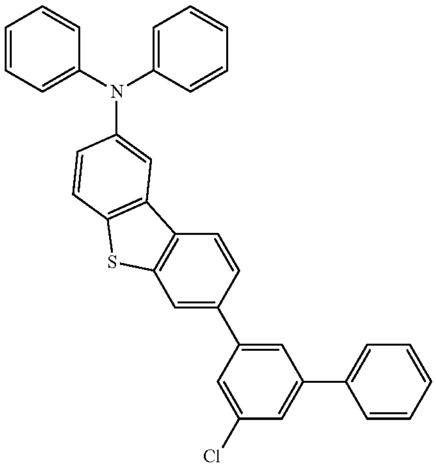
Sub 1-59
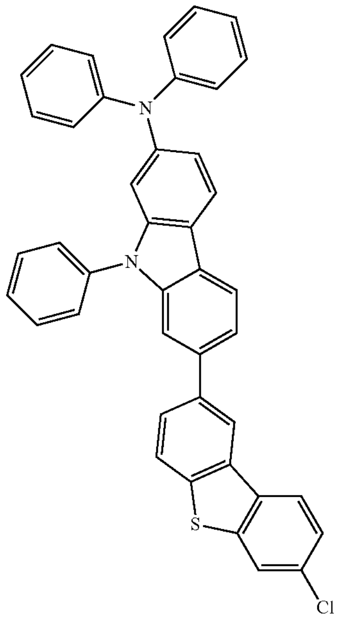
Sub 1-60
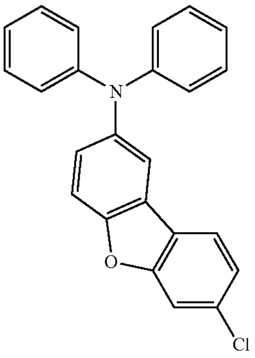
-continued
Sub 1-61
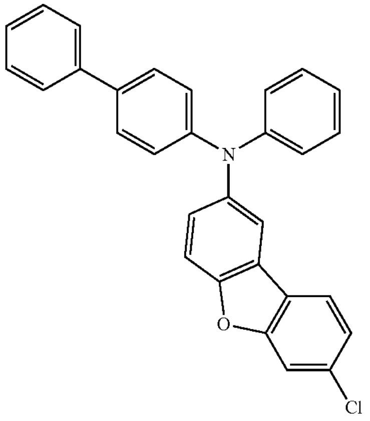
Sub 1-62
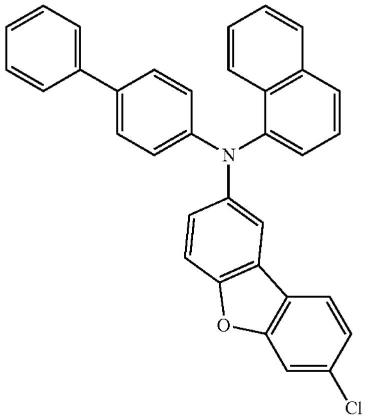
Sub 1-63
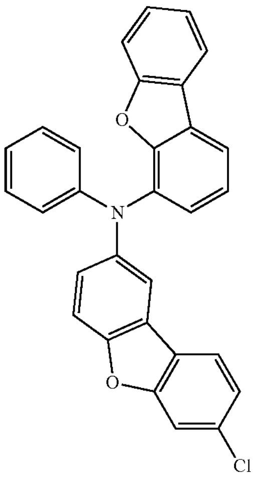

-continued
Sub 1-64
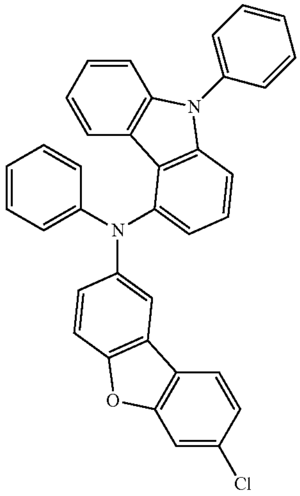
Sub 1-65
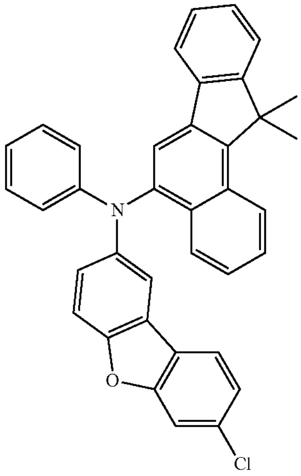
Sub 1-66
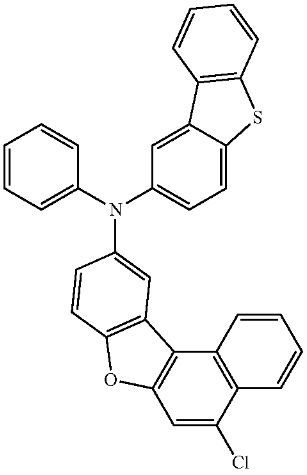
-continued
Sub 1-67
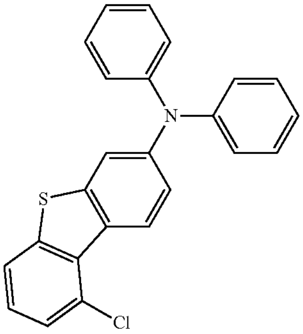
Sub 1-68
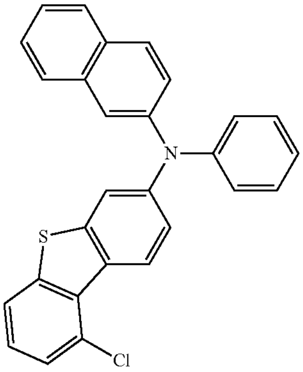
Sub 1-69
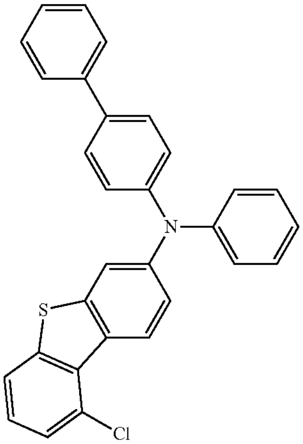
Sub 1-70
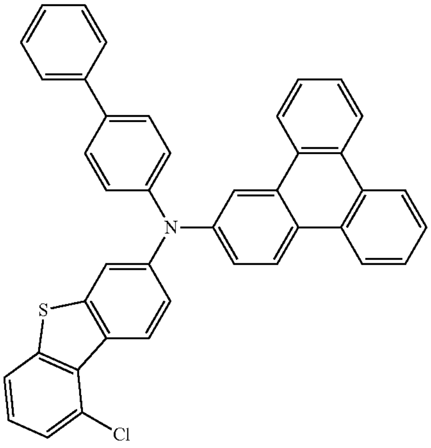

-continued
Sub 1-71
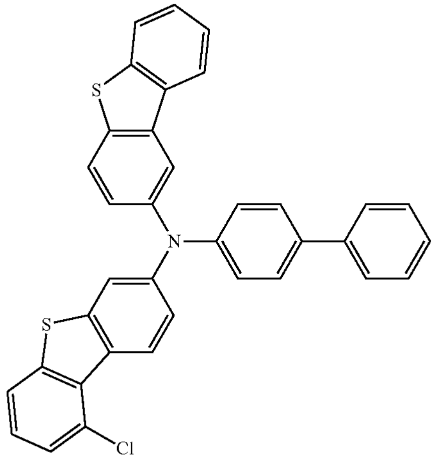
Sub 1-72
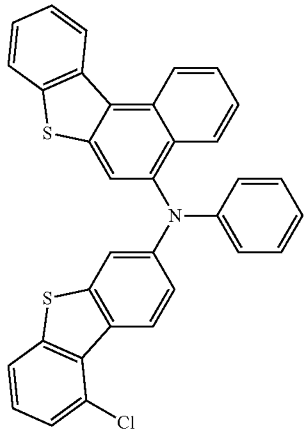
Sub 1-73
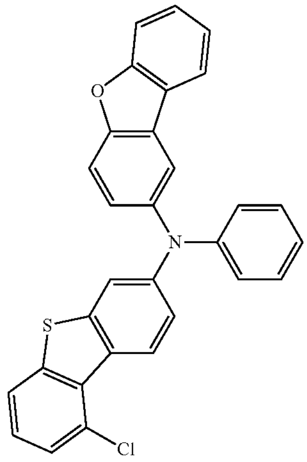
-continued
Sub 1-74
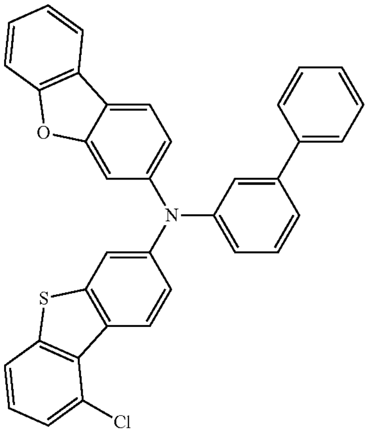
Sub 1-75
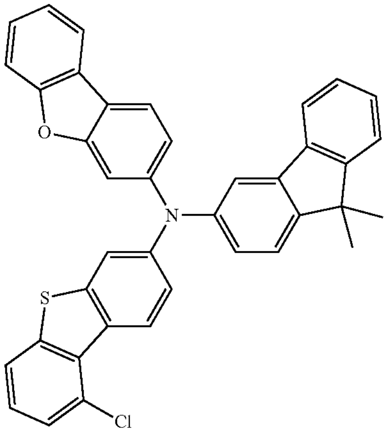
Sub 1-76
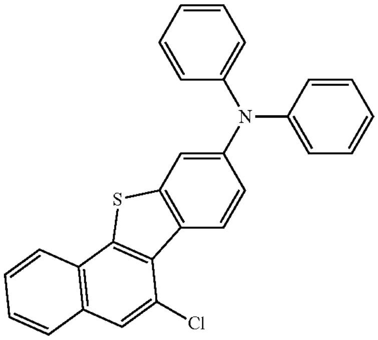
Sub 1-77
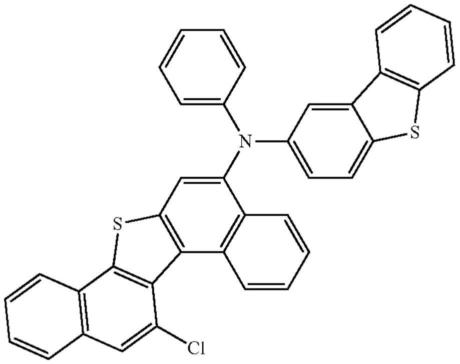

-continued
Sub 1-78
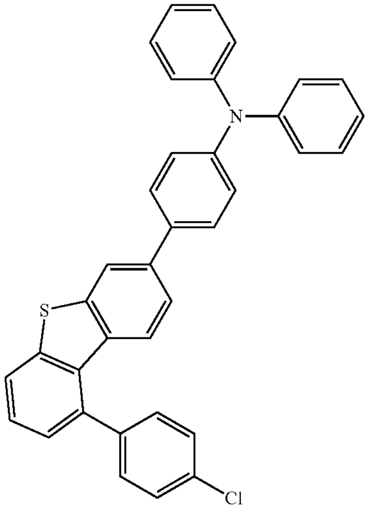
Sub 1-79
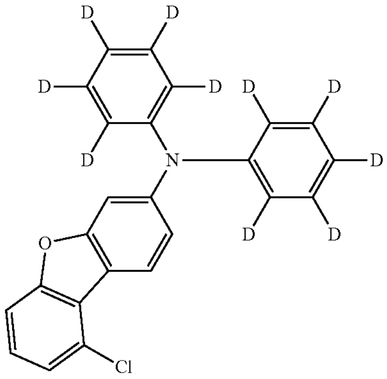
Sub 1-80
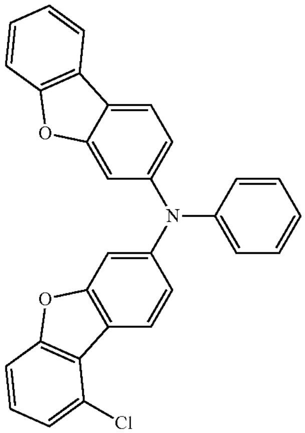
-continued
Sub 1-81
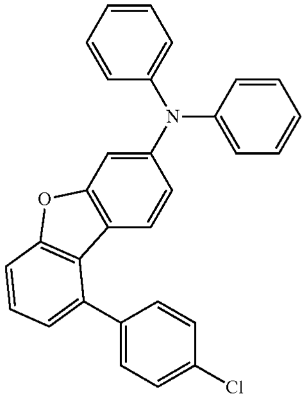
Sub 1-82
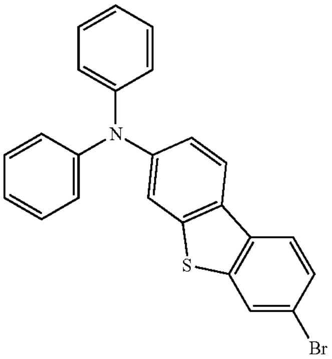
Sub 1-83
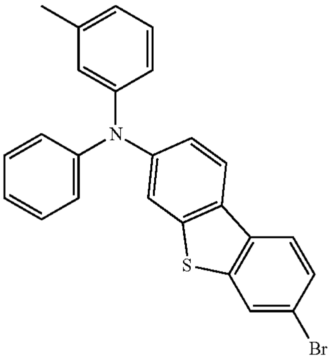
Sub 1-84
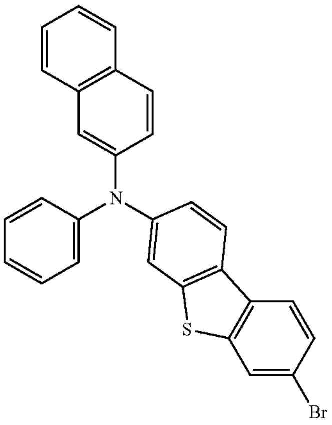

-continued
Sub 1-85
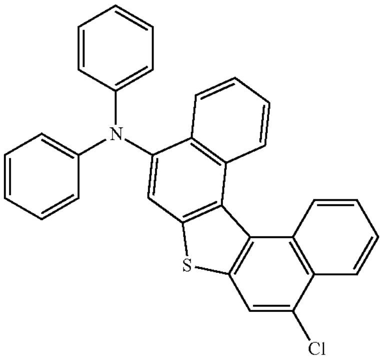
Sub 1-86
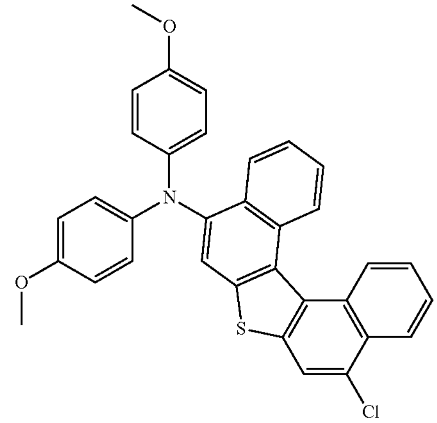
Sub 1-87
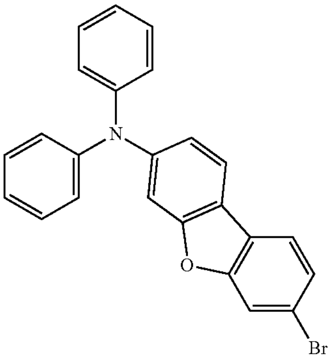
Sub 1-88
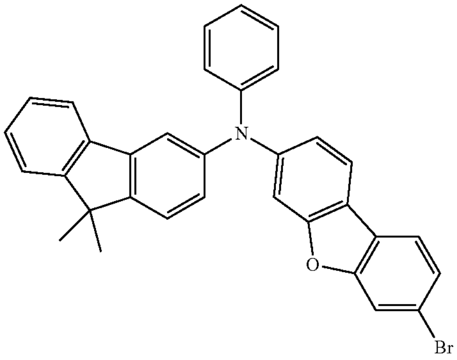
-continued
Sub 1-89
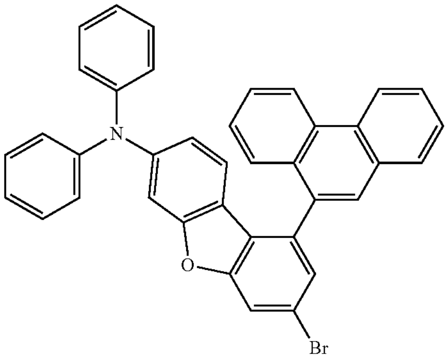
Sub 1-90
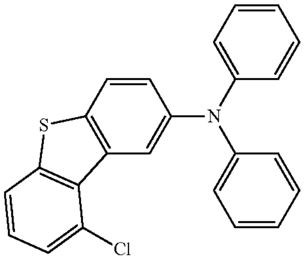
Sub 1-91
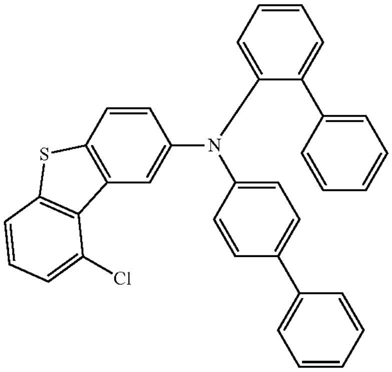
Sub 1-92
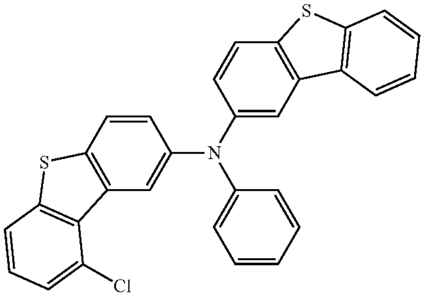

-continued
Sub 1-93
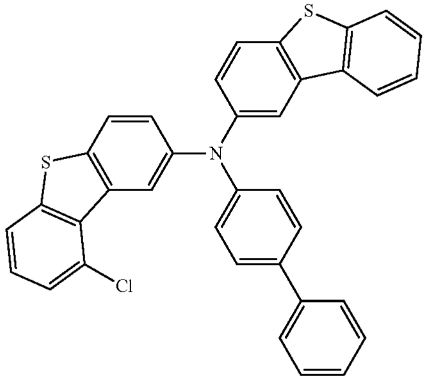
Sub 1-94
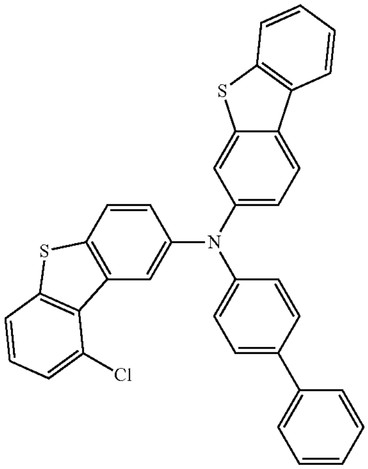
Sub 1-95
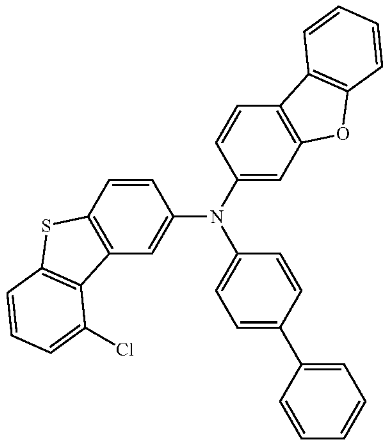
-continued
Sub 1-96
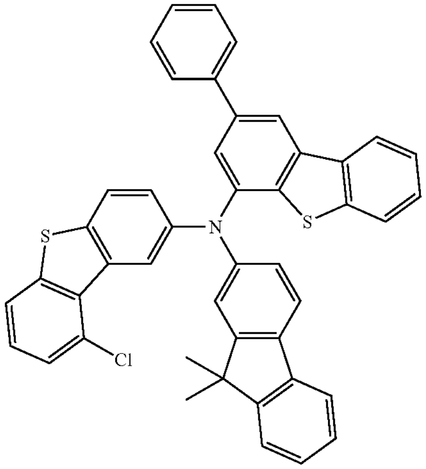
Sub 1-97
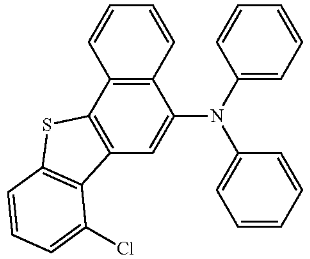
Sub 1-98
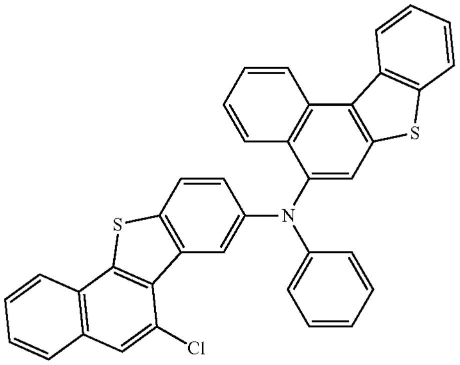
Sub 1-99
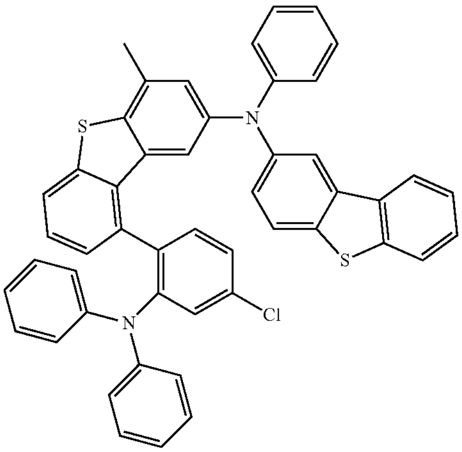

-continued
Sub 1-100
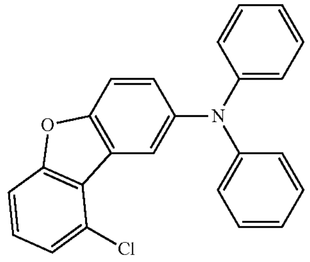
Sub 1-101
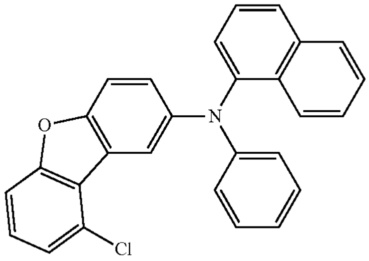
Sub 1-102
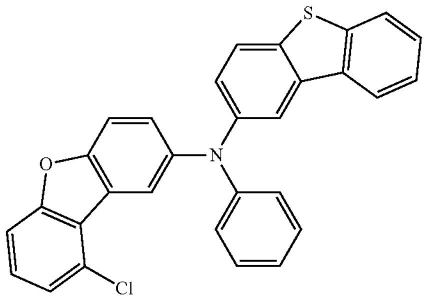
Sub 1-103
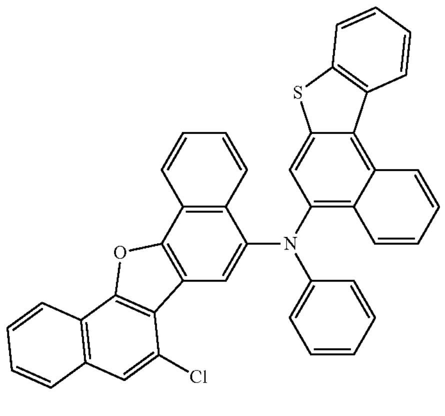
Sub 1-104
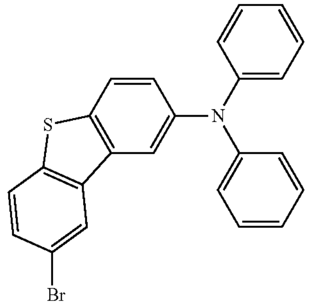
-continued
Sub 1-105
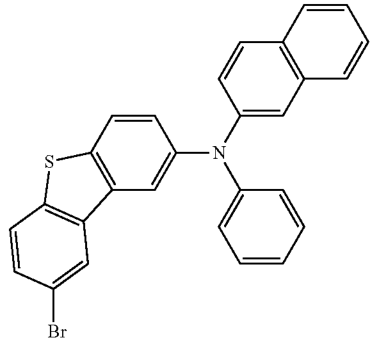
Sub 1-106
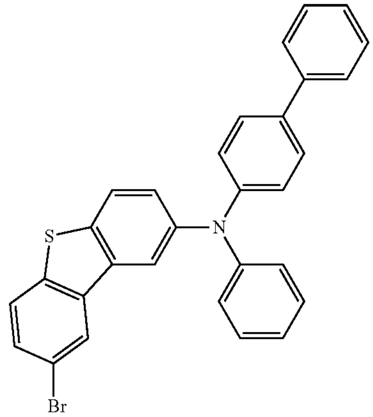
Sub 1-107
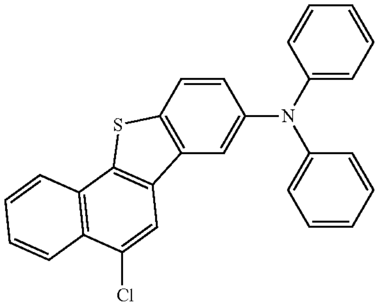
Sub 1-108
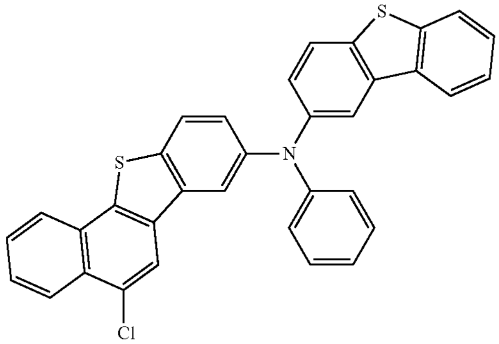

-continued
Sub 1-109
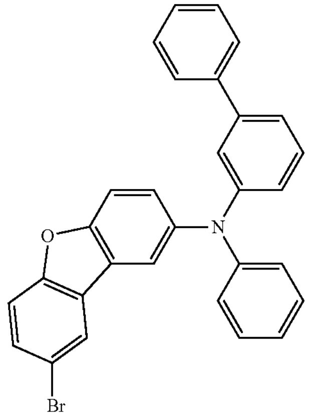
Sub 1-110
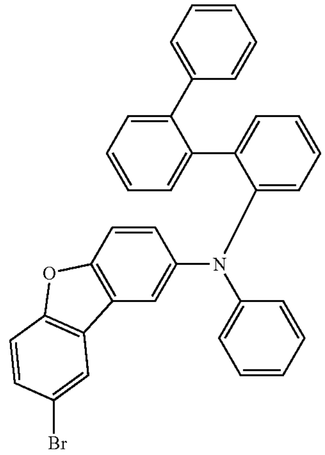
Sub 1-111
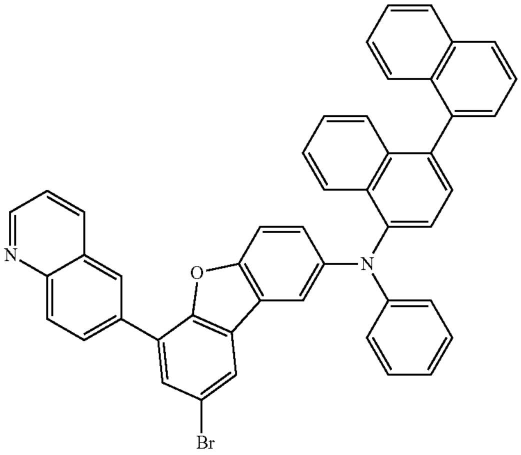
Sub 1-112
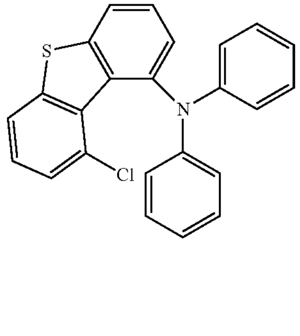
-continued
Sub 1-113
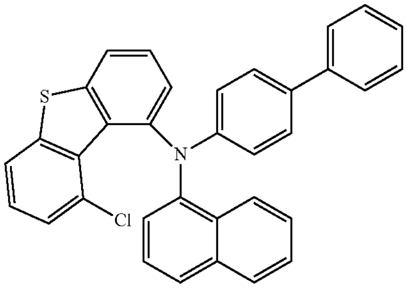
Sub 1-114
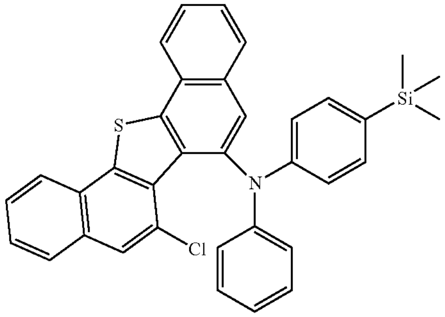
Sub 1-115
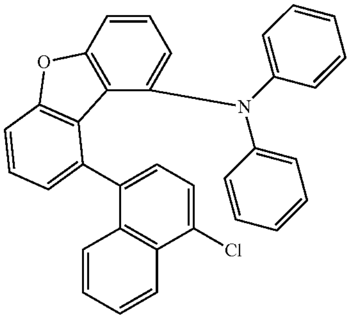
Sub 1-116
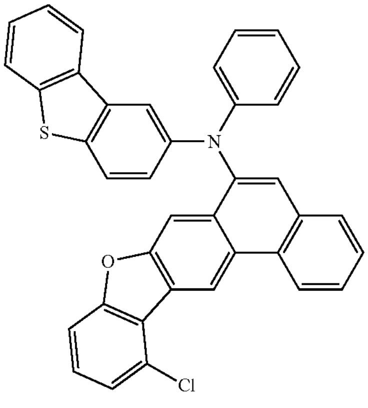

-continued

Sub 1-117

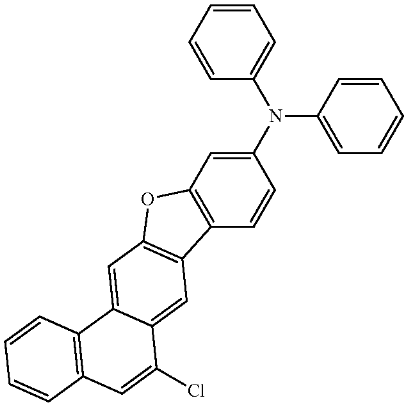

Sub 1-118

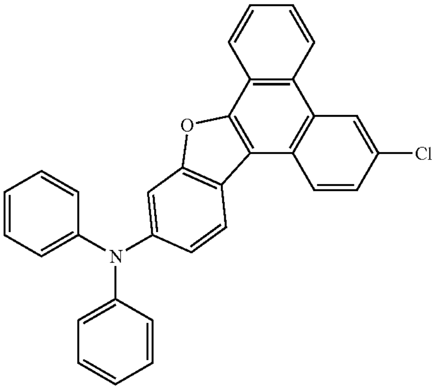

Sub 1-119

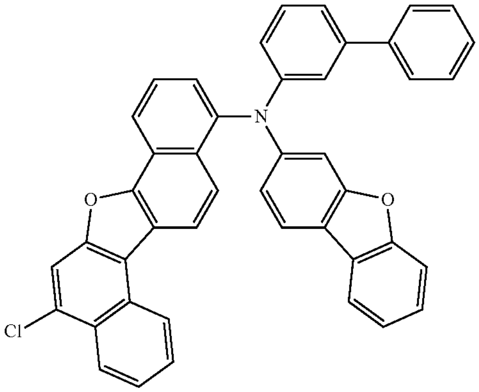

-continued

Sub 1-120

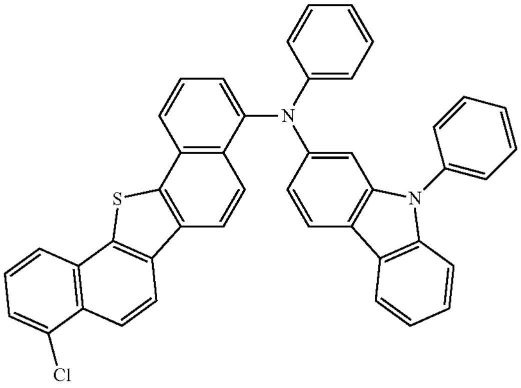

Sub 1-121

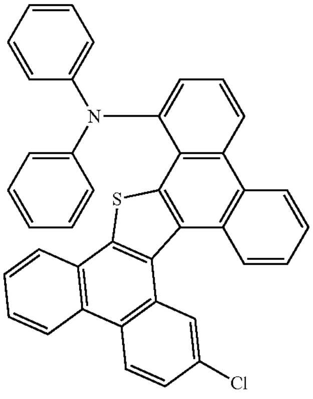

TABLE 1

| compound | FD-MS | compound | FD-MS |
|---|---|---|---|
| Sub 1-1 | m/z = 429.02($C_{24}H_{16}BrNS$ = 430.36) | Sub 1-2 | m/z = 413.04($C_{24}H_{16}BrNO$ = 414.30) |
| Sub 1-3 | m/z = 463.06($C_{28}H_{18}BrNO$ = 464.36) | Sub 1-4 | m/z = 385.07($C_{24}H_{16}ClNS$ = 385.91) |
| Sub 1-5 | m/z = 435.08($C_{28}H_{18}ClNS$ = 435.97) | Sub 1-6 | m/z = 567.09($C_{36}H_{22}ClNS_2$ = 568.15) |
| Sub 1-7 | m/z = 551.11($C_{36}H_{22}ClNOS$ = 552.09) | Sub 1-8 | m/z = 501.13($C_{33}H_{24}ClNS$ = 502.07) |
| Sub 1-9 | m/z = 445.12($C_{30}H_{20}ClNO$ = 445.95) | Sub 1-10 | m/z = 445.12($C_{30}H_{20}ClNO$ = 445.95) |
| Sub 1-11 | m/z = 385.07($C_{24}H_{16}ClNS$ = 385.91) | Sub 1-12 | m/z = 491.06($C_{30}H_{18}ClNS_2$ = 492.05) |
| Sub 1-13 | m/z = 567.09($C_{36}H_{22}ClNS_2$ = 568.15) | Sub 1-14 | m/z = 541.07($C_{34}H_{20}ClNS_2$ = 542.11) |
| Sub 1-15 | m/z = 575.11($C_{38}H_{22}ClNOS$ = 576.11) | Sub 1-16 | m/z = 552.11($C_{35}H_{21}ClN_2OS$ = 553.08) |
| Sub 1-17 | m/z = 626.16($C_{42}H_{27}ClN_2S$ = 627.20) | Sub 1-18 | m/z = 643.12($C_{42}H_{26}ClNS_2$ = 644.25) |
| Sub 1-19 | m/z = 435.08($C_{28}H_{18}ClNS$ = 435.97) | Sub 1-20 | m/z = 369.09($C_{24}H_{16}ClNO$ = 369.85) |
| Sub 1-21 | m/z = 475.08($C_{30}H_{18}ClNOS$ = 475.99) | Sub 1-22 | m/z = 565.09($C_{36}H_{20}ClNO_2S$ = 566.07) |
| Sub 1-23 | m/z = 519.14($C_{36}H_{22}ClNO$ = 520.03) | Sub 1-24 | m/z = 385.07($C_{24}H_{16}ClNS$ = 385.91) |
| Sub 1-25 | m/z = 435.08($C_{28}H_{18}ClNS$ = 435.97) | Sub 1-26 | m/z = 567.09($C_{36}H_{22}ClNS_2$ = 568.15) |
| Sub 1-27 | m/z = 597.04($C_{36}H_{20}ClNS_3$ = 598.19) | Sub 1-28 | m/z = 435.08($C_{28}H_{18}ClNS$ = 435.97) |

TABLE 1-continued

| compound | FD-MS | compound | FD-MS |
|---|---|---|---|
| Sub 1-29 | m/z = 435.08($C_{28}H_{18}ClNS$ = 435.97) | Sub 1-30 | m/z = 485.10($C_{32}H_{20}ClNS$ = 486.03) |
| Sub 1-31 | m/z = 591.14($C_{39}H_{26}ClNOS$ = 592.15) | Sub 1-32 | m/z = 559.13($C_{38}H_{22}ClNO_2$ = 560.05) |
| Sub 1-33 | m/z = 677.16($C_{46}H_{28}ClNOS$ = 678.25) | Sub 1-34 | m/z = 385.07($C_{24}H_{16}ClNS$ = 385.91) |
| Sub 1-35 | m/z = 399.08($C_{25}H_{18}ClNS$ = 399.94) | Sub 1-36 | m/z = 435.08($C_{28}H_{18}ClNS$ = 435.97) |
| Sub 1-37 | m/z = 461.10($C_{30}H_{20}ClNS$ = 462.01) | Sub 1-38 | m/z = 511.12($C_{34}H_{22}ClNS$ = 512.07) |
| Sub 1-39 | m/z = 399.08($C_{25}H_{18}ClNS$ = 399.94) | Sub 1-40 | m/z = 461.10($C_{30}H_{20}ClNS$ = 462.01) |
| Sub 1-41 | m/z = 491.06($C_{30}H_{18}ClNS_2$ = 492.05) | Sub 1-42 | m/z = 491.06($C_{30}H_{18}ClNS_2$ = 492.05) |
| Sub 1-43 | m/z = 491.06($C_{30}H_{18}ClNS_2$ = 492.05) | Sub 1-44 | m/z = 541.07($C_{34}H_{20}ClNS_2$ = 542.11) |
| Sub 1-45 | m/z = 643.12($C_{42}H_{26}ClNS_2$ = 644.25) | Sub 1-46 | m/z = 607.12($C_{39}H_{26}ClNS_2$ = 608.21) |
| Sub 1-47 | m/z = 541.07($C_{34}H_{20}ClNS_2$ = 542.11) | Sub 1-48 | m/z = 475.08($C_{30}H_{18}ClNOS$ = 475.99) |
| Sub 1-49 | m/z = 626.16($C_{42}H_{27}ClN_2S$ = 627.20) | Sub 1-50 | m/z = 435.08($C_{28}H_{18}ClNS$ = 435.97) |
| Sub 1-51 | m/z = 435.08($C_{28}H_{18}ClNS$ = 435.97) | Sub 1-52 | m/z = 435.08($C_{28}H_{18}ClNS$ = 435.97) |
| Sub 1-53 | m/z = 541.07($C_{34}H_{20}ClNS_2$ = 542.11) | Sub 1-54 | m/z = 555.09($C_{35}H_{22}ClNS_2$ = 556.14) |
| Sub 1-55 | m/z = 525.10($C_{34}H_{20}ClNOS$ = 526.05) | Sub 1-56 | m/z = 513.13($C_{34}H_{24}ClNS$ = 514.08) |
| Sub 1-57 | m/z = 485.10($C_{32}H_{20}ClNS$ = 486.03) | Sub 1-58 | m/z = 537.13($C_{36}H_{24}ClNS$ = 538.11) |
| Sub 1-59 | m/z = 626.16($C_{42}H_{27}ClN_2S$ = 627.20) | Sub 1-60 | m/z = 369.09($C_{24}H_{16}ClNO$ = 369.85) |
| Sub 1-61 | m/z = 445.12($C_{30}H_{20}ClNO$ = 445.95) | Sub 1-62 | m/z = 495.14($C_{34}H_{22}ClNO$ = 496.01) |
| Sub 1-63 | m/z = 459.10($C_{30}H_{18}ClNO_2$ = 459.93) | Sub 1-64 | m/z = 534.15($C_{36}H_{23}ClN_2O$ = 535.04) |
| Sub 1-65 | m/z = 535.17($C_{37}H_{26}ClNO$ = 536.07) | Sub 1-66 | m/z = 525.10($C_{34}H_{20}ClNOS$ = 526.05) |
| Sub 1-67 | m/z = 385.07($C_{24}H_{16}ClNS$ = 385.91) | Sub 1-68 | m/z = 435.08($C_{28}H_{18}ClNS$ = 435.97) |
| Sub 1-69 | m/z = 461.10($C_{30}H_{20}ClNS$ = 462.01) | Sub 1-70 | m/z = 611.15($C_{42}H_{26}ClNS$ = 612.19) |
| Sub 1-71 | m/z = 567.09($C_{36}H_{22}ClNS_2$ = 568.15) | Sub 1-72 | m/z = 541.07($C_{34}H_{20}ClNS_2$ = 542.11) |
| Sub 1-73 | m/z = 475.08($C_{30}H_{18}ClNOS$ = 475.99) | Sub 1-74 | m/z = 551.11($C_{36}H_{22}ClNOS$ = 552.09) |
| Sub 1-75 | m/z = 591.14($C_{39}H_{26}ClNOS$ = 592.15) | Sub 1-76 | m/z = 435.08($C_{28}H_{18}ClNS$ = 435.97) |
| Sub 1-77 | m/z = 591.09($C_{38}H_{22}ClNS_2$ = 592.17) | Sub 1-78 | m/z = 537.13($C_{36}H_{24}ClNS$ = 538.11) |
| Sub 1-79 | m/z = 379.15($C_{24}H_6D_{10}ClNO$ = 379.91) | Sub 1-80 | m/z = 459.10($C_{30}H_{18}ClNO_2$ = 459.93) |
| Sub 1-81 | m/z = 445.12($C_{30}H_{20}ClNO$ = 445.95) | Sub 1-82 | m/z = 429.02($C_{24}H_{16}BrNS$ = 430.36) |
| Sub 1-83 | m/z = 443.03($C_{25}H_{18}BrNS$ = 444.39) | Sub 1-84 | m/z = 479.03($C_{28}H_{18}BrNS$ = 480.42) |
| Sub 1-85 | m/z = 485.10($C_{32}H_{20}ClNS$ = 486.03) | Sub 1-86 | m/z = 545.12($C_{34}H_{24}ClNO_2S$ = 546.08) |
| Sub 1-87 | m/z = 413.04($C_{24}H_{16}BrNO$ = 414.30) | Sub 1-88 | m/z = 529.10($C_{33}H_{24}BrNO$ = 530.47) |
| Sub 1-89 | m/z = 589.10($C_{38}H_{24}BrNO$ = 590.52) | Sub 1-90 | m/z = 385.07($C_{24}H_{16}ClNS$ = 385.91) |
| Sub 1-91 | m/z = 537.13($C_{36}H_{24}ClNS$ = 538.11) | Sub 1-92 | m/z = 491.06($C_{30}H_{18}ClNS_2$ = 492.05) |
| Sub 1-93 | m/z = 567.09($C_{36}H_{22}ClNS_2$ = 568.15) | Sub 1-94 | m/z = 567.09($C_{36}H_{22}ClNS_2$ = 568.15) |
| Sub 1-95 | m/z = 551.11($C_{36}H_{22}ClNOS$ = 552.09) | Sub 1-96 | m/z = 683.15($C_{45}H_{30}ClNS_2$ = 684.31) |
| Sub 1-97 | m/z = 435.08($C_{28}H_{18}ClNS$ = 435.97) | Sub 1-98 | m/z = 591.09($C_{38}H_{22}ClNS_2$ = 592.17) |
| Sub 1-99 | m/z = 748.18($C_{49}H_{33}ClN_2S_2$ = 749.39) | Sub 1-100 | m/z = 369.09($C_{24}H_{16}ClNO$ = 369.85) |
| Sub 1-101 | m/z = 419.11($C_{28}H_{18}ClNO$ = 419.91) | Sub 1-102 | m/z = 475.08($C_{30}H_{18}ClNOS$ = 475.99) |
| Sub 1-103 | m/z = 625.13($C_{42}H_{24}ClNOS$ = 626.17) | Sub 1-104 | m/z = 429.02($C_{24}H_{16}BrNS$ = 430.36) |
| Sub 1-105 | m/z = 479.03($C_{28}H_{18}BrNS$ = 480.42) | Sub 1-106 | m/z = 505.05($C_{30}H_{20}BrNS$ = 506.46) |
| Sub 1-107 | m/z = 435.08($C_{28}H_{18}ClNS$ = 435.97) | Sub 1-108 | m/z = 541.07($C_{34}H_{20}ClNS_2$ = 542.11) |
| Sub 1-109 | m/z = 489.07($C_{30}H_{20}BrNO$ = 490.40) | Sub 1-110 | m/z = 565.10($C_{36}H_{24}BrNO$ = 566.50) |
| Sub 1-111 | m/z = 716.15($C_{47}H_{29}BrN_2O$ = 717.67) | Sub 1-112 | m/z = 385.07($C_{24}H_{16}ClNS$ = 385.91) |
| Sub 1-113 | m/z = 511.12($C_{34}H_{22}ClNS$ = 512.07) | Sub 1-114 | m/z = 557.14($C_{35}H_{28}ClNSSi$ = 558.21) |
| Sub 1-115 | m/z = 495.14($C_{34}H_{22}ClNO$ = 496.01) | Sub 1-116 | m/z = 575.11($C_{38}H_{22}ClNOS$ = 576.11) |
| Sub 1-117 | m/z = 469.12($C_{32}H_{20}ClNO$ = 469.97) | Sub 1-118 | m/z = 469.12($C_{32}H_{20}ClNO$ = 469.97) |
| Sub 1-119 | m/z = 635.17($C_{44}H_{26}ClNO_2$ = 636.15) | Sub 1-120 | m/z = 650.16($C_{44}H_{27}ClN_2S$ = 651.22) |
| Sub 1-121 | m/z = 585.13($C_{40}H_{24}ClNS$ = 586.15) | | |

II. Synthesis of Sub 2

Sub 2 of Reaction Scheme 3 may be synthesized (initiated in Korean Patent Registration No. 10-1251451 (registered on Apr. 5, 2013) of the applicant) by the reaction path of Reaction Scheme 3 below, but is not limited thereto.

$Z^1$ is $Ar^1$ or Ara, $Z^2$ is $Ar^2$ or $Ar^4$.

<Reaction Scheme3>

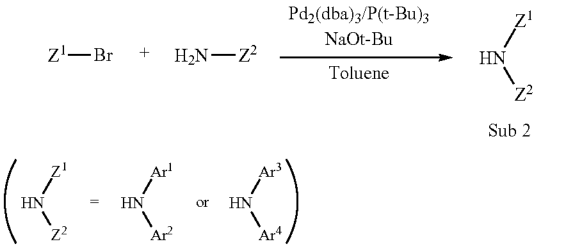

Sub 2

The compounds belonging to Sub 2 may be the following compounds, but is not limited thereto, and Table 2 shows the FD-MS (Field Desorption-Mass Spectrometry) values of some compounds belonging to Sub 2.

Sub 2-1

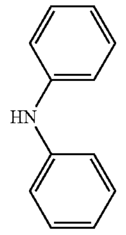

-continued
Sub 2-2
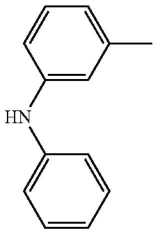
Sub 2-3
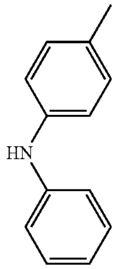
Sub 2-4
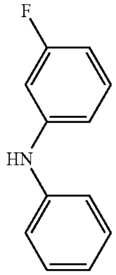
Sub 2-5
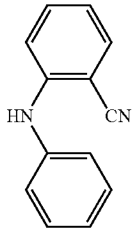
Sub 2-6
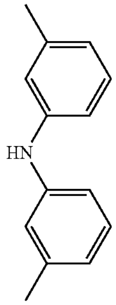
-continued
Sub 2-7
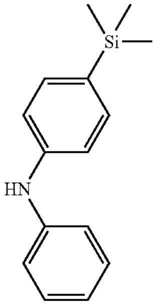
Sub 2-8
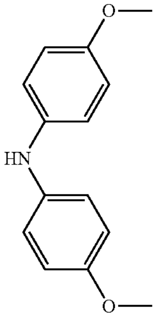
Sub 2-9
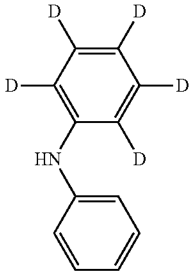
Sub 2-10
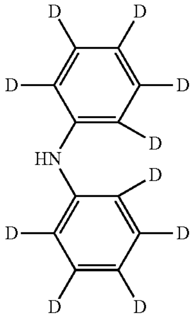
Sub 2-11
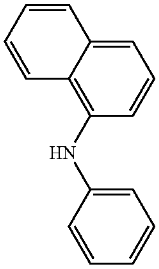

-continued
Sub 2-12
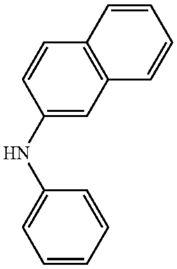
Sub 2-13
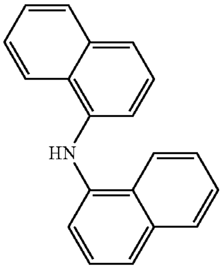
Sub 2-14
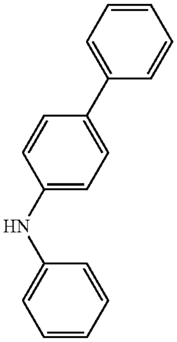
Sub 2-15
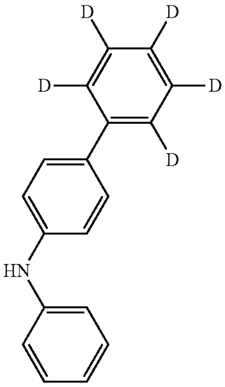
Sub 2-16
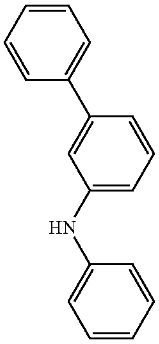
-continued
Sub 2-17
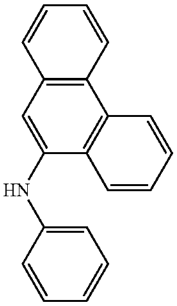
Sub 2-18
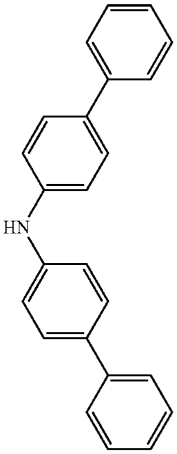
Sub 2-19
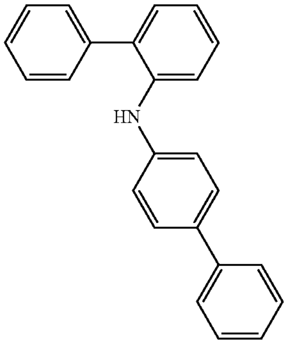
Sub 2-20
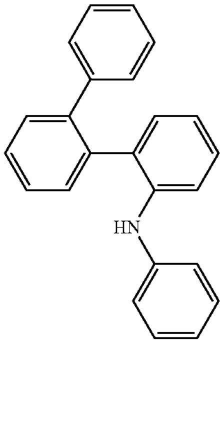

-continued
Sub 2-21
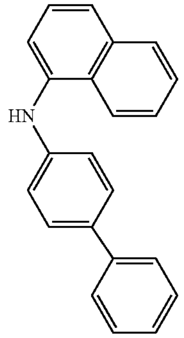
Sub 2-22
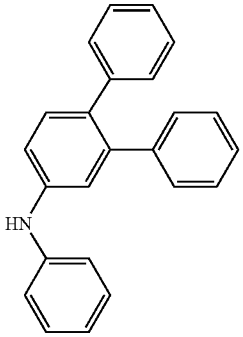
Sub 2-23
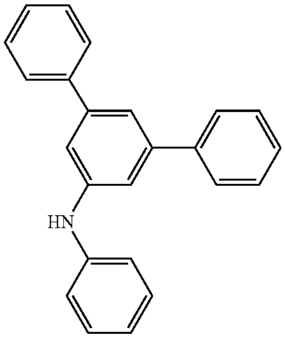
Sub 2-24
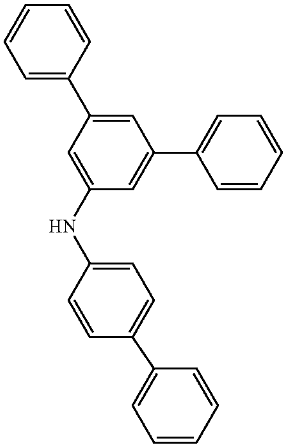
-continued
Sub 2-25
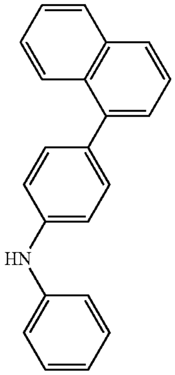
Sub 2-26
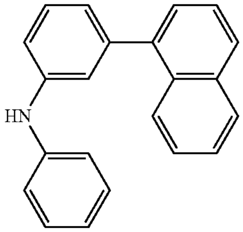
Sub 2-27
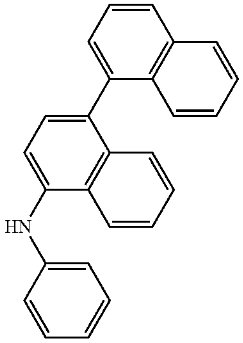
Sub 2-28
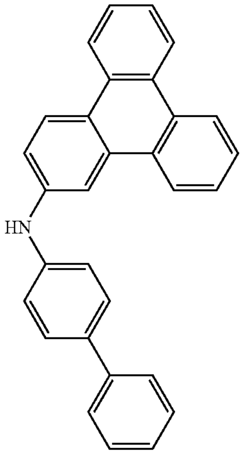

-continued
Sub 2-29
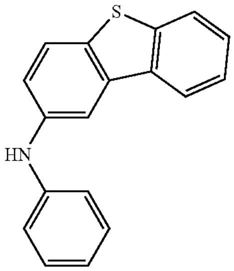
Sub 2-30
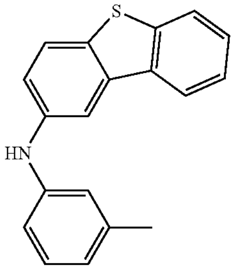
Sub 2-31
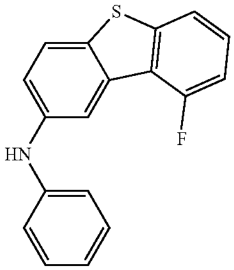
Sub 2-32
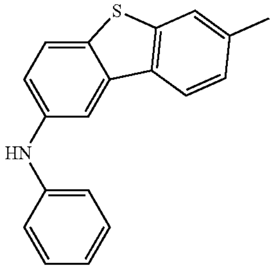
Sub 2-33
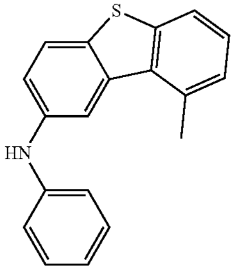
-continued
Sub 2-34
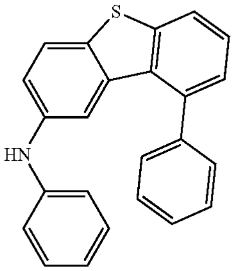
Sub 2-35
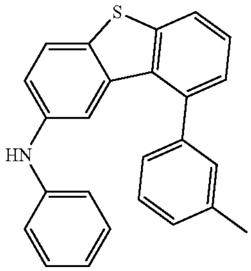
Sub 2-36
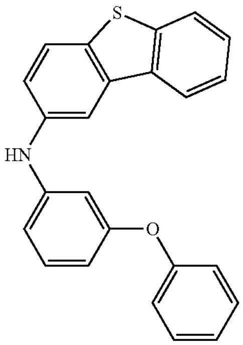
Sub 2-37
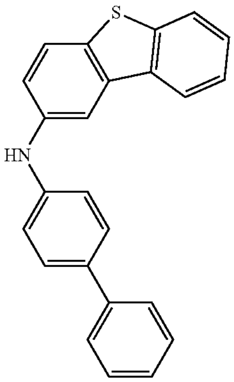
Sub 2-38
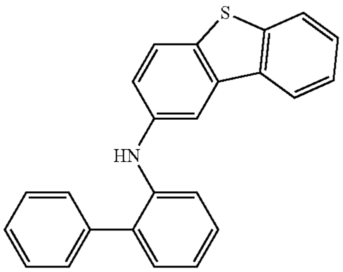

-continued
Sub 2-39
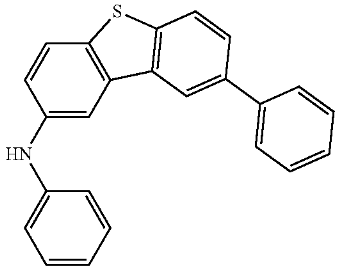
Sub 2-40
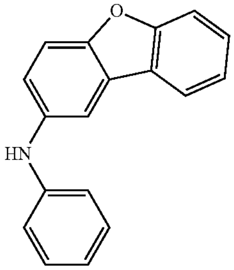
Sub 2-41
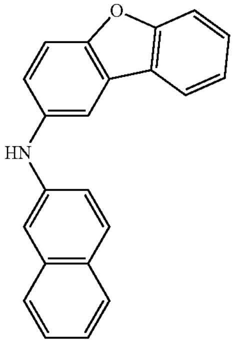
Sub 2-42
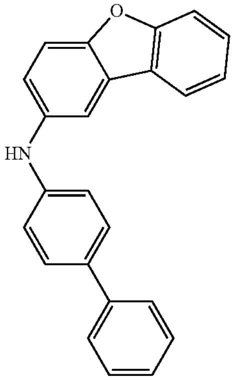
-continued
Sub 2-43
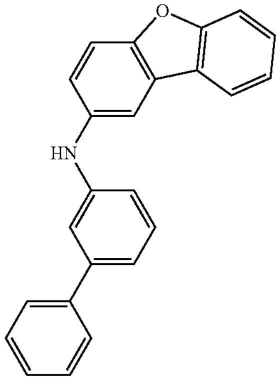
Sub 2-44
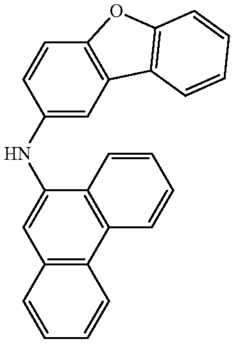
Sub 2-45
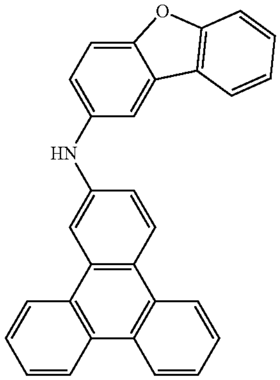
Sub 2-46
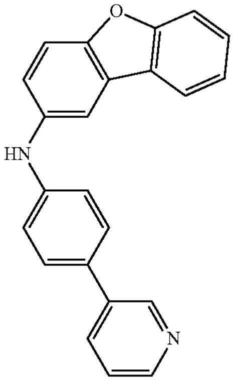

-continued
Sub 2-47
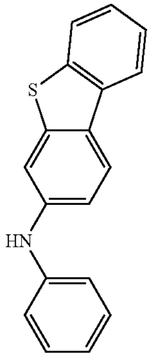
Sub 2-48
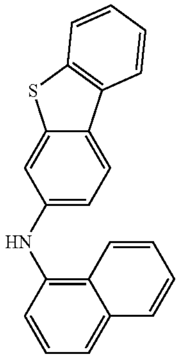
Sub 2-49
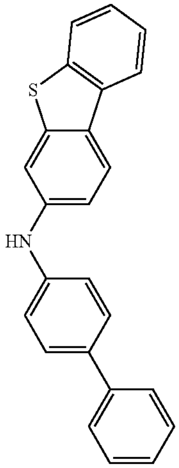
Sub 2-50
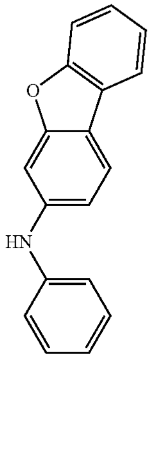
-continued
Sub 2-51
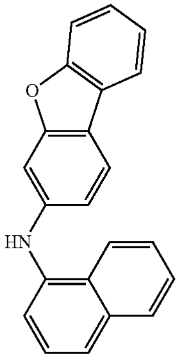
Sub 2-52
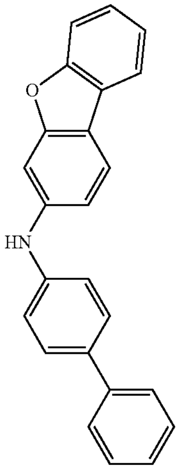
Sub 2-53
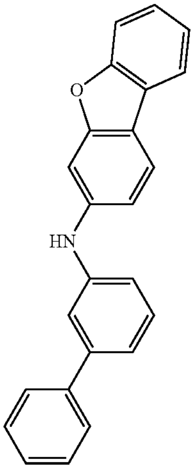

Sub 2-54
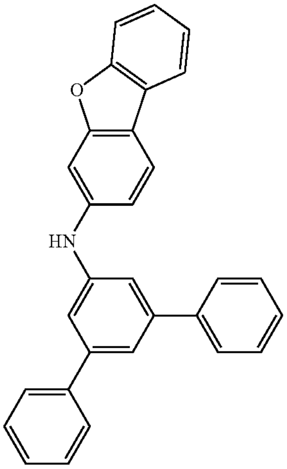
Sub 2-55
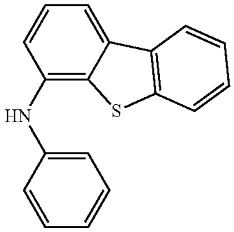
Sub 2-56
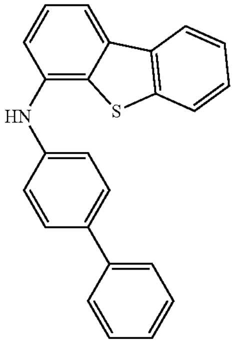
Sub 2-57
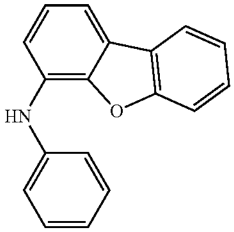
Sub 2-58
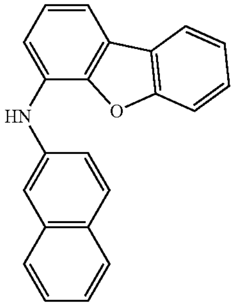
Sub 2-59
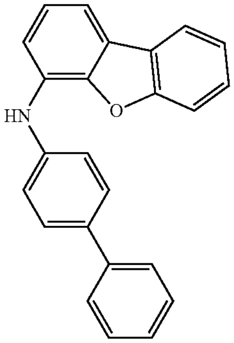
Sub 2-60
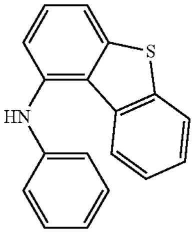
Sub 2-61
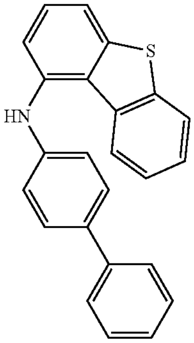
Sub 2-62
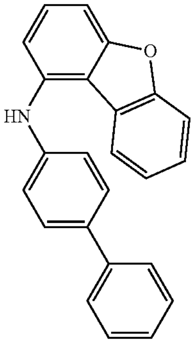

-continued
Sub 2-63
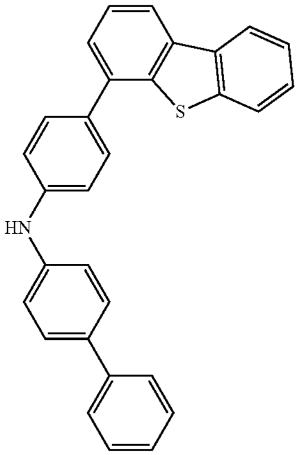
Sub 2-64
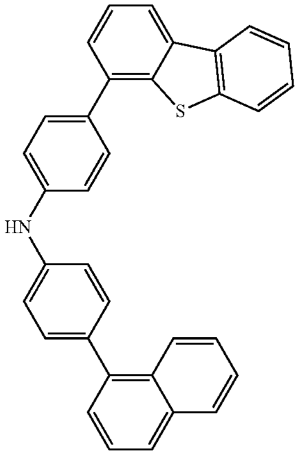
Sub 2-65
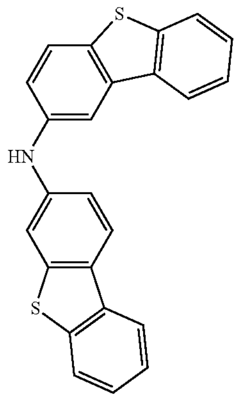
-continued
Sub 2-66
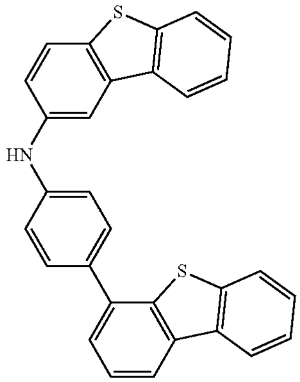
Sub 2-67
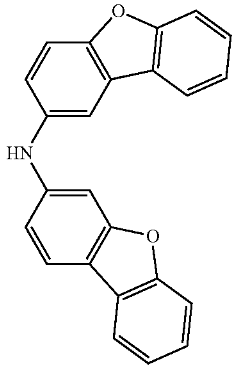
Sub 2-68
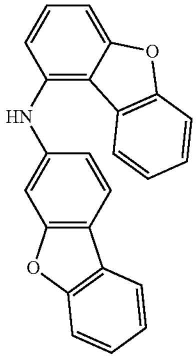
Sub 2-69
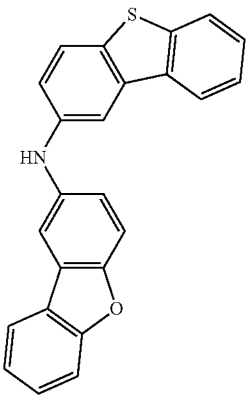

-continued
Sub 2-70
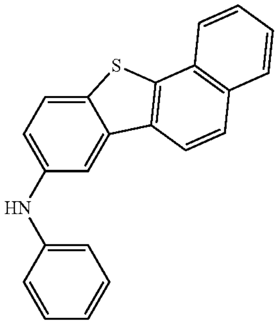
Sub 2-71
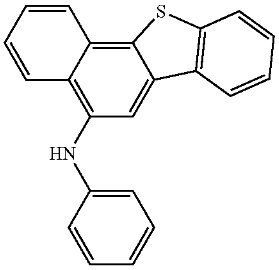
Sub 2-72
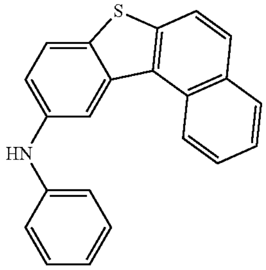
Sub 2-73
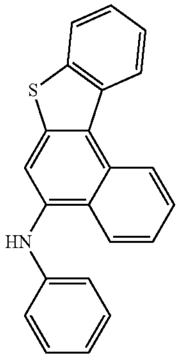
Sub 2-74
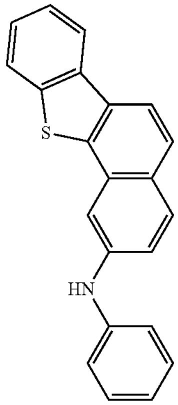
-continued
Sub 2-75
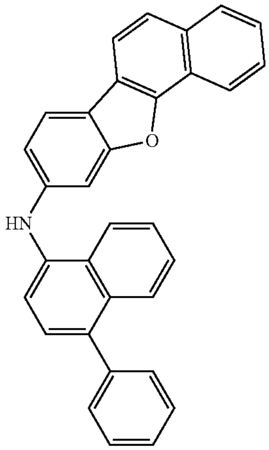
Sub 2-76
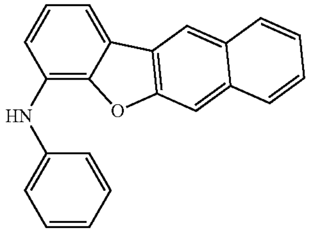
Sub 2-77
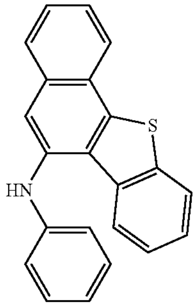
Sub 2-78
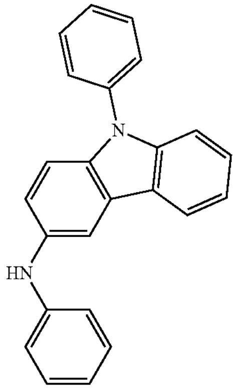

-continued
Sub 2-79
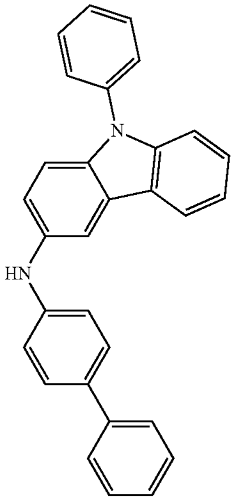
Sub 2-80
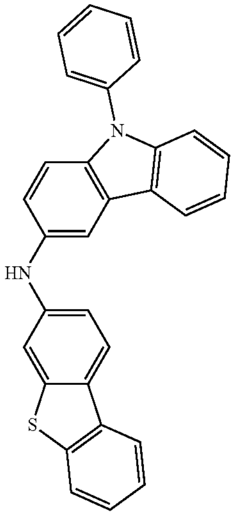
Sub 2-81
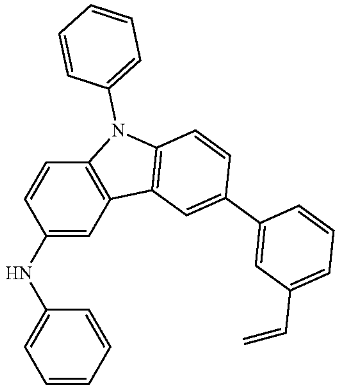
-continued
Sub 2-82
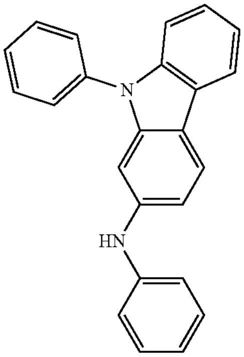
Sub 2-83
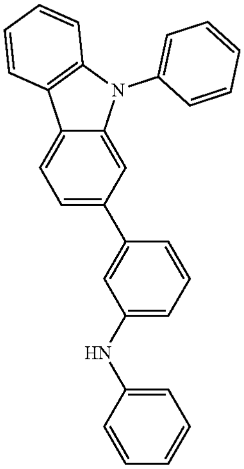
Sub 2-84
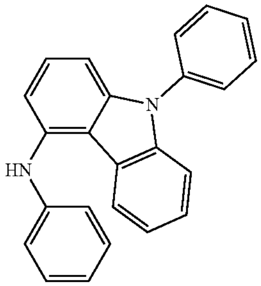
Sub 2-85
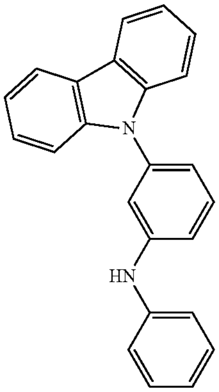

-continued
Sub 2-86
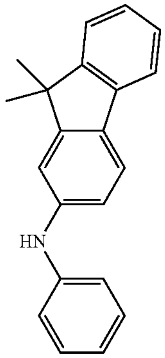
Sub 2-87
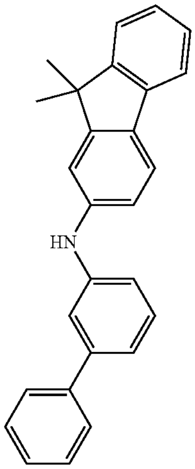
Sub 2-88
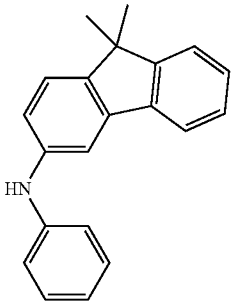
Sub 2-89
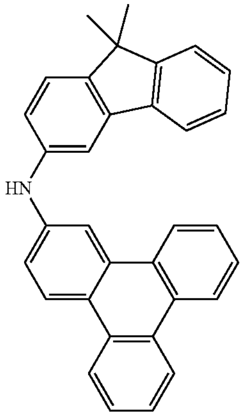
-continued
Sub 2-90
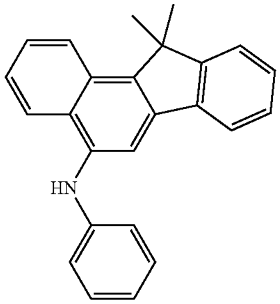
Sub 2-91
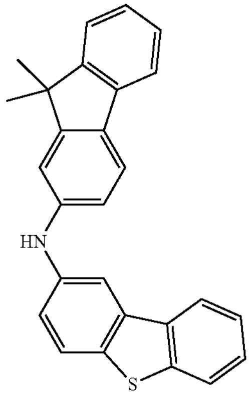
Sub 2-92
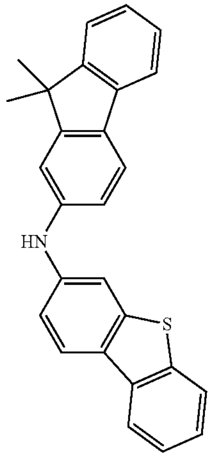
Sub 2-93
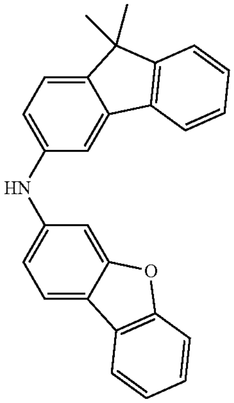

-continued

Sub 2-94

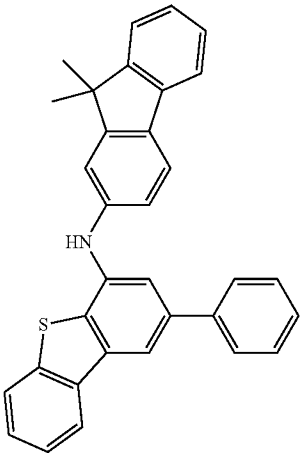

Sub 2-95

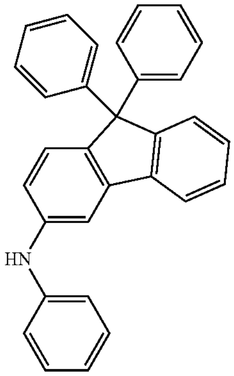

Sub 2-96

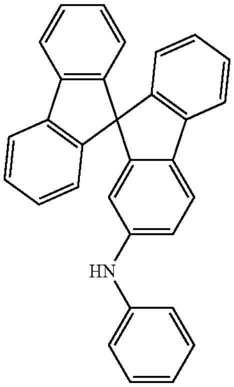

-continued

Sub 2-97

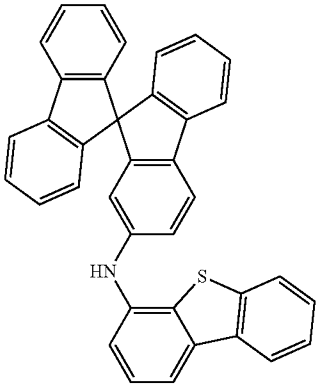

Sub 2-98

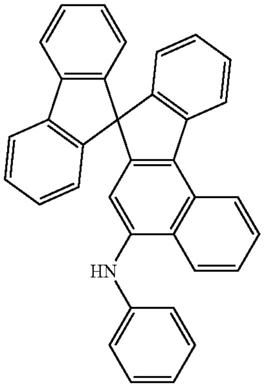

Sub 2-99

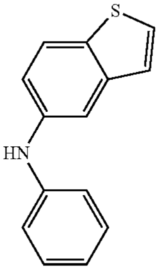

TABLE 2

| compound | FD-MS | compound | FD-MS |
|---|---|---|---|
| Sub 2-1 | m/z = 169.09($C_{12}H_{11}N$ = 169. 23) | Sub 2-2 | m/z = 183.10($C_{13}H_{13}N$ = 183.25) |
| Sub 2-3 | m/z = 183.10($C_{13}H_{13}N$ = 183.25) | Sub 2-4 | m/z = 187.08($C_{12}H_{10}FN$ = 187.22) |
| Sub 2-5 | m/z = 194.08($C_{13}H_{10}N_2$ = 194.24) | Sub 2-6 | m/z = 197.12($C_{14}H_{15}N$ = 197.28) |
| Sub 2-7 | m/z = 241.13($C_{15}H_{19}NSi$ = 241.41) | Sub 2-8 | m/z = 229.11($C_{14}H_{15}NO_2$ = 229.28) |
| Sub 2-9 | m/z = 174.12($C_{12}H_6D_5N$ = 174.26) | Sub 2-10 | m/z = 179.15($C_{12}HD_{10}N$ = 179.29) |
| Sub 2-11 | m/z = 219.10($C_{16}H_{13}N$ = 219.29) | Sub 2-12 | m/z = 219.10($C_{16}H_{13}N$ = 219.29) |
| Sub 2-13 | m/z = 269.12($C_{20}H_{15}N$ = 269.35) | Sub 2-14 | m/z = 245.12($C_{18}H_{15}N$ = 245.33) |
| Sub 2-15 | m/z = 250.15($C_{18}H_{10}D_5N$ = 250.36) | Sub 2-16 | m/z = 245.12($C_{18}H_{15}N$ = 245.33) |
| Sub 2-17 | m/z = 269.12($C_{20}H_{15}N$ = 269.35) | Sub 2-18 | m/z = 321.15($C_{24}H_{19}N$ = 321.42) |
| Sub 2-19 | m/z = 321.15($C_{24}H_{19}N$ = 321.42) | Sub 2-20 | m/z = 321.15($C_{24}H_{19}N$ = 321.42) |
| Sub 2-21 | m/z = 295.14($C_{22}H_{17}N$ = 295.39) | Sub 2-22 | m/z = 321.15($C_{24}H_{19}N$ = 321.42) |
| Sub 2-23 | m/z = 321.15($C_{24}H_{19}N$ = 321.42) | Sub 2-24 | m/z = 397.18($C_{30}H_{23}N$ = 397.52) |
| Sub 2-25 | m/z = 295.14($C_{22}H_{17}N$ = 295.39) | Sub 2-26 | m/z = 295.14($C_{22}H_{17}N$ = 295.39) |
| Sub 2-27 | m/z = 345.15($C_{26}H_{19}N$ = 345.45) | Sub 2-28 | m/z = 395.17($C_{30}H_{21}N$ = 395.51) |

TABLE 2-continued

| compound | FD-MS | compound | FD-MS |
|---|---|---|---|
| Sub 2-29 | m/z = 275.08($C_{18}H_{13}NS$ = 275.37) | Sub 2-30 | m/z = 289.09($C_{19}H_{15}NS$ = 289.40) |
| Sub 2-31 | m/z = 293.07($C_{18}H_{12}FNS$ = 293.36) | Sub 2-32 | m/z = 289.09($C_{19}H_{15}NS$ = 289.40) |
| Sub 2-33 | m/z = 289.09($C_{19}H_{15}NS$ = 289.40) | Sub 2-34 | m/z = 351.11($C_{24}H_{17}NS$ = 351.47) |
| Sub 2-35 | m/z = 365.12($C_{25}H_{19}NS$ = 365.49) | Sub 2-36 | m/z = 367.10($C_{24}H_{17}NOS$ = 367.47) |
| Sub 2-37 | m/z = 351.11($C_{24}H_{17}NS$ = 351.47) | Sub 2-38 | m/z = 351.11($C_{24}H_{17}NS$ = 351.47) |
| Sub 2-39 | m/z = 351.11($C_{24}H_{17}NS$ = 351.47) | Sub 2-40 | m/z = 259.10($C_{18}H_{13}NO$ = 259.31) |
| Sub 2-41 | m/z = 309.12($C_{22}H_{15}NO$ = 309.37) | Sub 2-42 | m/z = 335.13($C_{24}H_{17}NO$ = 335.41) |
| Sub 2-43 | m/z = 335.13($C_{24}H_{17}NO$ = 335.41) | Sub 2-44 | m/z = 359.13($C_{26}H_{17}NO$ = 359.43) |
| Sub 2-45 | m/z = 409.15($C_{30}H_{19}NO$ = 409.49) | Sub 2-46 | m/z = 336.13($C_{23}H_{16}N_2O$ = 336.39) |
| Sub 2-47 | m/z = 275.08($C_{18}H_{13}NS$ = 275.37) | Sub 2-48 | m/z = 325.09($C_{22}H_{15}NS$ = 325.43) |
| Sub 2-49 | m/z = 351.11($C_{24}H_{17}NS$ = 351.47) | Sub 2-50 | m/z = 259.10($C_{18}H_{13}NO$ = 259.31) |
| Sub 2-51 | m/z = 309.12($C_{22}H_{15}NO$ = 309.37) | Sub 2-52 | m/z = 335.13($C_{24}H_{17}NO$ = 335.41) |
| Sub 2-53 | m/z = 335.13($C_{24}H_{17}NO$ = 335.41) | Sub 2-54 | m/z = 411.16($C_{30}H_{21}NO$ = 411.50) |
| Sub 2-55 | m/z = 275.08($C_{18}H_{13}NS$ = 275.37) | Sub 2-56 | m/z = 351.11($C_{24}H_{17}NS$ = 351.47) |
| Sub 2-57 | m/z = 259.10($C_{18}H_{13}NO$ = 259.31) | Sub 2-58 | m/z = 309.12($C_{22}H_{15}NO$ = 309.37) |
| Sub 2-59 | m/z = 335.13($C_{24}H_{17}NO$ = 335.41) | Sub 2-60 | m/z = 275.08($C_{18}H_{13}NS$ = 275.37) |
| Sub 2-61 | m/z = 351.11($C_{24}H_{17}NS$ = 351.47) | Sub 2-62 | m/z = 335.13($C_{24}H_{17}NO$ = 335.41) |
| Sub 2-63 | m/z = 427.14($C_{30}H_{21}NS$ = 427.57) | Sub 2-64 | m/z = 477.16($C_{34}H_{23}NS$ = 477.63) |
| Sub 2-65 | m/z = 381.06($C_{24}H_{15}NS_2$ = 381.51) | Sub 2-66 | m/z = 457.10($C_{30}H_{19}NS_2$ = 457.61) |
| Sub 2-67 | m/z = 349.11($C_{24}H_{15}NO_2$ = 349.39) | Sub 2-68 | m/z = 349.11($C_{24}H_{15}NO_2$ = 349.39) |
| Sub 2-69 | m/z = 365.09($C_{24}H_{15}NOS$ = 365.45) | Sub 2-70 | m/z = 325.09($C_{22}H_{15}NS$ = 325.43) |
| Sub 2-71 | m/z = 325.09($C_{22}H_{15}NS$ = 325.43) | Sub 2-72 | m/z = 325.09($C_{22}H_{15}NS$ = 325.43) |
| Sub 2-73 | m/z = 325.09($C_{22}H_{15}NS$ = 325.43) | Sub 2-74 | m/z = 325.09($C_{22}H_{15}NS$ = 325.43) |
| Sub 2-75 | m/z = 435.16($C_{32}H_{21}NO$ = 435.53) | Sub 2-76 | m/z = 309.12($C_{22}H_{15}NO$ = 309.37) |
| Sub 2-77 | m/z = 325.09($C_{22}H_{15}NS$ = 325.43) | Sub 2-78 | m/z = 334.15($C_{24}H_{18}N_2$ = 334.42) |
| Sub 2-79 | m/z = 410.18($C_{30}H_{22}N_2$ = 410.52) | Sub 2-80 | m/z = 440.13($C_{30}H_{20}N_2S$ = 440.56) |
| Sub 2-81 | m/z = 436.19($C_{32}H_{24}N_2$ = 436.56) | Sub 2-82 | m/z = 334.15($C_{24}H_{18}N_2$ = 334.42) |
| Sub 2-83 | m/z = 410.18($C_{30}H_{22}N_2$ = 410.52) | Sub 2-84 | m/z = 334.15($C_{24}H_{18}N_2$ = 334.42) |
| Sub 2-85 | m/z = 334.15($C_{24}H_{18}N_2$ = 334.42) | Sub 2-86 | m/z = 285.15($C_{21}H_{19}N$ = 285.39) |
| Sub 2-87 | m/z = 361.18($C_{27}H_{23}N$ = 361.49) | Sub 2-88 | m/z = 285.15($C_{21}H_{19}N$ = 285.39) |
| Sub 2-89 | m/z = 435.20($C_{33}H_{25}N$ = 435.57) | Sub 2-90 | m/z = 335.17($C_{25}H_{21}N$ = 335.45) |
| Sub 2-91 | m/z = 391.14($C_{27}H_{21}NS$ = 391.53) | Sub 2-92 | m/z = 391.14($C_{27}H_{21}NS$ = 391.53) |
| Sub 2-93 | m/z = 375.16($C_{27}H_{21}NO$ = 375.47) | Sub 2-94 | m/z = 467.17($C_{33}H_{25}NS$ = 467.63) |
| Sub 2-95 | m/z = 409.18($C_{31}H_{23}N$ = 409.53) | Sub 2-96 | m/z = 407.17($C_{31}H_{21}N$ = 407.52) |
| Sub 2-97 | m/z = 513.16($C_{37}H_{23}NS$ = 513.66) | Sub 2-98 | m/z = 457.18($C_{35}H_{23}N$ = 457.58) |
| Sub 2-99 | m/z = 225.06($C_{14}H_{11}NS$ = 225.31) | | |

III. Synthesis of Final Product

After dissolving Sub 1 (1 eq.) with Toluene in a round bottom flask, Sub 2 (1 eq.), Pd2(dba)3 (0.03 eq.), (t-Bu)3P (1.00 eq.), and NaOt-Bu (2 eq.) were stirred at 100° C. When the reaction was completed, the resulting compound was extracted with $CH_2Cl_2$ and water, and the organic layer was dried over $MgSO_4$ and concentrated, and the resulting compound was recrystallized with a silicagel column to obtain Final product 1.

The Compounds of the present invention 1-30, 1-32, 1-35, 1-37, 1-67, 1-80, 1-86, 1-94, 1-111. 1-119, 1-133 are manufactured by the synthesis method disclosed in Korean Patent Registration No. 10-1668448 (registered on Oct. 17, 2016) and Korean Patent Registration No. 10-1789998 (registered on Oct. 19, 2017) of the applicant.

1. Synthesis Example of 1-1

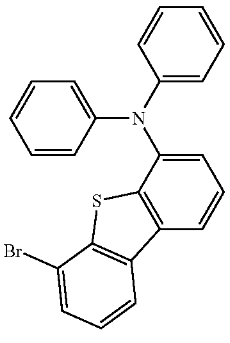

Sub 1-1

+

-continued

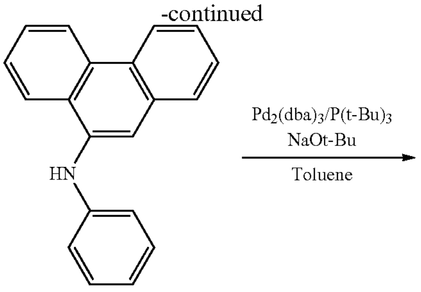

Sub 2-17

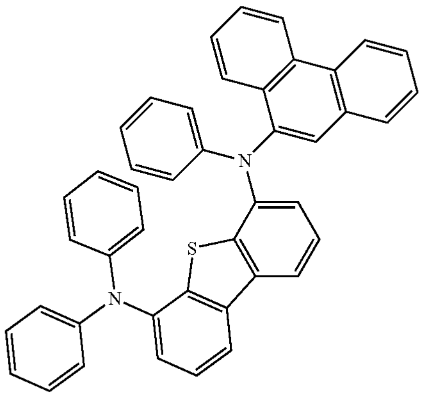

1-1

The obtained Sub 1-1 (5.97 g, 13.87 mmol) was added in a round bottom flask and dissolved in toluene (140 mL), Sub 2-17 (3.74 g, 13.87 mmol), $Pd_2(dba)_3$ (0.38 g, 0.42 mmol), $P(t\text{-}Bu)_3$ (0.28 g, 1.39 mmol), NaOt-Bu (2.67 g, 27.74 mmol) were added and stirred at 100° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 6.09 g of the product. (yield:71%)

2. Synthesis Example of 1-2

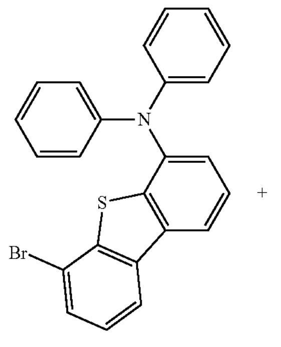

Sub 1-1

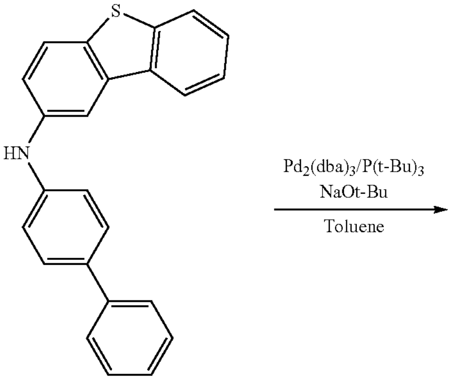

Sub 2-37

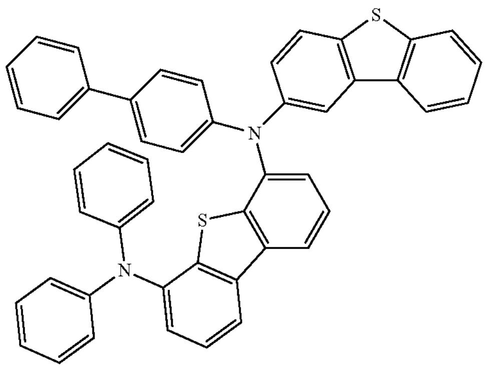

1-2

To Sub 1-1 (5.29 g, 12.29 mmol) obtained in the above synthesis, Sub 2-37 (4.32 g, 12.29 mmol), $Pd_2(dba)_3$ (0.34 g, 0.37 mmol) $P(t\text{-}Bu)_3$ (0.25 g, 1.23 mmol), NaOt-Bu (2.36 g, 24.58 mmol), toluene (125 ml) were added, and the same procedure as described in the synthesis method of 1-1 was carried out to obtain 6.81 g of the product. (yield:79%).

3. Synthesis Example of 1-4

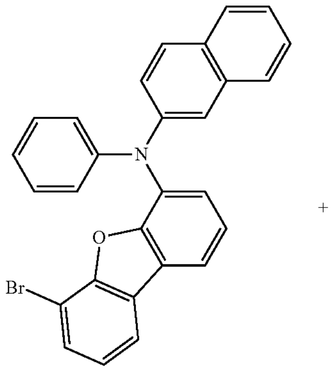

Sub 1-3

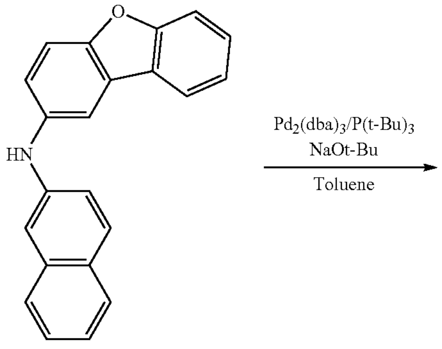

Sub 2-41

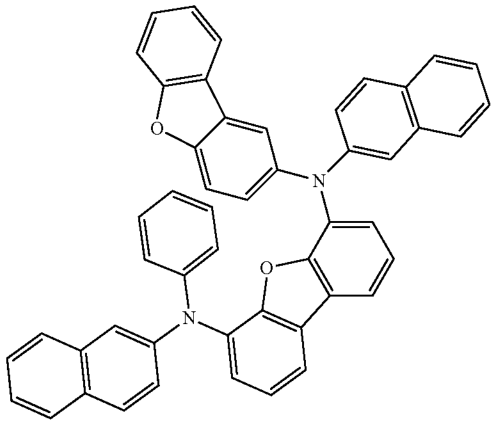

1-4

To Sub 1-3 (6.13 g, 13.20 mmol) obtained in the above synthesis, Sub 2-41 (4.08 g, 13.20 mmol), $Pd_2(dba)_3$ (0.36 g, 0.40 mmol) $P(t\text{-}Bu)_3$ (0.27 g, 1.32 mmol), NaOt-Bu (2.54 g, 26.40 mmol), toluene (130 ml) were added, and the same procedure as described in the synthesis method of 1-1 was carried out to obtain 7.32 g of the product. (yield:80%).

4. Synthesis Example of 1-10

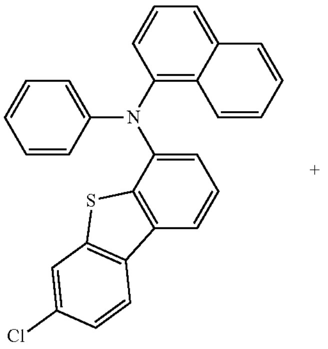

Sub 1-5

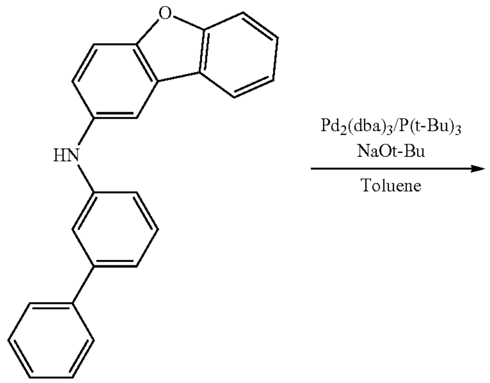

Sub 2-43

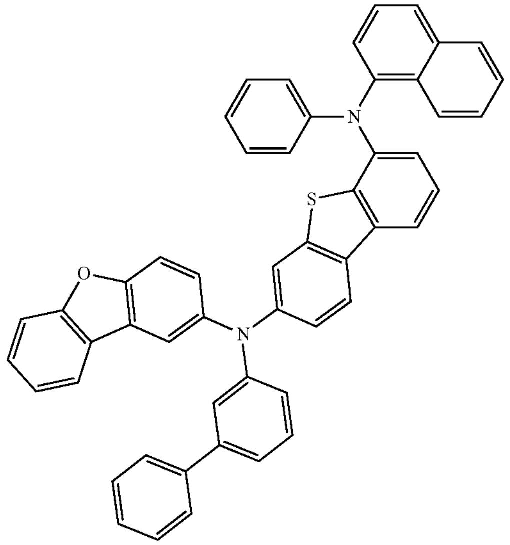

1-10

To Sub 1-5 (5.56 g, 12.75 mmol) obtained in the above synthesis, Sub 2-43 (4.28 g, 12.75 mmol), $Pd_2(dba)_3$ (0.35 g, 0.38 mmol) $P(t-Bu)_3$ (0.26 g, 1.28 mmol), NaOt-Bu (2.45 g, 25.51 mmol), toluene (130 ml) were added, and the same procedure as described in the synthesis method of 1-1 was carried out to obtain 8.06 g of the product. (yield:86%).

5. Synthesis Example of 1-24

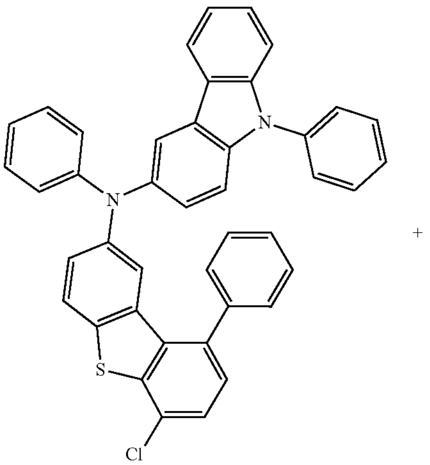

Sub 1-17

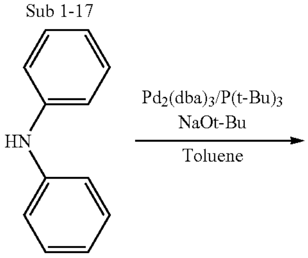

Sub 2-1

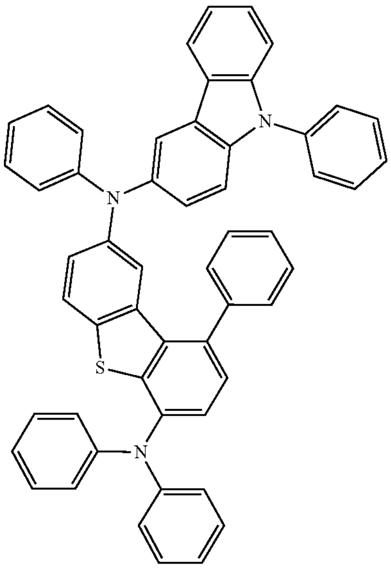

1-24

To Sub 1-17 (6.18 g, 9.85 mmol) obtained in the above synthesis, Sub 2-1 (1.67 g, 9.85 mmol), $Pd_2(dba)_3$ (0.27 g, 0.30 mmol) $P(t-Bu)_3$ (0.20 g, 0.99 mmol), NaOt-Bu (1.89 g, 19.71 mmol), toluene (100 ml) were added, and the same procedure as described in the synthesis method of 1-1 was carried out to obtain 5.62 g of the product. (yield:75%).

6. Synthesis Example of 1-122

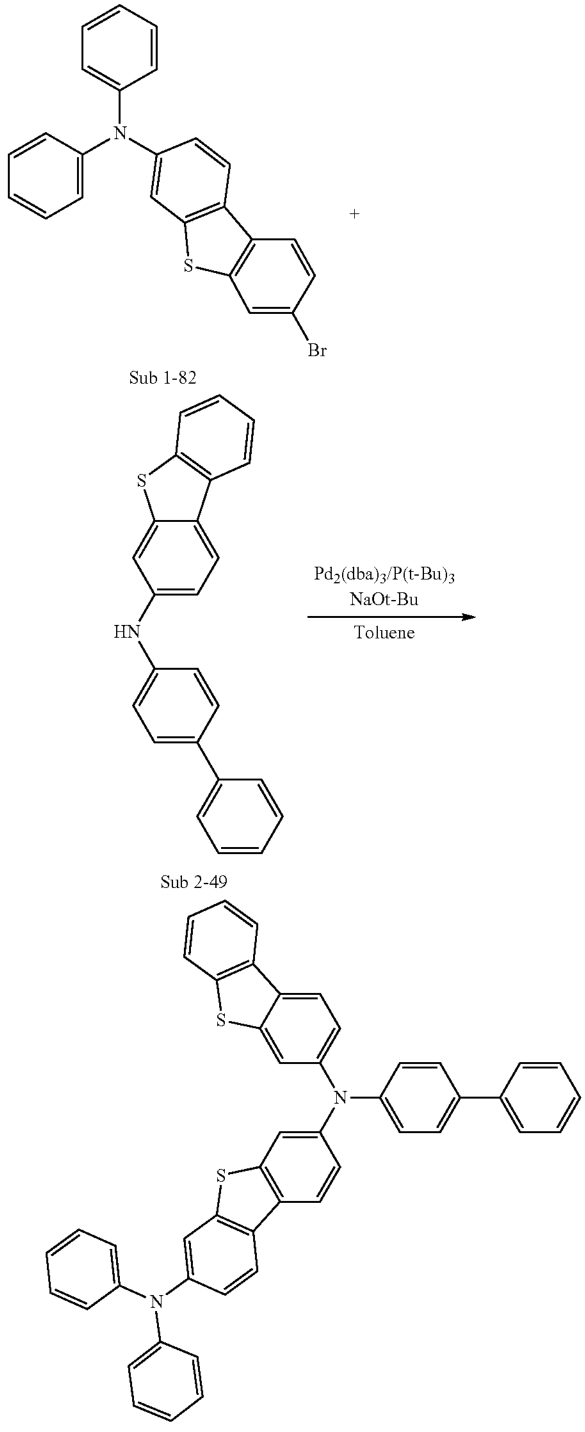

Sub 1-82

Sub 2-49

1-122

To Sub 1-82 (5.05 g, 11.73 mmol) obtained in the above synthesis, Sub 2-49 (4.12 g, 11.73 mmol), $Pd_2(dba)_3$ (0.32 g, 0.35 mmol) $P(t\text{-}Bu)_3$ (0.24 g, 1.17 mmol), NaOt-Bu (2.26 g, 23.47 mmol), toluene (120 ml) were added, and the same procedure as described in the synthesis method of 1-1 was carried out to obtain 7.65 g of the product. (yield:93%).

7. Synthesis Example of 1-125

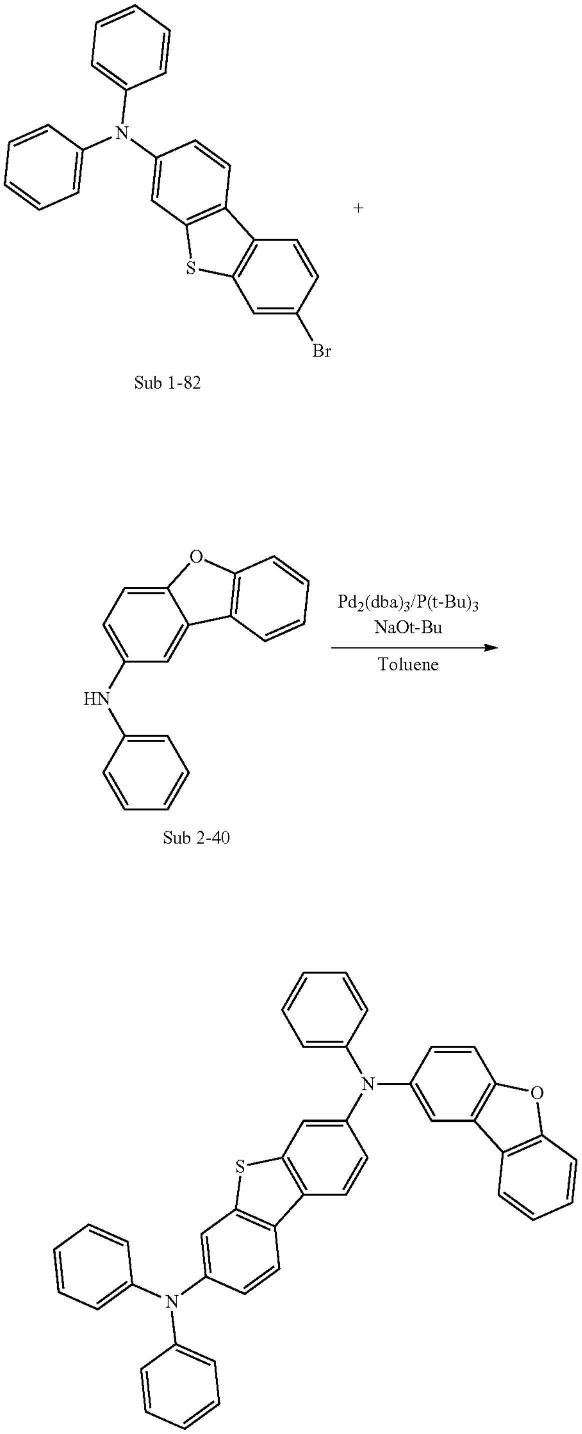

Sub 1-82

Sub 2-40

1-125

To Sub 1-82 (5.20 g, 12.08 mmol) obtained in the above synthesis, Sub 2-40 (3.13 g, 12.08 mmol), $Pd_2(dba)_3$ (0.33 g, 0.36 mmol) $P(t\text{-}Bu)_3$ (0.24 g, 1.21 mmol), NaOt-Bu (2.32 g, 24.17 mmol), toluene (120 ml) were added, and the same procedure as described in the synthesis method of 1-1 was carried out to obtain 6.69 g of the product. (yield:91%).

8. Synthesis Example of 1-141

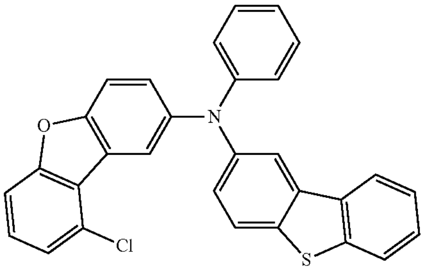

Sub 1-102

+

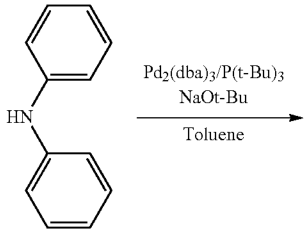

Sub 2-1

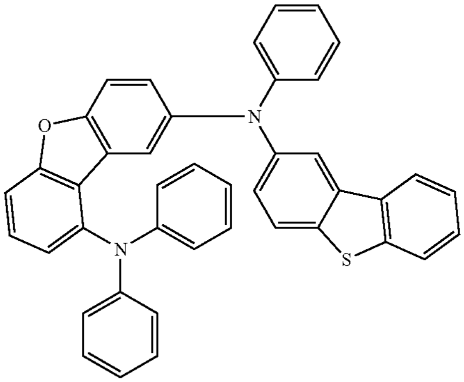

1-141

To Sub 1-102 (6.26 g, 13.15 mmol) obtained in the above synthesis, Sub 2-1 (2.23 g, 13.15 mmol), $Pd_2(dba)_3$ (0.36 g, 0.39 mmol) $P(t\text{-}Bu)_3$ (0.27 g, 1.32 mmol), NaOt-Bu (2.53 g, 26.30 mmol), toluene (130 ml) were added, and the same procedure as described in the synthesis method of 1-1 was carried out to obtain 6.57 g of the product. (yield:82%).

9. Synthesis Example of 1-146

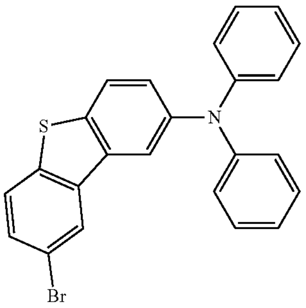

Sub 1-104

+

-continued

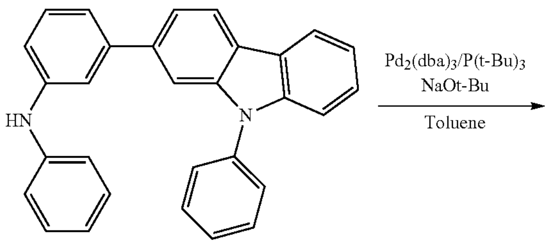

Sub 2-83

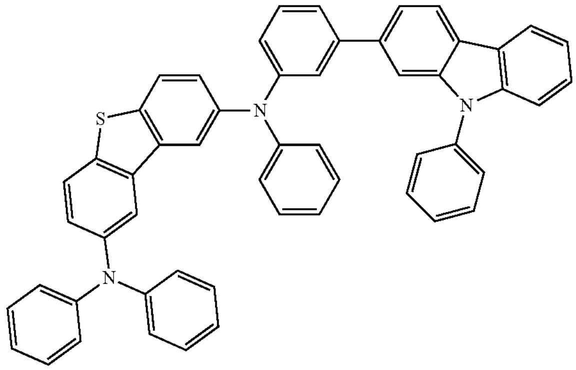

1-146

To Sub 1-104 (6.12 g, 14.22 mmol) obtained in the above synthesis, Sub 2-83 (5.84 g, 14.22 mmol), $Pd_2(dba)_3$ (0.39 g, 0.43 mmol) $P(t\text{-}Bu)_3$ (0.29 g, 1.42 mmol), NaOt-Bu (2.73 g, 28.43 mmol), toluene (140 ml) were added, and the same procedure as described in the synthesis method of 1-1 was carried out to obtain 8.00 g of the product. (yield:74%).

10. Synthesis Example of 1-158

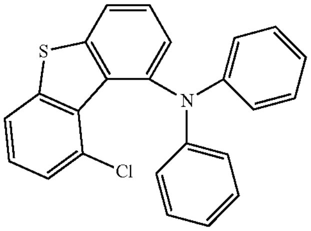

+

Sub 1-112

-continued

-continued

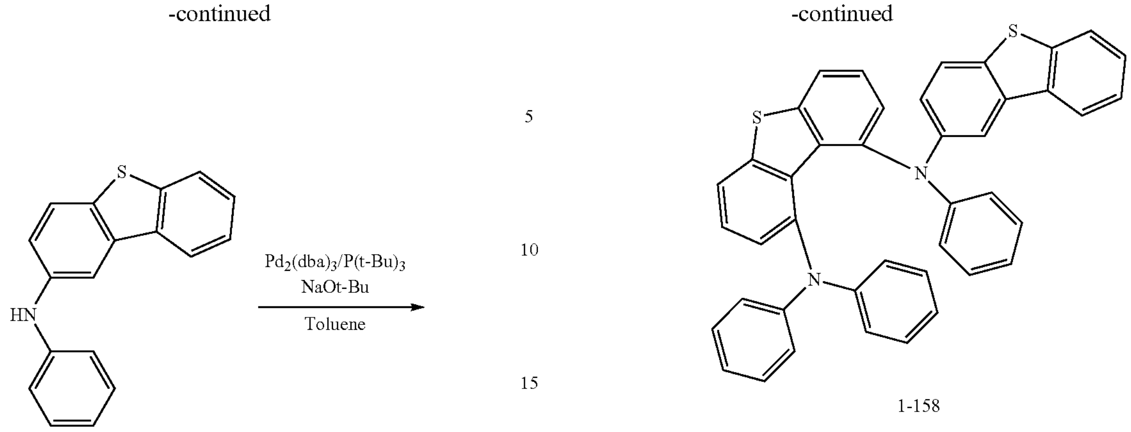

Sub 2-29

1-158

To Sub 1-112 (5.75 g, 14.90 mmol) obtained in the above synthesis, Sub 2-29 (4.10 g, 14.90 mmol), $Pd_2(dba)_3$ (0.41 g, 0.45 mmol) $P(t\text{-}Bu)_3$ (0.30 g, 1.49 mmol), NaOt-Bu (2.86 g, 29.80 mmol), toluene (150 ml) were added, and the same procedure as described in the synthesis method of 1-1 was carried out to obtain 6.24 g of the product. (yield:67%).

Meanwhile, FD-MS values of compounds 1-1 to 1-175 of the present invention prepared according to the synthesis example as described above are shown in Table 3 below.

TABLE 3

| compound | FD-MS | compound | FD-MS |
|---|---|---|---|
| 1-1 | m/z = 618.21($C_{44}H_{30}N_2S$ = 618.80) | 1-2 | m/z = 700.20($C_{48}H_{32}N_2S_2$ = 700.92) |
| 1-3 | m/z = 708.22($C_{50}H_{32}N_2OS$ = 708.88) | 1-4 | m/z = 692.25($C_{50}H_{32}N_2O_2$ = 692.82) |
| 1-5 | m/z = 742.30($C_{55}H_{38}N_2O$ = 742.92) | 1-6 | m/z = 654.27($C_{48}H_{34}N_2O$ = 654.81) |
| 1-7 | m/z = 700.20($C_{48}H_{32}N_2S_2$ = 700.92) | 1-8 | m/z = 760.25($C_{54}H_{36}N_2OS$ = 760.96) |
| 1-9 | m/z = 730.16($C_{48}H_{30}N_2S_3$ = 730.96) | 1-10 | m/z = 734.24($C_{52}H_{34}N_2OS$ = 734.92) |
| 1-11 | m/z = 872.32($C_{64}H_{44}N_2S$ = 873.13) | 1-12 | m/z = 718.26($C_{52}H_{34}N_2O_2$ = 718.86) |
| 1-13 | m/z = 568.20($C_{40}H_{28}N_2S$ = 568.74) | 1-14 | m/z = 624.17($C_{42}H_{28}N_2S_2$ = 624.82) |
| 1-15 | m/z = 658.21($C_{46}H_{30}N_2OS$ = 658.82) | 1-16 | m/z = 730.30($C_{54}H_{38}N_2O$ = 730.91) |
| 1-17 | m/z = 698.20($C_{48}H_{30}N_2O_2S$ = 698.84) | 1-18 | m/z = 624.17($C_{42}H_{28}N_2S_2$ = 624.82) |
| 1-19 | m/z = 700.20($C_{48}H_{32}N_2S_2$ = 700.92) | 1-20 | m/z = 708.22($C_{50}H_{32}N_2OS$ = 708.88) |
| 1-21 | m/z = 750.22($C_{52}H_{34}N_2S_2$ = 750.98) | 1-22 | m/z = 776.23($C_{54}H_{36}N_2S_2$ = 777.02) |
| 1-23 | m/z = 867.24($C_{59}H_{37}N_3OS_2$ = 868.09) | 1-24 | m/z = 759.27($C_{54}H_{37}N_3S$ = 759.97) |
| 1-25 | m/z = 608.19($C_{42}H_{28}N_2OS$ = 608.76) | 1-26 | m/z = 608.19($C_{42}H_{28}N_2OS$ = 608.76) |
| 1-27 | m/z = 692.25($C_{50}H_{32}N_2O_2$ = 692.82) | 1-28 | m/z = 894.20($C_{60}H_{34}N_2O_3S_2$ = 895.06) |
| 1-29 | m/z = 618.21($C_{44}H_{30}N_2S$ = 618.80) | 1-30 | m/z = 700.20($C_{48}H_{32}N_2S_2$ = 700.92) |
| 1-31 | m/z = 780.17($C_{52}H_{32}N_2S_3$ = 781.02) | 1-32 | m/z = 734.24($C_{52}H_{34}N_2OS$ = 734.92) |
| 1-33 | m/z = 834.31($C_{61}H_{42}N_2S$ = 835.08) | 1-34 | m/z = 700.20($C_{48}H_{32}N_2S_2$ = 700.92) |
| 1-35 | m/z = 724.25($C_{51}H_{36}N_2OS$ = 724.92) | 1-36 | m/z = 624.17($C_{42}H_{28}N_2S_2$ = 624.82) |
| 1-37 | m/z = 700.20($C_{48}H_{32}N_2S_2$ = 700.92) | 1-38 | m/z = 700.20($C_{48}H_{32}N_2S_2$ = 700.92) |
| 1-39 | m/z = 674.19($C_{46}H_{30}N_2S_2$ = 674.88) | 1-40 | m/z = 700.20($C_{48}H_{32}N_2S_2$ = 700.92) |
| 1-41 | m/z = 608.19($C_{42}H_{28}N_2OS$ = 608.76) | 1-42 | m/z = 684.22($C_{48}H_{32}N_2OS$ = 684.86) |
| 1-43 | m/z = 684.22($C_{48}H_{32}N_2OS$ = 684.86) | 1-44 | m/z = 624.17($C_{42}H_{28}N_2S_2$ = 624.82) |
| 1-45 | m/z = 674.19($C_{46}H_{30}N_2S_2$ = 674.88) | 1-46 | m/z = 700.20($C_{48}H_{32}N_2S_2$ = 700.92) |
| 1-47 | m/z = 826.25($C_{58}H_{38}N_2S_2$ = 827.08) | 1-48 | m/z = 608.19($C_{42}H_{28}N_2OS$ = 608.76) |
| 1-49 | m/z = 624.17($C_{42}H_{28}N_2S_2$ = 624.82) | 1-50 | m/z = 684.22($C_{48}H_{32}N_2OS$ = 684.86) |
| 1-51 | m/z = 700.20($C_{48}H_{32}N_2S_2$ = 700.92) | 1-52 | m/z = 684.22($C_{48}H_{32}N_2OS$ = 684.86) |
| 1-53 | m/z = 730.16($C_{48}H_{30}N_2S_3$ = 730.96) | 1-54 | m/z = 826.25($C_{58}H_{38}N_2S_2$ = 827.08) |
| 1-55 | m/z = 806.19($C_{54}H_{34}N_2S_3$ = 807.06) | 1-56 | m/z = 674.19($C_{46}H_{30}N_2S_2$ = 674.88) |
| 1-57 | m/z = 674.19($C_{46}H_{30}N_2S_2$ = 674.88) | 1-58 | m/z = 674.19($C_{46}H_{30}N_2S_2$ = 674.88) |
| 1-59 | m/z = 674.19($C_{46}H_{30}N_2S_2$ = 674.88) | 1-60 | m/z = 674.19($C_{46}H_{30}N_2S_2$ = 674.88) |
| 1-61 | m/z = 638.19($C_{43}H_{30}N_2S_2$ = 638.85) | 1-62 | m/z = 638.19($C_{43}H_{30}N_2S_2$ = 638.85) |
| 1-63 | m/z = 638.19($C_{43}H_{30}N_2S_2$ = 638.85) | 1-64 | m/z = 622.21($C_{43}H_{30}N_2OS$ = 622.79) |
| 1-65 | m/z = 688.20($C_{47}H_{32}N_2S_2$ = 688.91) | 1-66 | m/z = 700.20($C_{48}H_{32}N_2S_2$ = 700.92) |
| 1-67 | m/z = 789.23($C_{54}H_{35}N_3S_2$ = 790.02) | 1-68 | m/z = 638.19($C_{43}H_{30}N_2S_2$ = 638.85) |
| 1-69 | m/z = 638.19($C_{43}H_{30}N_2S_2$ = 638.85) | 1-70 | m/z = 642.16($C_{42}H_{27}FN_2S_2$ = 642.81) |
| 1-71 | m/z = 638.19($C_{43}H_{30}N_2S_2$ = 638.85) | 1-72 | m/z = 714.22($C_{49}H_{34}N_2S_2$ = 714.95) |
| 1-73 | m/z = 716.20($C_{48}H_{32}N_2OS_2$ = 716.92) | 1-74 | m/z = 670.24($C_{48}H_{34}N_2S$ = 670.87) |
| 1-75 | m/z = 634.24($C_{45}H_{34}N_2S$ = 634.84) | 1-76 | m/z = 759.27($C_{54}H_{37}N_3S$ = 759.97) |
| 1-77 | m/z = 674.19($C_{46}H_{30}N_2S_2$ = 674.88) | 1-78 | m/z = 708.22($C_{50}H_{32}N_2OS$ = 708.88) |
| 1-79 | m/z = 674.19($C_{46}H_{30}N_2S_2$ = 674.88) | 1-80 | m/z = 748.22($C_{52}H_{32}N_2O_2S$ = 748.90) |

TABLE 3-continued

| compound | FD-MS | compound | FD-MS |
|---|---|---|---|
| 1-81 | m/z = 821.29($C_{57}H_{35}D_5N_2S_2$ = 822.11) | 1-82 | m/z = 730.16($C_{48}H_{30}N_2S_3$ = 730.96) |
| 1-83 | m/z = 730.16($C_{48}H_{30}N_2S_3$ = 730.96) | 1-84 | m/z = 714.18($C_{48}H_{30}N_2OS_2$ = 714.90) |
| 1-85 | m/z = 882.22($C_{60}H_{38}N_2S_3$ = 883.16) | 1-86 | m/z = 624.17($C_{42}H_{28}N_2S_2$ = 624.82) |
| 1-87 | m/z = 700.20($C_{48}H_{32}N_2S_2$ = 700.92) | 1-88 | m/z = 674.19($C_{46}H_{30}N_2S_2$ = 674.88) |
| 1-89 | m/z = 674.19($C_{46}H_{30}N_2S_2$ = 674.88) | 1-90 | m/z = 708.22($C_{50}H_{32}N_2OS$ = 708.88) |
| 1-91 | m/z = 759.27($C_{54}H_{37}N_3S$ = 759.97) | 1-92 | m/z = 674.19($C_{46}H_{30}N_2S_2$ = 674.88) |
| 1-93 | m/z = 688.20($C_{47}H_{32}N_2S_2$ = 688.91) | 1-94 | m/z = 760.25($C_{54}H_{36}N_2OS$ = 760.96) |
| 1-95 | m/z = 759.27($C_{54}H_{37}N_3S$ = 759.97) | 1-96 | m/z = 608.19($C_{42}H_{28}N_2OS$ = 608.76) |
| 1-97 | m/z = 684.22($C_{48}H_{32}N_2OS$ = 684.86) | 1-98 | m/z = 622.21($C_{43}H_{30}N_2OS$ = 622.79) |
| 1-99 | m/z = 760.25($C_{54}H_{36}N_2OS$ = 760.96) | 1-100 | m/z = 658.21($C_{46}H_{30}N_2OS$ = 658.82) |
| 1-101 | m/z = 658.21($C_{46}H_{30}N_2OS$ = 658.82) | 1-102 | m/z = 692.25($C_{50}H_{32}N_2O_2$ = 692.82) |
| 1-103 | m/z = 628.25($C_{46}H_{32}N_2O$ = 628.78) | 1-104 | m/z = 693.28($C_{50}H_{35}N_3O$ = 693.85) |
| 1-105 | m/z = 723.23($C_{50}H_{33}N_3OS$ = 723.89) | 1-106 | m/z = 749.29($C_{54}H_{31}D_5N_2S$ = 749.99) |
| 1-107 | m/z = 700.20($C_{48}H_{32}N_2S_2$ = 700.92) | 1-108 | m/z = 674.19($C_{46}H_{30}N_2S_2$ = 674.88) |
| 1-109 | m/z = 684.22($C_{48}H_{32}N_2OS$ = 684.86) | 1-110 | m/z = 724.25($C_{51}H_{36}N_2OS$ = 724.92) |
| 1-111 | m/z = 674.19($C_{46}H_{30}N_2S_2$ = 674.88) | 1-112 | m/z = 674.19($C_{46}H_{30}N_2S_2$ = 674.88) |
| 1-113 | m/z = 780.17($C_{52}H_{32}N_2S_3$ = 781.02) | 1-114 | m/z = 684.22($C_{48}H_{32}N_2OS$ = 684.86) |
| 1-115 | m/z = 684.22($C_{48}H_{32}N_2OS$ = 684.86) | 1-116 | m/z = 698.20($C_{48}H_{30}N_2O_2S$ = 698.84) |
| 1-117 | m/z = 618.26($C_{42}H_{18}D_{10}N_2OS$ = 618.82) | 1-118 | m/z = 757.27($C_{54}H_{35}N_3O_2$ = 757.89) |
| 1-119 | m/z = 668.25($C_{48}H_{32}N_2O_2$ = 668.80) | 1-120 | m/z = 720.26($C_{52}H_{36}N_2S$ = 720.93) |
| 1-121 | m/z = 670.24($C_{48}H_{34}N_2S$ = 670.87) | 1-122 | m/z = 700.20($C_{48}H_{32}N_2S_2$ = 700.92) |
| 1-123 | m/z = 674.19($C_{46}H_{30}N_2S_2$ = 674.88) | 1-124 | m/z = 700.20($C_{48}H_{32}N_2S_2$ = 700.92) |
| 1-125 | m/z = 608.19($C_{42}H_{28}N_2OS$ = 608.76) | 1-126 | m/z = 860.25($C_{58}H_{40}N_2O_2S_2$ = 861.09) |
| 1-127 | m/z = 798.27($C_{57}H_{38}N_2OS$ = 799.00) | 1-128 | m/z = 734.33($C_{54}H_{42}N_2O$ = 734.94) |
| 1-129 | m/z = 742.26($C_{54}H_{34}N_2O_2$ = 742.88) | 1-130 | m/z = 945.37($C_{70}H_{47}N_3O$ = 946.17) |
| 1-131 | m/z = 670.24($C_{48}H_{34}N_2S$ = 670.87) | 1-132 | m/z = 624.17($C_{42}H_{28}N_2S_2$ = 624.82) |
| 1-133 | m/z = 700.20($C_{48}H_{32}N_2S_2$ = 700.92) | 1-134 | m/z = 724.20($C_{50}H_{32}N_2S_2$ = 724.94) |
| 1-135 | m/z = 816.26($C_{57}H_{40}N_2S_2$ = 817.08) | 1-136 | m/z = 760.25($C_{54}H_{36}N_2OS$ = 760.96) |
| 1-137 | m/z = 674.19($C_{46}H_{30}N_2S_2$ = 674.88) | 1-138 | m/z = 730.16($C_{48}H_{30}N_2S_3$ = 730.96) |
| 1-139 | m/z = 881.29($C_{61}H_{43}N_3S_2$ = 882.16) | 1-140 | m/z = 704.28($C_{52}H_{36}N_2O$ = 704.87) |
| 1-141 | m/z = 608.19($C_{42}H_{28}N_2OS$ = 608.76) | 1-142 | m/z = 682.23($C_{48}H_{30}N_2O_3$ = 682.78) |
| 1-143 | m/z = 670.24($C_{48}H_{34}N_2S$ = 670.87) | 1-144 | m/z = 776.23($C_{54}H_{36}N_2S_2$ = 777.02) |
| 1-145 | m/z = 674.19($C_{46}H_{30}N_2S_2$ = 674.88) | 1-146 | m/z = 759.27($C_{54}H_{37}N_3S$ = 759.97) |
| 1-147 | m/z = 758.24($C_{54}H_{34}N_2OS$ = 758.94) | 1-148 | m/z = 806.28($C_{59}H_{38}N_2S$ = 807.03) |
| 1-149 | m/z = 823.30($C_{59}H_{38}FN_3O$ = 823.97) | 1-150 | m/z = 743.29($C_{54}H_{37}N_3O$ = 743.91) |
| 1-151 | m/z = 998.33($C_{73}H_{46}N_2OS$ = 999.24) | 1-152 | m/z = 700.20($C_{48}H_{32}N_2S_2$ = 700.92) |
| 1-153 | m/z = 674.19($C_{46}H_{30}N_2S_2$ = 674.88) | 1-154 | m/z = 674.19($C_{46}H_{30}N_2S_2$ = 674.88) |
| 1-155 | m/z = 674.19($C_{46}H_{30}N_2S_2$ = 674.88) | 1-156 | m/z = 674.19($C_{46}H_{30}N_2S_2$ = 674.88) |
| 1-157 | m/z = 762.29($C_{50}H_{46}N_2SSi_2$ = 763.16) | 1-158 | m/z = 624.17($C_{42}H_{28}N_2S_2$ = 624.82) |
| 1-159 | m/z = 784.25($C_{56}H_{36}N_2OS$ = 784.98) | 1-160 | m/z = 810.27($C_{58}H_{38}N_2OS$ = 811.02) |
| 1-161 | m/z = 860.29($C_{62}H_{40}N_2OS$ = 861.08) | 1-162 | m/z = 708.22($C_{50}H_{32}N_2OS$ = 708.88) |
| 1-163 | m/z = 742.26($C_{54}H_{34}N_2O_2$ = 742.88) | 1-164 | m/z = 828.26($C_{58}H_{40}N_2S_2$ = 829.09) |
| 1-165 | m/z = 708.22($C_{50}H_{32}N_2OS$ = 708.88) | 1-166 | m/z = 724.20($C_{50}H_{32}N_2S_2$ = 724.94) |
| 1-167 | m/z = 834.27($C_{60}H_{38}N_2OS$ = 835.04) | 1-168 | m/z = 768.28($C_{56}H_{36}N_2O_2$ = 768.92) |
| 1-169 | m/z = 830.19($C_{56}H_{34}N_2S_3$ = 831.08) | 1-170 | m/z = 810.27($C_{58}H_{38}N_2OS$ = 811.02) |
| 1-171 | m/z = 810.31($C_{59}H_{42}N_2S$ = 811.06) | 1-172 | m/z = 692.25($C_{50}H_{32}N_2O_2$ = 692.82) |
| 1-173 | m/z = 758.24($C_{54}H_{34}N_2OS$ = 758.94) | 1-174 | m/z = 783.27($C_{56}H_{37}N_3S$ = 783.99) |
| 1-175 | m/z = 808.25($C_{58}H_{36}N_2OS$ = 809.00) | | |

Synthesis Example 2

The compound (final product) represented by Formula 2 according to the present invention may be prepared by reacting Sub 3 and Sub 4 as shown in Reaction Scheme 4 below, but is not limited thereto.

<Reaction Scheme 4>

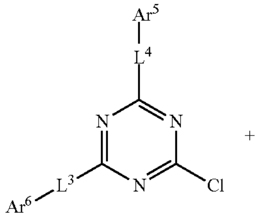

Sub 3

-continued

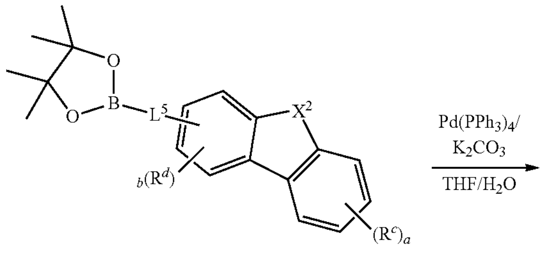

Sub 4

-continued

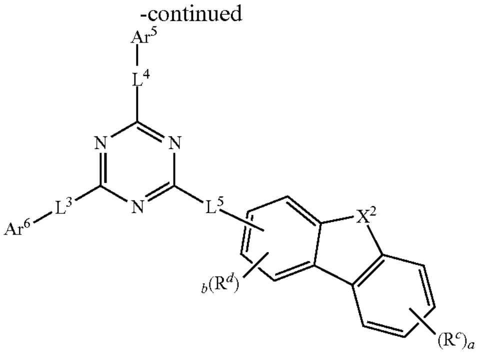

Final product 2

Synthesis Example of 1'-1

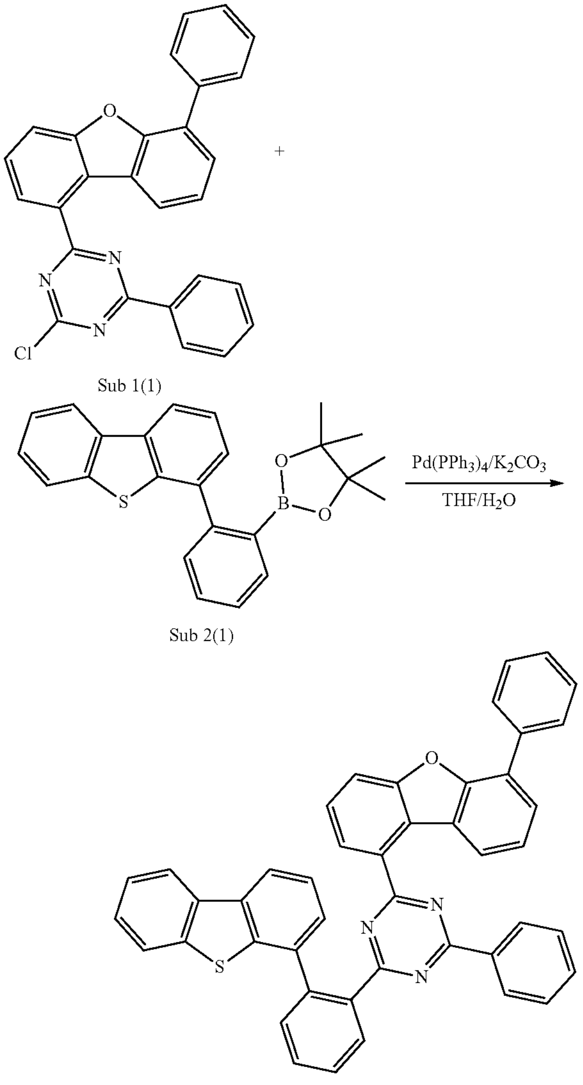

Sub 1(1)

Sub 2(1)

1'-1

After placing Sub 1(1) (34.7 g, 80 mmol) and Sub 2(1) (30.9 g, 80 mmol), K2CO3 (19.3 g, 140 mmol), Pd(PPh3)4 (2.8 g, 2.4 mmol) in a round bottom flask, THF and water were added to dissolve it, and then refluxed at 80° C. for 12 hours. When the reaction was completed, the temperature of the reaction product was cooled to room temperature, extracted with $CH_2Cl_2$, and washed with water. The organic layer was dried over $MgSO_4$, concentrated, and the resulting organic material was separated using a silicagel column to obtain the desired product (37.4 g, 71%).

Synthesis Example of 1'-6

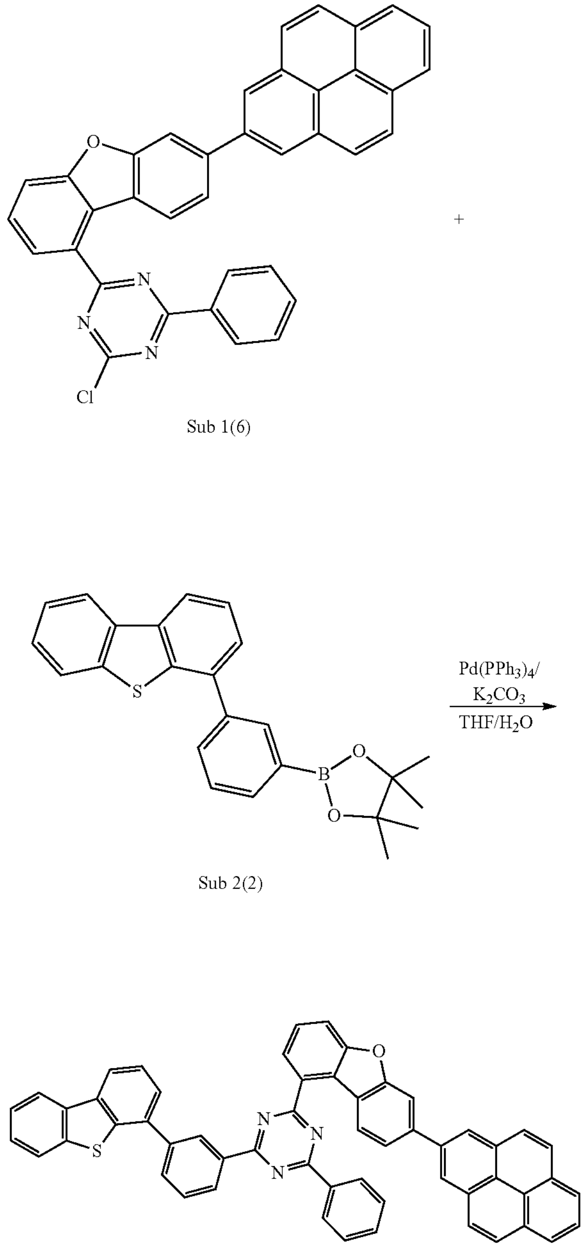

Sub 1(6)

Sub 2(2)

1'-6

Sub 1(6) (44.6 g, 80 mmol) and Sub 2(2) (30.9 g, 80 mmol) were used to obtain a product (43.2 g, 69%) using the synthesis method of 1'-1.

Synthesis Example of 1'-12
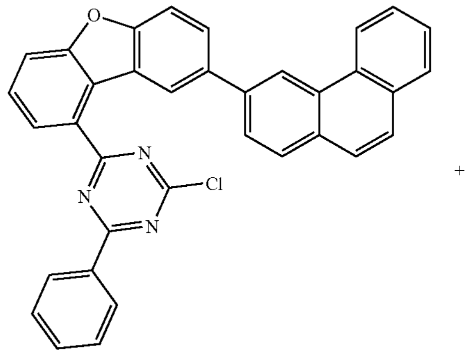
Sub 1(12)
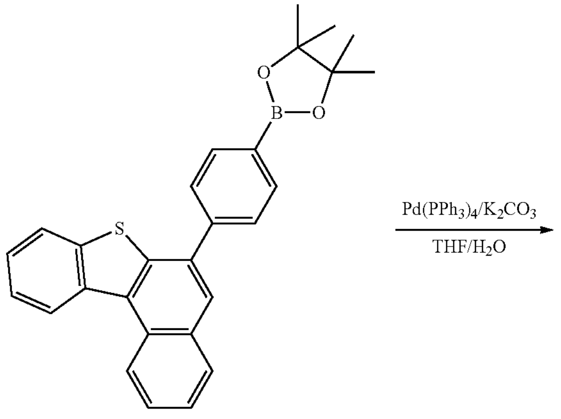
Sub 2(33)
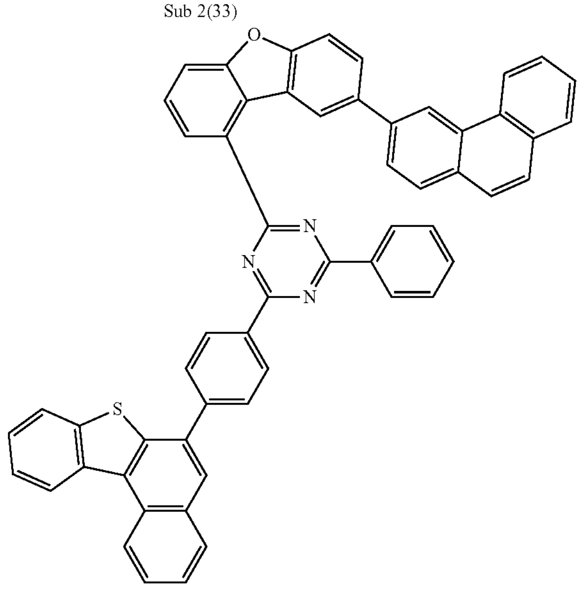
1'-12
Sub 1(12) (42.7 g, 80 mmol) and Sub 2(33) (34.9 g, 80 mmol) were used to obtain a product (42.7 g, 66%) using the synthesis method of 1'-1.
Synthesis Example of 1'-33
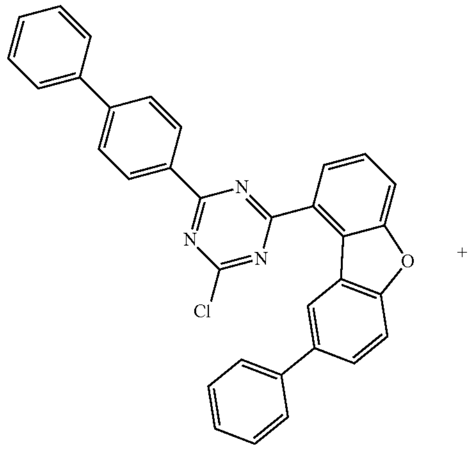
Sub 1(27)
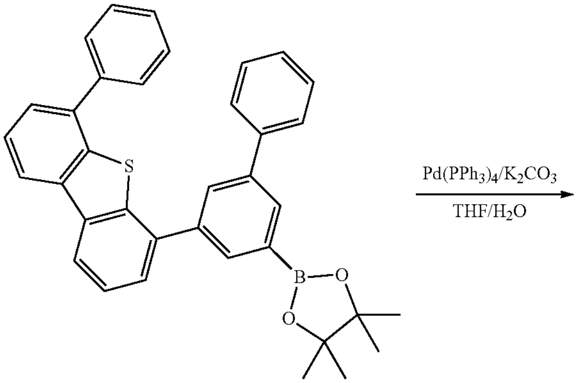
Sub 2(9)
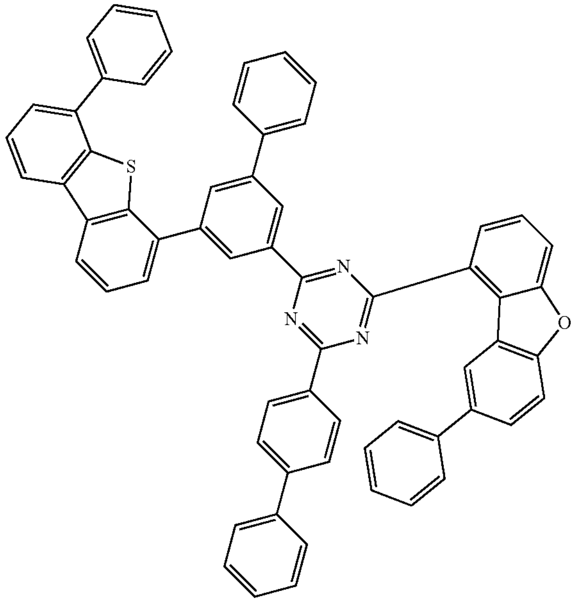
1'-33
Sub 1(27) (40.8 g, 80 mmol) and Sub 2(9) (43.1 g, 80 mmol) were used to obtain a product (51.0 g, 72%) using the synthesis method of 1'-1.

Synthesis Example of 1'-44
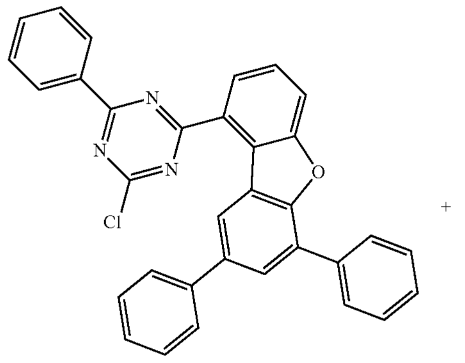
Sub 1(28)
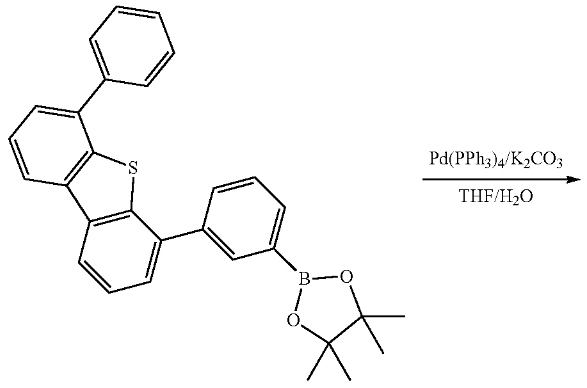
Sub 2(10)
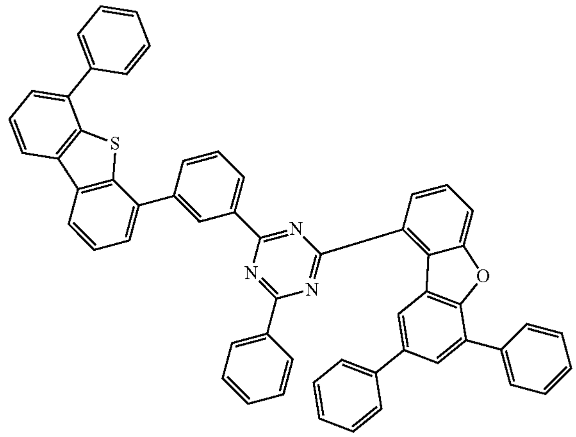
1'-44
Sub 1(27) (40.8 g, 80 mmol) and Sub 2(10) (37.0 g, 80 mmol) were used to obtain a product (45.4 g, 70%) using the synthesis method of 1'-1.
Synthesis Example of 1'-53
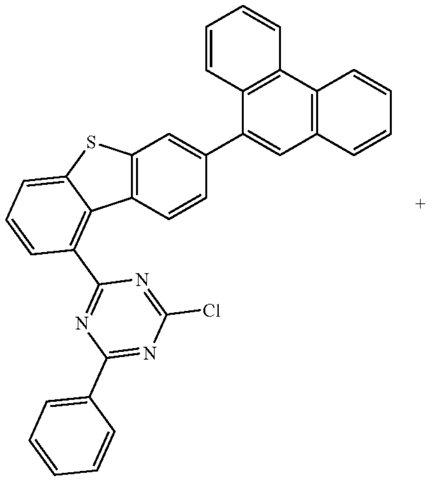
Sub 1(34)
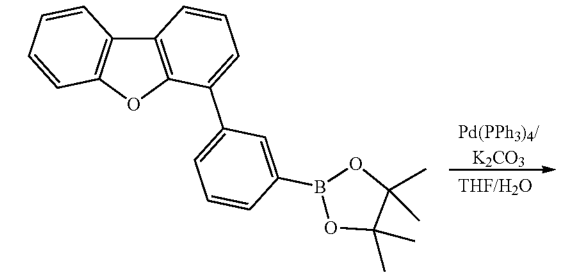
Sub 2(29)
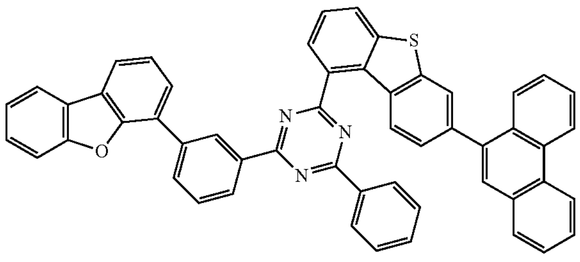
1'-53
Sub 1(34) (44.0 g, 80 mmol) and Sub 2(29) (29.6 g, 80 mmol) were used to obtain a product (41.2 g, 68%) using the synthesis method of 1'-1.

Synthesis Example of 1'-64
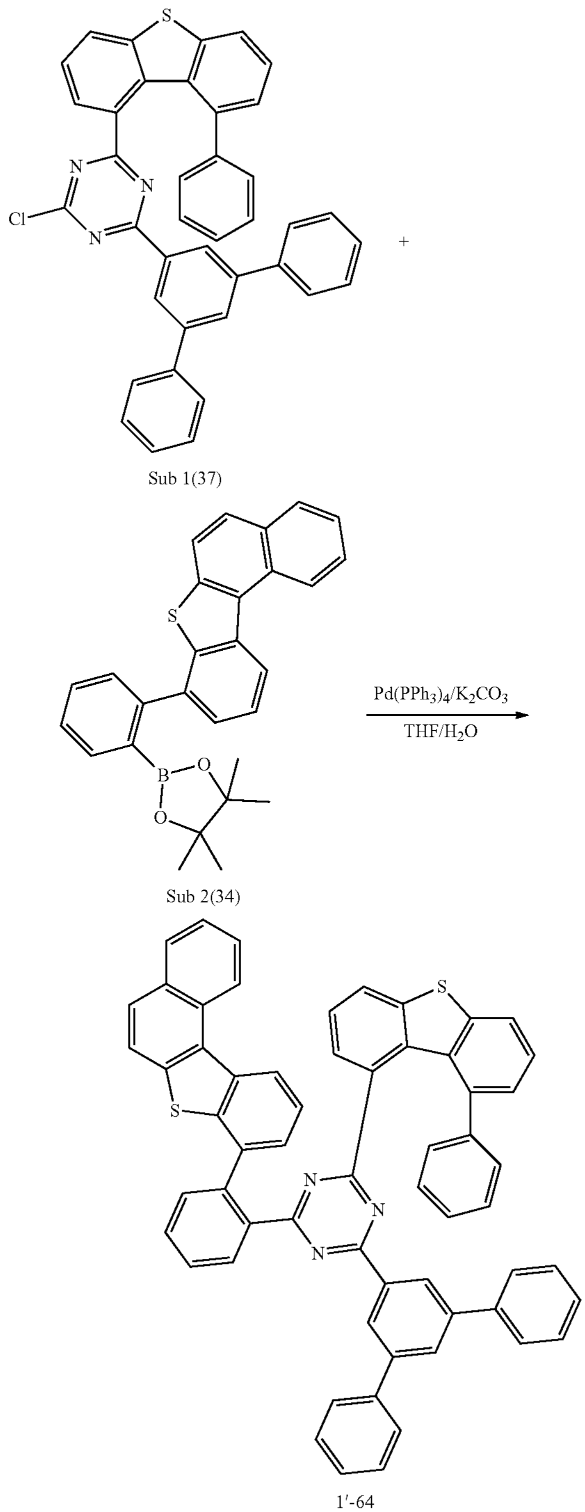
Sub 1(37)
Sub 2(34)
1'-64
Sub 1(37) (48.2 g, 80 mmol) and Sub 2(34) (34.9 g, 80 mmol) were used to obtain a product (45.6 g, 71%) using the synthesis method of 1'-1.
Synthesis Example of 1'-75
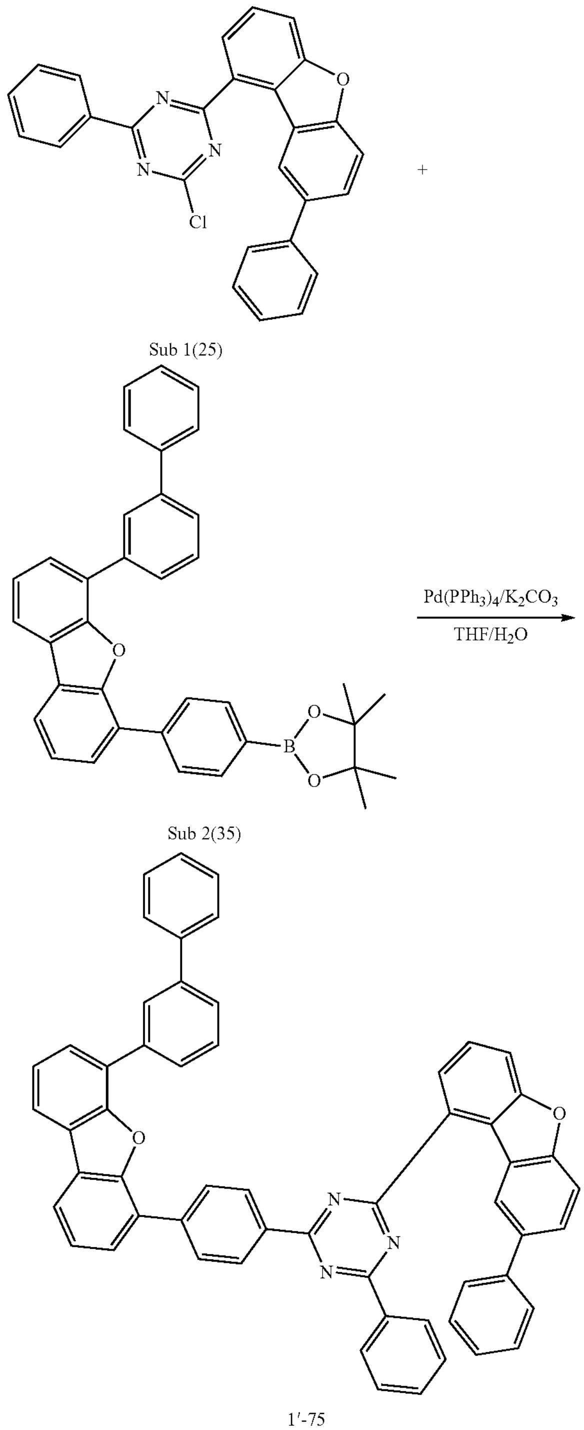
Sub 1(25)
Sub 2(35)
1'-75
Sub 1(25) (34.7 g, 80 mmol) and Sub 2(35) (41.8 g, 80 mmol) were used to obtain a product (46.4 g, 73%) using the synthesis method of 1'-1.

Synthesis Example of 2-1
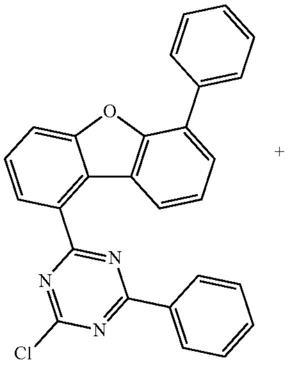
Sub 1(1)
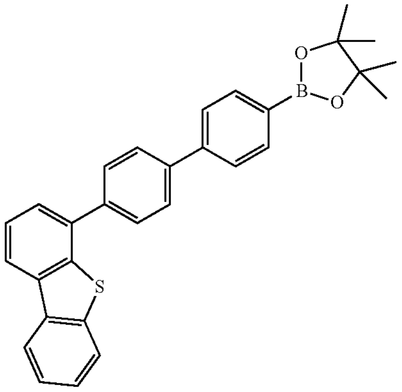
Sub 2(27)
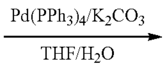
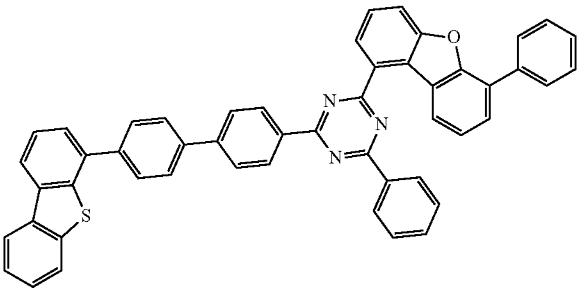
2-1
Sub 1(1) (34.7 g, 80 mmol) and Sub 2(27) (37.0 g, 80 mmol) were used to obtain a product (42.3 g, 72%) using the synthesis method of 1'-1.
Synthesis Example of 2-22
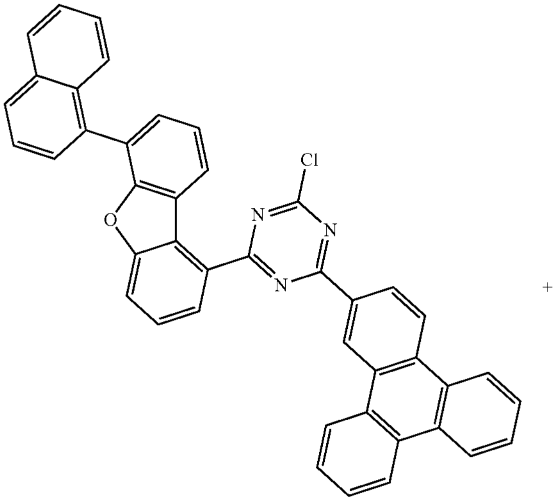
Sub 1(38)
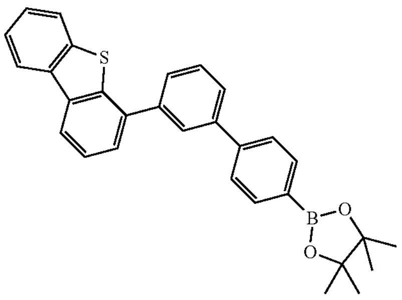
Sub 2(24)
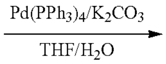
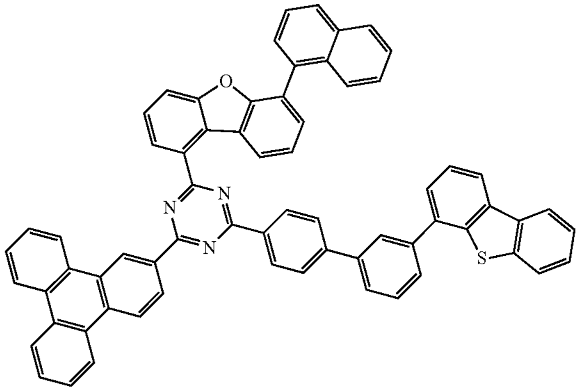
2-22
Sub 1(38) (50.7 g, 80 mmol) and Sub 2(24) (37.0 g, 80 mmol) were used to obtain a product (51.6 g, 69%) using the synthesis method of 1'-1.

Synthesis Example of 2-33
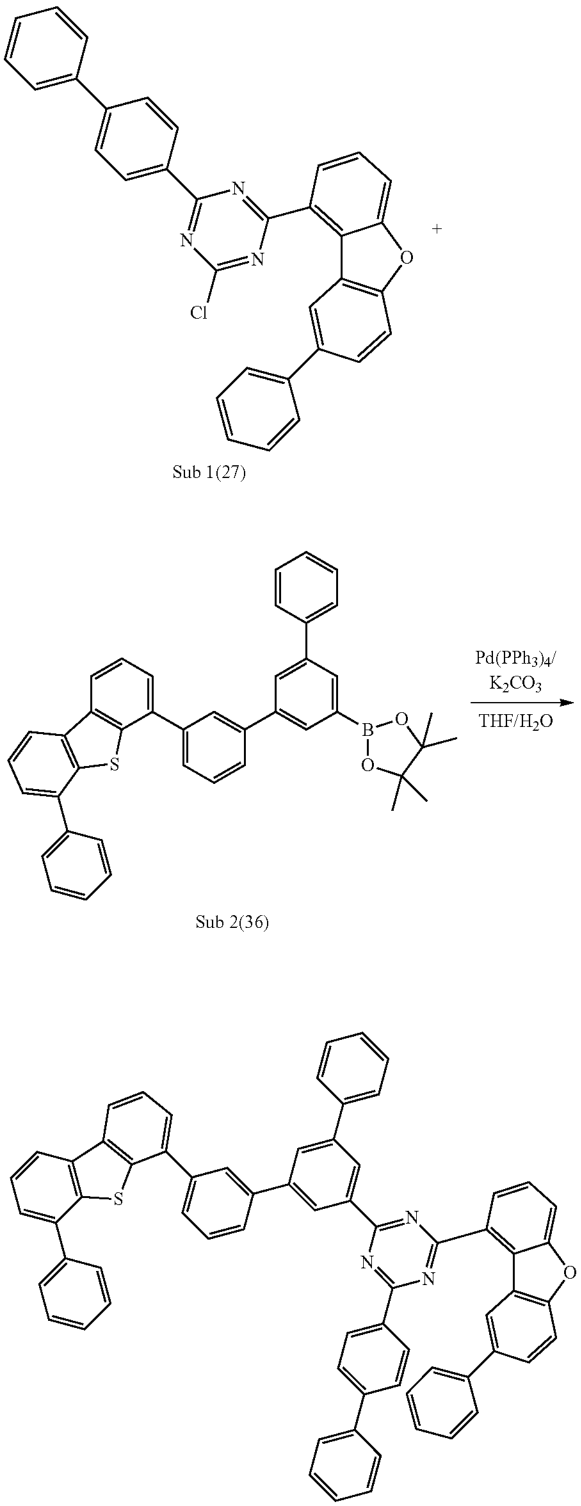
Sub 1(27)
Sub 2(36)
2-33
Sub 1(27) (40.8 g, 80 mmol) and Sub 2(36) (49.2 g, 80 mmol) were used to obtain a product (53.9 g, 70%) using the synthesis method of 1'-1.
Synthesis Example of 2-40
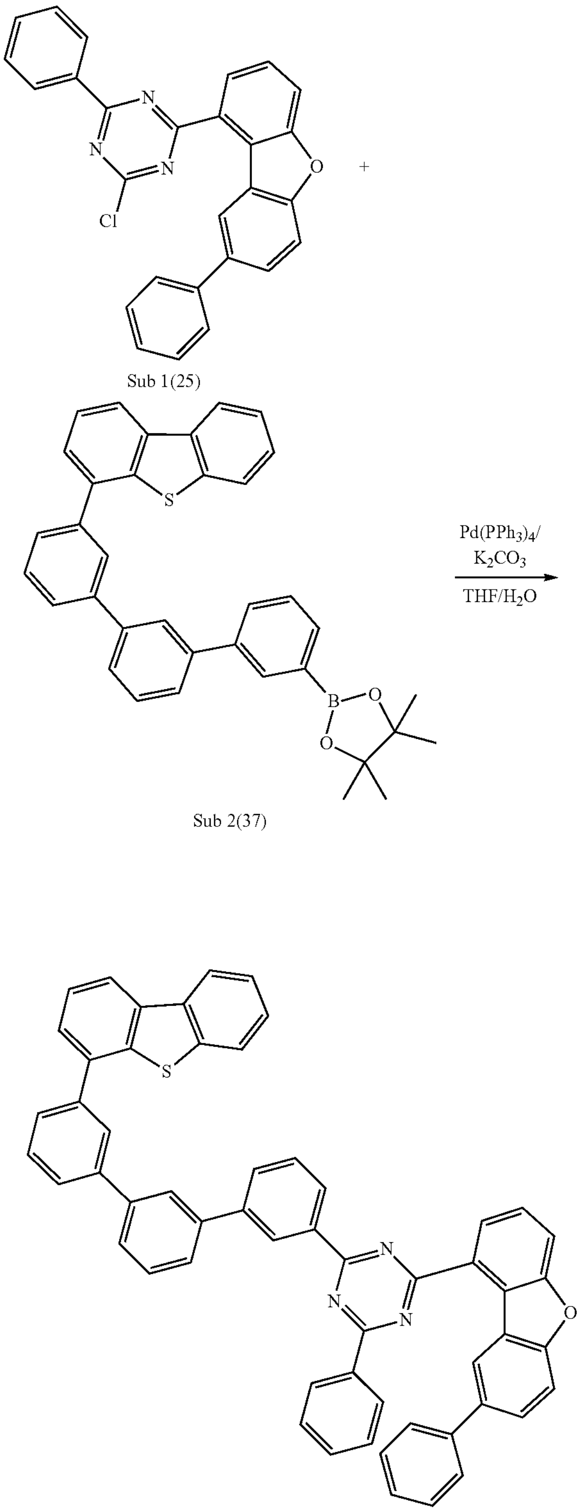
Sub 1(25)
Sub 2(37)
2-40
Sub 1(25) (34.7 g, 80 mmol) and Sub 2(37) (43.1 g, 80 mmol) were used to obtain a product (44.7 g, 69%) using the synthesis method of 1'-1.

Synthesis Example of 2-51
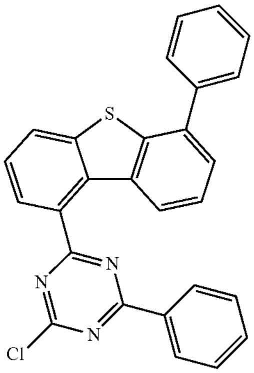
Sub 1(33)
+
-continued
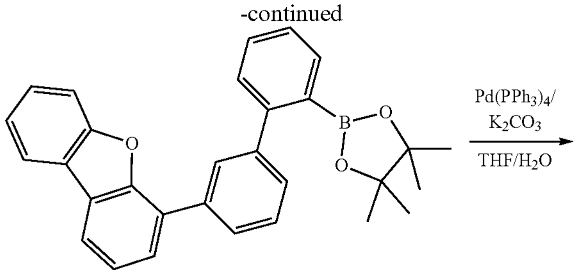
Sub 2(38)
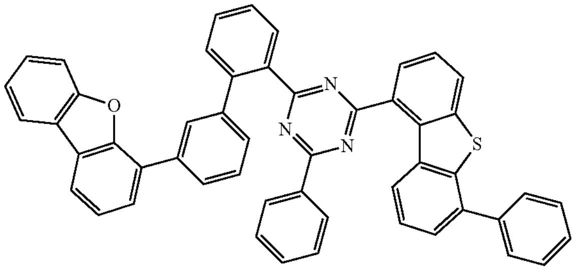
2-51
Sub 1(33) (36.0 g, 80 mmol) and Sub 2(38) (35.7 g, 80 mmol) were used to obtain a product (41.1 g, 70%) using the synthesis method of 1'-1.
Synthesis Example of 2-55
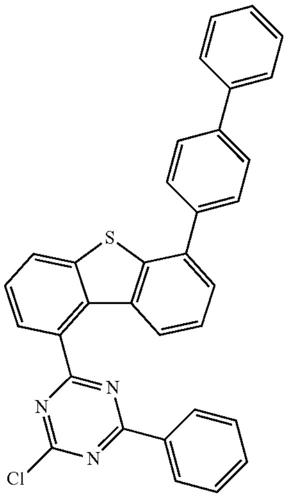
Sub 1(39)
+
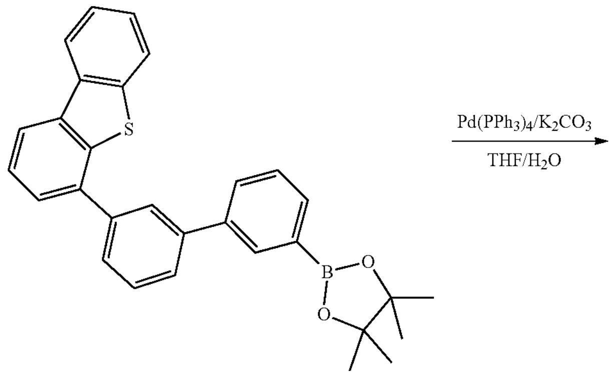
Sub 2(23)

-continued
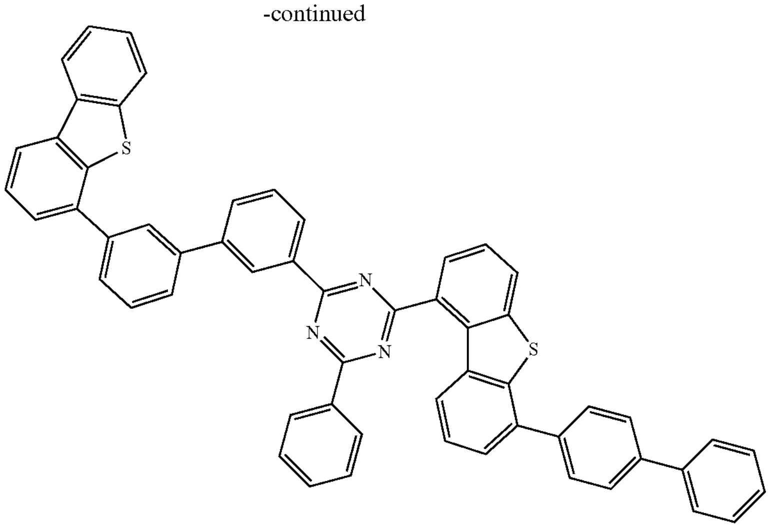
2-55
Sub 1(39) (42.1 g, 80 mmol) and Sub 2(23) (37.0 g, 80 mmol) were used to obtain a product (44.9 g, 68%) using the synthesis method of 1'-1.
Synthesis Example of 2-58
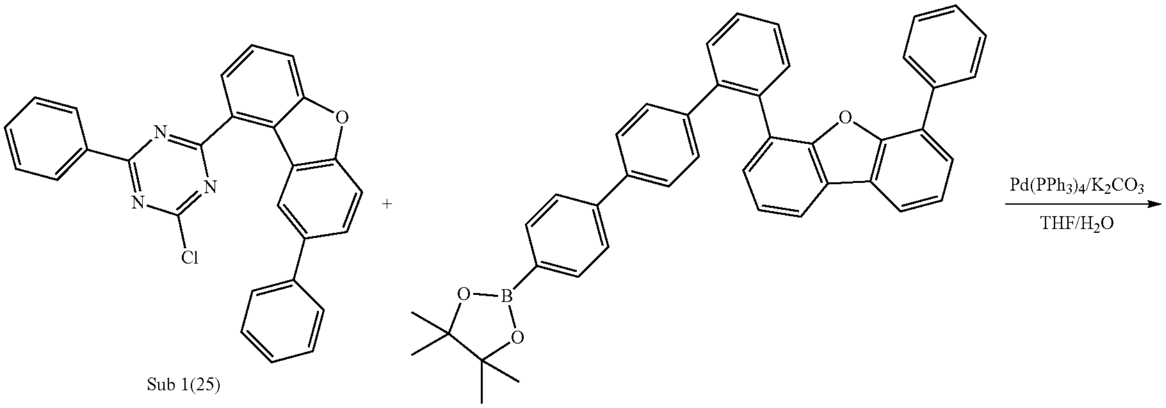
Sub 1(25)
Sub 2(39)
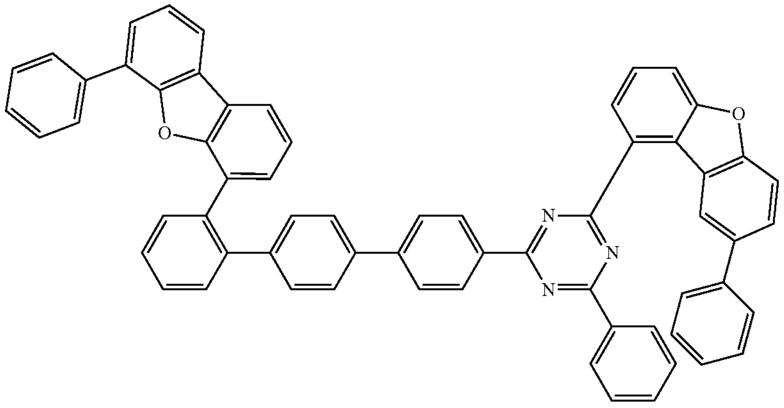
2-58

Sub 1(25) (34.7 g, 80 mmol) and Sub 2(39) (47.9 g, 80 mmol) were used to obtain a product (45.9 g, 66%) using the synthesis method of 1'-1.

Synthesis Example of 3-10

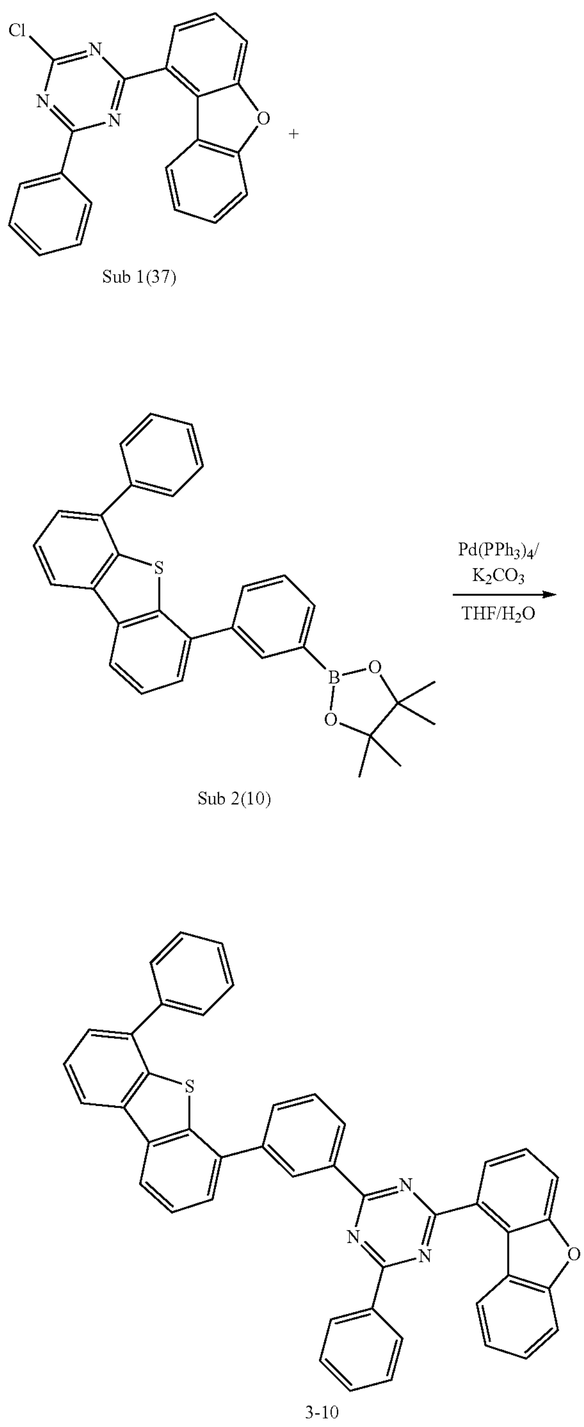

Sub 1(37)

Sub 2(10)

3-10

Sub 1(37) (28.6 g, 80 mmol) and Sub 2(10) (37.0 g, 80 mmol) were used to obtain a product (38.9 g, 74%) using the synthesis method of 1'-1.

Synthesis Example of P-41

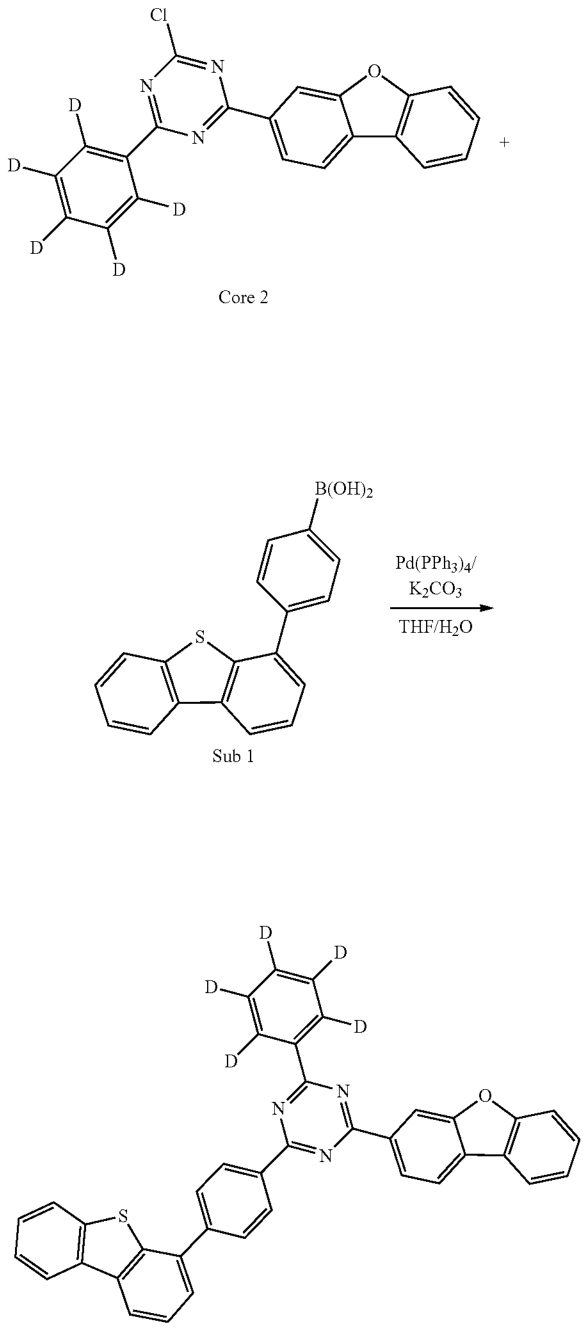

Core 2

Sub 1

P-41

Core 2 (5 g, 14 mmol), Sub 1 (4.6 g, 15.2 mmol), $Pd(PPh_3)_4$ (0.5 g, 0.4 mmol), K2CO3 (5.7 g, 41.3 mmol), THF and water were added in a round bottom flask and stirred at 90° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 4.6 g of P-41. (yield:57%)

Synthesis Example of P-91

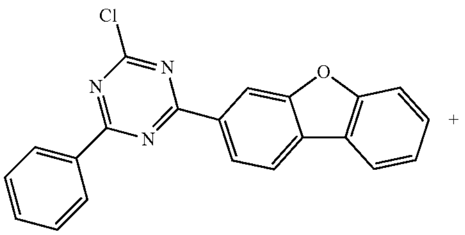

Core 1

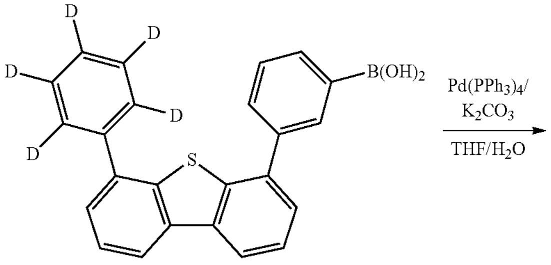

Sub 9

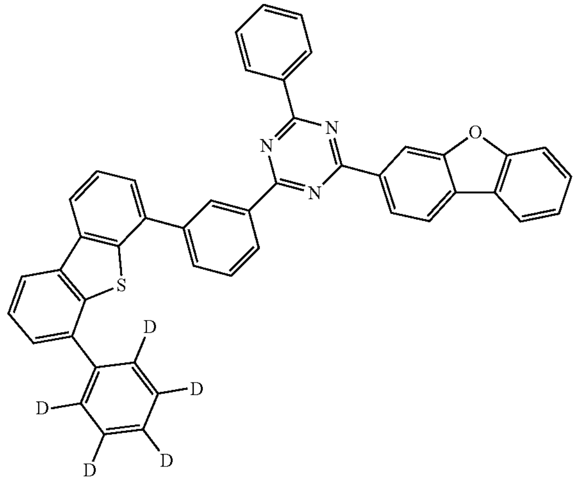

P-91

Core 1 (5 g, 14 mmol), Sub 9 (5.8 g, 15.4 mmol), $Pd(PPh_3)_4$ (0.5 g, 0.4 mmol), $K_2CO_3$ (5.8 g, 41.9 mmol), THF and water were added in a round bottom flask and stirred at 90° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 4.7 g of P-91. (yield:51%)

Synthesis Example of P-106

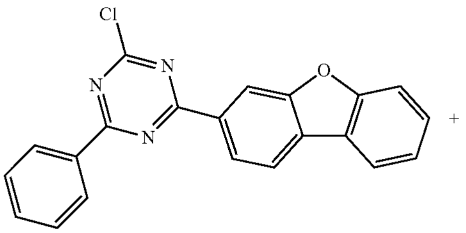

Core 1

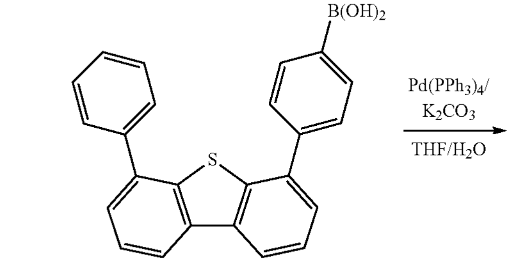

Sub 16

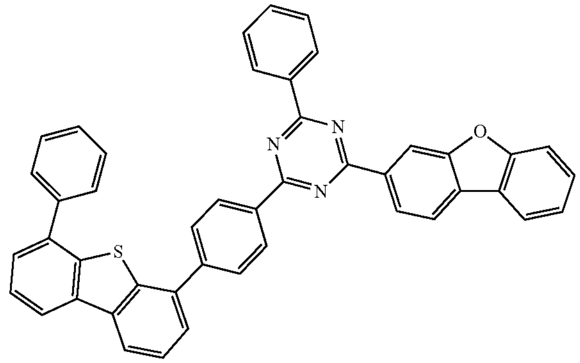

P-106

Core 1 (5 g, 14 mmol), Sub 16 (5.8 g, 15.4 mmol), $Pd(PPh_3)_4$ (0.5 g, 0.4 mmol), $K_2CO_3$ (5.8 g, 41.9 mmol), THF and water were added in a round bottom flask and stirred at 90° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 5.8 g of P-106. (yield:63%)

Synthesis Example of P-146

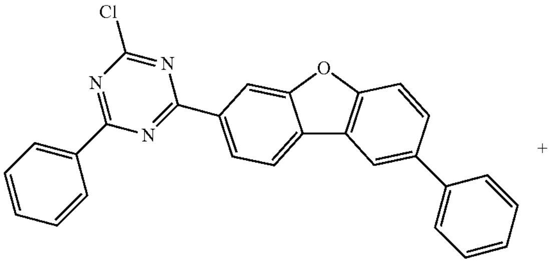

Core 11

-continued

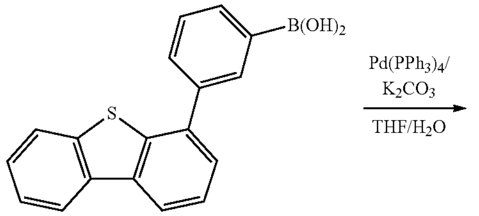

Sub 2

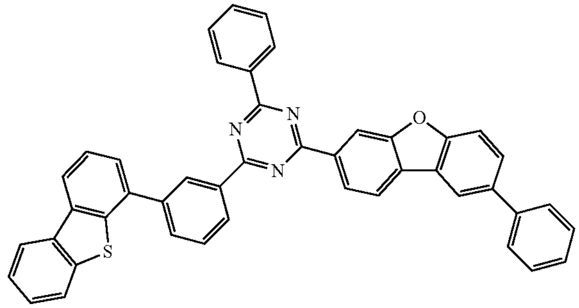

P-146

Core 1 (5 g, 14 mmol), Sub 2 (5.8 g, 15.4 mmol), $Pd(PPh_3)_4$ (0.5 g, 0.4 mmol), $K_2CO_3$ (5.8 g, 41.9 mmol), THF and water were added in a round bottom flask and stirred at 90° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 4.7 g of P-146. (yield:51%)

Synthesis Example of P-4

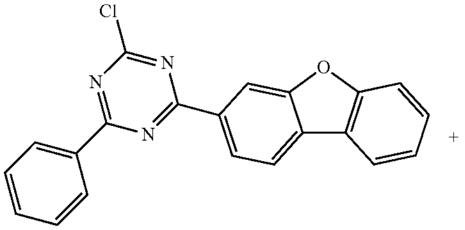

Core 1

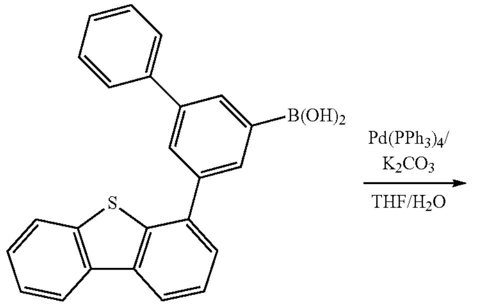

Sub 6

-continued

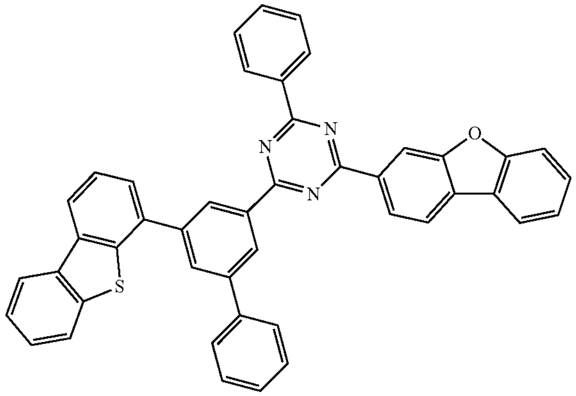

P-4

Core 1 (5 g, 14 mmol), Sub 6 (5.9 g, 15.4 mmol), $Pd(PPh_3)_4$ (0.5 g, 0.4 mmol), $K_2CO_3$ (5.8 g, 41.9 mmol), THF and water were added in a round bottom flask and stirred at 90° C. After the reaction was completed, the reaction mixture was extracted with $CH_2Cl_2$ and water. The organic layer was dried over $MgSO_4$ and concentrated. The resulting compound was separated by silicagel column chromatography and recrystallized to obtain 6.1 g of P-4. (yield: 66%)

Synthesis Example of 4-1

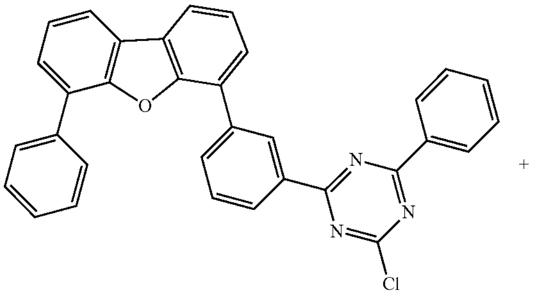

Sub 1-1′

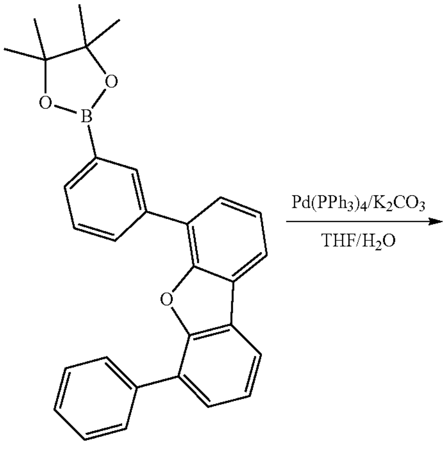

Sub 2-1′

-continued

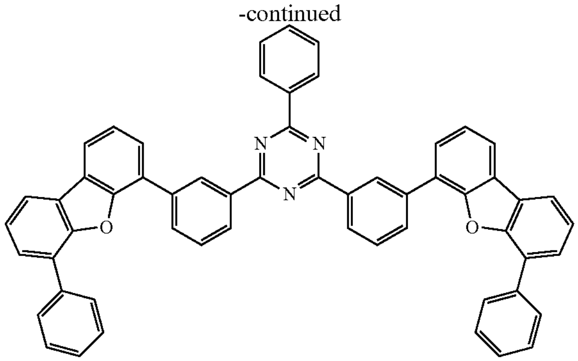

4-1

Sub 1-1' (50 g, 98.04 mmol) was added to a round bottom flask and dissolve with THF (359 mL), Sub 2-1'(52.51 g, 117.65 mmol), $Pd(PPh_3)_4$ (4.53 g, 3.92 mmol), $K_2CO_3$ (40.65 g, 294.12 mmol) and water (180 mL) were added and stirred to reflux. After the reaction was completed, the reaction mixture was extracted with $CH_2Cl_2$ and water. The organic layer was dried over $MgSO_4$ and concentrated. Thereafter, the concentrate was passed through a silicagel column and recrystallized to obtain 64.61 g of a product. (Yield: 83%)

Synthesis Example of 5-3

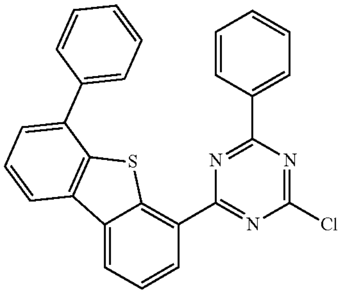

Sub 1-1''

+

-continued

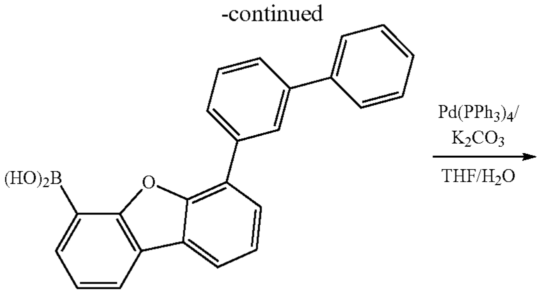

Sub 2-3''

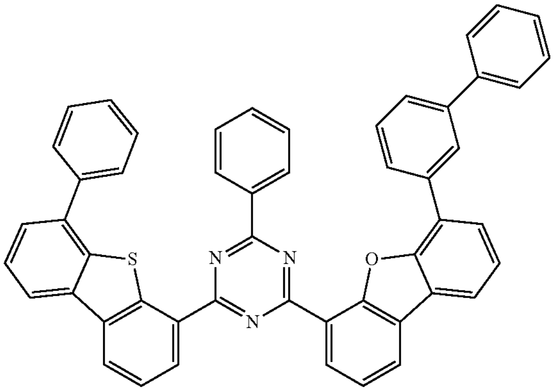

5-3

Sub 1-1" (60 g, 133.35 mmol) was added to a round bottom flask and dissolve with THF (489 mL), Sub 2-3" (58.28 g, 160.01 mmol), $Pd(PPh_3)_4$ (6.16 g, 5.33 mmol), $K_2CO_3$ (55.29 g, 400.04 mmol), and water (244 mL) were added and stirred to reflux. When the reaction is complete, the resulting compound was extracted with ether and water. The organic layer was dried over $MgSO_4$ and concentrated. The resulting compound was separated by silicagel column chromatography and recrystallized to obtain 73.40 g of the product. (yield:75%)

Synthesis Example of 7-8

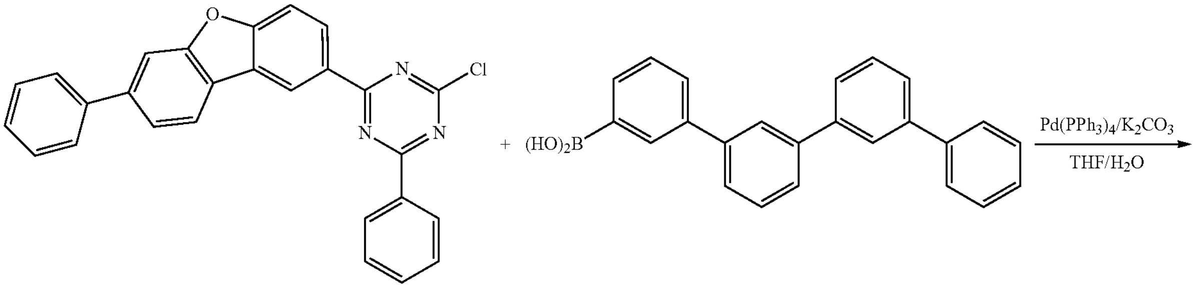

-continued

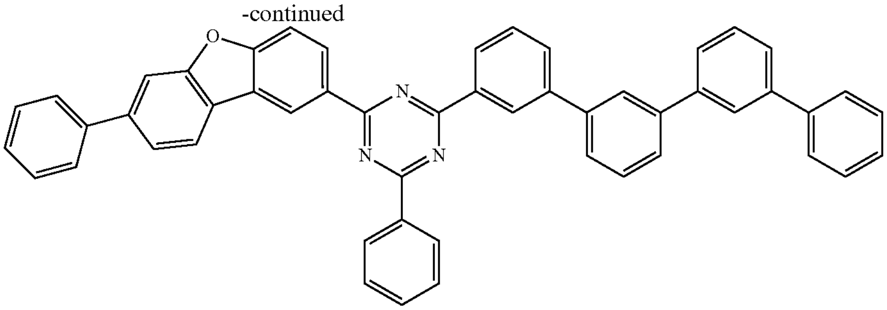

7-8

2-chloro-4-phenyl-6-(7-phenyldibenzo[b,d]furan-2-yl)-1,3,5-triazine (58 g, 133.35 mmol) was added to a round bottom flask and dissolve with THF (489 mL), [1,1':3',1":3",1'"-quaterphenyl]-3-ylboronic acid (56 g, 160.01 mmol), $Pd(PPh_3)_4$ (6.16 g, 5.33 mmol), $K_2CO_3$ (55.29 g, 400.04 mmol), and water (244 mL) were added and stirred to reflux. When the reaction is complete, the resulting compound was extracted with ether and water. The organic layer was dried over $MgSO_4$ and concentrated. The resulting compound was separated by silicagel column chromatography and recrystallized to obtain 71.33 g of the product. (yield:76%)

TABLE 4

| compound | FD-MS | compound | FD-MS |
|---|---|---|---|
| 1'-1 | m/z = 657.19($C_{45}H_{27}N_3OS$ = 657.79) | 1'-2 | m/z = 707.20($C_{49}H_{29}N_3OS$ = 707.85) |
| 1'-3 | m/z = 707.20($C_{49}H_{29}N_3OS$ = 707.85) | 1'-4 | m/z = 783.23($C_{55}H_{33}N_3OS$ = 783.95) |
| 1'-5 | m/z = 757.22($C_{53}H_{31}N_3OS$ = 757.91) | 1'-6 | m/z = 781.22($C_{55}H_{31}N_3OS$ = 781.93) |
| 1'-7 | m/z = 809.25($C_{57}H_{35}N_3OS$ = 809.99) | 1'-8 | m/z = 721.22($C_{50}H_{31}N_3OS$ = 721.88) |
| 1'-9 | m/z = 707.20($C_{49}H_{29}N_3OS$ = 707.85) | 1'-10 | m/z = 707.20($C_{49}H_{29}N_3OS$ = 707.85) |
| 1'-11 | m/z = 733.22($C_{51}H_{31}N_3OS$ = 733.89) | 1'-12 | m/z = 807.23($C_{57}H_{33}N_3OS$ = 807.97) |
| 1'-13 | m/z = 707.20($C_{49}H_{29}N_3OS$ = 707.85) | 1'-14 | m/z = 707.20($C_{49}H_{29}N_3OS$ = 707.85) |
| 1'-15 | m/z = 733.22($C_{51}H_{31}N_3OS$ = 733.89) | 1'-16 | m/z = 859.27($C_{61}H_{37}N_3OS$ = 860.05) |
| 1'-17 | m/z = 807.23($C_{57}H_{33}N_3OS$ = 807.97) | 1'-18 | m/z = 757.22($C_{53}H_{31}N_3OS$ = 757.91) |
| 1'-19 | m/z = 783.23($C_{55}H_{33}N_3OS$ = 783.95) | 1'-20 | m/z = 859.27($C_{61}H_{37}N_3OS$ = 860.05) |
| 1'-21 | m/z = 733.22($C_{51}H_{31}N_3OS$ = 733.89) | 1'-22 | m/z = 857.25($C_{61}H_{35}N_3OS$ = 858.03) |
| 1'-23 | m/z = 833.25($C_{59}H_{35}N_3OS$ = 834.01) | 1'-24 | m/z = 825.23($C_{57}H_{32}FN_3OS$ = 825.96) |
| 1'-25 | m/z = 657.19($C_{45}H_{27}N_3OS$ = 657.79) | 1'-26 | m/z = 733.22($C_{51}H_{31}N_3OS$ = 733.89) |
| 1'-27 | m/z = 809.25($C_{57}H_{35}N_3OS$ = 809.99) | 1'-28 | m/z = 809.25($C_{57}H_{35}N_3OS$ = 809.99) |
| 1'-29 | m/z = 732.22($C_{51}H_{31}N_3OS$ = 733.89) | 1'-30 | m/z = 733.22($C_{51}H_{31}N_3OS$ = 733.89) |
| 1'-31 | m/z = 657.19($C_{45}H_{27}N_3OS$ = 657.79) | 1'-32 | m/z = 809.25($C_{57}H_{35}N_3OS$ = 809.99) |
| 1'-33 | m/z = 885.28($C_{63}H_{39}N_3OS$ = 886.09) | 1'-34 | m/z = 733.22($C_{51}H_{31}N_3OS$ = 733.89) |
| 1'-35 | m/z = 733.22($C_{51}H_{31}N_3OS$ = 733.89) | 1'-36 | m/z = 809.25($C_{57}H_{35}N_3OS$ = 809.99) |
| 1'-37 | m/z = 733.22($C_{51}H_{31}N_3OS$ = 733.89) | 1'-38 | m/z = 733.22($C_{51}H_{31}N_3OS$ = 733.89) |
| 1'-39 | m/z = 809.25($C_{57}H_{35}N_3OS$ = 809.99) | 1'-40 | m/z = 657.19($C_{45}H_{27}N_3OS$ = 657.79) |
| 1'-41 | m/z = 783.23($C_{55}H_{33}N_3OS$ = 783.95) | 1'-42 | m/z = 733.22($C_{51}H_{31}N_3OS$ = 733.89) |
| 1'-43 | m/z = 733.22($C_{51}H_{31}N_3OS$ = 733.89) | 1'-44 | m/z = 809.25($C_{57}H_{35}N_3OS$ = 809.99) |
| 1'-45 | m/z = 809.25($C_{57}H_{35}N_3OS$ = 809.99) | 1'-46 | m/z = 809.25($C_{57}H_{35}N_3OS$ = 809.99) |
| 1'-47 | m/z = 885.28($C_{63}H_{39}N_3OS$ = 886.09) | 1'-48 | m/z = 783.23($C_{55}H_{33}N_3OS$ = 783.95) |
| 1'-49 | m/z = 657.19($C_{45}H_{27}N_3OS$ = 657.79) | 1'-50 | m/z = 707.20($C_{49}H_{29}N_3OS$ = 707.85) |
| 1'-51 | m/z = 707.20($C_{49}H_{29}N_3OS$ = 707.85) | 1'-52 | m/z = 783.23($C_{55}H_{33}N_3OS$ = 783.95) |
| 1'-53 | m/z = 757.22($C_{53}H_{31}N_3OS$ = 757.91) | 1'-54 | m/z = 781.22($C_{55}H_{31}N_3OS$ = 781.93) |
| 1'-55 | m/z = 809.25($C_{57}H_{35}N_3OS$ = 809.99) | 1'-56 | m/z = 721.22($C_{50}H_{31}N_3OS$ = 721.88) |
| 1'-57 | m/z = 707.20($C_{49}H_{29}N_3OS$ = 707.85) | 1'-58 | m/z = 707.20($C_{49}H_{29}N_3OS$ = 707.85) |
| 1'-59 | m/z = 733.22($C_{51}H_{31}N_3OS$ = 733.89) | 1'-60 | m/z = 807.23($C_{57}H_{33}N_3OS$ = 807.97) |
| 1'-61 | m/z = 723.18($C_{49}H_{29}N_3S_2$ = 723.91) | 1'-62 | m/z = 723.18($C_{49}H_{29}N_3S_2$ = 723.91) |
| 1'-63 | m/z = 749.20($C_{51}H_{31}N_3S_2$ = 749.95) | 1'-64 | m/z = 875.24($C_{61}H_{37}N_3S_2$ = 876.11) |
| 1'-65 | m/z = 823.21($C_{57}H_{33}N_3S_2$ = 824.03) | 1'-66 | m/z = 773.20($C_{53}H_{31}N_3S_2$ = 773.97) |
| 1'-67 | m/z = 799.21($C_{55}H_{33}N_3S_2$ = 800.01) | 1'-68 | m/z = 875.24($C_{61}H_{37}N_3S_2$ = 876.11) |
| 1'-69 | m/z = 749.20($C_{51}H_{31}N_3S_2$ = 749.95) | 1'-70 | m/z = 873.23($C_{61}H_{35}N_3S_2$ = 874.09) |
| 1'-71 | m/z = 849.23($C_{59}H_{35}N_3S_2$ = 850.07) | 1'-72 | m/z = 791.19($C_{53}H_{30}FN_3S_2$ = 791.96) |
| 1'-73 | m/z = 641.21($C_{45}H_{27}N_3O_2$ = 641.73) | 1'-74 | m/z = 717.24($C_{51}H_{31}N_3O_2$ = 717.83) |
| 1'-75 | m/z = 798.30($C_{57}H_{30}D_5N_3O_2$ = 799.0) | 1'-76 | m/z = 843.29($C_{61}H_{37}N_3O_2$ = 843.99) |
| 1'-77 | m/z = 717.24($C_{51}H_{31}N_3O_2$ = 717.83) | 1'-78 | m/z = 717.24($C_{51}H_{31}N_3O_3$ = 717.83) |
| 1'-79 | m/z = 641.21($C_{45}H_{27}N_3O_2$ = 641.73) | 1'-80 | m/z = 793.27($C_{57}H_{35}N_3O_2$ = 793.93) |
| 1'-81 | m/z = 869.30($C_{63}H_{39}N_3O_2$ = 870.02) | 1'-82 | m/z = 717.24($C_{51}H_{31}N_3O_2$ = 717.83) |
| 1'-83 | m/z = 722.27($C_{51}H_{26}D_5N_3O_2$ = 722.9) | 1'-84 | m/z = 793.27($C_{57}H_{35}N_3O_2$ = 793.93) |
| 2-1 | m/z = 733.22($C_{51}H_{31}N_3OS$ = 733.89) | 2-2 | m/z = 783.23($C_{55}H_{33}N_3OS$ = 783.95) |
| 2-3 | m/z = 783.23($C_{55}H_{33}N_3OS$ = 783.95) | 2-4 | m/z = 859.27($C_{61}H_{37}N_3OS$ = 860.05) |
| 2-5 | m/z = 833.25($C_{59}H_{35}N_3OS$ = 834.01) | 2-6 | m/z = 857.25($C_{61}H_{35}N_3OS$ = 858.03) |
| 2-7 | m/z = 885.28($C_{63}H_{39}N_3OS$ = 886.09) | 2-8 | m/z = 797.25($C_{56}H_{35}N_3OS$ = 797.98) |
| 2-9 | m/z = 783.23($C_{55}H_{33}N_3OS$ = 783.95) | 2-10 | m/z = 783.23($C_{55}H_{33}N_3OS$ = 783.95) |
| 2-11 | m/z = 809.25($C_{57}H_{35}N_3OS$ = 809.99) | 2-12 | m/z = 883.27($C_{63}H_{37}N_3OS$ = 884.07) |
| 2-13 | m/z = 783.23($C_{55}H_{33}N_3OS$ = 783.95) | 2-14 | m/z = 783.23($C_{55}H_{33}N_3OS$ = 783.95) |
| 2-15 | m/z = 809.25($C_{57}H_{35}N_3OS$ = 809.99) | 2-16 | m/z = 935.30($C_{67}H_{41}N_3OS$ = 936.15) |

TABLE 4-continued

| compound | FD-MS | compound | FD-MS |
|---|---|---|---|
| 2-17 | m/z = 883.27($C_{63}H_{37}N_3OS$ = 884.07) | 2-18 | m/z = 833.25($C_{59}H_{35}N_3OS$ = 834.01) |
| 2-19 | m/z = 885.28($C_{63}H_{39}N_3OS$ = 886.09) | 2-20 | m/z = 909.28($C_{65}H_{39}N_3OS$ = 910.11) |
| 2-21 | m/z = 809.25($C_{57}H_{35}N_3OS$ = 809.99) | 2-22 | m/z = 933.28($C_{67}H_{39}N_3OS$ = 934.13) |
| 2-23 | m/z = 909.28($C_{65}H_{39}N_3OS$ = 910.11) | 2-24 | m/z = 851.24($C_{59}H_{34}FN_3OS$ = 852.00) |
| 2-25 | m/z = 733.22($C_{51}H_{31}N_3OS$ = 733.89) | 2-26 | m/z = 809.25($C_{57}H_{35}N_3OS$ = 809.99) |
| 2-27 | m/z = 885.28($C_{63}H_{39}N_3OS$ = 886.09) | 2-28 | m/z = 935.30($C_{67}H_{41}N_3OS$ = 936.15) |
| 2-29 | m/z = 809.25($C_{57}H_{35}N_3OS$ = 809.99) | 2-30 | m/z = 809.25($C_{57}H_{35}N_3OS$ = 809.99) |
| 2-31 | m/z = 733.22($C_{51}H_{31}N_3OS$ = 733.89) | 2-32 | m/z = 885.28($C_{63}H_{39}N_3OS$ = 886.09) |
| 2-33 | m/z = 961.31($C_{69}H_{43}N_3OS$ = 962.18) | 2-34 | m/z = 809.25($C_{57}H_{35}N_3OS$ = 809.99) |
| 2-35 | m/z = 809.25($C_{57}H_{35}N_3OS$ = 809.99) | 2-36 | m/z = 885.28($C_{63}H_{39}N_3OS$ = 886.09) |
| 2-37 | m/z = 885.28($C_{63}H_{39}N_3OS$ = 886.09) | 2-38 | m/z = 885.28($C_{63}H_{39}N_3OS$ = 886.09) |
| 2-39 | m/z = 961.31($C_{69}H_{43}N_3OS$ = 962.18) | 2-40 | m/z = 809.25($C_{57}H_{35}N_3OS$ = 809.99) |
| 2-41 | m/z = 885.28($C_{63}H_{39}N_3OS$ = 886.09) | 2-42 | m/z = 885.28($C_{63}H_{39}N_3OS$ = 886.09) |
| 2-43 | m/z = 885.28($C_{63}H_{39}N_3OS$ = 886.09) | 2-44 | m/z = 1032.40($C_{74}H_{54}N_3OS$ = 1033.33) |
| 2-45 | m/z = 885.28($C_{63}H_{39}N_3OS$ = 886.09) | 2-46 | m/z = 885.28($C_{63}H_{39}N_3OS$ = 886.09) |
| 2-47 | m/z = 961.31($C_{69}H_{43}N_3OS$ = 962.18) | 2-48 | m/z = 859.27($C_{61}H_{37}N_3OS$ = 860.08) |
| 2-49 | m/z = 809.25($C_{57}H_{35}N_3OS$ = 809.99) | 2-50 | m/z = 809.25($C_{57}H_{35}N_3OS$ = 809.99) |
| 2-51 | m/z = 733.22($C_{51}H_{31}N_3OS$ = 733.89) | 2-52 | m/z = 885.28($C_{63}H_{39}N_3OS$ = 886.09) |
| 2-53 | m/z = 977.29($C_{69}H_{43}N_3S_2$ = 978.24) | 2-54 | m/z = 825.23($C_{57}H_{35}N_3S_2$ = 826.05) |
| 2-55 | m/z = 825.23($C_{57}H_{35}N_3S_2$ = 826.05) | 2-56 | m/z = 901.26($C_{63}H_{39}N_3S_2$ = 902.15) |
| 2-57 | m/z = 869.30($C_{63}H_{39}N_3O_2$ = 870.02) | 2-58 | m/z = 869.30($C_{63}H_{39}N_3O_2$ = 870.02) |
| 2-59 | m/z = 945.34($C_{69}H_{43}N_3O_2$ = 946.12) | 2-60 | m/z = 809.25($C_{57}H_{35}N_3OS$ = 809.99) |
| 3-1 | m/z = 581.16($C_{39}H_{23}N_3OS$ = 581.69) | 3-2 | m/z = 581.16($C_{39}H_{23}N_3OS$ = 581.69) |
| 3-3 | m/z = 581.16($C_{39}H_{23}N_3OS$ = 581.69) | 3-4 | m/z = 783.23($C_{55}H_{33}N_3OS$ = 783.95) |
| 3-5 | m/z = 631.17($C_{43}H_{25}N_3OS$ = 631.75) | 3-6 | m/z = 731.20($C_{51}H_{29}N_3OS$ = 731.87) |
| 3-7 | m/z = 581.16($C_{39}H_{23}N_3OS$ = 581.69) | 3-8 | m/z = 657.19($C_{45}H_{27}N_3OS$ = 657.79) |
| 3-9 | m/z = 581.16($C_{39}H_{23}N_3OS$ = 581.69) | 3-10 | m/z = 657.19($C_{45}H_{27}N_3OS$ = 657.79) |
| 3-11 | m/z = 657.19($C_{45}H_{27}N_3OS$ = 657.79) | 3-12 | m/z = 733.22($C_{51}H_{31}N_3OS$ = 733.89) |
| 3-13 | m/z = 631.17($C_{43}H_{25}N_3OS$ = 631.75) | 3-14 | m/z = 581.16($C_{39}H_{23}N_3OS$ = 581.69) |
| 3-15 | m/z = 581.16($C_{39}H_{23}N_3OS$ = 581.69) | 3-16 | m/z = 799.21($C_{55}H_{33}N_3S_2$ = 800.01) |
| 3-17 | m/z = 647.15($C_{43}H_{25}N_3S_2$ = 647.81) | 3-18 | m/z = 747.18($C_{51}H_{29}N_3S_2$ = 747.93) |
| 3-19 | m/z = 565.18($C_{39}H_{23}N_3O_2$ = 565.63) | 3-20 | m/z = 641.21($C_{45}H_{27}N_3O_2$ = 641.73) |
| 3-21 | m/z = 722.27($C_{51}H_{26}D_5N_3S_2$ = 722.86) | 3-22 | m/z = 657.19($C_{45}H_{27}N_3OS$ = 657.79) |
| 3-23 | m/z = 657.19($C_{45}H_{27}N_3OS$ = 657.79) | 3-24 | m/z = 707.20($C_{49}H_{29}N_3OS$ = 707.85) |
| 3-25 | m/z = 733.22($C_{51}H_{31}N_3OS$ = 733.89) | 3-26 | m/z = 707.20($C_{49}H_{29}N_3OS$ = 707.85) |
| 3-27 | m/z = 707.20($C_{49}H_{29}N_3OS$ = 707.85) | 3-28 | m/z = 859.27($C_{61}H_{37}N_3OS$ = 860.05) |
| 3-29 | m/z = 657.19($C_{45}H_{27}N_3OS$ = 657.79) | 3-30 | m/z = 733.22($C_{51}H_{31}N_3OS$ = 733.89) |
| 3-31 | m/z = 809.25($C_{57}H_{35}N_3OS$ = 809.99) | 3-32 | m/z = 809.25($C_{57}H_{35}N_3OS$ = 809.99) |
| 3-33 | m/z = 885.28($C_{63}H_{39}N_3OS$ = 886.09) | 3-34 | m/z = 809.25($C_{57}H_{35}N_3OS$ = 809.99) |
| 3-35 | m/z = 673.16($C_{45}H_{27}N_3S_2$ = 673.85) | 3-36 | m/z = 793.27($C_{57}H_{35}N_3O_2$ = 793.93) |
| P-1 | m/z = 581.16($C_{39}H_{23}N_3OS$ = 581.69) | P-2 | m/z = 631.17($C_{43}H_{25}N_3OS$ = 631.75) |
| P-3 | m/z = 631.17($C_{43}H_{25}N_3OS$ = 631.75) | P-4 | m/z = 657.19($C_{45}H_{27}N_3OS$ = 657.79) |
| P-5 | m/z = 681.19($C_{47}H_{27}N_3OS$ = 681.81) | P-6 | m/z = 631.17($C_{43}H_{25}N_3OS$ = 631.75) |
| P-7 | m/z = 631.17($C_{43}H_{25}N_3OS$ = 631.75) | P-8 | m/z = 657.19($C_{45}H_{27}N_3OS$ = 657.79) |
| P-9 | m/z = 657.19($C_{45}H_{27}N_3OS$ = 657.79) | P-10 | m/z = 657.19($C_{45}H_{27}N_3OS$ = 657.79) |
| P-11 | m/z = 586.19($C_{39}H_{18}D_5N_3OS$ = 586.7) | P-12 | m/z = 681.19($C_{47}H_{27}N_3OS$ = 681.81) |
| P-13 | m/z = 681.19($C_{47}H_{27}N_3OS$ = 681.81) | P-14 | m/z = 707.20($C_{49}H_{29}N_3OS$ = 707.85) |
| P-15 | m/z = 707.20($C_{49}H_{29}N_3OS$ = 707.85) | P-16 | m/z = 707.20($C_{49}H_{29}N_3OS$ = 707.85) |
| P-17 | m/z = 636.20($C_{43}H_{20}D_5N_3OS$ = 636.8) | P-18 | m/z = 681.19($C_{47}H_{27}N_3OS$ = 681.81) |
| P-19 | m/z = 681.19($C_{47}H_{27}N_3OS$ = 681.81) | P-20 | m/z = 707.20($C_{49}H_{29}N_3OS$ = 707.85) |
| P-21 | m/z = 707.20($C_{49}H_{29}N_3OS$ = 707.85) | P-22 | m/z = 707.20($C_{49}H_{29}N_3OS$ = 707.85) |
| P-23 | m/z = 636.20($C_{43}H_{20}D_5N_3OS$ = 636.8) | P-24 | m/z = 707.20($C_{49}H_{29}N_3OS$ = 707.85) |
| P-25 | m/z = 707.20($C_{49}H_{29}N_3OS$ = 707.85) | P-26 | m/z = 733.22($C_{51}H_{31}N_3OS$ = 733.89) |
| P-27 | m/z = 733.22($C_{51}H_{31}N_3OS$ = 733.89) | P-28 | m/z = 733.22($C_{51}H_{31}N_3OS$ = 733.89) |
| P-29 | m/z = 662.22($C_{45}H_{22}D_5N_3OS$ = 662.8) | P-30 | m/z = 662.22($C_{45}H_{22}D_5N_3OS$ = 662.82) |
| P-31 | m/z = 581.16($C_{39}H_{23}N_3OS$ = 581.69) | P-32 | m/z = 631.17($C_{43}H_{25}N_3OS$ = 631.75) |
| P-33 | m/z = 631.17($C_{43}H_{25}N_3OS$ = 631.75) | P-34 | m/z = 657.19($C_{45}H_{27}N_3OS$ = 657.79) |
| P-35 | m/z = 681.19($C_{47}H_{27}N_3OS$ = 681.81) | P-36 | m/z = 631.17($C_{43}H_{25}N_3OS$ = 631.75) |
| P-37 | m/z = 631.17($C_{43}H_{25}N_3OS$ = 631.75) | P-38 | m/z = 657.19($C_{45}H_{27}N_3OS$ = 657.79) |
| P-39 | m/z = 657.19($C_{45}H_{27}N_3OS$ = 657.79) | P-40 | m/z = 657.19($C_{45}H_{27}N_3OS$ = 657.79) |
| P-41 | m/z = 586.19($C_{39}H_{18}D_5N_3OS$ = 586.7) | P-42 | m/z = 681.19($C_{47}H_{27}N_3OS$ = 681.81) |
| P-43 | m/z = 681.19($C_{47}H_{27}N_3OS$ = 681.81) | P-44 | m/z = 707.20($C_{49}H_{29}N_3OS$ = 707.85) |
| P-45 | m/z = 707.20($C_{49}H_{29}N_3OS$ = 707.85) | P-46 | m/z = 707.20($C_{49}H_{29}N_3OS$ = 707.85) |
| P-47 | m/z = 636.20($C_{43}H_{20}D_5N_3OS$ = 636.8) | P-48 | m/z = 681.19($C_{47}H_{27}N_3OS$ = 681.81) |
| P-49 | m/z = 681.19($C_{47}H_{27}N_3OS$ = 681.81) | P-50 | m/z = 707.20($C_{49}H_{29}N_3OS$ = 707.85) |
| P-51 | m/z = 707.20($C_{49}H_{29}N_3OS$ = 707.85) | P-52 | m/z = 707.20($C_{49}H_{29}N_3OS$ = 707.85) |
| P-53 | m/z = 733.22($C_{51}H_{31}N_3OS$ = 733.89) | P-54 | m/z = 707.20($C_{49}H_{29}N_3OS$ = 707.85) |
| P-55 | m/z = 707.20($C_{49}H_{29}N_3OS$ = 707.85) | P-56 | m/z = 733.22($C_{51}H_{31}N_3OS$ = 733.89) |
| P-57 | m/z = 733.22($C_{51}H_{31}N_3OS$ = 733.89) | P-58 | m/z = 733.22($C_{51}H_{31}N_3OS$ = 733.89) |
| P-59 | m/z = 662.22($C_{45}H_{22}DN_3OS$ = 662.82) | P-60 | m/z = 662.22($C_{45}H_{22}DN_3OS$ = 662.82) |
| P-61 | m/z = 657.19($C_{45}H_{27}N_3OS$ = 657.79) | P-62 | m/z = 707.20($C_{49}H_{29}N_3OS$ = 707.85) |
| P-63 | m/z = 707.20($C_{49}H_{29}N_3OS$ = 707.85) | P-64 | m/z = 733.22($C_{51}H_{31}N_3OS$ = 733.89) |
| P-65 | m/z = 757.22($C_{53}H_{31}N_3OS$ = 757.91) | P-66 | m/z = 707.20($C_{49}H_{29}N_3OS$ = 707.85) |
| P-67 | m/z = 707.20($C_{49}H_{29}N_3OS$ = 707.85) | P-68 | m/z = 733.22($C_{51}H_{31}N_3OS$ = 733.89) |
| P-69 | m/z = 733.22($C_{51}H_{31}N_3OS$ = 733.89) | P-70 | m/z = 733.22($C_{51}H_{31}N_3OS$ = 733.89) |
| P-71 | m/z = 662.22($C_{45}H_{22}D_5N_3OS$ = 662.8) | P-72 | m/z = 757.22($C_{53}H_{31}N_3OS$ = 757.91) |
| P-73 | m/z = 757.22($C_{53}H_{31}N_3OS$ = 757.91) | P-74 | m/z = 783.23($C_{55}H_{33}N_3OS$ = 783.95) |
| P-75 | m/z = 783.23($C_{55}H_{33}N_3OS$ = 783.95) | P-76 | m/z = 783.23($C_{55}H_{33}N_3OS$ = 783.95) |

TABLE 4-continued

| compound | FD-MS | compound | FD-MS |
|---|---|---|---|
| P-77 | m/z = 712.23($C_{49}H_{24}D_5N_3OS$ = 712.9) | P-78 | m/z = 757.22($C_{53}H_{31}N_3OS$ = 757.91) |
| P-79 | m/z = 757.22($C_{53}H_{31}N_3OS$ = 757.91) | P-80 | m/z = 783.23($C_{55}H_{33}N_3OS$ = 783.95) |
| P-81 | m/z = 783.23($C_{55}H_{33}N_3OS$ = 783.95) | P-82 | m/z = 783.23($C_{55}H_{33}N_3OS$ = 783.95) |
| P-83 | m/z = 712.23($C_{49}H_{24}D_5N_3OS$ = 712.9) | P-84 | m/z = 783.23($C_{55}H_{33}N_3OS$ = 783.95) |
| P-85 | m/z = 783.23($C_{55}H_{33}N_3OS$ = 783.95) | P-86 | m/z = 809.25($C_{57}H_{35}N_3OS$ = 809.99) |
| P-87 | m/z = 809.25($C_{57}H_{35}N_3OS$ = 809.99) | P-88 | m/z = 809.25($C_{57}H_{35}N_3OS$ = 809.99) |
| P-89 | m/z = 738.25($C_{51}H_{26}D_5N_3OS$ = 738.9) | P-90 | m/z = 738.25($C_{51}H_{26}D_5N_3OS$ = 738.92) |
| P-91 | m/z = 662.22($C_{45}H_{22}DN_3OS$ = 662.82) | P-92 | m/z = 712.23($C_{49}H_{24}D_5N_3OS$ = 712.88) |
| P-93 | m/z = 712.23($C_{49}H_{24}D_5N_3OS$ = 712.9) | P-94 | m/z = 738.25($C_{51}H_{26}D_5N_3OS$ = 738.92) |
| P-95 | m/z = 762.25($C_{53}H_{26}D_5N_3OS$ = 762.9) | P-96 | m/z = 712.23($C_{49}H_{24}D_5N_3OS$ = 712.88) |
| P-97 | m/z = 712.23($C_{49}H_{24}D_5N_3OS$ = 712.9) | P-98 | m/z = 738.25($C_{51}H_{26}D_5N_3OS$ = 738.92) |
| P-99 | m/z = 738.25($C_{51}H_{26}D_5N_3OS$ = 738.9) | P-100 | m/z = 738.25($C_{51}H_{26}D_5N_3OS$ = 738.92) |
| P-101 | m/z = 667.2($C_{45}H_{17}D_{10}N_3OS$ = 667.9) | P-102 | m/z = 707.20($C_{49}H_{29}N_3OS$ = 707.85) |
| P-103 | m/z = 707.20($C_{49}H_{29}N_3OS$ = 707.85) | P-104 | m/z = 733.22($C_{51}H_{31}N_3OS$ = 733.89) |
| P-105 | m/z = 733.22($C_{51}H_{31}N_3OS$ = 733.89) | P-106 | m/z = 657.19($C_{45}H_{27}N_3OS$ = 657.79) |
| P-107 | m/z = 707.20($C_{49}H_{29}N_3OS$ = 707.85) | P-108 | m/z = 707.20($C_{49}H_{29}N_3OS$ = 707.85) |
| P-109 | m/z = 733.22($C_{51}H_{31}N_3OS$ = 733.89) | P-110 | m/z = 757.22($C_{53}H_{31}N_3OS$ = 757.91) |
| P-111 | m/z = 707.20($C_{49}H_{29}N_3OS$ = 707.85) | P-112 | m/z = 707.20($C_{49}H_{29}N_3OS$ = 707.85) |
| P-113 | m/z = 733.22($C_{51}H_{31}N_3OS$ = 733.89) | P-114 | m/z = 733.22($C_{51}H_{31}N_3OS$ = 733.89) |
| P-115 | m/z = 733.22($C_{51}H_{31}N_3OS$ = 733.89) | P-116 | m/z = 662.22($C_{45}H_{22}D_5N_3OS$ = 662.82) |
| P-117 | m/z = 757.22($C_{53}H_{31}N_3OS$ = 757.91) | P-118 | m/z = 757.22($C_{53}H_{31}N_3OS$ = 757.91) |
| P-119 | m/z = 783.23($C_{55}H_{33}N_3OS$ = 783.95) | P-120 | m/z = 783.23($C_{55}H_{33}N_3OS$ = 783.95) |
| P-121 | m/z = 783.23($C_{55}H_{33}N_3OS$ = 783.95) | P-122 | m/z = 712.23($C_{49}H_{24}D_5N_3OS$ = 712.88) |
| P-123 | m/z = 757.22($C_{53}H_{31}N_3OS$ = 757.91) | P-124 | m/z = 757.22($C_{53}H_{31}N_3OS$ = 757.91) |
| P-125 | m/z = 783.23($C_{55}H_{33}N_3OS$ = 783.95) | P-126 | m/z = 783.23($C_{55}H_{33}N_3OS$ = 783.95) |
| P-127 | m/z = 783.23($C_{55}H_{33}N_3OS$ = 783.95) | P-128 | m/z = 712.23($C_{49}H_{24}D_5N_3OS$ = 712.88) |
| P-129 | m/z = 783.23($C_{55}H_{33}N_3OS$ = 783.95) | P-130 | m/z = 783.23($C_{55}H_{33}N_3OS$ = 783.95) |
| P-131 | m/z = 809.25($C_{57}H_{35}N_3OS$ = 809.99) | P-132 | m/z = 809.25($C_{57}H_{35}N_3OS$ = 809.99) |
| P-133 | m/z = 809.25($C_{57}H_{35}N_3OS$ = 809.99) | P-134 | m/z = 738.25($C_{51}H_{26}D_5N_3OS$ = 738.92) |
| P-135 | m/z = 738.25($C_{51}H_{26}D_5N_3OS$ = 738.9) | P-136 | m/z = 662.22($C_{45}H_{22}D_5N_3OS$ = 662.82) |
| P-137 | m/z = 712.23($C_{49}H_{24}D_5N_3OS$ = 712.9) | P-138 | m/z = 712.23($C_{49}H_{24}D_5N_3OS$ = 712.88) |
| P-139 | m/z = 738.25($C_{51}H_{26}D_5N_3OS$ = 738.9) | P-140 | m/z = 762.25($C_{53}H_{26}D_5N_3OS$ = 762.94) |
| P-141 | m/z = 712.23($C_{49}H_{24}D_5N_3OS$ = 712.9) | P-142 | m/z = 712.23($C_{49}H_{24}D_5N_3OS$ = 712.88) |
| P-143 | m/z = 738.25($C_{51}H_{26}D_5N_3OS$ = 738.9) | P-144 | m/z = 738.25($C_{51}H_{26}D_5N_3OS$ = 738.92) |
| P-145 | m/z = 738.25($C_{51}H_{26}D_5N_3OS$ = 738.9) | P-146 | m/z = 657.19($C_{45}H_{27}N_3OS$ = 657.79) |
| P-147 | m/z = 733.22($C_{51}H_{31}N_3OS$ = 733.89) | P-148 | m/z = 662.22($C_{45}H_{22}D_5N_3OS$ = 662.82) |
| P-149 | m/z = 657.19($C_{45}H_{27}N_3OS$ = 657.79) | P-150 | m/z = 662.22($C_{45}H_{22}D_5N_3OS$ = 662.82) |
| P-151 | m/z = 657.19($C_{45}H_{27}N_3OS$ = 657.79) | P-152 | m/z = 733.22($C_{51}H_{31}N_3OS$ = 733.89) |
| P-153 | m/z = 662.22($C_{45}H_{22}D_5N_3OS$ = 662.8) | p-154 | m/z = 657.19($C_{45}H_{27}N_3OS$ = 657.79) |
| p-155 | m/z = 657.19($C_{45}H_{27}N_3OS$ = 657.79) | P-156 | m/z = 631.17($C_{43}H_{25}N_3OS$ = 631.75) |
| P-157 | m/z = 681.19($C_{45}H_{27}N_3OS$ = 681.81) | p-158 | m/z = 681.19($C_{45}H_{27}N_3OS$ = 681.81) |
| P-159 | m/z = 707.20($C_{49}H_{29}N_3OS$ = 707.85) | p-160 | m/z = 781.22($C_{55}H_{31}N_3OS$ = 781.93) |
| 4-1 | m/z = 793.27($C_{57}H_{35}N_3O_2$ = 793.93) | 4-2 | m/z = 869.30($C_{63}H_{39}N_3O_2$ = 870.02) |
| 4-4 | m/z = 798.3($C_{57}H_{30}D_5N_3O_2$ = 798.96) | 4-7 | m/z = 919.32($C_{67}H_{41}N_3O_2$ = 920.08) |
| 4-8 | m/z = 843.29($C_{61}H_{37}N_3O_2$ = 843.99) | 4-10 | m/z = 945.34($C_{69}H_{43}N_3O_2$ = 946.12) |
| 4-11 | m/z = 944.32($C_{68}H_{40}N_4O_2$ = 945.09) | 4-12 | m/z = 970.33($C_{70}H_{42}N_4O_2$ = 971.13) |
| 5-1 | m/z = 657.19($C_{45}H_{27}N_3OS$ = 657.79) | 5-2 | m/z = 733.22($C_{51}H_{31}N_3OS$ = 733.89) |
| 5-3 | m/z = 733.22($C_{51}H_{31}N_3OS$ = 733.89) | 5-4 | m/z = 733.22($C_{51}H_{31}N_3OS$ = 733.89) |
| 5-7 | m/z = 707.20($C_{49}H_{29}N_3OS$ = 707.85) | 5-8 | m/z = 757.22($C_{53}H_{31}N_3OS$ = 757.91) |
| 5-9 | m/z = 859.27($C_{61}H_{37}N_3OS$ = 860.05) | 5-10 | m/z = 707.20($C_{49}H_{29}N_3OS$ = 707.85) |
| 5-11 | m/z = 808.23($C_{56}H_{32}N_4OS$ = 808.96) | 5-12 | m/z = 890.31($C_{63}H_{34}D_5N_3OS$ = 891.1) |
| 5-13 | m/z = 824.24($C_{55}H_{32}N_6OS$ = 824.96) | 5-14 | m/z = 752.20($C_{50}H_{29}FN_4OS$ = 752.87) |
| 5-15 | m/z = 765.26($C_{51}H_{35}N_5OS$ = 765.94) | 5-16 | m/z = 765.17($C_{49}H_{27}N_5OS_2$ = 765.91) |
| 5-17 | m/z = 807.23($C_{57}H_{33}N_3OS$ = 807.97) | 5-18 | m/z = 833.25($C_{59}H_{35}N_3OS$ = 834.01) |
| 5-19 | m/z = 733.22($C_{51}H_{31}N_3OS$ = 733.89) | 5-20 | m/z = 733.22($C_{51}H_{31}N_3OS$ = 733.89) |
| 7-1 | m/z = 627.23($C_{45}H_{29}N_3O$ = 627.75) | 7-2 | m/z = 627.23($C_{45}H_{29}N_3O$ = 627.75) |
| 7-3 | m/z = 643.21($C_{45}H_{29}N_3S$ = 643.81) | 7-4 | m/z = 703.26($C_{51}H_{33}N_3O$ = 703.85) |
| 7-5 | m/z = 627.23($C_{45}H_{29}N_3O$ = 627.75) | 7-6 | m/z = 627.23($C_{45}H_{29}N_3O$ = 627.75) |
| 7-7 | m/z = 703.26($C_{51}H_{33}N_3O$ = 703.85) | 7-8 | m/z = 703.26($C_{51}H_{33}N_3O$ = 703.85) |
| 7-9 | m/z = 627.23($C_{45}H_{29}N_3O$ = 627.75) | 7-10 | m/z = 657.19($C_{45}H_{27}N_3OS$ = 657.79) |
| 7-11 | m/z = 657.19($C_{45}H_{27}N_3OS$ = 657.79) | 7-12 | m/z = 657.19($C_{45}H_{27}N_3OS$ = 657.79) |
| 7-13 | m/z = 641.21($C_{45}H_{27}N_3O_2$ = 641.73) | 7-14 | m/z = 641.21($C_{45}H_{27}N_3O_2$ = 641.73) |
| 7-15 | m/z = 641.21($C_{45}H_{27}N_3O_2$ = 641.73) | 7-16 | m/z = 717.24($C_{51}H_{31}N_3O_2$ = 717.83) |
| 7-17 | m/z = 717.24($C_{51}H_{31}N_3O_2$ = 717.83) | 7-18 | m/z = 581.16($C_{39}H_{23}N_3OS$ = 581.69) |
| 7-19 | m/z = 641.21($C_{45}H_{27}N_3O_2$ = 641.73) | 7-20 | m/z = 717.24($C_{51}H_{31}N_3O_2$ = 717.83) |
| 7-21 | m/z = 657.19($C_{45}H_{27}N_3OS$ = 657.79) | 7-22 | m/z = 641.21($C_{45}H_{27}N_3O_2$ = 641.73) |
| 7-23 | m/z = 641.21($C_{45}H_{27}N_3O_2$ = 641.73) | 7-24 | m/z = 641.21($C_{45}H_{27}N_3O_2$ = 641.73) |

Evaluation of Manufacture of Organic Electric Element

Example 1) Manufacture and Evaluation of Green Organic Light Emitting Diode

First, on an ITO layer(anode) formed on a glass substrate, N[1]-(naphthalen-2-yl)-N[4], N[4]-bis(4-(naphthalen-2-yl(phenyl)amino)phenyl)-N[1]-phenylbenzene-1,4-diamine (hereinafter will be abbreviated as 2-TNATA) was vacuum-deposited to form a hole injection layer with a thickness of 60 nm. 4,4-bis[N-(1-naphthyl)-N-phenylamino]biphenyl (hereinafter abbreviated as -NPD) was vacuum-deposited to form a hole transport layer with a thickness of 60 nm. Subsequently, as a host, a mixture of the compounds of the present invention represented by Formula 1 and Formula 2 at 6:4 was used, and a a dopant, by doping $Ir(ppy)_3$ [tris(2-phenylpyridine)-iridium] at 95:5 weight, an emitting layer having a thickness of 30 nm was deposited on the hole transport layer. (1,1'-bisphenyl)-4-olato)bis(2-methyl-8-quinolinolato)aluminum (hereinafter abbreviated as BAlq) was vacuum deposited as a hole blocking layer to a thickness of 10 nm, and tris(8-quinolinol)aluminum (hereinafter abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 5000 cd/$m^2$. In the following table, the manufacture of a device and the results of evaluation are shown.

Comparative Examples 1

An organic electroluminescent device was manufactured in the same manner as in Example 1, except that the comparative compound 1 was used as a host alone.

Comparative Examples 2

An organic electroluminescent device was manufactured in the same manner as in Example 1, except that the comparative compound 2 was used as a host alone.

Comparative Examples 3

An organic electroluminescent device was manufactured in the same manner as in Example 1, except that the comparative compound 3 was used as a host alone.

Comparative Examples 4, Comparative Examples 5

An organic electroluminescent device was manufactured in the same manner as in Example 1, except that the compound represented by Formula 2 was used as a host alone.

Comparative Examples 6

An organic electroluminescent device was manufactured in the same manner as in Example 1, except that comparative compound 1 and the compound represented by Formula 2 were mixed and used as a host.

Comparative Examples 7

An organic electroluminescent device was manufactured in the same manner as in Example 1, except that comparative compound 2 and the compound represented by Formula 2 were mixed and used as a host.

Comparative Examples 8

An organic electroluminescent device was manufactured in the same manner as in Example 1, except that comparative compound 3 and the compound represented by Formula 2 were mixed and used as a host.

[comparative compound 1]

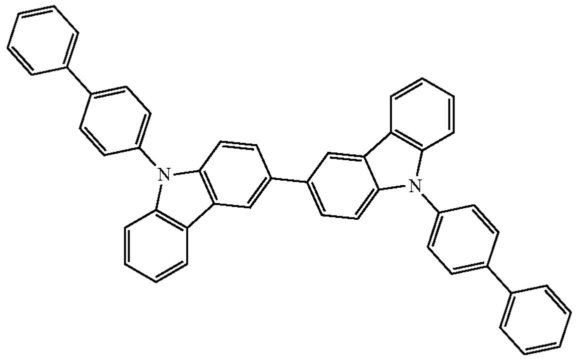

[comparative compound 2]

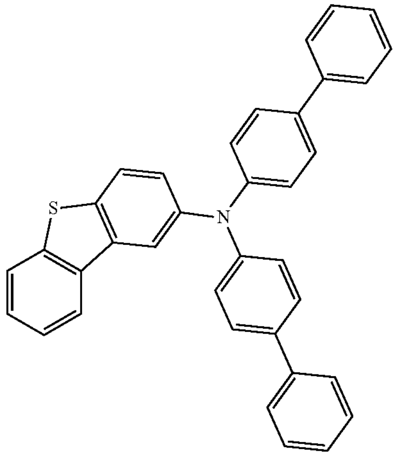

[comparative compound 3]

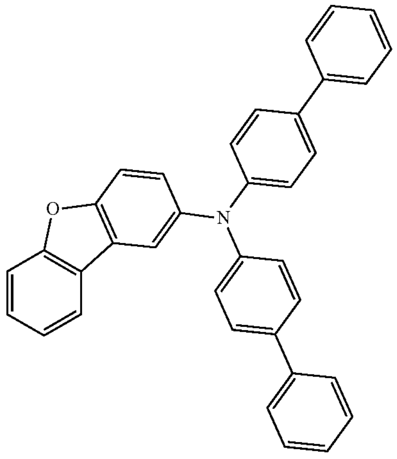

TABLE 5

| | First host | Second host | Voltage | Current Density | Brightness (cd/m2) | Efficiency | Lifetime T(95) |
|---|---|---|---|---|---|---|---|
| comparative example (1) | comparative compound 1 | — | 5.5 | 19.5 | 5000.0 | 25.6 | 80.4 |
| comparative example (2) | comparative compound 2 | — | 5.9 | 46.3 | 5000.0 | 10.8 | 20.3 |
| comparative example (3) | comparative compound 3 | — | 6.0 | 48.5 | 5000.0 | 10.3 | 23.8 |
| comparative example (4) | — | compound 1'-25 | 5.3 | 15.7 | 5000.0 | 31.9 | 60.8 |
| comparative example (5) | — | compound P-26 | 5.1 | 14.8 | 5000.0 | 33.8 | 58.2 |
| comparative example (6) | comparative compound 1 | compound P-26 | 4.8 | 12.3 | 5000.0 | 40.8 | 129.9 |
| comparative example (7) | comparative compound 2 | compound P-26 | 4.6 | 13.6 | 5000.0 | 36.9 | 70.4 |
| comparative example (8) | comparative compound 3 | compound P-26 | 4.5 | 12.9 | 5000.0 | 38.7 | 75.6 |
| example (1) | compound 1-2 | compound 1'-25 | 4.1 | 11.7 | 5000.0 | 42.8 | 130.3 |
| example (2) | | compound P-8 | 4.3 | 11.2 | 5000.0 | 44.5 | 130.1 |
| example (3) | | compound P-26 | 4.3 | 11.6 | 5000.0 | 43.2 | 131.0 |
| example (4) | | compound P-69 | 4.1 | 11.3 | 5000.0 | 44.3 | 130.9 |
| example (5) | | compound 4-5 | 4.1 | 11.5 | 5000.0 | 43.6 | 132.5 |
| example (6) | | compound 5-2 | 4.1 | 11.3 | 5000.0 | 44.2 | 132.9 |
| example (7) | | compound 6-4 | 4.2 | 11.5 | 5000.0 | 43.3 | 131.5 |
| example (8) | compound 1-16 | compound 1'-25 | 4.2 | 11.6 | 5000.0 | 43.2 | 132.5 |
| example (9) | | compound P-8 | 4.0 | 12.1 | 5000.0 | 41.5 | 132.8 |
| example (10) | | compound P-26 | 4.0 | 12.1 | 5000.0 | 41.2 | 131.8 |
| example (11) | | compound P-69 | 4.1 | 12.5 | 5000.0 | 40.1 | 131.3 |
| example (12) | | compound 4-5 | 4.3 | 11.9 | 5000.0 | 42.0 | 130.2 |
| example (13) | | compound 5-2 | 4.2 | 11.2 | 5000.0 | 44.8 | 130.7 |
| example (14) | | compound 6-4 | 4.1 | 11.3 | 5000.0 | 44.2 | 130.7 |
| example (15) | compound 1-36 | compound 1'-25 | 3.7 | 10.3 | 5000.0 | 48.4 | 136.8 |
| example (16) | | compound P-8 | 3.8 | 10.2 | 5000.0 | 48.8 | 136.1 |
| example (17) | | compound P-26 | 3.8 | 10.3 | 5000.0 | 48.6 | 137.5 |
| example (18) | | compound P-69 | 3.8 | 10.1 | 5000.0 | 49.5 | 139.0 |
| example (19) | | compound 4-5 | 3.8 | 10.1 | 5000.0 | 49.3 | 136.2 |
| example (20) | | compound 5-2 | 3.9 | 11.0 | 5000.0 | 45.3 | 139.9 |
| example (21) | | compound 6-4 | 3.8 | 10.5 | 5000.0 | 47.7 | 136.0 |
| example (22) | compound 1-64 | compound 1'-25 | 3.8 | 10.5 | 5000.0 | 47.7 | 136.5 |
| example (23) | | compound P-8 | 3.8 | 10.1 | 5000.0 | 49.7 | 135.5 |
| example (24) | | compound P-26 | 3.8 | 10.3 | 5000.0 | 48.4 | 136.4 |
| example (25) | | compound P-69 | 3.8 | 10.4 | 5000.0 | 47.9 | 137.6 |
| example (26) | | compound 4-5 | 3.8 | 10.6 | 5000.0 | 47.3 | 139.5 |
| example (27) | | compound 5-2 | 3.7 | 10.1 | 5000.0 | 49.6 | 136.1 |
| example (28) | | compound 6-4 | 3.9 | 10.2 | 5000.0 | 48.8 | 139.8 |
| example (29) | compound 1-74 | compound 1'-25 | 4.2 | 10.4 | 5000.0 | 48.1 | 138.7 |
| example (30) | | compound P-8 | 4.1 | 10.1 | 5000.0 | 49.7 | 135.4 |
| example (31) | | compound P-26 | 4.2 | 10.6 | 5000.0 | 47.3 | 136.6 |
| example (32) | | compound P-69 | 4.0 | 10.2 | 5000.0 | 49.0 | 136.8 |
| example (33) | | compound 4-5 | 4.1 | 10.7 | 5000.0 | 46.7 | 138.5 |
| example (34) | | compound 5-2 | 4.2 | 10.2 | 5000.0 | 48.9 | 135.1 |
| example (35) | | compound 6-4 | 4.3 | 10.7 | 5000.0 | 46.7 | 139.6 |
| example (36) | compound 1-100 | compound 1'-25 | 3.8 | 10.2 | 5000.0 | 49.2 | 137.4 |
| example (37) | | compound P-8 | 3.8 | 10.1 | 5000.0 | 49.5 | 139.8 |
| example (38) | | compound P-26 | 3.9 | 10.2 | 5000.0 | 49.2 | 138.4 |
| example (39) | | compound P-69 | 3.8 | 10.9 | 5000.0 | 46.1 | 140.0 |
| example (40) | | compound 4-5 | 3.7 | 10.7 | 5000.0 | 46.9 | 135.4 |
| example (41) | | compound 5-2 | 3.8 | 10.9 | 5000.0 | 45.8 | 138.4 |
| example (42) | | compound 6-4 | 3.7 | 10.5 | 5000.0 | 47.5 | 138.3 |
| example (43) | compound 1-122 | compound 1'-25 | 3.8 | 12.5 | 5000.0 | 40.0 | 130.6 |
| example (44) | | compound P-8 | 3.8 | 11.5 | 5000.0 | 43.5 | 131.9 |
| example (45) | | compound P-26 | 3.9 | 11.6 | 5000.0 | 43.1 | 131.5 |
| example (46) | | compound P-69 | 3.7 | 12.0 | 5000.0 | 41.6 | 132.9 |
| example (47) | | compound 4-5 | 3.7 | 11.3 | 5000.0 | 44.2 | 132.3 |
| example (48) | | compound 5-2 | 3.8 | 11.2 | 5000.0 | 44.6 | 130.6 |
| example (49) | | compound 6-4 | 3.8 | 11.7 | 5000.0 | 42.9 | 131.4 |
| example (50) | compound 1-141 | compound 1'-25 | 4.3 | 11.8 | 5000.0 | 42.5 | 130.7 |
| example (51) | | compound P-8 | 4.1 | 12.5 | 5000.0 | 40.1 | 132.2 |
| example (52) | | compound P-26 | 4.2 | 11.2 | 5000.0 | 44.7 | 132.7 |
| example (53) | | compound P-69 | 4.2 | 11.3 | 5000.0 | 44.3 | 132.9 |
| example (54) | | compound 4-5 | 4.3 | 11.6 | 5000.0 | 42.9 | 130.7 |
| example (55) | | compound 5-2 | 4.1 | 11.4 | 5000.0 | 44.0 | 130.6 |
| example (56) | | compound 6-4 | 4.2 | 12.1 | 5000.0 | 41.3 | 131.7 |

As can be seen from the results of Table 5, when the material for an organic electroluminescent device of the present invention represented by Formula 1 and Formula 2 is mixed and used as a phosphorescent host (Examples 1 to 56), compared to devices using a single compound (Comparative Examples 1 to 5) or devices mixed with a comparative compound (Comparative Examples 6 to 8), the driving voltage, efficiency, and lifespan are significantly improved. When the tertiary amine compounds, Comparative Compound 2 and Comparative Compound 3, were used as a phosphorescent host as a single material, both driving, efficiency and lifespan showed poor results, and Comparative compound 1 was the best in lifespan. When the compound represented by Formula 2 was used alone, there was a slight increase in driving and efficiency compared to the comparative compounds, but when Comparative Compounds 1 to 3 and the compound represented by Formula 2 were mixed and used as a phosphorescent host, all effects were improved compared to when used as a single compound. When Comparative Compound 1 with strong hole transport ability and the compound represented by Formula 2 were mixed, it showed a remarkable effect in terms of lifespan, and when the tertiary amine compounds, Comparative Compound 2 and Comparative Compound 3 were mixed, a remarkable effect was exhibited in terms of driving. From this result alone, it can be seen that even a compound with poor performance with a single host can improve the effect when mixed with a compound with a good charge balance.

In addition, it was confirmed that Examples 1 to 56 in which the compounds of Formula 1 and Formula 2 of the present invention were mixed and used as a host were significantly improved than in the case of Comparative Examples 1 to 8.

Based on the above experimental results, the present inventors determined that in the case of a mixture of the compound of Formula 1 and the compound of Formula 2, each of the compounds has novel properties other than those of the compound, and measured the PL lifetime using the compound of Formula 1, the compound of Formula 2, and the mixture of the present invention, respectively. As a result, it was confirmed that when the compounds of the present invention, Formula 1 and Formula 2, were mixed, a new PL wavelength was formed unlike the single compound, and the decrease and disappearance time of the newly formed PL wavelength increased from about 60 times to about 360 times less than the decrease and disappearance time of each of the compounds of Formula 1 and Formula 2. It is considered when mixed with the compound of the present invention, not only electrons and holes are moved through the energy level of each compound, but also the efficiency and life span are increased by electron, hole transport or energy transfer by a new region(exciplex) having a new energy level formed due to mixing. As a result, when the mixture of the present invention is used, the mixed thin film is an important example showing exciplex energy transfer and light emitting process.

Also, the reason why the combination of the present invention is superior to Comparative Examples 6 to 8 in which a comparative compound is mixed and used as a phosphorescent host is that the hole characteristics are improved by using a compound represented by Formula 1 in which one more amine group is added in Comparative Compounds 2 and 3, and has a good electrochemical synergy effect with the compound represented by Formula 2, which has strong electron properties. Accordingly, the charge balance between holes and electrons in the emission layer is increased, so that light emission is well performed inside the emitting layer rather than the hole transport layer interface, thereby reducing deterioration at the HTL interface, maximizing the driving voltage, efficiency, and lifespan of the entire device.

Example 2) Manufacture and Evaluation of Green Organic Light Emitting Diode by Mixing Ratio

TABLE 6

| | First host | Second host | Mixing ratio (first host: second host) | Voltage | Current Density | Brightness (cd/m2) | Efficiency | Lifetime T(95) |
|---|---|---|---|---|---|---|---|---|
| example (57) | compound | compound | 7:3 | 3.9 | 10.2 | 5000.0 | 49.1 | 140.2 |
| example (58) | 1-36 | 1'-25 | 5:5 | 3.8 | 10.7 | 5000.0 | 46.8 | 130.3 |
| example (59) | | | 4:6 | 3.6 | 11.1 | 5000.0 | 45.2 | 125.7 |
| example (60) | | | 3:7 | 3.8 | 11.2 | 5000.0 | 44.6 | 120.6 |
| example (61) | compound | compound | 7:3 | 4.0 | 10.0 | 5000.0 | 50.1 | 139.4 |
| example (62) | 1-64 | P-26 | 5:5 | 3.7 | 10.9 | 5000.0 | 45.8 | 130.5 |
| example (63) | | | 4:6 | 3.6 | 11.5 | 5000.0 | 43.5 | 123.4 |
| example (64) | | | 3:7 | 3.8 | 12.3 | 5000.0 | 40.7 | 120.2 |

As shown in Table 6, a device was manufactured and measured in the same manner as in Example 1 by using a mixture of the compounds of the present invention in different ratios (7:3, 5:5, 4:6, 3:7). As a result of measuring by ratio, in the case of 7:3, it was similar to the result of Example 1, which was measured as 6:4, but in the case of 5:5, 4:6, and 3:7 where the ratio of the first host decreases, the results of driving voltage, efficiency, and lifespan gradually declined. This can be explained because when an appropriate amount of the compound represented by Formula 1 having strong hole properties such as 7:3 and 4:6 is mixed, the charge balance in the emitting layer is maximized.

Example 3) Manufacture and Evaluation of Green Organic Light Emitting Diode

First, on an ITO layer(anode) formed on a glass substrate, $N^1$-(naphthalen-2-yl)-$N^4$,$N^4$-bis(4-(naphthalen-2-yl(phenyl)amino)phenyl)-$N^1$-phenylbenzene-1,4-diamine (hereinafter will be abbreviated as 2-TNATA) was vacuum-deposited to form a hole injection layer with a thickness of 60 nm. Subsequently, 4,4-bis[N-(1-naphthyl)-N-phenylamino]biphenyl (hereinafter abbreviated as -NPD) was vacuum-deposited on the film to form a hole transport layer with a thickness of 60 nm. Subsequently, as a host, the compounds of the present invention represented by Formula 19 and Formula 21 was used, and as a dopant, by doping $Ir(ppy)_3$ [tris(2-phenylpyridine)-iridium] at 5:5 weight, an emitting layer having a thickness of 30 nm was deposited on the hole transport layer. (1,1'-bisphenyl)-4-olato)bis(2-methyl-8-quinolinolato)aluminum (hereinafter abbreviated as BAlq) was vacuum deposited as a hole blocking layer to a thickness of 10 nm, and tris(8-quinolinol)aluminum (hereinafter abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 5000 cd/m$^2$. In the following table, the manufacture of a device and the results of evaluation are shown.

Comparative Examples 9~12

An organic electroluminescent device was manufactured in the same manner as in Example 3, except that Comparative Compounds 4 to 7 were used as a single host, respectively.

[comparative compound 4]

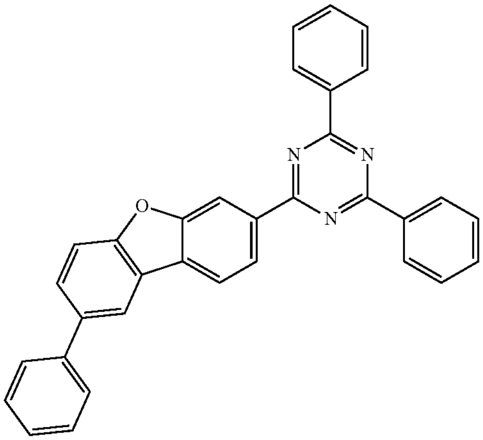

-continued

[comparative compound 5]

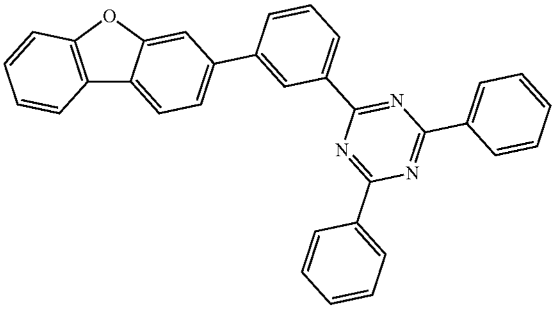

[comparative compound 6]

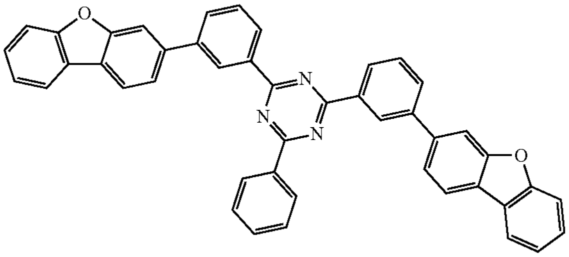

[comparative compound 7]

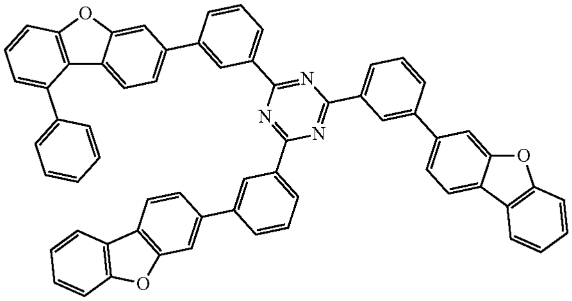

TABLE 7

| | compound | Voltage | Current Density | Brightness (cd/m$^2$) | Efficiency (cd/A) | T(95) | CIE x | CIE y |
|---|---|---|---|---|---|---|---|---|
| comparative example (9) | comparative compound 4 | 5.5 | 17.6 | 5000.0 | 28.4 | 74.2 | 0.30 | 0.63 |
| comparative example (10) | comparative compound 5 | 5.9 | 14.4 | 5000.0 | 34.7 | 65.4 | 0.34 | 0.65 |
| comparative example (11) | comparative compound 6 | 6.2 | 11.4 | 5000.0 | 43.8 | 80.6 | 0.33 | 0.60 |
| comparative example (12) | comparative compound 7 | 6.6 | 11.3 | 5000.0 | 44.1 | 84.3 | 0.33 | 0.62 |
| example (65) | compound (7-1) | 5.2 | 9.3 | 5000.0 | 53.8 | 100.5 | 0.32 | 0.61 |
| example (66) | compound (7-7) | 5.2 | 9.6 | 5000.0 | 52.0 | 104.8 | 0.31 | 0.62 |
| example (67) | compound (7-10) | 5.1 | 9.3 | 5000.0 | 53.8 | 100.7 | 0.35 | 0.62 |
| example (68) | compound (7-13) | 4.9 | 8.8 | 5000.0 | 56.7 | 104.7 | 0.31 | 0.63 |
| example (69) | compound (7-19) | 5.2 | 9.1 | 5000.0 | 54.7 | 103.0 | 0.30 | 0.63 |
| example (70) | compound (7-21) | 5.1 | 9.3 | 5000.0 | 53.6 | 102.0 | 0.30 | 0.61 |

As described above, it can be seen that the organic electroluminescent device using the compound of the present invention as a phosphorescent host significantly improves all of the driving voltage, efficiency, and lifespan compared to the organic electroluminescent device using the comparative compound. The difference between Comparative Compound 4 and the present invention is the difference in the presence or absence of a linking group of m-phenylene, and Comparative Compound 5 and Comparative Compound 6 differ in the presence or absence of secondary substituents such as phenyl and biphenyl in dibenzofuran, and Comparative compound 7 differs according to the number of substitutions of dibenzofuran.

Comprehensively judging the device data, it was confirmed that the linker of m-phenylene has an effect of improving the efficiency, and the secondary substituent of dibenzouran has the effect of remarkably improving the lifespan, in particular. This means that even with the same core, the energy level of the compound (HOMO level, LUMO level, T1 level) is significantly different as a specific substituent is substituted, this difference in physical properties of the compound acts as a major factor (for example, energy balance) to improve device performance during device deposition, suggesting that these different device results may be derived.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

INDUSTRIAL AVAILABILITY

According to the present invention, it is possible to manufacture an organic device having excellent device characteristics of high luminance, high light emission and long life, and thus has industrial applicability.

What is claimed is:

1. An organic electronic element comprising a first electrode, a second electrode, and an organic material layer formed between the first electrode and the second electrode, wherein the organic material layer comprises an emitting layer comprising a phosphorescent dopant, wherein the emitting layer comprises a first host compound represented by Formula 1 and a second host compound represented by Formula 2:

Formula 1

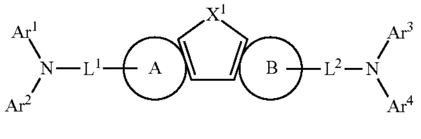

-continued

Formula 2

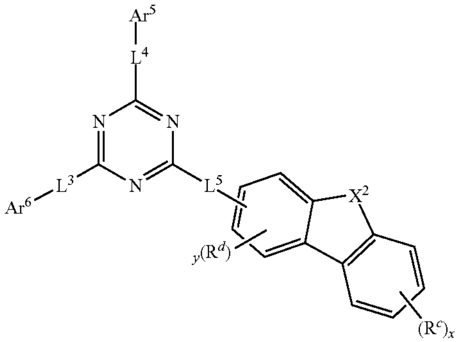

in Formula 1 and Formula 2,

1) $Ar^1$, $Ar^2$, $Ar^3$, $Ar^4$, $Ar^5$, $Ar^6$ and $Ar^7$ are each independently selected from the group consisting of hydrogen; deuterium; halogen; a $C_6$-$C_{60}$ aryl group; a fluorenyl group; a $C_2$-$C_{60}$ heterocyclic group including at least one hetero atom of O, N, S, Si, P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R^a$)($R^b$), and also $Ar^1$ and $Ar^2$, or $Ar^3$ and $Ar^4$ may combine each other to form a ring,
2) L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R^a$ and $R^b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P,
3) $L^1$, $L^2$, $L^3$, $L^4$ and $L^5$ are independently selected from the group consisting of a single bond, a $C_6$-$C_{60}$ arylene group; a fluorenylene group; or a $C_2$-$C_{60}$ heteroarylene group containing at least one hetero atom of O, N, S, Si, and P,
4) $X^1$is O or S,
5) Ring A and B are independently a $C_6$-$C_{60}$ aryl group; or a $C_2$-$C_{20}$ heterocyclic group,
6) $X^2$ is N-$L^6$-$Ar^7$, O, S or CR'R", wherein R' and R" are independently hydrogen; a $C_6$-$C_{60}$ aryl group; a fluorenyl group; a $C_3$-$C_{60}$ heterocyclic group; or a $C_1$-$C_{50}$ alkyl group; R' and R" may be bonded to each other to form a spiro ring,
7) x is an integer of 0 to 4, y is an integer of 0 to 3, $R^c$ and $R^d$ are each independently selected from the group consisting of hydrogen; a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and L-N($R^a$)($R^b$), and
8) the aryl group, fluorenyl group, arylene group, heterocyclic group, fused ring group, alkyl group, alkenyl group, alkoxy group and aryloxy group may be substituted with one or more substituents selected from the group consisting of deuterium; halogen; a silane group; siloxane group; boron group; germanium group; cyano group; nitro group; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may combine each other and form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The organic electronic element of claim 1, wherein A and B in Formula 1 each independently include a structure of formulas a-1 to a-7:

Formula a-1

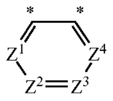

Formula a-2

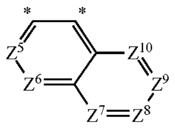

Formula a-3

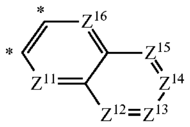

Formula a-4

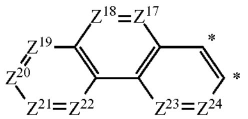

Formula a-5

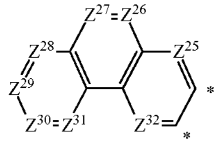

Formula a-6

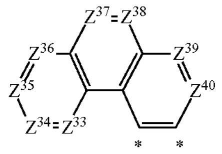

Formula a-7

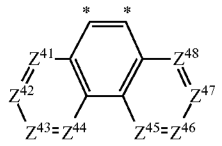

wherein $Z^1$ to $Z^{48}$ are each independently $CR^c$ or N, $Z^1$ to $Z^{48}$ bonded to $L^1$ or $L^3$ are carbon (C), $R^c$ is the same as the definition of $R^a$ in claim 1,

* indicates the position to be condensed.

3. The organic electronic element of claim 1, wherein $L^1$ to $L^5$ in Formula 1 or Formula 2 are represented by one of Formulas b-1 to b-13:

Formula b-1

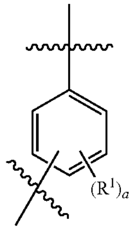

Formula b-2

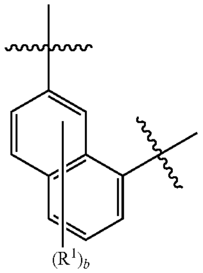

Formula b-3

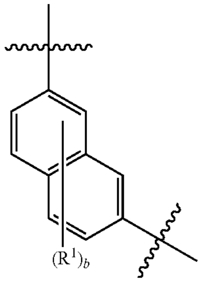

Formula b-4

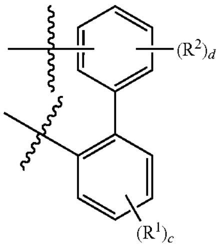

Formula b-5

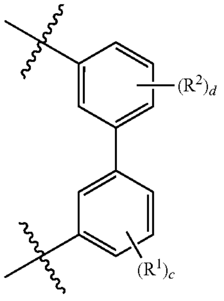

-continued

Formula b-6

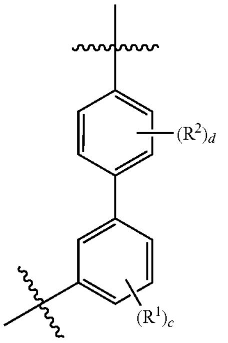

Formula b-7

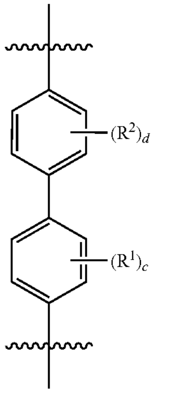

Formula b-8

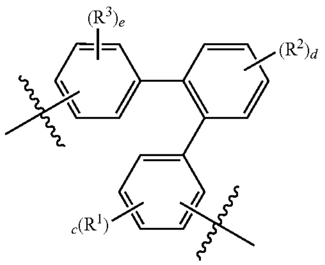

Formula b-9

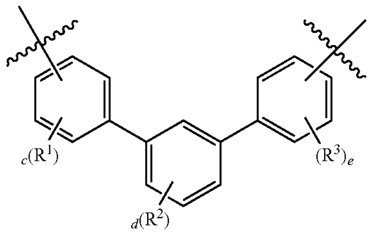

Formula b-10

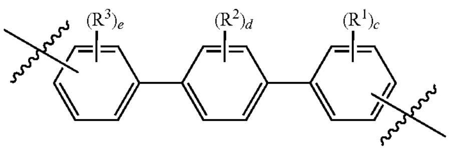

Formula b-11

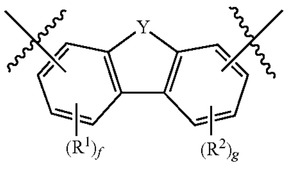

-continued

Formula b-12

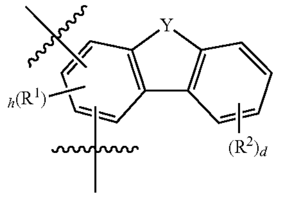

Formula b-13

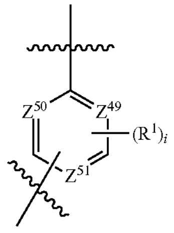

wherein

Y is N-$L^5$-$Ar^7$, O, S or $CR^dR^e$, $L^5$ is the same as the definition of $L^3$ in claim 1, $Ar^7$ is the same as the definition of $Ar^5$ in claim 1, $R^d$ and $R^e$ are the same as the definition of $R^a$ in claim 1, a, c, d and e are each independently an integer of 0 to 4, b is an integer of 0 to 6, f and g are each independently an integer of 0 to 3, h is an integer of 0 to 2, i is an integer of 0 or 1, $R^1$, $R^2$ and $R^3$ are each independently hydrogen; deuterium; tritium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -$L^a$-N($R^f$)($R^g$); or in case a, b, c, d, e, f and g are 2 or more, and h is 2 or more, each as plurality are the same as or different from each other, and a plurality of $R^1$ or a plurality of $R^2$ or a plurality of $R^3$ or adjacent $R^1$ and $R^2$, or adjacent $R^2$ and $R^3$ may be bonded to each other to form an aromatic or a heteroaromatic ring, $L^a$ is selected from the group consisting of a single bond; a $C_6$-$C_{60}$ arylene group; a fluorenylene group; a $C_2$-$C_{60}$ heterocyclic group containing at least one hetero atom of O, N, S, Si, and P; a fused ring group of a $C_3$-$C_{60}$ aliphatic ring and a $C_6$-$C_{60}$ aromatic ring; and $C_3$-$C_{60}$ aliphatic hydrocarbon group;

$R^f$ and $R^g$ are each independently selected from the group consisting of a $C_6$-$C_{60}$ aryl group; a fluorenyl group; a $C_2$-$C_{60}$ heterocyclic group containing at least one hetero atom selected from the group consisting of O, N, S, Si, and P; a fused ring group of a $C_3$-$C_{60}$ aliphatic ring and a $C_6$-$C_{60}$ aromatic ring, $Z^{49}$, $Z^{50}$, and $Z^{51}$ are each independently $CR^h$ or N, at least one of $Z^{49}$, $Z_{50}$, and $Z^{51}$ is N, and $R^h$ is selected from the group consisting of hydrogen; deuterium; tritium; halogen; cyano group; nitro group; $C_6$-$C_{60}$ aryl group; a fluorenyl group; a $C_2$-$C_{60}$ heterocyclic group including at least one heteroatom selected from the group consisting of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and adjacent $R^1$ and $R^h$ may be bonded to each other to form an aromatic or a heteroaromatic ring.

4. The organic electronic element of claim 1, wherein the first host compound represented by Formula 1 comprises a compound represented by one of Formula 3 to Formula 5:

Formula 3

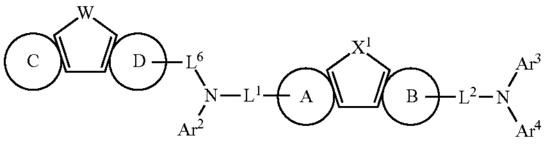

Formula 4

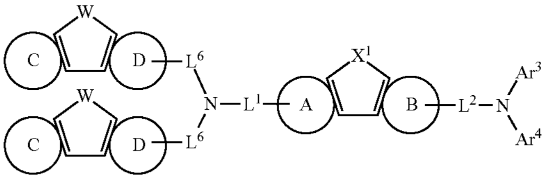

Formula 5

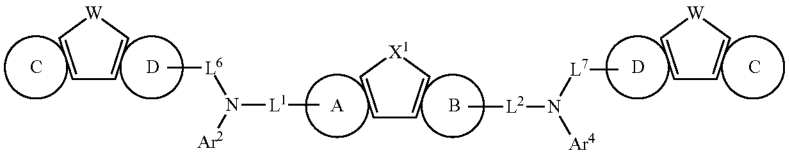

wherein $X^1$, A, B, $L^1$, $L^2$, $Ar^2$, $Ar^3$ and $Ar^4$ are the same as defined in claim 1, C and D are the same as the definition of A in claim 1, W is N-$L^7$-$Ar^8$, O, S, or $CR^iR^j$, $L^6$ and $L^7$ are the same as the definition of $L^4$ in claim 1, $Ar^8$ is the same as the definition of $Ar^5$ in claim 1, $R^i$ and $R^j$ are the same as the definition of $R^a$ in claim 1, and wherein in formulae 4 and 5, the two $Ar^8$ are each the same or different, the two W are each the same or different, the two C are each the same or different, the two D are each the same or different.

5. The organic electronic element of claim 1, wherein the first host compound represented by Formula 1 comprises a compound represented by Formula 6:

Formula 6

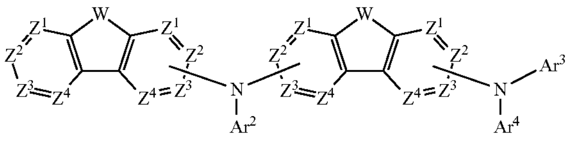

wherein $X^1$, $Ar^2$, $Ar^3$ and $Ar^4$ are the same as defined in claim 1, $Z^1$, $Z^2$, $Z^3$ and $Z^4$ are each independently $CR^c$ or N, $Z^1$ to $Z^4$ bonded to N is carbon (C), $R^c$ is the same as the definition of $R^a$ in claim 1, W is N-$L^7$-$Ar^8$, O, S, or $CR^iR^j$, $L^7$ are the same as the definition of $L^4$ in claim 1, $Ar^8$ is the same as the definition of $Ar^5$ in claim 1, $R^i$ and $R^j$ are the same as the definition of $R^a$ in claim 1.

6. The organic electronic element of claim 1, wherein the first host compound represented by Formula 1 comprises a compound represented by Formula 7 or 8 or 9:

Formula 7

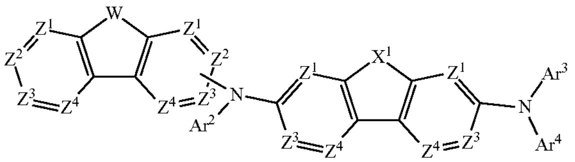

Formula 8

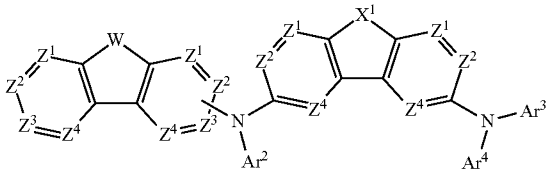

Formula 9

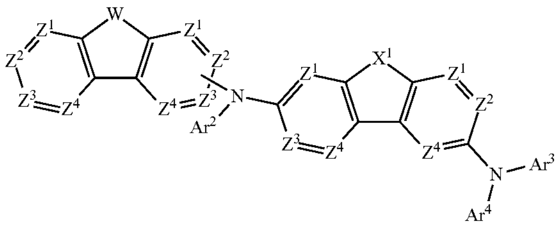

wherein $X^1$, $Ar^2$, $Ar^3$ and $Ar^4$ are the same as defined in claim 1, $Z^1$, $Z^2$, $Z^3$, $Z^4$ and W are the same as defined in claim 5.

7. The organic electronic element of claim 1, wherein the second host compound represented by Formula 2 comprises a compound represented by any one of Formulas 10 to 13:

Formula 10

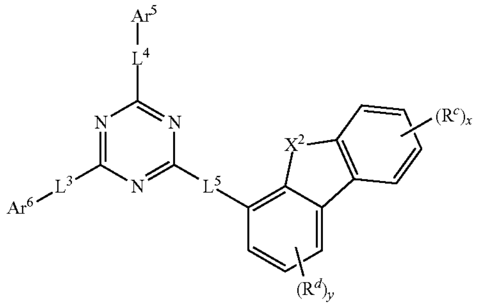

Formula 11

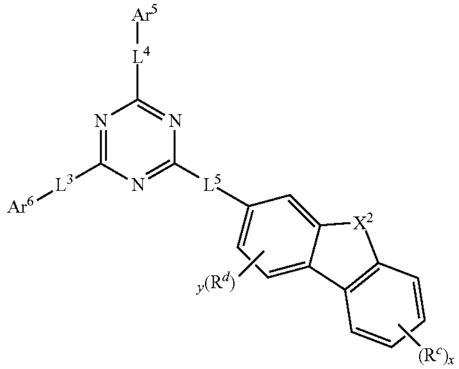

Formula 12

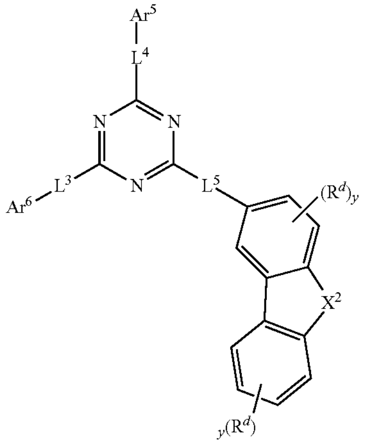

-continued

Formula 13

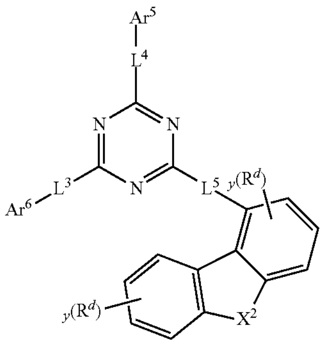

wherein $X^2$, $L^3$, $L^4$, $L^5$, $Ar^5$, $Ar^6$, $R^c$, $R^d$, x and y are the same as defined in claim 1.

8. The organic electronic element of claim 1, wherein the second host compound represented by Formula 2 comprises a compound represented by Formula 14:

Formula 14

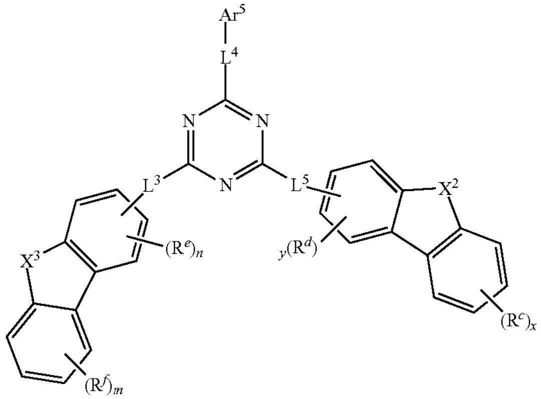

wherein

1) $X^2$, $L^3$, $L^4$, $L^5$, $Ar^5$, $R^c$, $R^d$x and y are the same as defined in claim 1, 2) $X^3$ is the same as the definition of $X^2$ in claim 1, 3) $R^e$ and $R^f$ are the same as the definition of $R^d$ and $R^c$ in claim 1, 4) n is the same as the definition of y, m is the same as the definition of x.

9. The organic electronic element of claim 1, wherein the second host compound represented by Formula 2 comprises a compound represented by one of Formulas 15 to 18:

Formula 15

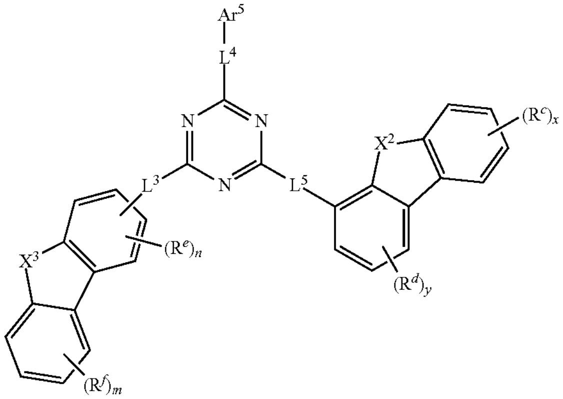

Formula 16

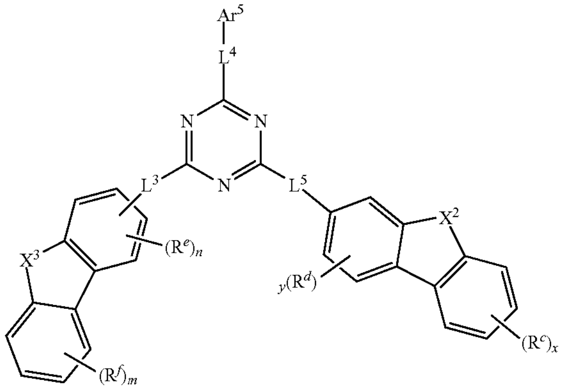

Formula 17

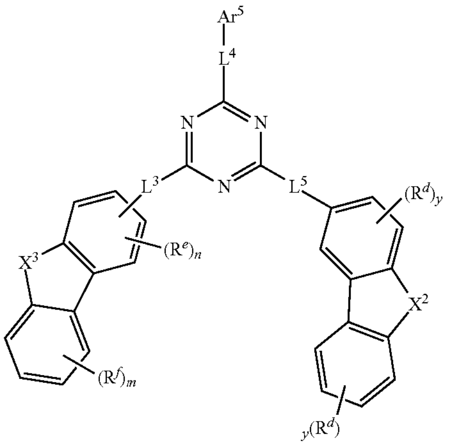

-continued

Formula 18

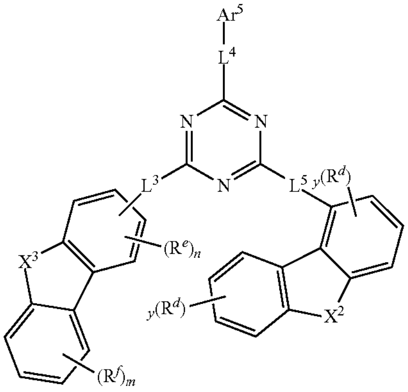

wherein

1) $X^2$, $L^3$, $L^4$, $L^5$, $Ar^5$, $R^c$, $R^d$, x and y are the same as defined in claim 1, 2) $X^3$, is the same as definition of $X^2$ in claim 1, 3) $R^e$ and $R^f$, are the same as definition of $R^c$ and $R^d$ in claim 1, 4) n is the same as the definition of y, m is the same as the definition of x.

10. The organic electronic element of claim 1, wherein the first host compound represented by Formula 1 is any one of Compound 1-1 to Compound 1-175:

1-1

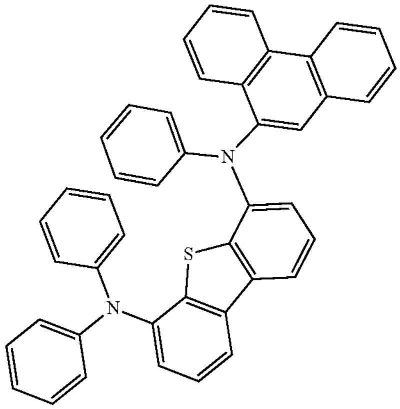

1-2

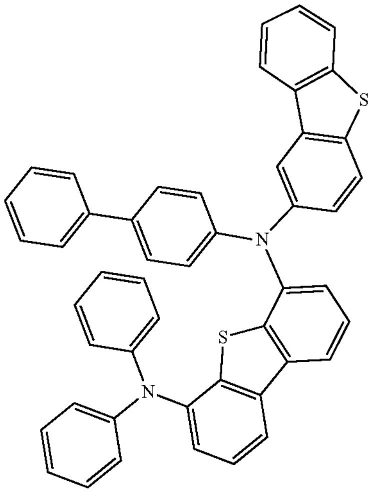

-continued
1-3
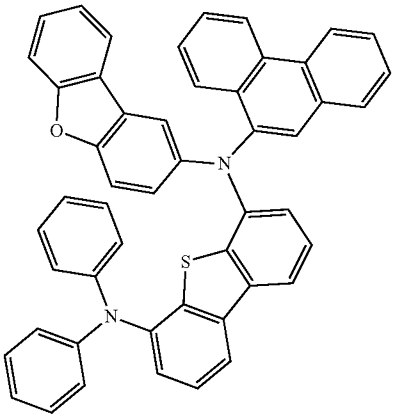
1-4
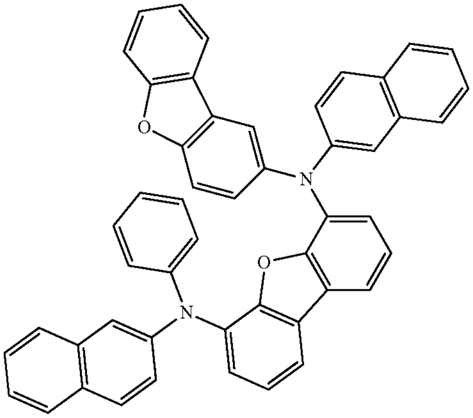
1-5
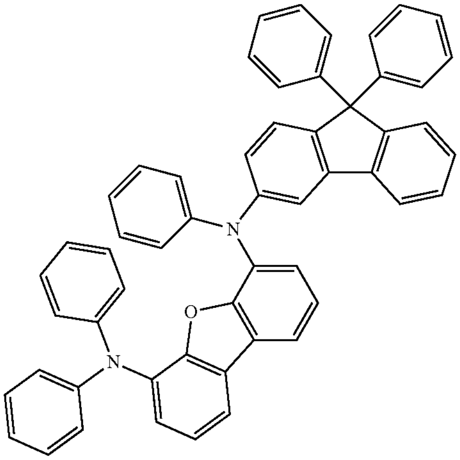
-continued
1-6
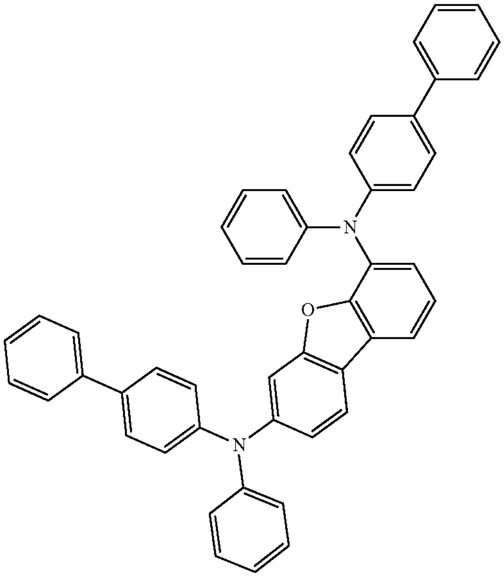
1-7
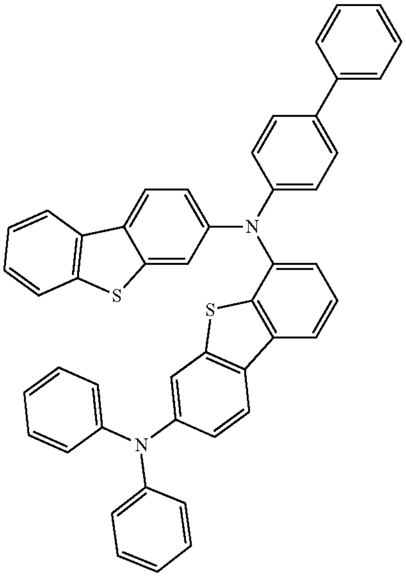

-continued
1-8
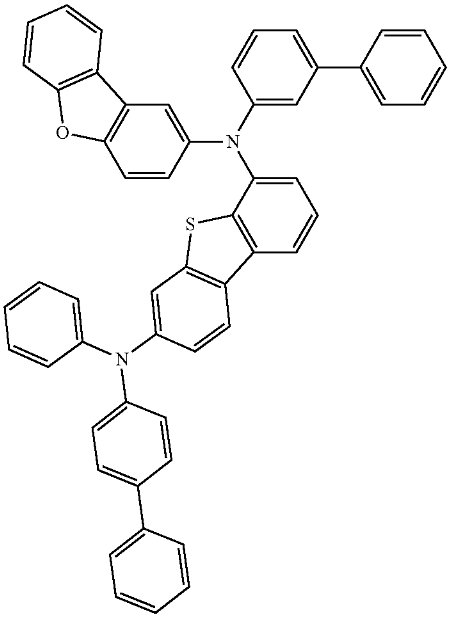
1-9
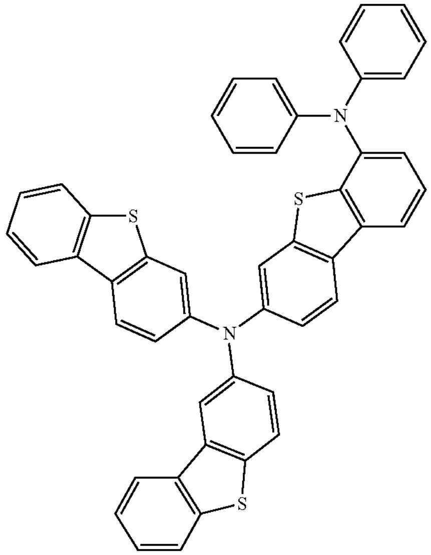
-continued
1-10
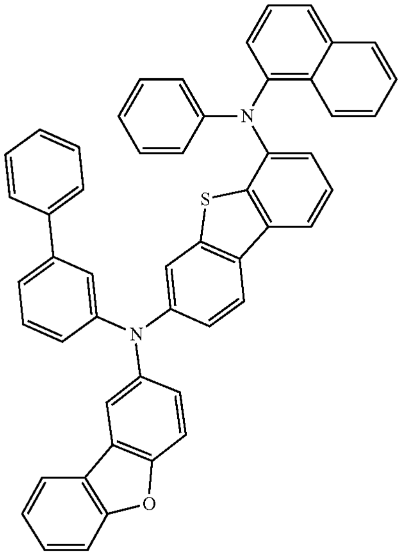
1-11
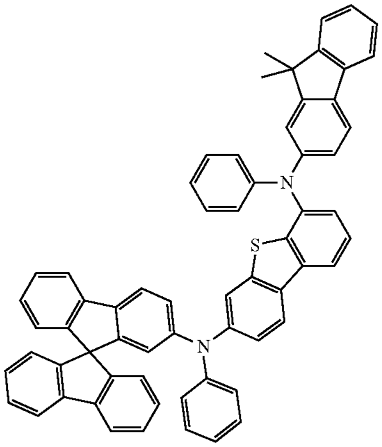
1-12
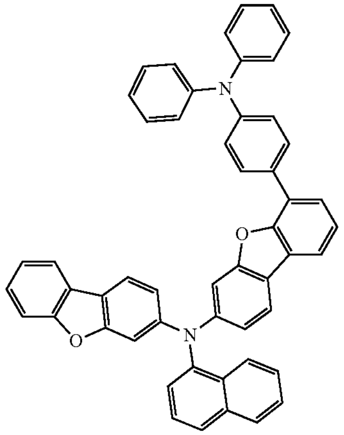

-continued
1-13
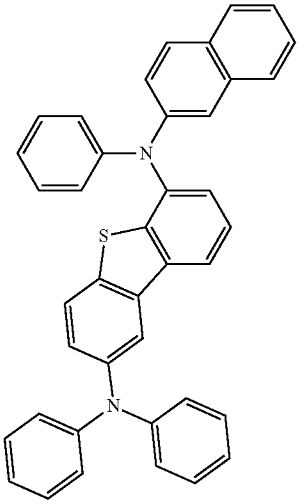
1-14
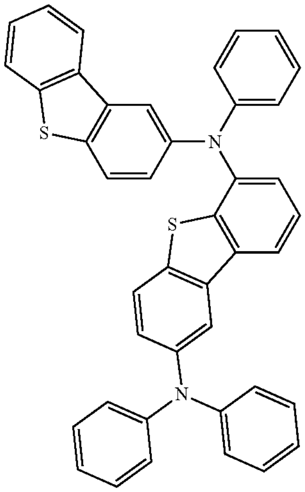
1-15
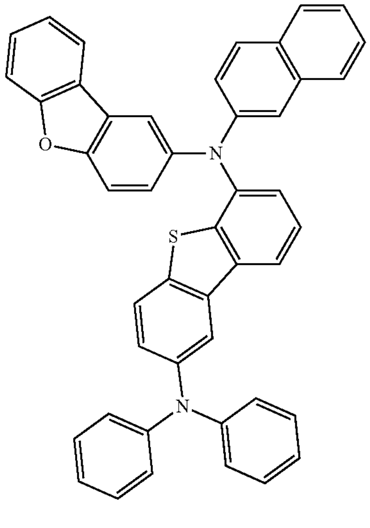
-continued
1-16
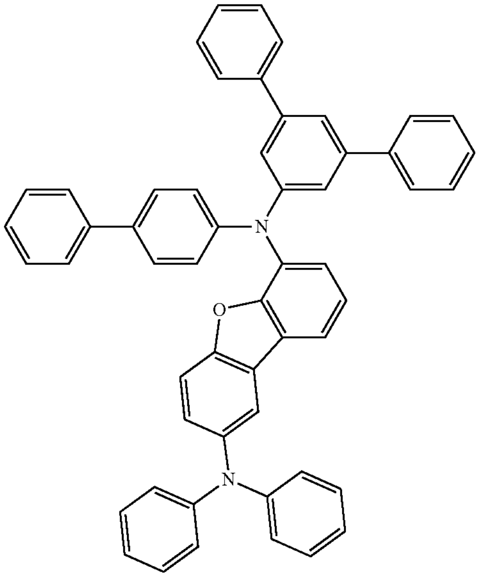
1-17
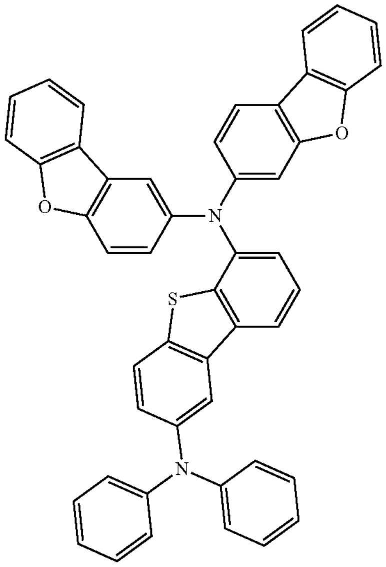

-continued
1-18
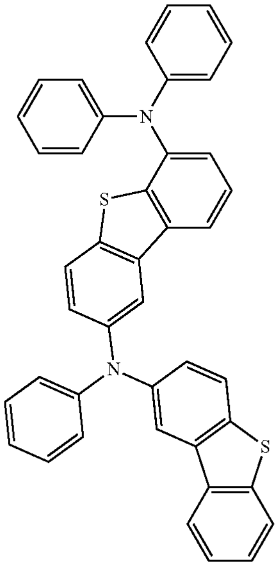
1-19
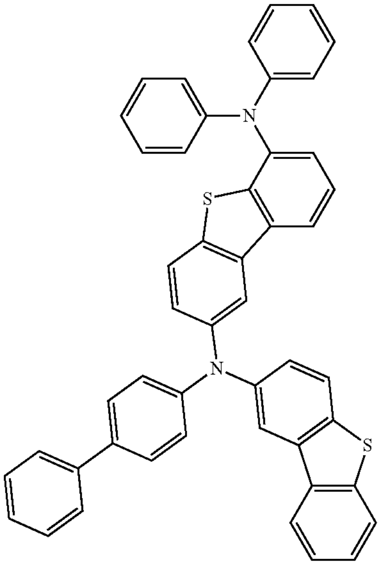
-continued
1-20
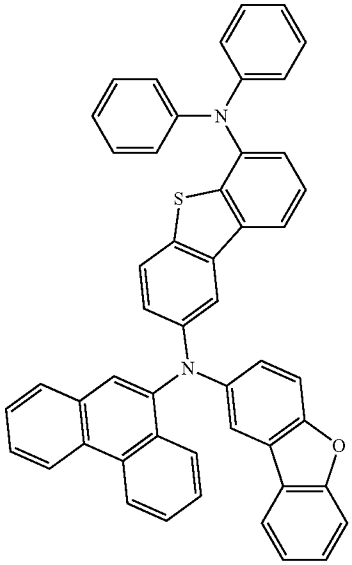
1-21
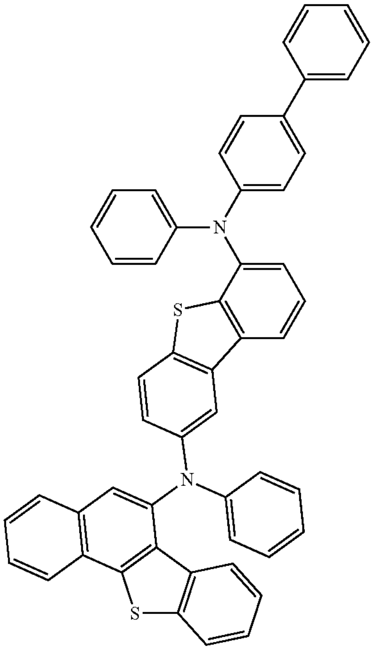

-continued
1-22
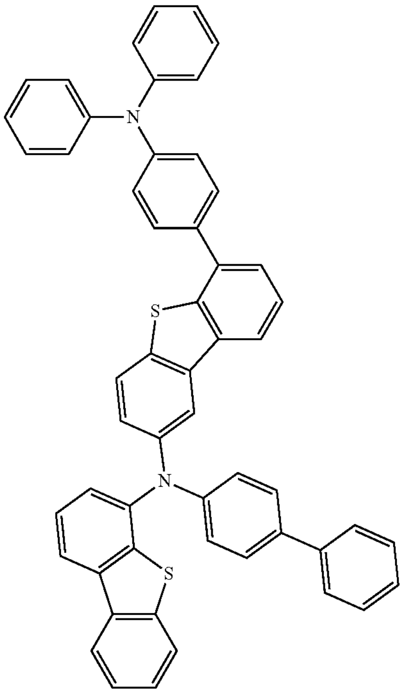
1-23
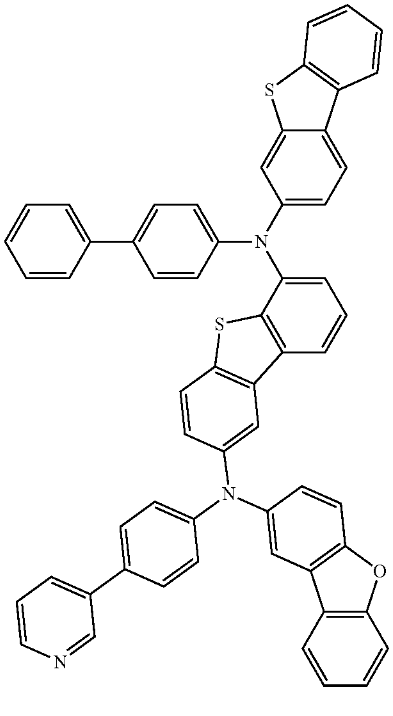
-continued
1-24
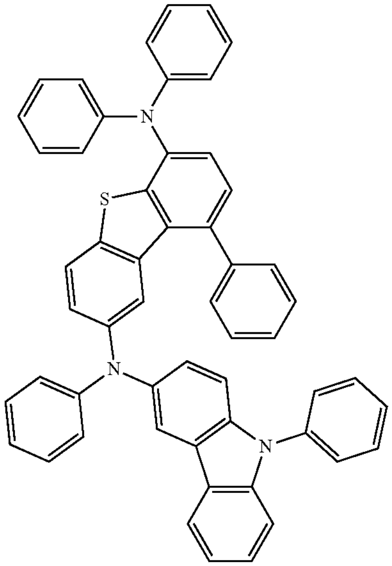
1-25
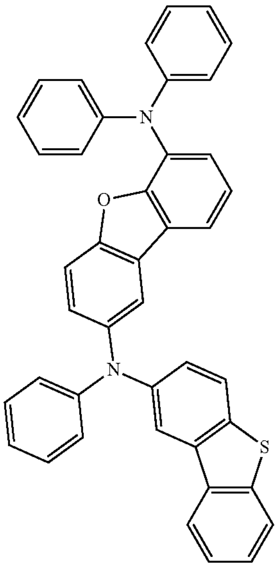
1-26
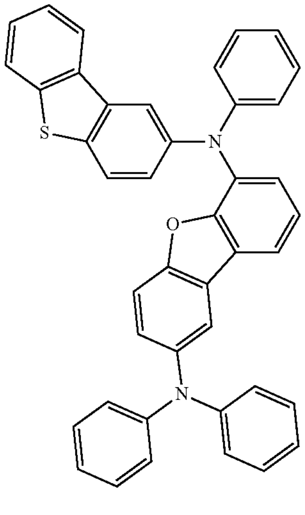

-continued
1-27
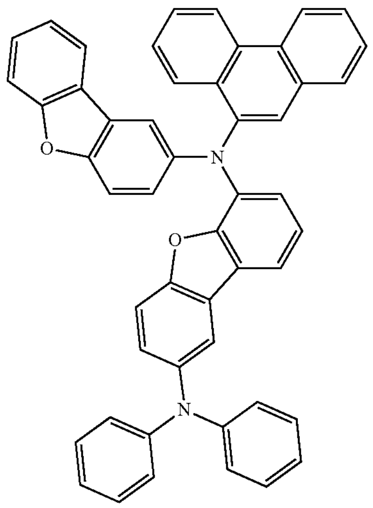
1-28
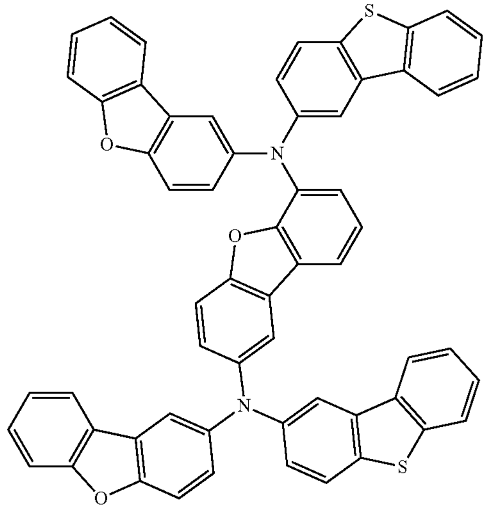
1-29
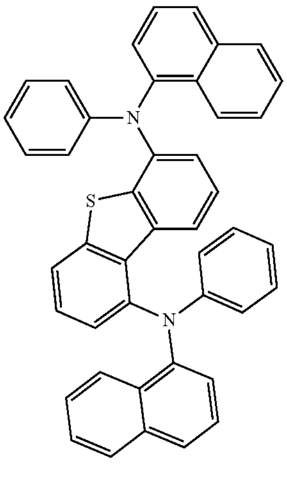
-continued
1-30
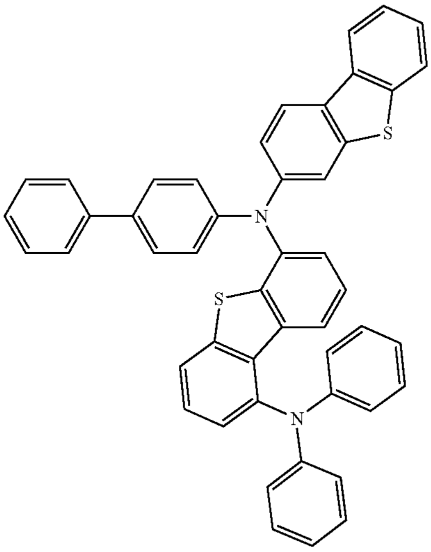
1-31
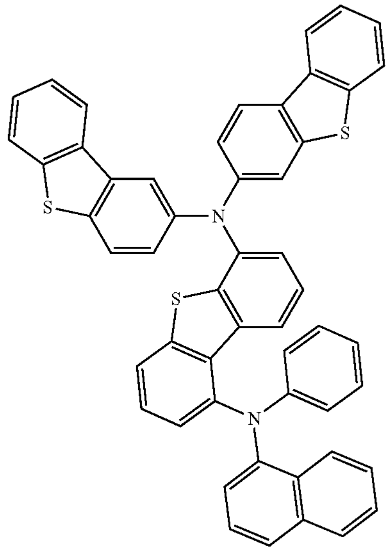
1-32
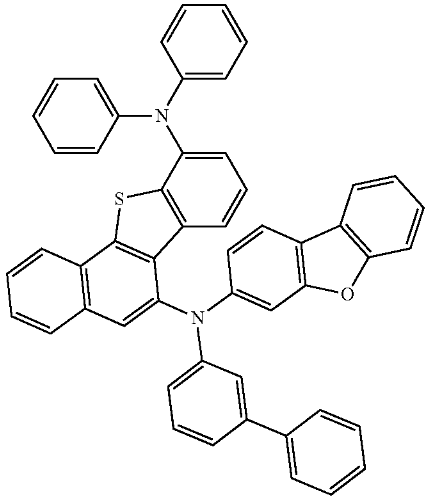

-continued
1-33
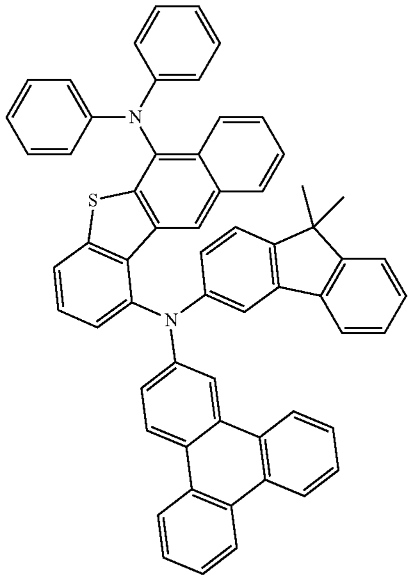
1-34
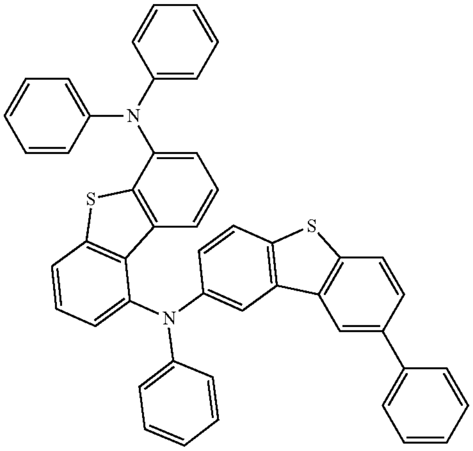
1-35
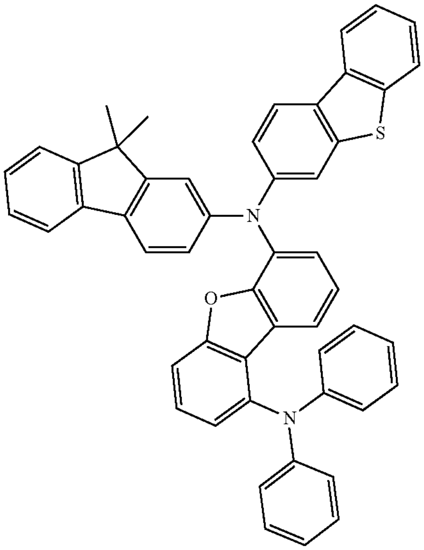
-continued
1-36
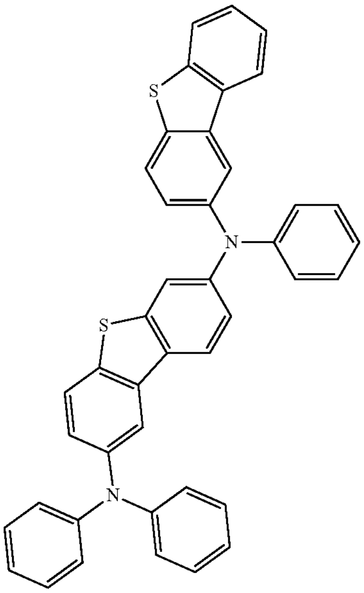
1-37
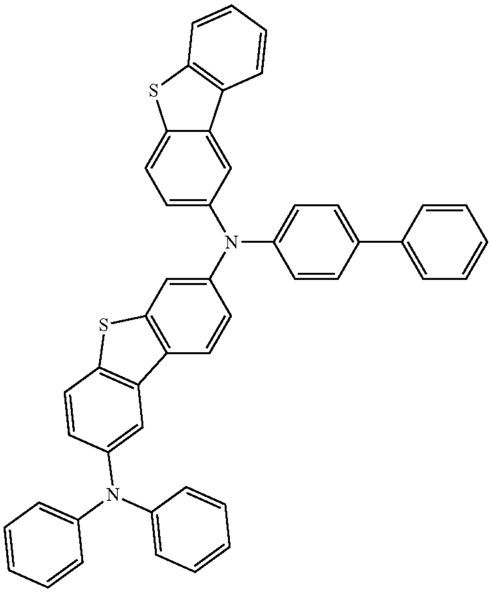

-continued
1-38
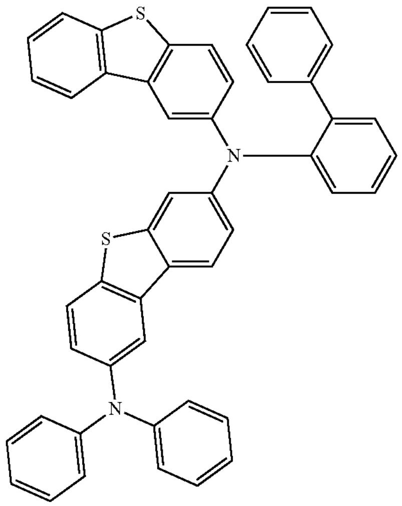
1-39
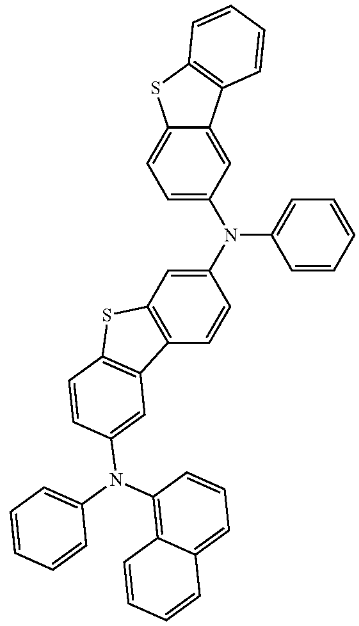
-continued
1-40
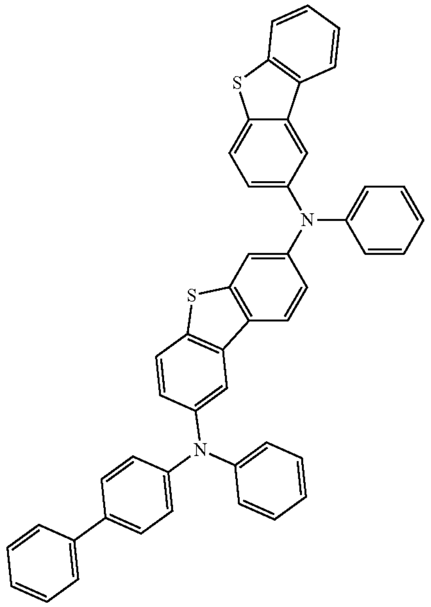
1-41
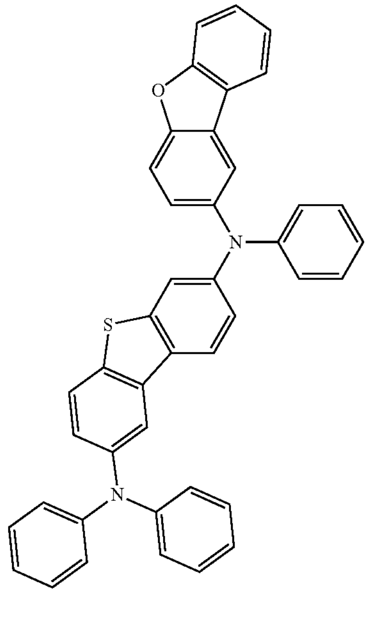

-continued
1-42
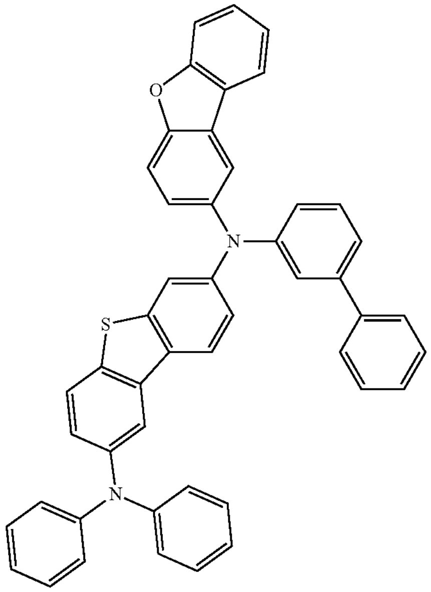
1-43
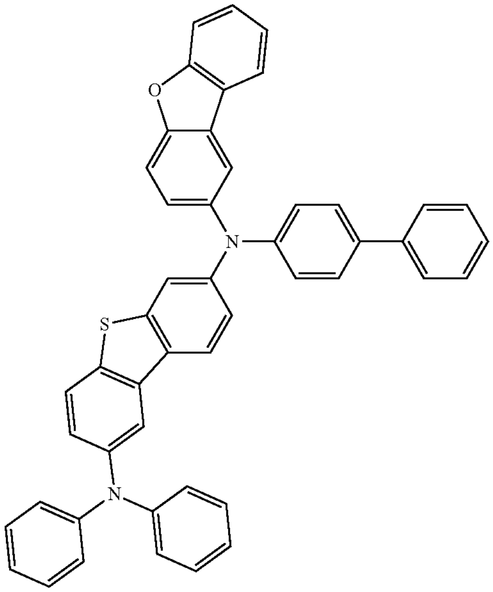
-continued
1-44
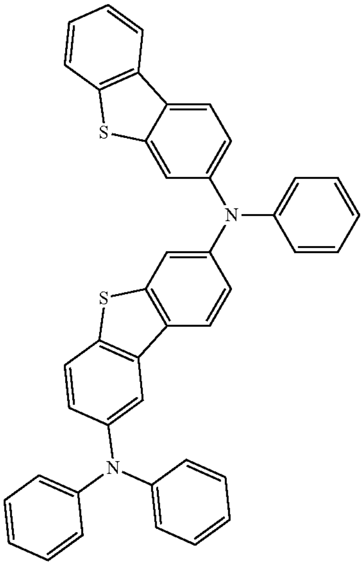
1-45
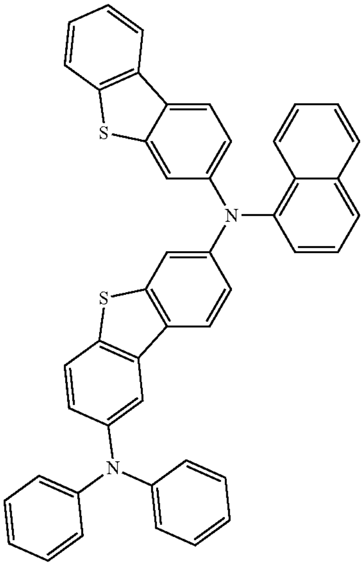

-continued
1-46
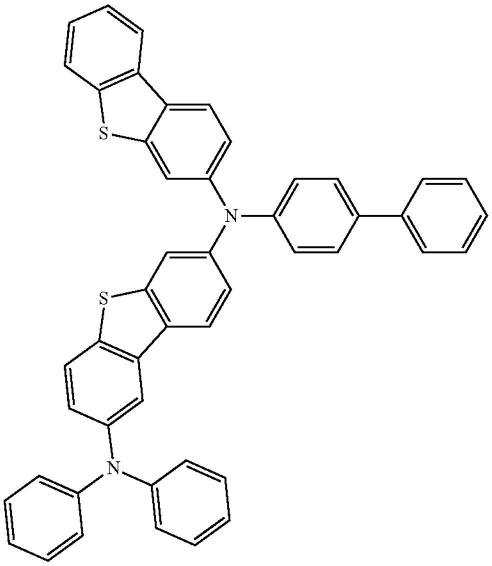
1-47
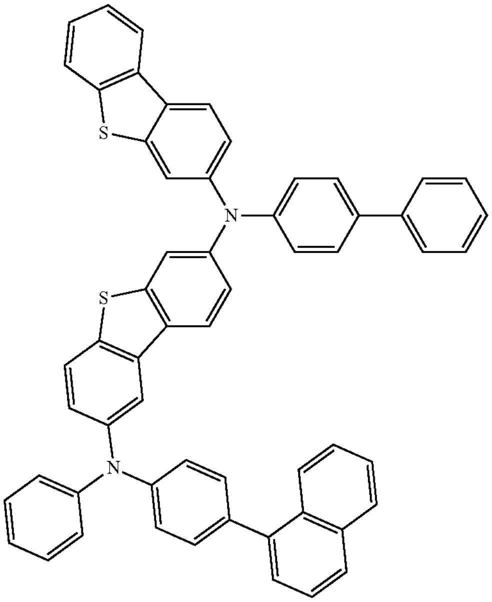
-continued
1-48
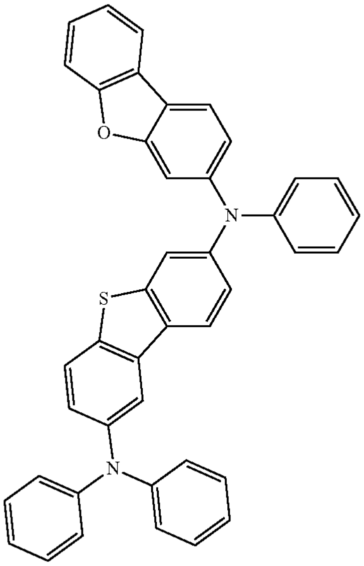
1-49
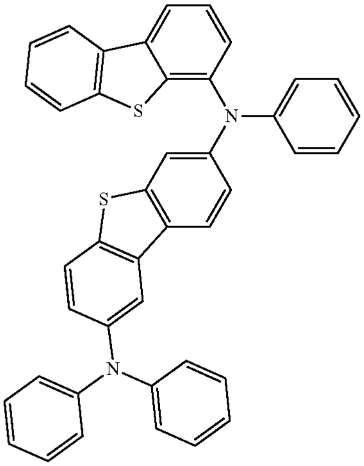
1-50
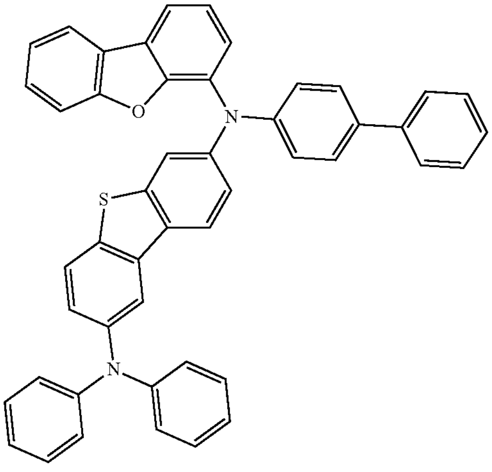

-continued
1-51
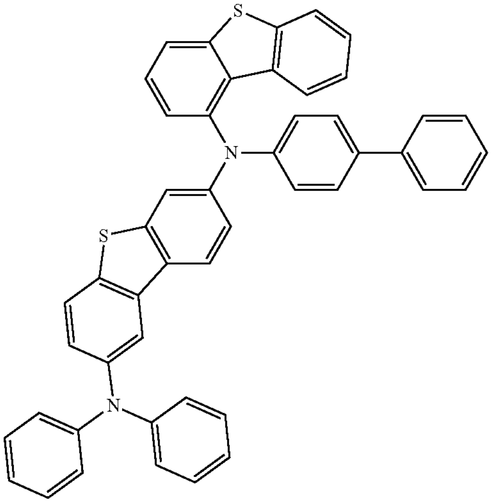
1-52
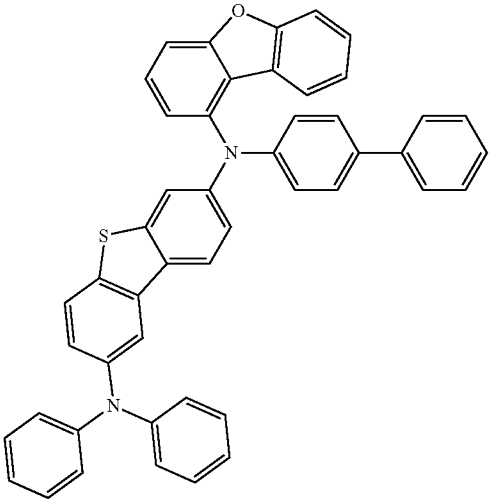
1-53
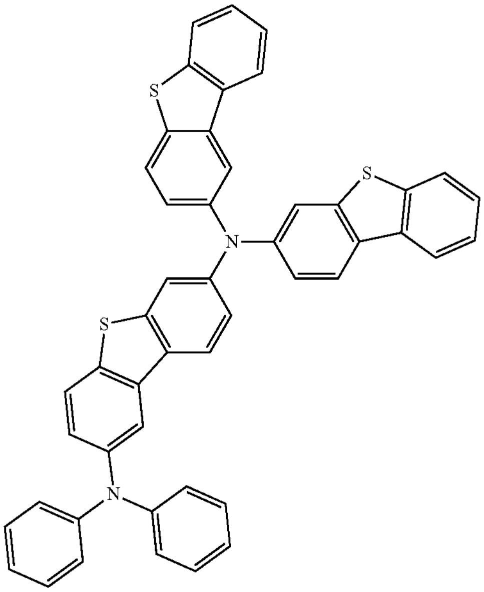
-continued
1-54
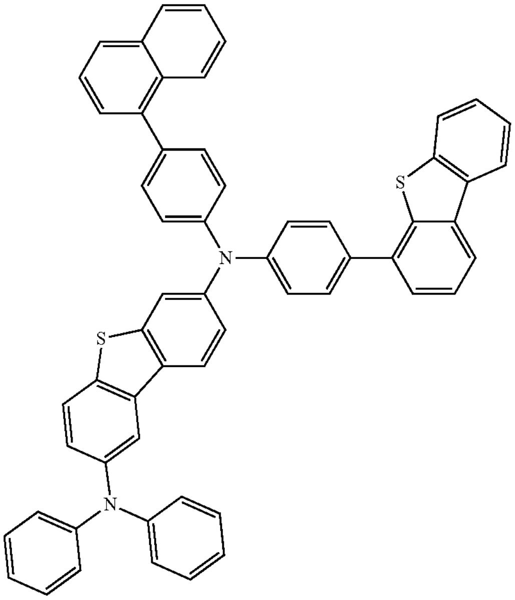
1-55
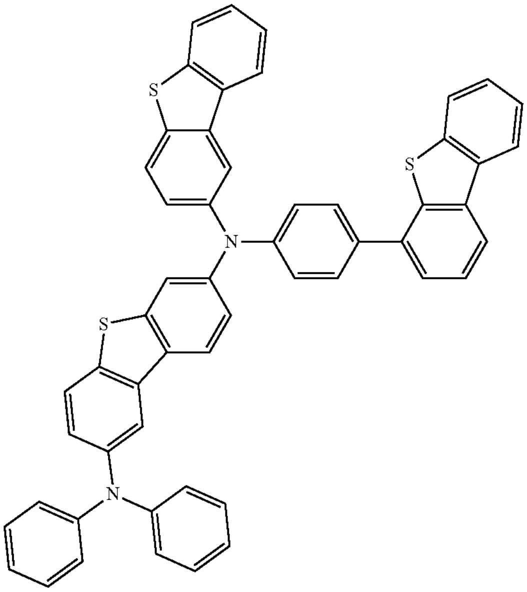

-continued
1-56
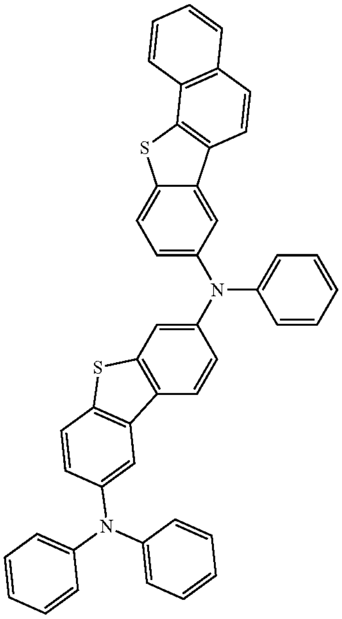
1-57
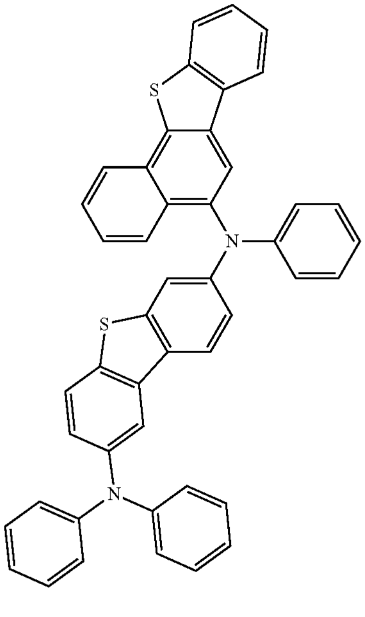
-continued
1-58
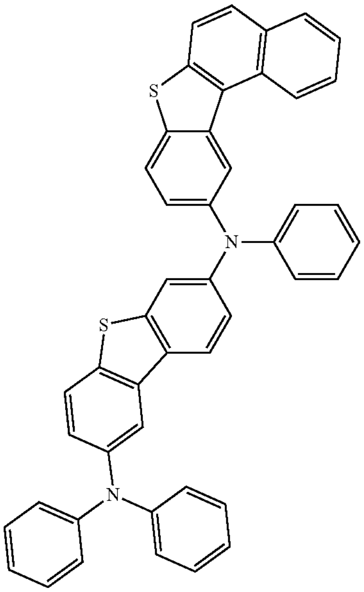
1-59
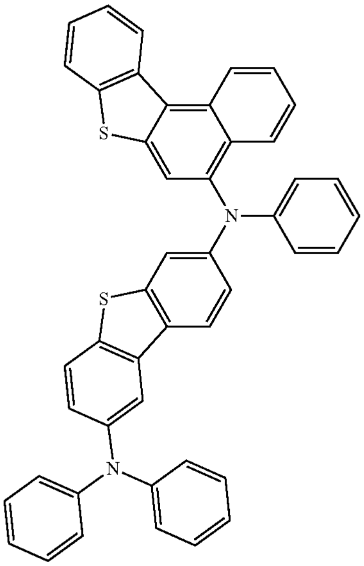
1-60
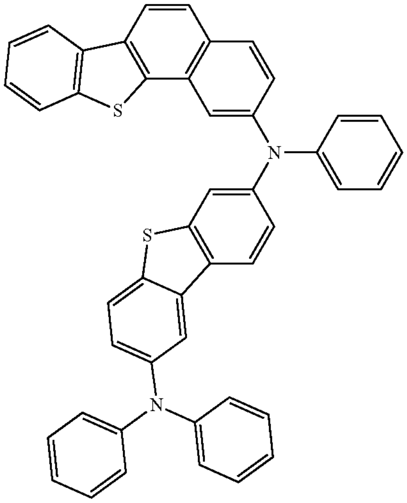

-continued
1-61
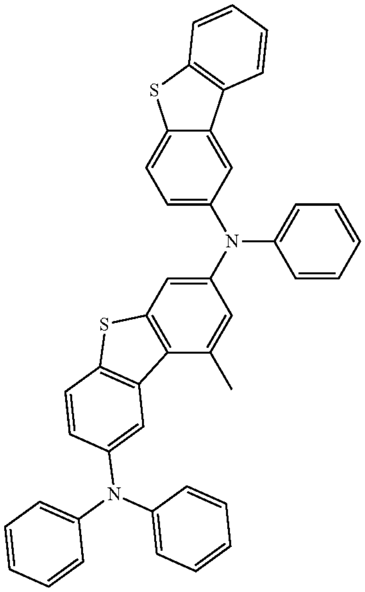
1-62
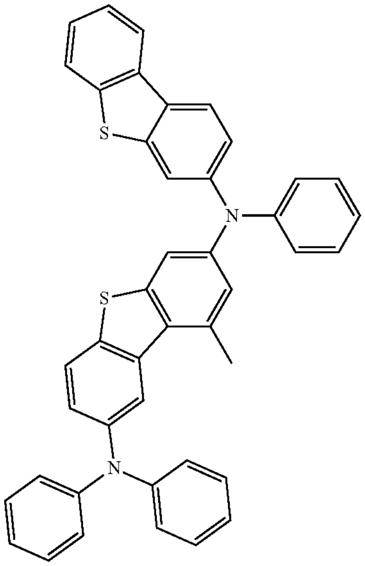
1-63
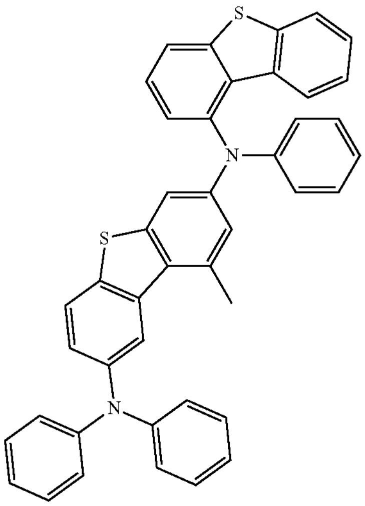
-continued
1-64
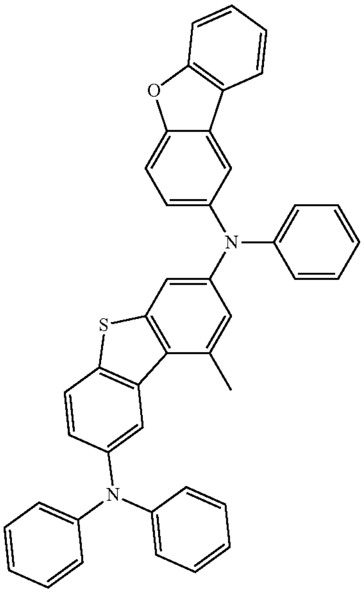
1-65
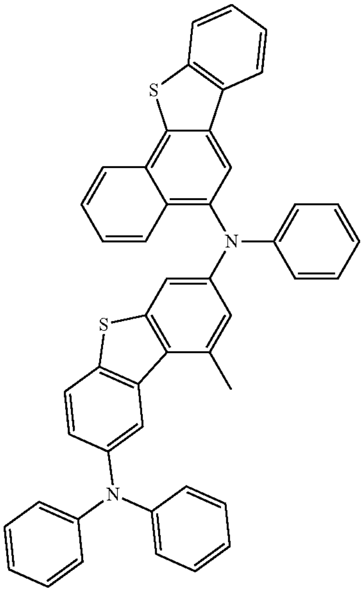

-continued
1-66
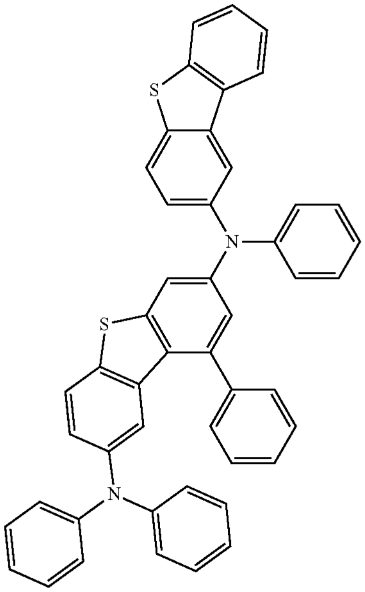
1-67
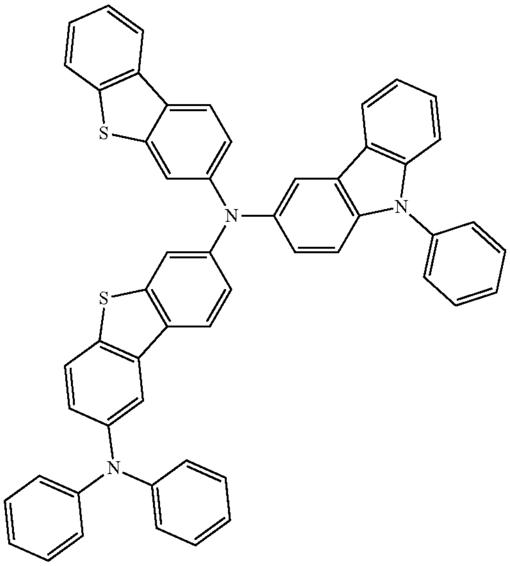
-continued
1-68
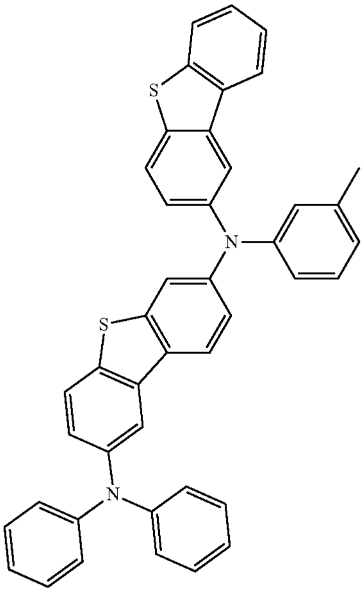
1-69
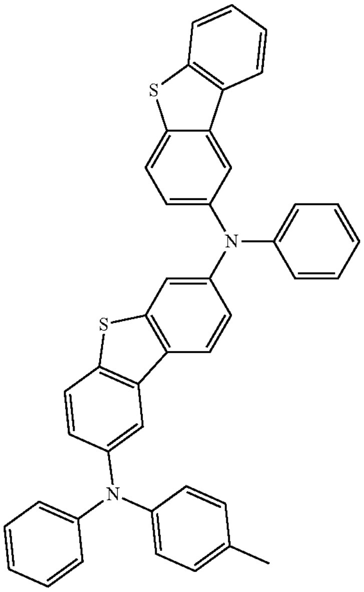

-continued
1-70
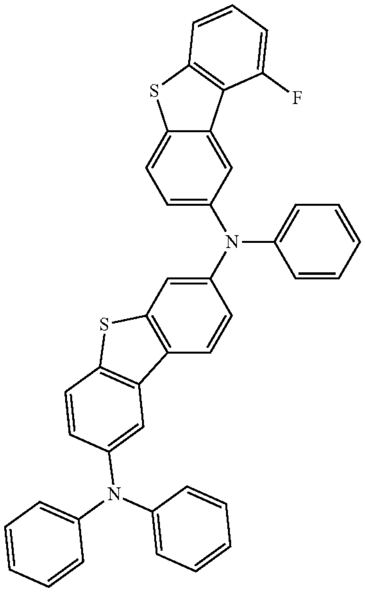
1-71
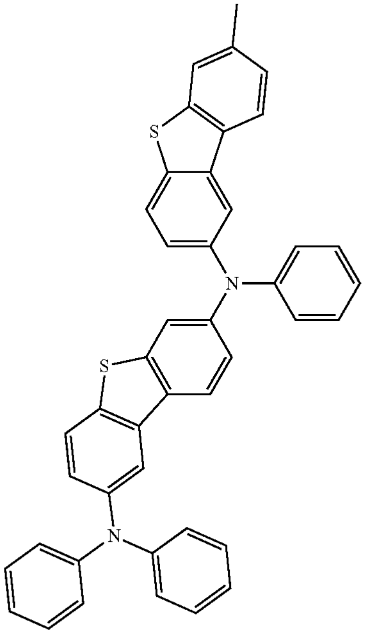
-continued
1-72
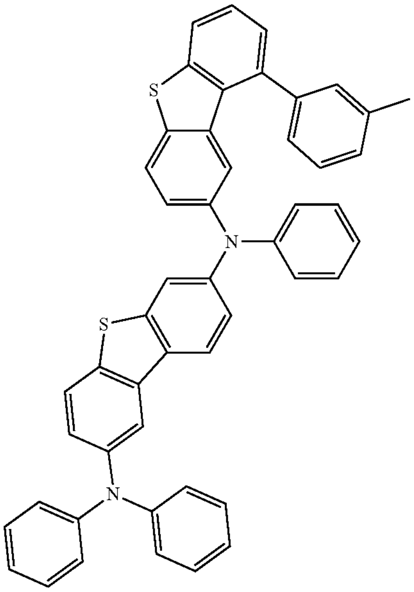
1-73
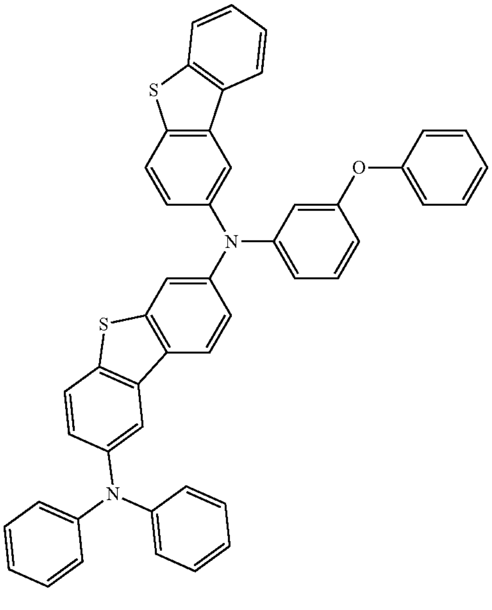

-continued
1-74
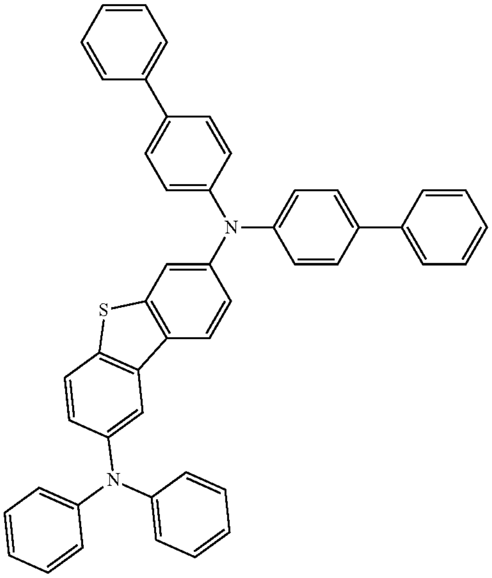
1-75
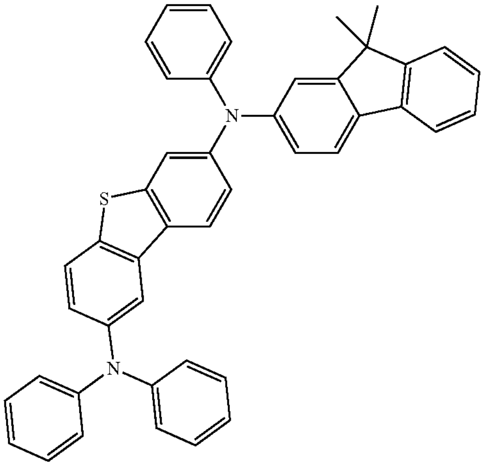
1-76
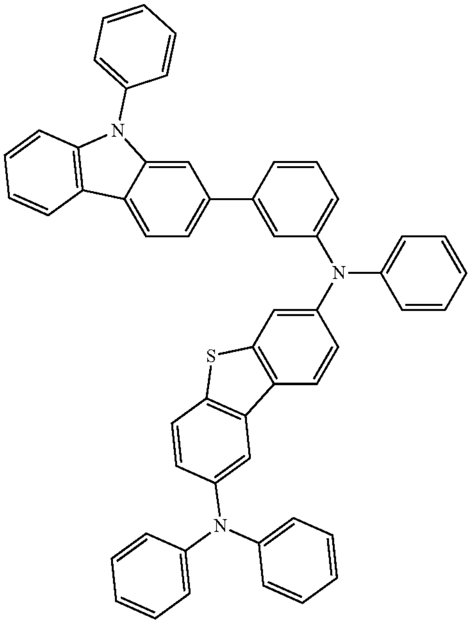
-continued
1-77
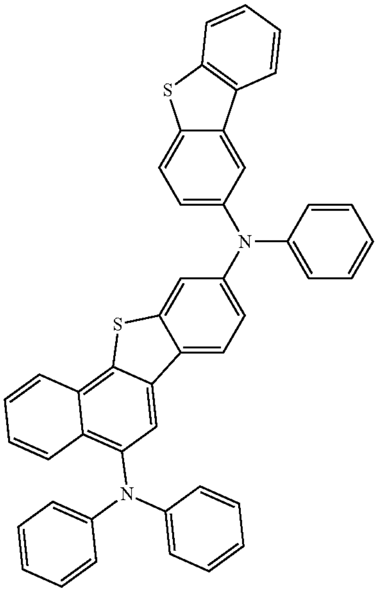
1-78
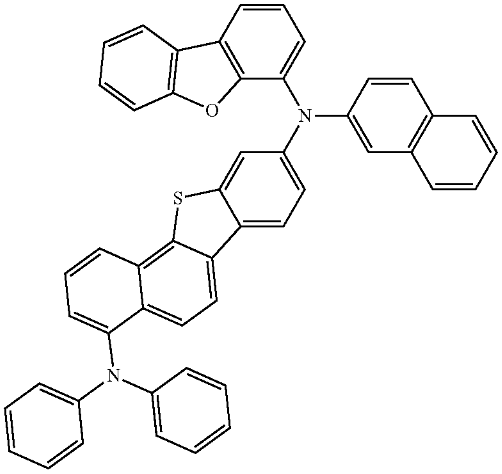
1-79
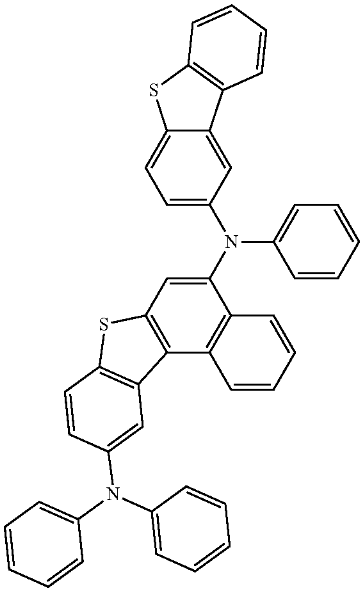

-continued
1-80
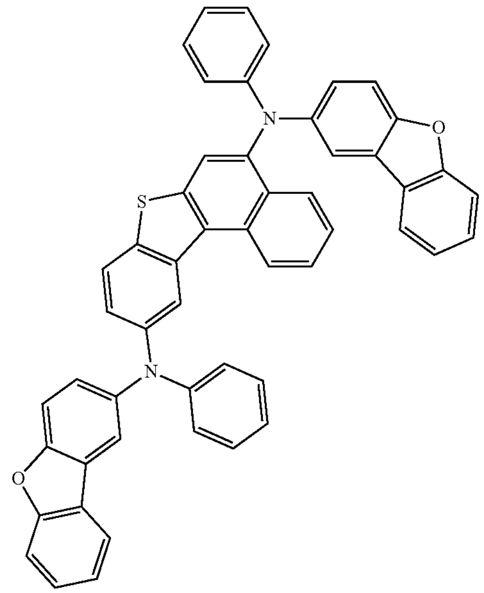
1-81
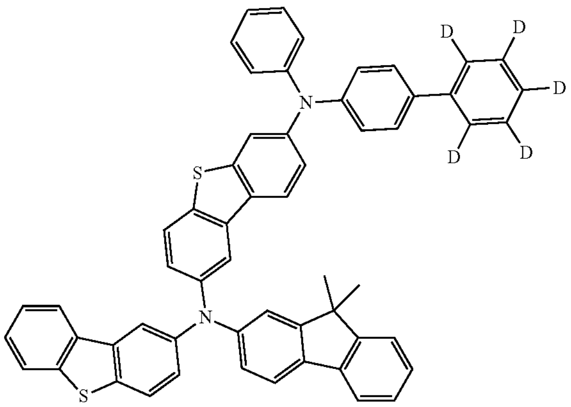
1-82
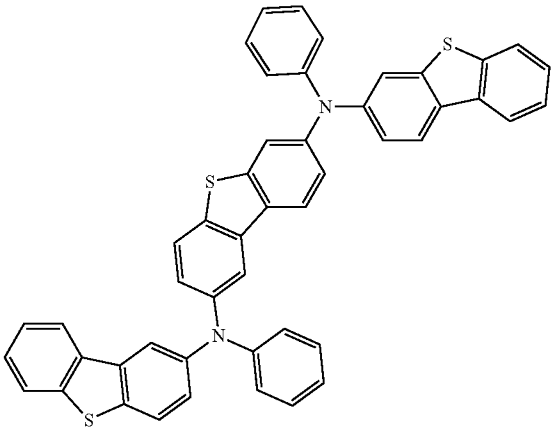
-continued
1-83
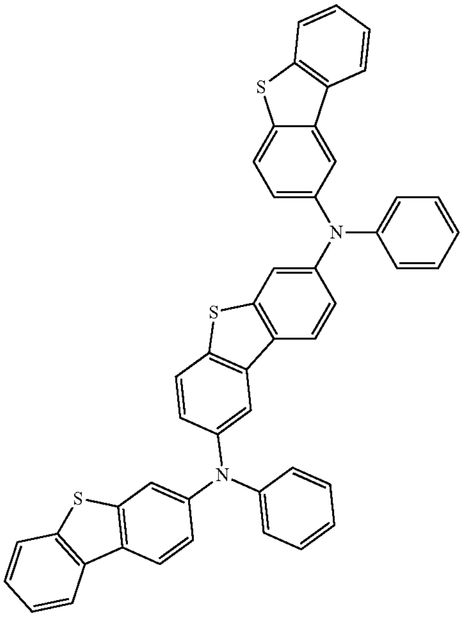
1-84
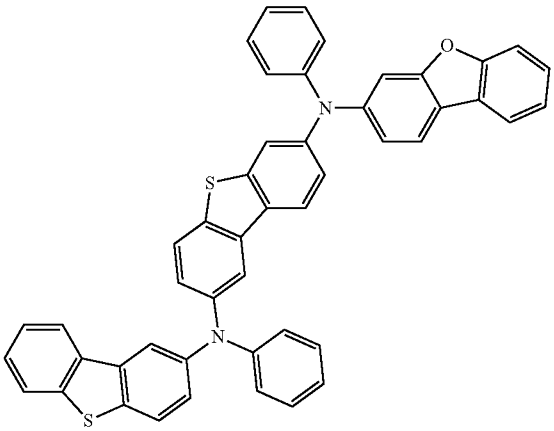

-continued
1-85
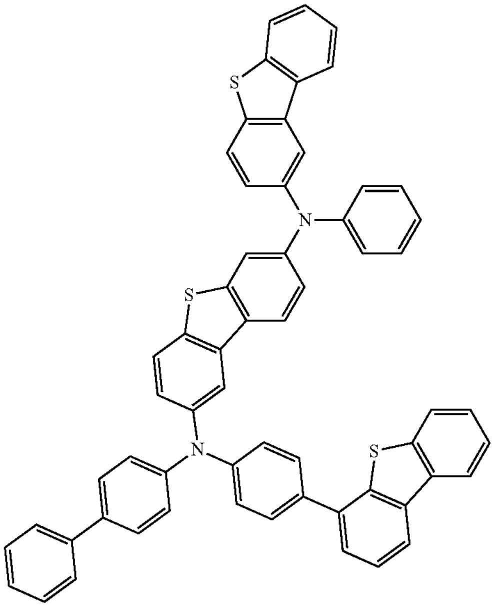
1-86
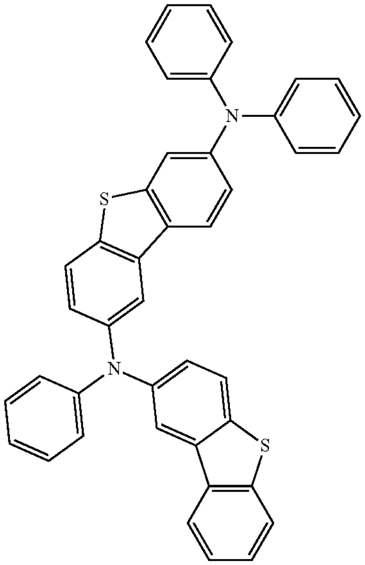
-continued
1-87
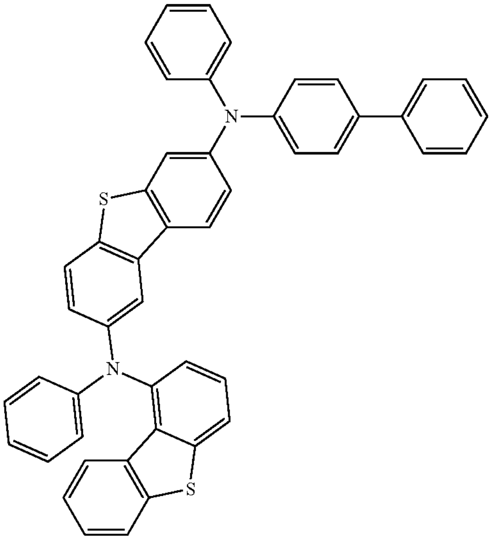
1-88
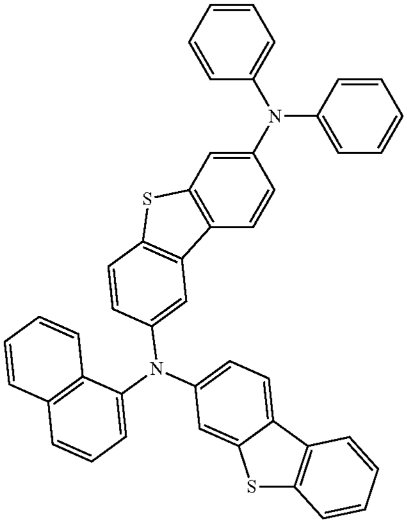
1-89
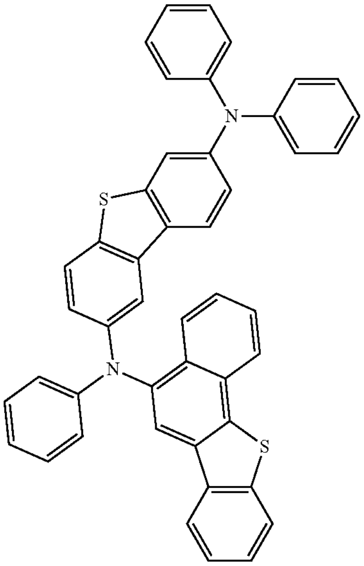

-continued
1-90
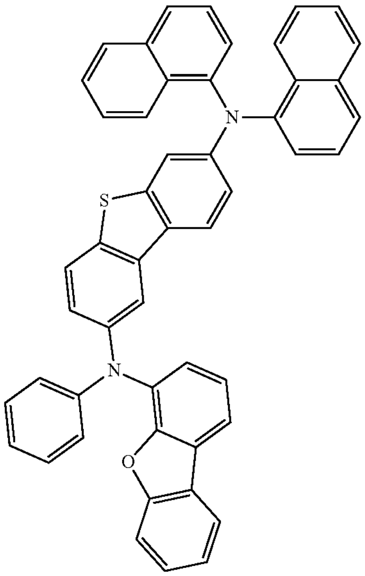
-continued
1-92
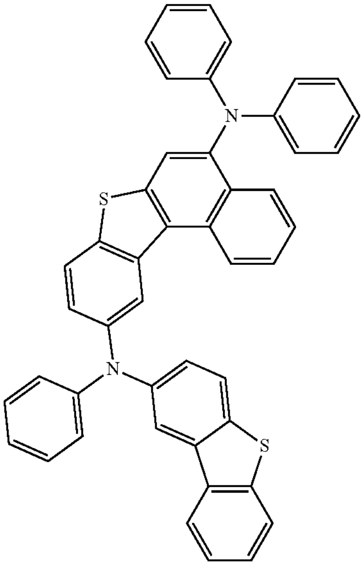
1-91
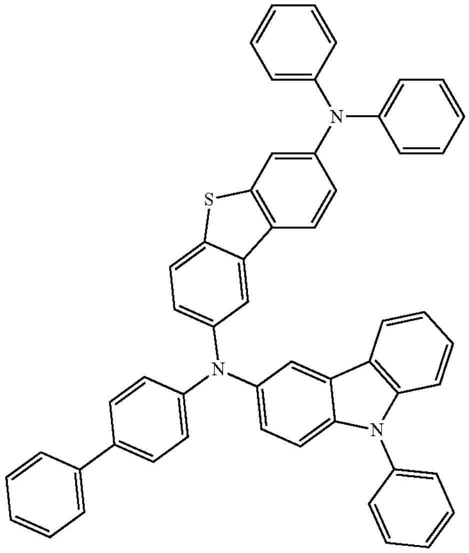
1-93
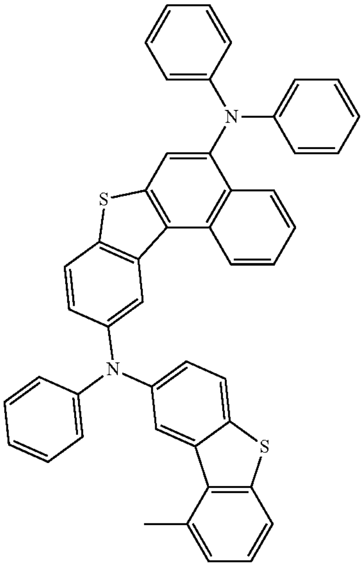

-continued
1-94
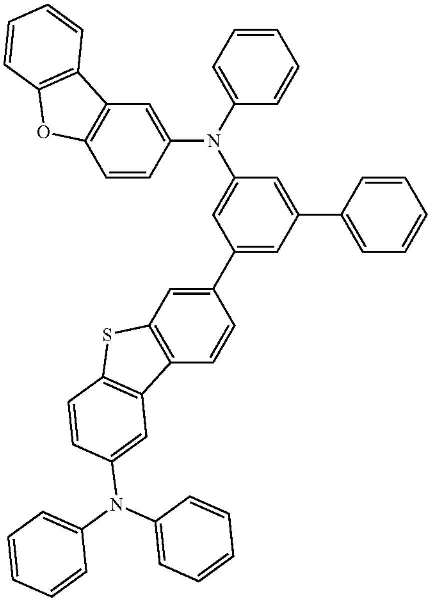
1-95
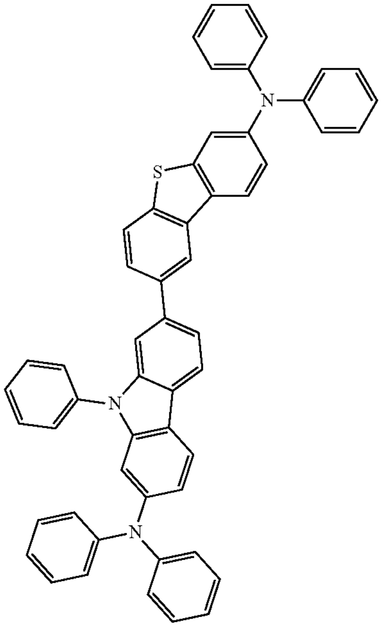
-continued
1-96
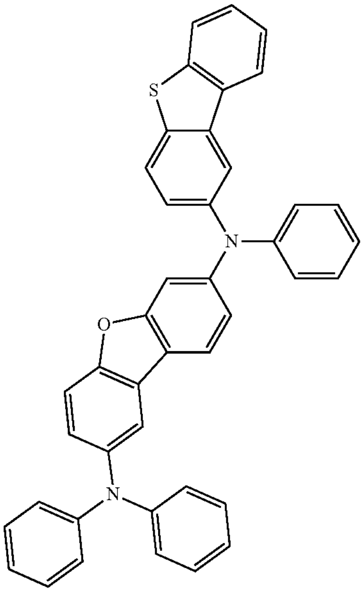
1-97
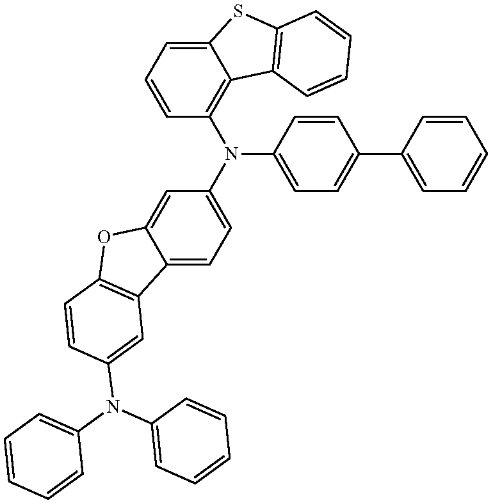

-continued
1-98
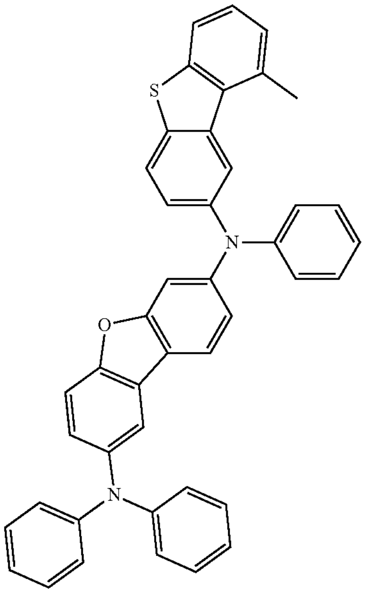
1-99
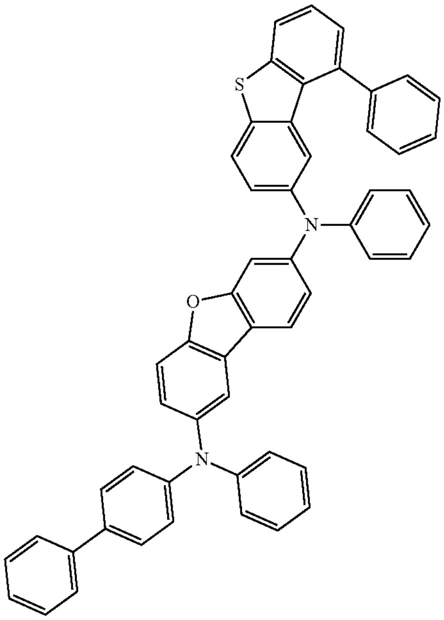
-continued
1-100
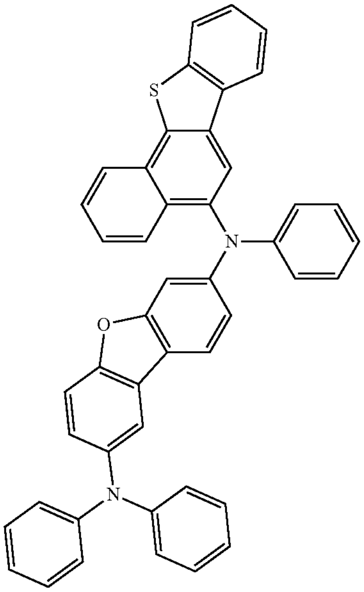
1-101
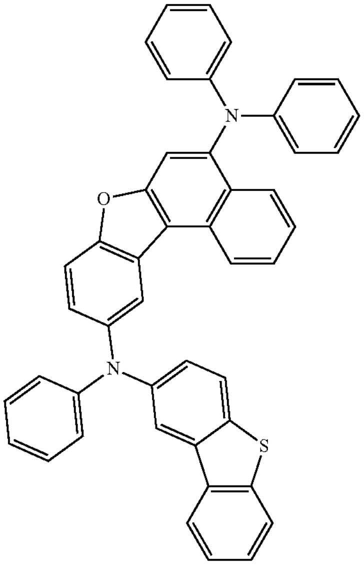

-continued
1-102
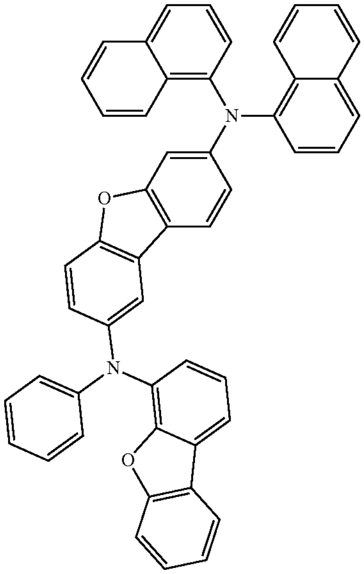
1-103
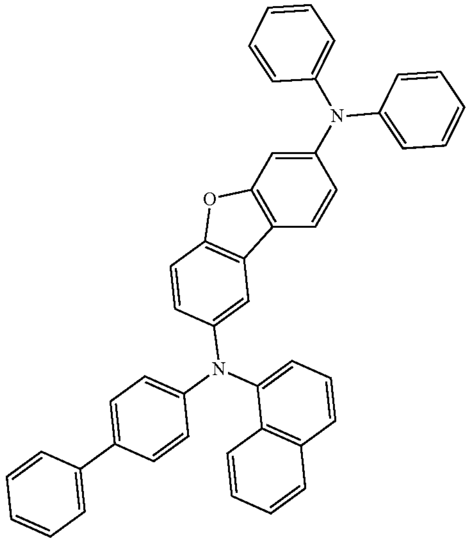
-continued
1-104
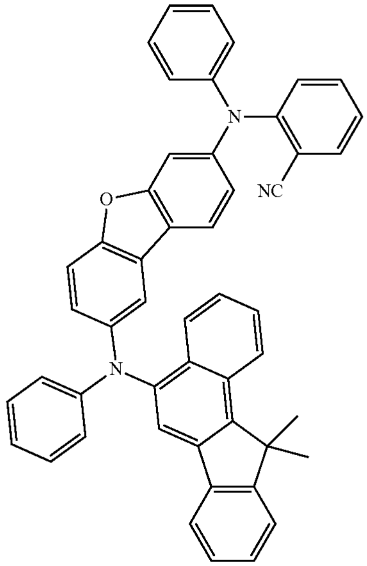
1-105
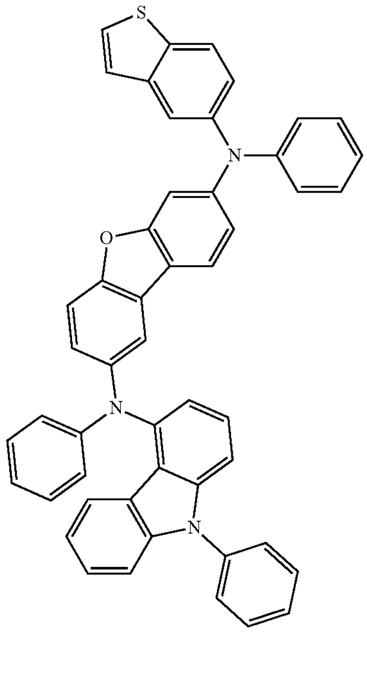

-continued
1-106
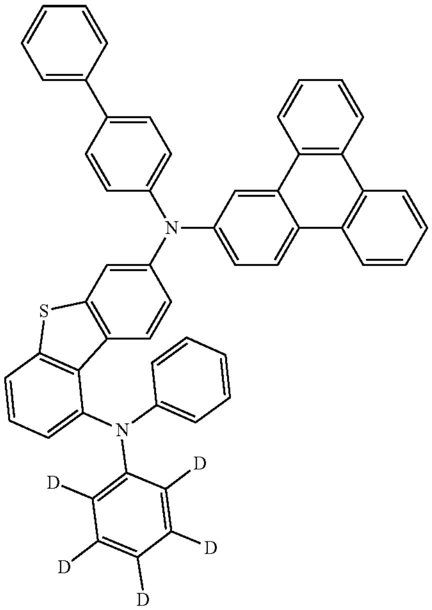
1-107
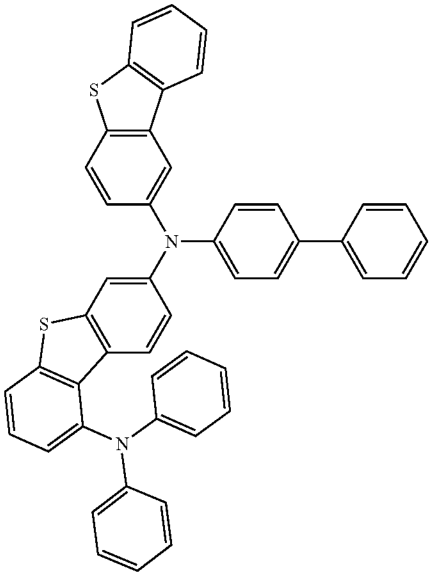
-continued
1-108
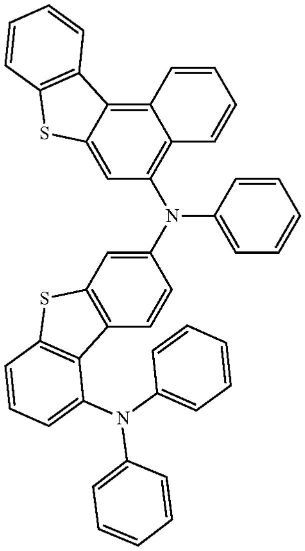
1-109
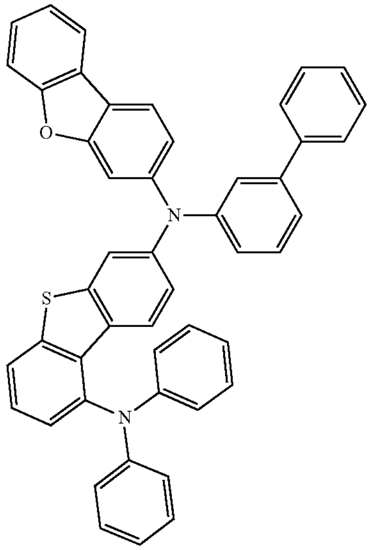
1-110
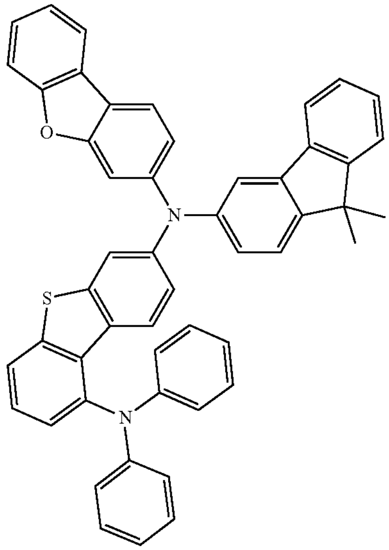

-continued
1-111
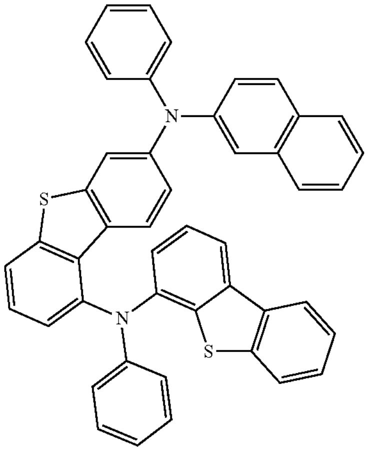
1-112
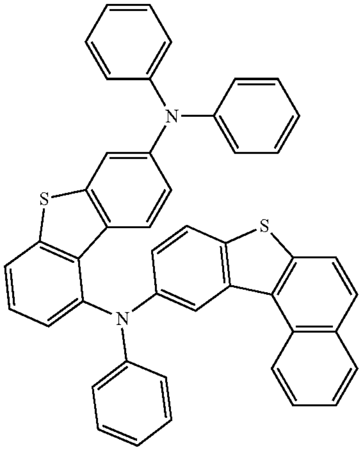
1-113
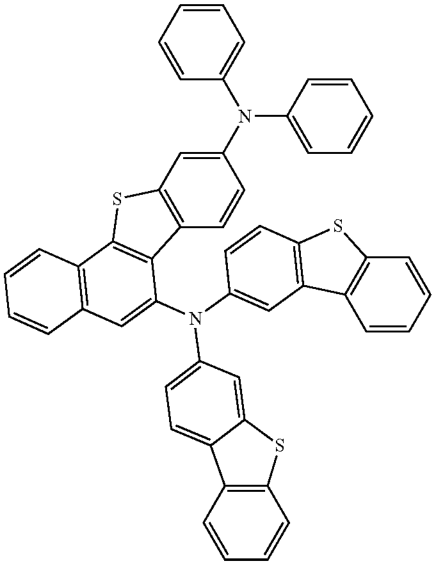
-continued
1-114
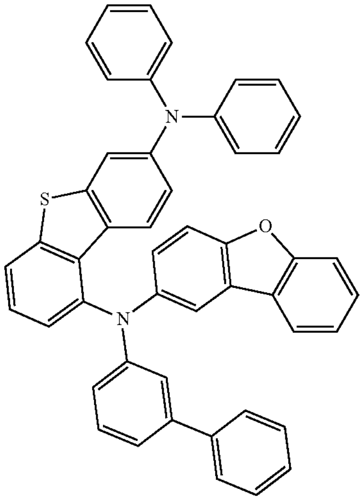
1-115
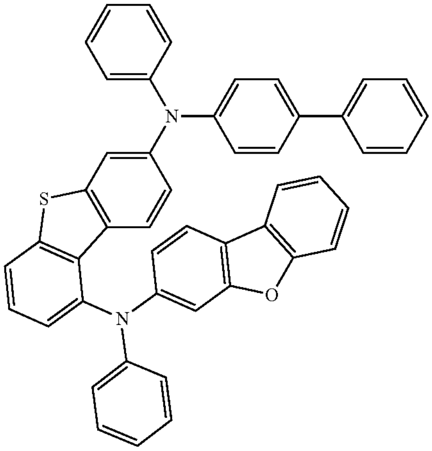
1-116
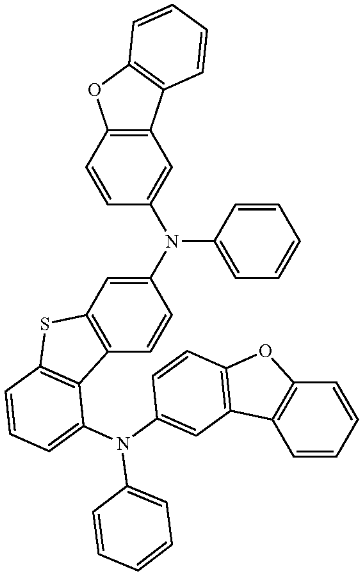

-continued
1-117
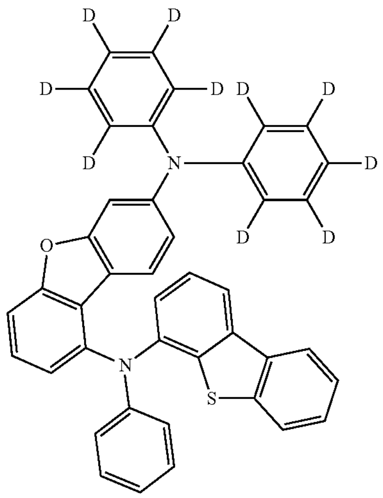
1-118
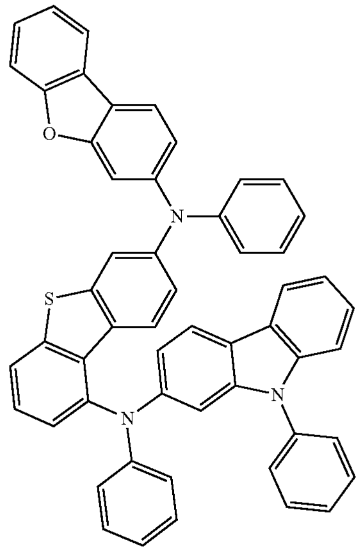
1-119
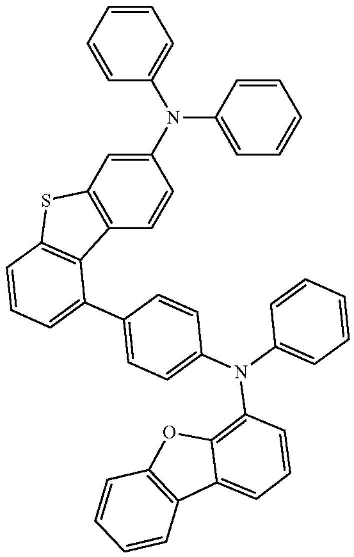
-continued
1-120
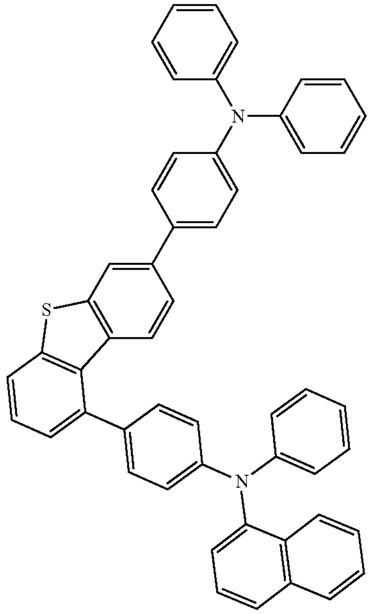
1-121
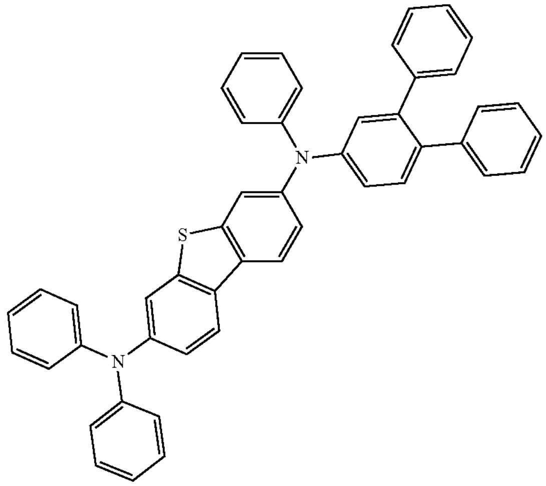

-continued
1-122
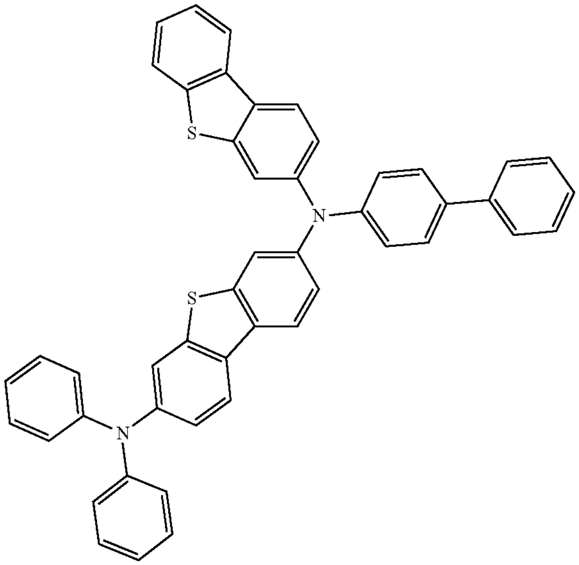
1-123
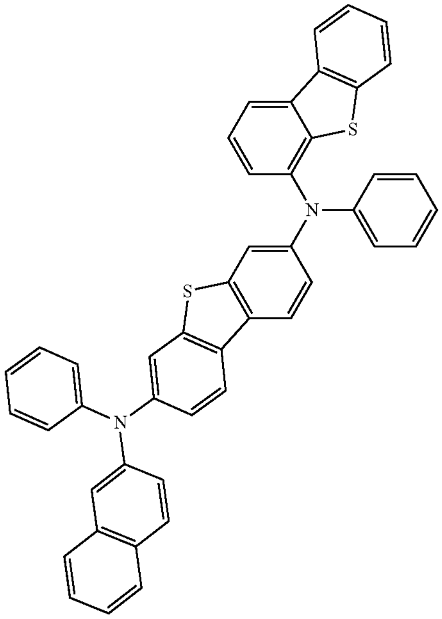
-continued
1-124
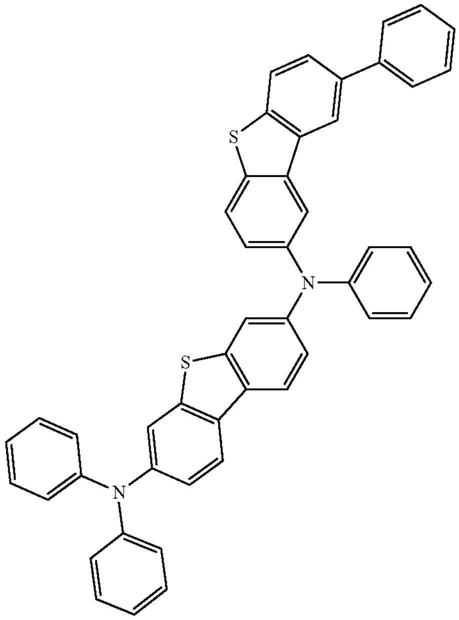
1-125
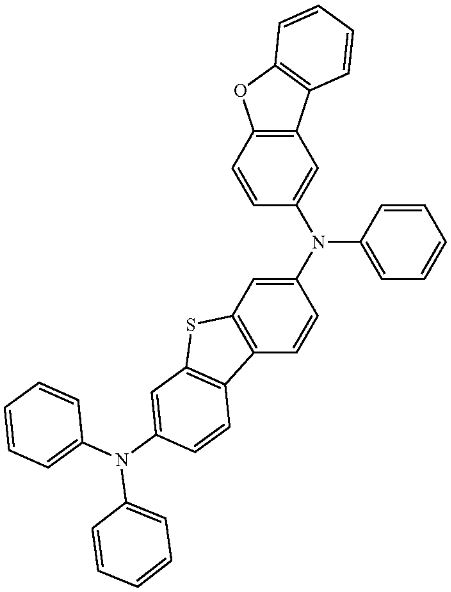

-continued
1-126
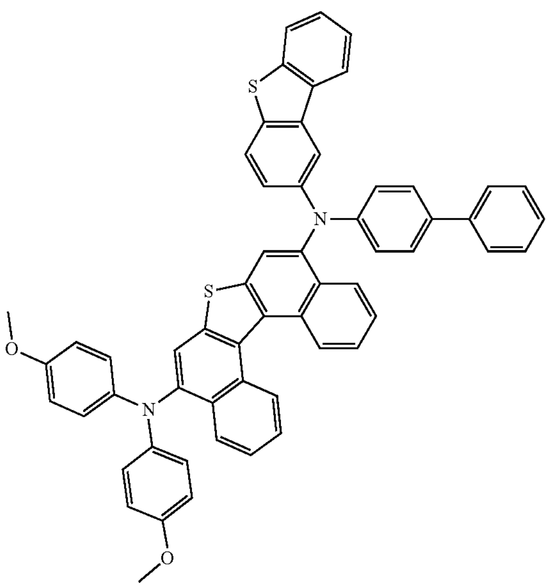
1-127
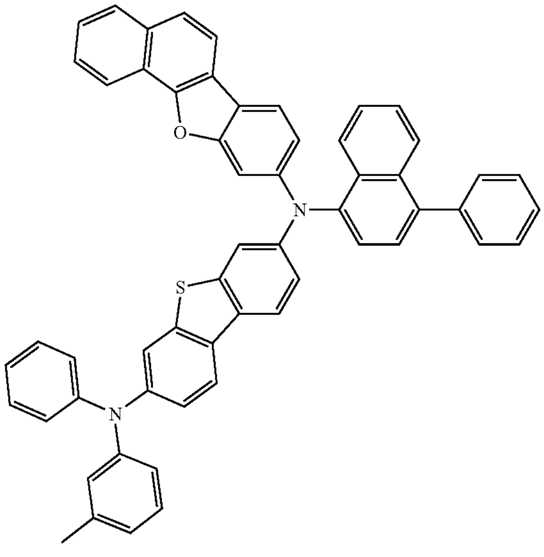
-continued
1-128
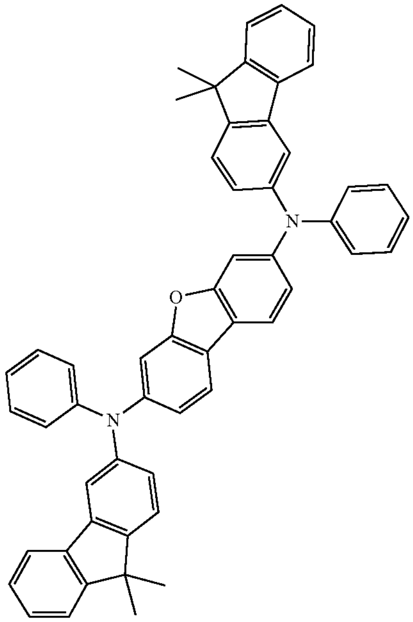
1-129
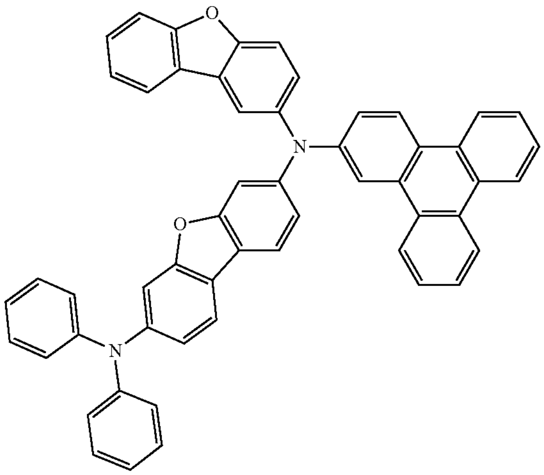

-continued
1-130
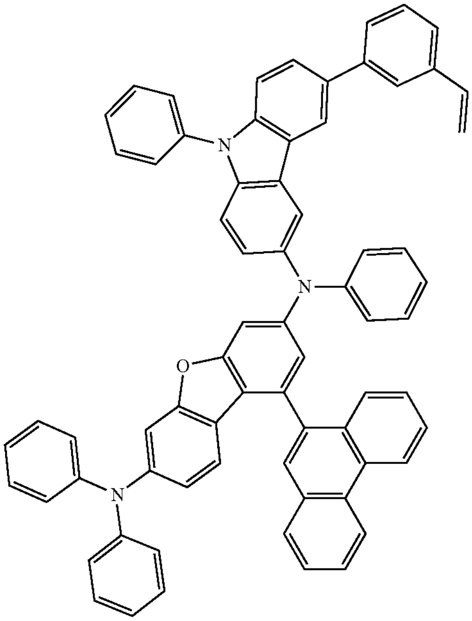
1-131
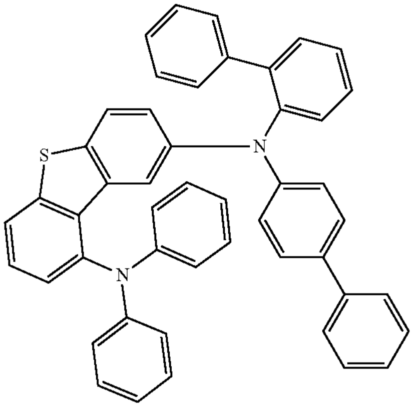
1-132
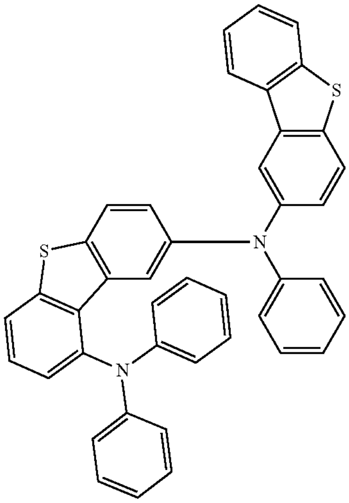
-continued
1-133
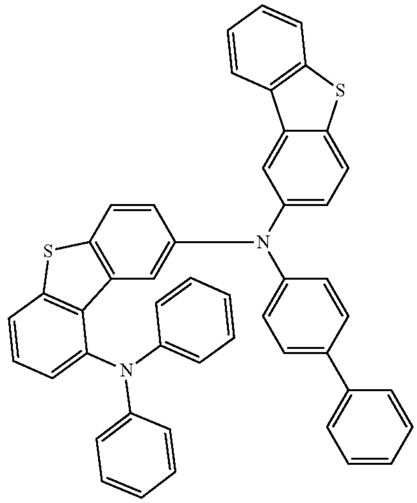
1-134
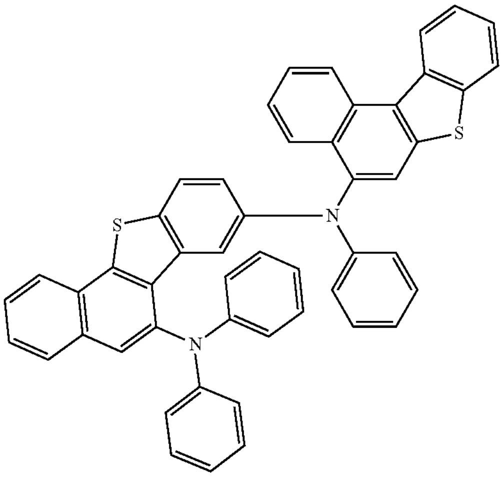
1-135
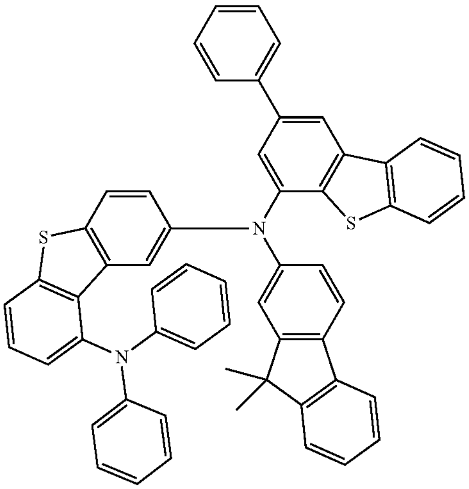

-continued
1-136
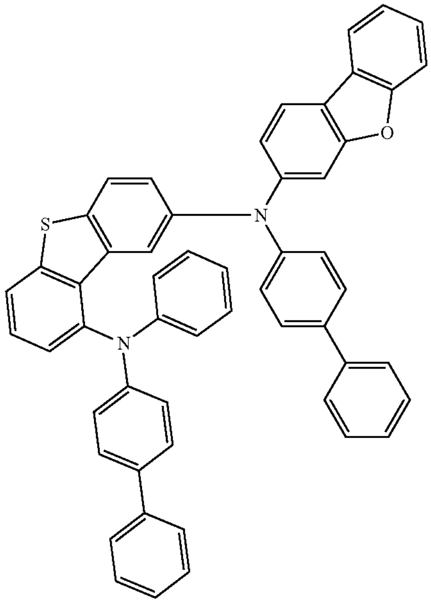
1-137
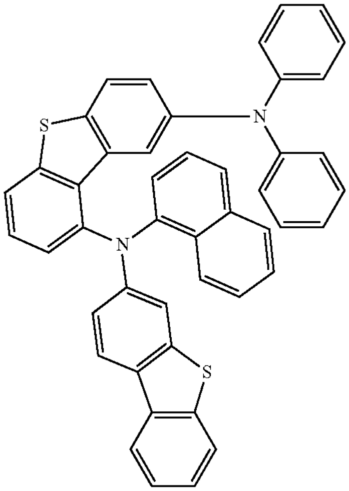
1-138
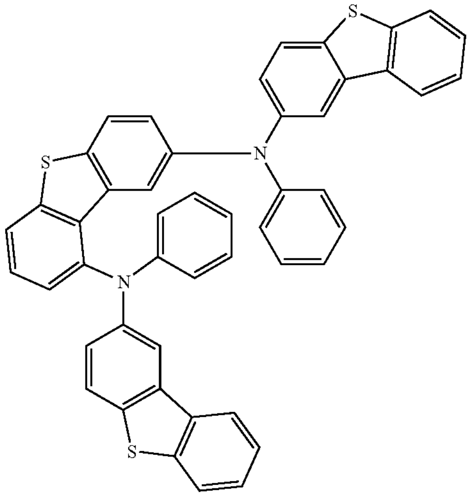
-continued
1-139
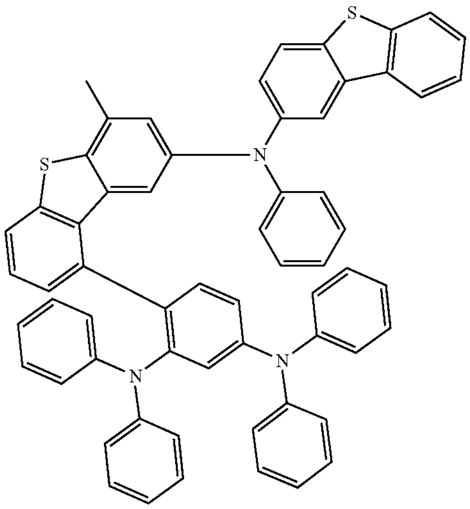
1-140
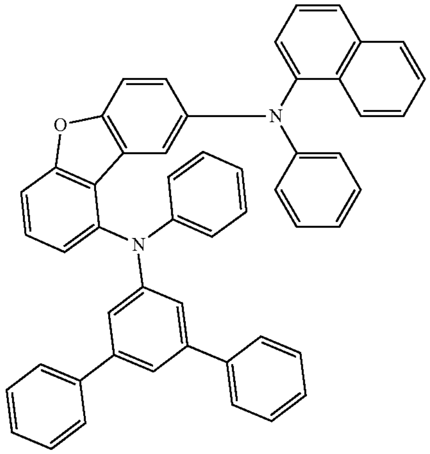
1-141
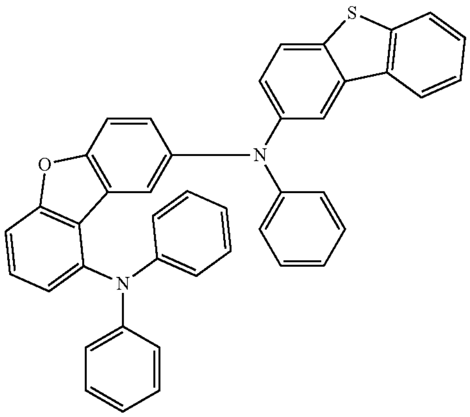

-continued
1-142
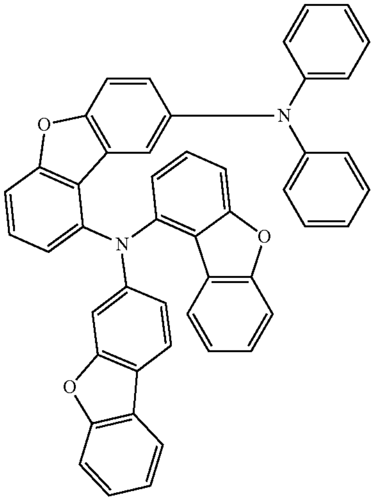
1-143
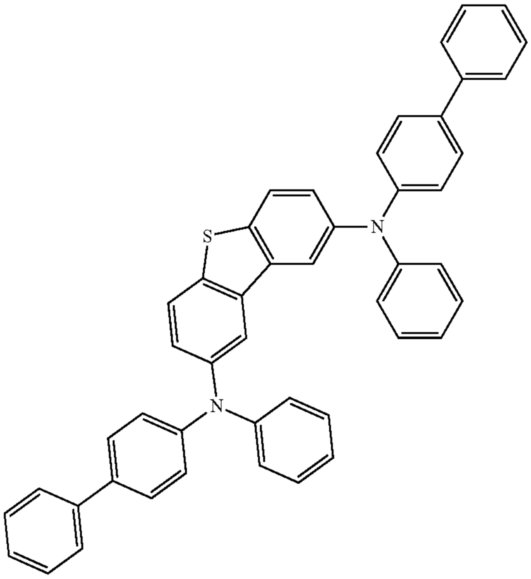
1-144
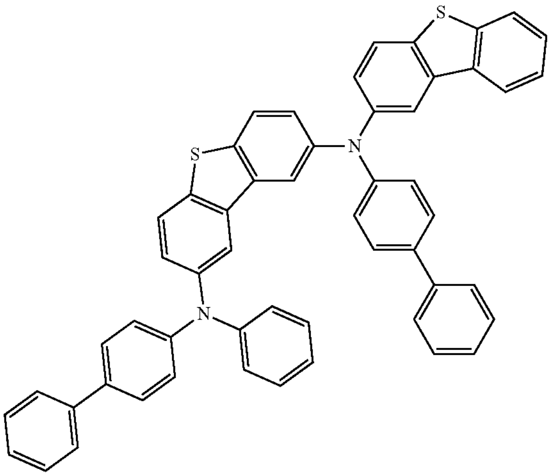
-continued
1-145
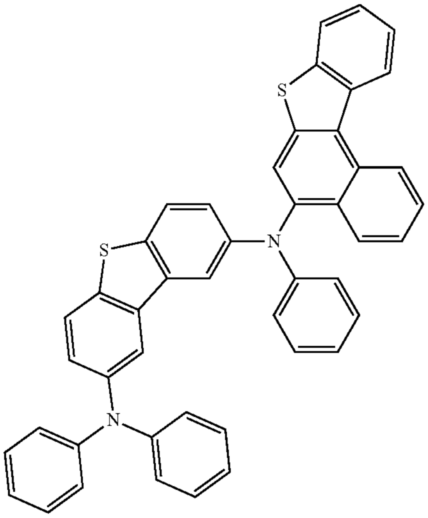
1-146
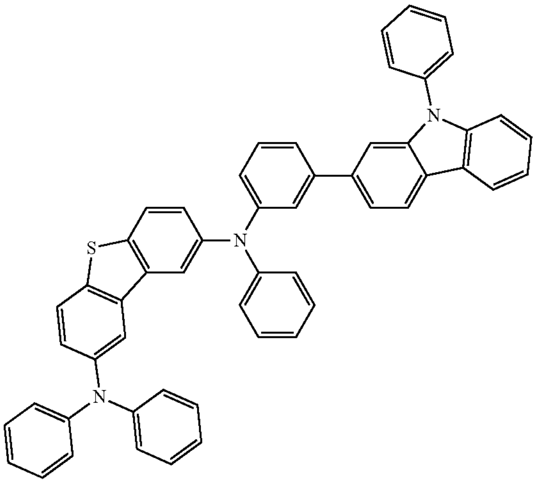
1-147
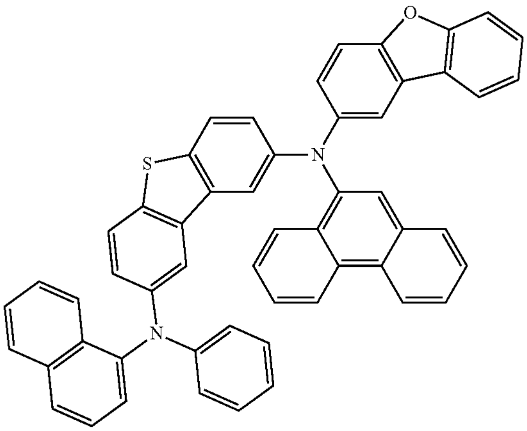

-continued
1-148
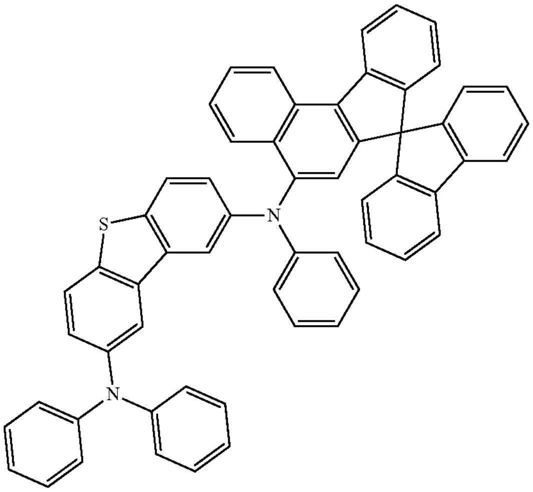
1-149
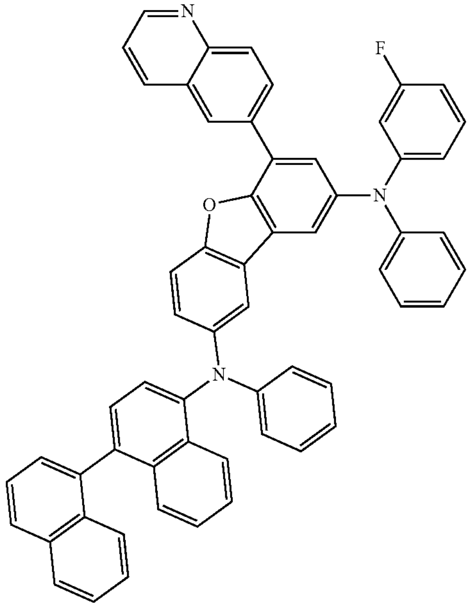
1-150
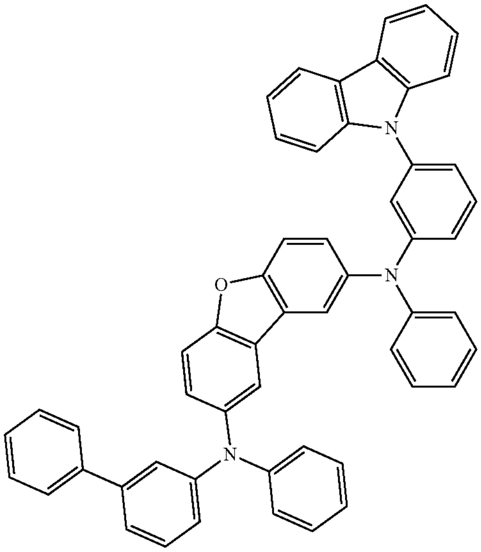
-continued
1-151
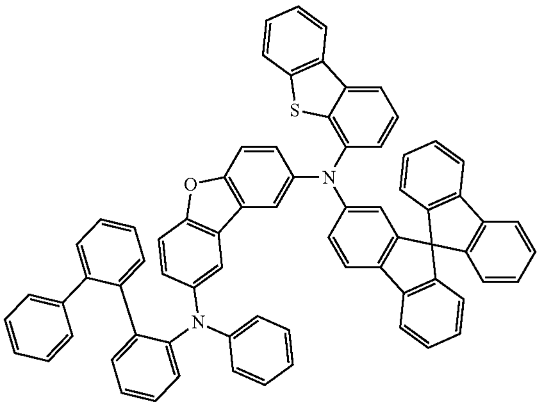
1-152
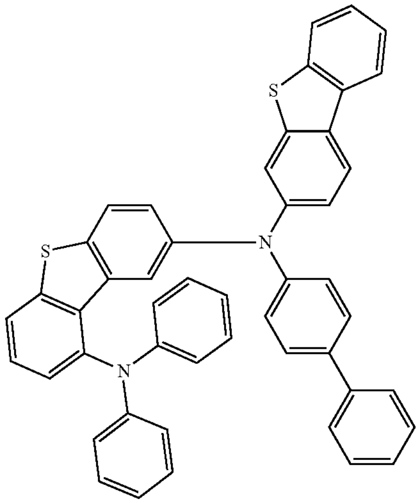
1-153
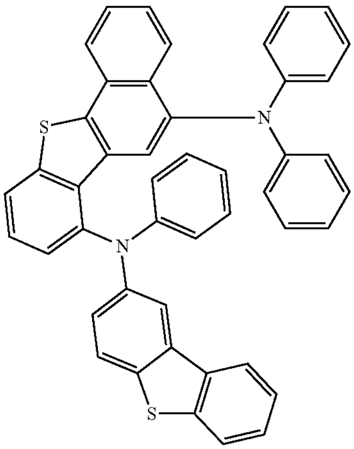

-continued
1-154
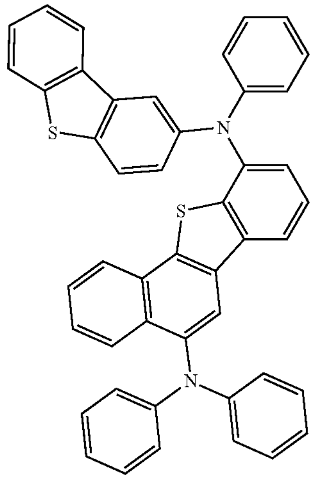
1-155
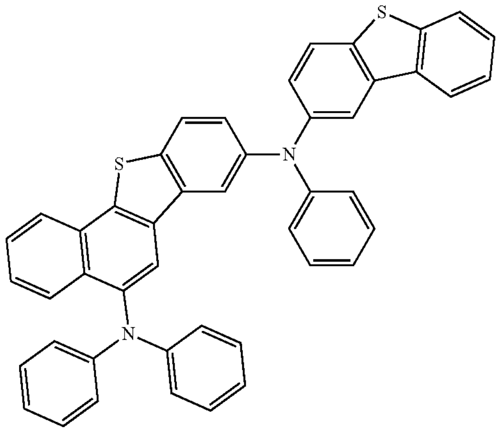
1-156
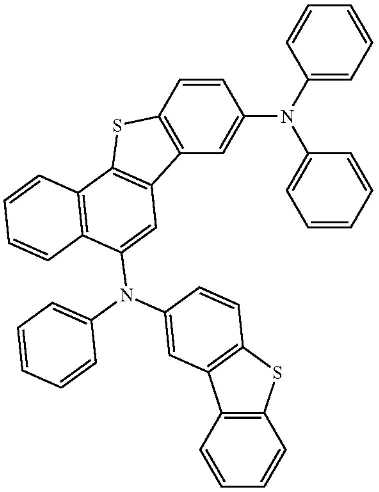
-continued
1-157
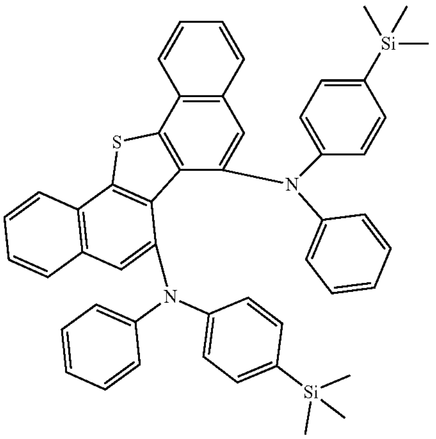
1-158
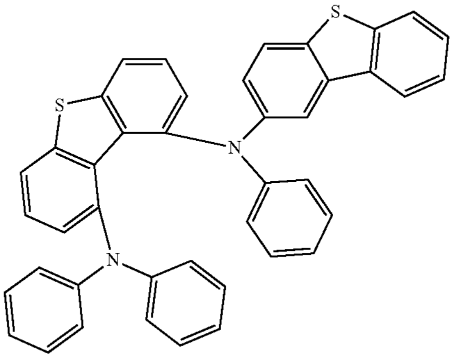
1-159
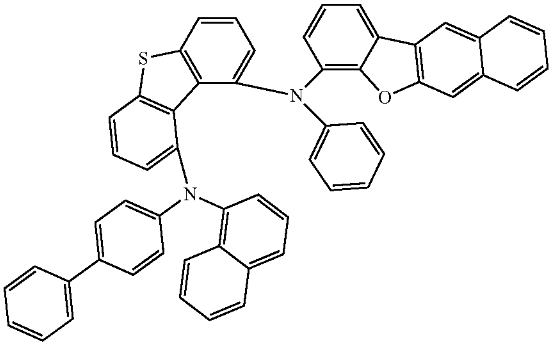
1-160
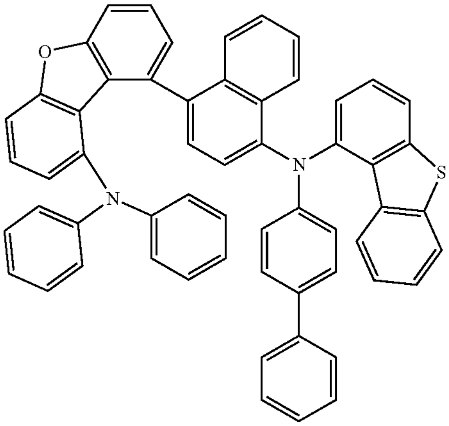

-continued
1-161
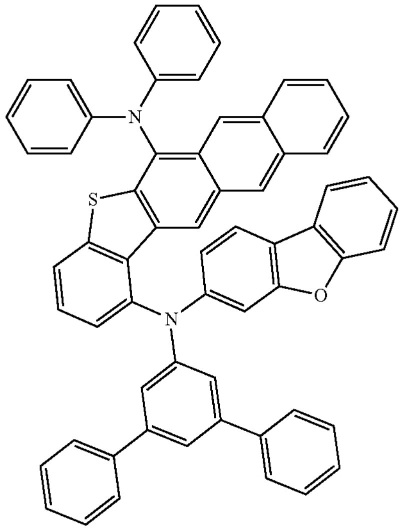
1-162
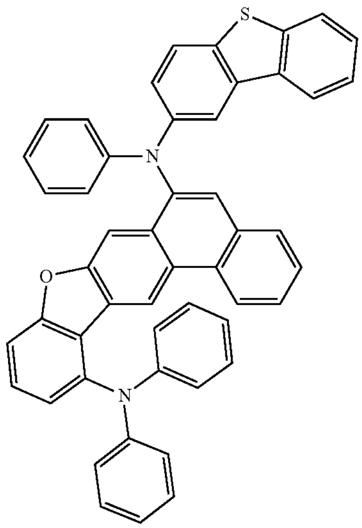
1-163
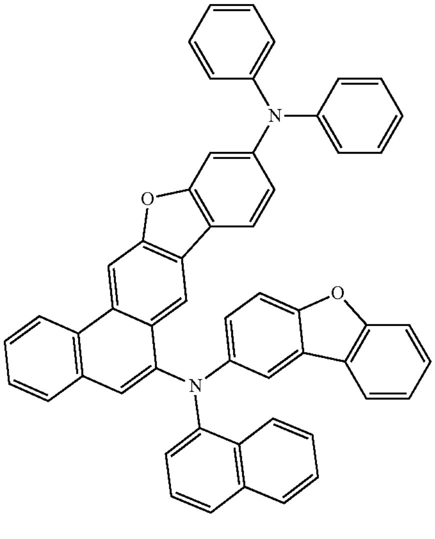
-continued
1-164
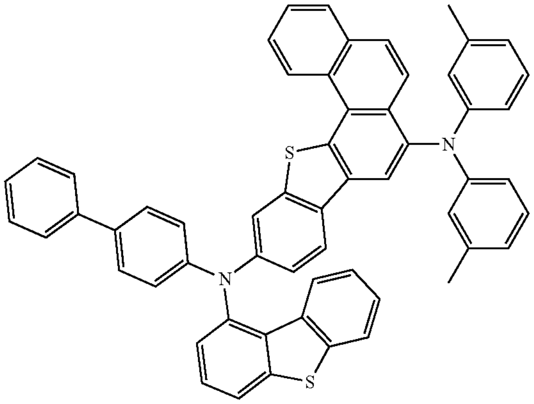
1-165
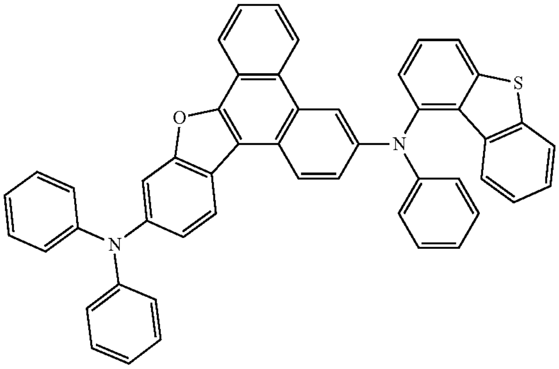
1-166
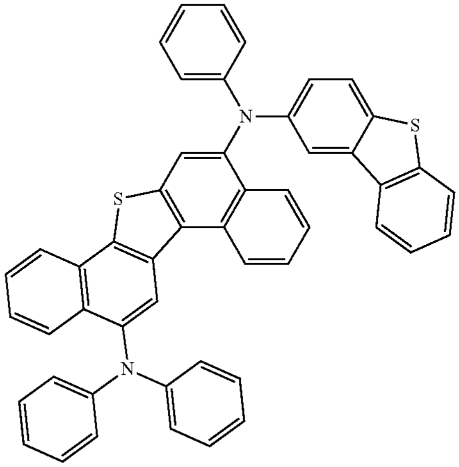
1-167
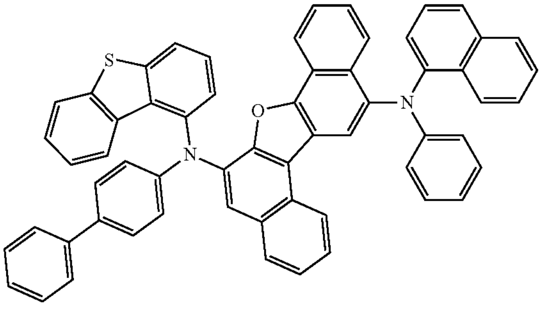

-continued
1-168
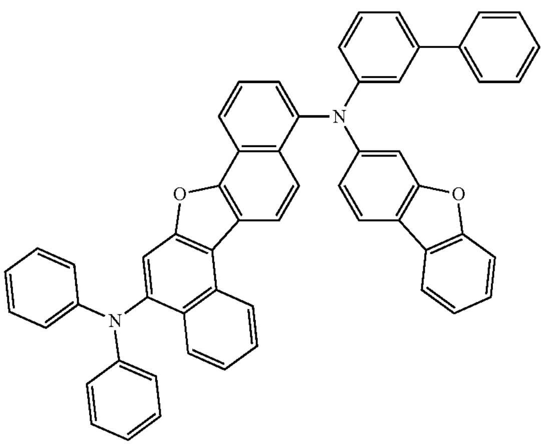
1-169
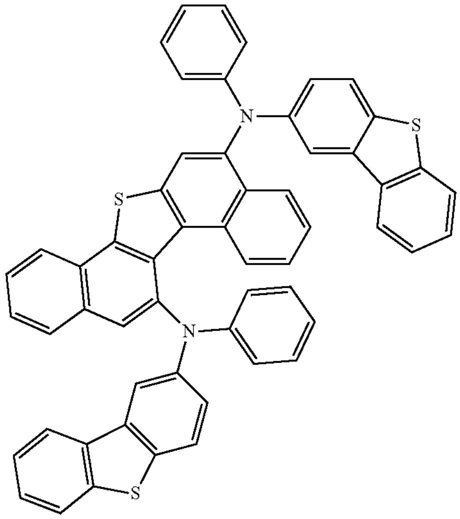
1-170
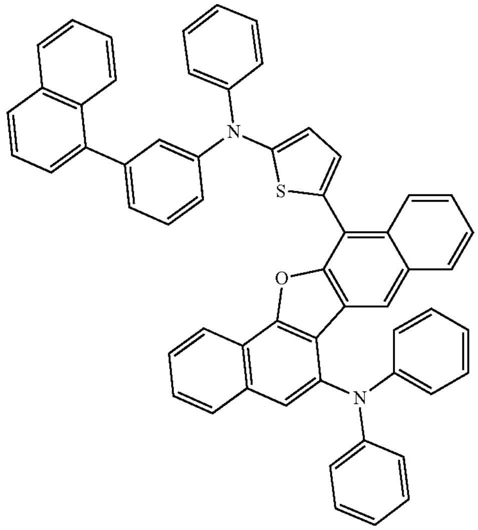
-continued
1-171
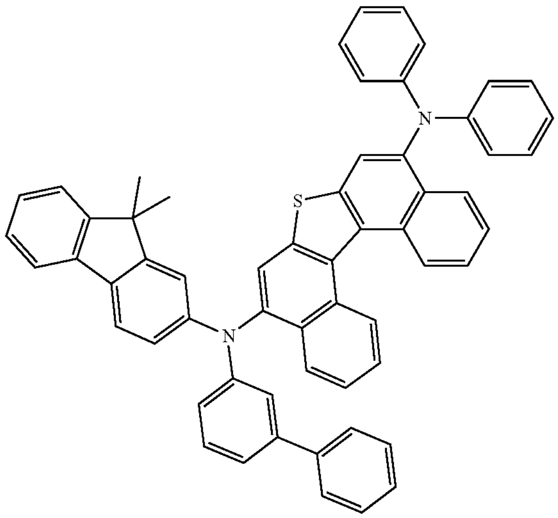
1-172
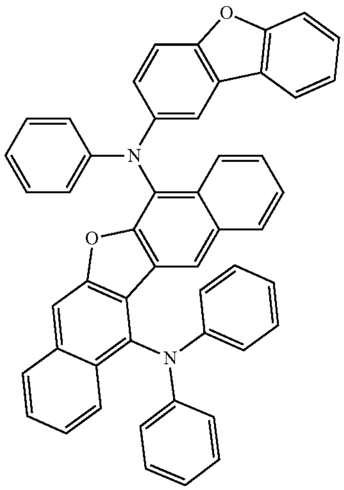
1-173
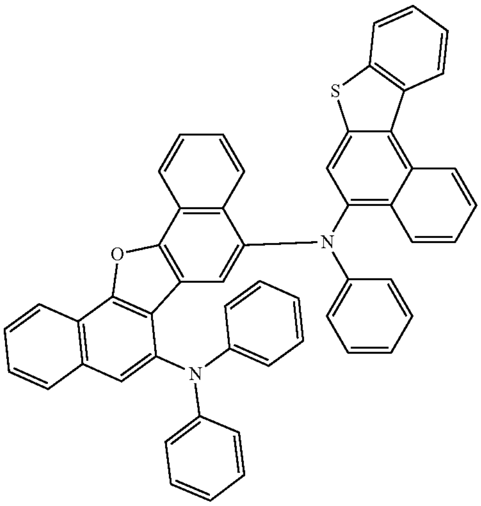

-continued
1-174
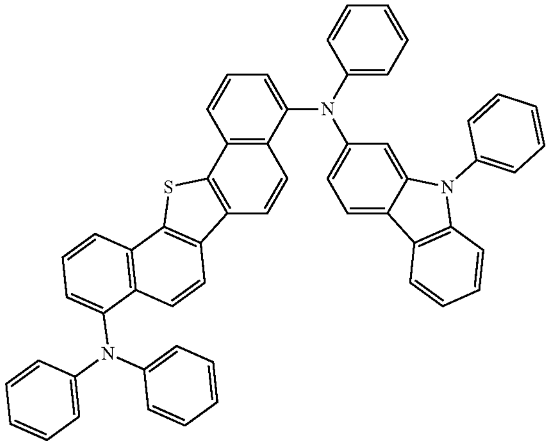
1-175
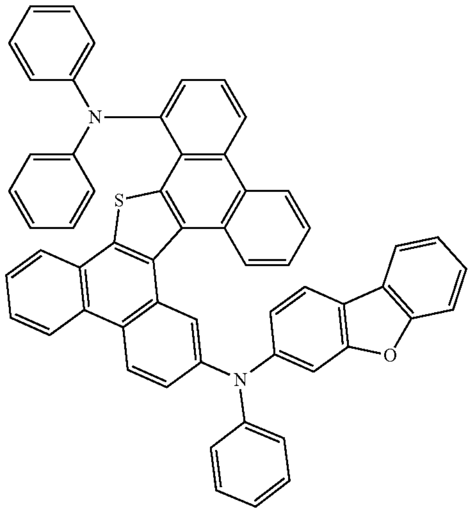
.
11. The organic electronic element of claim 1, wherein the second host compound represented by Chemical Formula 2 is any one of the following compounds:
1'-1
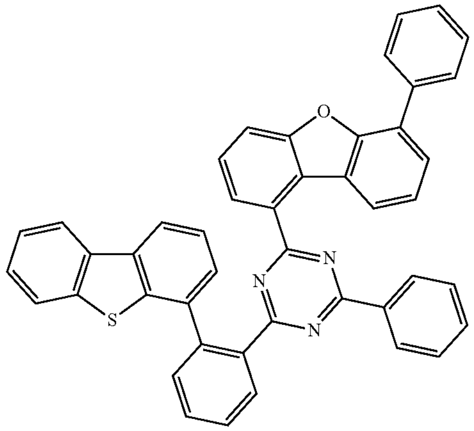
-continued
1'-2
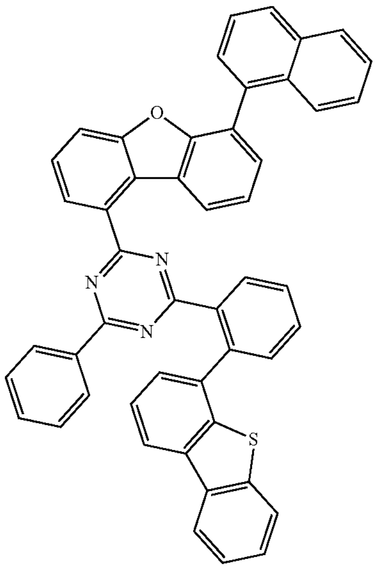
1'-3
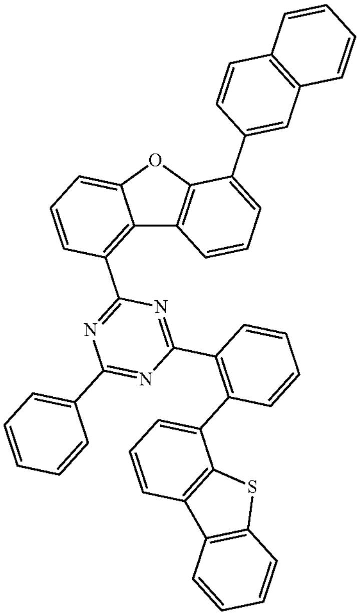

1'-4
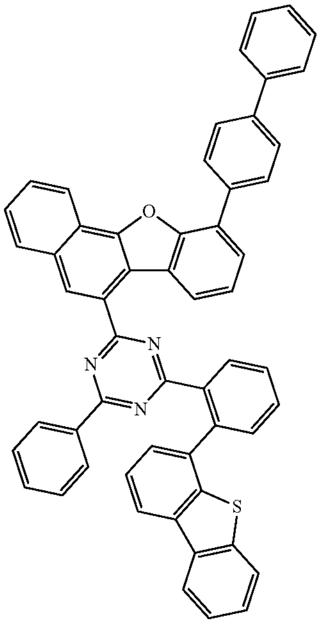
1'-5
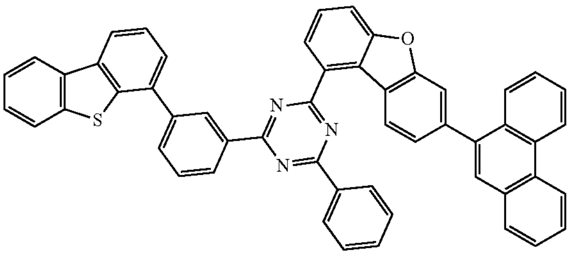
1'-6
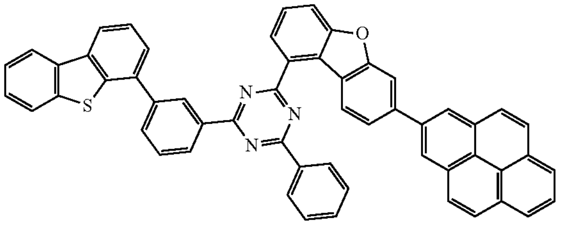
1'-7
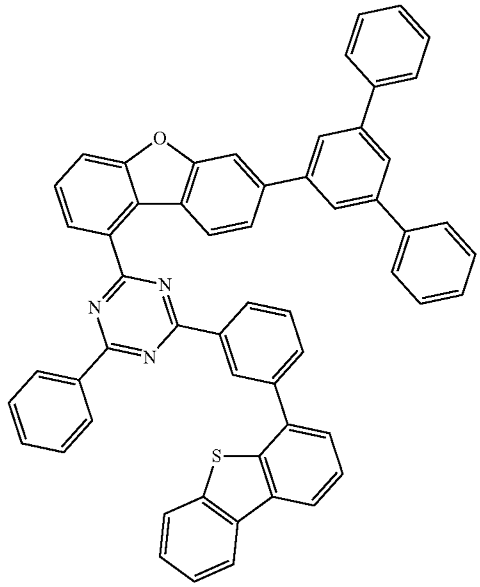
1'-8
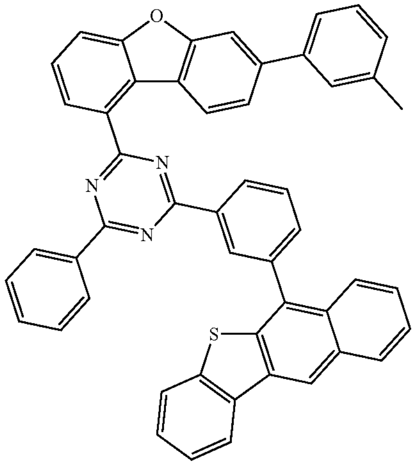
1'-9
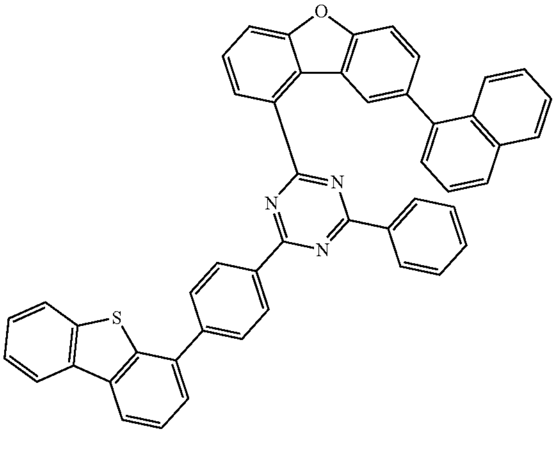

-continued
1'-10
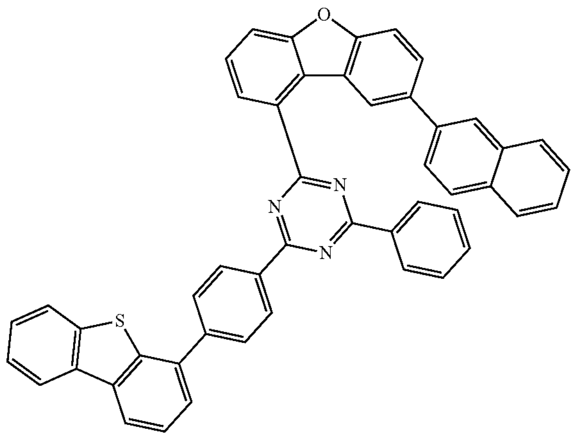
1'-11
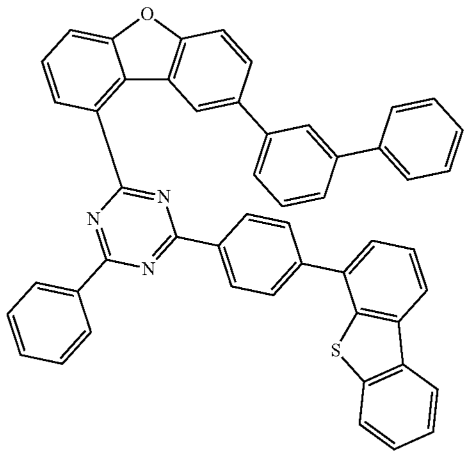
1'-12
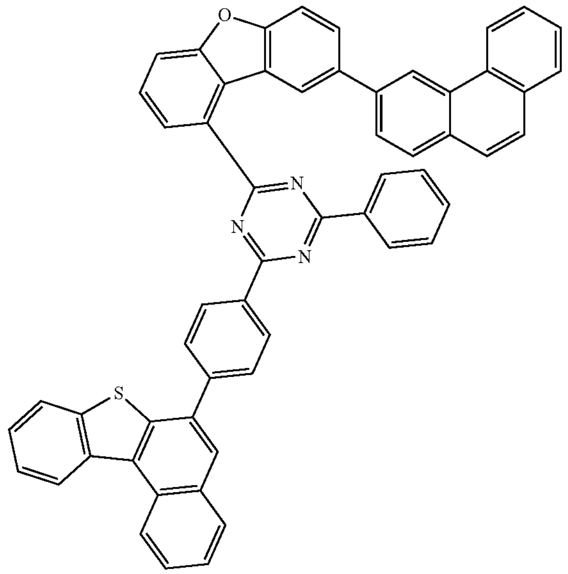
-continued
1'-13
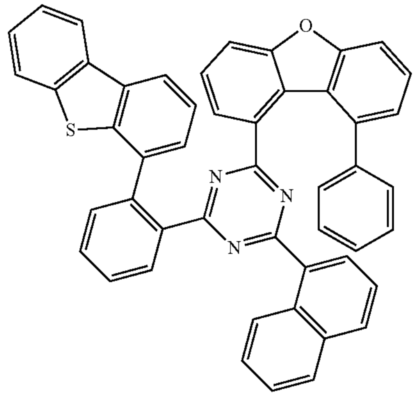
1'-14
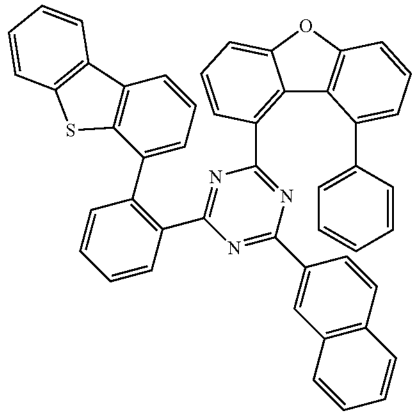
1'-15
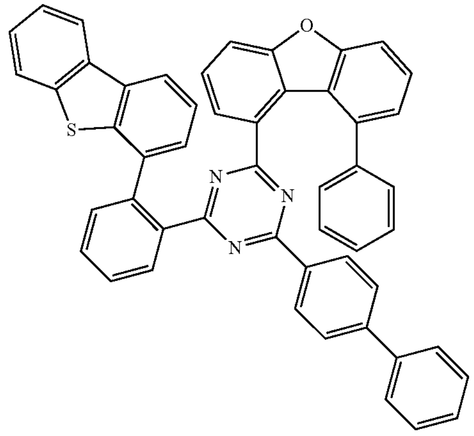

-continued
1'-16
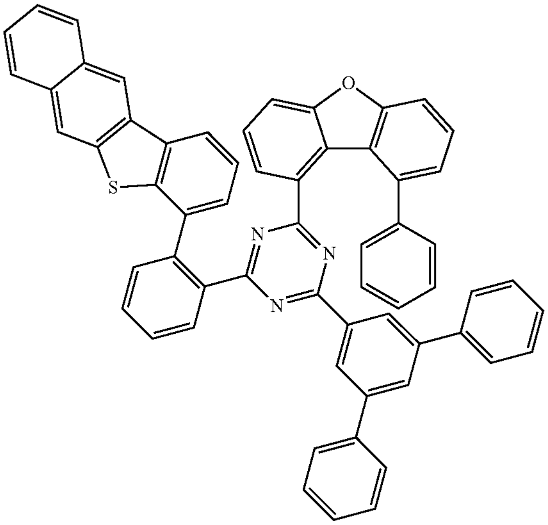
1'-17
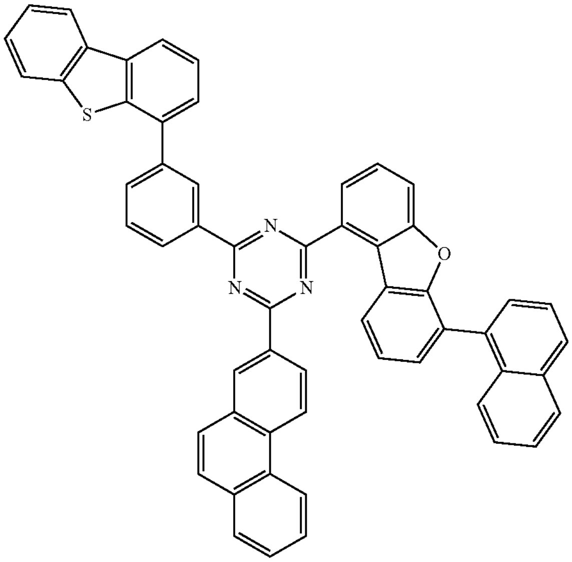
1'-18
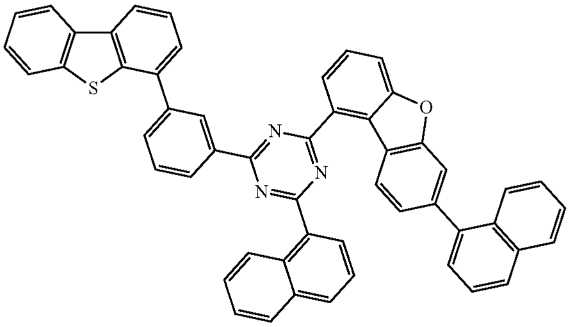
-continued
1'-19
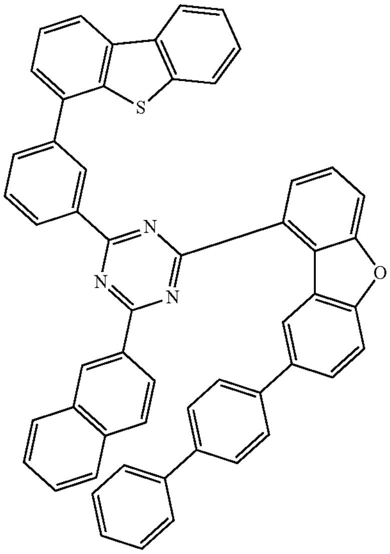
1'-20
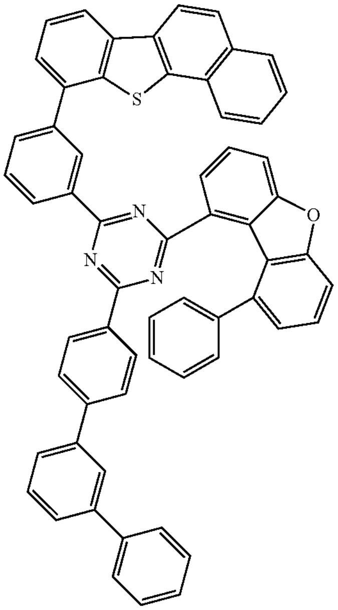
1'-21
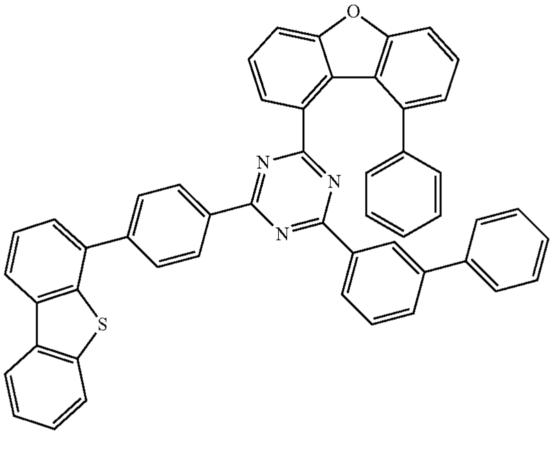

-continued
1'-22
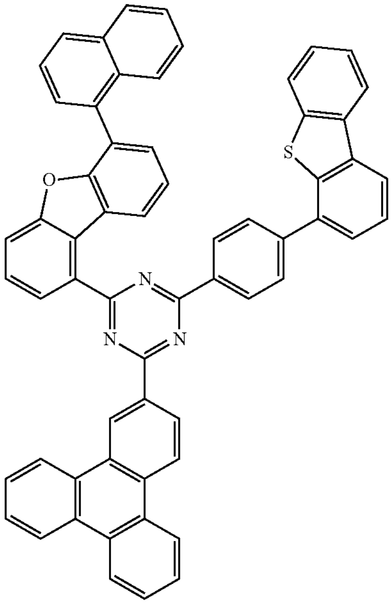
1'-23
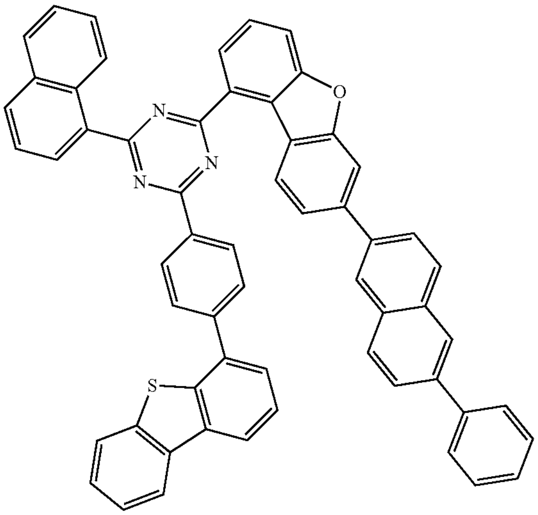
1'-24
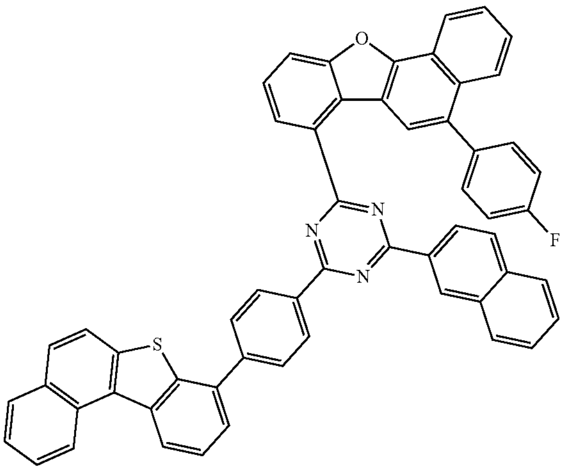
-continued
1'-25
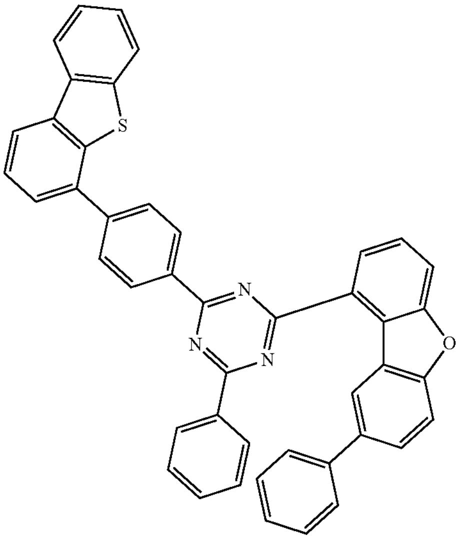
1'-26
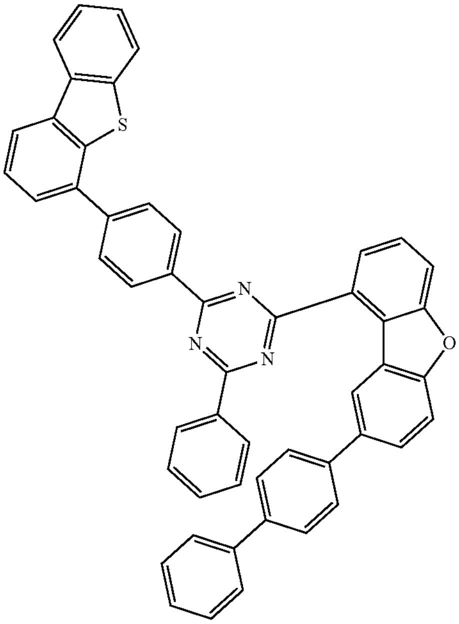

-continued
1′-27
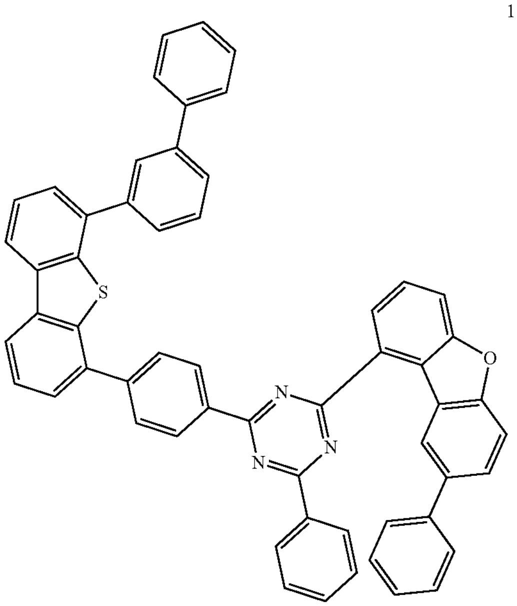
1′-28
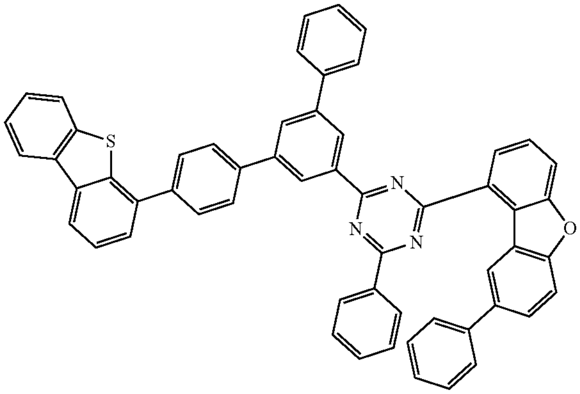
1′-29
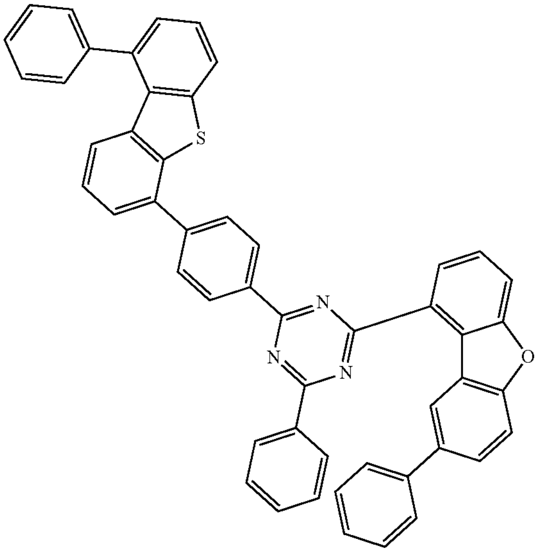
-continued
1′-30
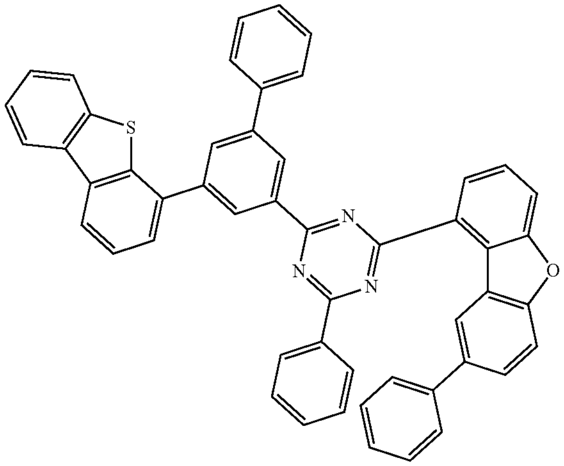
1′-31
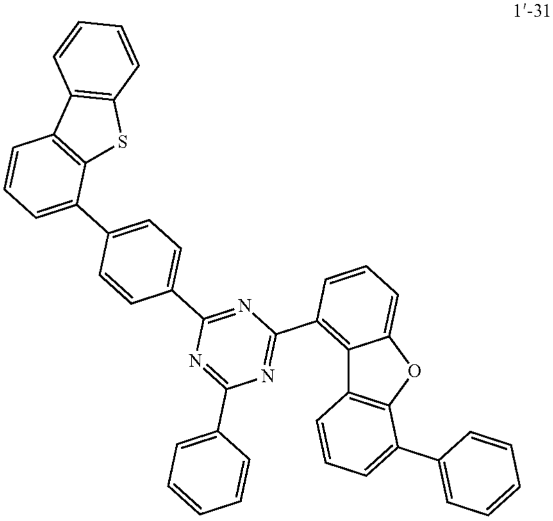
1′-32
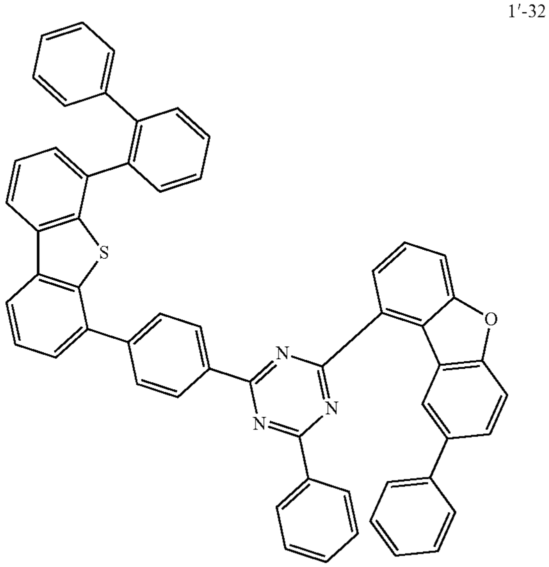

-continued
1′-33
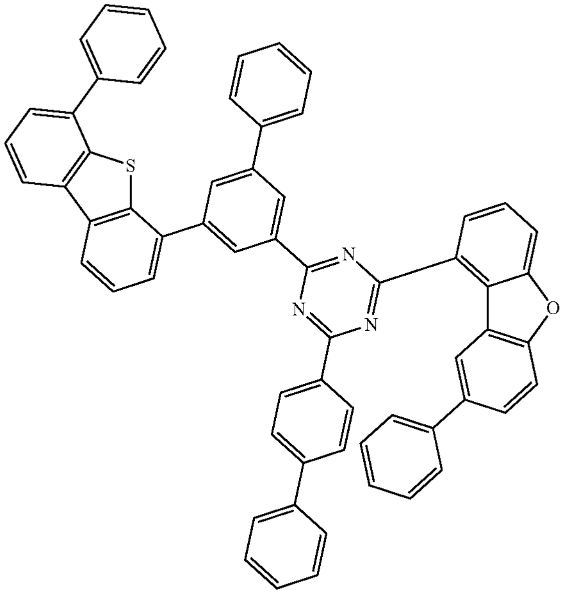
1′-34
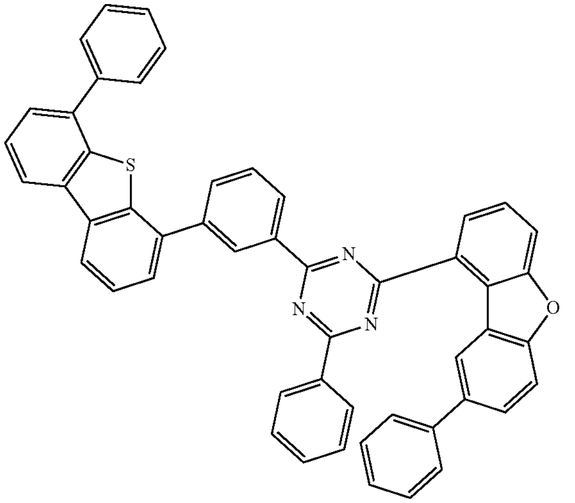
1′-35
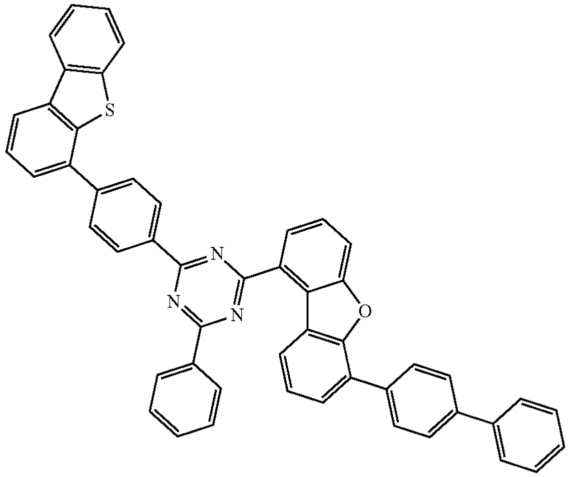
-continued
1′-36
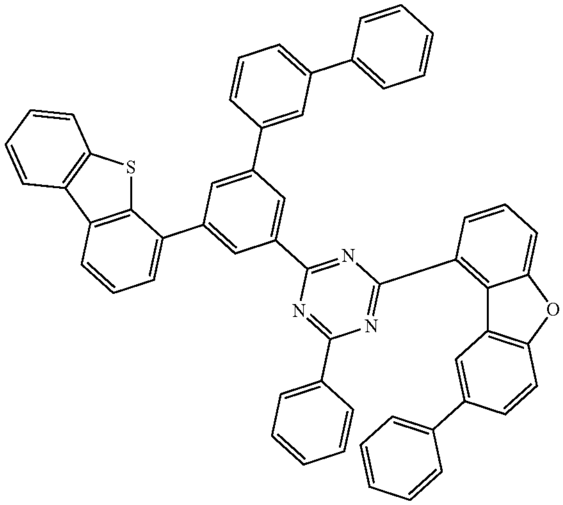
1′-37
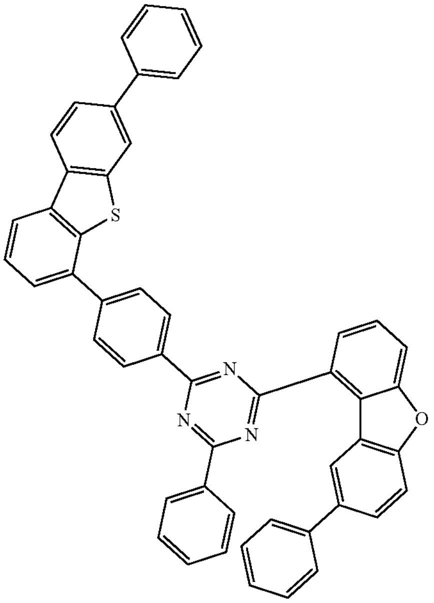
1′-38
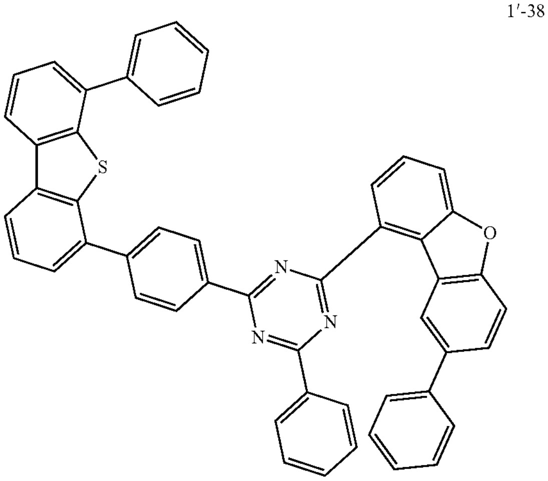

-continued
1′-39
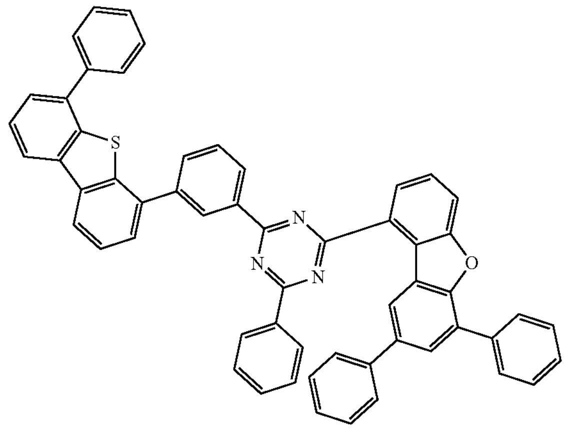
1′-40
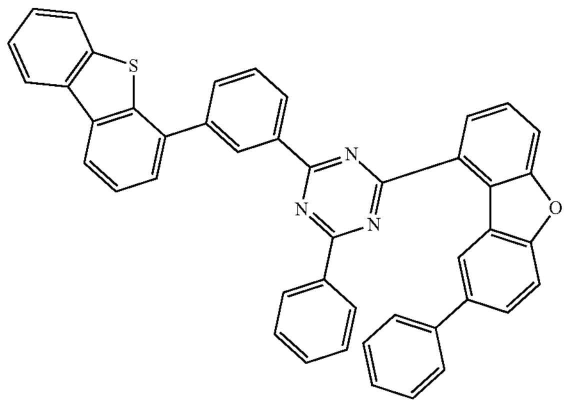
1′-41
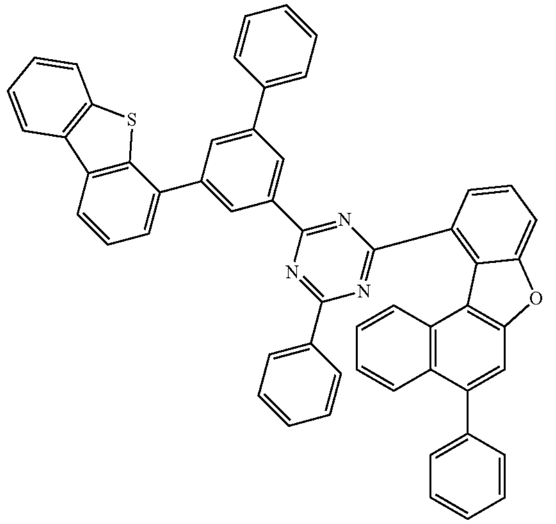
-continued
1′-42
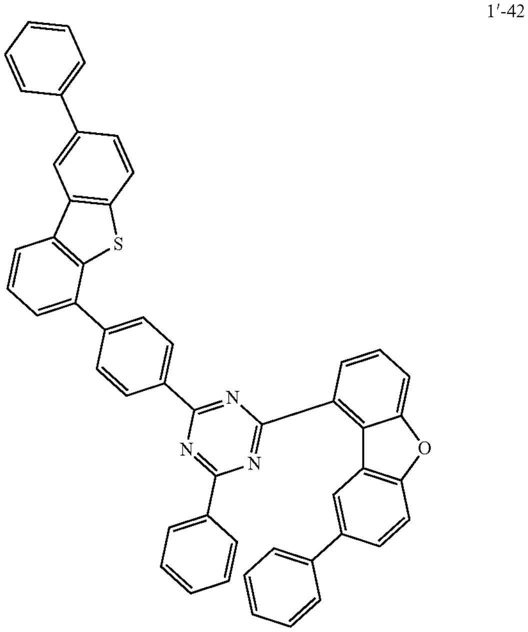
1′-43
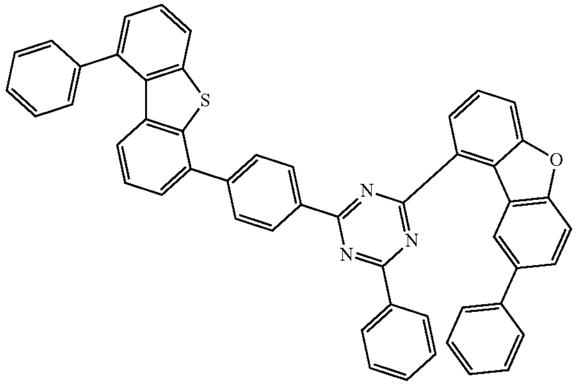
1′-44
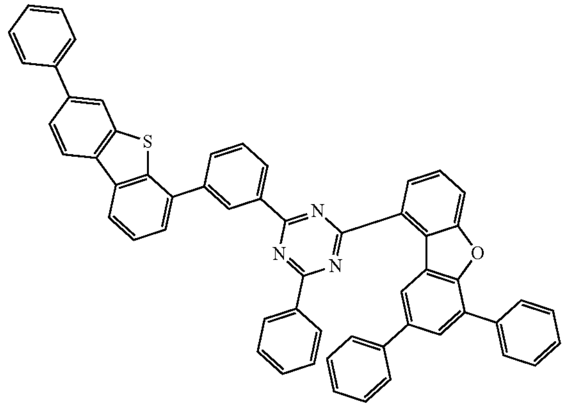

-continued
1'-45
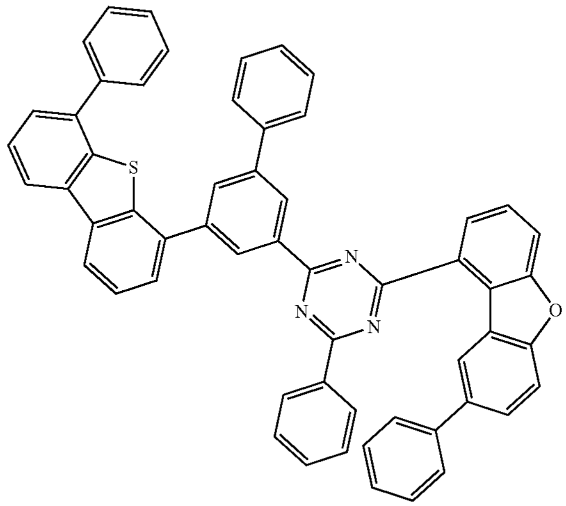
1'-46
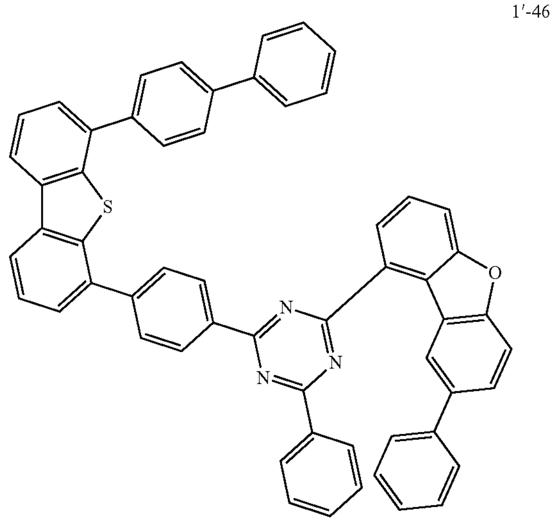
1'-47
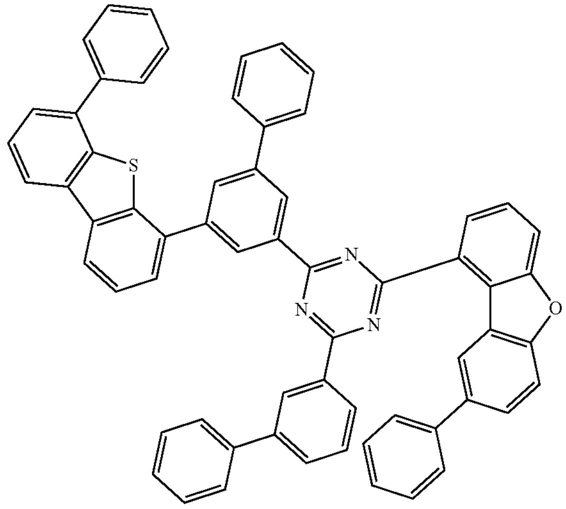
-continued
1'-48
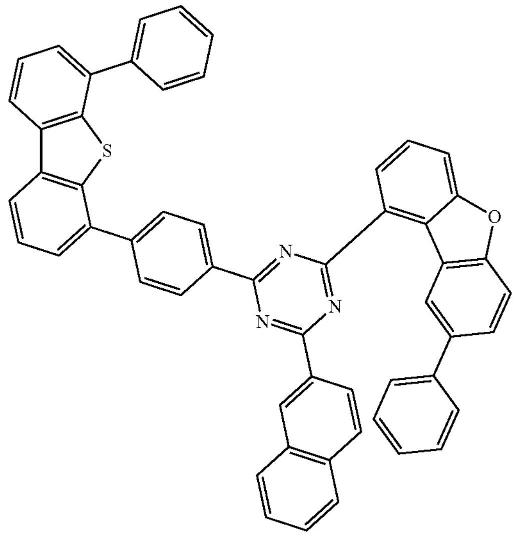
1'-49
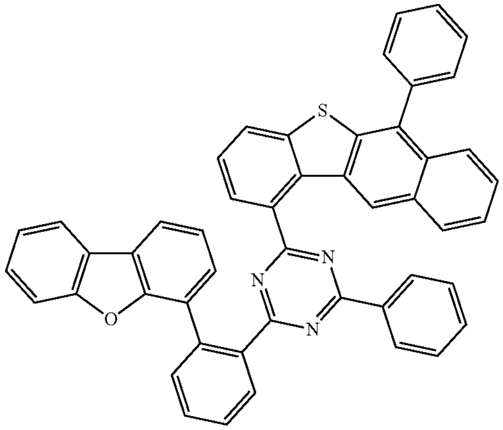
1'-150
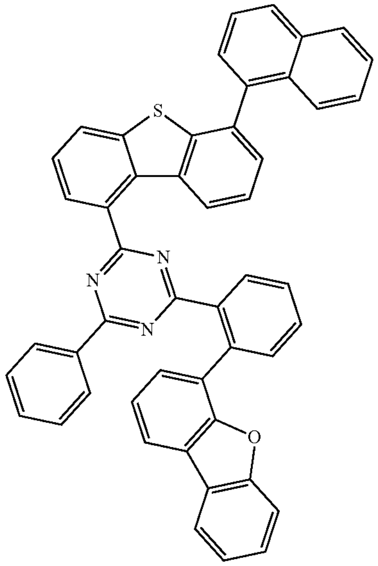

-continued
1′-51
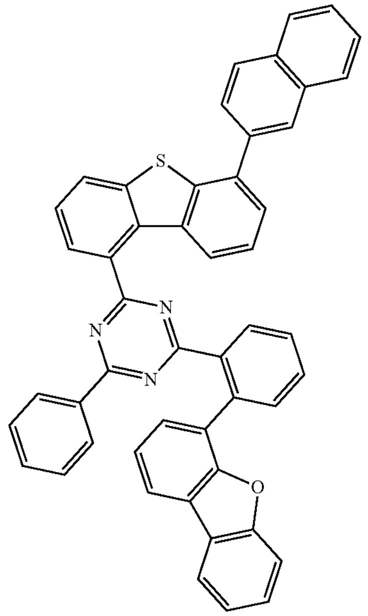
1′-52
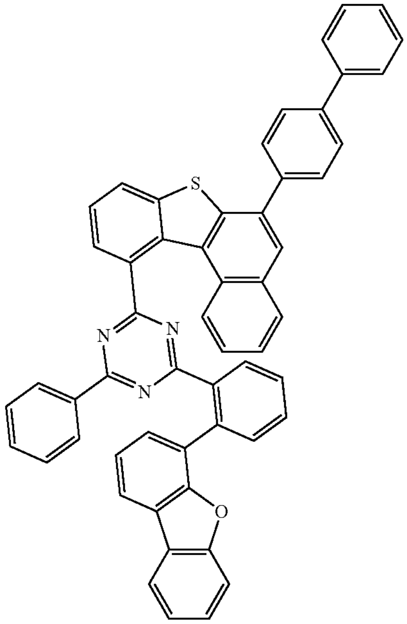
1′-53
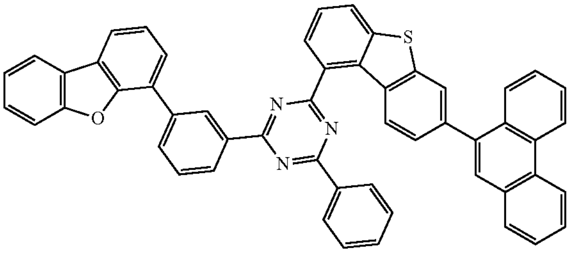
-continued
1′-54
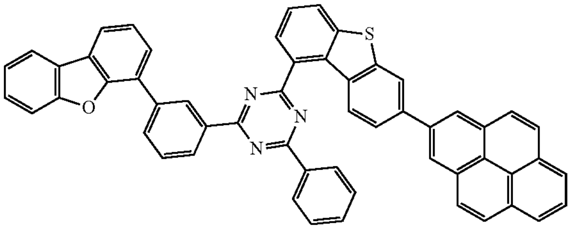
1′-55
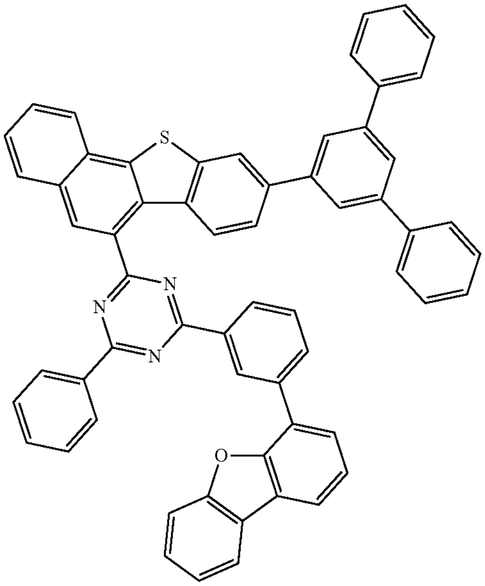
1′-56
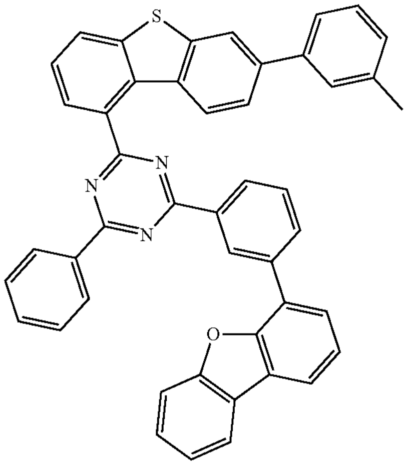

-continued
1′-57
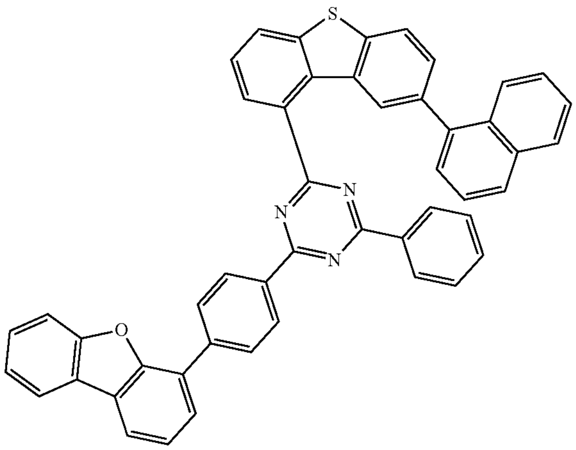
1′-58
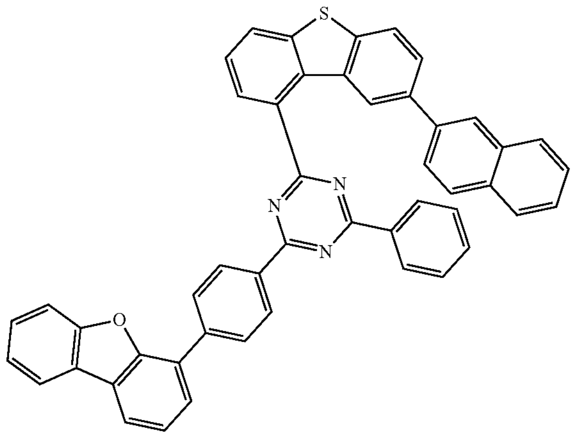
1′-59
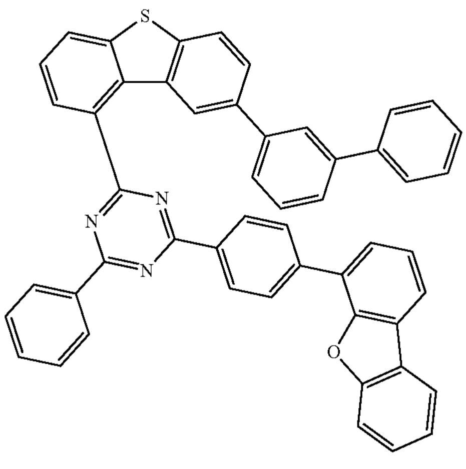
-continued
1′-60
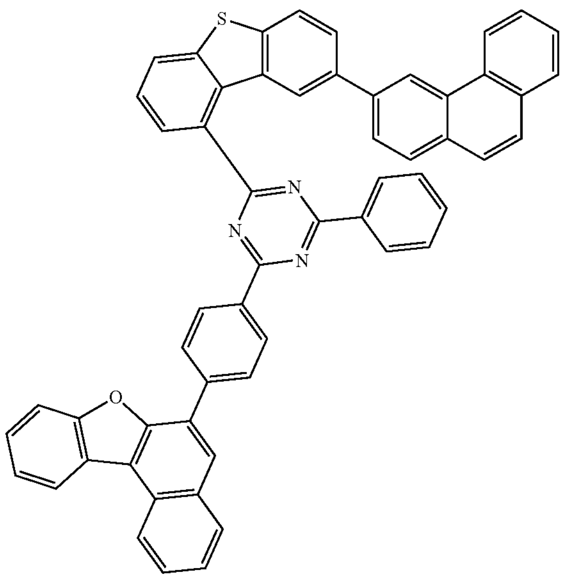
1′-61
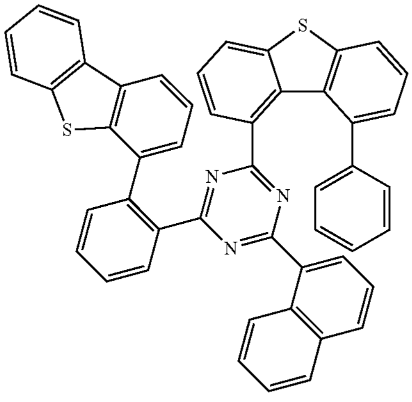
1′-62
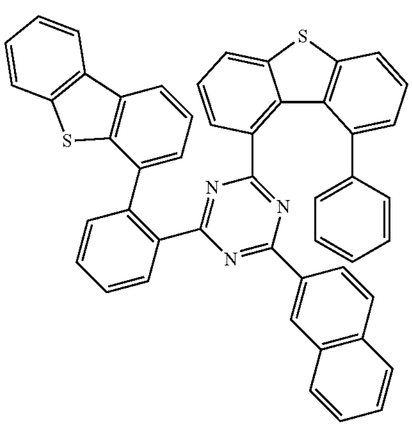

-continued
1′-63
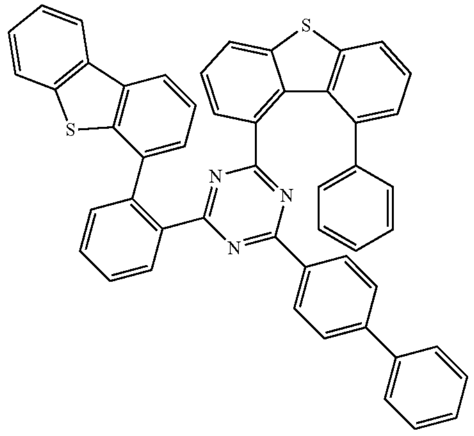
1′-64
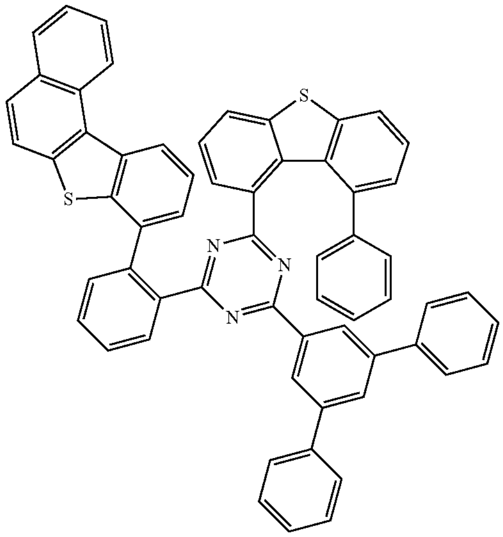
1′-65
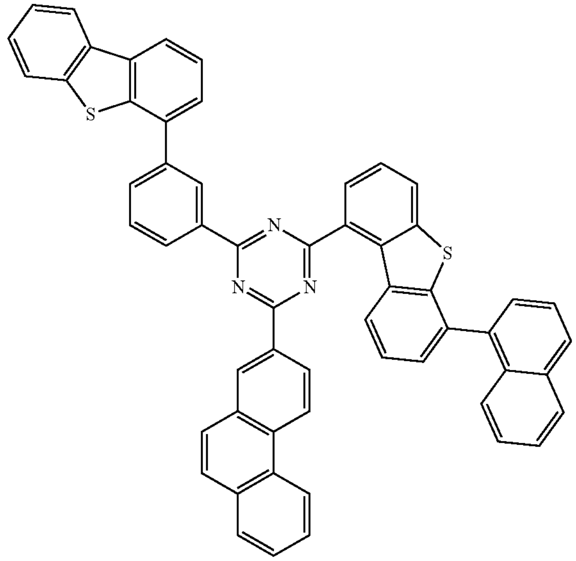
-continued
1′-66
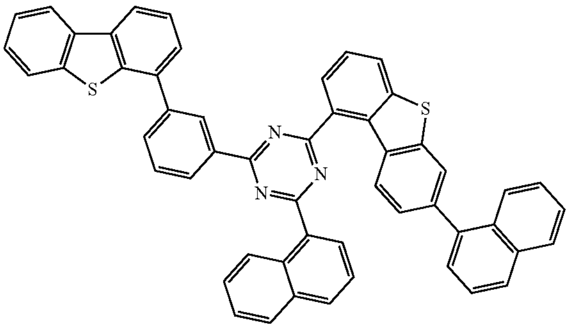
1′-67
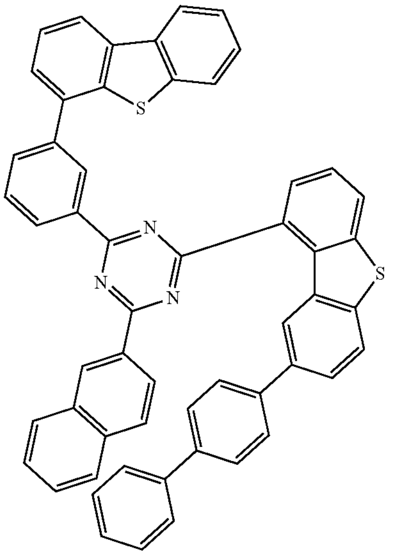
1′-68
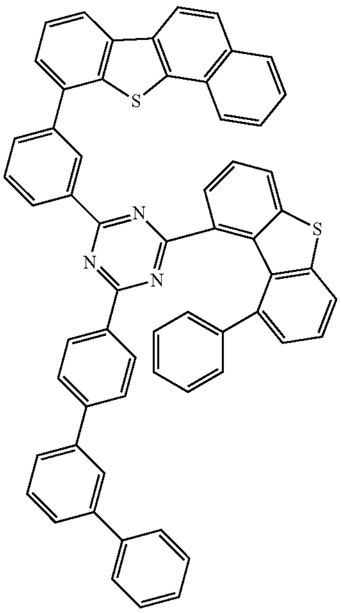

-continued
1'-69
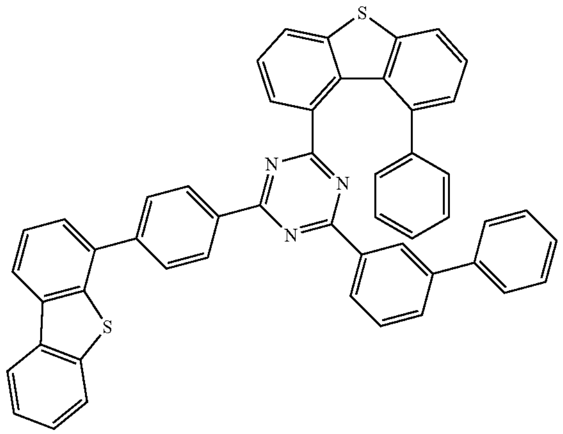
1'-70
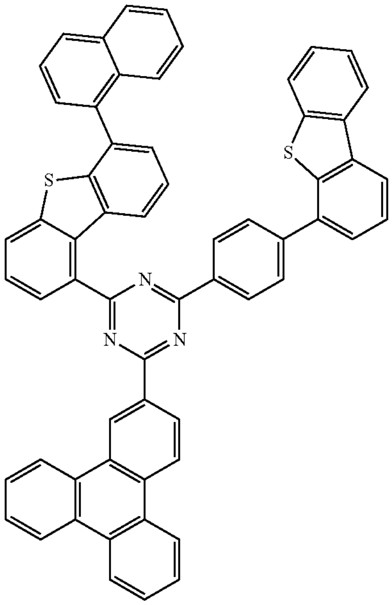
1'-71
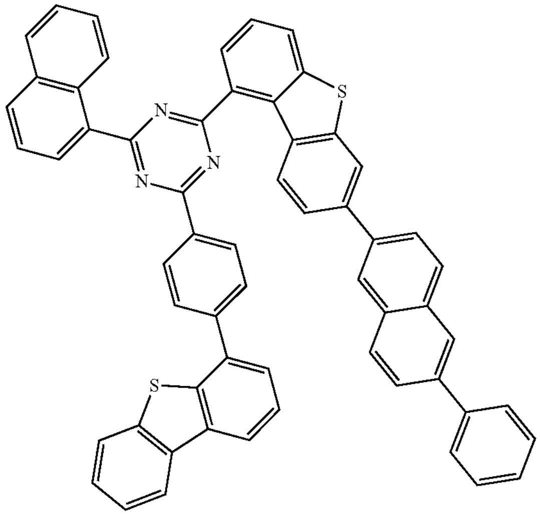
-continued
1'-72
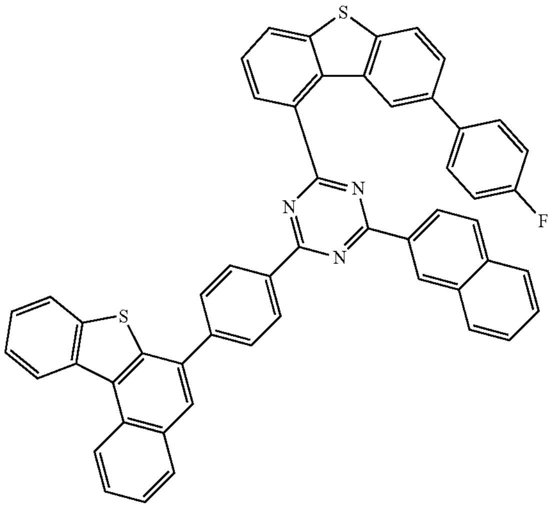
1'-73
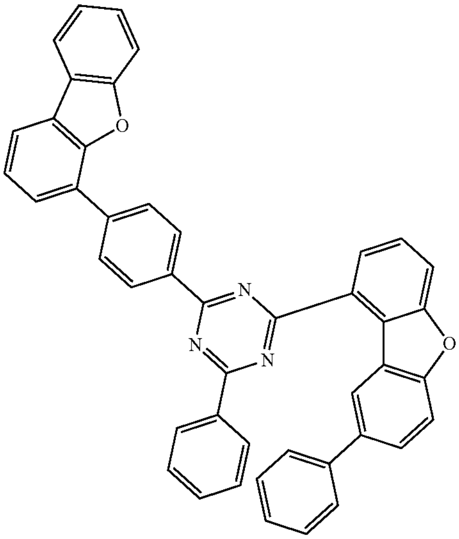

-continued
1'-74
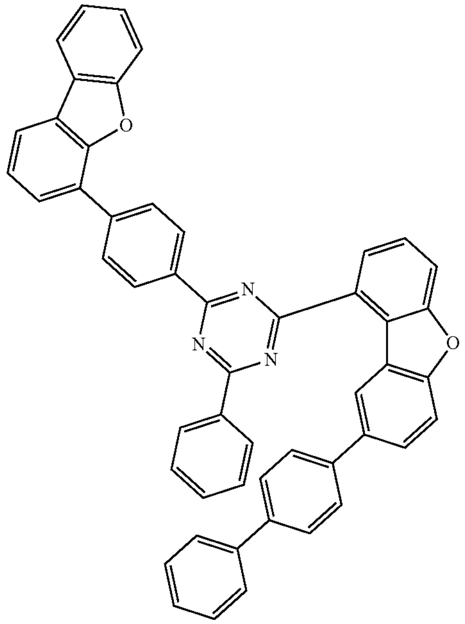
1'-75
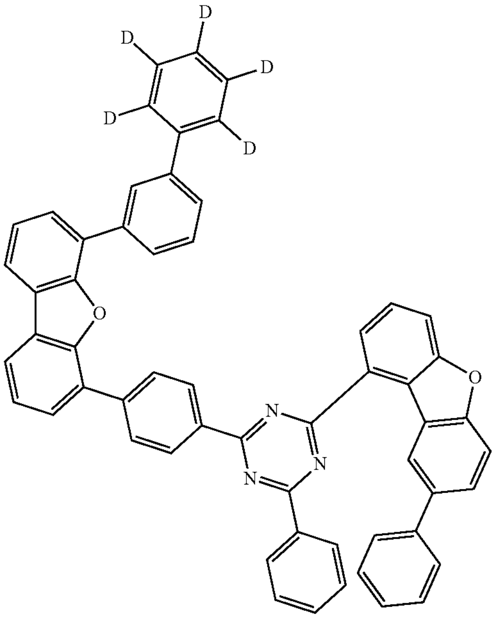
1'-76
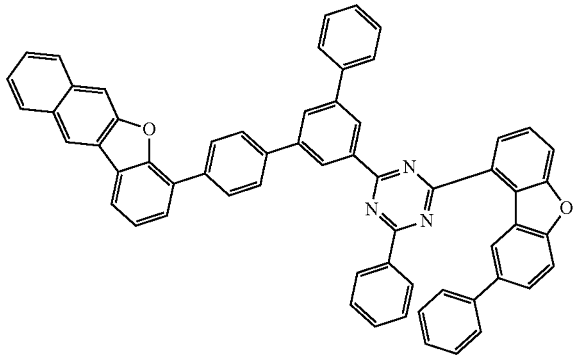
-continued
1'-77
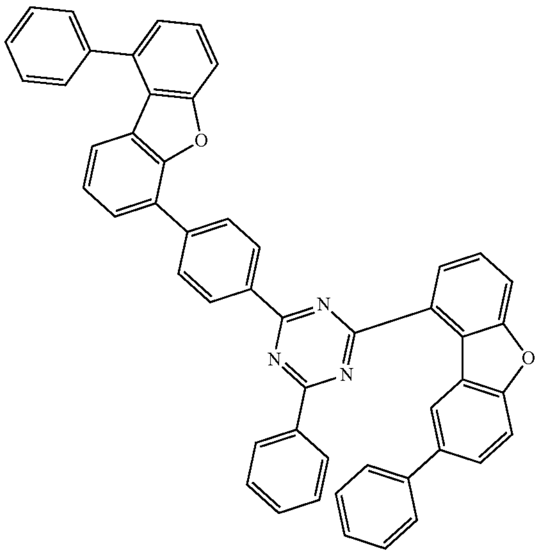
1'-78
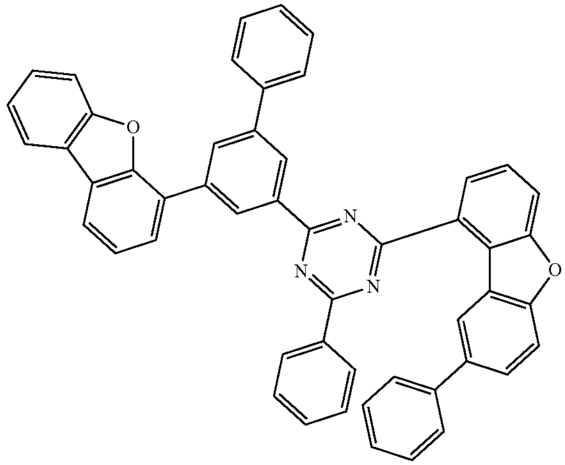
1'-79
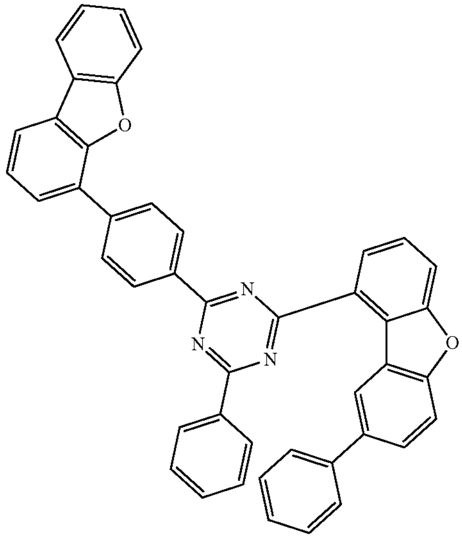

-continued
1′-80
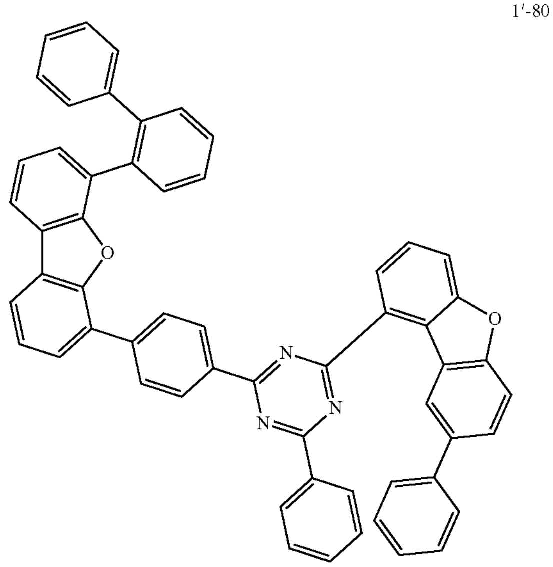
1′-81
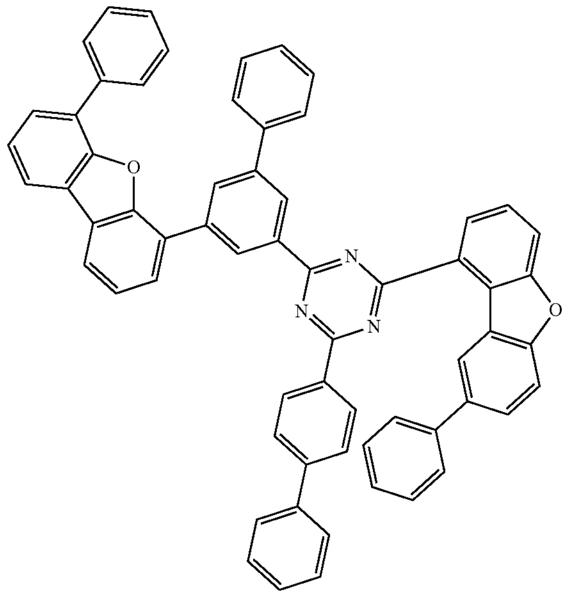
-continued
1′-82
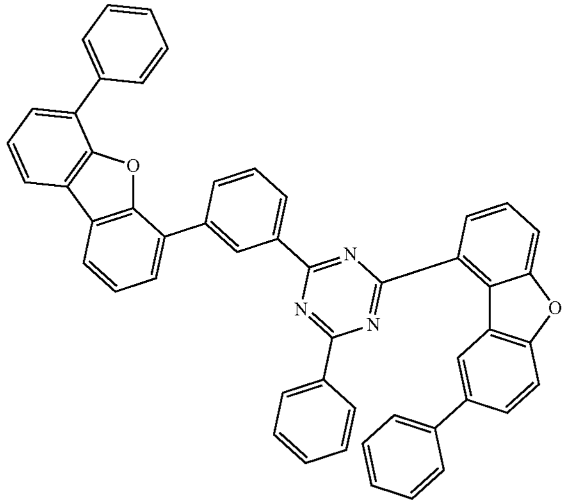
1′-83
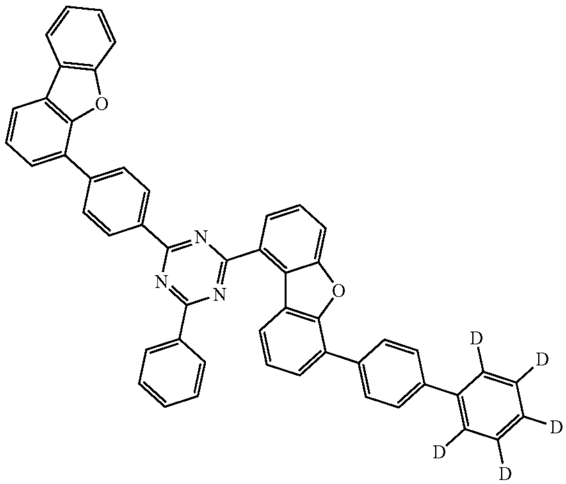
1′-84
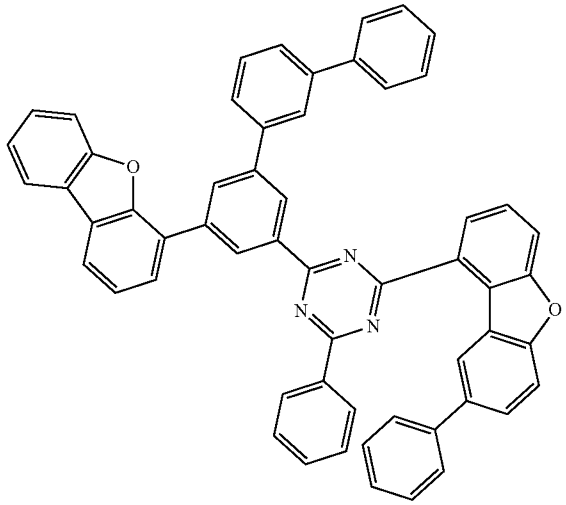

-continued
2-1
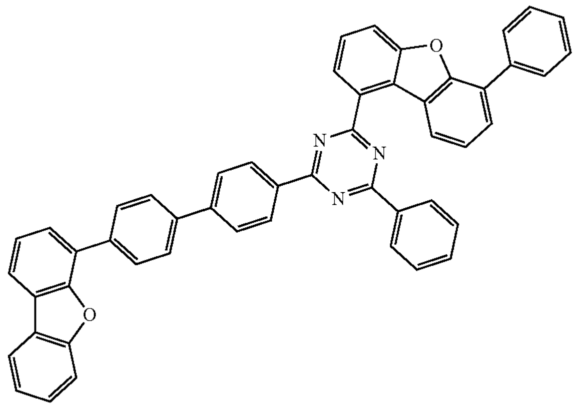
2-2
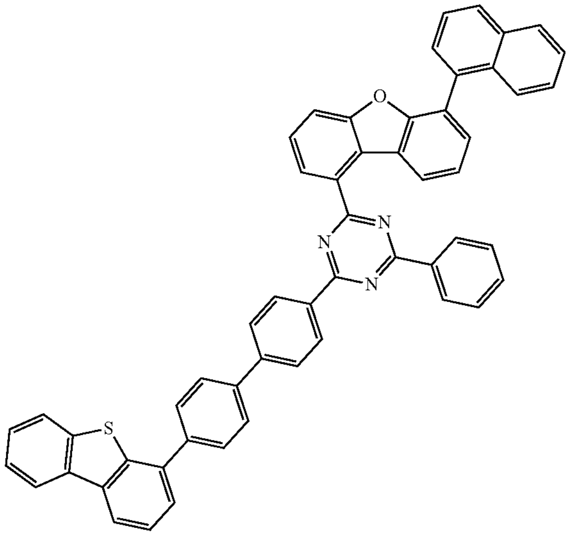
2-3
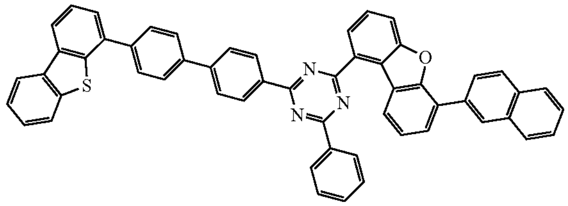
2-4
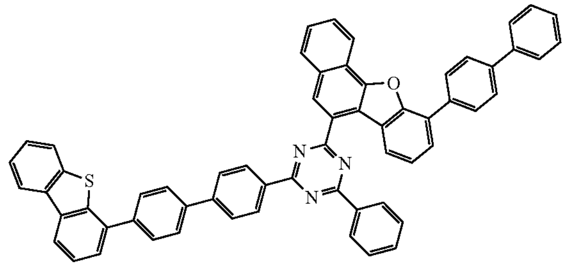
-continued
2-5
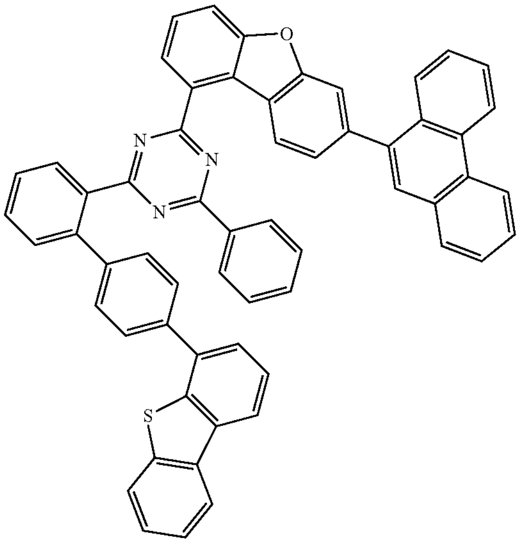
2-6
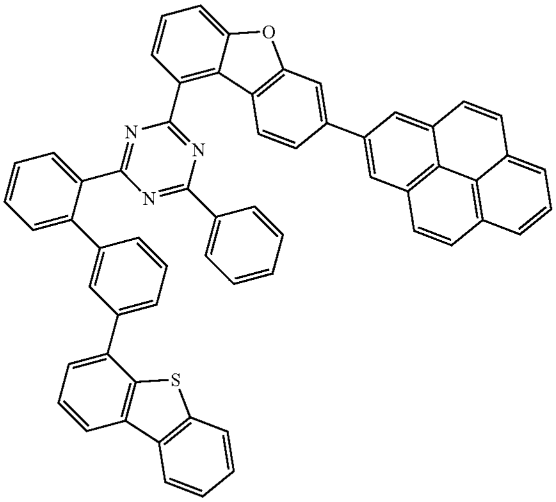

-continued
2-7
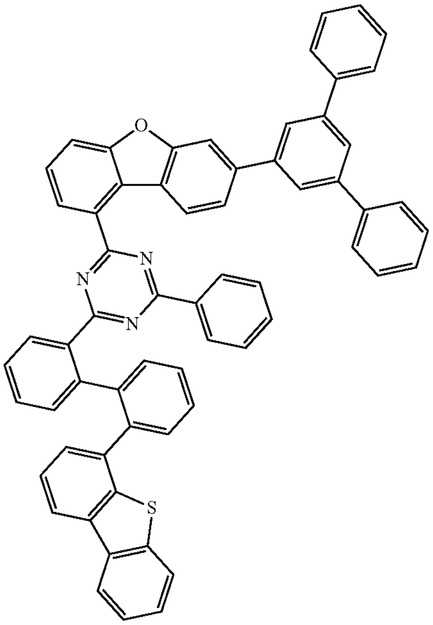
2-8
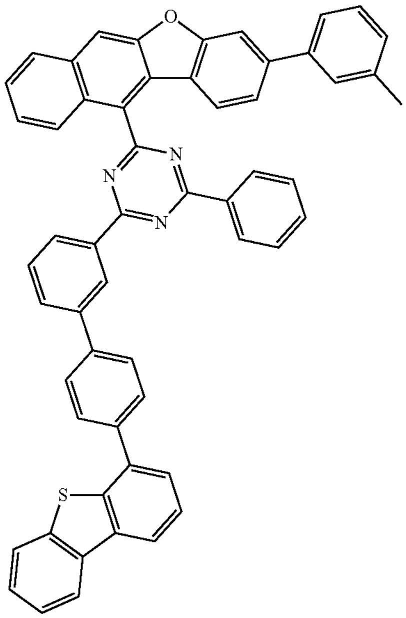
-continued
2-9
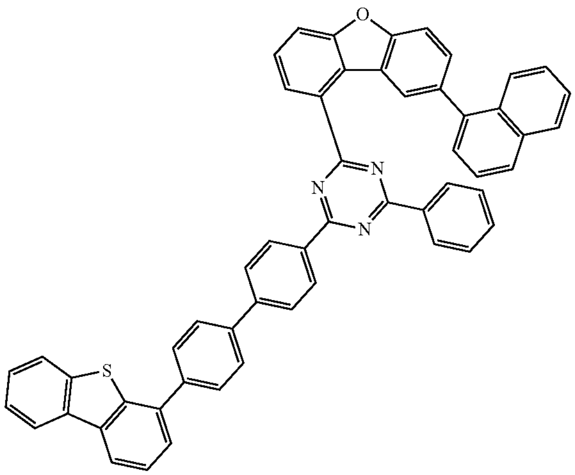
2-10
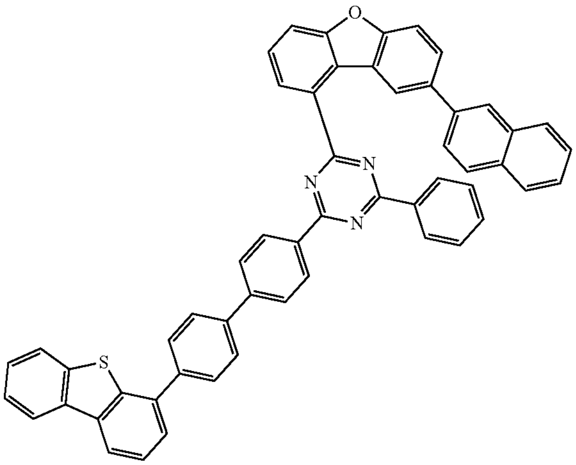
2-11
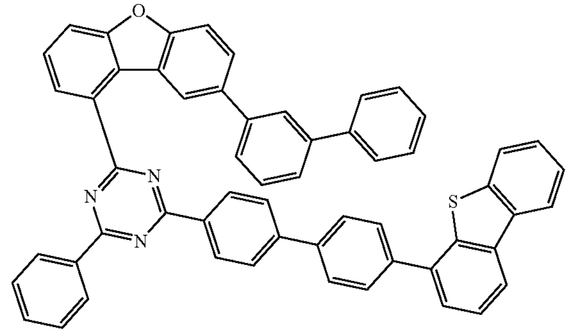
2-12
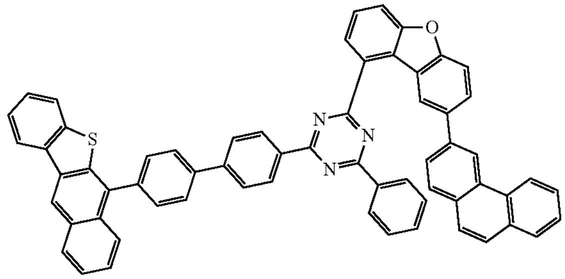

-continued
2-13
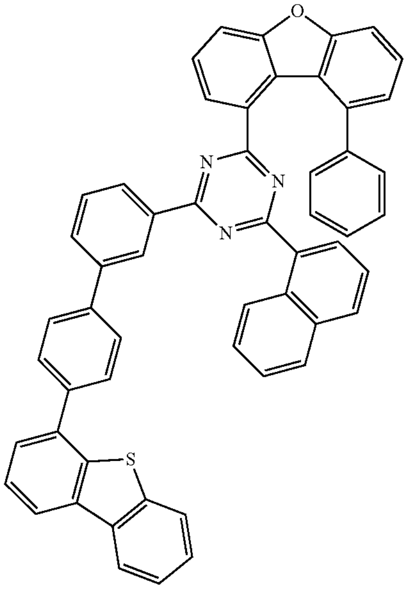
2-14
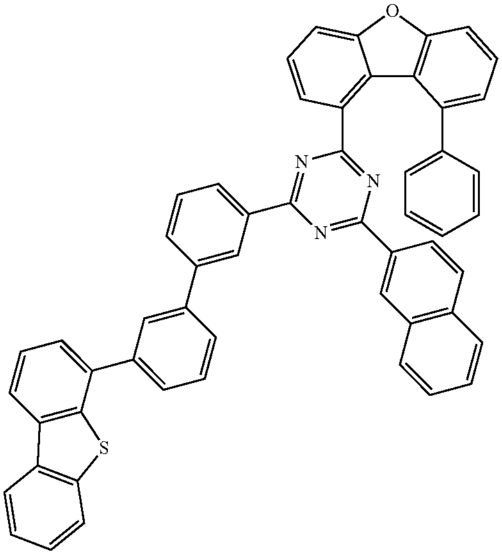
2-15
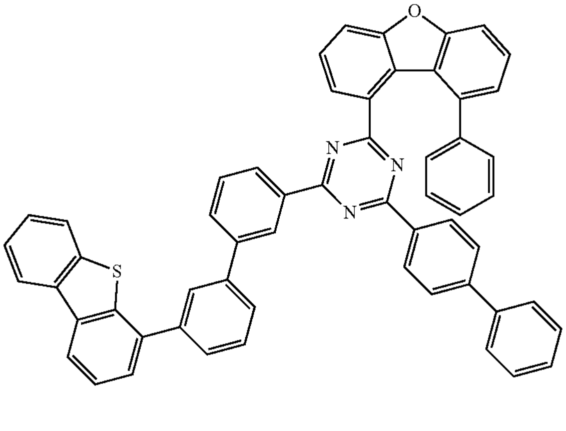
-continued
2-16
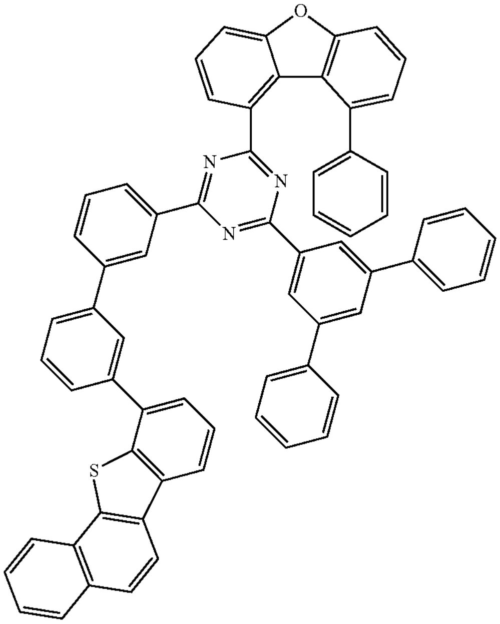
2-17
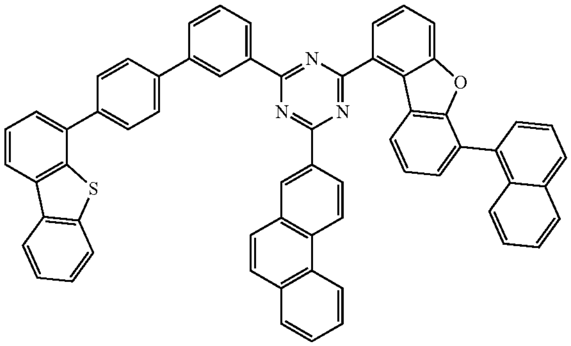
2-18
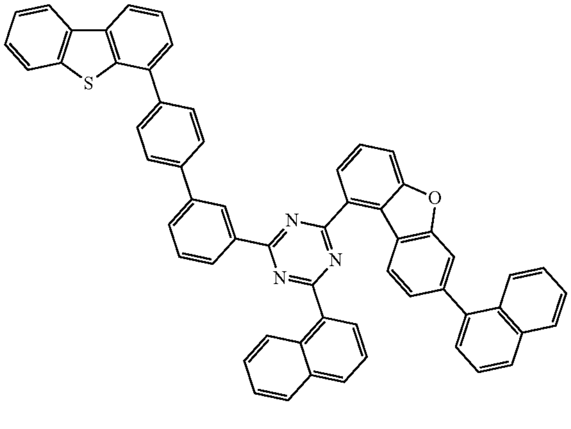

-continued
2-19
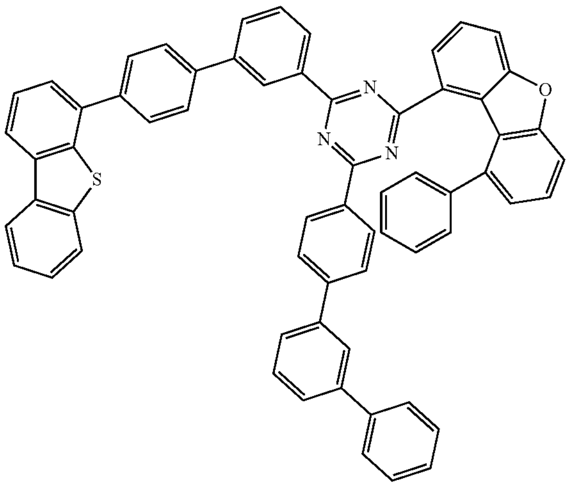
2-20
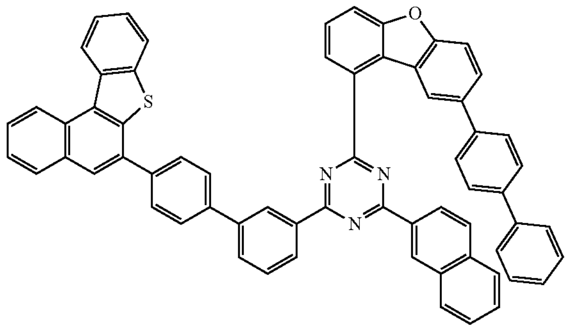
2-21
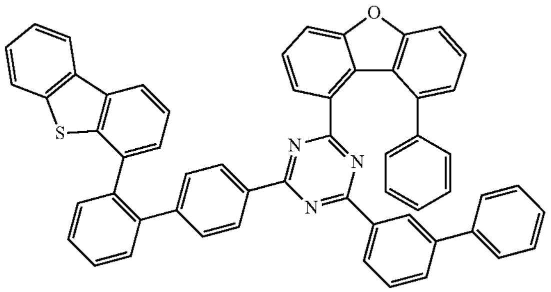
2-22
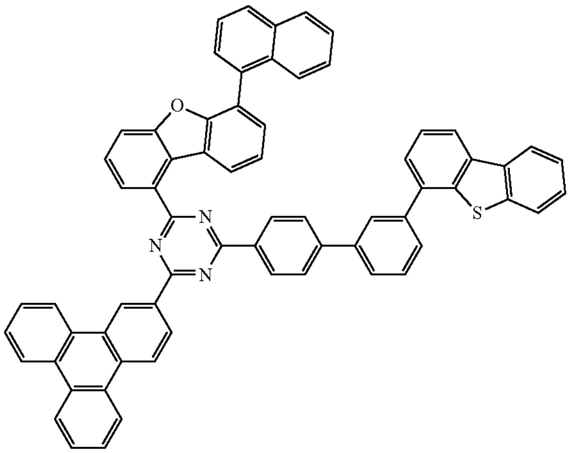
-continued
2-23
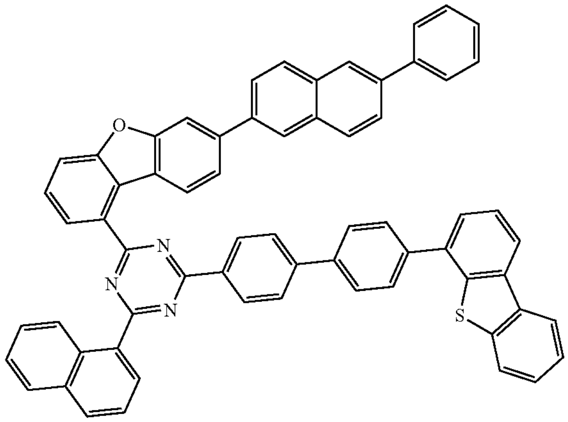
2-24
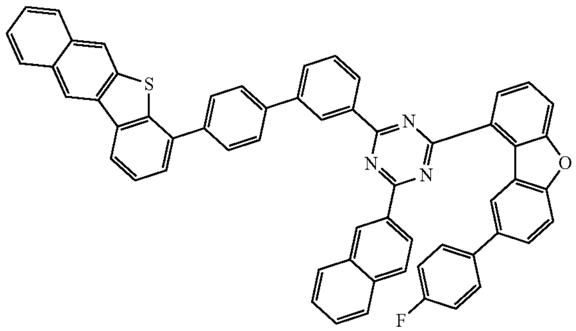
2-25
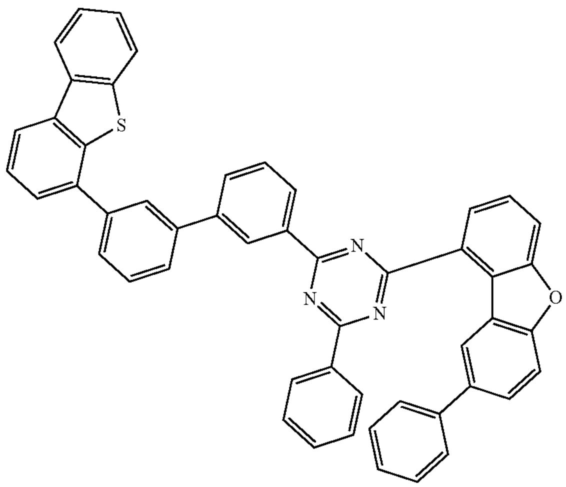

-continued
2-26
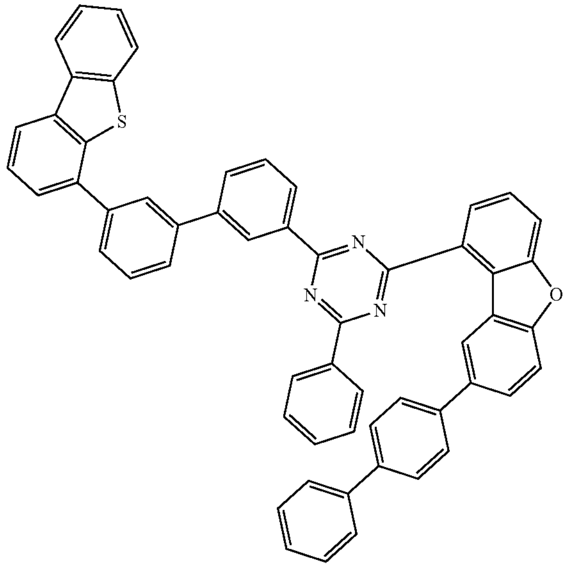
2-27
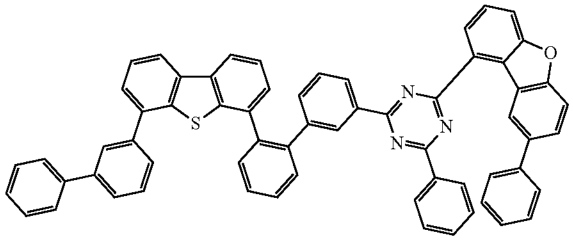
2-28
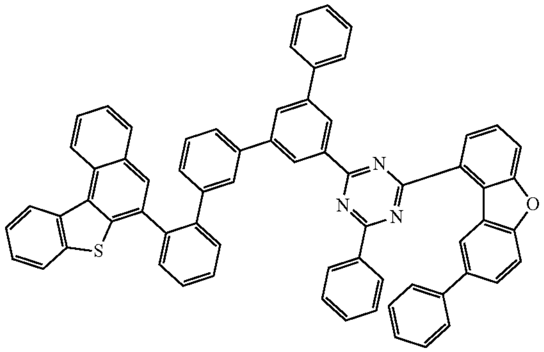
-continued
2-29
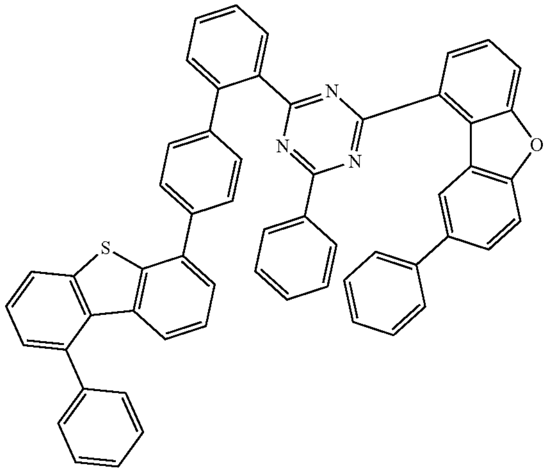
2-30
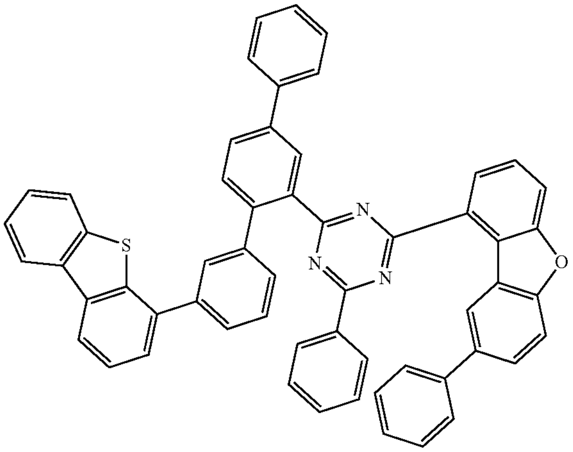
2-31
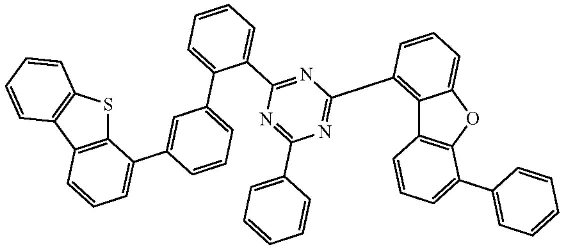

-continued
2-32
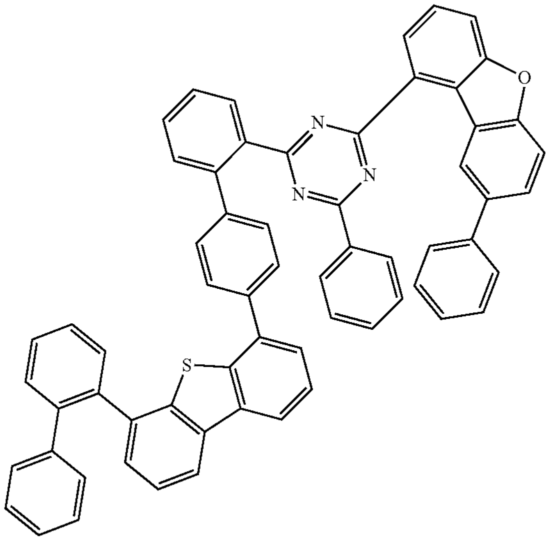
2-33
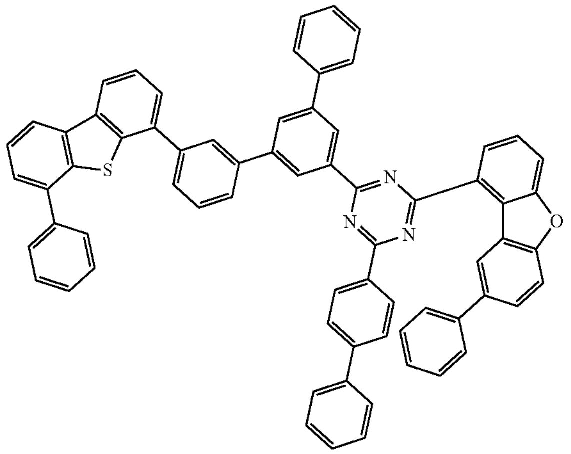
3-34
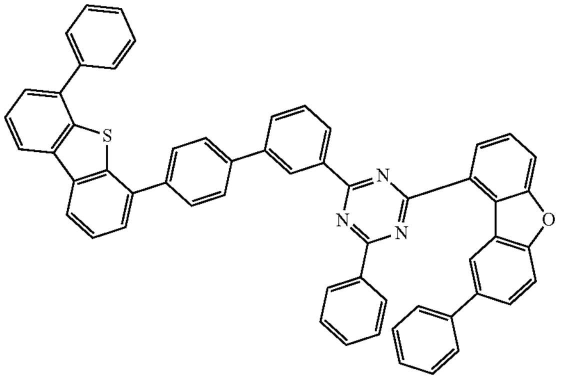
-continued
2-35
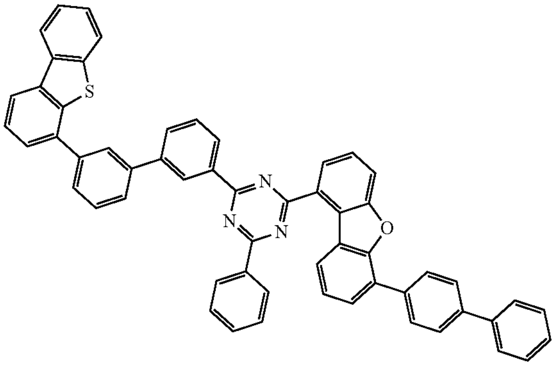
2-36
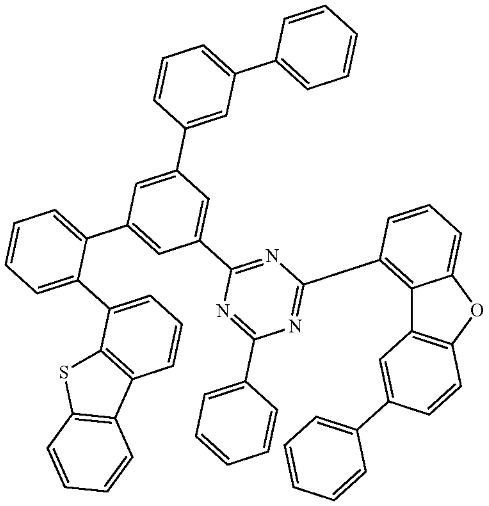
2-37
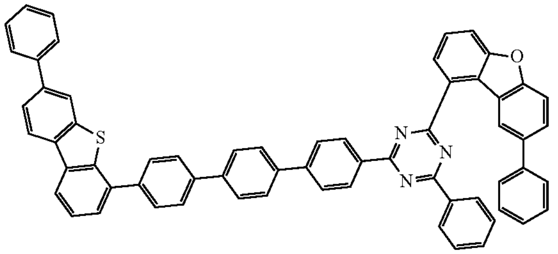
2-38
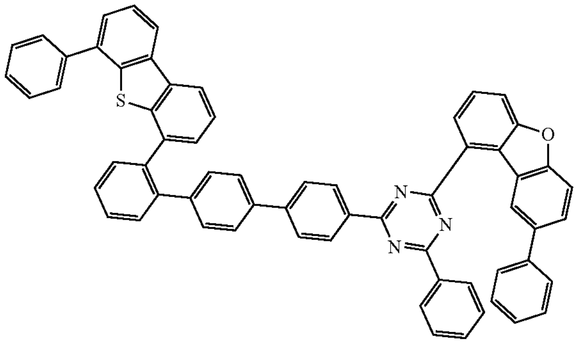

-continued
2-39
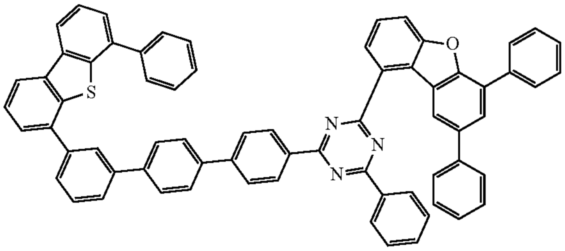
2-40
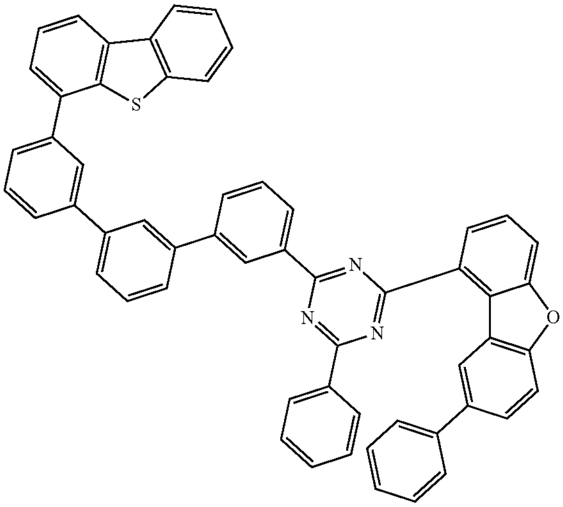
2-41
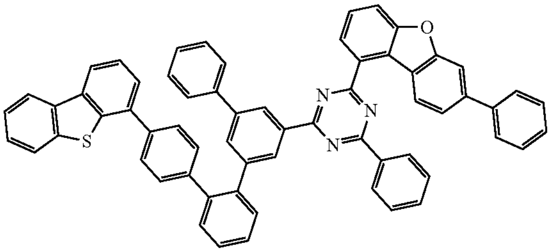
2-42
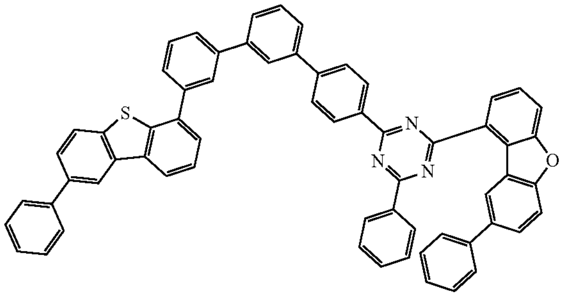
-continued
2-43
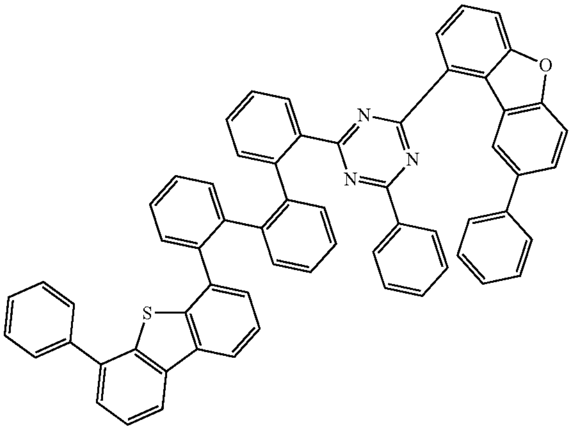
2-44
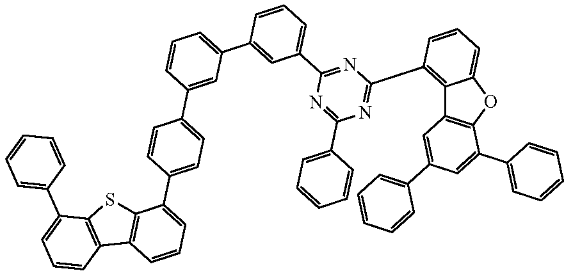
2-45
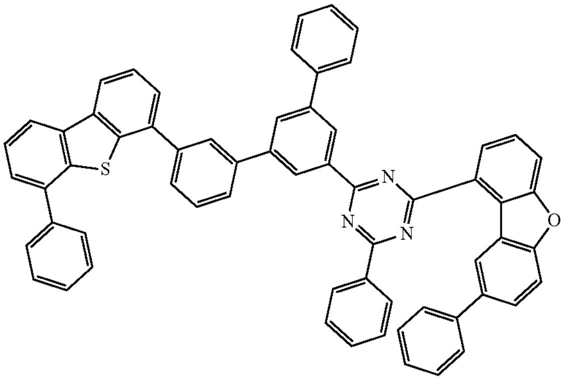

-continued
2-46
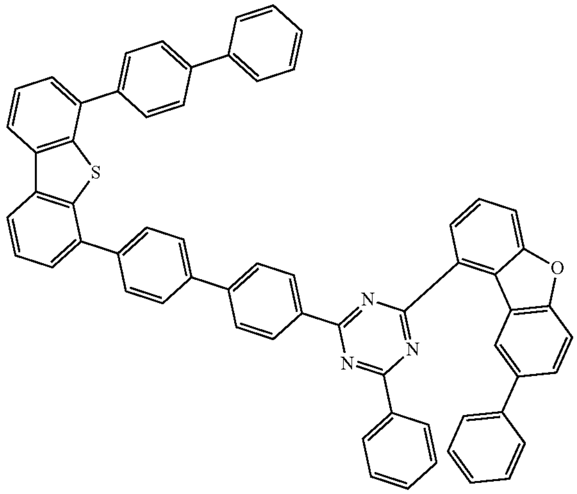
2-47
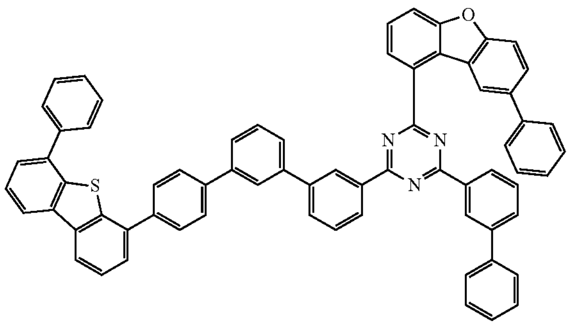
2-48
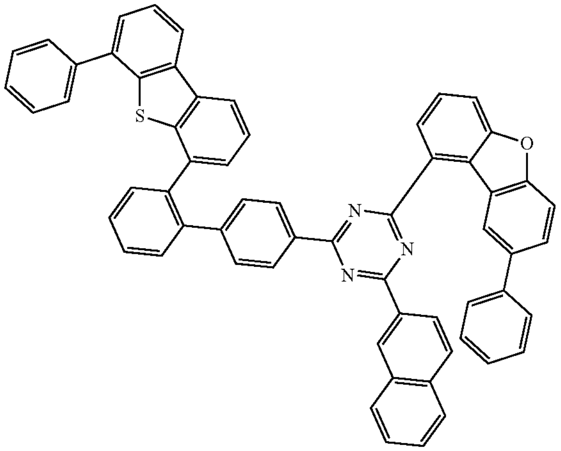
-continued
2-49
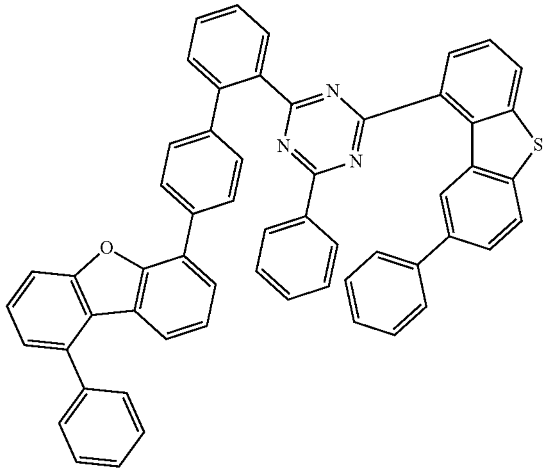
2-50
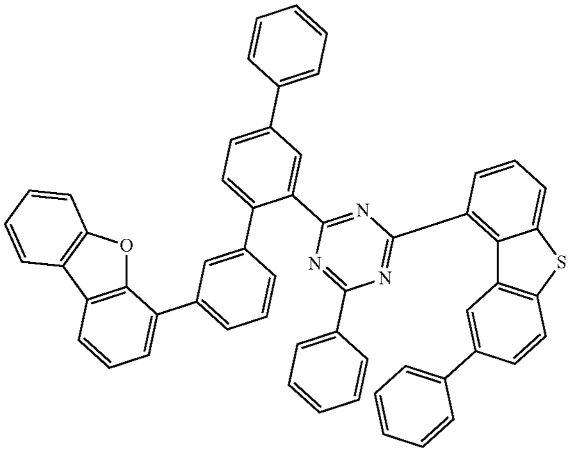
2-51
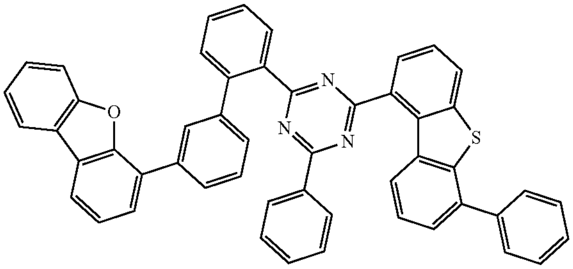

-continued
2-52
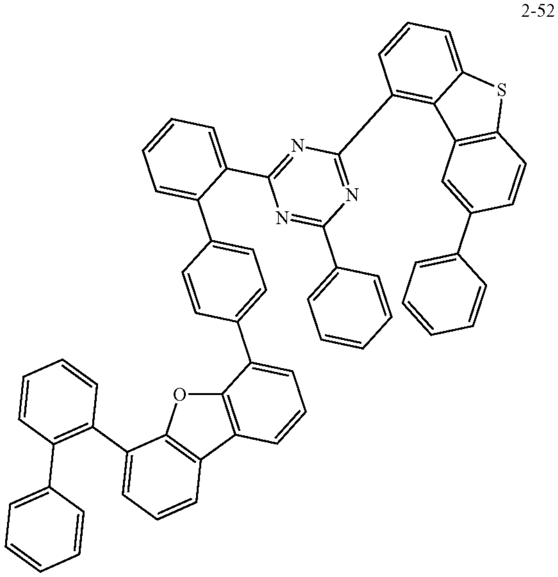
2-53
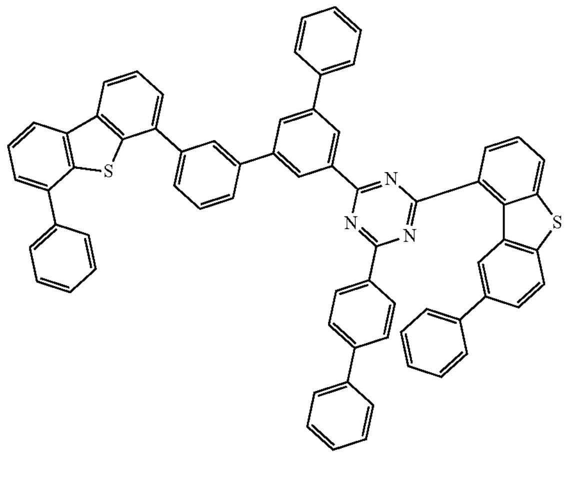
2-54
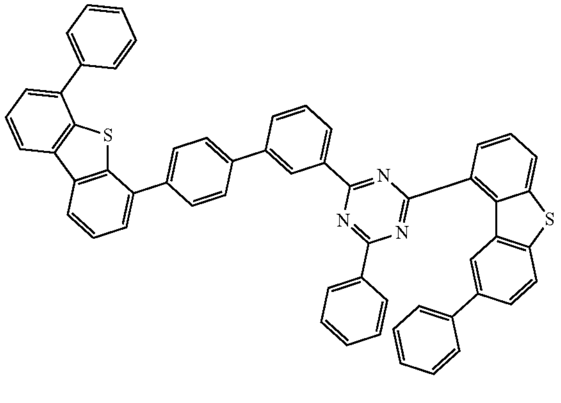
-continued
2-55
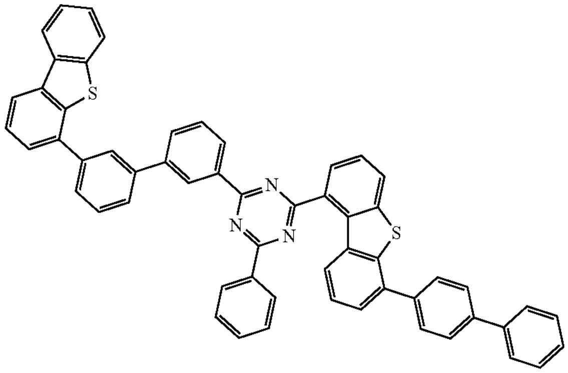
2-56
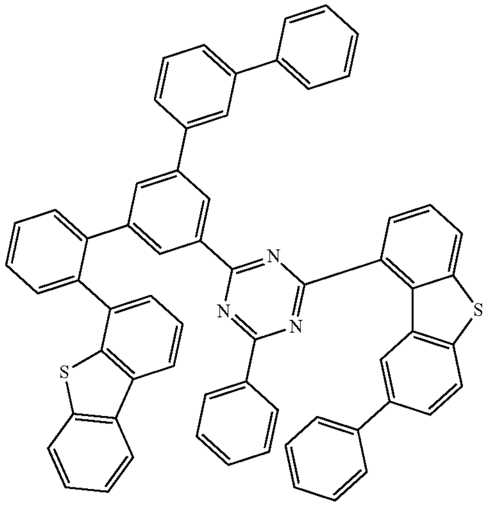
2-57
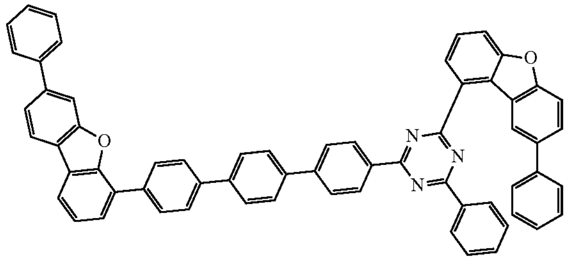
2-58
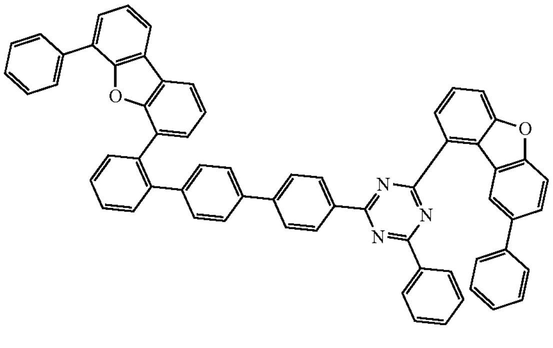

-continued
2-59
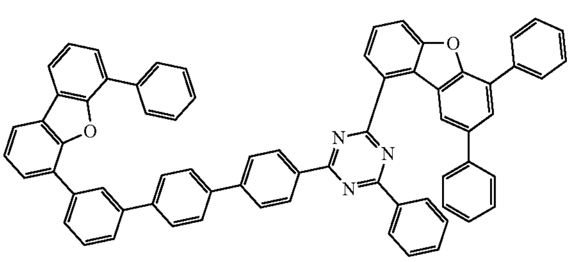
2-60
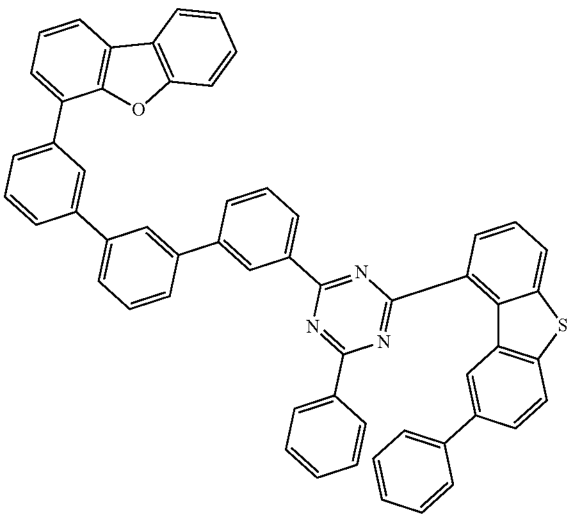
3-1
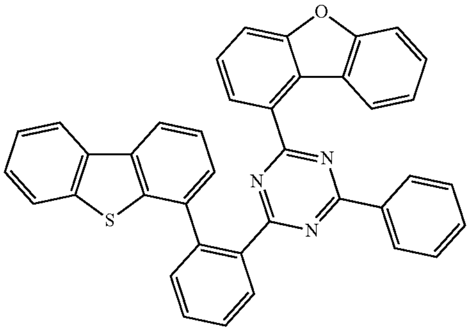
3-2
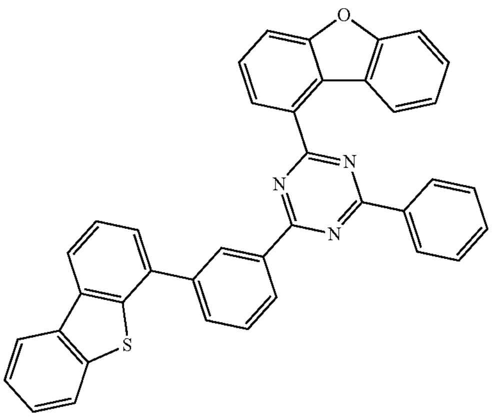
-continued
3-3
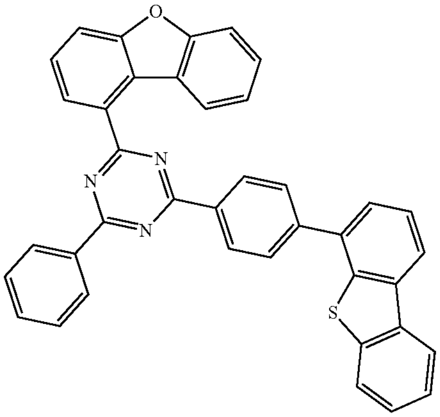
3-4
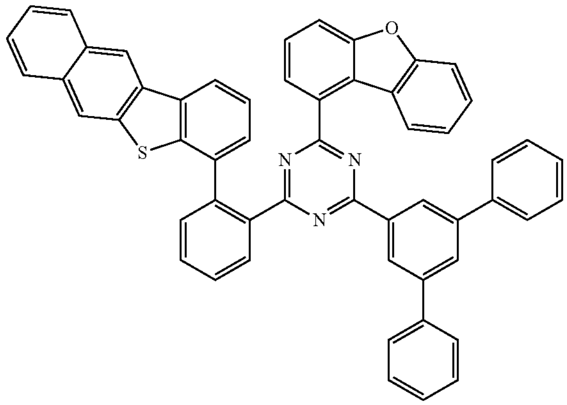
3-5
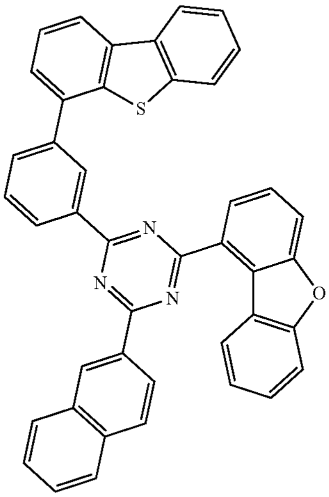

-continued
3-6
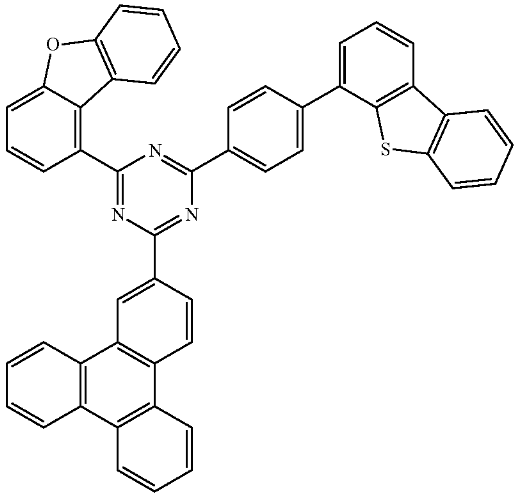
3-7
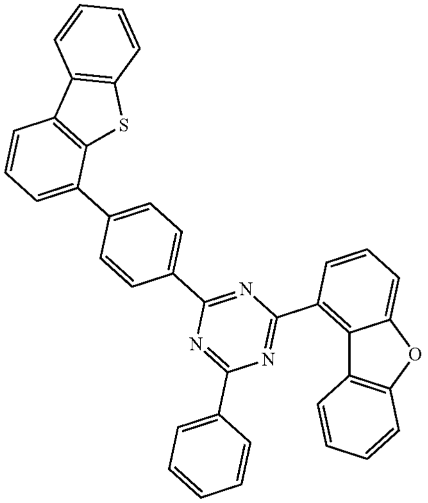
3-8
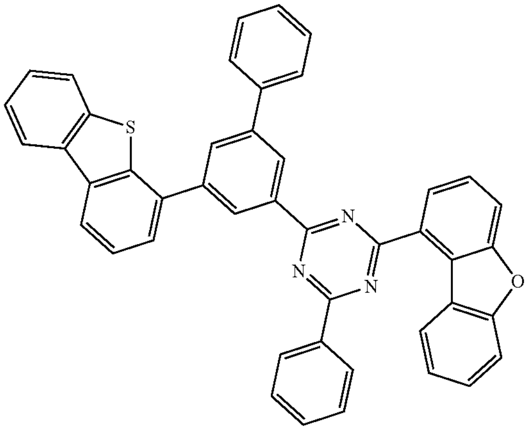
-continued
3-9
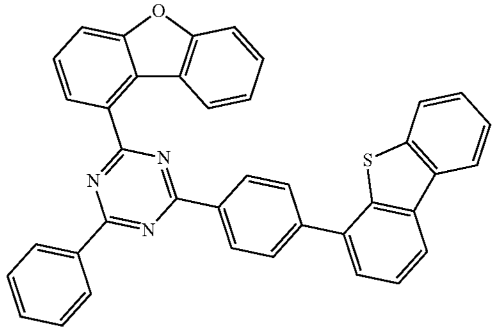
3-10
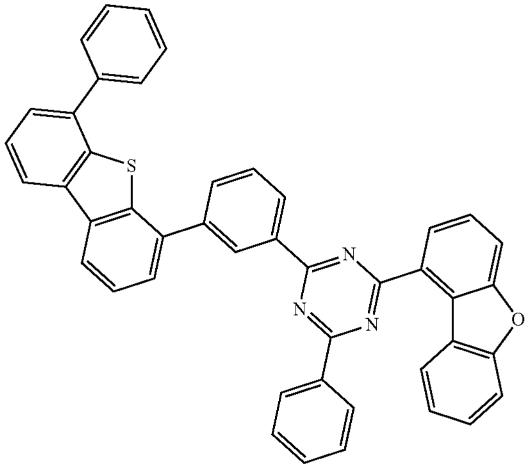
3-11
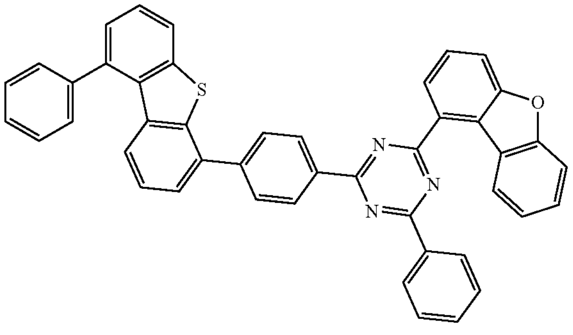

-continued
3-12
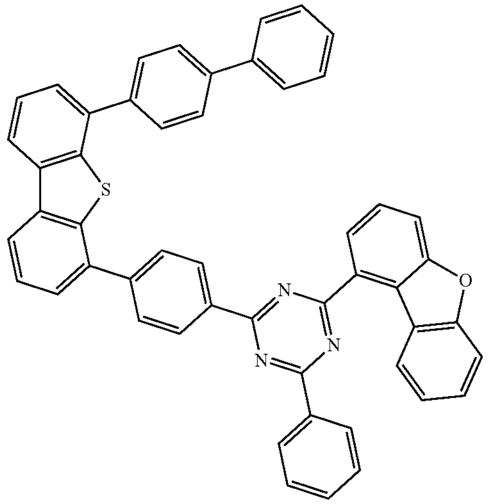
3-13
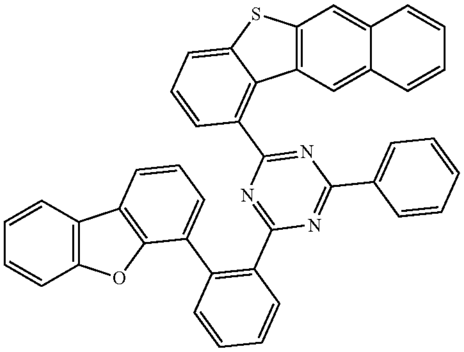
3-14
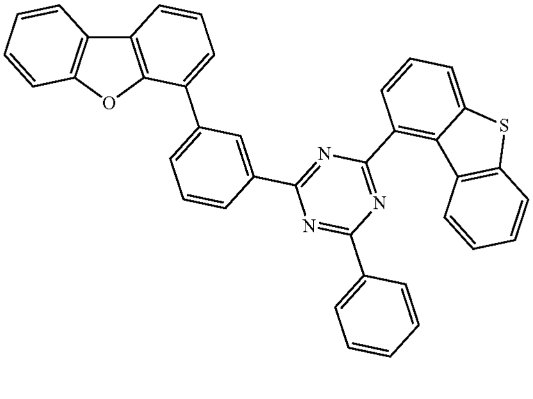
-continued
3-15
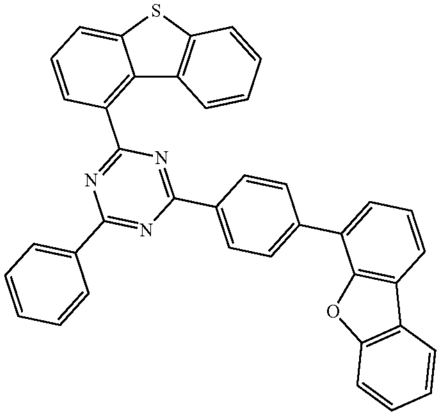
3-16
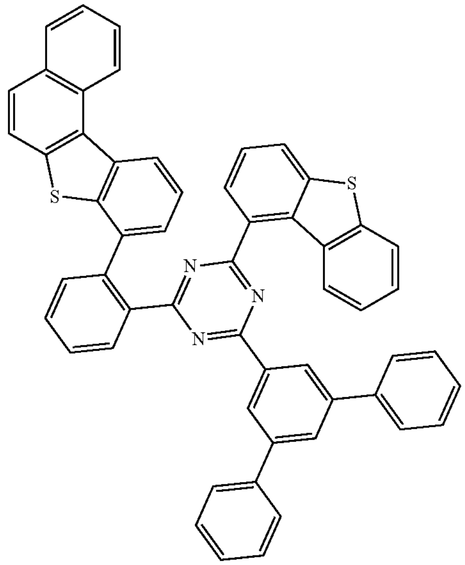
3-17
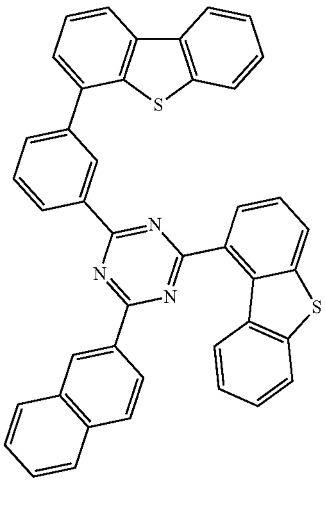

-continued
3-18
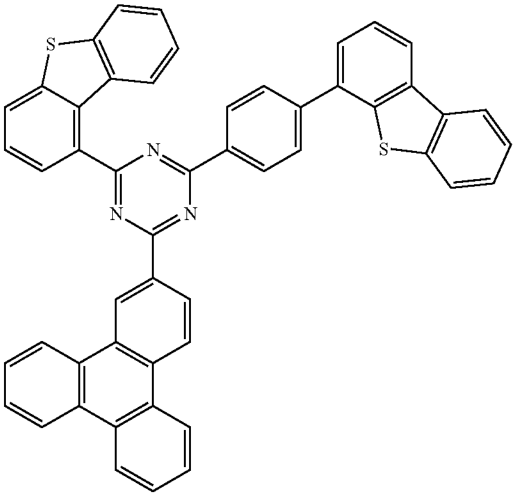
3-19
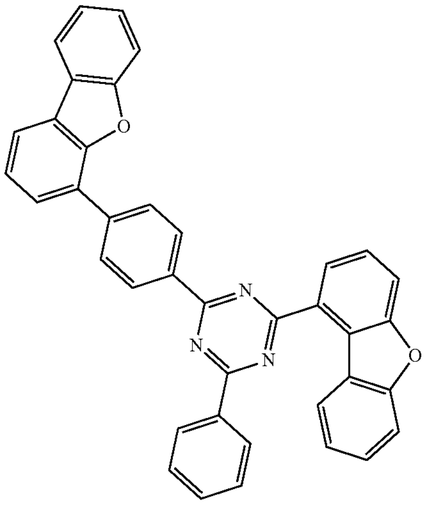
3-20
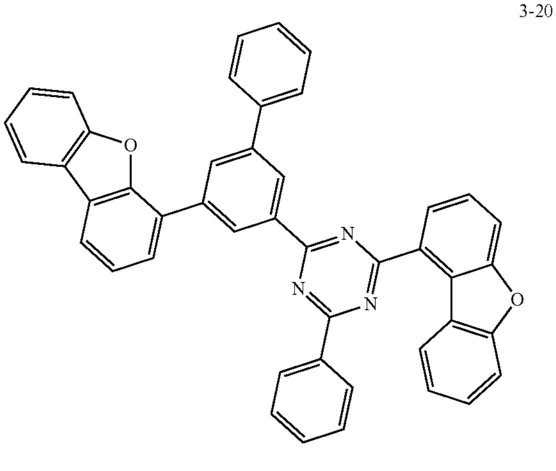
-continued
3-21
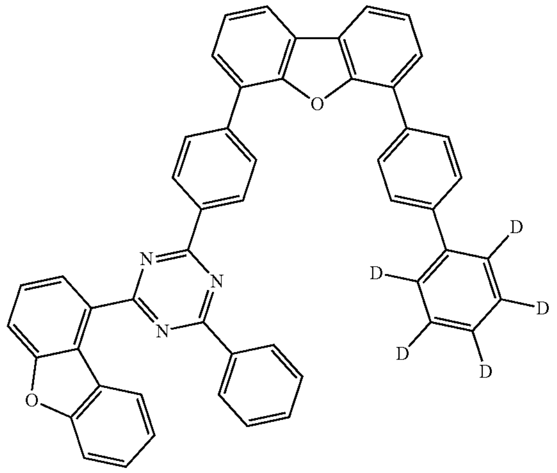
3-22
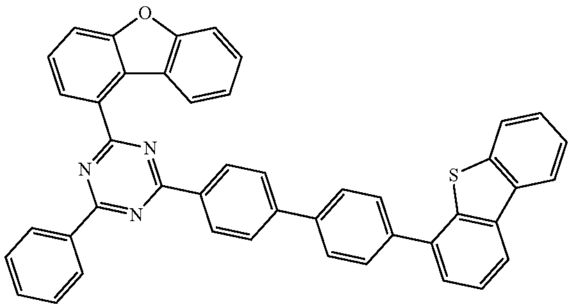
3-23
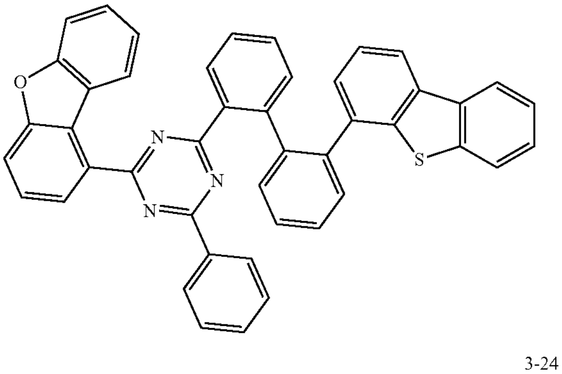
3-24
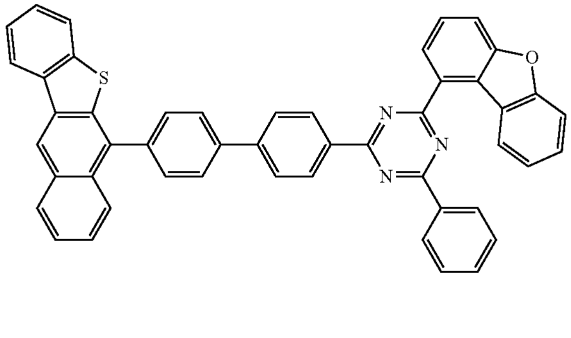

3-25
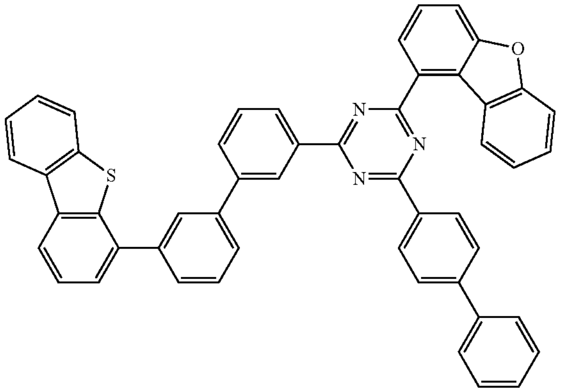
3-26
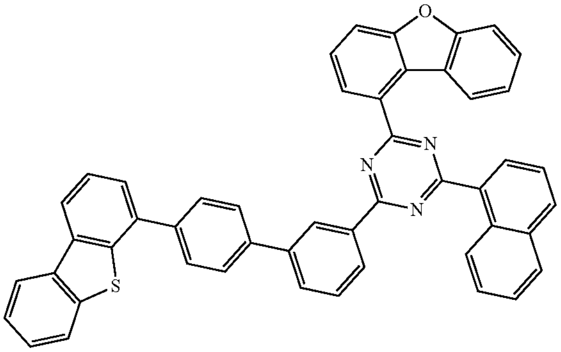
3-27
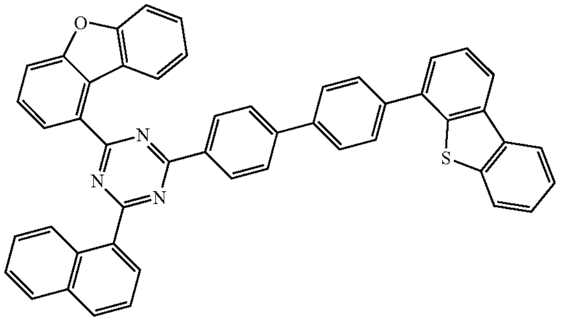
3-28
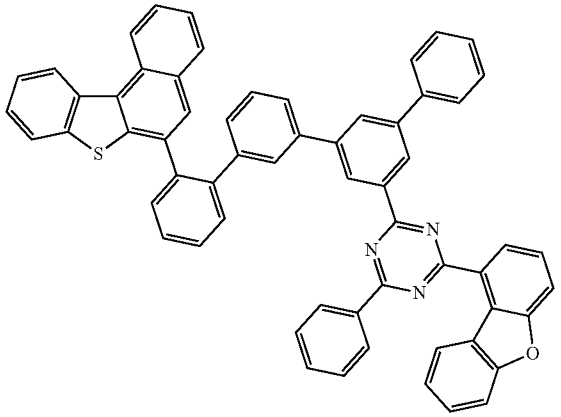
3-29
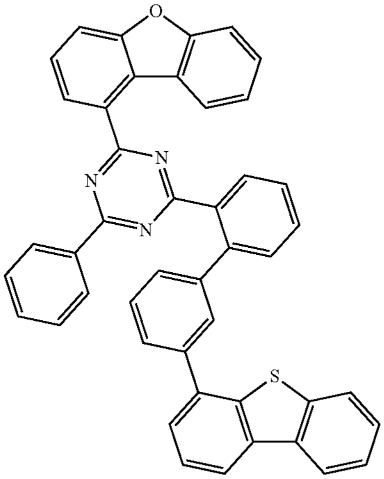
3-30
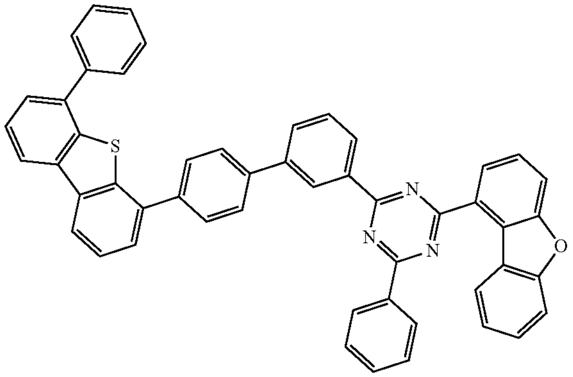
3-31
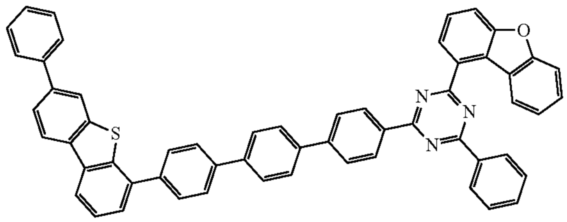
3-32
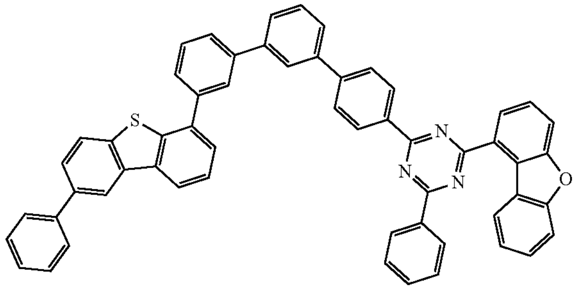

3-33
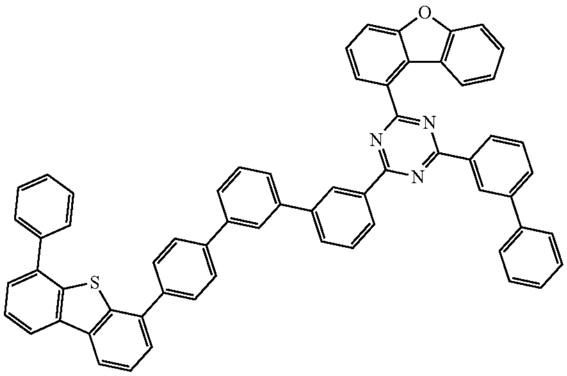
3-34
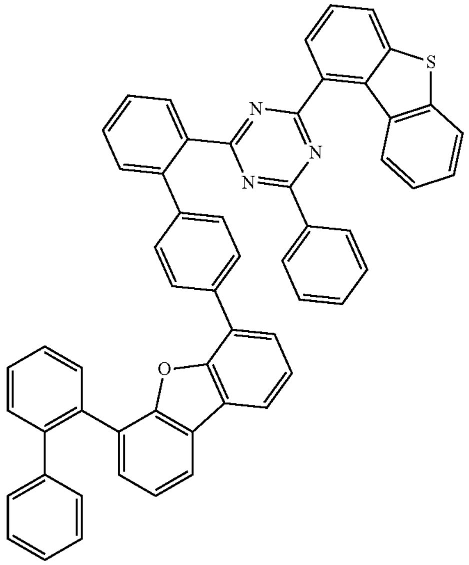
3-35
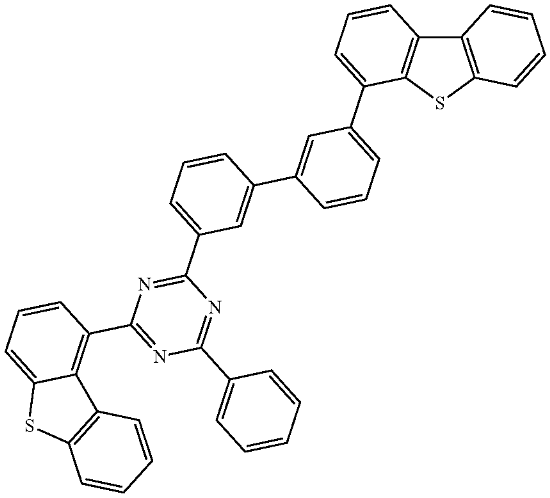
3-36
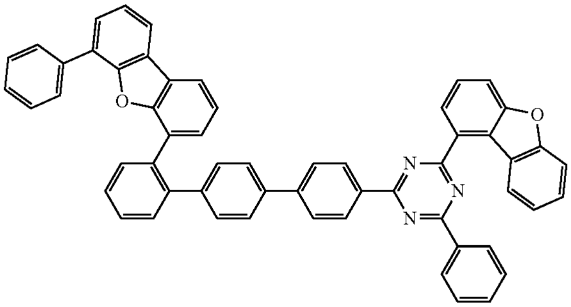
P-1
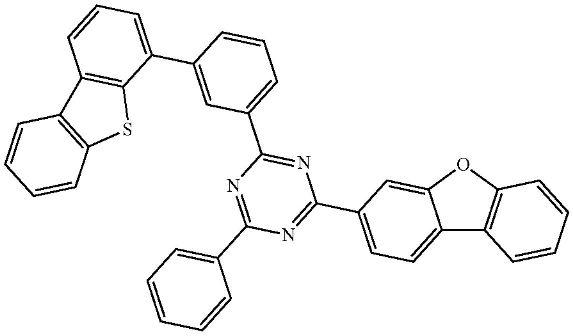
P-2
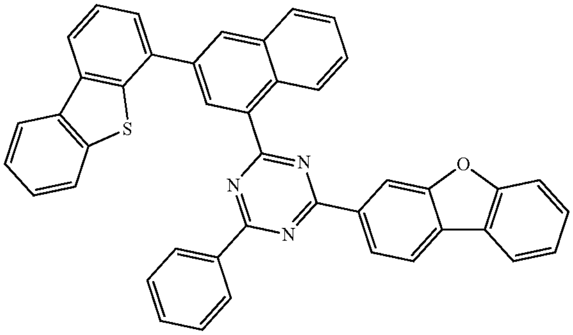
P-3
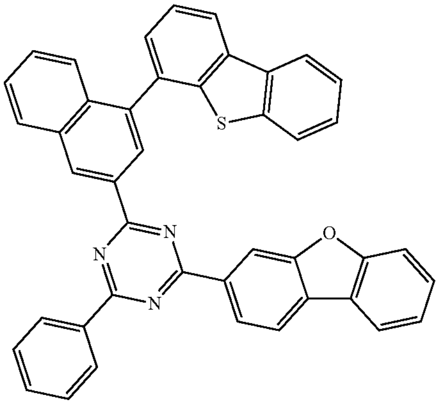

-continued
P-4
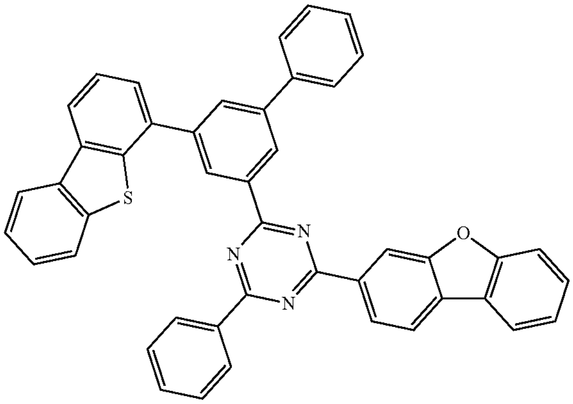
P-5
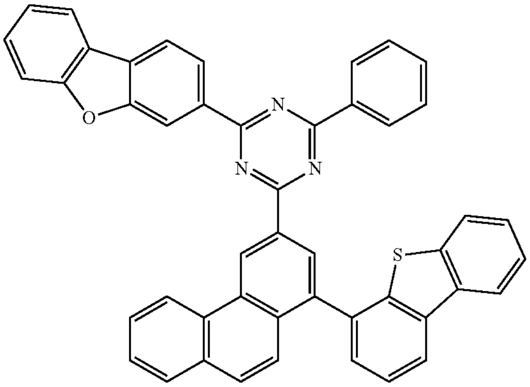
P-6
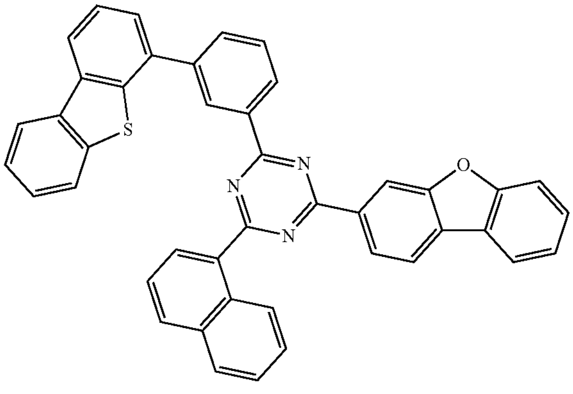
-continued
P-7
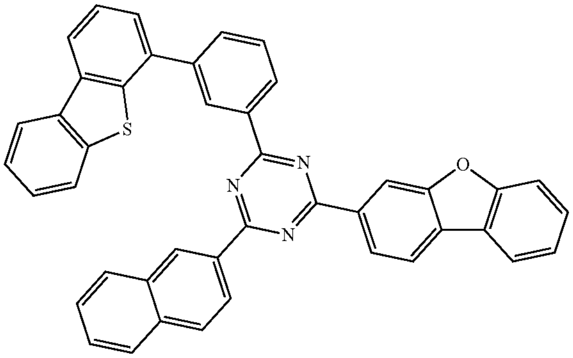
P-8
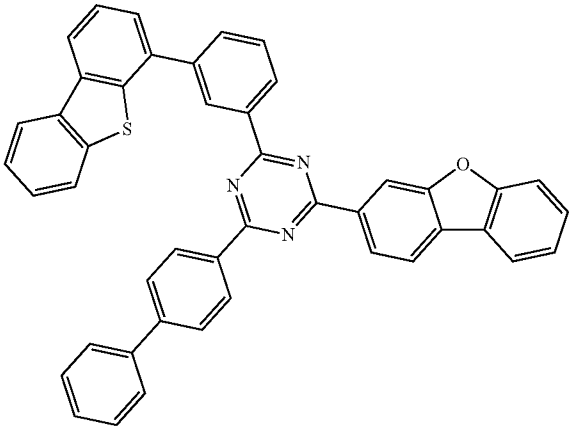
P-9
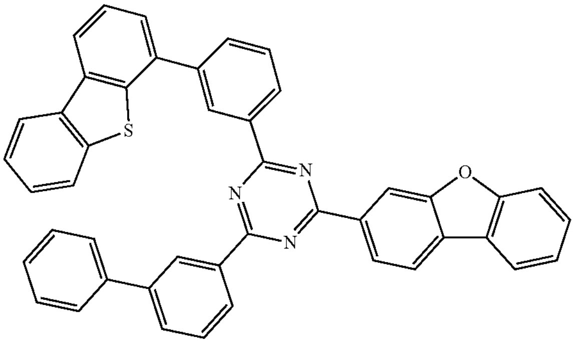
P-10
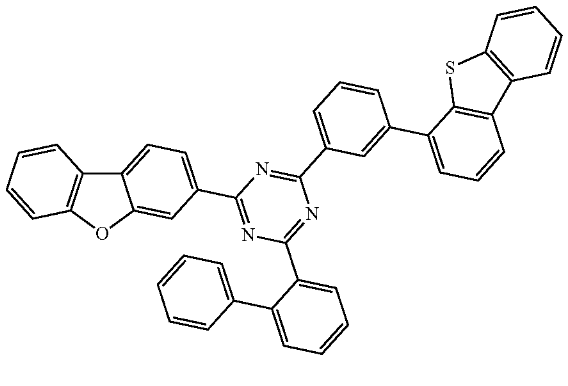

-continued
P-11
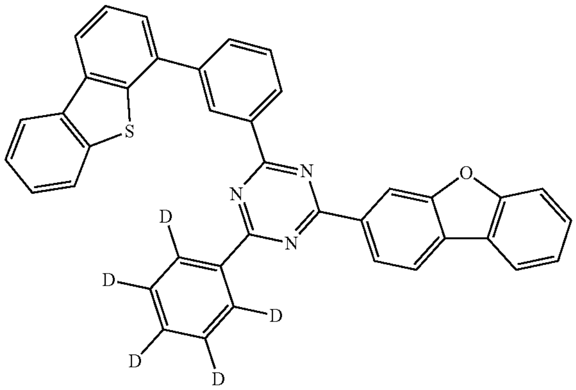
P-12
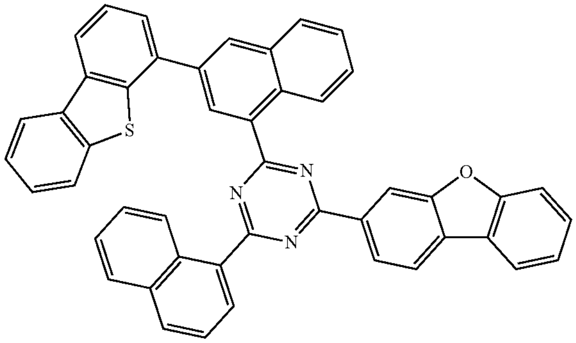
P-13
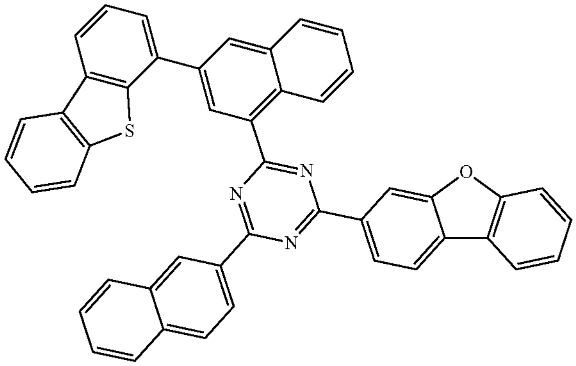
P-14
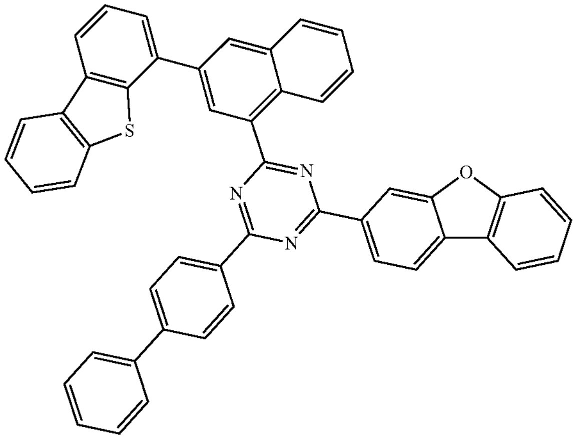
-continued
P-15
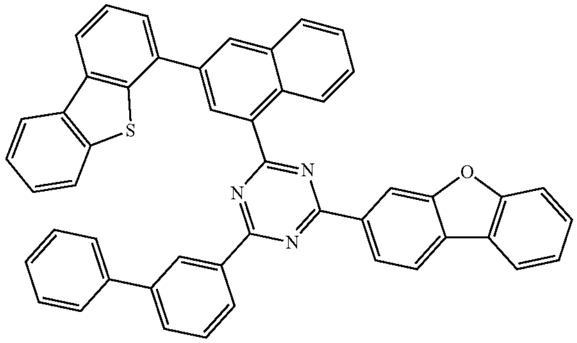
P-16
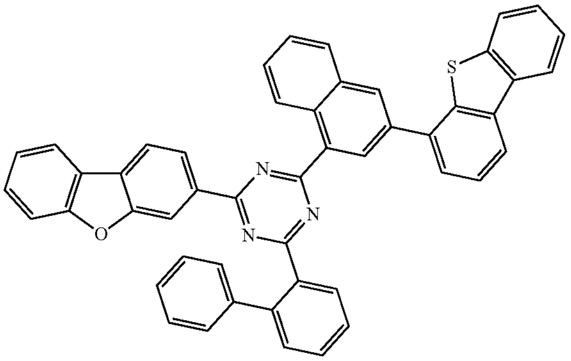
P-17
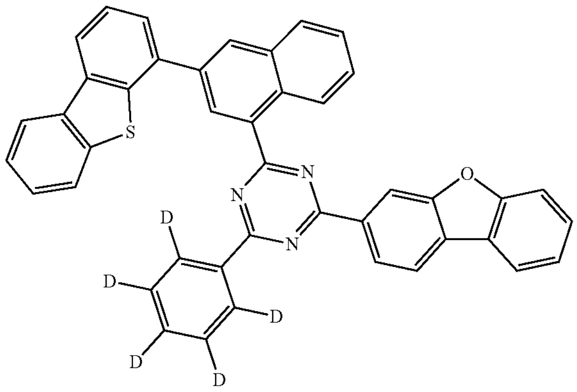
P-18
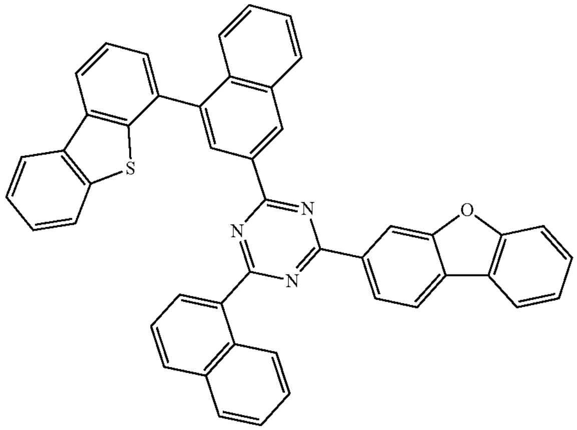

-continued
P-19
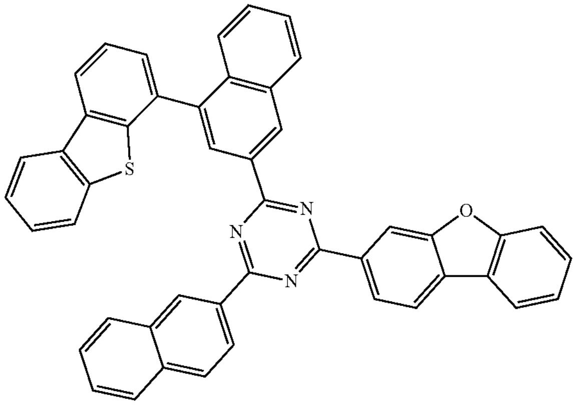
P-20
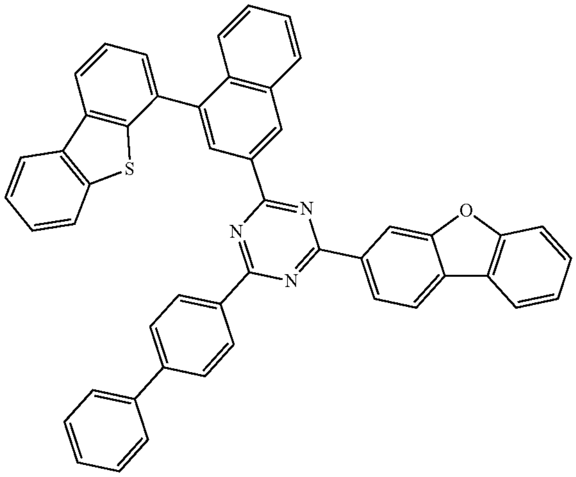
P-21
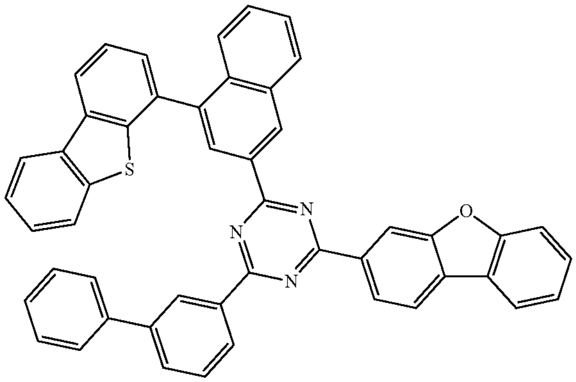
-continued
P-22
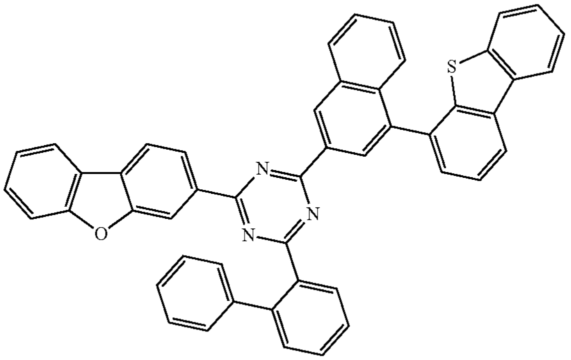
P-23
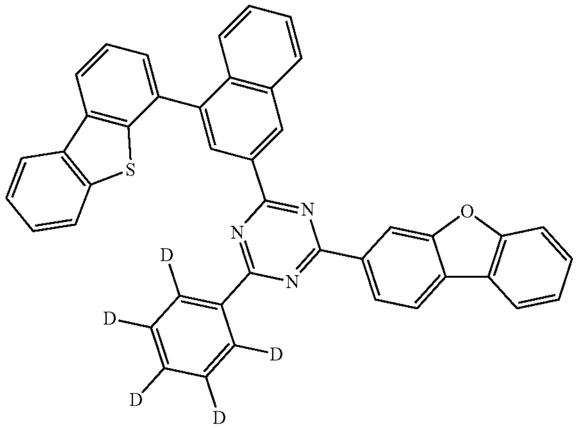
P-24
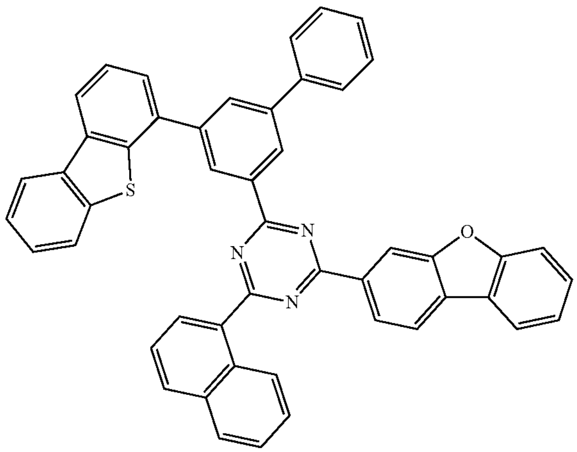

-continued
P-25
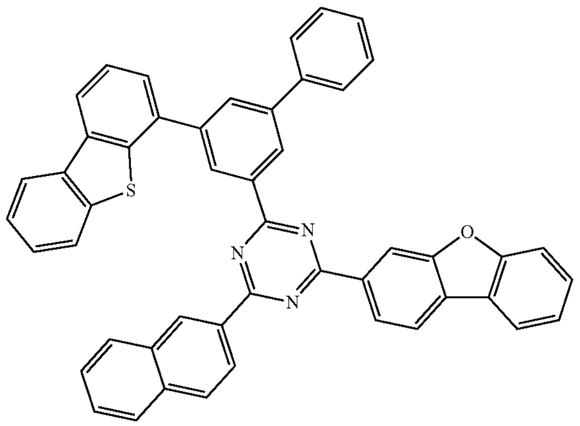
P-26
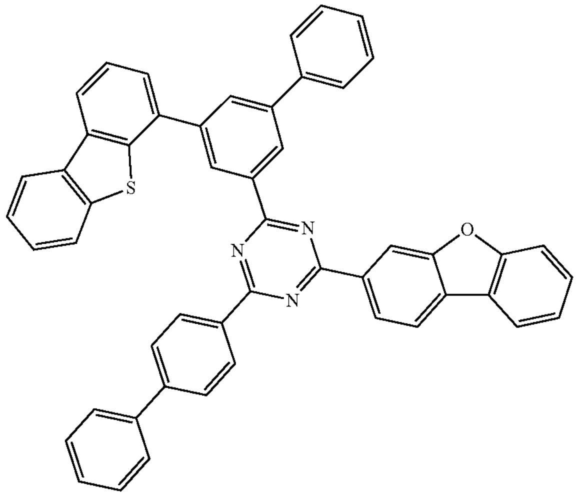
P-27
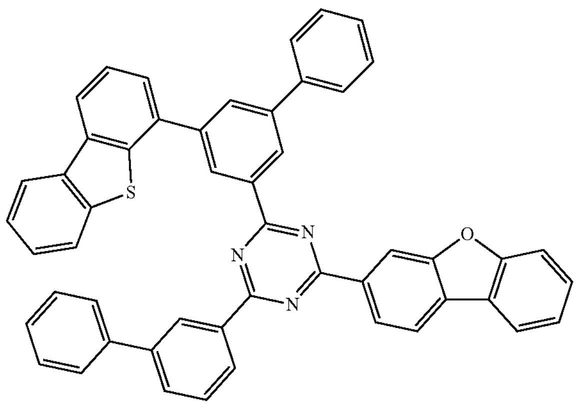
-continued
P-28
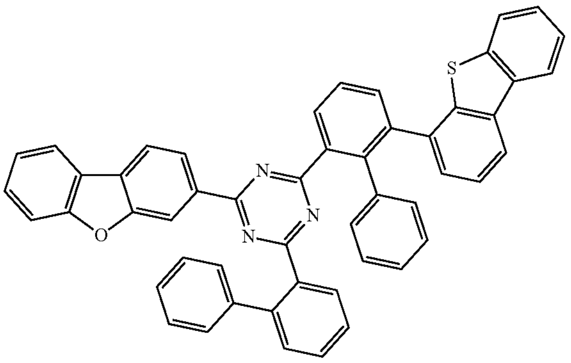
P-29
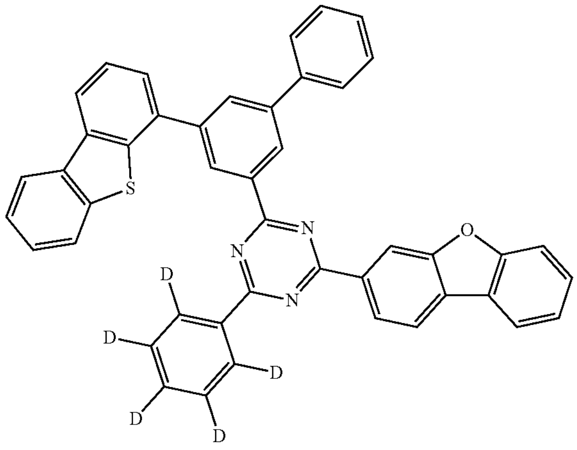
P-30
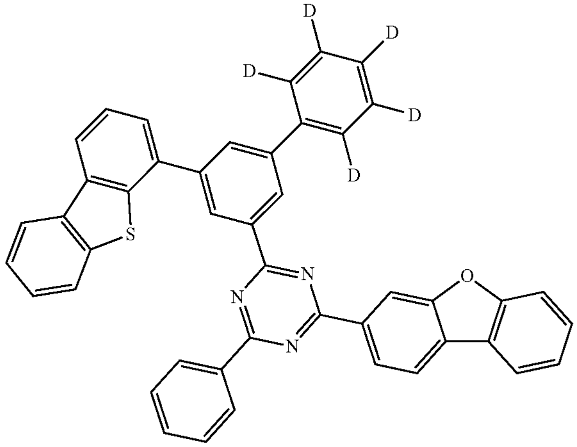

-continued
P-31
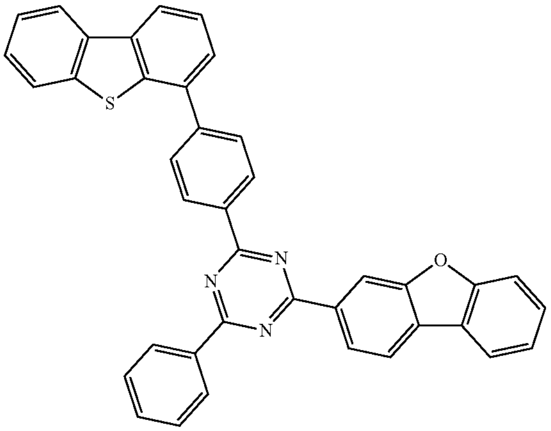
P-32
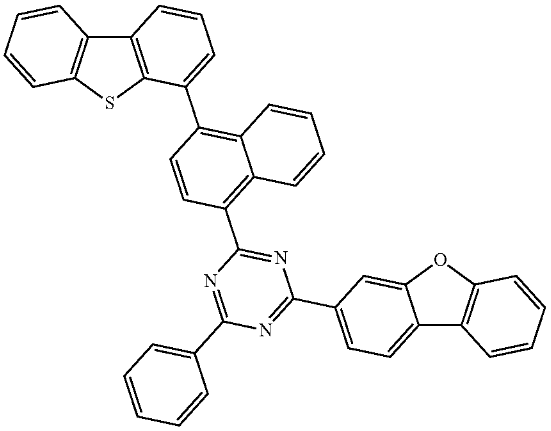
P-33
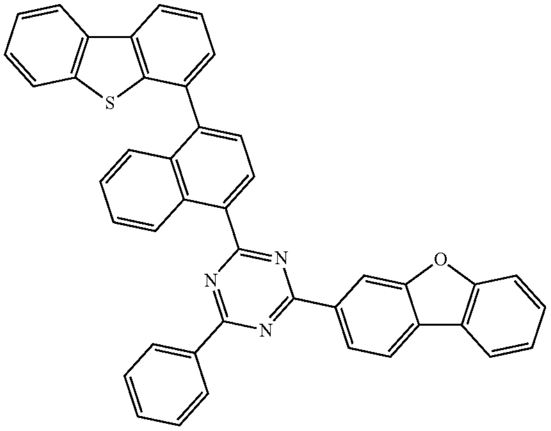
-continued
P-34
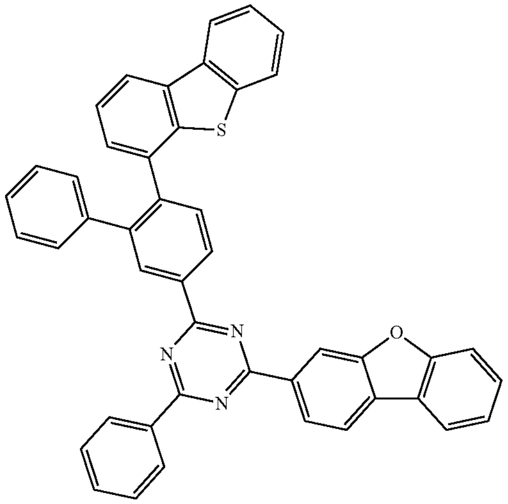
P-35
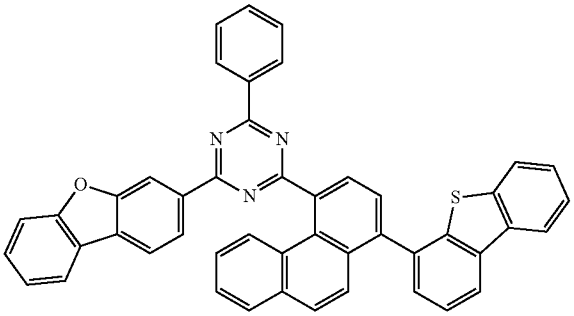
P-36
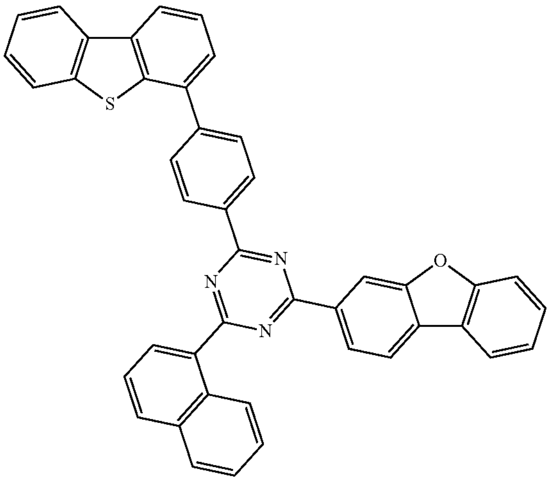

-continued
P-37
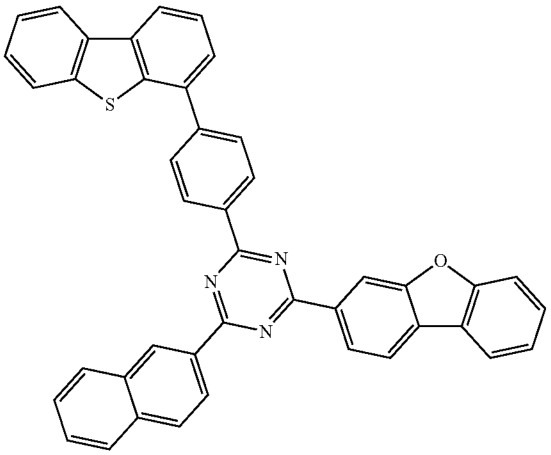
P-38
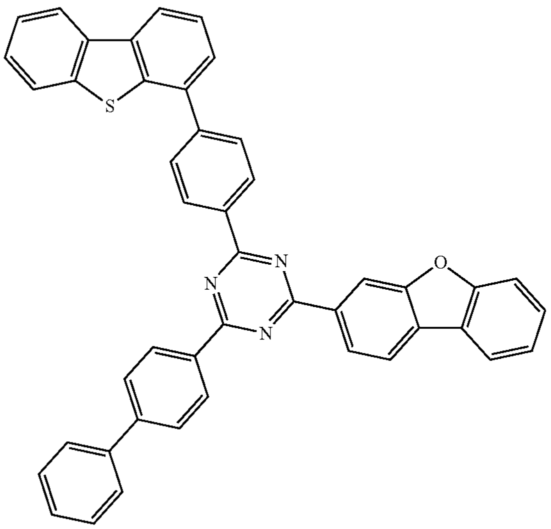
P-39
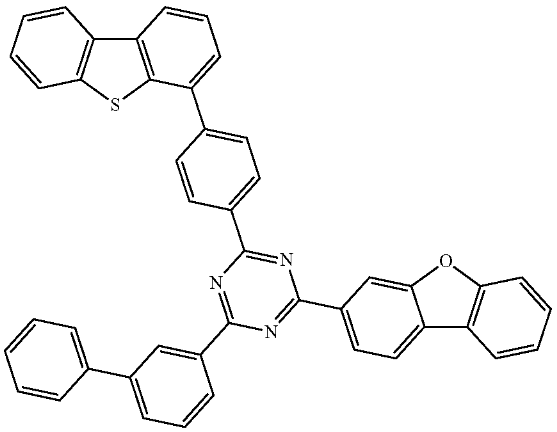
-continued
P-40
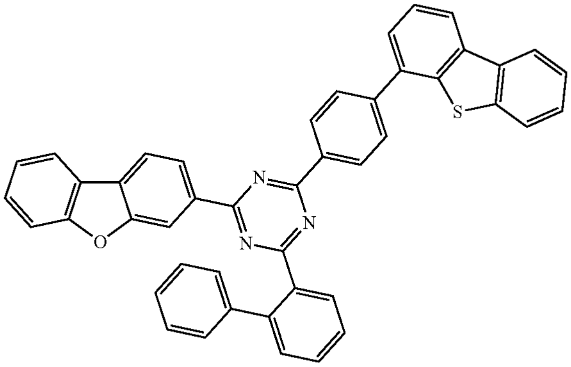
P-41
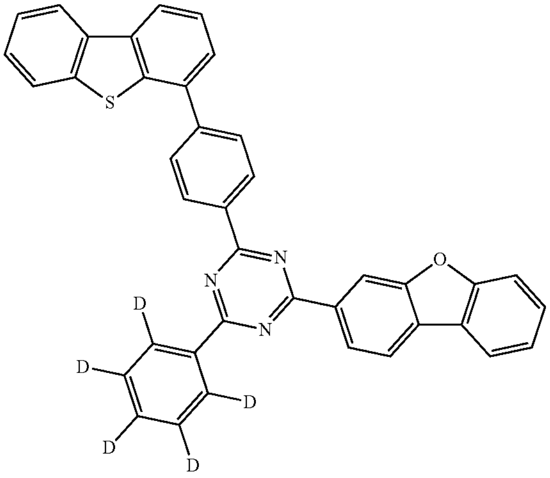
P-42
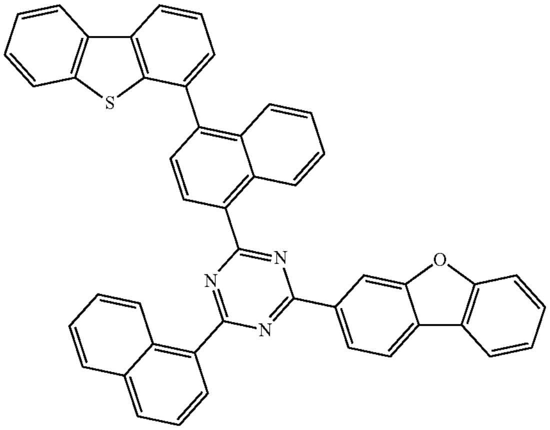

-continued
P-43
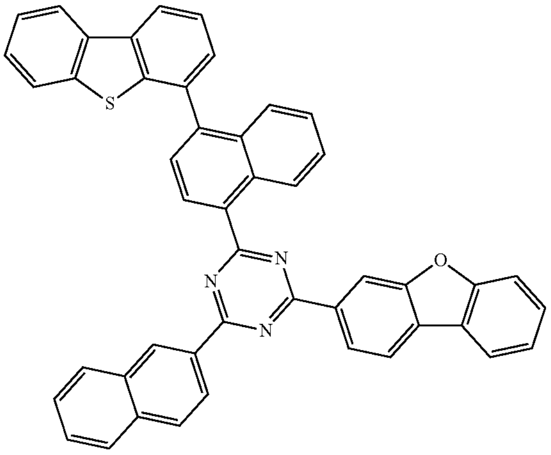
P-44
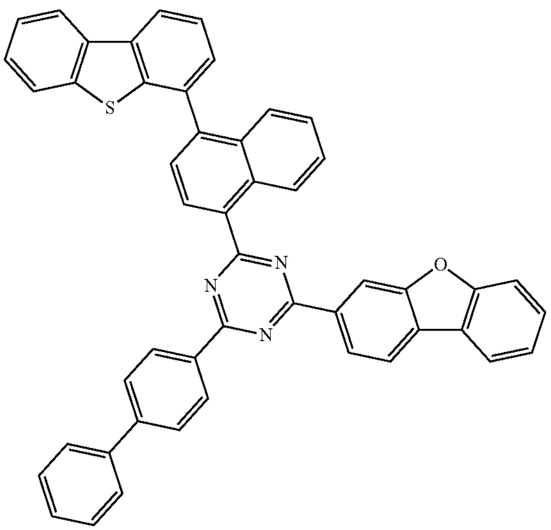
P-45
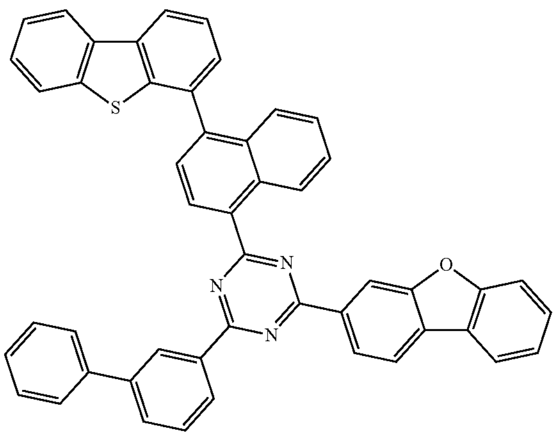
-continued
P-46
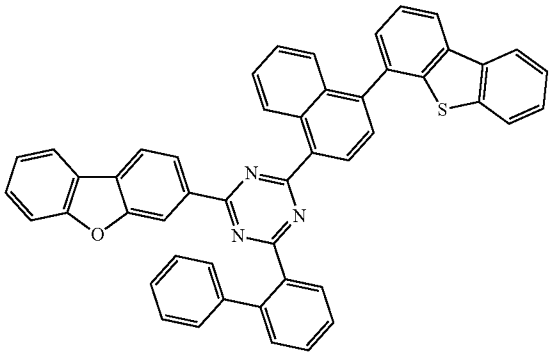
P-47
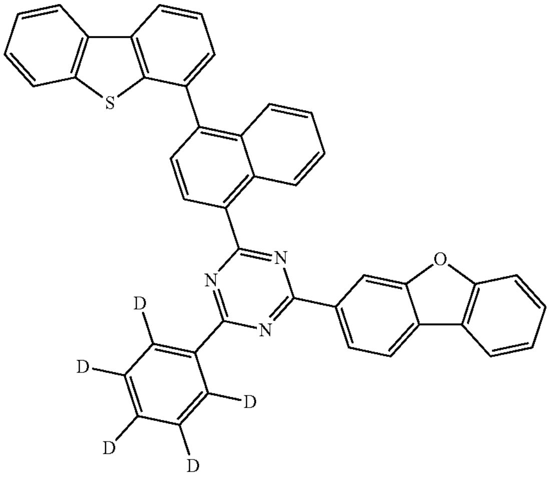
P-48
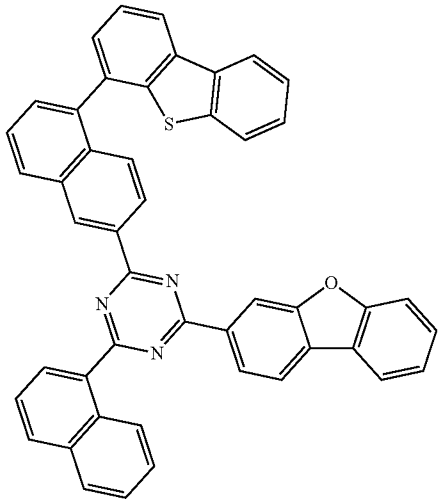

-continued
P-49
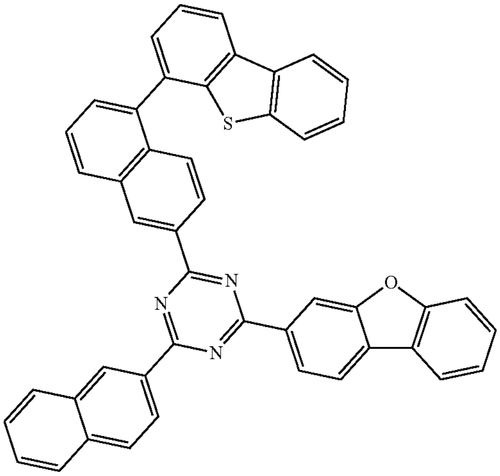
P-50
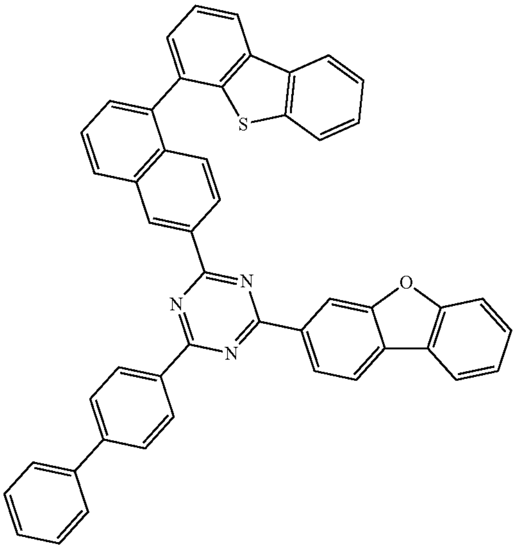
P-51
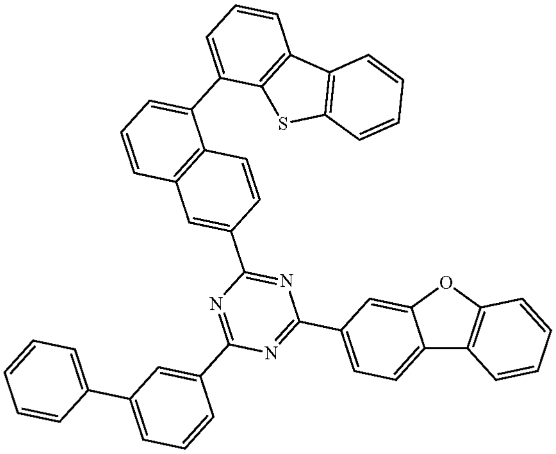
-continued
P-52
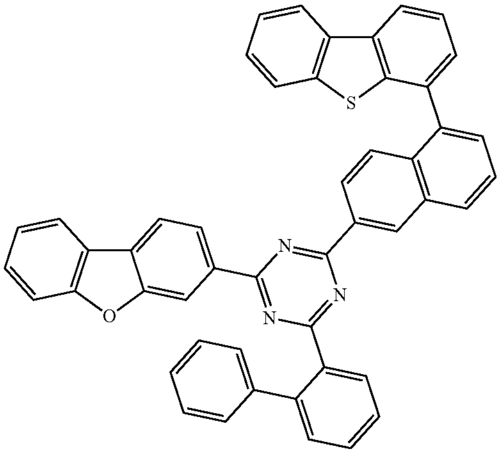
P-53
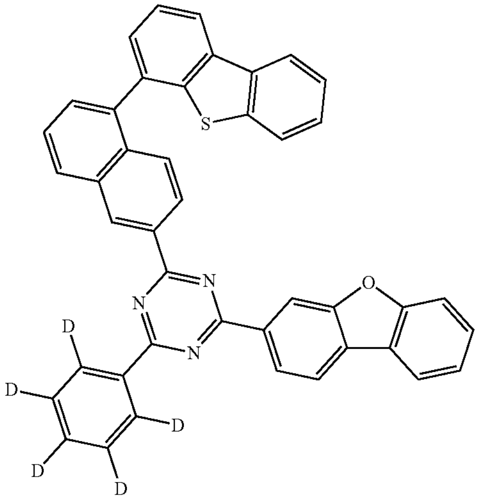
P-54
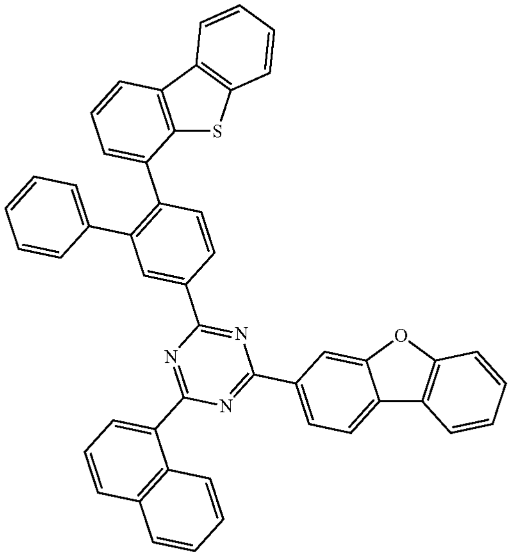

-continued
P-55
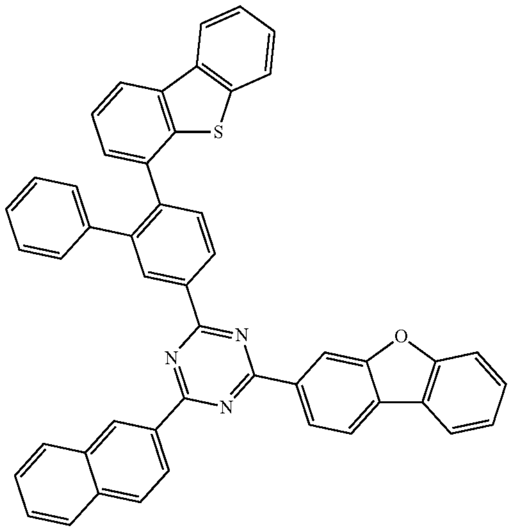
P-56
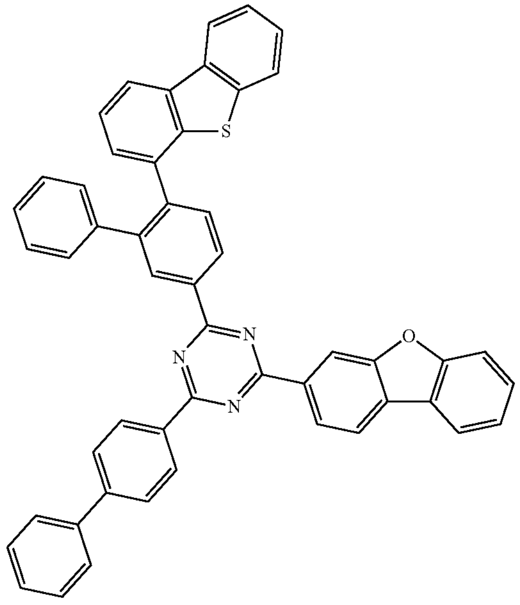
-continued
P-57
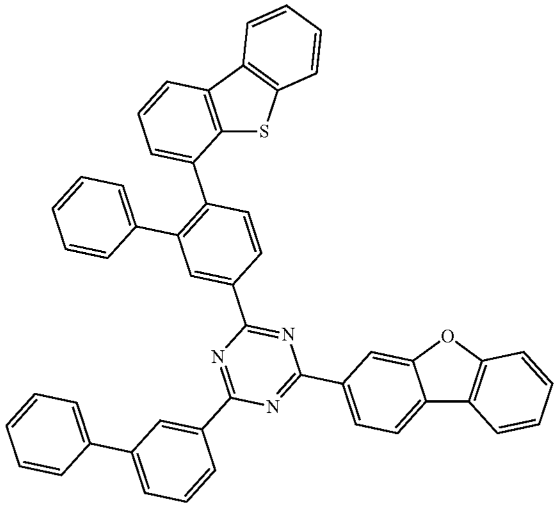
P-58
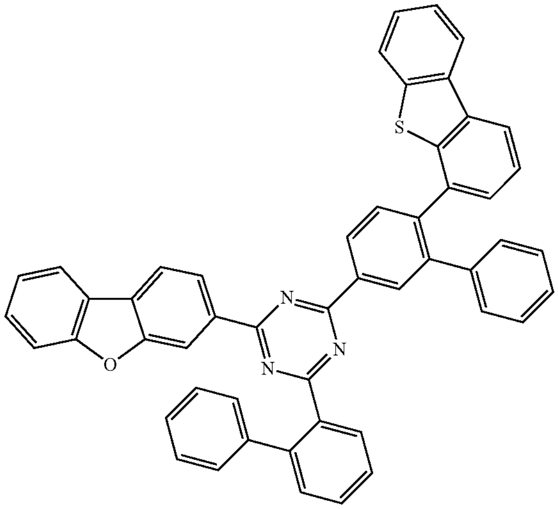
P-59
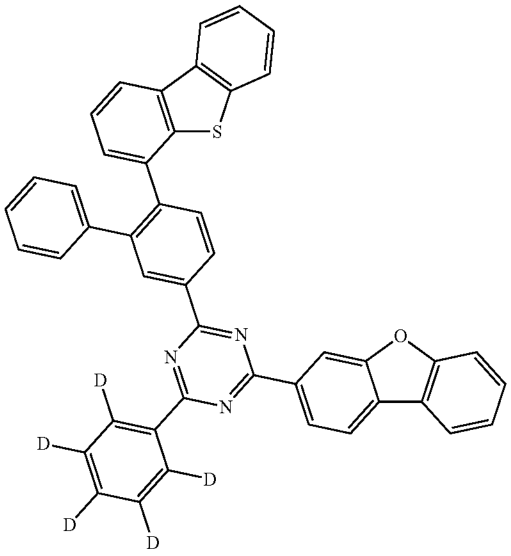

-continued
P-60
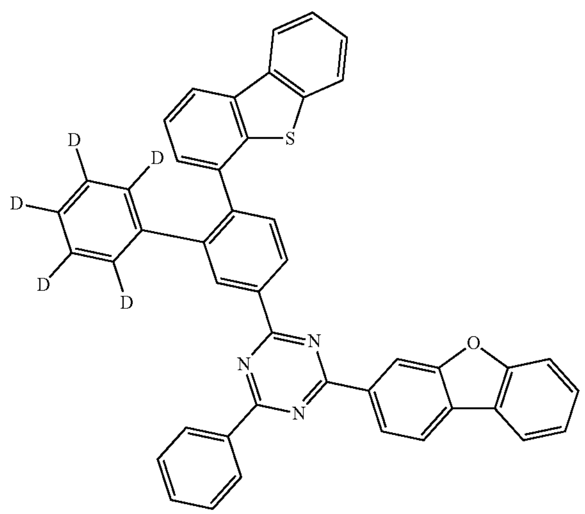
P-61
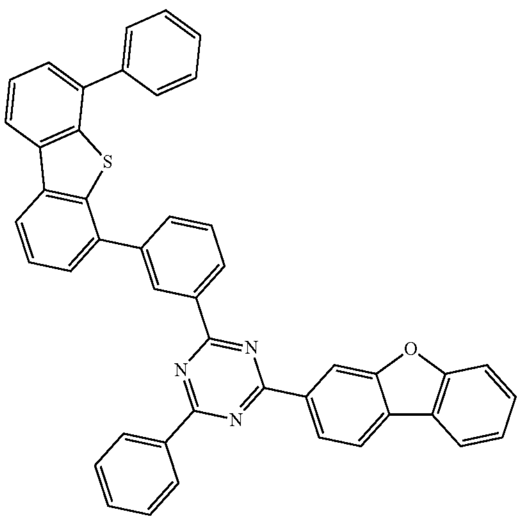
P-62
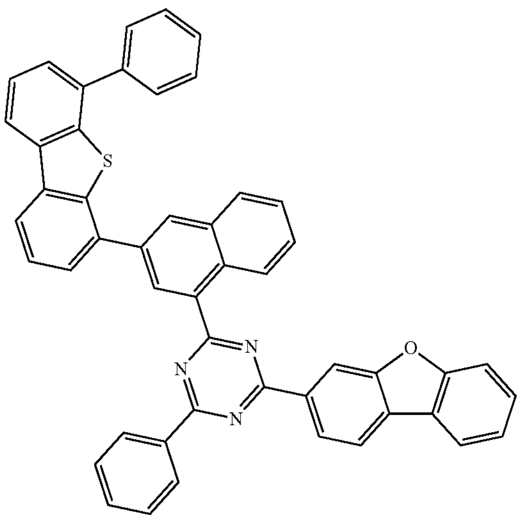
-continued
P-63
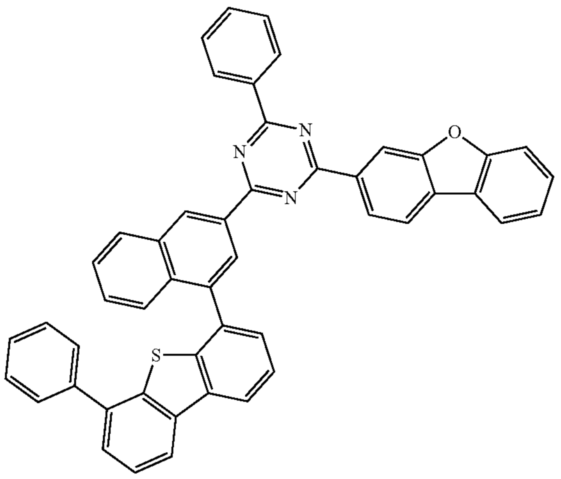
P-64
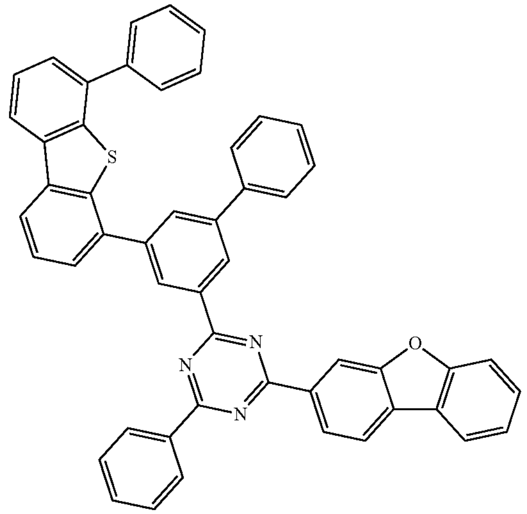
P-65
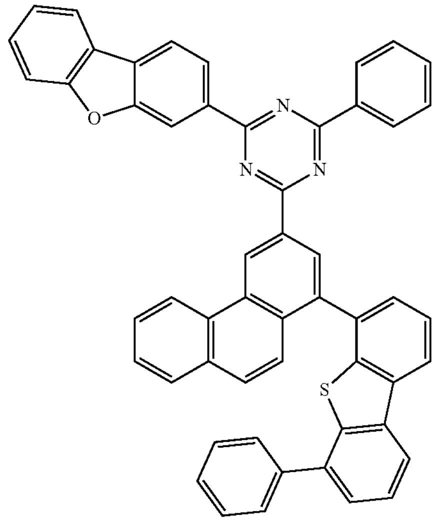

-continued
P-66
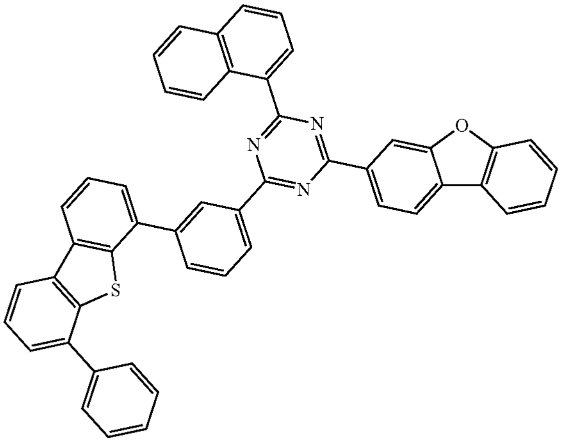
P-67
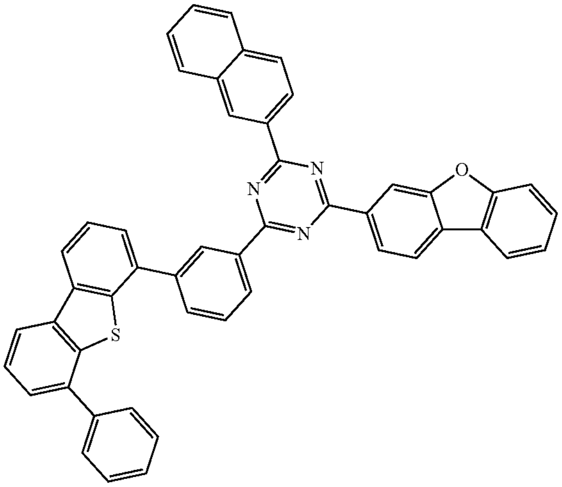
P-68
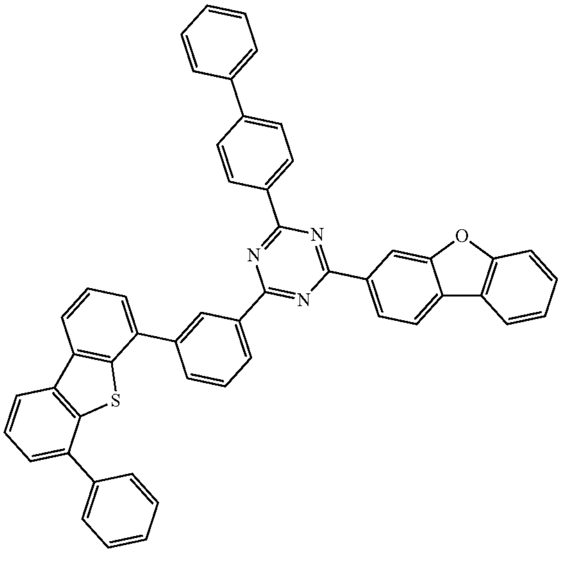
-continued
P-69
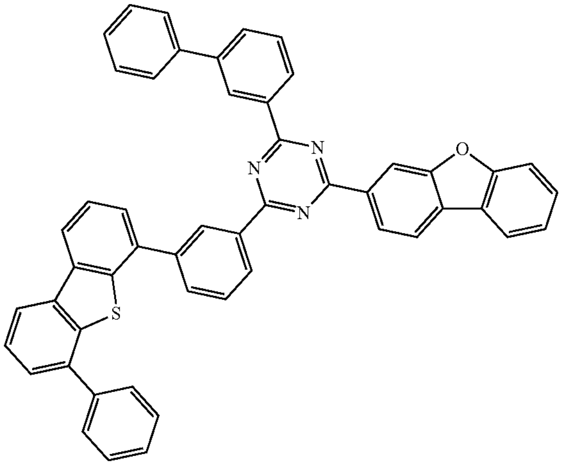
P-70
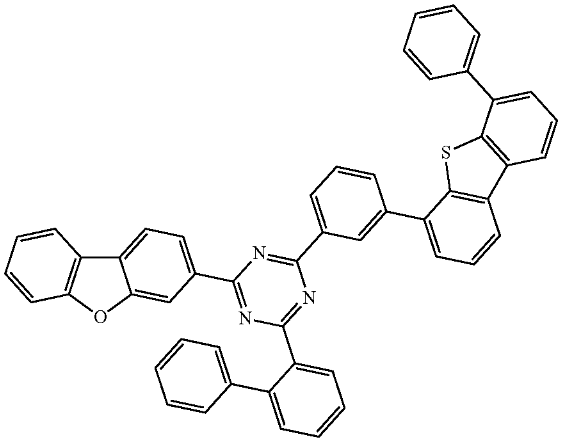
P-71
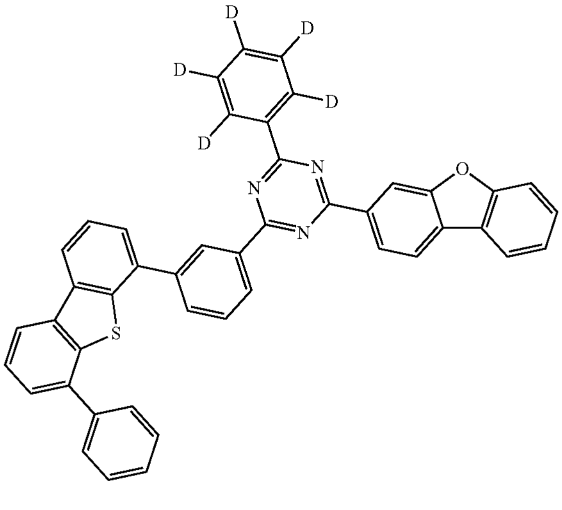

-continued
P-72
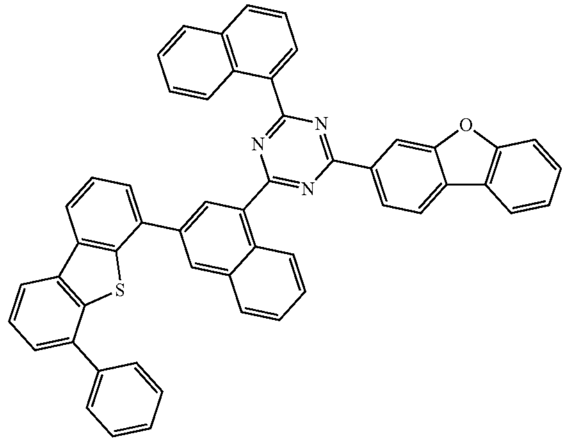
P-73
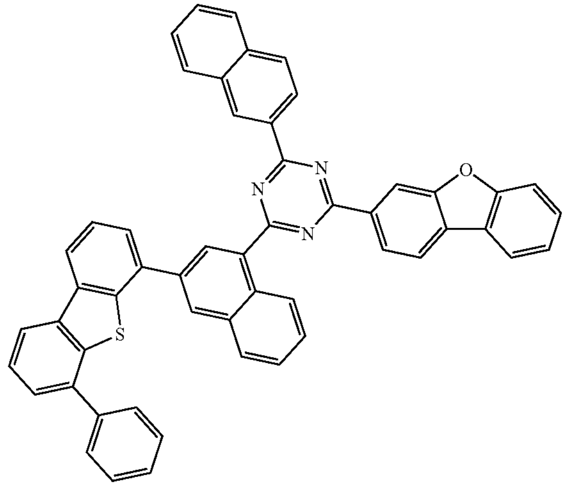
P-74
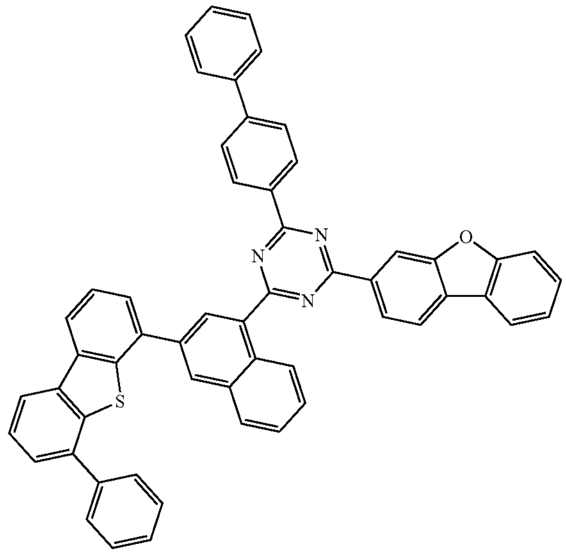
-continued
P-75
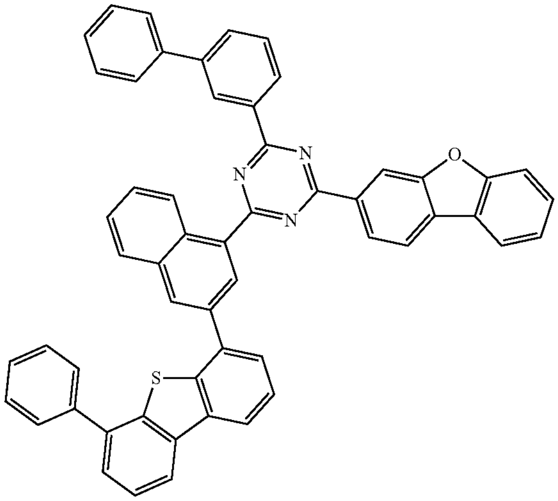
P-76
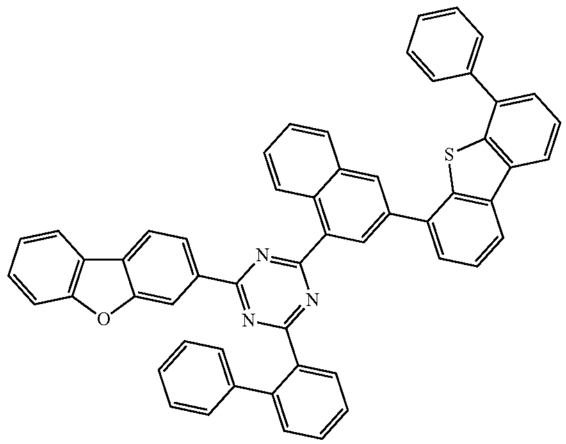
P-77
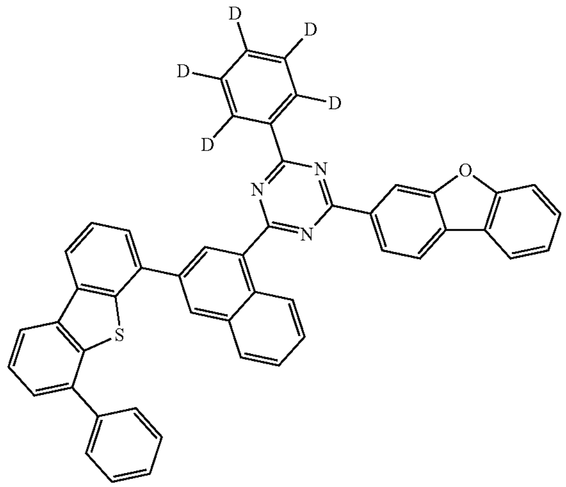

-continued
P-78
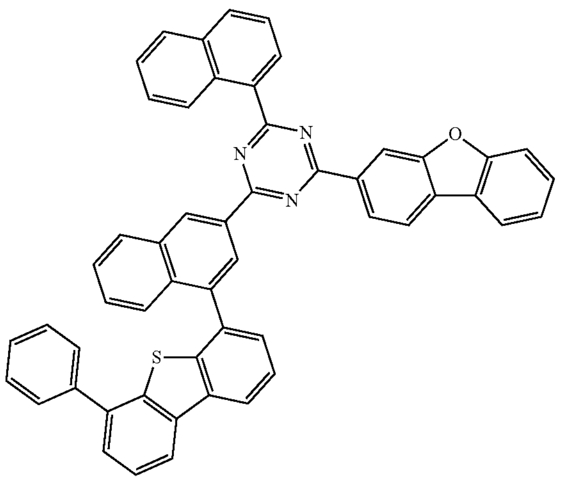
P-79
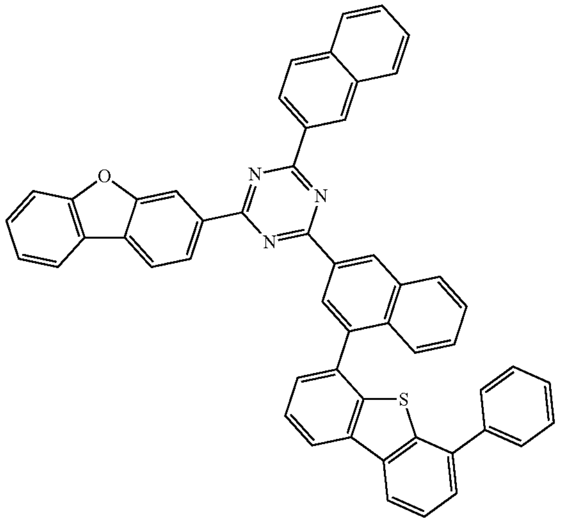
P-80
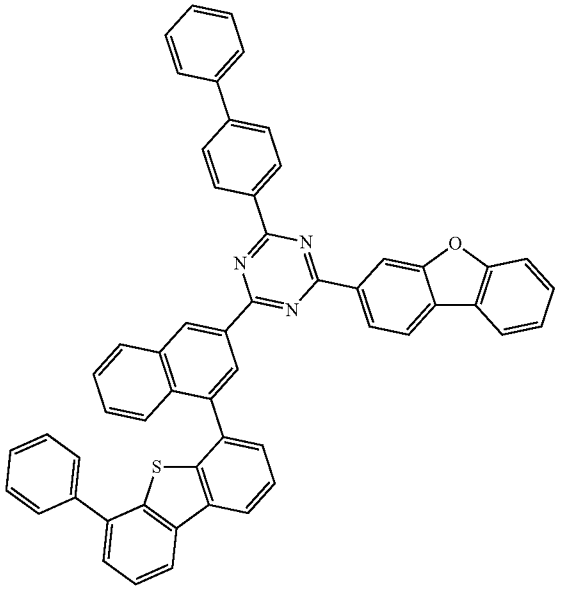
-continued
P-81
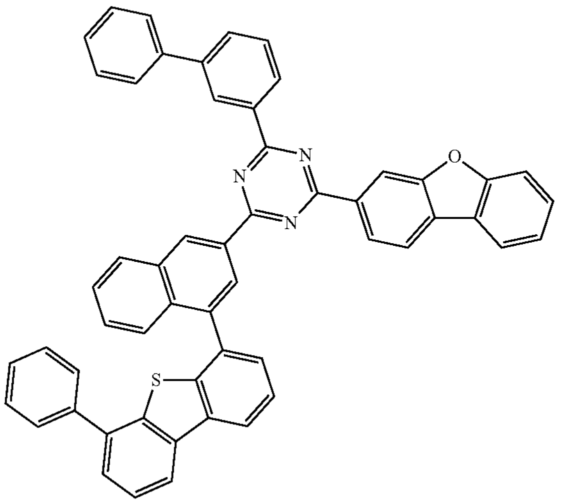
P-82
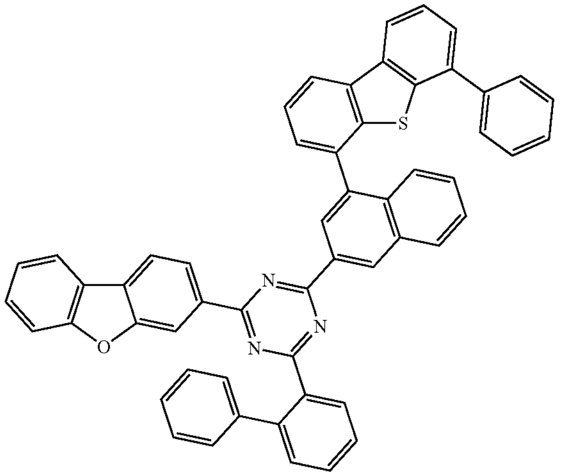
P-83
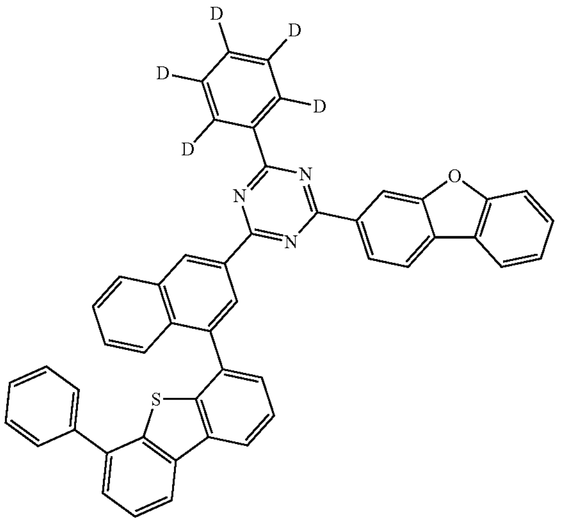

-continued
P-84
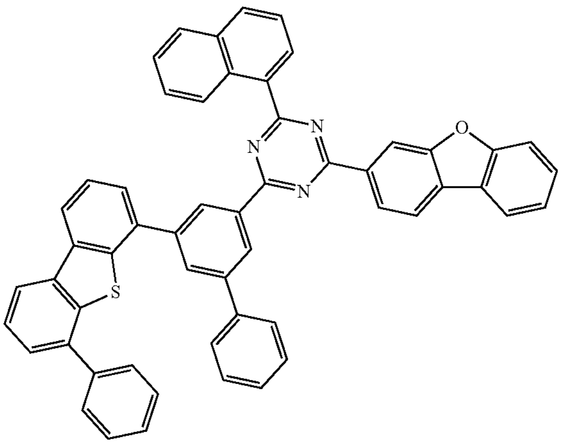
P-85
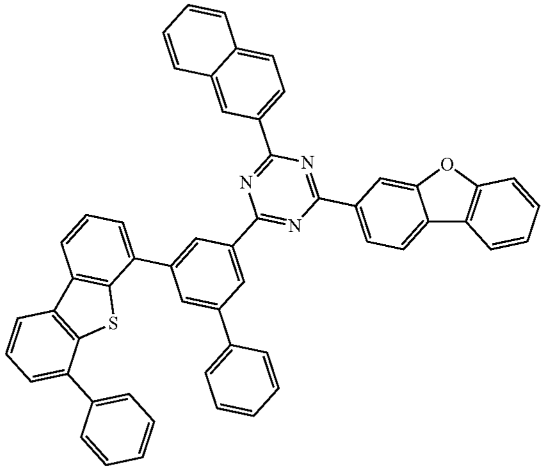
P-86
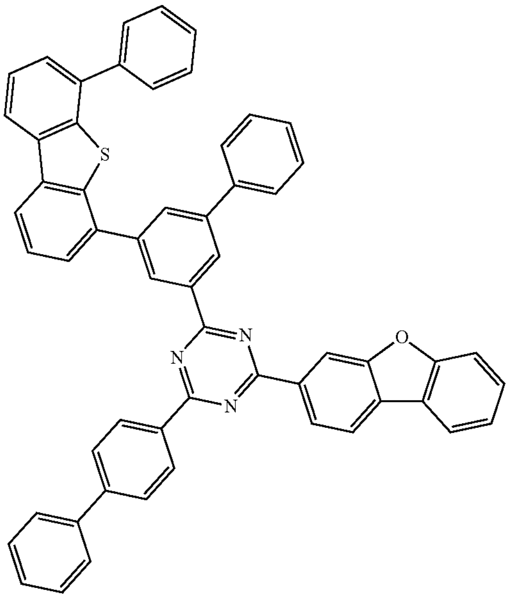
-continued
P-87
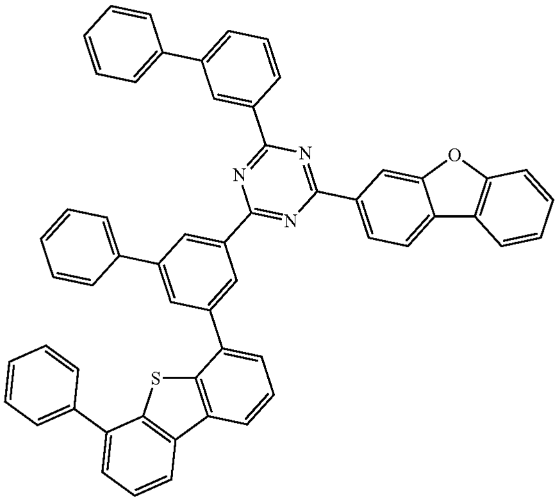
P-88
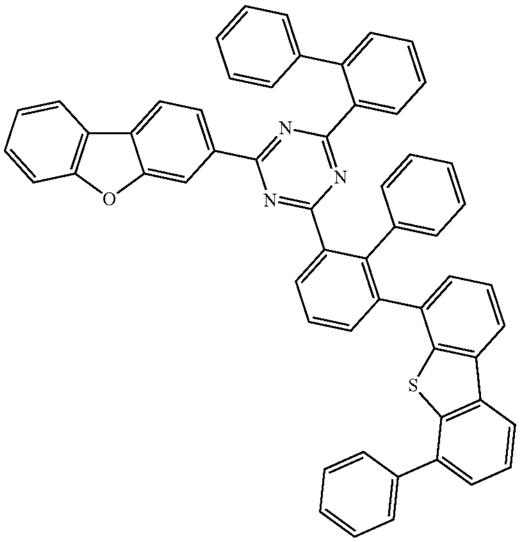
P-89
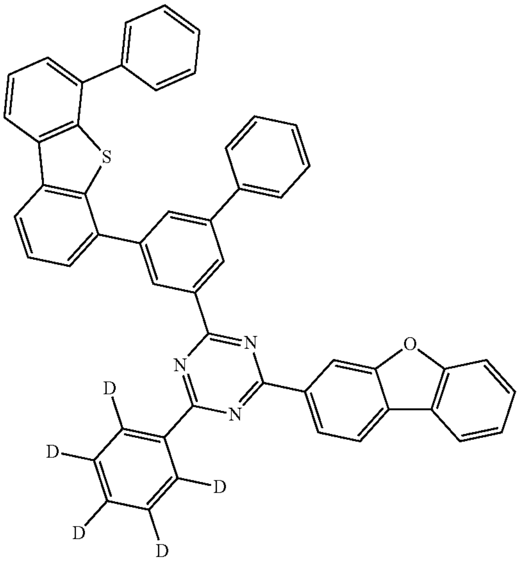

-continued
P-90
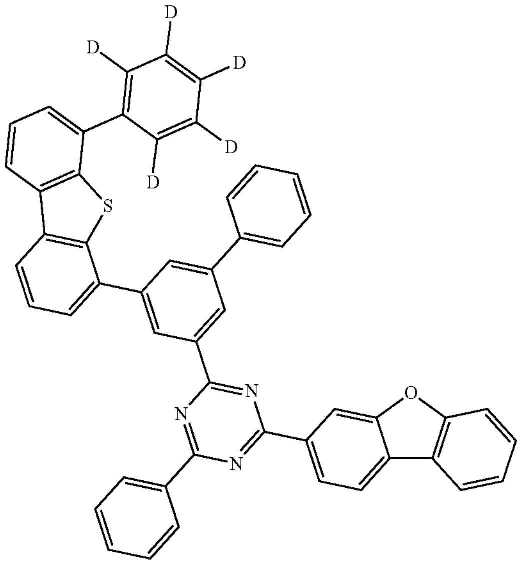
P-91
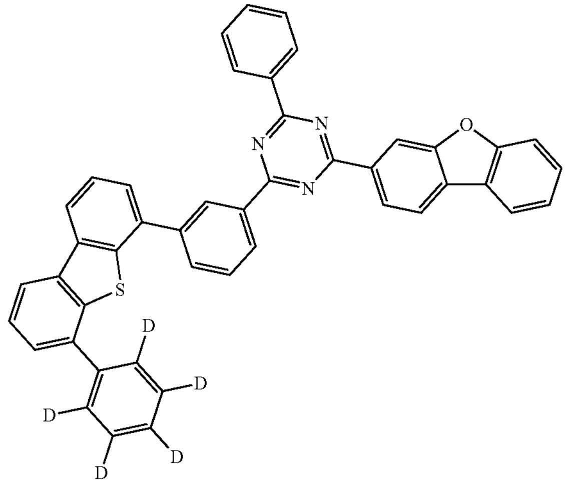
P-92
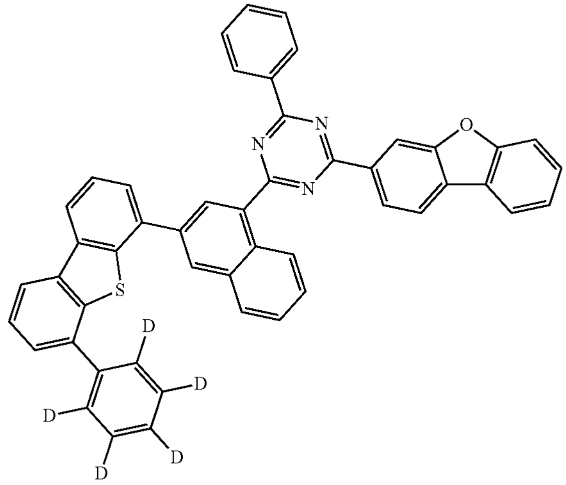
-continued
P-93
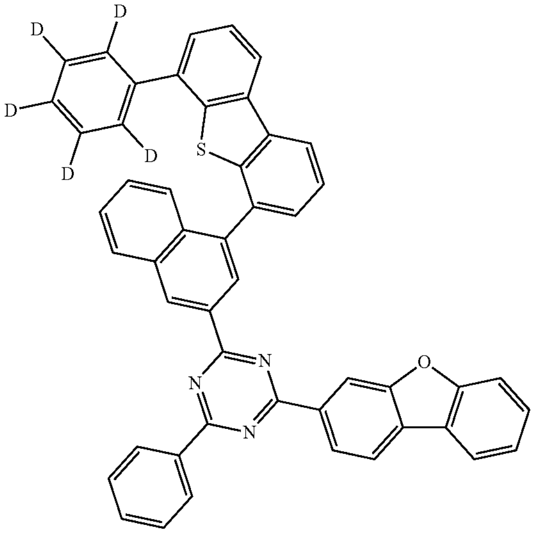
P-94
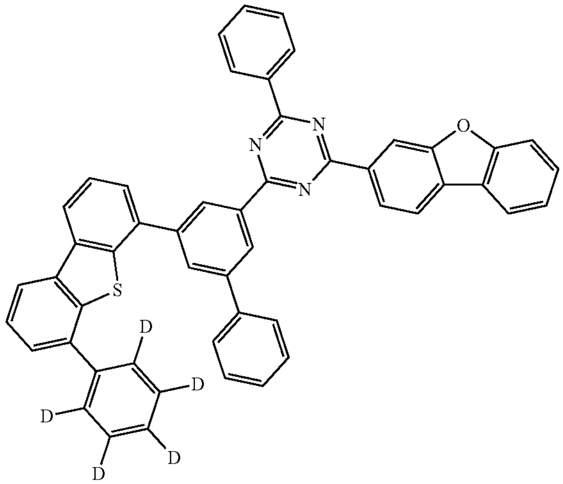
P-95
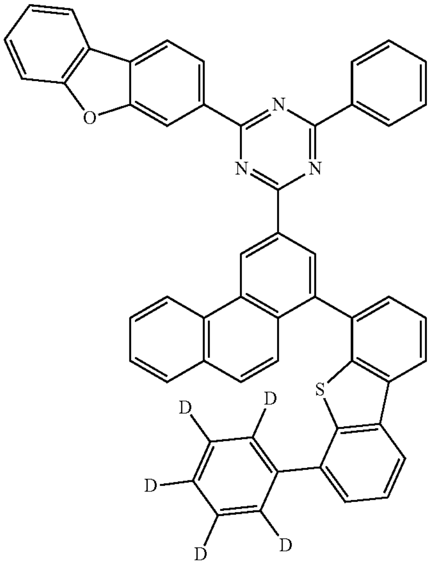

-continued
P-96
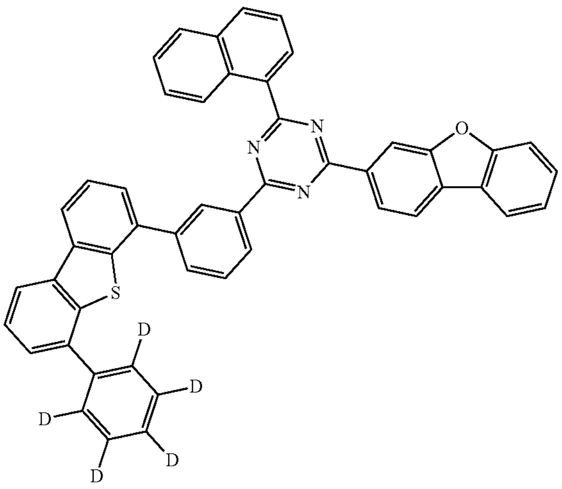
P-97
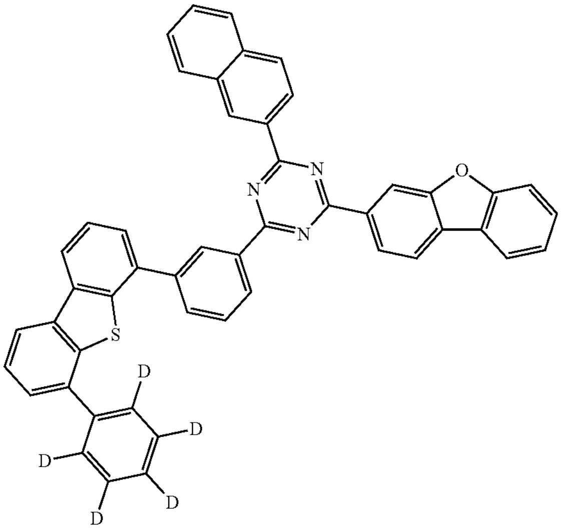
P-98
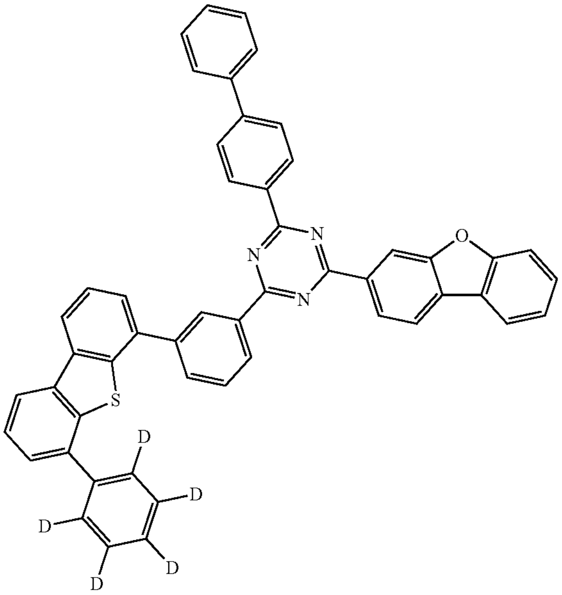
-continued
P-99
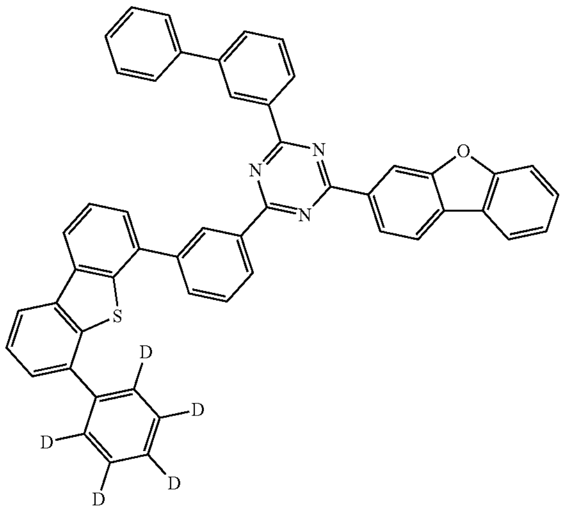
P-100
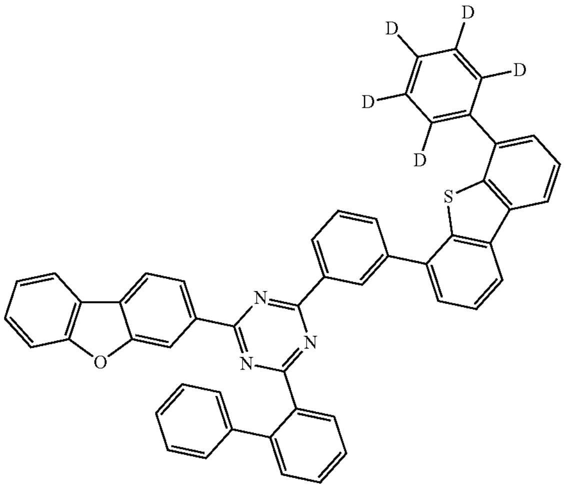
P-101
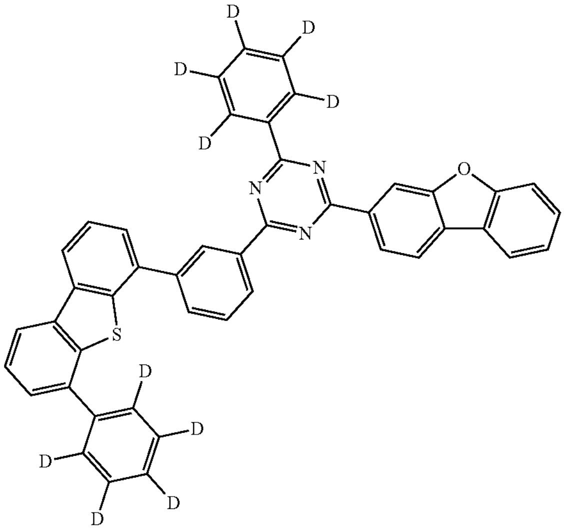

-continued
P-102
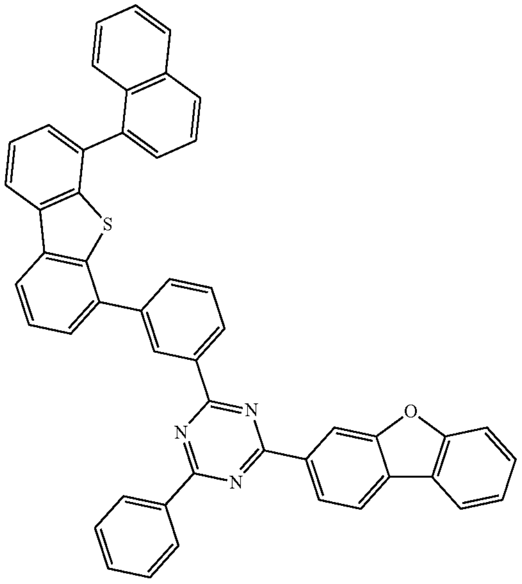
P-103
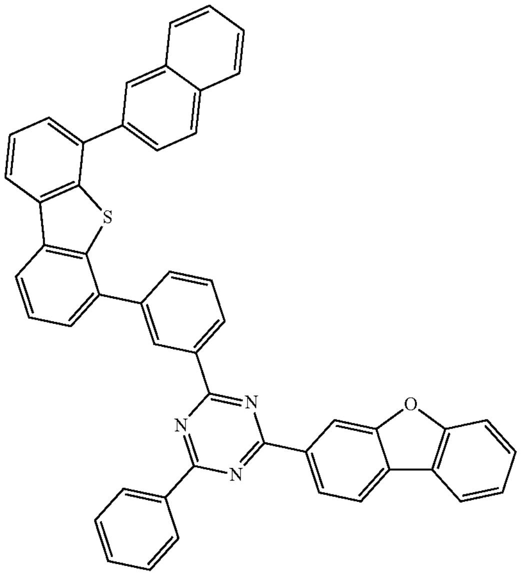
-continued
P-104
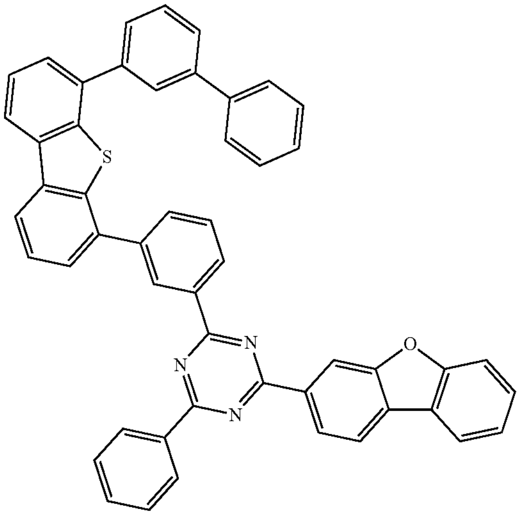
P-105
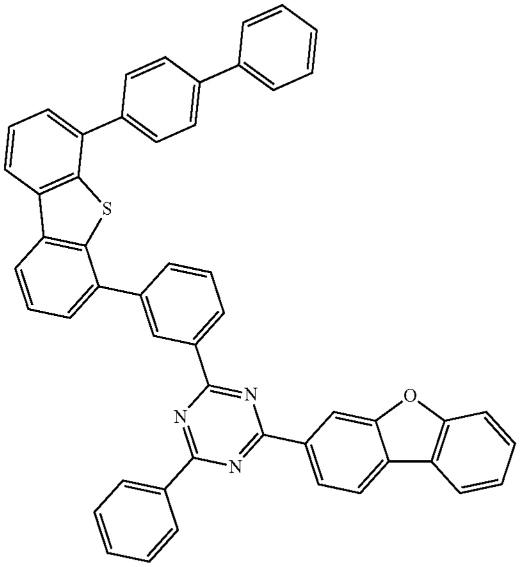
P-106
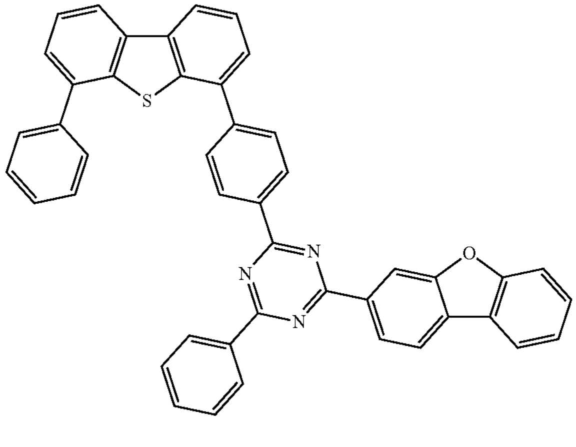

P-107
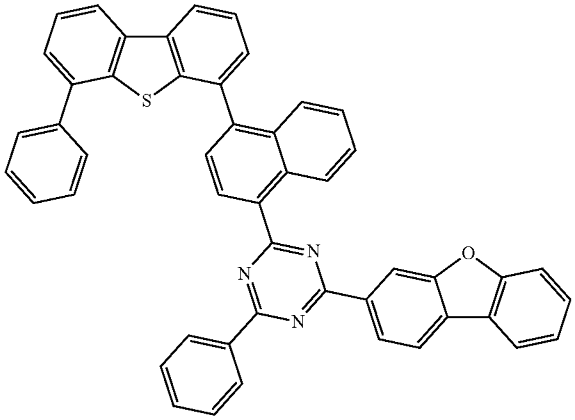
P-108
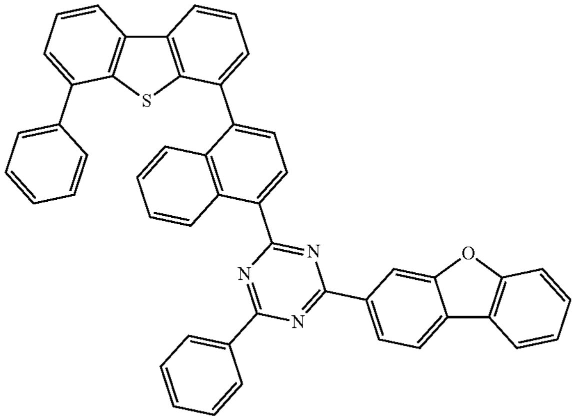
P-109
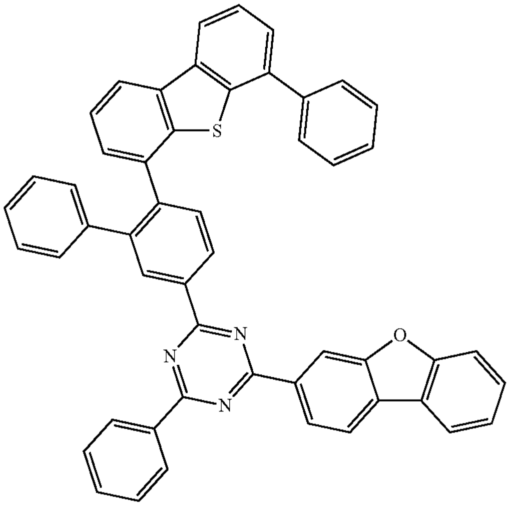
P-110
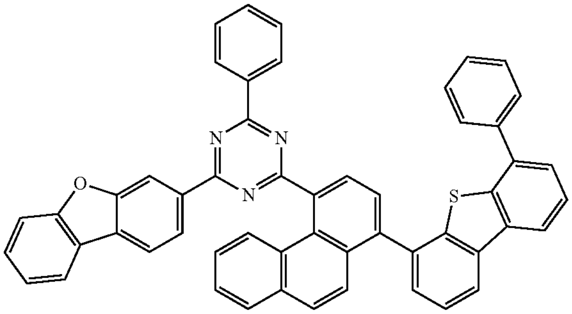
P-111
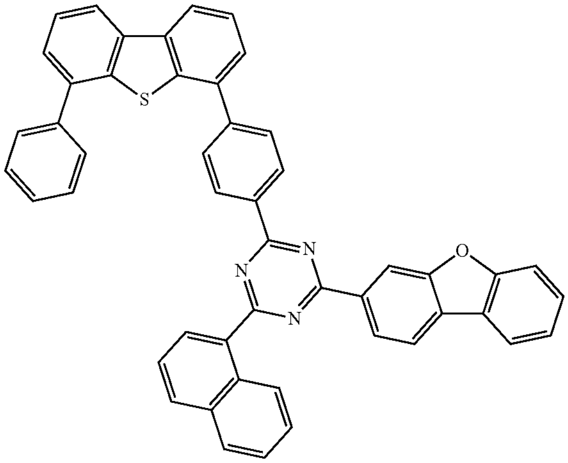
P-112
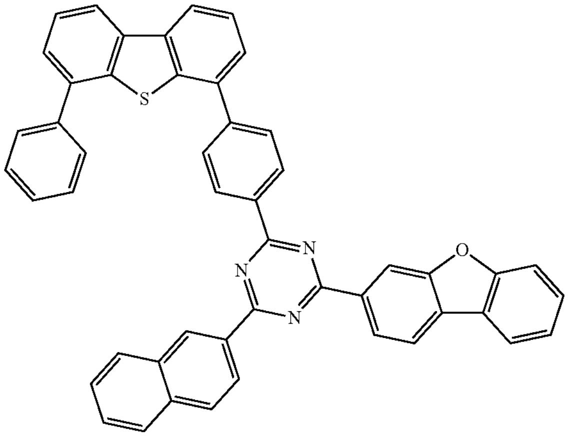

-continued
P-113
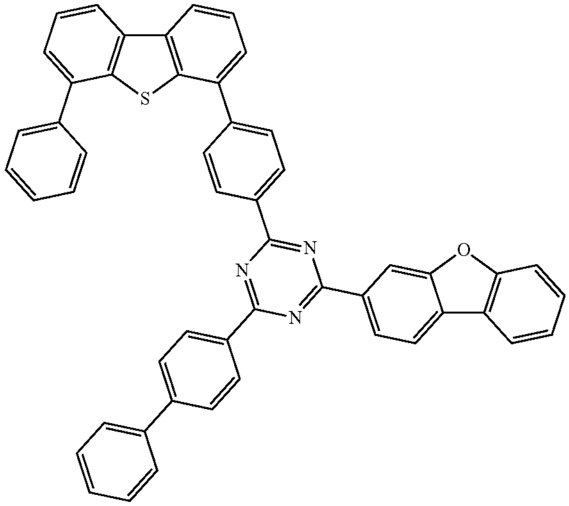
P-114
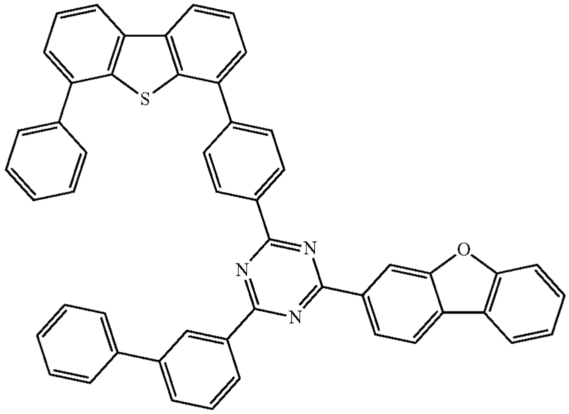
P-115
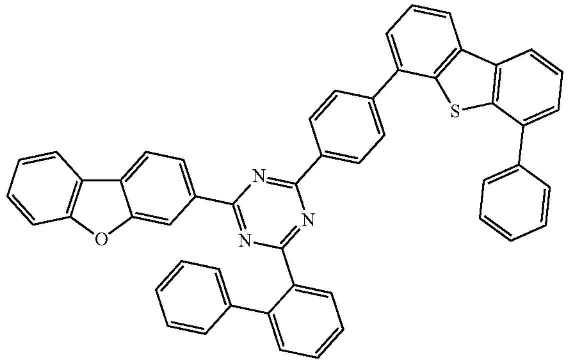
-continued
P-116
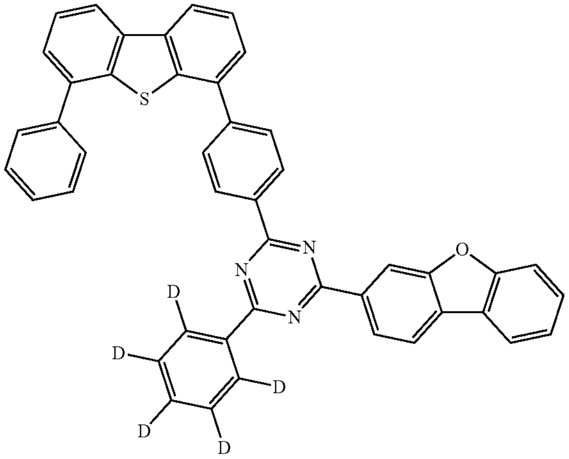
P-117
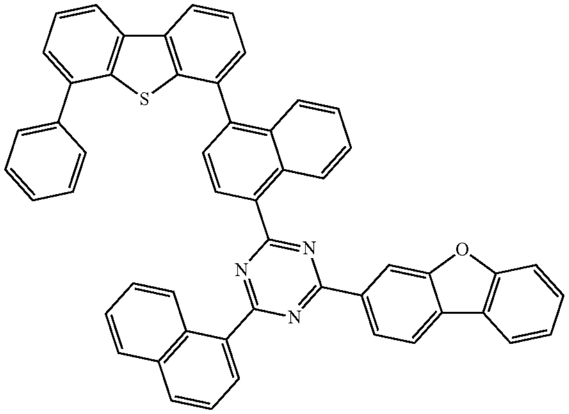
P-118
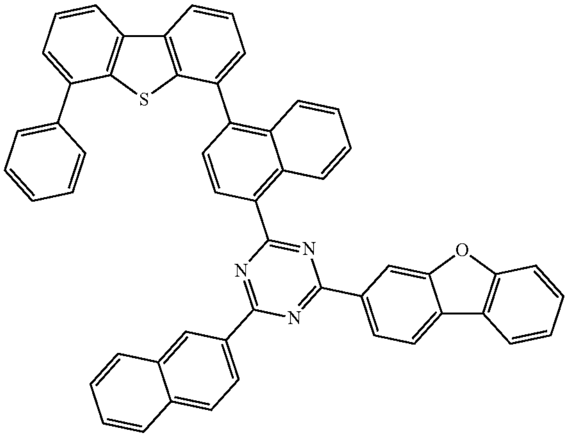

-continued
P-119
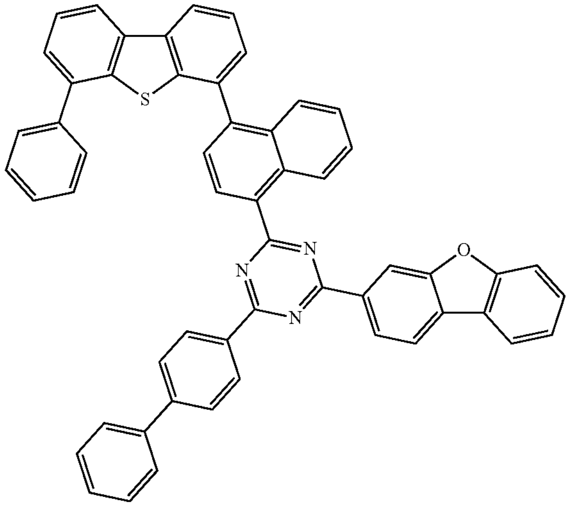
P-120
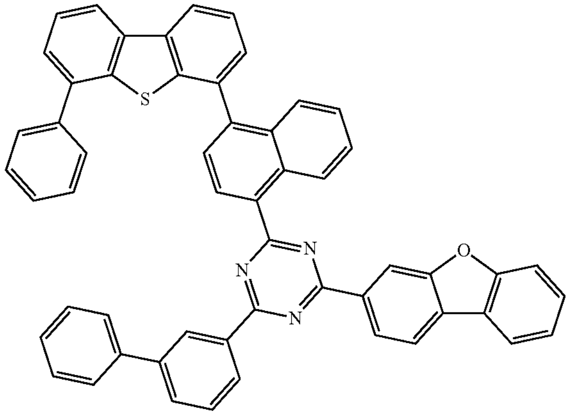
4-1
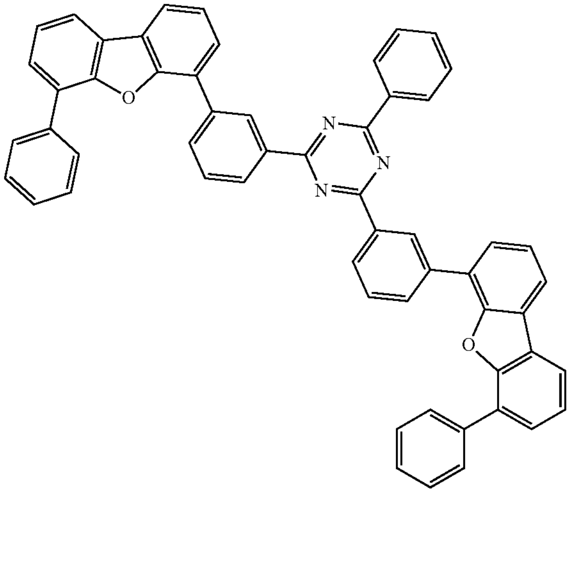
-continued
4-2
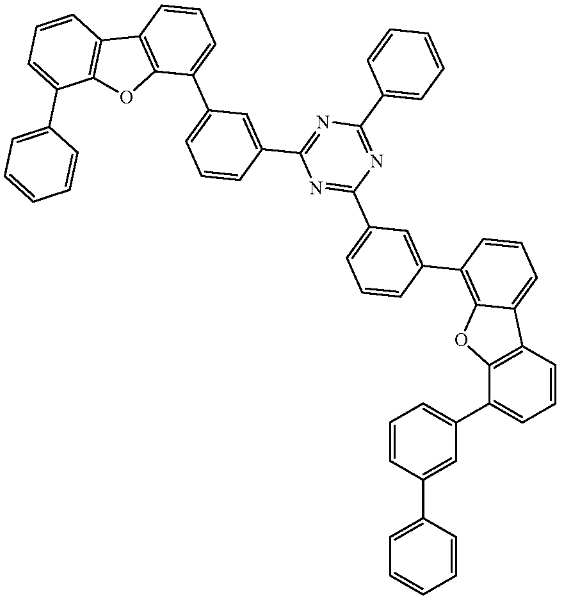
4-3
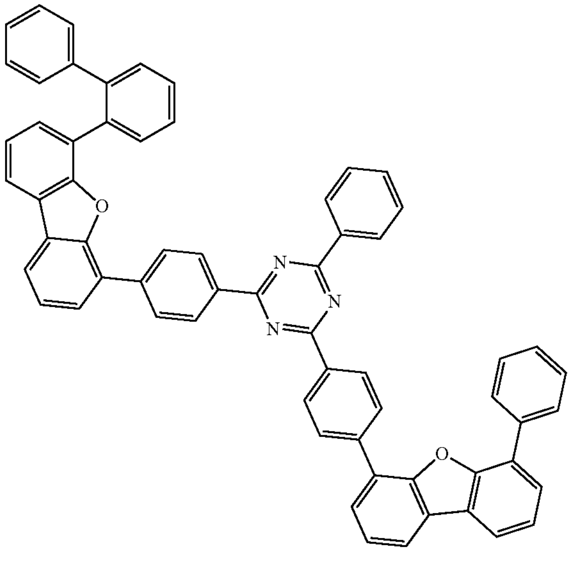

-continued
4-4
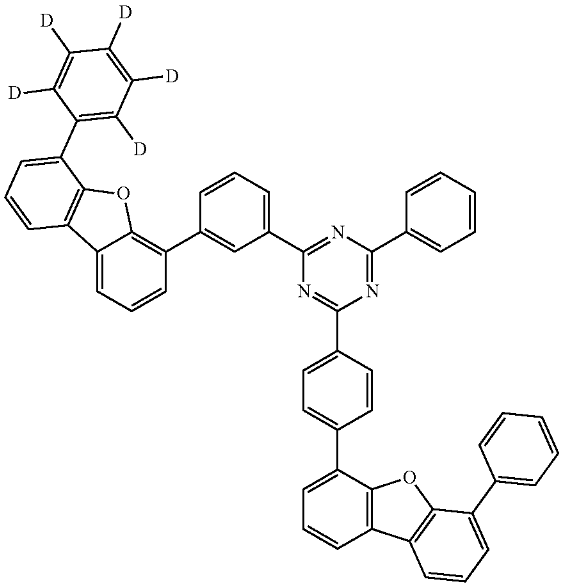
-continued
4-6
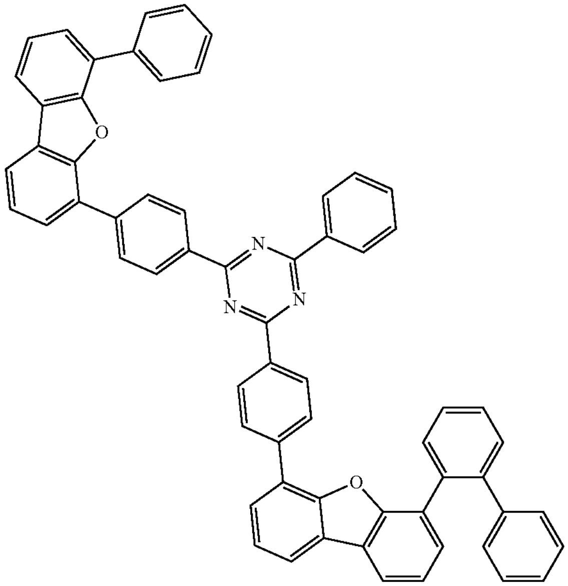
4-5
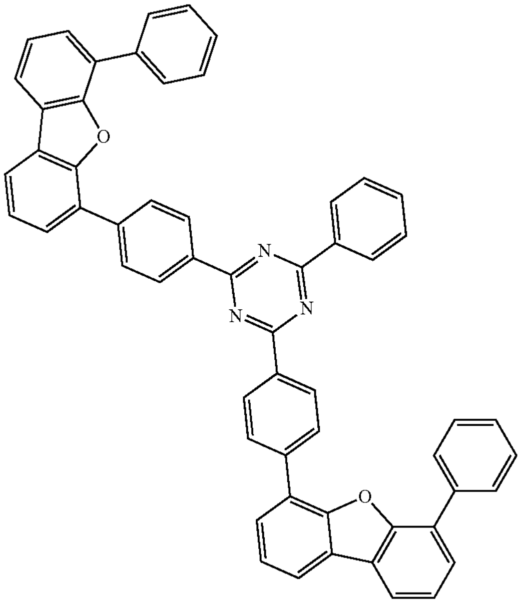
4-7
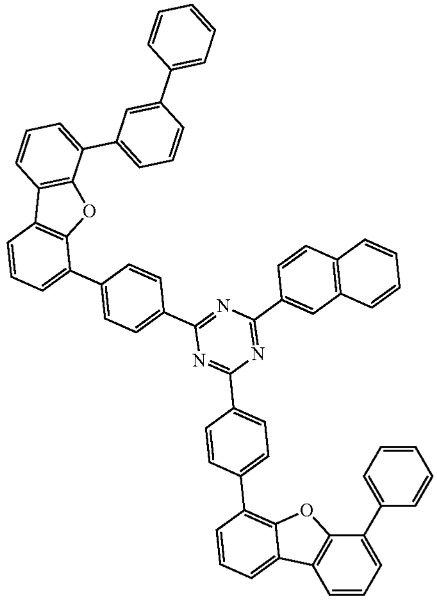

-continued
4-8
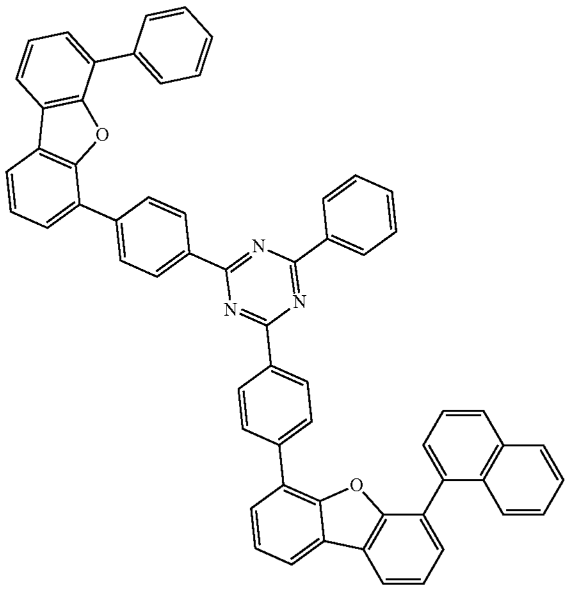
4-9
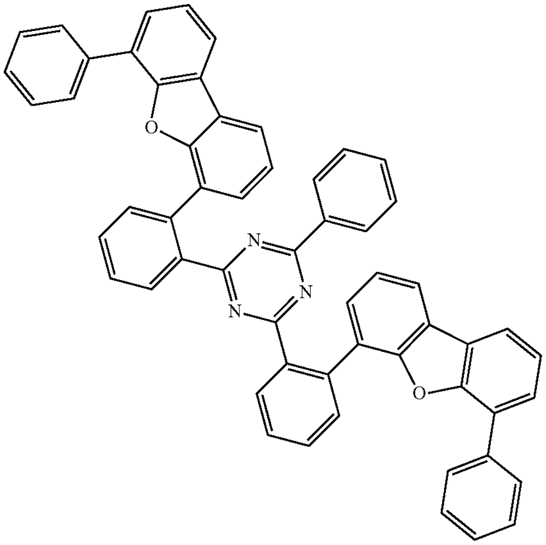
4-10
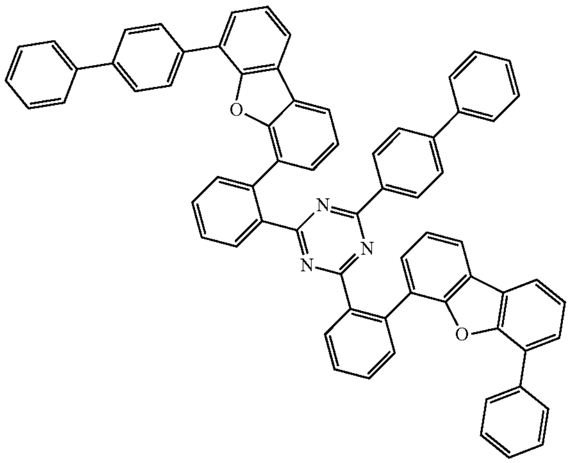
-continued
4-11
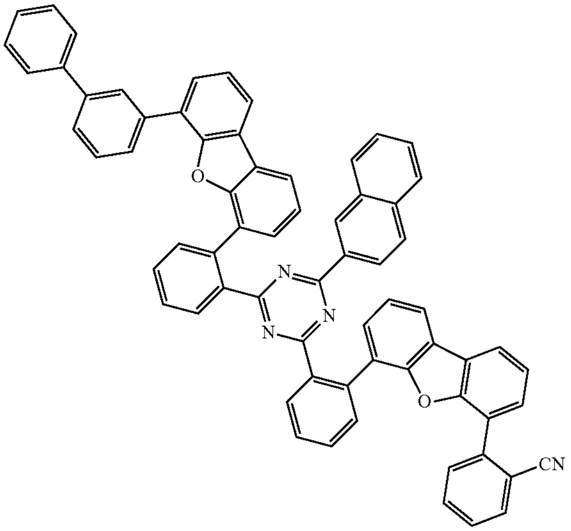
4-12
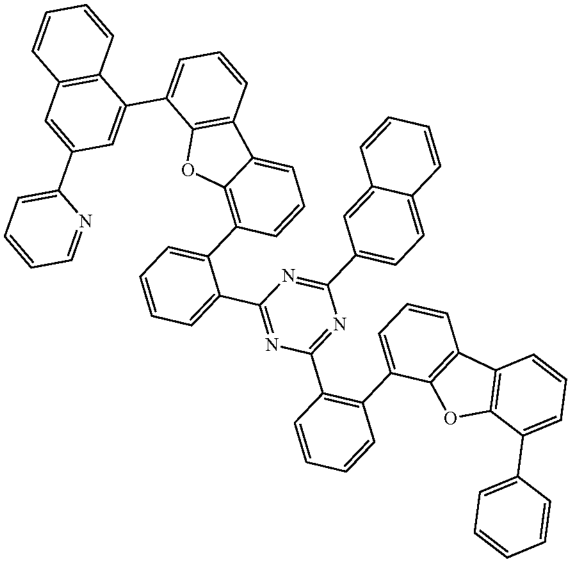
5-1
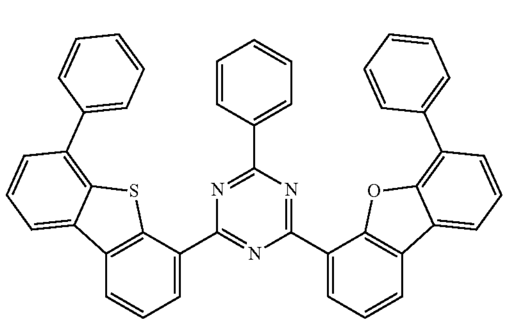

-continued
5-2
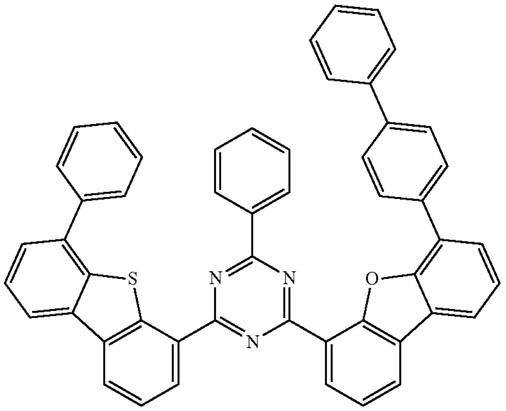
5-3
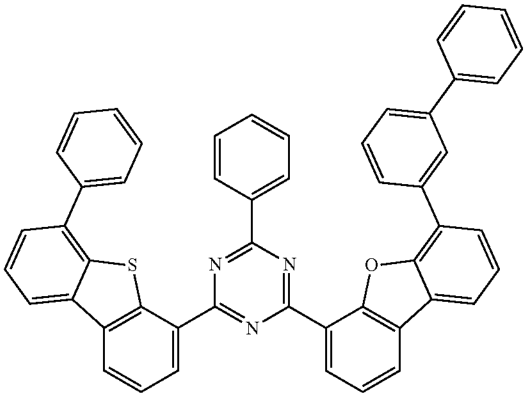
5-4
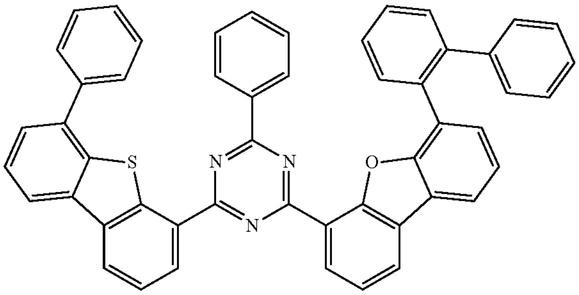
5-5
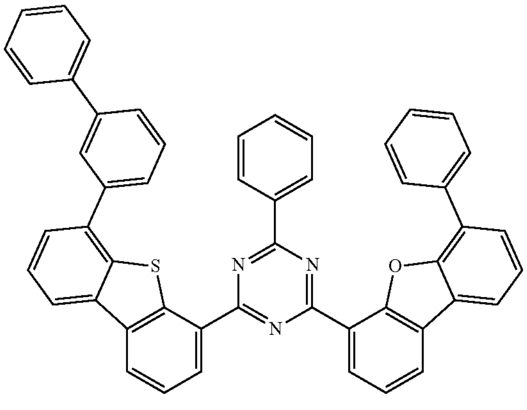
-continued
5-6
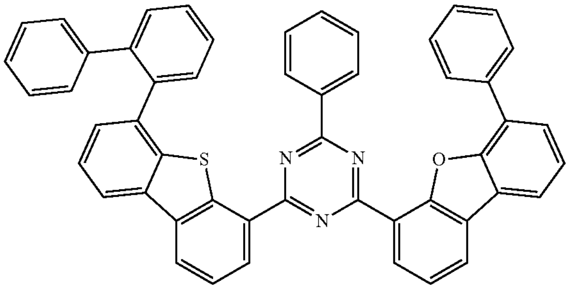
5-7
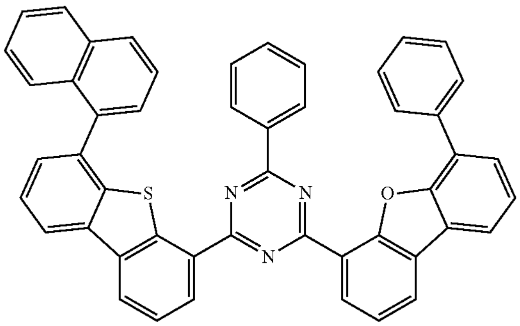
5-8
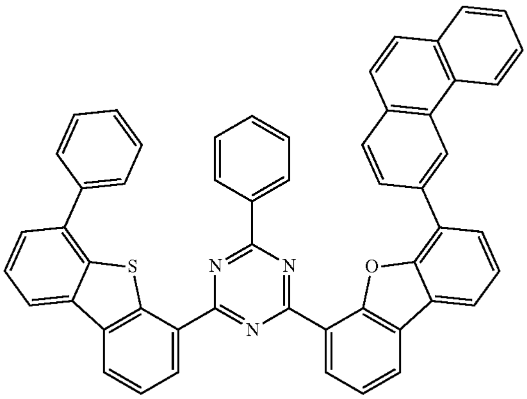
5-9
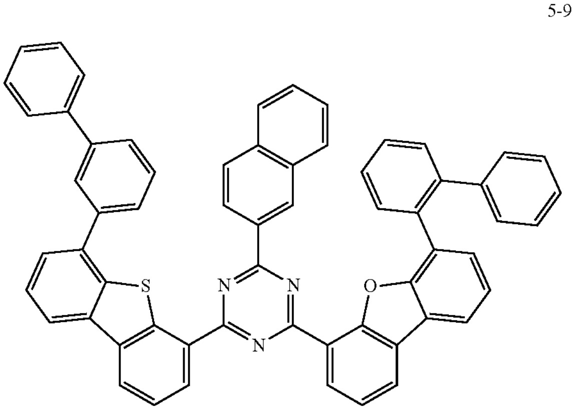

-continued
5-10
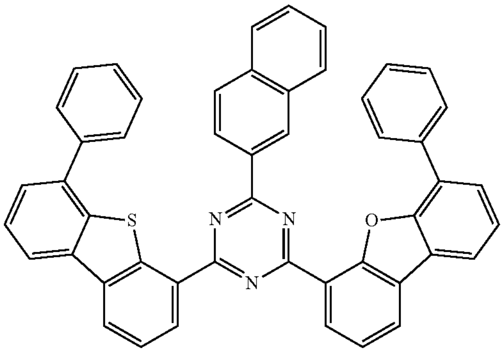
5-11
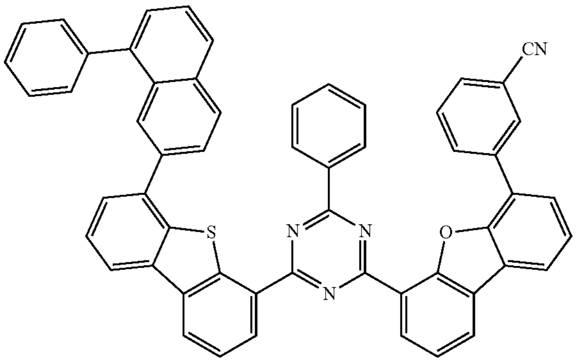
5-12
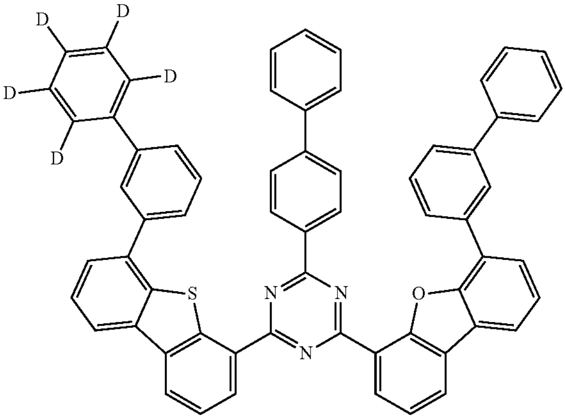
5-13
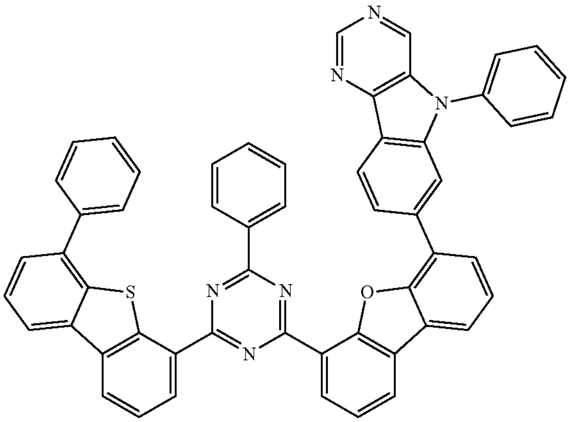
-continued
5-14
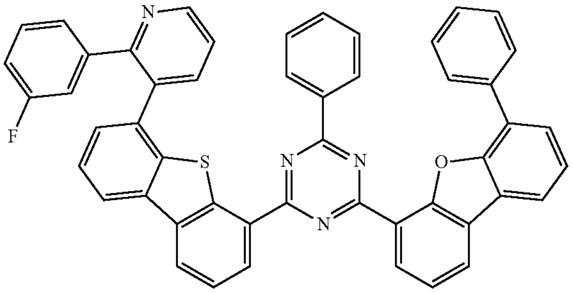
5-15
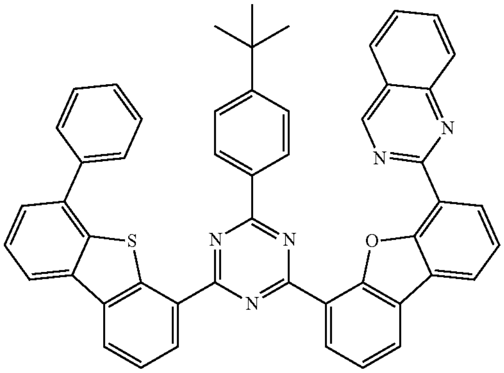
5-16
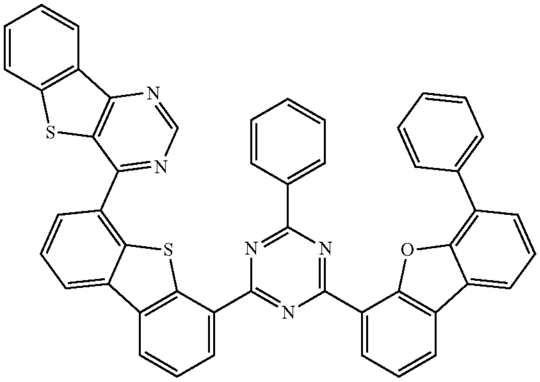
5-17
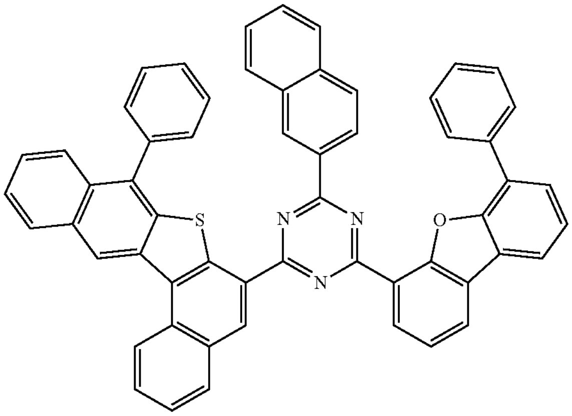

-continued
5-18
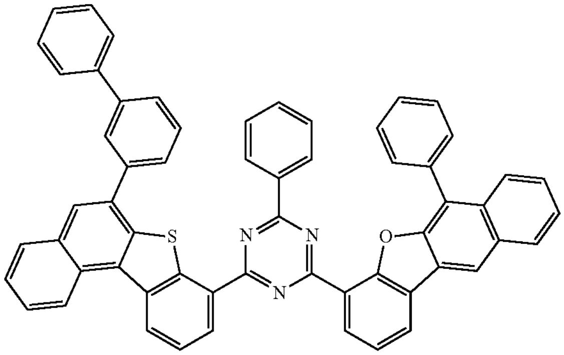
5-19
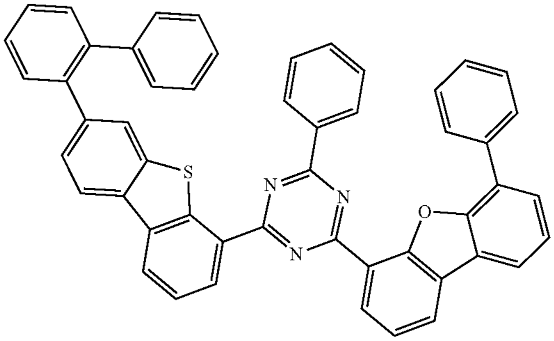
5-20
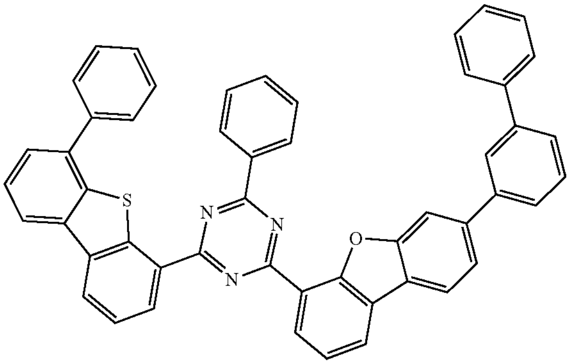
6-1
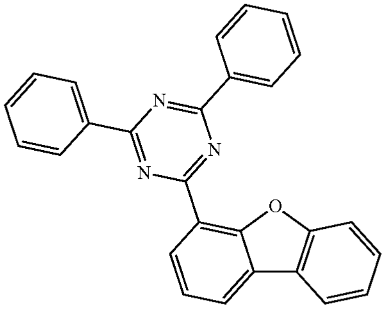
-continued
6-2
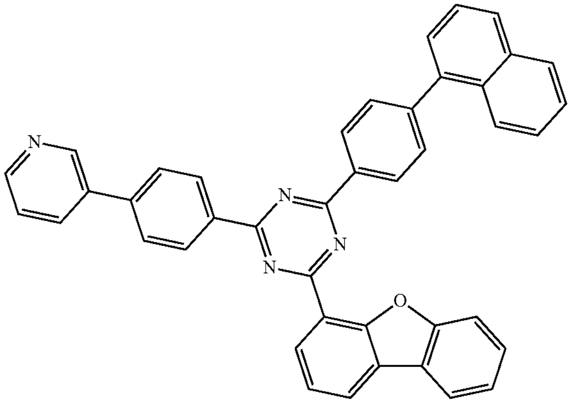
6-3
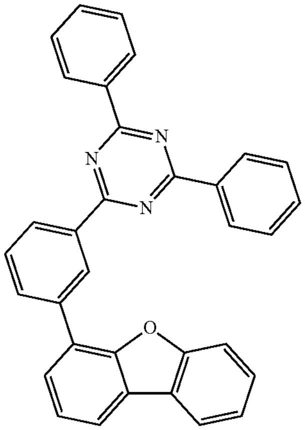
6-4
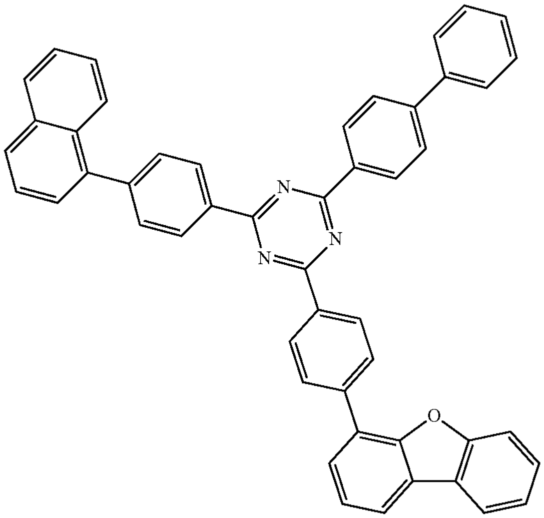

6-5
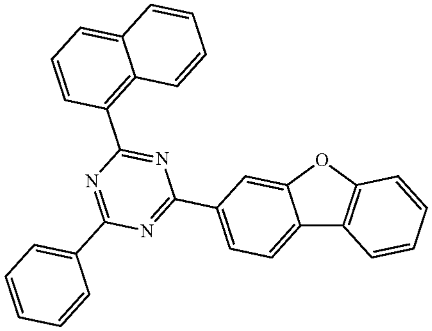
6-6
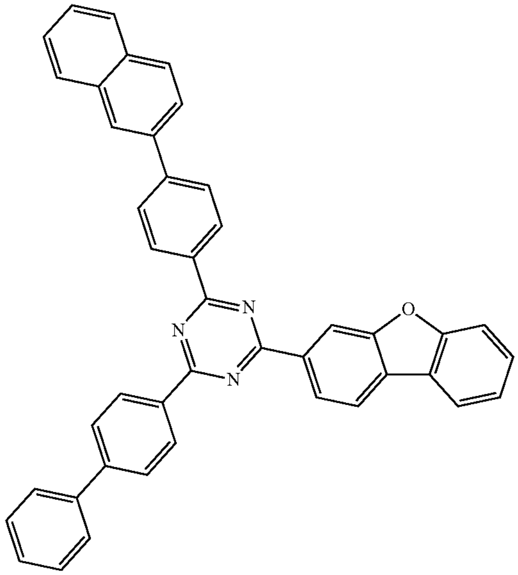
6-7
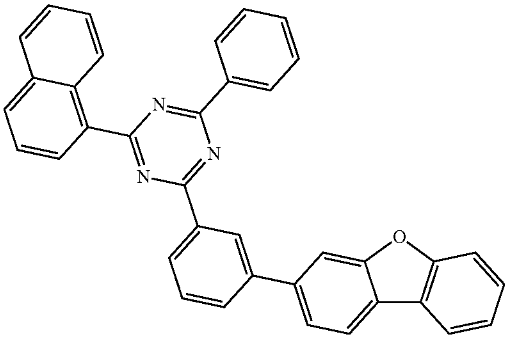
6-8
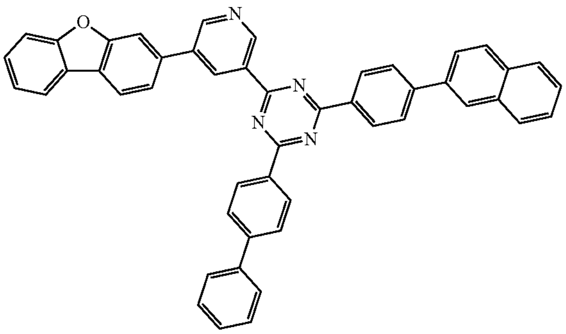
6-9
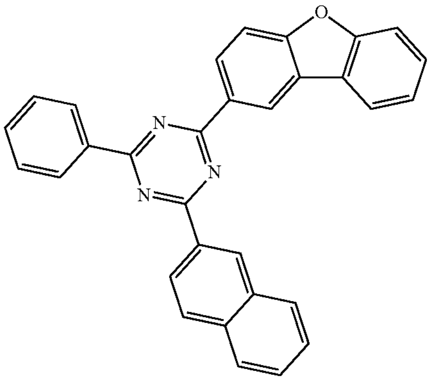
6-10
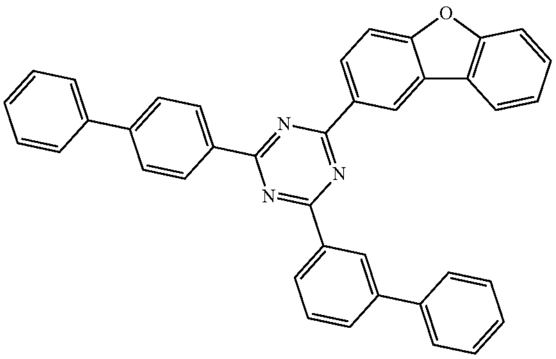
6-11
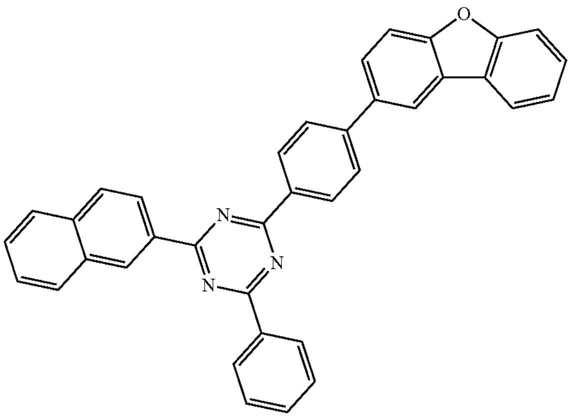

-continued 6-12

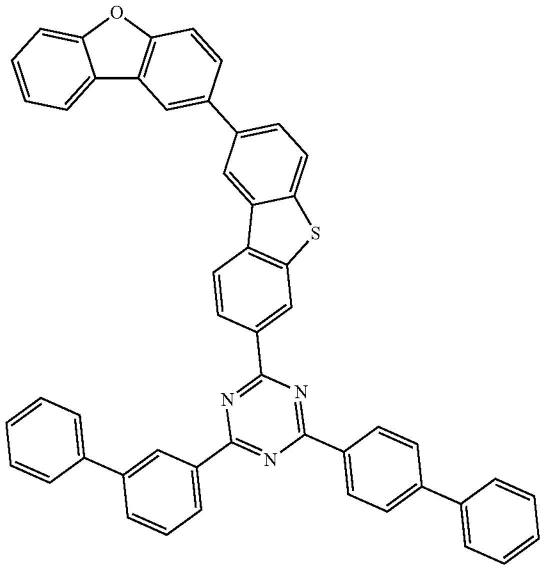

6-13

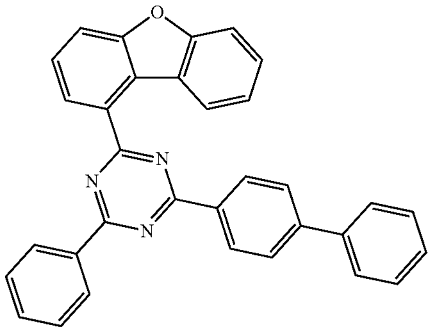

6-14

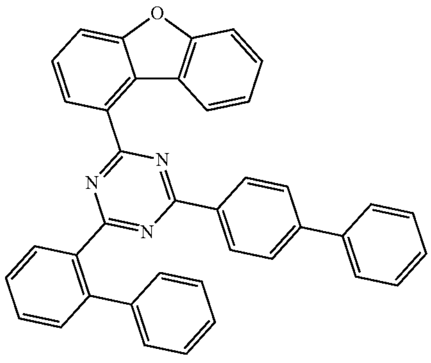

-continued 6-15

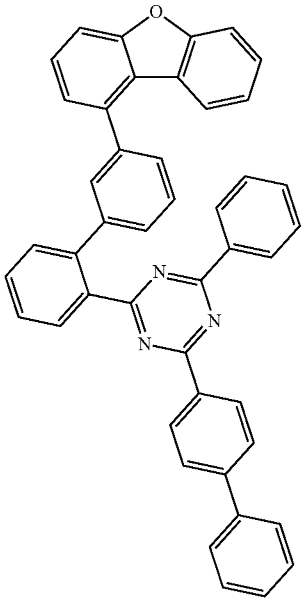

6-16

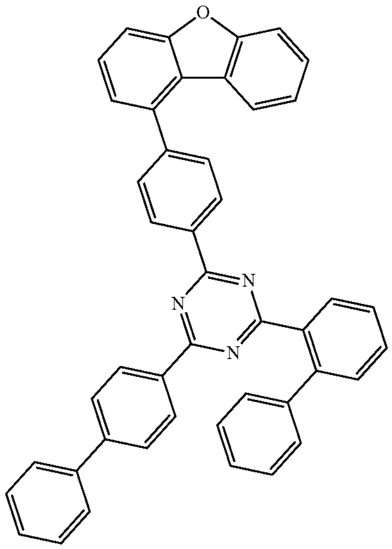

.

12. The organic electronic element of claim 1, comprising between the first electrode and the emitting layer, a hole transport layer and/or an emitting auxiliary layer comprising the compound represented by Formula 1.

13. The organic electronic element of claim 1, wherein the compounds represented by Formula 1 and by Formula 2 are mixed in a ratio of 1:9 to 9:1 and included in the emitting layer.

14. The organic electronic element of claim 1, wherein the compounds represented by Formula 1 and by Formula 2 are mixed in a ratio of 1:9 to 5:5 and included in the emitting layer.

15. The organic electronic element of claim 1, wherein the compounds represented by Formula 1 and by Formula 2 are mixed in a ratio of 2:8 or 3:7 and included in the emitting layer.

16. The organic electronic element of claim 1, comprising a light efficiency enhancing layer formed on one side of the first electrode and/or of the second electrode, the side being opposite to the organic material layer and not facing the organic material layer.

17. The organic electronic element of claim 1, wherein the organic material layer is formed by one of a spin coating process, a nozzle printing process, an inkjet printing process, a slot coating process, a dip coating process and a roll-to-roll process.

18. An electronic device comprising: a display device including the organic electric element of claim 1; and a control unit for driving the display device.

19. The electronic device of claim 18, wherein the organic electric element is at least one of an OLED, an organic solar cell, an organic photo conductor, an organic transistor and an element for monochromic or white illumination.

20. A compound represented by Formula 20 or 21:

<Formula 20>

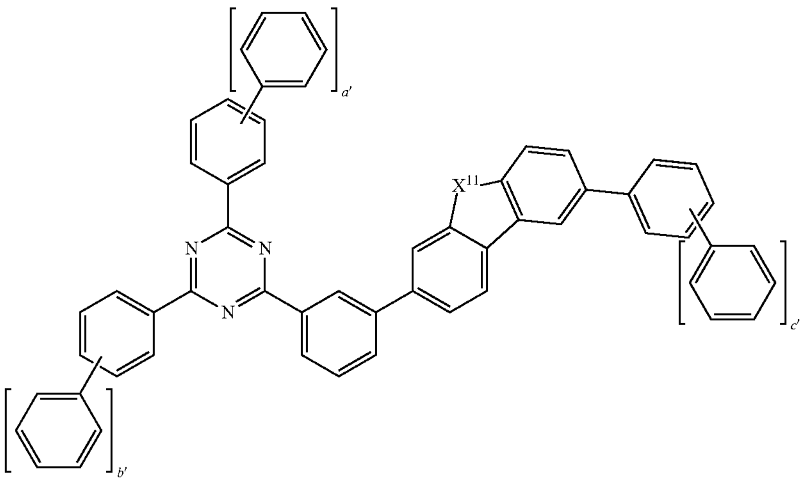

<Formula 21>

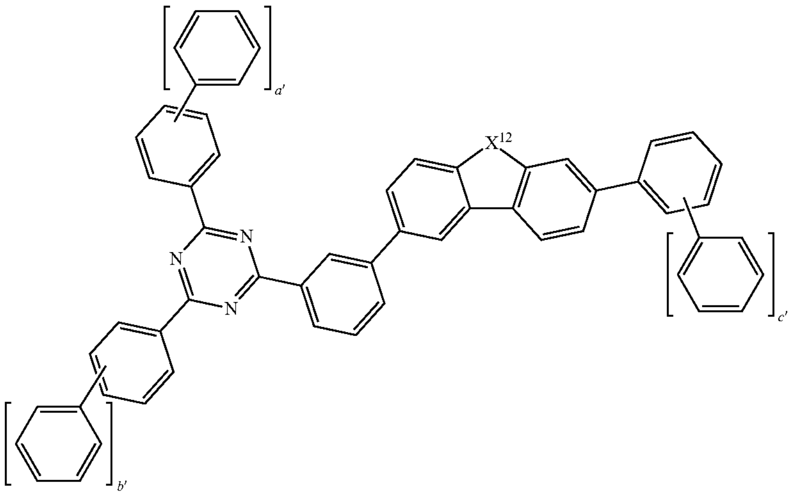

wherein $X^{11}$ and $X^{12}$ are each independently O or S, and a', b', c' and d' are each independently 0 or 1.

21. A compound represented by Formula 22:

<Formula 22>

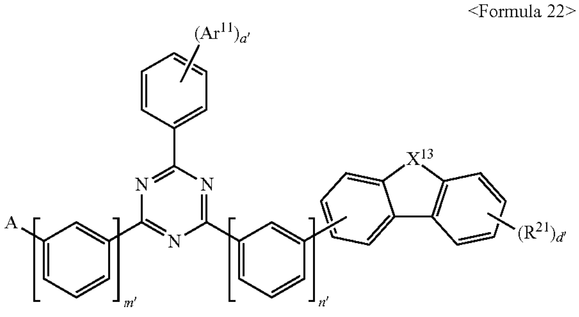

wherein

A is the following Formula A-1 or A-2,

<Formula A-1>

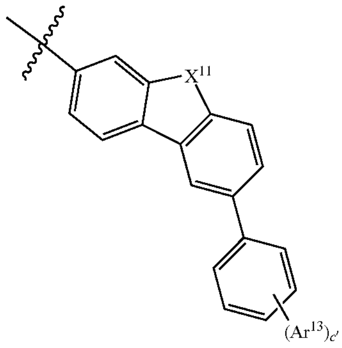

-continued

<Formula A-2>

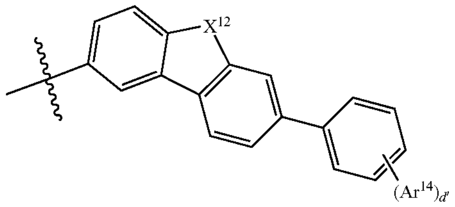

$Ar^{11}$ is a $C_6$-$C_{18}$ aryl group, $X^{11}$, $X^{12}$ and $X^{13}$ are each independently O or S, m' and n' are each independently 0 or 1, a' and c' each independently an integer of 0 to 5, d' is an integer of any one of 0 to 4, $R^{21}$ is a $C_6$-$C_{18}$ aryl group, and $Ar^{13}$ and $Ar^{14}$ are each independently a $C_6$-$C_{18}$ aryl group, with the proviso that: (1) where m'+n'=0, c' is not an integer of 0 and d' is not an integer of 0, and (2) where $X^{11}$, $X^{12}$ and $X^{13}$ are O, m'+n'=1 or 2.

22. The compound of claim 21, wherein the compound represented by Formula 22 is represented by Formula 23 or Formula 24:

Formula 23

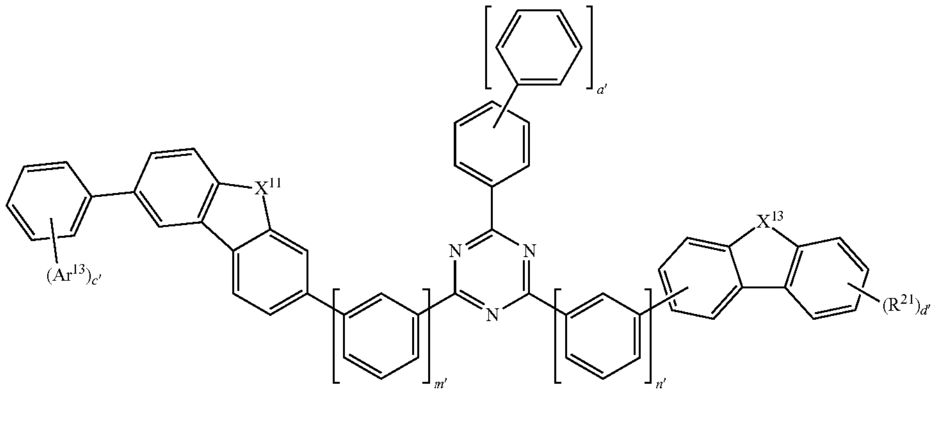

Formula 24

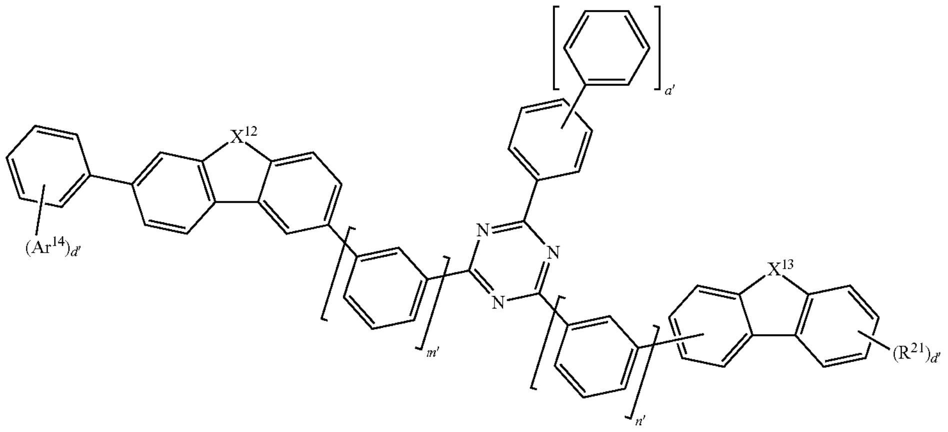

wherein
$X^{11}$, $X^{12}$, $X^{13}$, a', c', d', m', n', $Ar^{13}$, $Ar^{14}$, $R^{21}$ are the same as defined in claim 21.
23. A compound selected from the group consisting of the following compounds:
7-1
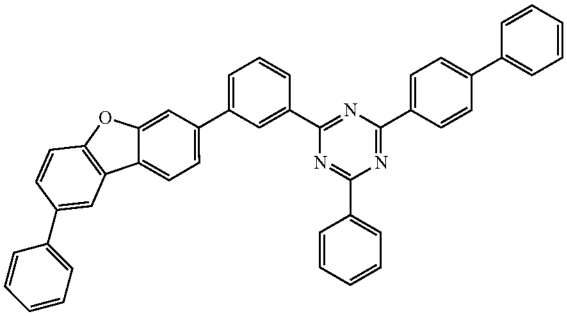
7-2
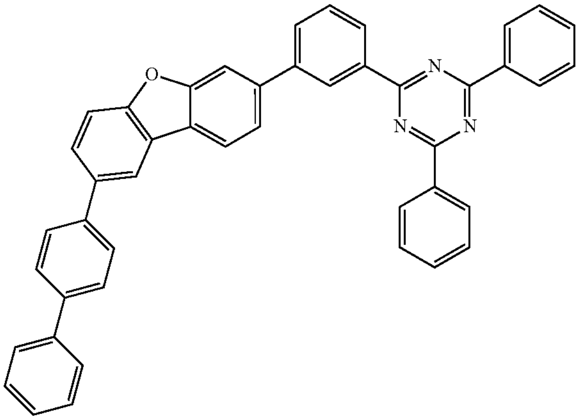
7-3
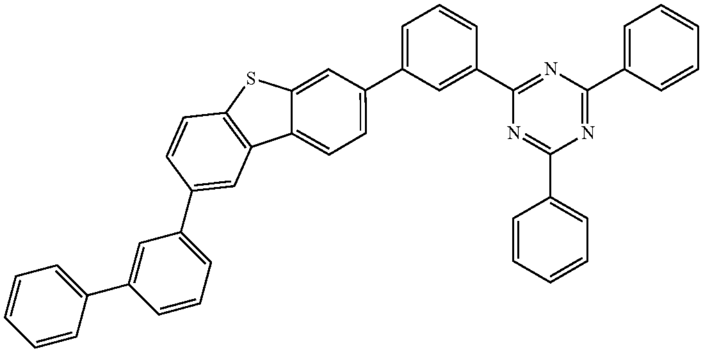
7-4
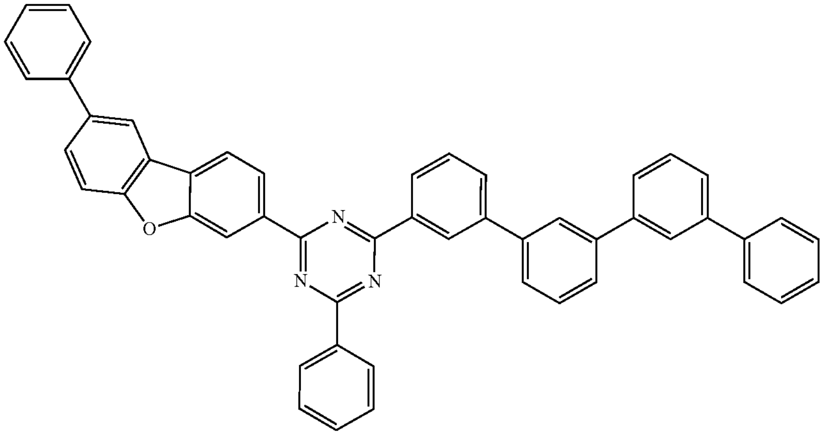

-continued
7-5
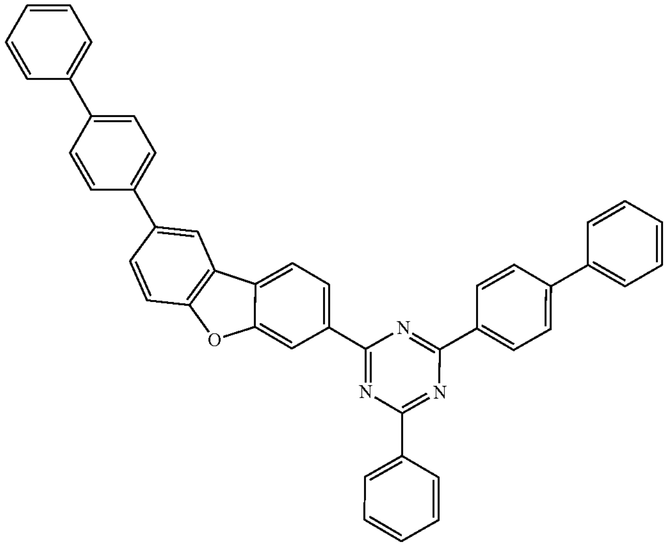
7-6
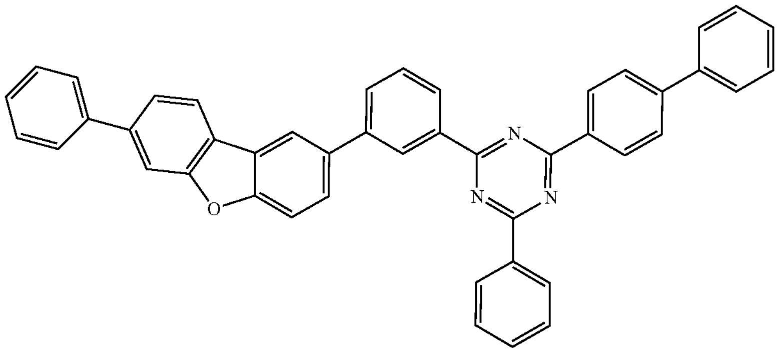
7-7
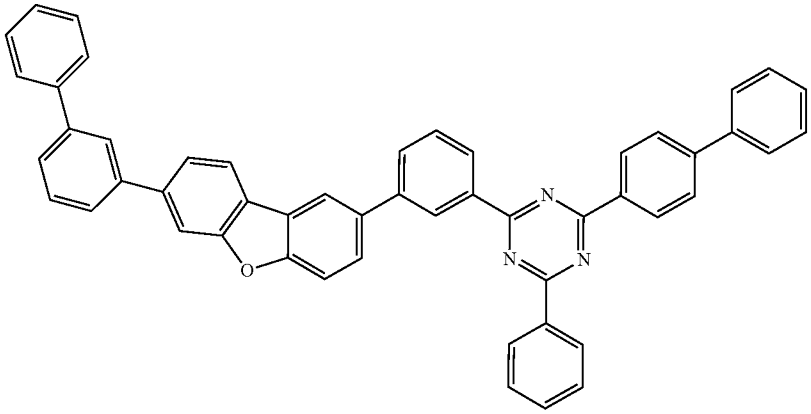
7-8
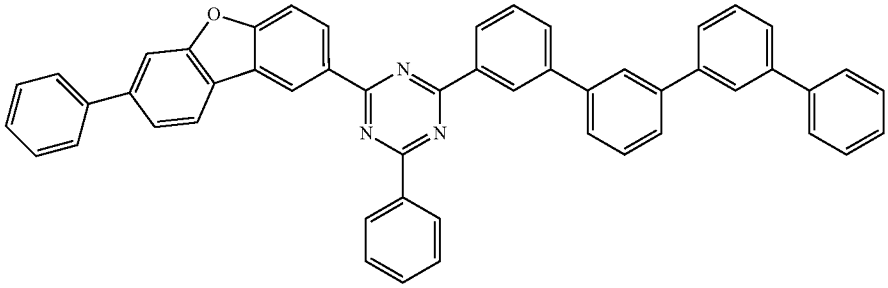

-continued
7-9
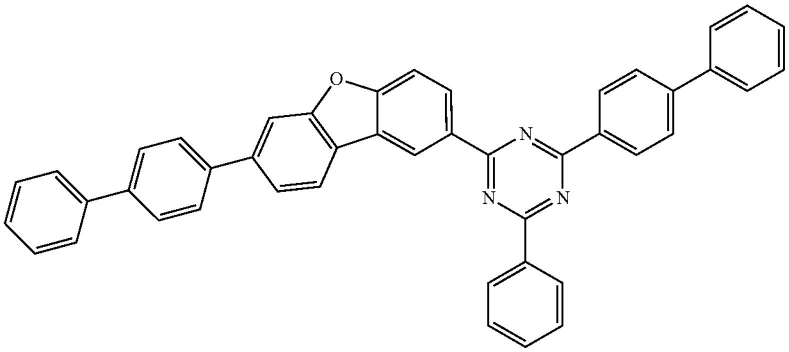
24. A compound selected from the group consisting of the following compounds:
7-10
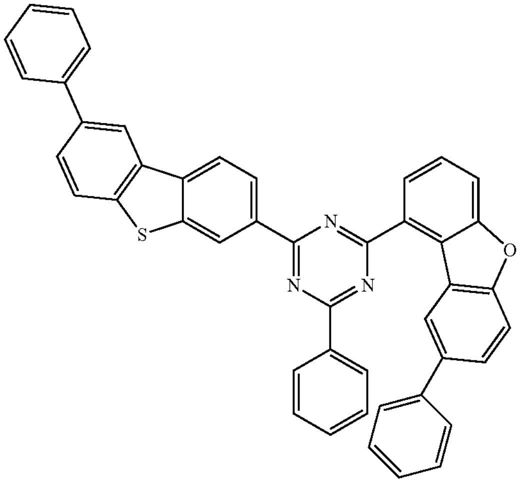
7-11
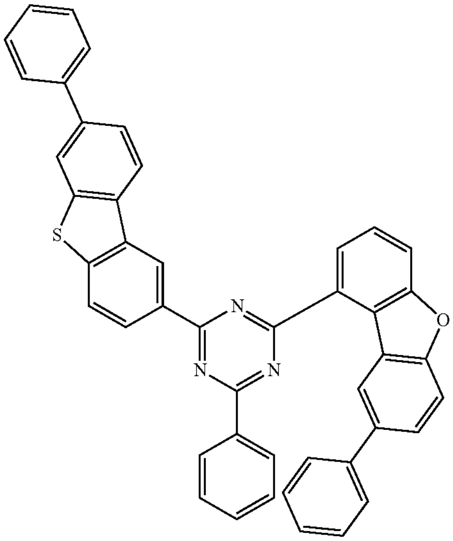
-continued
7-12
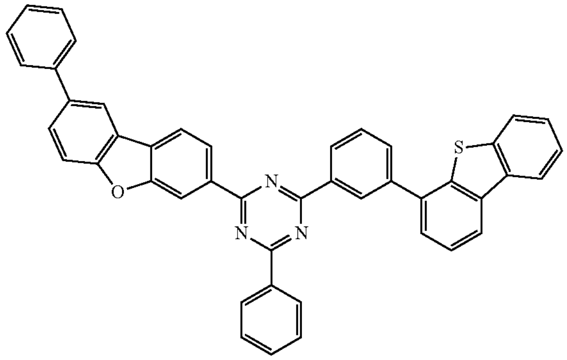
7-13
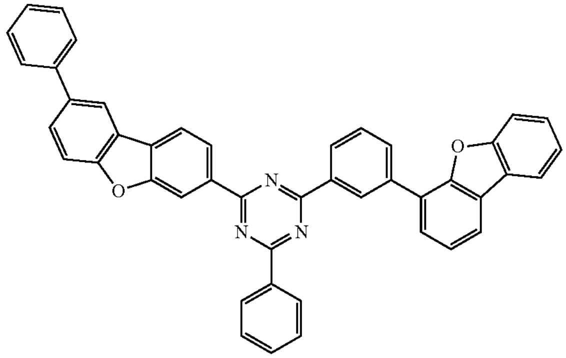
7-14
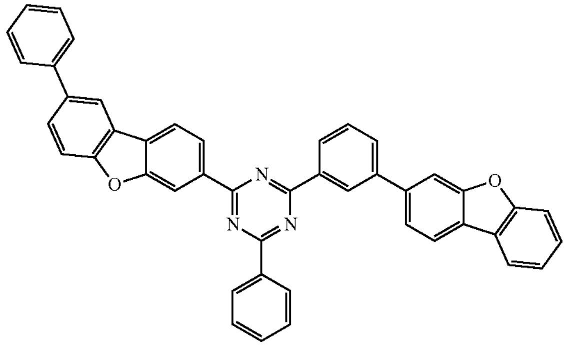

-continued
7-15
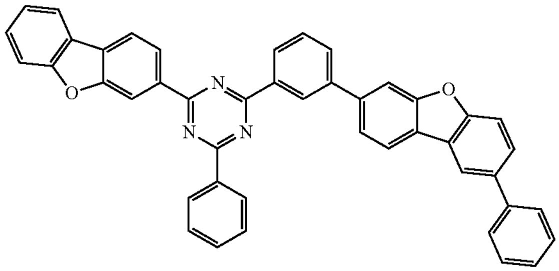
7-16
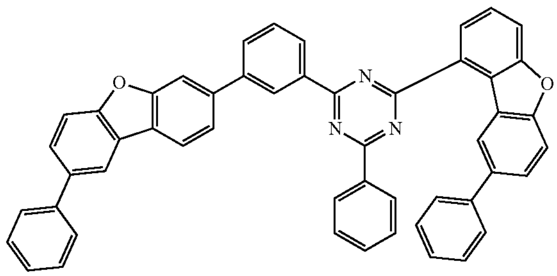
7-17
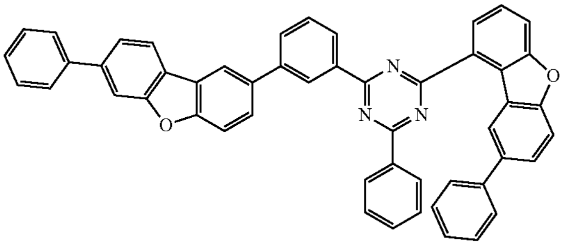
7-18
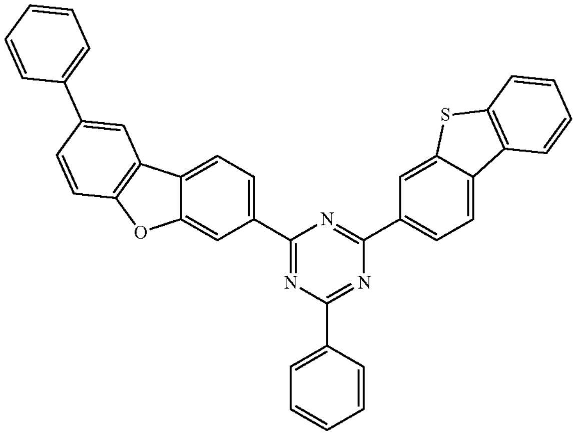
-continued
7-19
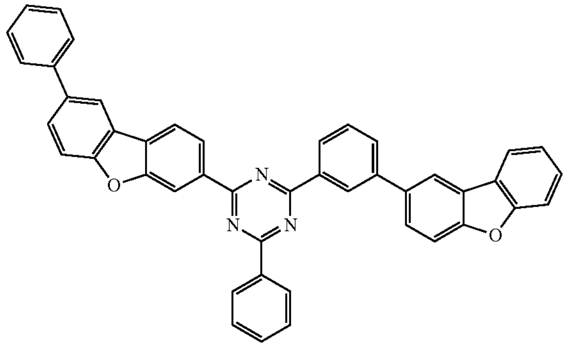
7-20
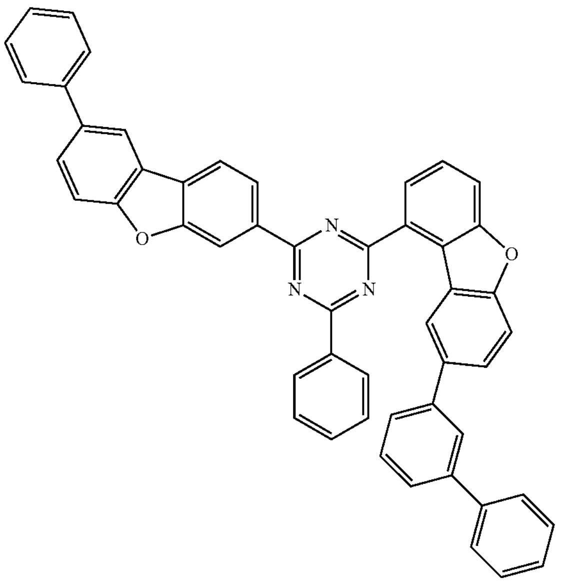
7-21
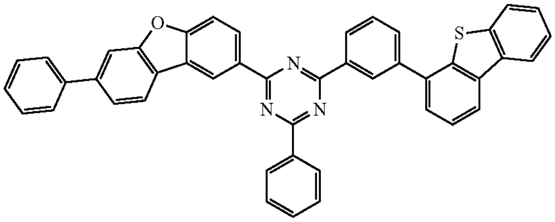
7-22
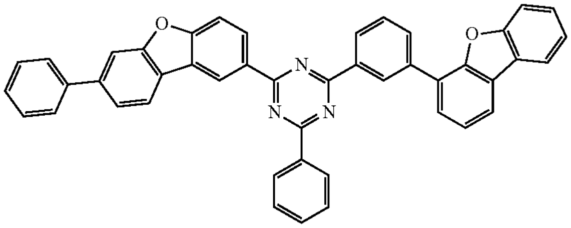

-continued
7-23
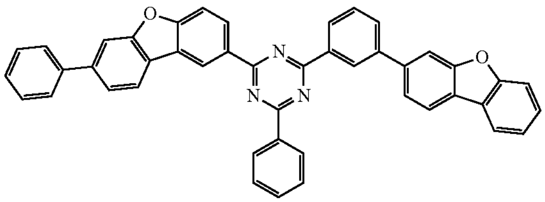
7-24
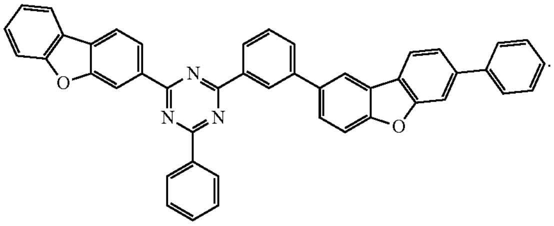
.
* * * * *